US012605104B2

(12) United States Patent
Poltorak

(10) Patent No.: US 12,605,104 B2
(45) Date of Patent: Apr. 21, 2026

(54) METHOD AND APPARATUS FOR NEUROENHANCEMENT

(71) Applicant: Neuroenhancement Lab, LLC, Pomona, NY (US)

(72) Inventor: Alexander I. Poltorak, Pomona, NY (US)

(73) Assignee: NeuroLight, Inc., Pomona, NY (US)

( * ) Notice: Subject to any disclaimer, the term of this patent is extended or adjusted under 35 U.S.C. 154(b) by 7 days.

(21) Appl. No.: 18/233,835

(22) Filed: Aug. 14, 2023

(65) Prior Publication Data

US 2023/0380749 A1 Nov. 30, 2023

Related U.S. Application Data

(62) Division of application No. 16/134,309, filed on Sep. 18, 2018, now Pat. No. 11,723,579.

(60) Provisional application No. 62/594,452, filed on Dec. 4, 2017, provisional application No. 62/568,610, filed on Oct. 5, 2017, provisional application No. 62/560,502, filed on Sep. 19, 2017.

(51) Int. Cl.
| | |
|---|---|
| *A61B 5/369* | (2021.01) |
| *A61B 5/00* | (2006.01) |
| *A61B 5/316* | (2021.01) |
| *A61B 5/377* | (2021.01) |
| *A61M 21/00* | (2006.01) |
| *G06N 3/02* | (2006.01) |

(52) U.S. Cl.
CPC .............. *A61B 5/369* (2021.01); *A61B 5/316* (2021.01); *A61B 5/377* (2021.01); *A61B*

*5/7267* (2013.01); *A61M 21/00* (2013.01); *G06N 3/02* (2013.01); *G06F 2218/12* (2023.01)

(58) Field of Classification Search
CPC ..................................................... A61M 21/00
See application file for complete search history.

(56) References Cited

U.S. PATENT DOCUMENTS

| | | | |
|---|---|---|---|
| 3,951,134 | A | 4/1976 | Malech |
| 4,172,014 | A | 10/1979 | Sequeira, Jr. et al. |
| 4,296,756 | A | 10/1981 | Dunning et al. |
| 4,367,527 | A | 1/1983 | Desjacques |
| 4,407,299 | A | 10/1983 | Culver |

(Continued)

FOREIGN PATENT DOCUMENTS

| | | |
|---|---|---|
| EP | 1304073 A2 | 4/2003 |
| EP | 1304073 A3 | 9/2003 |

(Continued)

*Primary Examiner* — John R Downey
(74) *Attorney, Agent, or Firm* — Hoffberg & Associates; Steven M Hoffberg

(57) ABSTRACT

A method of facilitating a skill learning process or improving performance of a task, comprising: determining a brainwave pattern reflecting neuronal activity of a skilled subject while engaged in a respective skill or task; processing the determined brainwave pattern with at least one automated processor; and subjecting a subject training in the respective skill or task to brain entrainment by a stimulus selected from the group consisting of one or more of a sensory excitation, a peripheral excitation, a transcranial excitation, and a deep brain stimulation, dependent on the processed temporal pattern extracted from brainwaves reflecting neuronal activity of the skilled subject.

23 Claims, 11 Drawing Sheets

(56)                    References Cited

U.S. PATENT DOCUMENTS

| | | | |
|---|---|---|---|
| 4,408,616 A | 10/1983 | Duffy et al. |
| 4,421,122 A | 12/1983 | Duffy |
| 4,437,064 A | 3/1984 | Overton, Jr. et al. |
| 4,493,327 A | 1/1985 | Bergelson et al. |
| 4,550,736 A | 11/1985 | Broughton et al. |
| 4,557,270 A | 12/1985 | John |
| 4,562,540 A | 12/1985 | Devaney |
| 4,579,125 A | 4/1986 | Strobl et al. |
| 4,583,190 A | 4/1986 | Salb |
| 4,585,011 A | 4/1986 | Broughton et al. |
| 4,591,787 A | 5/1986 | Hoenig |
| 4,594,662 A | 6/1986 | Devaney |
| 4,610,259 A | 9/1986 | Cohen et al. |
| 4,613,817 A | 9/1986 | Hoenig |
| 4,649,482 A | 3/1987 | Raviv et al. |
| 4,689,559 A | 8/1987 | Hastings et al. |
| 4,693,000 A | 9/1987 | Hoenig |
| 4,700,135 A | 10/1987 | Hoenig |
| 4,705,049 A | 11/1987 | John |
| 4,733,180 A | 3/1988 | Hoenig et al. |
| 4,736,307 A | 4/1988 | Salb |
| 4,736,751 A | 4/1988 | Gevins et al. |
| 4,744,029 A | 5/1988 | Raviv et al. |
| 4,749,946 A | 6/1988 | Hoenig |
| 4,753,246 A | 6/1988 | Freeman |
| 4,761,611 A | 8/1988 | Hoenig |
| 4,776,345 A | 10/1988 | Cohen et al. |
| 4,792,145 A | 12/1988 | Eisenberg et al. |
| 4,794,533 A | 12/1988 | Cohen |
| 4,801,882 A | 1/1989 | Daalmans |
| 4,846,190 A | 7/1989 | John |
| 4,862,359 A | 8/1989 | Trivedi et al. |
| 4,883,067 A | 11/1989 | Knispel et al. |
| 4,907,597 A | 3/1990 | Chamoun |
| 4,913,152 A | 4/1990 | Ko et al. |
| 4,924,875 A | 5/1990 | Chamoun |
| 4,937,525 A | 6/1990 | Daalmans |
| 4,940,058 A | 7/1990 | Taff et al. |
| 4,947,480 A | 8/1990 | Lewis |
| 4,949,725 A | 8/1990 | Raviv et al. |
| 4,951,674 A | 8/1990 | Zanakis et al. |
| 4,974,602 A | 12/1990 | Abraham-Fuchs et al. |
| 4,977,505 A | 12/1990 | Pelizzari et al. |
| 4,982,157 A | 1/1991 | Seifert |
| 4,983,912 A | 1/1991 | Roehrlein et al. |
| 4,996,479 A | 2/1991 | Hoenig |
| 5,008,622 A | 4/1991 | Overton, Jr. et al. |
| 5,010,891 A | 4/1991 | Chamoun |
| 5,012,190 A | 4/1991 | Dossel |
| 5,020,538 A | 6/1991 | Morgan et al. |
| 5,020,540 A | 6/1991 | Chamoun |
| 5,027,817 A | 7/1991 | John |
| 5,029,082 A | 7/1991 | Shen et al. |
| 5,059,814 A | 10/1991 | Mead et al. |
| 5,061,680 A | 10/1991 | Paulson et al. |
| 5,069,218 A | 12/1991 | Ikeda |
| 5,070,399 A | 12/1991 | Martel |
| 5,083,571 A | 1/1992 | Prichep |
| 5,088,497 A | 2/1992 | Ikeda |
| 5,092,341 A | 3/1992 | Kelen |
| 5,092,835 A | 3/1992 | Schurig et al. |
| 5,095,270 A | 3/1992 | Ludeke |
| 5,105,354 A | 4/1992 | Nishimura |
| 5,109,862 A | 4/1992 | Kelen et al. |
| 5,118,606 A | 6/1992 | Lynch et al. |
| 5,126,315 A | 6/1992 | Nishino et al. |
| RE34,015 E | 8/1992 | Duffy |
| 5,136,687 A | 8/1992 | Edelman et al. |
| 5,158,932 A | 10/1992 | Hinshaw et al. |
| 5,159,703 A | 10/1992 | Lowery |
| 5,159,928 A | 11/1992 | Keppel |
| 5,166,614 A | 11/1992 | Yokosawa et al. |
| 5,187,327 A | 2/1993 | Ohta et al. |
| 5,198,977 A | 3/1993 | Salb |
| 5,213,338 A | 5/1993 | Brotz |

| | | | | |
|---|---|---|---|---|
| 5,213,562 A | * | 5/1993 | Monroe | G09B 5/04 |
| | | | | 600/545 |
| 5,215,086 A | | 6/1993 | Terry, Jr. et al. | |
| 5,218,530 A | | 6/1993 | Jastrzebski et al. | |
| 5,224,203 A | | 6/1993 | Skeirik | |
| 5,230,344 A | | 7/1993 | Ozdamar et al. | |
| 5,230,346 A | | 7/1993 | Leuchter et al. | |
| 5,231,988 A | | 8/1993 | Wernicke et al. | |
| 5,233,517 A | | 8/1993 | Jindra | |
| 5,241,967 A | | 9/1993 | Yasushi et al. | |
| 5,243,281 A | | 9/1993 | Ahonen et al. | |
| 5,243,517 A | | 9/1993 | Schmidt et al. | |
| 5,263,488 A | | 11/1993 | Van Veen et al. | |
| 5,265,611 A | | 11/1993 | Hoenig et al. | |
| 5,269,315 A | | 12/1993 | Leuchter et al. | |
| 5,269,325 A | | 12/1993 | Robinson et al. | |
| 5,273,038 A | | 12/1993 | Beavin | |
| 5,280,791 A | | 1/1994 | Lavie | |
| 5,282,474 A | | 2/1994 | Valdes Sosa et al. | |
| 5,283,523 A | | 2/1994 | Uhl et al. | |
| 5,287,859 A | | 2/1994 | John | |
| 5,291,888 A | | 3/1994 | Tucker | |
| 5,293,187 A | | 3/1994 | Knapp et al. | |
| 5,299,569 A | | 4/1994 | Wernicke et al. | |
| 5,303,705 A | | 4/1994 | Nenov | |
| 5,306,228 A | | 4/1994 | Rubins | |
| 5,307,807 A | | 5/1994 | Valdes Sosa et al. | |
| 5,309,095 A | | 5/1994 | Ahonen et al. | |
| 5,309,917 A | | 5/1994 | Wang et al. | |
| 5,309,923 A | | 5/1994 | Leuchter et al. | |
| 5,311,129 A | | 5/1994 | Ludwig et al. | |
| 5,320,109 A | | 6/1994 | Chamoun et al. | |
| 5,323,777 A | | 6/1994 | Ahonen et al. | |
| 5,325,862 A | | 7/1994 | Lewis et al. | |
| 5,326,745 A | | 7/1994 | Nishino et al. | |
| 5,331,970 A | | 7/1994 | Gevins et al. | |
| 5,335,657 A | | 8/1994 | Terry, Jr. et al. | |
| 5,339,811 A | | 8/1994 | Ohta et al. | |
| 5,339,826 A | | 8/1994 | Schmidt et al. | |
| 5,343,871 A | | 9/1994 | Bittman et al. | |
| 5,356,368 A | * | 10/1994 | Monroe | A61M 21/00 |
| | | | | 600/545 |
| 5,359,363 A | | 10/1994 | Kuban et al. | |
| 5,377,100 A | | 12/1994 | Pope et al. | |
| 5,384,588 A | | 1/1995 | Martin et al. | |
| 5,406,956 A | | 4/1995 | Farwell | |
| 5,406,957 A | | 4/1995 | Tansey | |
| 5,409,445 A | | 4/1995 | Rubins | |
| 5,417,211 A | | 5/1995 | Abraham-Fuchs et al. | |
| 5,418,512 A | | 5/1995 | Ohta et al. | |
| 5,422,689 A | | 6/1995 | Knapp et al. | |
| 5,442,289 A | | 8/1995 | DiIorio et al. | |
| 5,443,073 A | | 8/1995 | Wang et al. | |
| 5,447,154 A | | 9/1995 | Cinquin et al. | |
| 5,447,166 A | | 9/1995 | Gevins | |
| 5,458,117 A | | 10/1995 | Chamoun et al. | |
| 5,458,142 A | | 10/1995 | Farmer et al. | |
| 5,459,536 A | | 10/1995 | Shalon et al. | |
| 5,461,699 A | | 10/1995 | Arbabi et al. | |
| 5,469,057 A | | 11/1995 | Robinson | |
| 5,474,082 A | | 12/1995 | Junker | |
| 5,476,438 A | | 12/1995 | Edrich et al. | |
| 5,491,492 A | | 2/1996 | Knapp et al. | |
| 5,496,798 A | | 3/1996 | Sakai et al. | |
| 5,503,149 A | | 4/1996 | Beavin | |
| 5,513,649 A | | 5/1996 | Gevins et al. | |
| 5,515,301 A | | 5/1996 | Corby, Jr. et al. | |
| 5,522,863 A | | 6/1996 | Spano et al. | |
| 5,546,943 A | | 8/1996 | Gould | |
| 5,552,375 A | | 9/1996 | Nishino et al. | |
| 5,555,889 A | | 9/1996 | Karagueuzian et al. | |
| 5,568,816 A | | 10/1996 | Gevins et al. | |
| 5,571,150 A | | 11/1996 | Wernicke et al. | |
| 5,579,241 A | | 11/1996 | Corby, Jr. et al. | |
| 5,594,849 A | | 1/1997 | Kuc et al. | |
| 5,600,243 A | | 2/1997 | Colclough | |
| 5,601,081 A | | 2/1997 | Tomita et al. | |
| 5,611,350 A | | 3/1997 | John | |
| 5,617,856 A | | 4/1997 | Tamura et al. | |

(56)                    References Cited

U.S. PATENT DOCUMENTS

| | | | |
|---|---|---|---|
| 5,619,995 A | 4/1997 | Lobodzinski |
| 5,622,168 A | 4/1997 | Keusch et al. |
| 5,626,145 A | 5/1997 | Clapp et al. |
| 5,632,272 A | 5/1997 | Diab et al. |
| 5,640,493 A | 6/1997 | Skeirik |
| 5,643,325 A | 7/1997 | Karagueuzian et al. |
| 5,649,061 A | 7/1997 | Smyth |
| 5,650,726 A | 7/1997 | Gasnier et al. |
| 5,656,937 A | 8/1997 | Cantor |
| 5,662,109 A | 9/1997 | Hutson |
| 5,671,740 A | 9/1997 | Tomita et al. |
| 5,678,561 A | 10/1997 | Karagueuzian et al. |
| 5,682,889 A | 11/1997 | Tomita et al. |
| 5,685,313 A | 11/1997 | Mayevsky |
| 5,692,517 A | 12/1997 | Junker |
| 5,694,939 A | 12/1997 | Cowings |
| 5,699,808 A | 12/1997 | John |
| 5,701,909 A | 12/1997 | Amir et al. |
| 5,706,402 A | 1/1998 | Bell |
| 5,706,811 A | 1/1998 | Takeda et al. |
| 5,711,305 A | 1/1998 | Swanson et al. |
| 5,715,821 A | 2/1998 | Faupel |
| 5,719,561 A | 2/1998 | Gonzales |
| 5,720,619 A | 2/1998 | Fisslinger |
| 5,722,418 A | 3/1998 | Bro |
| 5,724,987 A | 3/1998 | Gevins et al. |
| 5,729,046 A | 3/1998 | Nishino et al. |
| 5,730,146 A | 3/1998 | Itil et al. |
| 5,736,543 A | 4/1998 | Rogers et al. |
| 5,737,485 A | 4/1998 | Flanagan et al. |
| 5,740,812 A | 4/1998 | Cowan |
| 5,742,748 A | 4/1998 | Sever, Jr. |
| 5,743,854 A | 4/1998 | Dobson et al. |
| 5,743,860 A | 4/1998 | Hively et al. |
| 5,747,492 A | 5/1998 | Lynch et al. |
| 5,752,514 A | 5/1998 | Okamura et al. |
| 5,752,521 A | 5/1998 | Dardik |
| 5,752,911 A | 5/1998 | Canedo et al. |
| 5,755,227 A | 5/1998 | Tomita et al. |
| 5,755,739 A | 5/1998 | Sun et al. |
| 5,761,332 A | 6/1998 | Wischmann et al. |
| 5,762,611 A | 6/1998 | Lewis et al. |
| 5,767,043 A | 6/1998 | Cantor et al. |
| 5,771,261 A | 6/1998 | Anbar |
| 5,771,893 A | 6/1998 | Kassai et al. |
| 5,771,894 A | 6/1998 | Richards et al. |
| 5,771,897 A | 6/1998 | Zufrin |
| 5,791,342 A | 8/1998 | Woodard |
| 5,794,623 A | 8/1998 | Forbes |
| 5,795,304 A | 8/1998 | Sun et al. |
| 5,797,840 A | 8/1998 | Akselrod et al. |
| 5,797,853 A | 8/1998 | Musha et al. |
| 5,810,737 A | 9/1998 | Dardik |
| 5,813,993 A | 9/1998 | Kaplan et al. |
| 5,815,413 A | 9/1998 | Hively et al. |
| 5,816,247 A | 10/1998 | Maynard |
| 5,825,830 A | 10/1998 | Kopf |
| 5,827,195 A | 10/1998 | Lander |
| 5,840,040 A | 11/1998 | Altschuler et al. |
| 5,842,986 A | 12/1998 | Avrin et al. |
| 5,845,639 A | 12/1998 | Hochman et al. |
| 5,846,189 A | 12/1998 | Pincus |
| 5,846,208 A | 12/1998 | Pichlmayr et al. |
| 5,853,005 A | 12/1998 | Scanlon |
| 5,857,978 A | 1/1999 | Hively et al. |
| 5,859,533 A | 1/1999 | Gasnier et al. |
| 5,871,517 A | 2/1999 | Abrams et al. |
| 5,877,801 A | 3/1999 | Martin et al. |
| 5,884,626 A | 3/1999 | Kuroda et al. |
| 5,885,976 A | 3/1999 | Sandyk |
| 5,891,131 A | 4/1999 | Rajan et al. |
| 5,899,867 A | 5/1999 | Collura |
| 5,911,581 A | 6/1999 | Reynolds et al. |
| 5,916,171 A | 6/1999 | Mayevsky |
| 5,921,245 A | 7/1999 | O'Donnell, Jr. |
| 5,928,272 A | 7/1999 | Adkins et al. |
| 5,938,598 A | 8/1999 | Takeda et al. |
| 5,938,688 A | 8/1999 | Schiff |
| 5,954,662 A | 9/1999 | Swanson et al. |
| 5,970,499 A | 10/1999 | Smith et al. |
| 5,971,923 A | 10/1999 | Finger |
| 5,983,129 A | 11/1999 | Cowan et al. |
| 5,995,868 A | 11/1999 | Dorfmeister et al. |
| 5,999,856 A | 12/1999 | Kennedy |
| 6,002,254 A | 12/1999 | Kassai et al. |
| 6,002,952 A | 12/1999 | Diab et al. |
| 6,011,990 A | 1/2000 | Schultz et al. |
| 6,011,991 A | 1/2000 | Mardirossian |
| 6,016,444 A | 1/2000 | John |
| 6,021,345 A | 2/2000 | Karagueuzian et al. |
| 6,023,161 A | 2/2000 | Dantsker et al. |
| 6,026,173 A | 2/2000 | Svenson et al. |
| 6,032,072 A | 2/2000 | Greenwald et al. |
| 6,042,548 A | 3/2000 | Giuffre |
| 6,044,292 A | 3/2000 | Heyrend et al. |
| 6,050,940 A | 4/2000 | Braun et al. |
| 6,050,962 A | 4/2000 | Kramer et al. |
| 6,052,619 A | 4/2000 | John |
| 6,053,739 A | 4/2000 | Stewart et al. |
| 6,057,846 A | 5/2000 | Sever, Jr. |
| 6,066,084 A | 5/2000 | Edrich et al. |
| 6,067,462 A | 5/2000 | Diab et al. |
| 6,067,467 A | 5/2000 | John |
| 6,069,369 A | 5/2000 | Nishino et al. |
| 6,070,098 A | 5/2000 | Moore-Ede et al. |
| 6,071,246 A | 6/2000 | Sturzebecher et al. |
| 6,080,164 A | 6/2000 | Oshio et al. |
| 6,081,735 A | 6/2000 | Diab et al. |
| 6,088,611 A | 7/2000 | Lauterbur et al. |
| 6,092,058 A | 7/2000 | Smyth |
| 6,097,980 A | 8/2000 | Monastra et al. |
| 6,097,981 A | 8/2000 | Freer |
| 6,099,319 A | 8/2000 | Zaltman et al. |
| 6,104,956 A | 8/2000 | Naritoku et al. |
| 6,115,631 A | 9/2000 | Heyrend et al. |
| 6,117,075 A | 9/2000 | Barnea |
| 6,129,681 A | 10/2000 | Kuroda et al. |
| 6,132,724 A | 10/2000 | Blum |
| 6,144,872 A | 11/2000 | Graetz |
| 6,149,586 A | 11/2000 | Elkind |
| 6,154,026 A | 11/2000 | Dantsker et al. |
| 6,155,966 A | 12/2000 | Parker |
| 6,155,993 A | 12/2000 | Scott |
| 6,157,850 A | 12/2000 | Diab et al. |
| 6,157,857 A | 12/2000 | Dimpfel |
| 6,161,031 A | 12/2000 | Hochman et al. |
| 6,167,298 A | 12/2000 | Levin |
| 6,167,311 A | 12/2000 | Rezai |
| 6,171,239 B1 | 1/2001 | Humphrey |
| 6,171,258 B1 | 1/2001 | Karakasoglu et al. |
| 6,182,013 B1 | 1/2001 | Malinverno et al. |
| 6,188,924 B1 | 2/2001 | Swanson et al. |
| 6,195,576 B1 | 2/2001 | John |
| 6,196,972 B1 | 3/2001 | Moehring |
| 6,205,359 B1 | 3/2001 | Boveja |
| 6,208,902 B1 | 3/2001 | Boveja |
| 6,224,549 B1 | 5/2001 | Drongelen |
| 6,226,418 B1 | 5/2001 | Miller et al. |
| 6,230,037 B1 | 5/2001 | Tsukada et al. |
| 6,236,872 B1 | 5/2001 | Diab et al. |
| 6,239,145 B1 | 5/2001 | Utsumi et al. |
| 6,240,308 B1 | 5/2001 | Hardy et al. |
| 6,241,686 B1 | 6/2001 | Balkin et al. |
| 6,248,126 B1 | 6/2001 | Lesser et al. |
| 6,259,399 B1 | 7/2001 | Krasner |
| 6,263,189 B1 | 7/2001 | Reagor |
| 6,266,453 B1 | 7/2001 | Hibbard et al. |
| 6,269,270 B1 | 7/2001 | Boveja |
| 6,272,370 B1 | 8/2001 | Gillies et al. |
| 6,280,393 B1 | 8/2001 | Granger et al. |
| 6,287,328 B1 | 9/2001 | Snyder et al. |
| 6,290,638 B1 | 9/2001 | Canedo et al. |
| 6,292,688 B1 | 9/2001 | Patton |
| 6,293,904 B1 | 9/2001 | Blazey et al. |

(56)                References Cited

U.S. PATENT DOCUMENTS

| | | | |
|---|---|---|---|
| 6,294,917 B1 | 9/2001 | Nichols |
| 6,298,259 B1 | 10/2001 | Kucharczyk et al. |
| 6,305,943 B1 | 10/2001 | Pougatchev et al. |
| 6,306,077 B1 | 10/2001 | Prabhu et al. |
| 6,309,342 B1 | 10/2001 | Blazey et al. |
| 6,309,361 B1 | 10/2001 | Thornton |
| 6,315,736 B1 | 11/2001 | Tsutsumi et al. |
| 6,317,627 B1 | 11/2001 | Ennen et al. |
| 6,319,205 B1 | 11/2001 | Goor et al. |
| 6,322,515 B1 | 11/2001 | Goor et al. |
| 6,325,475 B1 | 12/2001 | Hayes et al. |
| 6,325,761 B1 | 12/2001 | Jay |
| 6,331,164 B1 | 12/2001 | Shaw et al. |
| 6,332,087 B1 | 12/2001 | Svenson et al. |
| 6,338,713 B1 | 1/2002 | Chamoun et al. |
| 6,339,725 B1 | 1/2002 | Naritoku et al. |
| 6,341,236 B1 | 1/2002 | Osorio et al. |
| 6,343,229 B1 | 1/2002 | Siebler et al. |
| 6,354,087 B1 | 3/2002 | Nakahara et al. |
| 6,354,299 B1 | 3/2002 | Fischell et al. |
| 6,356,079 B1 | 3/2002 | Mizoguchi et al. |
| 6,356,781 B1 | 3/2002 | Lee et al. |
| 6,356,788 B2 | 3/2002 | Boveja |
| 6,358,201 B1 | 3/2002 | Childre et al. |
| 6,364,845 B1 | 4/2002 | Duffy et al. |
| 6,366,813 B1 | 4/2002 | DiLorenzo |
| 6,366,814 B1 | 4/2002 | Boveja et al. |
| 6,370,414 B1 | 4/2002 | Robinson |
| 6,370,423 B1 | 4/2002 | Guerrero et al. |
| 6,374,131 B1 | 4/2002 | Tomita et al. |
| 6,375,614 B1 | 4/2002 | Braun et al. |
| 6,377,833 B1 | 4/2002 | Albert |
| 6,385,479 B1 | 5/2002 | Sibbitt et al. |
| 6,385,486 B1 | 5/2002 | John et al. |
| 6,390,979 B1 | 5/2002 | Njemanze |
| 6,393,363 B1 | 5/2002 | Wilt et al. |
| 6,394,963 B1 | 5/2002 | Blazey et al. |
| 6,402,520 B1 | 6/2002 | Freer |
| 6,402,689 B1 | 6/2002 | Scarantino et al. |
| 6,408,107 B1 | 6/2002 | Miller et al. |
| 6,418,344 B1 | 7/2002 | Rezai et al. |
| 6,419,629 B1 | 7/2002 | Balkin et al. |
| 6,427,086 B1 | 7/2002 | Fischell et al. |
| 6,428,490 B1 | 8/2002 | Kramer et al. |
| 6,430,443 B1 | 8/2002 | Karell |
| 6,435,878 B1 | 8/2002 | Reynolds et al. |
| 6,442,421 B1 | 8/2002 | Le Van Quyen et al. |
| 6,442,948 B1 | 9/2002 | Takeda |
| 6,466,816 B2 | 10/2002 | Granger et al. |
| 6,470,220 B1 | 10/2002 | Kraus, Jr. et al. |
| 6,475,163 B1 | 11/2002 | Smits et al. |
| 6,482,165 B1 | 11/2002 | Patton et al. |
| 6,487,441 B1 | 11/2002 | Swanson et al. |
| 6,488,617 B1 | 12/2002 | Katz |
| 6,490,472 B1 | 12/2002 | Li et al. |
| 6,493,577 B1 | 12/2002 | Williams |
| 6,496,724 B1 | 12/2002 | Levendowski et al. |
| 6,497,658 B2 | 12/2002 | Roizen et al. |
| 6,497,699 B1 | 12/2002 | Ludvig et al. |
| 6,503,085 B1 | 1/2003 | Elkind |
| 6,507,754 B2 | 1/2003 | Le Van Quyen et al. |
| 6,510,340 B1 | 1/2003 | Jordan |
| 6,511,424 B1 | 1/2003 | Moore-Ede et al. |
| 6,516,246 B2 | 2/2003 | Derakhshan |
| 6,520,905 B1 | 2/2003 | Surve et al. |
| 6,520,921 B1 | 2/2003 | Patton et al. |
| 6,522,906 B1 | 2/2003 | Salisbury, Jr. et al. |
| 6,524,249 B2 | 2/2003 | Moehring et al. |
| 6,526,297 B1 | 2/2003 | Merilainen |
| 6,526,415 B2 | 2/2003 | Smith et al. |
| 6,527,715 B2 | 3/2003 | Balkin et al. |
| 6,527,730 B2 | 3/2003 | Blazey et al. |
| 6,529,759 B1 | 3/2003 | Tucker et al. |
| 6,529,773 B1 | 3/2003 | Dewan |
| 6,530,884 B2 | 3/2003 | Balkin et al. |
| 6,534,986 B2 | 3/2003 | Nichols |
| 6,538,436 B1 | 3/2003 | Simola et al. |
| 6,539,245 B2 | 3/2003 | Tsukada et al. |
| 6,539,263 B1 | 3/2003 | Schiff et al. |
| 6,544,170 B1 | 4/2003 | Kajihara et al. |
| 6,546,378 B1 | 4/2003 | Cook |
| 6,547,736 B1 | 4/2003 | Moehring et al. |
| 6,547,746 B1 | 4/2003 | Marino |
| 6,549,804 B1 | 4/2003 | Osorio et al. |
| 6,551,243 B2 | 4/2003 | Bocionek et al. |
| 6,553,252 B2 | 4/2003 | Balkin et al. |
| 6,556,695 B1 | 4/2003 | Packer et al. |
| 6,556,861 B1 | 4/2003 | Prichep |
| 6,556,868 B2 | 4/2003 | Naritoku et al. |
| 6,557,558 B1 | 5/2003 | Tajima et al. |
| 6,560,486 B1 | 5/2003 | Osorio et al. |
| 6,565,518 B2 | 5/2003 | Blazey et al. |
| 6,574,573 B1 | 6/2003 | Asano |
| 6,587,727 B2 | 7/2003 | Osorio et al. |
| 6,587,729 B2 | 7/2003 | O'Loughlin et al. |
| 6,591,132 B2 | 7/2003 | Gotman et al. |
| 6,591,137 B1 | 7/2003 | Fischell et al. |
| 6,594,524 B2 | 7/2003 | Esteller et al. |
| 6,597,954 B1 | 7/2003 | Pless et al. |
| 6,602,202 B2 | 8/2003 | John et al. |
| 6,603,502 B2 | 8/2003 | Martin et al. |
| 6,609,030 B1 | 8/2003 | Rezai et al. |
| 6,611,698 B1 | 8/2003 | Yamashita et al. |
| 6,615,158 B2 | 9/2003 | Wenzel et al. |
| 6,616,611 B1 | 9/2003 | Moehring |
| 6,622,036 B1 | 9/2003 | Suffin |
| 6,622,047 B2 | 9/2003 | Barrett et al. |
| 6,625,485 B2 | 9/2003 | Levendowski et al. |
| 6,626,676 B2 | 9/2003 | Freer |
| 6,633,686 B1 | 10/2003 | Bakircioglu et al. |
| 6,644,976 B2 | 11/2003 | Kullok et al. |
| 6,648,822 B2 | 11/2003 | Hamamoto et al. |
| 6,648,880 B2 | 11/2003 | Chauvet et al. |
| 6,650,917 B2 | 11/2003 | Diab et al. |
| 6,652,458 B2 | 11/2003 | Blazey et al. |
| 6,652,470 B2 | 11/2003 | Patton et al. |
| 6,654,632 B2 | 11/2003 | Lange et al. |
| 6,654,729 B1 | 11/2003 | Hickman et al. |
| 6,656,137 B1 | 12/2003 | Tyldsley et al. |
| 6,658,287 B1 | 12/2003 | Litt et al. |
| 6,663,571 B1 | 12/2003 | Njemanze |
| 6,665,552 B2 | 12/2003 | Yokosawa et al. |
| 6,665,553 B2 | 12/2003 | Kandori et al. |
| 6,665,562 B2 | 12/2003 | Gluckman et al. |
| 6,671,555 B2 | 12/2003 | Gielen et al. |
| 6,671,556 B2 | 12/2003 | Osorio et al. |
| 6,678,548 B1 | 1/2004 | Echauz et al. |
| 6,684,098 B2 | 1/2004 | Oshio et al. |
| 6,684,105 B2 | 1/2004 | Cohen et al. |
| 6,687,525 B2 | 2/2004 | Llinas et al. |
| 6,695,761 B2 | 2/2004 | Oschman et al. |
| 6,697,660 B1 | 2/2004 | Robinson |
| RE38,476 E | 3/2004 | Diab et al. |
| 6,699,194 B1 | 3/2004 | Diab et al. |
| 6,701,173 B2 | 3/2004 | Nowinski et al. |
| 6,703,838 B2 | 3/2004 | Conti |
| 6,708,051 B1 | 3/2004 | Durousseau |
| 6,708,064 B2 | 3/2004 | Rezai |
| 6,708,184 B2 | 3/2004 | Smith et al. |
| 6,709,399 B1 | 3/2004 | Shen et al. |
| 6,725,080 B2 | 4/2004 | Melkent et al. |
| 6,726,624 B2 | 4/2004 | Keirsbilck et al. |
| 6,728,424 B1 | 4/2004 | Zhu et al. |
| 6,728,564 B2 | 4/2004 | Lahteenmaki |
| 6,731,975 B1 | 5/2004 | Viertio-Oja et al. |
| 6,735,460 B2 | 5/2004 | Tsukada et al. |
| 6,735,467 B2 | 5/2004 | Wilson |
| 6,735,475 B1 | 5/2004 | Whitehurst et al. |
| 6,740,032 B2 | 5/2004 | Balkin et al. |
| 6,743,167 B2 | 6/2004 | Balkin et al. |
| 6,743,182 B2 | 6/2004 | Miller et al. |
| 6,745,060 B2 | 6/2004 | Diab et al. |
| 6,745,156 B2 | 6/2004 | Cook |
| 6,746,409 B2 | 6/2004 | Keirsbilck et al. |

(56)                    References Cited

U.S. PATENT DOCUMENTS

| 6,751,499 B2 | 6/2004 | Lange et al. |
| 6,758,813 B2 | 7/2004 | Meadows |
| 6,768,920 B2 | 7/2004 | Lange et al. |
| 6,773,400 B2 | 8/2004 | Njemanze |
| 6,774,929 B1 | 8/2004 | Kopp |
| 6,775,405 B1 | 8/2004 | Zhu |
| 6,782,292 B2 | 8/2004 | Whitehurst |
| 6,785,409 B1 | 8/2004 | Suri |
| 6,788,975 B1 | 9/2004 | Whitehurst et al. |
| 6,791,331 B2 | 9/2004 | Conti |
| 6,795,724 B2 | 9/2004 | Hogan |
| 6,798,898 B1 | 9/2004 | Fedorovskaya et al. |
| 6,801,648 B2 | 10/2004 | Cheng |
| 6,801,803 B2 | 10/2004 | Viertio-Oja |
| 6,804,558 B2 | 10/2004 | Haller et al. |
| 6,804,661 B2 | 10/2004 | Cook |
| 6,815,949 B2 | 11/2004 | Kandori et al. |
| 6,816,744 B2 | 11/2004 | Garfield et al. |
| 6,819,956 B2 | 11/2004 | DiLorenzo |
| 6,826,426 B2 | 11/2004 | Lange et al. |
| 6,843,774 B2 | 1/2005 | Foust et al. |
| 6,853,186 B2 | 2/2005 | Li |
| 6,856,830 B2 | 2/2005 | He |
| 6,863,127 B2 | 3/2005 | Clark et al. |
| 6,865,494 B2 | 3/2005 | Duensing et al. |
| 6,873,872 B2 | 3/2005 | Gluckman et al. |
| 6,875,174 B2 | 4/2005 | Braun et al. |
| 6,876,196 B1 | 4/2005 | Taulu et al. |
| 6,879,859 B1 | 4/2005 | Boveja |
| 6,882,881 B1 | 4/2005 | Lesser et al. |
| 6,885,192 B2 | 4/2005 | Clarke et al. |
| 6,885,886 B2 | 4/2005 | Bauch et al. |
| 6,886,964 B2 | 5/2005 | Gardiner et al. |
| 6,893,407 B1 | 5/2005 | Brooks et al. |
| 6,896,655 B2 | 5/2005 | Patton et al. |
| RE38,749 E | 6/2005 | Dardik |
| 6,907,280 B2 | 6/2005 | Becerra et al. |
| 6,915,241 B2 | 7/2005 | Kohlmorgen et al. |
| 6,920,357 B2 | 7/2005 | Osorio et al. |
| 6,926,921 B2 | 8/2005 | Stasiak et al. |
| 6,928,354 B2 | 8/2005 | Ryu et al. |
| 6,931,274 B2 | 8/2005 | Williams |
| 6,931,275 B2 | 8/2005 | Collura |
| 6,936,012 B2 | 8/2005 | Wells |
| 6,947,790 B2 | 9/2005 | Gevins et al. |
| 6,950,697 B2 | 9/2005 | Jordan |
| 6,950,698 B2 | 9/2005 | Sarkela et al. |
| 6,959,215 B2 | 10/2005 | Gliner et al. |
| 6,961,618 B2 | 11/2005 | Osorio et al. |
| 6,963,770 B2 | 11/2005 | Scarantino et al. |
| 6,963,771 B2 | 11/2005 | Scarantino et al. |
| 6,978,179 B1 | 12/2005 | Flagg et al. |
| 6,980,863 B2 | 12/2005 | van Venrooij et al. |
| 6,981,947 B2 | 1/2006 | Melker |
| 6,983,184 B2 | 1/2006 | Price |
| 6,983,264 B2 | 1/2006 | Shimizu |
| 6,985,769 B2 | 1/2006 | Jordan |
| 6,988,056 B2 | 1/2006 | Cook |
| 6,990,377 B2 | 1/2006 | Gliner et al. |
| 6,993,380 B1 | 1/2006 | Modarres |
| 6,996,261 B2 | 2/2006 | deCharms |
| 6,996,549 B2 | 2/2006 | Zhang et al. |
| 7,003,352 B1 | 2/2006 | Whitehurst |
| 7,006,872 B2 | 2/2006 | Gielen et al. |
| 7,010,340 B2 | 3/2006 | Scarantino et al. |
| 7,010,351 B2 | 3/2006 | Firlik et al. |
| 7,011,410 B2 | 3/2006 | Bolger et al. |
| 7,011,814 B2 | 3/2006 | Suddarth et al. |
| 7,014,613 B2 | 3/2006 | John et al. |
| 7,016,722 B2 | 3/2006 | Prichep |
| 7,022,083 B2 | 4/2006 | Tanaka et al. |
| 7,023,206 B2 | 4/2006 | Viehland et al. |
| 7,024,247 B2 | 4/2006 | Gliner et al. |
| 7,030,617 B2 | 4/2006 | Conti |
| 7,035,686 B2 | 4/2006 | Hogan |
| 7,037,260 B2 | 5/2006 | Keirsbilck et al. |
| 7,038,450 B2 | 5/2006 | Romalis et al. |
| 7,039,266 B1 | 5/2006 | Doty |
| 7,039,547 B2 | 5/2006 | Wilson |
| 7,043,293 B1 | 5/2006 | Baura |
| 7,053,610 B2 | 5/2006 | Clarke et al. |
| 7,054,454 B2 | 5/2006 | Causevic et al. |
| 7,062,391 B2 | 6/2006 | Wilson |
| 7,063,535 B2 | 6/2006 | Stamm et al. |
| 7,070,571 B2 | 7/2006 | Kramer et al. |
| 7,079,977 B2 | 7/2006 | Osorio et al. |
| 7,089,927 B2 | 8/2006 | John et al. |
| 7,092,748 B2 | 8/2006 | Valdes Sosa et al. |
| 7,099,714 B2 | 8/2006 | Houben |
| 7,104,947 B2 | 9/2006 | Riehl |
| 7,104,963 B2 | 9/2006 | Melker et al. |
| 7,105,824 B2 | 9/2006 | Stoddart et al. |
| 7,107,090 B2 | 9/2006 | Salisbury, Jr. et al. |
| 7,116,102 B2 | 10/2006 | Clarke et al. |
| 7,117,026 B2 | 10/2006 | Shao et al. |
| 7,119,553 B2 | 10/2006 | Yang et al. |
| 7,120,486 B2 | 10/2006 | Leuthardt et al. |
| 7,123,955 B1 | 10/2006 | Gao et al. |
| 7,127,100 B2 | 10/2006 | Wenzel et al. |
| 7,128,713 B2 | 10/2006 | Moehring et al. |
| 7,130,673 B2 | 10/2006 | Tolvanen-Laakso et al. |
| 7,130,675 B2 | 10/2006 | Ewing et al. |
| 7,130,691 B2 | 10/2006 | Falci |
| 7,145,333 B2 | 12/2006 | Romalis et al. |
| 7,146,211 B2 | 12/2006 | Frei et al. |
| 7,146,217 B2 | 12/2006 | Firlik et al. |
| 7,146,218 B2 | 12/2006 | Esteller et al. |
| 7,149,572 B2 | 12/2006 | Frei et al. |
| 7,149,773 B2 | 12/2006 | Haller et al. |
| 7,150,710 B2 | 12/2006 | Haber et al. |
| 7,150,715 B2 | 12/2006 | Collura et al. |
| 7,150,717 B2 | 12/2006 | Katura et al. |
| 7,150,718 B2 | 12/2006 | Okada et al. |
| 7,151,961 B1 | 12/2006 | Whitehurst et al. |
| 7,155,279 B2 | 12/2006 | Whitehurst et al. |
| 7,163,512 B1 | 1/2007 | Childre et al. |
| 7,164,941 B2 | 1/2007 | Misczynski et al. |
| 7,167,751 B1 | 1/2007 | Whitehurst et al. |
| 7,170,294 B2 | 1/2007 | Kasevich |
| 7,171,252 B1 | 1/2007 | Scarantino et al. |
| 7,171,339 B2 | 1/2007 | Repucci et al. |
| 7,174,206 B2 | 2/2007 | Frei et al. |
| 7,176,680 B1 | 2/2007 | Veryaskin |
| 7,177,675 B2 | 2/2007 | Suffin et al. |
| 7,177,678 B1 | 2/2007 | Osorio et al. |
| 7,181,505 B2 | 2/2007 | Haller et al. |
| 7,183,381 B2 | 2/2007 | Varadhachary et al. |
| 7,184,837 B2 | 2/2007 | Goetz |
| 7,186,209 B2 | 3/2007 | Jacobson et al. |
| 7,187,169 B2 | 3/2007 | Clarke et al. |
| 7,190,826 B2 | 3/2007 | Russell et al. |
| 7,190,995 B2 | 3/2007 | Chervin et al. |
| 7,193,413 B2 | 3/2007 | Kandori et al. |
| 7,196,514 B2 | 3/2007 | Li |
| 7,197,352 B2 | 3/2007 | Gott et al. |
| 7,199,708 B2 | 4/2007 | Terauchi et al. |
| 7,203,548 B2 | 4/2007 | Whitehurst et al. |
| 7,207,948 B2 | 4/2007 | Coyle |
| 7,209,787 B2 | 4/2007 | DiLorenzo |
| 7,209,788 B2 | 4/2007 | Nicolelis et al. |
| 7,212,851 B2 | 5/2007 | Donoghue et al. |
| 7,215,986 B2 | 5/2007 | Diab et al. |
| 7,215,994 B2 | 5/2007 | Huiku |
| 7,218,104 B2 | 5/2007 | Clarke et al. |
| 7,221,981 B2 | 5/2007 | Gliner |
| 7,222,964 B2 | 5/2007 | Gotze et al. |
| 7,224,282 B2 | 5/2007 | Terauchi et al. |
| 7,225,013 B2 | 5/2007 | Geva et al. |
| 7,228,167 B2 | 6/2007 | Kara et al. |
| 7,228,169 B2 | 6/2007 | Viertio-Oja et al. |
| 7,228,171 B2 | 6/2007 | Lesser et al. |
| 7,228,178 B2 | 6/2007 | Carroll et al. |
| 7,231,245 B2 | 6/2007 | Greenwald et al. |
| 7,231,254 B2 | 6/2007 | DiLorenzo |

(56)　　　　　　References Cited

U.S. PATENT DOCUMENTS

| | | | |
|---|---|---|---|
| 7,236,830 B2 | 6/2007 | Gliner |
| 7,236,831 B2 | 6/2007 | Firlik et al. |
| 7,239,731 B1 | 7/2007 | Semenov et al. |
| 7,239,926 B2 | 7/2007 | Goetz |
| 7,242,983 B2 | 7/2007 | Frei et al. |
| 7,242,984 B2 | 7/2007 | DiLorenzo |
| 7,252,090 B2 | 8/2007 | Goetz |
| 7,254,433 B2 | 8/2007 | Diab et al. |
| 7,254,439 B2 | 8/2007 | Misczynski et al. |
| 7,254,500 B2 | 8/2007 | Makeig et al. |
| 7,257,439 B2 | 8/2007 | Llinas |
| 7,258,659 B2 | 8/2007 | Anninou et al. |
| 7,260,430 B2 | 8/2007 | Wu et al. |
| 7,267,644 B2 | 9/2007 | Thomas et al. |
| 7,267,652 B2 | 9/2007 | Coyle et al. |
| 7,269,455 B2 | 9/2007 | Pineda |
| 7,269,456 B2 | 9/2007 | Collura |
| 7,269,516 B2 | 9/2007 | Brunner et al. |
| 7,276,916 B2 | 10/2007 | Hammer |
| 7,277,758 B2 | 10/2007 | DiLorenzo |
| 7,278,966 B2 | 10/2007 | Hjelt et al. |
| 7,280,861 B2 | 10/2007 | Thomas et al. |
| 7,280,867 B2 | 10/2007 | Frei et al. |
| 7,280,870 B2 | 10/2007 | Nurmikko et al. |
| 7,282,030 B2 | 10/2007 | Frei et al. |
| 7,283,861 B2 | 10/2007 | Bystritsky |
| 7,286,871 B2 | 10/2007 | Cohen |
| 7,288,066 B2 | 10/2007 | Drew |
| 7,292,890 B2 | 11/2007 | Whitehurst et al. |
| 7,295,019 B2 | 11/2007 | Yang et al. |
| 7,297,110 B2 | 11/2007 | Goyal et al. |
| 7,299,088 B1 | 11/2007 | Thakor et al. |
| 7,299,096 B2 | 11/2007 | Balzer et al. |
| 7,302,298 B2 | 11/2007 | Lowry et al. |
| 7,305,268 B2 | 12/2007 | Gliner et al. |
| 7,309,315 B2 | 12/2007 | Kullok et al. |
| 7,313,442 B2 | 12/2007 | Velasco et al. |
| 7,321,837 B2 | 1/2008 | Osorio et al. |
| 7,324,845 B2 | 1/2008 | Mietus et al. |
| 7,324,851 B1 | 1/2008 | DiLorenzo |
| 7,328,053 B1 | 2/2008 | Diab et al. |
| 7,330,032 B2 | 2/2008 | Donnangelo |
| 7,333,619 B2 | 2/2008 | Causevic et al. |
| 7,333,851 B2 | 2/2008 | Echauz et al. |
| 7,334,892 B2 | 2/2008 | Goodall et al. |
| 7,338,171 B2 | 3/2008 | Hsieh et al. |
| 7,338,455 B2 | 3/2008 | White et al. |
| 7,340,125 B1 | 3/2008 | Doty |
| 7,340,289 B2 | 3/2008 | Kandori et al. |
| 7,343,198 B2 | 3/2008 | Behbehani et al. |
| 7,346,382 B2 | 3/2008 | McIntyre et al. |
| 7,346,395 B2 | 3/2008 | Lozano et al. |
| 7,353,064 B2 | 4/2008 | Gliner et al. |
| 7,353,065 B2 | 4/2008 | Morrell |
| 7,355,597 B2 | 4/2008 | Laidlaw et al. |
| 7,359,837 B2 | 4/2008 | Drew |
| 7,363,164 B2 | 4/2008 | Little et al. |
| 7,366,571 B2 | 4/2008 | Armstrong |
| 7,367,807 B1 | 5/2008 | Pennebaker |
| 7,367,949 B2 | 5/2008 | Korhonen et al. |
| 7,369,896 B2 | 5/2008 | Gesotti |
| 7,371,365 B2 | 5/2008 | Poduslo et al. |
| 7,373,198 B2 | 5/2008 | Bibian et al. |
| 7,376,453 B1 | 5/2008 | Diab et al. |
| 7,376,459 B2 | 5/2008 | Rosenfeld |
| 7,378,056 B2 | 5/2008 | Black |
| 7,381,185 B2 | 6/2008 | Zhirnov et al. |
| 7,383,070 B2 | 6/2008 | Diab et al. |
| 7,383,237 B2 | 6/2008 | Zhang et al. |
| 7,386,347 B2 | 6/2008 | Chung et al. |
| 7,389,144 B1 | 6/2008 | Osorio et al. |
| 7,392,079 B2 | 6/2008 | Donoghue et al. |
| 7,394,246 B2 | 7/2008 | Chieh et al. |
| 7,395,292 B2 | 7/2008 | Johnson |
| 7,396,333 B2 | 7/2008 | Stahmann et al. |
| 7,399,282 B2 | 7/2008 | John et al. |
| 7,400,984 B2 | 7/2008 | Kandori et al. |
| 7,403,809 B2 | 7/2008 | Tsukada et al. |
| 7,403,814 B2 | 7/2008 | Cox et al. |
| 7,403,815 B2 | 7/2008 | Katz et al. |
| 7,403,820 B2 | 7/2008 | DiLorenzo |
| 7,407,485 B2 | 8/2008 | Huiku |
| 7,409,321 B2 | 8/2008 | Repucci et al. |
| 7,418,290 B2 | 8/2008 | Devlin et al. |
| 7,420,033 B2 | 9/2008 | Varadhachary et al. |
| 7,422,555 B2 | 9/2008 | Zabara |
| 7,429,247 B2 | 9/2008 | Okada et al. |
| 7,437,196 B2 | 10/2008 | Wyler et al. |
| 7,440,789 B2 | 10/2008 | Hannula et al. |
| 7,440,806 B1 | 10/2008 | Whitehurst et al. |
| 7,444,184 B2 | 10/2008 | Boveja et al. |
| 7,450,986 B2 | 11/2008 | Nguyen et al. |
| 7,453,263 B2 | 11/2008 | Kim et al. |
| 7,454,240 B2 | 11/2008 | Diab et al. |
| 7,454,243 B2 | 11/2008 | Silberstein |
| 7,454,245 B2 | 11/2008 | Armstrong et al. |
| 7,454,387 B2 | 11/2008 | Abercrombie et al. |
| 7,457,653 B2 | 11/2008 | Fujimaki |
| 7,457,665 B1 | 11/2008 | Osorio et al. |
| 7,461,045 B1 | 12/2008 | Chaovalitwongse et al. |
| 7,462,151 B2 | 12/2008 | Childre et al. |
| 7,462,155 B2 | 12/2008 | England |
| 7,463,024 B2 | 12/2008 | Simola et al. |
| 7,463,142 B2 | 12/2008 | Lindsay |
| 7,463,927 B1 | 12/2008 | Chaouat |
| 7,466,132 B2 | 12/2008 | Clarke et al. |
| 7,468,040 B2 | 12/2008 | Hartley et al. |
| 7,468,350 B2 | 12/2008 | Gong et al. |
| 7,469,697 B2 | 12/2008 | Lee et al. |
| 7,471,971 B2 | 12/2008 | Diab et al. |
| 7,471,978 B2 | 12/2008 | John et al. |
| 7,478,108 B2 | 1/2009 | Townsend et al. |
| 7,482,298 B2 | 1/2009 | Nepela |
| 7,483,747 B2 | 1/2009 | Gliner et al. |
| 7,486,986 B1 | 2/2009 | Osorio et al. |
| 7,488,294 B2 | 2/2009 | Torch |
| 7,489,958 B2 | 2/2009 | Diab et al. |
| 7,489,964 B2 | 2/2009 | Suffin et al. |
| 7,490,085 B2 | 2/2009 | Walker et al. |
| 7,491,173 B2 | 2/2009 | Heim |
| 7,493,171 B1 | 2/2009 | Whitehurst et al. |
| 7,493,172 B2 | 2/2009 | Whitehurst et al. |
| 7,496,393 B2 | 2/2009 | Diab et al. |
| 7,497,828 B1 | 3/2009 | Wilk et al. |
| 7,499,741 B2 | 3/2009 | Diab et al. |
| 7,499,745 B2 | 3/2009 | Littrup et al. |
| 7,499,752 B2 | 3/2009 | Maschino et al. |
| 7,499,894 B2 | 3/2009 | Marom et al. |
| 7,502,720 B2 | 3/2009 | Taulu |
| 7,509,154 B2 | 3/2009 | Diab et al. |
| 7,509,161 B2 | 3/2009 | Viertio-Oja |
| 7,509,163 B1 | 3/2009 | Luo et al. |
| 7,510,531 B2 | 3/2009 | Lee et al. |
| 7,510,699 B2 | 3/2009 | Black et al. |
| 7,515,054 B2 | 4/2009 | Torch |
| 7,530,955 B2 | 5/2009 | Diab et al. |
| 7,537,568 B2 | 5/2009 | Moehring |
| 7,539,528 B2 | 5/2009 | Xiong et al. |
| 7,539,532 B2 | 5/2009 | Tran |
| 7,539,533 B2 | 5/2009 | Tran |
| 7,539,543 B2 | 5/2009 | Schiff et al. |
| 7,547,284 B2 | 6/2009 | Brainard, II |
| 7,553,810 B2 | 6/2009 | Gong et al. |
| 7,558,622 B2 | 7/2009 | Tran |
| 7,559,903 B2 | 7/2009 | Moussavi et al. |
| 7,561,918 B2 | 7/2009 | Armstrong et al. |
| 7,565,193 B2 | 7/2009 | Laken |
| 7,565,199 B2 | 7/2009 | Sheffield et al. |
| 7,565,200 B2 | 7/2009 | Wyler et al. |
| 7,565,809 B2 | 7/2009 | Takeda |
| 7,567,693 B2 | 7/2009 | deCharms |
| 7,570,054 B1 | 8/2009 | Lin |
| 7,570,991 B2 | 8/2009 | Milgramm et al. |
| 7,572,225 B2 | 8/2009 | Stahmann et al. |

(56) References Cited

U.S. PATENT DOCUMENTS

| | | | |
|---|---|---|---|
| 7,573,264 B2 | 8/2009 | Xu et al. |
| 7,573,268 B2 | 8/2009 | Volegov et al. |
| 7,574,007 B2 | 8/2009 | Shaw et al. |
| 7,574,254 B2 | 8/2009 | Milgramm et al. |
| 7,577,472 B2 | 8/2009 | Li et al. |
| 7,577,481 B2 | 8/2009 | Firlik et al. |
| 7,580,798 B2 | 8/2009 | Brunner et al. |
| 7,582,062 B2 | 9/2009 | Magill et al. |
| 7,583,857 B2 | 9/2009 | Xu et al. |
| 7,593,767 B1 | 9/2009 | Modarres |
| 7,594,122 B2 | 9/2009 | Milgramm et al. |
| 7,594,889 B2 | 9/2009 | St. Ores et al. |
| 7,596,535 B2 | 9/2009 | de Voir et al. |
| 7,597,665 B2 | 10/2009 | Wilk et al. |
| 7,603,168 B2 | 10/2009 | Bibian et al. |
| 7,603,174 B2 | 10/2009 | De Ridder |
| 7,604,603 B2 | 10/2009 | Sackner et al. |
| 7,606,405 B2 | 10/2009 | Sawyer et al. |
| 7,608,579 B2 | 10/2009 | Gong et al. |
| 7,610,083 B2 | 10/2009 | Drew et al. |
| 7,610,094 B2 | 10/2009 | Stahmann et al. |
| 7,610,096 B2 | 10/2009 | McDonald, III |
| 7,610,100 B2 | 10/2009 | Jaax et al. |
| 7,613,502 B2 | 11/2009 | Yamamoto et al. |
| 7,613,519 B2 | 11/2009 | De Ridder |
| 7,613,520 B2 | 11/2009 | De Ridder |
| 7,617,002 B2 | 11/2009 | Goetz |
| 7,618,381 B2 | 11/2009 | Krebs et al. |
| 7,620,455 B2 | 11/2009 | Maschino |
| 7,620,456 B2 | 11/2009 | Gliner et al. |
| 7,623,912 B2 | 11/2009 | Akselrod et al. |
| 7,623,927 B2 | 11/2009 | Rezai |
| 7,623,928 B2 | 11/2009 | DiLorenzo |
| 7,624,293 B2 | 11/2009 | Osorio et al. |
| 7,625,340 B2 | 12/2009 | Sarkela |
| 7,627,370 B2 | 12/2009 | Marks |
| 7,629,889 B2 | 12/2009 | Sachanandani et al. |
| 7,630,757 B2 | 12/2009 | Dorfmeister et al. |
| 7,634,317 B2 | 12/2009 | Ben-David et al. |
| 7,640,055 B2 | 12/2009 | Geva et al. |
| 7,643,655 B2 | 1/2010 | Liang et al. |
| 7,643,881 B2 | 1/2010 | Armstrong |
| 7,647,097 B2 | 1/2010 | Flaherty et al. |
| 7,647,098 B2 | 1/2010 | Prichep |
| 7,648,498 B2 | 1/2010 | Hempel |
| 7,649,351 B2 | 1/2010 | Kajola et al. |
| 7,653,433 B2 | 1/2010 | Lozano et al. |
| 7,654,948 B2 | 2/2010 | Kaplan et al. |
| 7,657,316 B2 | 2/2010 | Jaax et al. |
| 7,668,579 B2 | 2/2010 | Lynn |
| 7,668,591 B2 | 2/2010 | Lee et al. |
| 7,670,838 B2 | 3/2010 | Deisseroth et al. |
| 7,672,707 B2 | 3/2010 | Takeda |
| 7,672,717 B1 * | 3/2010 | Zikov .................... A61B 5/726 |
| | | 600/509 |
| 7,672,730 B2 | 3/2010 | Firlik et al. |
| 7,676,263 B2 | 3/2010 | Harris et al. |
| 7,678,047 B2 | 3/2010 | Shiomi et al. |
| 7,678,061 B2 | 3/2010 | Lee et al. |
| 7,678,767 B2 | 3/2010 | Gong et al. |
| 7,680,526 B2 | 3/2010 | McIntyre et al. |
| 7,680,540 B2 | 3/2010 | Jensen et al. |
| 7,684,856 B2 | 3/2010 | Virtanen et al. |
| 7,684,858 B2 | 3/2010 | He et al. |
| 7,684,866 B2 | 3/2010 | Fowler et al. |
| 7,684,867 B2 | 3/2010 | Jaax et al. |
| 7,697,979 B2 | 4/2010 | Martinerie et al. |
| 7,702,387 B2 | 4/2010 | Stevenson et al. |
| 7,702,502 B2 | 4/2010 | Ricci et al. |
| 7,706,871 B2 | 4/2010 | Devlin et al. |
| 7,706,992 B2 | 4/2010 | Ricci et al. |
| 7,711,417 B2 | 5/2010 | John et al. |
| 7,711,432 B2 | 5/2010 | Thimineur et al. |
| 7,714,936 B1 | 5/2010 | Martin et al. |
| 7,715,894 B2 | 5/2010 | Dunseath et al. |
| 7,715,910 B2 | 5/2010 | Hargrove et al. |
| 7,715,919 B2 | 5/2010 | Osorio et al. |
| 7,720,519 B2 | 5/2010 | Ruohonen |
| 7,720,530 B2 | 5/2010 | Causevic |
| 7,725,174 B2 | 5/2010 | Kern et al. |
| 7,725,192 B2 | 5/2010 | Eskandar et al. |
| 7,727,161 B2 | 6/2010 | Coyle et al. |
| 7,729,740 B2 | 6/2010 | Kraus, Jr. et al. |
| 7,729,753 B2 | 6/2010 | Kremliovsky et al. |
| 7,729,755 B2 | 6/2010 | Laken |
| 7,729,773 B2 | 6/2010 | Sloan |
| 7,733,224 B2 | 6/2010 | Tran |
| 7,733,973 B2 | 6/2010 | Moriya et al. |
| 7,734,334 B2 | 6/2010 | Mietus et al. |
| 7,734,340 B2 | 6/2010 | De Ridder |
| 7,734,355 B2 | 6/2010 | Cohen et al. |
| 7,736,382 B2 | 6/2010 | Webb et al. |
| 7,737,687 B2 | 6/2010 | Na et al. |
| 7,738,683 B2 | 6/2010 | Cahill et al. |
| 7,740,592 B2 | 6/2010 | Graham et al. |
| 7,742,820 B2 | 6/2010 | Wyler et al. |
| 7,746,979 B2 | 6/2010 | Dilmanian et al. |
| 7,747,318 B2 | 6/2010 | John et al. |
| 7,747,325 B2 | 6/2010 | Dilorenzo |
| 7,747,326 B2 | 6/2010 | Velasco et al. |
| 7,747,551 B2 | 6/2010 | Snyder |
| 7,749,155 B1 | 7/2010 | Anderson et al. |
| 7,751,877 B2 | 7/2010 | Flaherty et al. |
| 7,751,878 B1 | 7/2010 | Merkle et al. |
| 7,753,836 B2 | 7/2010 | Peterchev |
| 7,754,190 B2 | 7/2010 | Suffin |
| 7,756,564 B2 | 7/2010 | Matsui et al. |
| 7,756,568 B2 | 7/2010 | Scarantino et al. |
| 7,756,584 B2 | 7/2010 | Sheffield et al. |
| 7,757,690 B2 | 7/2010 | Stahmann et al. |
| 7,758,503 B2 | 7/2010 | Lynn et al. |
| 7,763,588 B2 | 7/2010 | van Praag et al. |
| 7,764,987 B2 | 7/2010 | Dorr et al. |
| 7,765,088 B2 | 7/2010 | Drew |
| 7,766,827 B2 | 8/2010 | Balkin et al. |
| 7,769,424 B2 | 8/2010 | Sato |
| 7,769,431 B2 | 8/2010 | Scarantino et al. |
| 7,769,461 B2 | 8/2010 | Whitehurst et al. |
| 7,769,464 B2 | 8/2010 | Gerber et al. |
| 7,771,341 B2 | 8/2010 | Rogers |
| 7,771,364 B2 | 8/2010 | Arbel et al. |
| 7,774,052 B2 | 8/2010 | Burton et al. |
| 7,774,064 B2 | 8/2010 | Meyer et al. |
| 7,775,993 B2 | 8/2010 | Heruth et al. |
| 7,778,490 B2 | 8/2010 | Quist |
| 7,778,692 B2 | 8/2010 | Scarantino et al. |
| 7,778,693 B2 | 8/2010 | Barbour et al. |
| 7,783,362 B2 | 8/2010 | Whitehurst et al. |
| 7,787,937 B2 | 8/2010 | Scarantino et al. |
| 7,787,946 B2 | 8/2010 | Stahmann et al. |
| 7,792,575 B2 | 9/2010 | Fujimaki et al. |
| 7,794,403 B2 | 9/2010 | Schaafsma |
| 7,794,406 B2 | 9/2010 | Reisfeld et al. |
| 7,797,040 B2 | 9/2010 | Pesaran et al. |
| 7,800,493 B2 | 9/2010 | Terauchi et al. |
| 7,801,591 B1 | 9/2010 | Shusterman |
| 7,801,592 B2 | 9/2010 | Shan et al. |
| 7,801,593 B2 | 9/2010 | Behbehani et al. |
| 7,801,601 B2 | 9/2010 | Maschino et al. |
| 7,801,686 B2 | 9/2010 | Hyde et al. |
| 7,803,118 B2 | 9/2010 | Reisfeld et al. |
| 7,803,119 B2 | 9/2010 | Reisfeld |
| 7,804,441 B1 | 9/2010 | DeChiaro, Jr. |
| 7,805,203 B2 | 9/2010 | Ben-David et al. |
| 7,809,433 B2 | 10/2010 | Keenan |
| 7,809,434 B2 | 10/2010 | Kofol et al. |
| 7,811,279 B2 | 10/2010 | John |
| 7,819,794 B2 | 10/2010 | Becker |
| 7,819,812 B2 | 10/2010 | John et al. |
| 7,822,481 B2 | 10/2010 | Gerber et al. |
| D627,476 S | 11/2010 | Gaw et al. |
| 7,829,562 B2 | 11/2010 | Shamloo et al. |
| 7,831,302 B2 | 11/2010 | Thomas |
| 7,831,305 B2 | 11/2010 | Gliner |

(56)                    References Cited

U.S. PATENT DOCUMENTS

| | | | |
|---|---|---|---|
| 7,834,627 | B2 | 11/2010 | Sakai et al. |
| 7,835,787 | B2 | 11/2010 | Sajda et al. |
| 7,840,039 | B2 | 11/2010 | Fuchs |
| 7,840,248 | B2 | 11/2010 | Fuchs et al. |
| 7,840,250 | B2 | 11/2010 | Tucker |
| 7,840,257 | B2 | 11/2010 | Chance |
| 7,840,280 | B2 | 11/2010 | Parnis et al. |
| 7,841,986 | B2 | 11/2010 | He et al. |
| 7,844,324 | B2 | 11/2010 | Sarkela et al. |
| 7,848,803 | B1 | 12/2010 | Jaax et al. |
| 7,852,087 | B2 | 12/2010 | Wilt et al. |
| 7,853,321 | B2 | 12/2010 | Jaax et al. |
| 7,853,322 | B2 | 12/2010 | Bourget et al. |
| 7,853,323 | B2 | 12/2010 | Goetz |
| 7,853,329 | B2 | 12/2010 | DiLorenzo |
| 7,856,264 | B2 | 12/2010 | Firlik et al. |
| 7,860,548 | B2 | 12/2010 | McIntyre et al. |
| 7,860,552 | B2 | 12/2010 | Borsook et al. |
| 7,860,561 | B1 | 12/2010 | Modarres |
| 7,860,570 | B2 | 12/2010 | Whitehurst et al. |
| 7,863,272 | B2 | 1/2011 | Oksenberg et al. |
| 7,865,234 | B1 | 1/2011 | Modarres |
| 7,865,235 | B2 | 1/2011 | Le et al. |
| 7,865,244 | B2 | 1/2011 | Giftakis et al. |
| 7,869,867 | B2 | 1/2011 | Armstrong et al. |
| 7,869,884 | B2 | 1/2011 | Scott et al. |
| 7,869,885 | B2 | 1/2011 | Begnaud et al. |
| 7,872,235 | B2 | 1/2011 | Rousso et al. |
| 7,873,411 | B2 | 1/2011 | Eda et al. |
| 7,876,938 | B2 | 1/2011 | Huang et al. |
| 7,878,965 | B2 | 2/2011 | Haber et al. |
| 7,879,043 | B2 | 2/2011 | Meneghini et al. |
| 7,881,760 | B2 | 2/2011 | Matsui et al. |
| 7,881,770 | B2 | 2/2011 | Melkent et al. |
| 7,881,780 | B2 | 2/2011 | Flaherty |
| 7,882,135 | B2 | 2/2011 | Brunner et al. |
| 7,884,101 | B2 | 2/2011 | Teegarden et al. |
| 7,887,493 | B2 | 2/2011 | Stahmann et al. |
| 7,890,155 | B2 | 2/2011 | Burns et al. |
| 7,890,176 | B2 | 2/2011 | Jaax et al. |
| 7,890,185 | B2 | 2/2011 | Cohen et al. |
| 7,891,814 | B2 | 2/2011 | Harada et al. |
| 7,892,764 | B2 | 2/2011 | Xiong et al. |
| 7,894,890 | B2 | 2/2011 | Sun et al. |
| 7,894,903 | B2 | 2/2011 | John |
| 7,895,033 | B2 | 2/2011 | Joublin et al. |
| 7,896,807 | B2 | 3/2011 | Clancy et al. |
| 7,899,524 | B2 | 3/2011 | Kozel |
| 7,899,525 | B2 | 3/2011 | John et al. |
| 7,899,539 | B2 | 3/2011 | Whitehurst et al. |
| 7,899,545 | B2 | 3/2011 | John |
| 7,901,211 | B2 | 3/2011 | Pennebaker |
| 7,904,134 | B2 | 3/2011 | McIntyre et al. |
| 7,904,139 | B2 | 3/2011 | Chance |
| 7,904,144 | B2 | 3/2011 | Causevic et al. |
| 7,904,151 | B2 | 3/2011 | Ben-David et al. |
| 7,904,175 | B2 | 3/2011 | Scott et al. |
| 7,904,507 | B2 | 3/2011 | Jung et al. |
| 7,907,994 | B2 | 3/2011 | Stolarski et al. |
| 7,907,998 | B2 | 3/2011 | Arad (Abboud) |
| 7,908,008 | B2 | 3/2011 | Ben-David et al. |
| 7,908,009 | B2 | 3/2011 | Wyler et al. |
| 7,909,771 | B2 | 3/2011 | Meyer et al. |
| 7,912,530 | B2 | 3/2011 | Seki et al. |
| 7,917,199 | B2 | 3/2011 | Drew et al. |
| 7,917,206 | B2 | 3/2011 | Frei et al. |
| 7,917,221 | B2 | 3/2011 | Tass |
| 7,917,225 | B2 | 3/2011 | Wyler et al. |
| 7,918,779 | B2 | 4/2011 | Haber et al. |
| 7,920,914 | B2 | 4/2011 | Shieh et al. |
| 7,920,915 | B2 | 4/2011 | Mann et al. |
| 7,920,916 | B2 | 4/2011 | Johnson et al. |
| 7,925,353 | B1 | 4/2011 | Whitehurst et al. |
| 7,929,693 | B2 | 4/2011 | Terauchi et al. |
| 7,930,035 | B2 | 4/2011 | DiLorenzo |
| 7,932,225 | B2 | 4/2011 | Gong et al. |
| 7,933,645 | B2 | 4/2011 | Strychacz et al. |
| 7,933,646 | B2 | 4/2011 | Frei et al. |
| 7,933,727 | B2 | 4/2011 | Taulu et al. |
| 7,937,138 | B2 | 5/2011 | Liley |
| 7,937,152 | B1 | 5/2011 | Lozano |
| 7,937,222 | B2 | 5/2011 | Donadille et al. |
| 7,938,782 | B2 | 5/2011 | Stahmann et al. |
| 7,938,785 | B2 | 5/2011 | Aguilar et al. |
| 7,941,209 | B2 | 5/2011 | Hughes et al. |
| 7,942,824 | B1 | 5/2011 | Kayyali et al. |
| 7,944,551 | B2 | 5/2011 | Addison et al. |
| 7,945,304 | B2 | 5/2011 | Feinberg |
| 7,945,316 | B2 | 5/2011 | Giftakis et al. |
| 7,945,330 | B2 | 5/2011 | Gliner et al. |
| 7,957,796 | B2 | 6/2011 | Maschino |
| 7,957,797 | B2 | 6/2011 | Bourget et al. |
| 7,957,806 | B2 | 6/2011 | Stevenson et al. |
| 7,957,809 | B2 | 6/2011 | Bourget et al. |
| 7,961,922 | B2 | 6/2011 | Spence et al. |
| 7,962,204 | B2 | 6/2011 | Suffin et al. |
| 7,962,214 | B2 | 6/2011 | Byerman et al. |
| 7,962,219 | B2 | 6/2011 | Jaax et al. |
| 7,962,220 | B2 | 6/2011 | Kolafa et al. |
| 7,970,734 | B2 | 6/2011 | Townsend et al. |
| 7,972,278 | B2 | 7/2011 | Graham et al. |
| 7,974,688 | B2 | 7/2011 | Armstrong et al. |
| 7,974,693 | B2 | 7/2011 | Ben-David et al. |
| 7,974,696 | B1 | 7/2011 | DiLorenzo |
| 7,974,697 | B2 | 7/2011 | Maschino et al. |
| 7,974,701 | B2 | 7/2011 | Armstrong |
| 7,974,787 | B2 | 7/2011 | Hyde et al. |
| 7,976,465 | B2 | 7/2011 | Frei et al. |
| 7,983,740 | B2 | 7/2011 | Culver et al. |
| 7,983,741 | B2 | 7/2011 | Chance |
| 7,983,757 | B2 | 7/2011 | Miyazawa et al. |
| 7,983,762 | B2 | 7/2011 | Gliner et al. |
| 7,986,991 | B2 | 7/2011 | Prichep |
| 7,988,613 | B2 | 8/2011 | Becker |
| 7,988,969 | B2 | 8/2011 | Poduslo et al. |
| 7,991,461 | B2 | 8/2011 | Flaherty et al. |
| 7,991,477 | B2 | 8/2011 | McDonald, III |
| 7,993,279 | B2 | 8/2011 | Hartley et al. |
| 7,996,075 | B2 | 8/2011 | Korzinov et al. |
| 7,996,079 | B2 | 8/2011 | Armstrong |
| 8,000,767 | B2 | 8/2011 | Eden et al. |
| 8,000,773 | B2 | 8/2011 | Rousso et al. |
| 8,000,788 | B2 | 8/2011 | Giftakis et al. |
| 8,000,793 | B2 | 8/2011 | Libbus |
| 8,000,794 | B2 | 8/2011 | Lozano |
| 8,000,795 | B2 | 8/2011 | Lozano |
| 8,001,179 | B2 | 8/2011 | Jung et al. |
| 8,002,553 | B2 | 8/2011 | Hatlestad et al. |
| 8,005,534 | B2 | 8/2011 | Greenwald et al. |
| 8,005,624 | B1 | 8/2011 | Starr |
| 8,005,894 | B2 | 8/2011 | Jung et al. |
| 8,010,178 | B2 | 8/2011 | Seki et al. |
| 8,010,347 | B2 | 8/2011 | Ricci et al. |
| 8,012,107 | B2 | 9/2011 | Einav et al. |
| 8,014,847 | B2 | 9/2011 | Shastri et al. |
| 8,014,870 | B2 | 9/2011 | Seidman |
| 8,016,597 | B2 | 9/2011 | Becker et al. |
| 8,019,400 | B2 | 9/2011 | Diab et al. |
| 8,019,410 | B1 | 9/2011 | Bharmi et al. |
| 8,024,029 | B2 | 9/2011 | Drew et al. |
| 8,024,032 | B1 | 9/2011 | Osorio et al. |
| 8,025,404 | B2 | 9/2011 | Bolger et al. |
| 8,027,730 | B2 | 9/2011 | John |
| 8,029,553 | B2 | 10/2011 | Nemenov |
| 8,031,076 | B2 | 10/2011 | Sachanandani et al. |
| 8,032,209 | B2 | 10/2011 | He et al. |
| 8,032,229 | B2 | 10/2011 | Gerber et al. |
| 8,032,486 | B2 | 10/2011 | Townsend et al. |
| 8,033,996 | B2 | 10/2011 | Behar |
| 8,036,434 | B2 | 10/2011 | Hewett et al. |
| 8,036,728 | B2 | 10/2011 | Diab et al. |
| 8,036,736 | B2 | 10/2011 | Snyder et al. |
| 8,036,745 | B2 | 10/2011 | Ben-David et al. |
| 8,041,136 | B2 | 10/2011 | Causevic |

(56)                References Cited

U.S. PATENT DOCUMENTS

| | | | |
|---|---|---|---|
| 8,041,418 B2 | 10/2011 | Giftakis et al. |
| 8,041,419 B2 | 10/2011 | Giftakis et al. |
| 8,046,041 B2 | 10/2011 | Diab et al. |
| 8,046,042 B2 | 10/2011 | Diab et al. |
| 8,046,076 B2 | 10/2011 | Whitehurst et al. |
| 8,050,768 B2 | 11/2011 | Firlik et al. |
| 8,055,348 B2 | 11/2011 | Heruth et al. |
| 8,055,591 B2 | 11/2011 | Jung et al. |
| 8,059,879 B2 | 11/2011 | Tsukimoto |
| 8,060,181 B2 | 11/2011 | Rodriguez Ponce et al. |
| 8,060,194 B2 | 11/2011 | Flaherty |
| 8,064,994 B2 | 11/2011 | Pardo et al. |
| 8,065,011 B2 | 11/2011 | Echauz et al. |
| 8,065,012 B2 | 11/2011 | Firlik et al. |
| 8,065,017 B2 | 11/2011 | Cornejo Cruz et al. |
| 8,065,240 B2 | 11/2011 | Jung et al. |
| 8,065,360 B2 | 11/2011 | Jung et al. |
| 8,066,637 B2 | 11/2011 | Childre et al. |
| 8,066,647 B2 | 11/2011 | Armitstead |
| 8,068,904 B2 | 11/2011 | Sun et al. |
| 8,068,911 B2 | 11/2011 | Giftakis et al. |
| 8,069,125 B2 | 11/2011 | Jung et al. |
| 8,073,534 B2 | 12/2011 | Low |
| 8,073,546 B2 | 12/2011 | Sheffield et al. |
| 8,073,631 B2 | 12/2011 | Wilber et al. |
| 8,075,499 B2 | 12/2011 | Nathan et al. |
| 8,079,953 B2 | 12/2011 | Braun et al. |
| 8,082,031 B2 | 12/2011 | Ochs |
| 8,082,033 B2 | 12/2011 | Rezai et al. |
| 8,082,215 B2 | 12/2011 | Jung et al. |
| 8,083,786 B2 | 12/2011 | Gafni et al. |
| 8,086,294 B2 | 12/2011 | Echauz et al. |
| 8,086,296 B2 | 12/2011 | Bystritsky |
| 8,086,563 B2 | 12/2011 | Jung et al. |
| 8,088,057 B2 | 1/2012 | Honeycutt et al. |
| 8,089,283 B2 | 1/2012 | Kaplan et al. |
| 8,090,164 B2 | 1/2012 | Bullitt et al. |
| 8,092,549 B2 | 1/2012 | Hillis et al. |
| 8,095,209 B2 | 1/2012 | Flaherty |
| 8,095,210 B2 | 1/2012 | Burdick et al. |
| 8,097,926 B2 | 1/2012 | De Graff et al. |
| 8,099,299 B2 | 1/2012 | Sirohey et al. |
| 8,103,333 B2 | 1/2012 | Tran |
| 8,108,033 B2 | 1/2012 | Drew et al. |
| 8,108,036 B2 | 1/2012 | Tran |
| 8,108,038 B2 | 1/2012 | Giftakis et al. |
| 8,108,039 B2 | 1/2012 | Saliga et al. |
| 8,108,042 B1 | 1/2012 | Johnson et al. |
| 8,112,148 B2 | 2/2012 | Giftakis et al. |
| 8,112,153 B2 | 2/2012 | Giftakis et al. |
| 8,114,021 B2 | 2/2012 | Robertson et al. |
| 8,116,874 B2 | 2/2012 | Tass |
| 8,116,877 B2 | 2/2012 | Lozano |
| 8,116,883 B2 | 2/2012 | Williams et al. |
| 8,121,361 B2 | 2/2012 | Ernst et al. |
| 8,121,673 B2 | 2/2012 | Tran |
| 8,121,694 B2 | 2/2012 | Molnar et al. |
| 8,121,695 B2 | 2/2012 | Gliner et al. |
| 8,126,228 B2 | 2/2012 | Fueyo et al. |
| 8,126,243 B2 | 2/2012 | Hamada et al. |
| 8,126,528 B2 | 2/2012 | Diab et al. |
| 8,126,542 B2 | 2/2012 | Grey |
| 8,126,567 B2 | 2/2012 | Gerber et al. |
| 8,126,568 B2 | 2/2012 | Gliner |
| 8,128,572 B2 | 3/2012 | Diab et al. |
| 8,131,354 B2 | 3/2012 | Arad (Abboud) |
| 8,131,526 B2 | 3/2012 | Neville |
| 8,133,172 B2 | 3/2012 | Shachar et al. |
| 8,135,472 B2 | 3/2012 | Fowler et al. |
| 8,135,957 B2 | 3/2012 | Dinges et al. |
| 8,137,269 B2 | 3/2012 | Sheikhzadeh-Nadjar et al. |
| 8,137,270 B2 | 3/2012 | Keenan et al. |
| 8,140,152 B2 | 3/2012 | John et al. |
| 8,145,295 B2 | 3/2012 | Boyden et al. |
| 8,145,310 B2 | 3/2012 | Dong et al. |
| 8,148,417 B2 | 4/2012 | Teegarden et al. |
| 8,148,418 B2 | 4/2012 | Teegarden et al. |
| 8,150,508 B2 | 4/2012 | Craig |
| 8,150,523 B2 | 4/2012 | Schiff et al. |
| 8,150,524 B2 | 4/2012 | Maschino et al. |
| 8,150,796 B2 | 4/2012 | Jung et al. |
| 8,152,732 B2 | 4/2012 | Lynn et al. |
| 8,155,726 B2 | 4/2012 | Seki et al. |
| 8,155,736 B2 | 4/2012 | Sullivan et al. |
| 8,160,273 B2 | 4/2012 | Visser et al. |
| 8,160,317 B2 | 4/2012 | Amunts et al. |
| 8,160,680 B2 | 4/2012 | Boyden et al. |
| 8,160,689 B2 | 4/2012 | Jadidi |
| 8,160,696 B2 | 4/2012 | Bendett et al. |
| 8,165,687 B2 | 4/2012 | Cornejo Cruz et al. |
| 8,167,784 B1 | 5/2012 | Honeycutt et al. |
| 8,167,826 B2 | 5/2012 | Oohashi et al. |
| 8,170,315 B2 | 5/2012 | Mistretta et al. |
| 8,170,347 B2 | 5/2012 | Ancelin |
| 8,172,759 B2 | 5/2012 | Bukhman |
| 8,172,766 B1 | 5/2012 | Kayyali et al. |
| 8,174,430 B1 | 5/2012 | DeChiaro, Jr. |
| 8,175,359 B2 | 5/2012 | O'Halloran et al. |
| 8,175,360 B2 | 5/2012 | Razifar et al. |
| 8,175,686 B2 | 5/2012 | Utsugi et al. |
| 8,175,696 B2 | 5/2012 | Liley et al. |
| 8,175,700 B2 | 5/2012 | Johnson et al. |
| 8,177,724 B2 | 5/2012 | Derchak et al. |
| 8,177,726 B2 | 5/2012 | John |
| 8,177,727 B2 | 5/2012 | Kwak |
| 8,180,125 B2 | 5/2012 | Avinash et al. |
| 8,180,148 B2 | 5/2012 | Cover et al. |
| 8,180,420 B2 | 5/2012 | Diab et al. |
| 8,180,436 B2 | 5/2012 | Boyden et al. |
| 8,180,601 B2 | 5/2012 | Butson et al. |
| 8,185,186 B2 | 5/2012 | Ross et al. |
| 8,185,207 B2 | 5/2012 | Molnar et al. |
| 8,185,382 B2 | 5/2012 | Joublin et al. |
| 8,187,181 B2 | 5/2012 | Osorio et al. |
| 8,187,201 B2 | 5/2012 | Lynn |
| 8,188,749 B2 | 5/2012 | Wilt et al. |
| 8,190,227 B2 | 5/2012 | Diab et al. |
| 8,190,248 B2 | 5/2012 | Besio et al. |
| 8,190,249 B1 | 5/2012 | Gharieb et al. |
| 8,190,251 B2 | 5/2012 | Molnar et al. |
| 8,190,264 B2 | 5/2012 | Lozano et al. |
| 8,195,295 B2 | 6/2012 | Stevenson et al. |
| 8,195,298 B2 | 6/2012 | Lozano |
| 8,195,300 B2 | 6/2012 | Gliner et al. |
| 8,195,593 B2 | 6/2012 | Jung et al. |
| 8,197,395 B2 | 6/2012 | Jassemidis et al. |
| 8,197,437 B2 | 6/2012 | Kalafut et al. |
| 8,199,982 B2 | 6/2012 | Fueyo et al. |
| 8,199,985 B2 | 6/2012 | Jakobsson et al. |
| 8,200,319 B2 | 6/2012 | Pu et al. |
| 8,200,340 B2 | 6/2012 | Skelton et al. |
| 8,204,583 B2 | 6/2012 | Sackellares et al. |
| 8,204,603 B2 | 6/2012 | Maschino |
| 8,209,009 B2 | 6/2012 | Giftakis et al. |
| 8,209,018 B2 | 6/2012 | Osorio et al. |
| 8,209,019 B2 | 6/2012 | Giftakis et al. |
| 8,209,224 B2 | 6/2012 | Pradeep et al. |
| 8,211,035 B2 | 7/2012 | Melker et al. |
| 8,212,556 B1 | 7/2012 | Schwindt et al. |
| 8,213,670 B2 | 7/2012 | Lai |
| 8,214,007 B2 | 7/2012 | Baker et al. |
| 8,214,035 B2 | 7/2012 | Giftakis et al. |
| 8,219,188 B2 | 7/2012 | Craig |
| 8,221,330 B2 | 7/2012 | Sarkela et al. |
| 8,222,378 B2 | 7/2012 | Masure |
| 8,223,023 B2 | 7/2012 | Sachanandani et al. |
| 8,224,431 B2 | 7/2012 | Drew |
| 8,224,433 B2 | 7/2012 | Suffin et al. |
| 8,224,444 B2 | 7/2012 | Ben-David et al. |
| 8,224,451 B2 | 7/2012 | Jaax et al. |
| 8,229,540 B2 | 7/2012 | Sami et al. |
| 8,229,559 B2 | 7/2012 | Westendorp et al. |
| 8,233,682 B2 | 7/2012 | Fessler et al. |
| 8,233,689 B2 | 7/2012 | Razifar et al. |

(56)                    References Cited

U.S. PATENT DOCUMENTS

| | | | |
|---|---|---|---|
| 8,233,965 B2 | 7/2012 | Bjornerud et al. |
| 8,233,990 B2 | 7/2012 | Goetz |
| 8,235,907 B2 | 8/2012 | Wilk et al. |
| 8,236,005 B2 | 8/2012 | Meneghini et al. |
| 8,236,038 B2 | 8/2012 | Nofzinger |
| 8,239,014 B2 | 8/2012 | Ochs |
| 8,239,028 B2 | 8/2012 | Scott |
| 8,239,029 B2 | 8/2012 | De Ridder |
| 8,239,030 B1 | 8/2012 | Hagedorn et al. |
| 8,241,213 B2 | 8/2012 | Lynn et al. |
| 8,244,340 B2 | 8/2012 | Wu et al. |
| 8,244,341 B2 | 8/2012 | Hinrikus et al. |
| 8,244,347 B2 | 8/2012 | Lozano |
| 8,244,475 B2 | 8/2012 | Aguilar et al. |
| 8,244,552 B2 | 8/2012 | Firminger et al. |
| 8,244,553 B2 | 8/2012 | Firminger et al. |
| 8,248,069 B2 | 8/2012 | Buracas |
| 8,249,316 B2 | 8/2012 | Hu et al. |
| 8,249,698 B2 | 8/2012 | Mugler et al. |
| 8,249,718 B2 | 8/2012 | Skelton et al. |
| 8,249,815 B2 | 8/2012 | Taylor |
| 8,260,426 B2 | 9/2012 | Armstrong et al. |
| 8,262,714 B2 | 9/2012 | Hulvershorn et al. |
| 8,263,574 B2 | 9/2012 | Schaller et al. |
| 8,267,851 B1 | 9/2012 | Kroll |
| 8,270,814 B2 | 9/2012 | Pradeep et al. |
| 8,271,077 B1 | 9/2012 | Rotenberg |
| 8,280,502 B2 | 10/2012 | Hargrove et al. |
| 8,280,503 B2 | 10/2012 | Linderman |
| 8,280,505 B2 | 10/2012 | Craig |
| 8,280,514 B2 | 10/2012 | Lozano et al. |
| 8,280,517 B2 | 10/2012 | Skelton et al. |
| 8,285,351 B2 | 10/2012 | Johnson et al. |
| 8,285,368 B2 | 10/2012 | Chen et al. |
| 8,290,575 B2 | 10/2012 | Tarassenko et al. |
| 8,290,596 B2 | 10/2012 | Wei et al. |
| 8,295,914 B2 | 10/2012 | Kalafut et al. |
| 8,295,934 B2 | 10/2012 | Leyde |
| 8,295,935 B2 | 10/2012 | Okun et al. |
| 8,296,108 B2 | 10/2012 | Tanaka |
| 8,298,078 B2 | 10/2012 | Sutton et al. |
| 8,298,140 B2 | 10/2012 | Beck-Nielsen et al. |
| 8,301,222 B2 | 10/2012 | Rongen et al. |
| 8,301,232 B2 | 10/2012 | Albert et al. |
| 8,301,233 B2 | 10/2012 | Zhang et al. |
| 8,301,257 B2 | 10/2012 | Hsu et al. |
| 8,303,636 B2 | 11/2012 | Schiffer |
| 8,304,246 B2 | 11/2012 | Cook et al. |
| 8,305,078 B2 | 11/2012 | Savukov et al. |
| 8,306,607 B1 | 11/2012 | Levi et al. |
| 8,306,610 B2 | 11/2012 | Mirow |
| 8,306,627 B2 | 11/2012 | Armstrong |
| 8,308,646 B2 | 11/2012 | Belohlavek et al. |
| 8,308,661 B2 | 11/2012 | Miesel et al. |
| 8,311,622 B2 | 11/2012 | Snyder et al. |
| 8,311,747 B2 | 11/2012 | Taylor |
| 8,311,748 B2 | 11/2012 | Taylor et al. |
| 8,311,750 B2 | 11/2012 | Taylor |
| 8,313,441 B2 | 11/2012 | Dalton |
| 8,314,707 B2 | 11/2012 | Kobetski et al. |
| 8,315,703 B2 | 11/2012 | Lozano |
| 8,315,704 B2 | 11/2012 | Jaax et al. |
| 8,315,710 B2 | 11/2012 | Skelton et al. |
| 8,315,812 B2 | 11/2012 | Taylor |
| 8,315,813 B2 | 11/2012 | Taylor et al. |
| 8,315,814 B2 | 11/2012 | Taylor et al. |
| 8,315,962 B1 | 11/2012 | Horne |
| 8,315,970 B2 | 11/2012 | Zalay et al. |
| 8,320,649 B2 | 11/2012 | Shahaf et al. |
| 8,321,150 B2 | 11/2012 | Taylor |
| 8,323,188 B2 | 12/2012 | Tran |
| 8,323,189 B2 | 12/2012 | Tran et al. |
| 8,323,204 B2 | 12/2012 | Stahmann et al. |
| 8,326,418 B2 | 12/2012 | Sommer et al. |
| 8,326,420 B2 | 12/2012 | Skelton et al. |
| 8,326,433 B2 | 12/2012 | Blum et al. |
| 8,328,718 B2 | 12/2012 | Tran |
| 8,332,017 B2 | 12/2012 | Tarassenko et al. |
| 8,332,024 B2 | 12/2012 | Rapoport et al. |
| 8,332,038 B2 | 12/2012 | Heruth et al. |
| 8,332,041 B2 | 12/2012 | Skelton et al. |
| 8,332,191 B2 | 12/2012 | Rosthal et al. |
| 8,334,690 B2 | 12/2012 | Kitching et al. |
| 8,335,561 B1 | 12/2012 | Modarres |
| 8,335,664 B2 | 12/2012 | Eberle |
| 8,335,715 B2 | 12/2012 | Pradeep et al. |
| 8,335,716 B2 | 12/2012 | Pradeep et al. |
| 8,337,404 B2 | 12/2012 | Osorio |
| 8,340,752 B2 | 12/2012 | Cox et al. |
| 8,340,753 B2 | 12/2012 | Hardt |
| 8,340,771 B2 | 12/2012 | Thimineur et al. |
| 8,343,026 B2 | 1/2013 | Gardiner et al. |
| 8,343,027 B1 | 1/2013 | DiMino et al. |
| 8,343,066 B1 | 1/2013 | Eagleman et al. |
| 8,346,331 B2 | 1/2013 | Bunce et al. |
| 8,346,342 B2 | 1/2013 | Kalafut |
| 8,346,349 B2 | 1/2013 | Guttag et al. |
| 8,346,354 B2 | 1/2013 | Hyde et al. |
| 8,346,365 B2 | 1/2013 | Lozano |
| 8,350,804 B1 | 1/2013 | Moll |
| 8,352,023 B2 | 1/2013 | John et al. |
| 8,352,031 B2 | 1/2013 | Rousso et al. |
| 8,353,837 B2 | 1/2013 | John et al. |
| 8,354,438 B2 | 1/2013 | Chez |
| 8,354,881 B2 | 1/2013 | Denison |
| 8,355,768 B2 | 1/2013 | Masmanidis et al. |
| 8,356,004 B2 | 1/2013 | Jung et al. |
| 8,356,594 B2 | 1/2013 | Ujhazy et al. |
| 8,358,818 B2 | 1/2013 | Miga et al. |
| 8,359,080 B2 | 1/2013 | Diab et al. |
| 8,362,780 B2 | 1/2013 | Rosthal et al. |
| 8,364,226 B2 | 1/2013 | Diab et al. |
| 8,364,254 B2 | 1/2013 | Jacquin et al. |
| 8,364,255 B2 | 1/2013 | Isenhart et al. |
| 8,364,271 B2 | 1/2013 | De Ridder |
| 8,364,272 B2 | 1/2013 | Goetz |
| 8,369,940 B2 | 2/2013 | Sun et al. |
| 8,374,411 B2 | 2/2013 | Ernst et al. |
| 8,374,412 B2 | 2/2013 | Kimura |
| 8,374,690 B2 | 2/2013 | Ma |
| 8,374,696 B2 | 2/2013 | Sanchez et al. |
| 8,374,701 B2 | 2/2013 | Hyde et al. |
| 8,374,703 B2 | 2/2013 | Imran |
| 8,376,965 B2 | 2/2013 | Schuette et al. |
| 8,379,947 B2 | 2/2013 | Garg et al. |
| 8,379,952 B2 | 2/2013 | McIntyre et al. |
| 8,380,289 B2 | 2/2013 | Zellers et al. |
| 8,380,290 B2 | 2/2013 | Scarantino et al. |
| 8,380,296 B2 | 2/2013 | Lee et al. |
| 8,380,314 B2 | 2/2013 | Panken et al. |
| 8,380,316 B2 | 2/2013 | Hagedorn et al. |
| 8,380,658 B2 | 2/2013 | Jung et al. |
| 8,382,667 B2 | 2/2013 | Osorio |
| 8,386,188 B2 | 2/2013 | Taylor et al. |
| 8,386,244 B2 | 2/2013 | Ricci et al. |
| 8,386,312 B2 | 2/2013 | Pradeep et al. |
| 8,386,313 B2 | 2/2013 | Pradeep et al. |
| RE44,097 E | 3/2013 | Wilber et al. |
| 8,388,529 B2 | 3/2013 | Fueyo et al. |
| 8,388,530 B2 | 3/2013 | Shusterman |
| 8,388,555 B2 | 3/2013 | Panken et al. |
| 8,391,942 B2 | 3/2013 | Benni |
| 8,391,956 B2 | 3/2013 | Zellers et al. |
| 8,391,966 B2 | 3/2013 | Luo et al. |
| 8,392,250 B2 | 3/2013 | Pradeep et al. |
| 8,392,251 B2 | 3/2013 | Pradeep et al. |
| 8,392,253 B2 | 3/2013 | Pradeep et al. |
| 8,392,254 B2 | 3/2013 | Pradeep et al. |
| 8,392,255 B2 | 3/2013 | Pradeep et al. |
| 8,396,542 B2 | 3/2013 | Johnson et al. |
| 8,396,545 B2 | 3/2013 | Berridge et al. |
| 8,396,546 B2 | 3/2013 | Hirata et al. |
| 8,396,557 B2 | 3/2013 | DiLorenzo |
| 8,396,565 B2 | 3/2013 | Singhal et al. |

(56) References Cited

U.S. PATENT DOCUMENTS

| | | | |
|---|---|---|---|
| 8,396,744 B2 | 3/2013 | Pradeep et al. |
| 8,398,692 B2 | 3/2013 | Deisseroth et al. |
| 8,401,624 B2 | 3/2013 | Govari |
| 8,401,626 B2 | 3/2013 | Mietus et al. |
| 8,401,634 B2 | 3/2013 | Whitehurst et al. |
| 8,401,654 B1 | 3/2013 | Foster et al. |
| 8,401,655 B2 | 3/2013 | De Ridder |
| 8,401,666 B2 | 3/2013 | Skelton et al. |
| 8,403,848 B2 | 3/2013 | Mietus et al. |
| 8,406,838 B2 | 3/2013 | Kato |
| 8,406,841 B2 | 3/2013 | Lin et al. |
| 8,406,848 B2 | 3/2013 | Wu et al. |
| 8,406,862 B2 | 3/2013 | Hopenfeld |
| 8,406,890 B2 | 3/2013 | Goetz |
| 8,412,334 B2 | 4/2013 | Whitehurst et al. |
| 8,412,335 B2 | 4/2013 | Gliner et al. |
| 8,412,337 B2 | 4/2013 | Lozano |
| 8,412,338 B2 | 4/2013 | Faltys |
| 8,412,655 B2 | 4/2013 | Colman et al. |
| 8,415,123 B2 | 4/2013 | Pilla et al. |
| 8,417,344 B2 | 4/2013 | Colborn et al. |
| 8,423,118 B2 | 4/2013 | Wenzel et al. |
| 8,423,125 B2 | 4/2013 | Rousso et al. |
| 8,423,144 B2 | 4/2013 | Tass et al. |
| 8,423,155 B1 | 4/2013 | Jaax et al. |
| 8,423,297 B2 | 4/2013 | Wilber |
| 8,425,415 B2 | 4/2013 | Tran |
| 8,425,583 B2 | 4/2013 | Nofzinger |
| 8,428,696 B2 | 4/2013 | Foo |
| 8,428,703 B2 | 4/2013 | Hopenfeld |
| 8,428,704 B2 | 4/2013 | Johnson et al. |
| 8,428,726 B2 | 4/2013 | Ignagni et al. |
| 8,429,225 B2 | 4/2013 | Jung et al. |
| 8,430,805 B2 | 4/2013 | Burnett et al. |
| 8,430,816 B2 | 4/2013 | Avinash et al. |
| 8,431,537 B2 | 4/2013 | Gong et al. |
| 8,433,388 B2 | 4/2013 | Blunt et al. |
| 8,433,410 B2 | 4/2013 | Stevenson et al. |
| 8,433,414 B2 | 4/2013 | Gliner et al. |
| 8,433,418 B2 | 4/2013 | DeRidder |
| 8,435,166 B2 | 5/2013 | Burnett et al. |
| 8,437,843 B1 | 5/2013 | Kayyali et al. |
| 8,437,844 B2 | 5/2013 | Syed Momen et al. |
| 8,437,861 B2 | 5/2013 | Skelton et al. |
| 8,439,845 B2 | 5/2013 | Folkerts et al. |
| 8,442,626 B2 | 5/2013 | Zavoronkovs et al. |
| 8,444,571 B2 | 5/2013 | Folkerts et al. |
| 8,445,021 B2 | 5/2013 | Akhtari et al. |
| 8,445,851 B2 | 5/2013 | Rousso et al. |
| 8,447,392 B2 | 5/2013 | Llinas |
| 8,447,407 B2 | 5/2013 | Talathi et al. |
| 8,447,411 B2 | 5/2013 | Skelton et al. |
| 8,449,471 B2 | 5/2013 | Tran |
| 8,452,387 B2 | 5/2013 | Osorio et al. |
| 8,452,544 B2 | 5/2013 | Hymel |
| 8,454,555 B2 | 6/2013 | Struijk et al. |
| 8,456,164 B2 | 6/2013 | Subbarao |
| 8,456,166 B2 | 6/2013 | DePavia et al. |
| 8,456,309 B2 | 6/2013 | Sachanandani et al. |
| 8,457,730 B2 | 6/2013 | Makinen |
| 8,457,746 B2 | 6/2013 | Libbus |
| 8,457,747 B2 | 6/2013 | Terry, Jr. |
| 8,461,988 B2 | 6/2013 | Tran |
| 8,463,006 B2 | 6/2013 | Prokoski |
| 8,463,007 B2 | 6/2013 | Steinberg et al. |
| 8,463,349 B2 | 6/2013 | Diab et al. |
| 8,463,370 B2 | 6/2013 | Korhonen et al. |
| 8,463,374 B2 | 6/2013 | Hudson et al. |
| 8,463,378 B2 | 6/2013 | Tass |
| 8,463,386 B2 | 6/2013 | Tass |
| 8,463,387 B2 | 6/2013 | De Ridder |
| 8,464,288 B2 | 6/2013 | Pradeep et al. |
| 8,465,408 B2 | 6/2013 | Phillips et al. |
| 8,467,877 B2 | 6/2013 | Imran |
| 8,467,878 B2 | 6/2013 | Lozano et al. |
| 8,473,024 B2 | 6/2013 | Causevic et al. |
| 8,473,044 B2 | 6/2013 | Lee et al. |
| 8,473,306 B2 | 6/2013 | Seely |
| 8,473,345 B2 | 6/2013 | Pradeep et al. |
| 8,475,354 B2 | 7/2013 | Phillips et al. |
| 8,475,368 B2 | 7/2013 | Tran et al. |
| 8,475,371 B2 | 7/2013 | Derchak et al. |
| 8,475,387 B2 | 7/2013 | Derchak et al. |
| 8,475,506 B1 | 7/2013 | Bendett et al. |
| 8,478,389 B1 | 7/2013 | Brockway et al. |
| 8,478,394 B2 | 7/2013 | Prichep et al. |
| 8,478,402 B2 | 7/2013 | Wahlstrand et al. |
| 8,478,417 B2 | 7/2013 | Drew et al. |
| 8,478,428 B2 | 7/2013 | Cowley |
| 8,480,554 B2 | 7/2013 | Phillips et al. |
| 8,483,795 B2 | 7/2013 | Okada |
| 8,483,815 B2 | 7/2013 | Liley |
| 8,483,816 B1 | 7/2013 | Payton et al. |
| 8,484,081 B2 | 7/2013 | Pradeep et al. |
| 8,484,270 B2 | 7/2013 | Kurtz et al. |
| 8,485,979 B2 | 7/2013 | Giftakis et al. |
| 8,487,760 B2 | 7/2013 | Kangas et al. |
| 8,489,185 B2 | 7/2013 | Kilgard et al. |
| 8,492,336 B2 | 7/2013 | Masure |
| 8,494,610 B2 | 7/2013 | Pradeep et al. |
| 8,494,829 B2 | 7/2013 | Teixeira |
| 8,494,857 B2 | 7/2013 | Pakhomov |
| 8,494,905 B2 | 7/2013 | Pradeep et al. |
| 8,496,594 B2 | 7/2013 | Taylor et al. |
| 8,498,697 B2 | 7/2013 | Yong et al. |
| 8,498,699 B2 | 7/2013 | Wells et al. |
| 8,498,708 B2 | 7/2013 | Bentwich |
| RE44,408 E | 8/2013 | Lindsay |
| 8,500,282 B2 | 8/2013 | Bolger et al. |
| 8,500,636 B2 | 8/2013 | Tran |
| 8,504,150 B2 | 8/2013 | Skelton |
| 8,506,469 B2 | 8/2013 | Dietrich et al. |
| 8,509,879 B2 | 8/2013 | Durkin et al. |
| 8,509,881 B2 | 8/2013 | Thiagarajan et al. |
| 8,509,885 B2 | 8/2013 | Snyder et al. |
| 8,509,904 B2 | 8/2013 | Rickert et al. |
| 8,512,219 B2 | 8/2013 | Ferren et al. |
| 8,512,221 B2 | 8/2013 | Kaplan et al. |
| 8,512,240 B1 | 8/2013 | Zuckerman-Stark et al. |
| 8,515,535 B2 | 8/2013 | Hopper et al. |
| 8,515,538 B1 | 8/2013 | Osorio et al. |
| 8,515,541 B1 | 8/2013 | Jaax et al. |
| 8,515,549 B2 | 8/2013 | Panken et al. |
| 8,515,550 B2 | 8/2013 | Skelton et al. |
| 8,517,909 B2 | 8/2013 | Honeycutt et al. |
| 8,517,912 B2 | 8/2013 | Clare |
| 8,519,705 B2 | 8/2013 | Savukov et al. |
| 8,519,853 B2 | 8/2013 | Eskandarian et al. |
| 8,520,974 B2 | 8/2013 | Fujita et al. |
| 8,521,284 B2 | 8/2013 | Kim et al. |
| 8,523,779 B2 | 9/2013 | Taylor et al. |
| 8,525,673 B2 | 9/2013 | Tran |
| 8,525,687 B2 | 9/2013 | Tran |
| 8,527,029 B2 | 9/2013 | Okada |
| 8,527,035 B2 | 9/2013 | Diamond |
| 8,527,435 B1 | 9/2013 | Han et al. |
| 8,529,463 B2 | 9/2013 | Della Santina et al. |
| 8,531,291 B2 | 9/2013 | Tran |
| 8,532,756 B2 | 9/2013 | Schalk et al. |
| 8,532,757 B2 | 9/2013 | Molnar et al. |
| 8,533,042 B2 | 9/2013 | Pradeep et al. |
| 8,536,667 B2 | 9/2013 | de Graff et al. |
| 8,538,108 B2 | 9/2013 | Shekhar et al. |
| 8,538,512 B1 | 9/2013 | Bibian et al. |
| 8,538,513 B2 | 9/2013 | Molnar et al. |
| 8,538,514 B2 | 9/2013 | Sun et al. |
| 8,538,523 B2 | 9/2013 | Sommer et al. |
| 8,538,536 B2 | 9/2013 | Rezai et al. |
| 8,538,543 B2 | 9/2013 | McIntyre et al. |
| 8,538,700 B2 | 9/2013 | Badri et al. |
| 8,538,705 B2 | 9/2013 | Greenwald |
| 8,542,900 B2 | 9/2013 | Tolkowsky et al. |
| 8,542,916 B2 | 9/2013 | Tognoli et al. |
| 8,543,189 B2 | 9/2013 | Paitel et al. |

(56) References Cited

U.S. PATENT DOCUMENTS

| | | | |
|---|---|---|---|
| 8,543,199 B2 | 9/2013 | Snyder et al. |
| 8,543,214 B2 | 9/2013 | Osorio et al. |
| 8,543,219 B2 | 9/2013 | Tass |
| 8,545,378 B2 | 10/2013 | Peterchev |
| 8,545,416 B1 | 10/2013 | Kayyali et al. |
| 8,545,420 B2 | 10/2013 | Einav et al. |
| 8,545,436 B2 | 10/2013 | Robertson et al. |
| 8,548,583 B2 | 10/2013 | Rousso et al. |
| 8,548,594 B2 | 10/2013 | Thimineur et al. |
| 8,548,604 B2 | 10/2013 | Whitehurst et al. |
| 8,548,786 B2 | 10/2013 | Plenz |
| 8,548,852 B2 | 10/2013 | Pradeep et al. |
| 8,553,956 B2 | 10/2013 | Wu et al. |
| 8,554,311 B2 | 10/2013 | Warner et al. |
| 8,554,325 B2 | 10/2013 | Molnar et al. |
| 8,559,645 B2 | 10/2013 | Corona-Strauss et al. |
| 8,560,034 B1 | 10/2013 | Diab et al. |
| 8,560,041 B2 | 10/2013 | Flaherty et al. |
| 8,560,073 B2 | 10/2013 | Osorio |
| 8,562,525 B2 | 10/2013 | Nakashima et al. |
| 8,562,526 B2 | 10/2013 | Heneghan et al. |
| 8,562,527 B2 | 10/2013 | Braun et al. |
| 8,562,536 B2 | 10/2013 | Osorio et al. |
| 8,562,540 B2 | 10/2013 | Goodall et al. |
| 8,562,548 B2 | 10/2013 | Shimada et al. |
| 8,562,660 B2 | 10/2013 | Peyman |
| 8,562,951 B2 | 10/2013 | Suffin et al. |
| 8,565,606 B2 | 10/2013 | Kim et al. |
| 8,565,864 B2 | 10/2013 | Drew et al. |
| 8,565,867 B2 | 10/2013 | Armstrong et al. |
| 8,565,883 B2 | 10/2013 | Lozano |
| 8,565,886 B2 | 10/2013 | Nelson et al. |
| 8,568,231 B2 | 10/2013 | Solanki et al. |
| 8,568,329 B2 | 10/2013 | Lee et al. |
| 8,571,293 B2 | 10/2013 | Ernst et al. |
| 8,571,629 B2 | 10/2013 | Faro et al. |
| 8,571,642 B2 | 10/2013 | Gill et al. |
| 8,571,643 B2 | 10/2013 | Osorio et al. |
| 8,571,653 B2 | 10/2013 | Ben-David et al. |
| 8,574,164 B2 | 11/2013 | Mashiach |
| 8,574,279 B2 | 11/2013 | Schiffer |
| 8,577,103 B2 | 11/2013 | Vija et al. |
| 8,577,464 B2 | 11/2013 | Mashiach |
| 8,577,465 B2 | 11/2013 | Mashiach |
| 8,577,466 B2 | 11/2013 | Mashiach |
| 8,577,467 B2 | 11/2013 | Mashiach et al. |
| 8,577,468 B2 | 11/2013 | Mashiach et al. |
| 8,577,472 B2 | 11/2013 | Mashiach et al. |
| 8,577,478 B2 | 11/2013 | Mashiach et al. |
| 8,579,786 B2 | 11/2013 | Osorio et al. |
| 8,579,793 B1 | 11/2013 | Honeycutt et al. |
| 8,579,795 B2 | 11/2013 | Martel |
| 8,579,834 B2 | 11/2013 | Davis et al. |
| 8,583,238 B1 | 11/2013 | Heldman et al. |
| 8,583,252 B2 | 11/2013 | Skelton et al. |
| 8,585,568 B2 | 11/2013 | Phillips et al. |
| 8,586,019 B2 | 11/2013 | Satchi-Fainaro et al. |
| 8,586,932 B2 | 11/2013 | Rousso et al. |
| 8,587,304 B2 | 11/2013 | Budker et al. |
| 8,588,486 B2 | 11/2013 | Virtue et al. |
| 8,588,552 B2 | 11/2013 | Garg et al. |
| 8,588,899 B2 | 11/2013 | Schiff |
| 8,588,929 B2 | 11/2013 | Skelton et al. |
| 8,588,933 B2 | 11/2013 | Floyd et al. |
| 8,588,941 B2 | 11/2013 | Mashiach |
| 8,589,316 B2 | 11/2013 | Lujan et al. |
| 8,591,419 B2 | 11/2013 | Tyler |
| 8,591,498 B2 | 11/2013 | John |
| 8,593,141 B1 | 11/2013 | Radparvar et al. |
| 8,593,154 B2 | 11/2013 | Ross |
| 8,594,798 B2 | 11/2013 | Osorio et al. |
| 8,594,800 B2 | 11/2013 | Butson et al. |
| 8,594,950 B2 | 11/2013 | Taylor |
| 8,597,171 B2 | 12/2013 | Altman et al. |
| 8,597,193 B2 | 12/2013 | Grunwald et al. |
| 8,600,493 B2 | 12/2013 | Tanner et al. |
| 8,600,502 B2 | 12/2013 | Lovett et al. |
| 8,600,513 B2 | 12/2013 | Aur et al. |
| 8,600,521 B2 | 12/2013 | Armstrong et al. |
| 8,600,696 B2 | 12/2013 | Zafiris |
| 8,603,790 B2 | 12/2013 | Deisseroth et al. |
| 8,606,349 B2 | 12/2013 | Rousso et al. |
| 8,606,351 B2 | 12/2013 | Wheeler |
| 8,606,356 B2 | 12/2013 | Lee et al. |
| 8,606,360 B2 | 12/2013 | Butson et al. |
| 8,606,361 B2 | 12/2013 | Gliner et al. |
| 8,606,530 B2 | 12/2013 | Taylor |
| 8,606,592 B2 | 12/2013 | Hyde et al. |
| 8,612,005 B2 | 12/2013 | Rezai et al. |
| 8,613,695 B2 | 12/2013 | Von Ohlsen et al. |
| 8,613,905 B2 | 12/2013 | El-Agnaf |
| 8,614,254 B2 | 12/2013 | Llinas et al. |
| 8,614,873 B1 | 12/2013 | Beran |
| 8,615,293 B2 | 12/2013 | Jacobson et al. |
| 8,615,309 B2 | 12/2013 | Craig |
| 8,615,479 B2 | 12/2013 | Jung et al. |
| 8,615,664 B2 | 12/2013 | Jung et al. |
| 8,618,799 B1 | 12/2013 | Radparvar et al. |
| 8,620,206 B2 | 12/2013 | Brown et al. |
| 8,620,419 B2 | 12/2013 | Rotenberg et al. |
| 8,626,264 B1 | 1/2014 | Beran |
| 8,626,301 B2 | 1/2014 | Libbus |
| 8,628,328 B2 | 1/2014 | Palacios |
| 8,628,480 B2 | 1/2014 | Derchak |
| 8,630,699 B2 | 1/2014 | Baker et al. |
| 8,630,705 B2 | 1/2014 | Mann et al. |
| 8,630,812 B2 | 1/2014 | Taylor |
| 8,632,465 B1 | 1/2014 | Brockway |
| 8,632,750 B2 | 1/2014 | Suffin et al. |
| 8,634,616 B2 | 1/2014 | Den Harder et al. |
| 8,634,922 B1 | 1/2014 | Osorio et al. |
| 8,635,105 B2 | 1/2014 | Pradeep et al. |
| 8,636,640 B2 | 1/2014 | Chang |
| 8,638,950 B2 | 1/2014 | Anderson et al. |
| 8,641,632 B2 | 2/2014 | Quintin et al. |
| 8,641,646 B2 | 2/2014 | Colborn |
| 8,644,754 B2 | 2/2014 | Brown |
| 8,644,910 B2 | 2/2014 | Rousso et al. |
| 8,644,914 B2 | 2/2014 | Hunt |
| 8,644,921 B2 | 2/2014 | Wilson |
| 8,644,945 B2 | 2/2014 | Skelton et al. |
| 8,644,946 B2 | 2/2014 | Butson et al. |
| 8,644,954 B2 | 2/2014 | Jaax et al. |
| 8,644,957 B2 | 2/2014 | Mashiach |
| 8,647,278 B2 | 2/2014 | Ji et al. |
| 8,648,017 B2 | 2/2014 | Umansky et al. |
| 8,649,845 B2 | 2/2014 | McIntyre et al. |
| 8,649,866 B2 | 2/2014 | Brooke |
| 8,649,871 B2 | 2/2014 | Frei et al. |
| 8,652,038 B2 | 2/2014 | Tran et al. |
| 8,652,187 B2 | 2/2014 | Wells et al. |
| 8,652,189 B2 | 2/2014 | Gafni et al. |
| 8,655,428 B2 | 2/2014 | Pradeep et al. |
| 8,655,437 B2 | 2/2014 | Pradeep et al. |
| 8,655,817 B2 | 2/2014 | Hasey et al. |
| 8,657,732 B2 | 2/2014 | Vasishta |
| 8,657,756 B2 | 2/2014 | Stahmann et al. |
| 8,658,149 B2 | 2/2014 | Satchi-Fainaro et al. |
| 8,660,642 B2 | 2/2014 | Ferren et al. |
| 8,660,649 B2 | 2/2014 | Ruffini et al. |
| 8,660,666 B2 | 2/2014 | Craig |
| 8,660,799 B2 | 2/2014 | Watson et al. |
| 8,664,258 B2 | 3/2014 | Teegarden et al. |
| 8,666,099 B2 | 3/2014 | Nielsen et al. |
| 8,666,467 B2 | 3/2014 | Lynn et al. |
| 8,666,478 B2 | 3/2014 | LaViolette et al. |
| 8,666,501 B2 | 3/2014 | Kilgard et al. |
| 8,668,496 B2 | 3/2014 | Nolen |
| 8,670,603 B2 | 3/2014 | Tolkowsky et al. |
| 8,672,852 B2 | 3/2014 | Gavish |
| 8,675,936 B2 | 3/2014 | Vija et al. |
| 8,675,945 B2 | 3/2014 | Barnhorst et al. |
| 8,675,983 B2 | 3/2014 | Yahil |
| 8,676,324 B2 | 3/2014 | Simon et al. |

(56)                    References Cited

U.S. PATENT DOCUMENTS 8,676,325 B2   3/2014   Lindenthaler et al.
8,676,330 B2   3/2014   Simon et al.
8,679,009 B2   3/2014   Osorio
8,680,119 B2   3/2014   Teegarden et al.
8,680,991 B2   3/2014   Tran
8,682,422 B2   3/2014   Hopenfeld
8,682,441 B2   3/2014   De Ridder
8,682,449 B2   3/2014   Simon
8,682,687 B2   3/2014   Hyde et al.
8,684,742 B2   4/2014   Siefert
8,684,900 B2   4/2014   Tran
8,684,921 B2   4/2014   Osorio
8,684,922 B2   4/2014   Tran
8,684,926 B2   4/2014   Arndt
8,688,209 B2   4/2014   Verbitskiy
8,690,748 B1   4/2014   Fu
8,693,756 B2   4/2014   Tolkowsky et al.
8,693,765 B2   4/2014   Mercier et al.
8,694,087 B2   4/2014   Schiff
8,694,089 B2   4/2014   Arad (Abboud)
8,694,092 B2   4/2014   Ferren et al.
8,694,107 B2   4/2014   Falci
8,694,118 B2   4/2014   Armstrong
8,694,157 B2   4/2014   Wenderow et al.
8,696,722 B2   4/2014   Deisseroth et al.
8,696,724 B2   4/2014   Rogers
8,698,639 B2   4/2014   Fung et al.
8,700,137 B2   4/2014   Albert
8,700,141 B2   4/2014   Causevic
8,700,142 B2   4/2014   John et al.
8,700,163 B2   4/2014   Terry, Jr. et al.
8,700,167 B2   4/2014   Sabel
8,700,174 B2   4/2014   Skelton et al.
8,700,183 B2   4/2014   Mashiach
8,703,114 B2   4/2014   Satchi-Fainaro et al.
8,706,183 B2   4/2014   Cui et al.
8,706,205 B2   4/2014   Shahaf et al.
8,706,206 B2   4/2014   Kanai et al.
8,706,207 B2   4/2014   Flint
8,706,237 B2   4/2014   Giftakis et al.
8,706,241 B2   4/2014   Firlik et al.
8,706,518 B2   4/2014   Hyde et al.
8,708,903 B2   4/2014   Tran
8,708,934 B2   4/2014   Skelton et al.
8,711,655 B2   4/2014   Gzara et al.
8,712,507 B2   4/2014   Cazares et al.
8,712,512 B2   4/2014   Doidge et al.
8,712,513 B1   4/2014   Modarres
8,712,547 B2   4/2014   Whitehurst et al.
8,716,447 B2   5/2014   Deisseroth et al.
8,717,430 B2   5/2014   Simon et al.
8,718,747 B2   5/2014   Bjornerud et al.
8,718,776 B2   5/2014   Mashiach et al.
8,718,777 B2   5/2014   Lowry et al.
8,718,779 B2   5/2014   Whitehurst et al.
8,721,695 B2   5/2014   Tass et al.
8,724,871 B1   5/2014   Biagiotti et al.
8,725,238 B2   5/2014   Liu et al.
8,725,243 B2   5/2014   Dilorenzo et al.
8,725,311 B1   5/2014   Breed
8,725,668 B2   5/2014   Georgopoulos
8,725,669 B1   5/2014   Fu
8,725,796 B2   5/2014   Serena
8,727,978 B2   5/2014   Tran et al.
8,728,001 B2   5/2014   Lynn
8,729,040 B2   5/2014   Deisseroth et al.
8,731,650 B2   5/2014   Sajda et al.
8,731,656 B2   5/2014   Bourget et al.
8,731,987 B2   5/2014   Chen et al.
8,733,290 B2   5/2014   Gerashchenko
8,734,356 B2   5/2014   Taylor
8,734,357 B2   5/2014   Taylor
8,734,498 B2   5/2014   DiMauro et al.
8,738,121 B2   5/2014   Virag et al.
8,738,126 B2   5/2014   Craig
8,738,136 B2   5/2014   Frei et al.
8,738,140 B2   5/2014   De Ridder
8,738,395 B2   5/2014   Hyde et al.
8,744,562 B2   6/2014   Giftakis et al.
8,744,563 B2   6/2014   Yoshida
8,747,313 B2   6/2014   Tran et al.
8,747,336 B2   6/2014   Tran
8,747,382 B2   6/2014   D'Souza et al.
8,750,971 B2   6/2014   Tran
8,750,974 B2   6/2014   Baker et al.
8,750,992 B2   6/2014   Hopper et al.
8,751,008 B2   6/2014   Carlton et al.
8,751,011 B2   6/2014   Skelton et al.
8,753,296 B2   6/2014   Einav et al.
8,754,238 B2   6/2014   Teegarden et al.
8,755,854 B2   6/2014   Addison et al.
8,755,856 B2   6/2014   Diab et al.
8,755,868 B2   6/2014   Yazicioglu
8,755,869 B2   6/2014   Zhang et al.
8,755,871 B2   6/2014   Weng et al.
8,755,877 B2   6/2014   Zoica
8,755,901 B2   6/2014   Skelton et al.
8,756,017 B2   6/2014   Hu et al.
8,758,274 B2   6/2014   Sahasrabudhe et al.
8,761,438 B2   6/2014   Lee et al.
8,761,866 B2   6/2014   Chance
8,761,868 B2   6/2014   Giftakis et al.
8,761,869 B2   6/2014   Leuthardt et al.
8,761,889 B2   6/2014   Wingeier et al.
8,762,065 B2   6/2014   DiLorenzo
8,762,202 B2   6/2014   Pradeep et al.
8,764,651 B2   7/2014   Tran
8,764,652 B2   7/2014   Lee et al.
8,764,653 B2   7/2014   Kaminska et al.
8,764,673 B2   7/2014   McCraty et al.
8,768,022 B2   7/2014   Miga et al.
8,768,427 B2   7/2014   Sjaaheim et al.
8,768,431 B2   7/2014   Ross et al.
8,768,446 B2   7/2014   Drew et al.
8,768,447 B2   7/2014   Ermes et al.
8,768,449 B2   7/2014   Pesaran et al.
8,768,471 B2   7/2014   Colborn et al.
8,768,477 B2   7/2014   Spitzer et al.
8,768,718 B2   7/2014   Cazares et al.
8,771,194 B2   7/2014   John et al.
8,774,923 B2   7/2014   Rom
8,775,340 B2   7/2014   Waxman et al.
8,781,193 B2   7/2014   Steinberg et al.
8,781,197 B2   7/2014   Wang et al.
8,781,557 B2   7/2014   Dean et al.
8,781,563 B2   7/2014   Foo
8,781,595 B2   7/2014   Grevious et al.
8,781,597 B2   7/2014   DiLorenzo
8,781,796 B2   7/2014   Mott et al.
8,784,109 B2   7/2014   Gottfried
8,784,322 B2   7/2014   Kim et al.
8,785,441 B2   7/2014   Teegarden et al.
8,786,624 B2   7/2014   Echauz et al.
8,787,637 B2   7/2014   Duchesnay et al.
8,788,030 B1   7/2014   Payton et al.
8,788,033 B2   7/2014   Rossi
8,788,044 B2   7/2014   John
8,788,055 B2   7/2014   Gerber et al.
8,788,057 B2   7/2014   Stevenson et al.
8,790,255 B2   7/2014   Behar
8,790,272 B2   7/2014   Sackner et al.
8,790,297 B2   7/2014   Bromander et al.
8,792,972 B2   7/2014   Zaidel et al.
8,792,974 B2   7/2014   Rothman
8,792,991 B2   7/2014   Gerber et al.
8,795,175 B2   8/2014   Funane et al.
8,798,717 B2   8/2014   Roscher
8,798,728 B2   8/2014   Drew et al.
8,798,735 B1   8/2014   Bibian et al.
8,798,736 B2   8/2014   Sullivan et al.
8,798,773 B2   8/2014   Mashiach
8,801,620 B2   8/2014   Melker et al.
8,805,516 B2   8/2014   Bentwich
8,805,518 B2   8/2014   King et al.

(56)         References Cited

U.S. PATENT DOCUMENTS

| | | | |
|---|---|---|---|
| 8,812,126 B2 | 8/2014 | Butson et al. |
| 8,812,237 B2 | 8/2014 | Wilt et al. |
| 8,812,245 B2 | 8/2014 | Taylor |
| 8,812,246 B2 | 8/2014 | Taylor |
| 8,814,923 B2 | 8/2014 | Nissila et al. |
| 8,815,582 B2 | 8/2014 | Deisseroth et al. |
| 8,821,376 B2 | 9/2014 | Tolkowsky |
| 8,821,408 B2 | 9/2014 | Hu et al. |
| 8,821,559 B2 | 9/2014 | DiMauro et al. |
| 8,825,149 B2 | 9/2014 | Kraus et al. |
| 8,825,166 B2 | 9/2014 | John |
| 8,825,167 B2 | 9/2014 | Tass et al. |
| 8,825,428 B2 | 9/2014 | Addison et al. |
| 8,827,912 B2 | 9/2014 | Bukhman |
| 8,827,917 B2 | 9/2014 | Watson et al. |
| 8,829,908 B2 | 9/2014 | Roshtal et al. |
| 8,831,705 B2 | 9/2014 | Dobak |
| 8,831,731 B2 | 9/2014 | Blum et al. |
| 8,831,732 B2 | 9/2014 | Frei et al. |
| 8,834,392 B2 | 9/2014 | Panken et al. |
| 8,834,546 B2 | 9/2014 | Deisseroth et al. |
| 8,838,201 B2 | 9/2014 | Mori et al. |
| 8,838,225 B2 | 9/2014 | Ahonen et al. |
| 8,838,226 B2 | 9/2014 | Bibian et al. |
| 8,838,227 B2 | 9/2014 | Causevic et al. |
| 8,838,247 B2 | 9/2014 | Hagedorn et al. |
| 8,843,199 B2 | 9/2014 | Kim et al. |
| 8,843,201 B1 | 9/2014 | Heldman et al. |
| 8,843,210 B2 | 9/2014 | Simon et al. |
| 8,845,545 B2 | 9/2014 | Folkerts et al. |
| 8,849,390 B2 | 9/2014 | Echauz et al. |
| 8,849,392 B2 | 9/2014 | Lozano |
| 8,849,407 B1 | 9/2014 | Danilov et al. |
| 8,849,409 B2 | 9/2014 | Colborn et al. |
| 8,849,632 B2 | 9/2014 | Sparks et al. |
| 8,849,681 B2 | 9/2014 | Hargrove et al. |
| 8,852,073 B2 | 10/2014 | Genereux et al. |
| 8,852,100 B2 | 10/2014 | Osorio |
| 8,852,103 B2 | 10/2014 | Rothberg et al. |
| 8,855,758 B2 | 10/2014 | Rodriquez-Villegas et al. |
| 8,855,773 B2 | 10/2014 | Kokones et al. |
| 8,855,775 B2 | 10/2014 | Leyde |
| 8,858,440 B2 | 10/2014 | Tyler |
| 8,858,449 B2 | 10/2014 | Inan et al. |
| 8,861,819 B2 | 10/2014 | Lee et al. |
| 8,862,196 B2 | 10/2014 | Lynn |
| 8,862,210 B2 | 10/2014 | Yazicioglu et al. |
| 8,862,236 B2 | 10/2014 | Wolpaw et al. |
| 8,862,581 B2 | 10/2014 | Zhang et al. |
| 8,864,310 B2 | 10/2014 | Gross et al. |
| 8,864,806 B2 | 10/2014 | Wells et al. |
| 8,868,148 B2 | 10/2014 | Engelbrecht et al. |
| 8,868,163 B2 | 10/2014 | Guttag et al. |
| 8,868,172 B2 | 10/2014 | Leyde et al. |
| 8,868,173 B2 | 10/2014 | Nelson et al. |
| 8,868,174 B2 | 10/2014 | Sato et al. |
| 8,868,175 B2 | 10/2014 | Simon et al. |
| 8,868,177 B2 | 10/2014 | Simon et al. |
| 8,868,189 B2 | 10/2014 | Stevenson et al. |
| 8,868,201 B2 | 10/2014 | Roberts et al. |
| 8,870,737 B2 | 10/2014 | Phillips et al. |
| 8,871,797 B2 | 10/2014 | Teegarden et al. |
| 8,872,640 B2 | 10/2014 | Horseman |
| 8,874,205 B2 | 10/2014 | Simon et al. |
| 8,874,218 B2 | 10/2014 | Terry, Jr. |
| 8,874,227 B2 | 10/2014 | Simon et al. |
| 8,874,439 B2 | 10/2014 | Kim et al. |
| 8,880,207 B2 | 11/2014 | Abeyratne et al. |
| 8,880,576 B2 | 11/2014 | Ochs et al. |
| 8,886,299 B2 | 11/2014 | Yazicioglu et al. |
| 8,886,302 B2 | 11/2014 | Skelton et al. |
| 8,888,672 B2 | 11/2014 | Phillips et al. |
| 8,888,673 B2 | 11/2014 | Phillips et al. |
| 8,888,702 B2 | 11/2014 | Osorio |
| 8,888,708 B2 | 11/2014 | Diab et al. |
| 8,888,723 B2 | 11/2014 | Einav |
| 8,892,207 B2 | 11/2014 | Nelson et al. |
| 8,893,120 B2 | 11/2014 | Pinsky et al. |
| 8,898,037 B2 | 11/2014 | Watson et al. |
| 8,900,284 B2 | 12/2014 | DiMauro et al. |
| 8,902,070 B2 | 12/2014 | Kobetski et al. |
| 8,903,479 B2 | 12/2014 | Zoicas |
| 8,903,483 B2 | 12/2014 | Sun et al. |
| 8,903,486 B2 | 12/2014 | Bourget et al. |
| 8,903,494 B2 | 12/2014 | Goldwasser et al. |
| 8,906,360 B2 | 12/2014 | Deisseroth et al. |
| 8,907,668 B2 | 12/2014 | Okada |
| 8,909,345 B1 | 12/2014 | Danilov et al. |
| 8,910,638 B2 | 12/2014 | Boyden et al. |
| 8,913,810 B2 | 12/2014 | Panin et al. |
| 8,914,100 B2 | 12/2014 | Adachi et al. |
| 8,914,115 B2 | 12/2014 | Giftakis et al. |
| 8,914,119 B2 | 12/2014 | Wu et al. |
| 8,914,122 B2 | 12/2014 | Simon et al. |
| 8,915,741 B2 | 12/2014 | Hatlestad et al. |
| 8,915,871 B2 | 12/2014 | Einav |
| 8,918,162 B2 | 12/2014 | Prokoski |
| 8,918,176 B2 | 12/2014 | Nelson et al. |
| 8,918,178 B2 | 12/2014 | Simon et al. |
| 8,918,183 B2 | 12/2014 | Carlton et al. |
| 8,921,320 B2 | 12/2014 | Paul et al. |
| 8,922,376 B2 | 12/2014 | Kangas et al. |
| 8,922,788 B2 | 12/2014 | Addison et al. |
| 8,923,958 B2 | 12/2014 | Gupta et al. |
| 8,924,235 B2 | 12/2014 | Seely |
| RE45,336 E | 1/2015 | Teegarden et al. |
| RE45,337 E | 1/2015 | Teegarden et al. |
| 8,926,959 B2 | 1/2015 | Deisseroth et al. |
| 8,929,991 B2 | 1/2015 | Fowler et al. |
| 8,929,999 B2 | 1/2015 | Maschiach |
| 8,932,218 B1 | 1/2015 | Thompson |
| 8,932,227 B2 | 1/2015 | Lynn |
| 8,932,562 B2 | 1/2015 | Deisseroth et al. |
| 8,933,696 B2 | 1/2015 | Nishikawa |
| 8,934,685 B2 | 1/2015 | Avinash et al. |
| 8,934,965 B2 | 1/2015 | Rogers et al. |
| 8,934,967 B2 | 1/2015 | Kilgard et al. |
| 8,934,979 B2 | 1/2015 | Moffitt |
| 8,934,986 B2 | 1/2015 | Goetz |
| 8,936,629 B2 | 1/2015 | Boyden et al. |
| 8,936,630 B2 | 1/2015 | Denison et al. |
| 8,938,102 B2 | 1/2015 | Carroll |
| 8,938,289 B2 | 1/2015 | Einav et al. |
| 8,938,290 B2 | 1/2015 | Wingeier et al. |
| 8,938,301 B2 | 1/2015 | Hagedorn |
| 8,939,903 B2 | 1/2015 | Roberts et al. |
| 8,942,777 B2 | 1/2015 | Diab et al. |
| 8,942,813 B1 | 1/2015 | Hagedorn et al. |
| 8,942,817 B2 | 1/2015 | Hyde et al. |
| 8,945,006 B2 | 2/2015 | Osorio |
| 8,948,834 B2 | 2/2015 | Diab et al. |
| 8,948,849 B2 | 2/2015 | Diamond et al. |
| 8,948,855 B2 | 2/2015 | Osorio et al. |
| 8,948,860 B2 | 2/2015 | Causevic |
| 8,951,189 B2 | 2/2015 | Osorio |
| 8,951,190 B2 | 2/2015 | Chmiel et al. |
| 8,951,192 B2 | 2/2015 | Osorio |
| 8,951,203 B2 | 2/2015 | Patangay et al. |
| 8,954,139 B2 | 2/2015 | Hopenfeld et al. |
| 8,954,146 B2 | 2/2015 | Hopper et al. |
| 8,954,293 B2 | 2/2015 | Klinkenbusch |
| 8,955,010 B2 | 2/2015 | Pradeep et al. |
| 8,955,974 B2 | 2/2015 | Gross et al. |
| 8,956,277 B2 | 2/2015 | Mishelevich |
| 8,956,363 B2 | 2/2015 | Schneider et al. |
| 8,958,868 B2 | 2/2015 | Ghovanloo et al. |
| 8,958,870 B2 | 2/2015 | Gerber et al. |
| 8,958,882 B1 | 2/2015 | Hagedorn |
| 8,961,187 B2 | 2/2015 | Boers et al. |
| 8,961,385 B2 | 2/2015 | Pilla et al. |
| 8,961,386 B2 | 2/2015 | Phillips et al. |
| 8,962,042 B2 | 2/2015 | Geng |
| 8,962,589 B2 | 2/2015 | Deisseroth et al. |
| 8,964,298 B2 | 2/2015 | Haddick et al. |

(56)                    References Cited

U.S. PATENT DOCUMENTS

| | | | |
|---|---|---|---|
| 8,965,492 | B2 | 2/2015 | Baker et al. |
| 8,965,513 | B2 | 2/2015 | Wingeier et al. |
| 8,965,514 | B2 | 2/2015 | Bikson et al. |
| 8,968,172 | B2 | 3/2015 | Wang et al. |
| 8,968,176 | B2 | 3/2015 | Altman et al. |
| 8,968,195 | B2 | 3/2015 | Tran |
| 8,968,376 | B2 | 3/2015 | Wells et al. |
| 8,971,936 | B2 | 3/2015 | Derchak |
| 8,972,004 | B2 | 3/2015 | Simon et al. |
| 8,972,013 | B2 | 3/2015 | Maschino |
| 8,974,365 | B2 | 3/2015 | Best |
| 8,977,024 | B1 | 3/2015 | Rex et al. |
| 8,977,110 | B2 | 3/2015 | Pradeep et al. |
| 8,977,362 | B2 | 3/2015 | Saab |
| 8,980,891 | B2 | 3/2015 | Stirn et al. |
| 8,983,155 | B2 | 3/2015 | McIntyre et al. |
| 8,983,591 | B2 | 3/2015 | Leininger et al. |
| 8,983,620 | B2 | 3/2015 | Cinbis |
| 8,983,628 | B2 | 3/2015 | Simon et al. |
| 8,983,629 | B2 | 3/2015 | Simon et al. |
| 8,985,119 | B1 | 3/2015 | Webb et al. |
| 8,986,207 | B2 | 3/2015 | Li et al. |
| 8,989,835 | B2 | 3/2015 | Badower et al. |
| 8,989,836 | B2 | 3/2015 | Machon et al. |
| 8,989,863 | B2 | 3/2015 | Osorio |
| 8,989,867 | B2 | 3/2015 | Chow et al. |
| 8,989,868 | B2 | 3/2015 | Mashiach et al. |
| 8,989,871 | B2 | 3/2015 | Ollivier |
| 8,992,230 | B2 | 3/2015 | Tuchschmid et al. |
| 8,993,623 | B2 | 3/2015 | Goodenowe |
| 8,996,112 | B2 | 3/2015 | Brooke |
| 8,996,120 | B1 | 3/2015 | Calle et al. |
| 8,998,828 | B2 | 4/2015 | Reichow et al. |
| 9,002,458 | B2 | 4/2015 | Pal et al. |
| 9,002,471 | B2 | 4/2015 | Stevenson et al. |
| 9,002,477 | B2 | 4/2015 | Burnett |
| 9,004,687 | B2 | 4/2015 | Stack |
| 9,005,102 | B2 | 4/2015 | Burnett et al. |
| 9,005,126 | B2 | 4/2015 | Beach et al. |
| 9,005,649 | B2 | 4/2015 | Ho et al. |
| 9,008,367 | B2 | 4/2015 | Tolkowsky et al. |
| 9,008,754 | B2 | 4/2015 | Steinberg et al. |
| 9,008,771 | B2 | 4/2015 | Dong et al. |
| 9,008,780 | B2 | 4/2015 | Nudo et al. |
| 9,008,970 | B2 | 4/2015 | Donderici et al. |
| 9,011,329 | B2 | 4/2015 | Ferren et al. |
| 9,014,216 | B2 | 4/2015 | Lazar et al. |
| 9,014,453 | B2 | 4/2015 | Steinberg et al. |
| 9,014,804 | B2 | 4/2015 | Giftakis et al. |
| 9,014,811 | B2 | 4/2015 | Pal et al. |
| 9,014,819 | B2 | 4/2015 | Lee et al. |
| 9,014,823 | B2 | 4/2015 | Simon et al. |
| 9,015,057 | B2 | 4/2015 | Phillips et al. |
| 9,015,087 | B2 | 4/2015 | Li et al. |
| 9,020,576 | B2 | 4/2015 | Nagatani |
| 9,020,582 | B2 | 4/2015 | Osorio et al. |
| 9,020,585 | B2 | 4/2015 | John et al. |
| 9,020,586 | B2 | 4/2015 | Yamada et al. |
| 9,020,598 | B2 | 4/2015 | Simon et al. |
| 9,020,612 | B1 | 4/2015 | Danilov et al. |
| 9,020,789 | B2 | 4/2015 | Butson et al. |
| 9,022,930 | B2 | 5/2015 | Sachanandani et al. |
| 9,022,936 | B2 | 5/2015 | Rothberg et al. |
| 9,025,845 | B2 | 5/2015 | Carroll |
| 9,026,194 | B2 | 5/2015 | Okada |
| 9,026,202 | B2 | 5/2015 | Albert |
| 9,026,217 | B2 | 5/2015 | Kokones et al. |
| 9,026,218 | B2 | 5/2015 | Lozano et al. |
| 9,026,372 | B2 | 5/2015 | O'Donnell, Jr. et al. |
| 9,028,405 | B2 | 5/2015 | Tran |
| 9,028,412 | B2 | 5/2015 | Rothberg et al. |
| 9,031,644 | B2 | 5/2015 | Johnson et al. |
| 9,031,653 | B2 | 5/2015 | Mashiach |
| 9,031,655 | B2 | 5/2015 | Osorio et al. |
| 9,031,658 | B2 | 5/2015 | Chiao et al. |
| 9,033,884 | B2 | 5/2015 | Rothberg et al. |
| 9,034,055 | B2 | 5/2015 | Vinjamuri et al. |
| 9,034,911 | B2 | 5/2015 | Selvey et al. |
| 9,034,923 | B2 | 5/2015 | Goodenowe |
| 9,035,657 | B2 | 5/2015 | Zhang et al. |
| 9,036,844 | B1 | 5/2015 | Suhami et al. |
| 9,037,224 | B1 | 5/2015 | Fu |
| 9,037,225 | B1 | 5/2015 | Saliga et al. |
| 9,037,254 | B2 | 5/2015 | John |
| 9,037,256 | B2 | 5/2015 | Bokil |
| 9,037,530 | B2 | 5/2015 | Tan et al. |
| 9,042,074 | B1 | 5/2015 | Beran |
| 9,042,201 | B2 | 5/2015 | Tyler et al. |
| 9,042,952 | B2 | 5/2015 | Lynn et al. |
| 9,042,958 | B2 | 5/2015 | Karmarkar et al. |
| 9,042,988 | B2 | 5/2015 | DiLorenzo |
| 9,043,001 | B2 | 5/2015 | Simon et al. |
| 9,044,188 | B2 | 6/2015 | DiLorenzo et al. |
| 9,044,612 | B2 | 6/2015 | Mashiach et al. |
| 9,050,469 | B1 | 6/2015 | Osorio et al. |
| 9,050,470 | B2 | 6/2015 | Carlton et al. |
| 9,050,471 | B2 | 6/2015 | Skelton et al. |
| 9,053,516 | B2 | 6/2015 | Stempora |
| 9,053,534 | B2 | 6/2015 | Ross et al. |
| 9,055,871 | B2 | 6/2015 | Inan et al. |
| 9,055,974 | B2 | 6/2015 | Goetz |
| 9,056,195 | B2 | 6/2015 | Sabesan |
| 9,058,473 | B2 | 6/2015 | Navratil et al. |
| 9,060,671 | B2 | 6/2015 | Badower et al. |
| 9,060,683 | B2 | 6/2015 | Tran |
| 9,060,695 | B2 | 6/2015 | Peters |
| 9,060,722 | B2 | 6/2015 | Teixeira |
| 9,060,746 | B2 | 6/2015 | Weng et al. |
| 9,061,132 | B1 | 6/2015 | Zweber et al. |
| 9,061,133 | B2 | 6/2015 | Wurster et al. |
| 9,061,151 | B2 | 6/2015 | Mashiach et al. |
| 9,061,153 | B1 | 6/2015 | Lebovitz et al. |
| 9,063,183 | B2 | 6/2015 | Toda et al. |
| 9,063,643 | B2 | 6/2015 | Sparks et al. |
| 9,064,036 | B2 | 6/2015 | Hyde et al. |
| 9,067,052 | B2 | 6/2015 | Moses et al. |
| 9,067,054 | B2 | 6/2015 | Simon et al. |
| 9,067,070 | B2 | 6/2015 | Connor |
| 9,069,031 | B2 | 6/2015 | Guedes et al. |
| 9,069,097 | B2 | 6/2015 | Zhang et al. |
| 9,070,492 | B2 | 6/2015 | Yarmush et al. |
| 9,072,449 | B2 | 7/2015 | Semenov |
| 9,072,482 | B2 | 7/2015 | Sarkela et al. |
| 9,072,832 | B2 | 7/2015 | Frei et al. |
| 9,072,870 | B2 | 7/2015 | Wu et al. |
| 9,072,905 | B2 | 7/2015 | Kokones et al. |
| 9,074,976 | B2 | 7/2015 | Adolphi et al. |
| 9,076,212 | B2 | 7/2015 | Ernst et al. |
| 9,078,564 | B2 | 7/2015 | Taylor |
| 9,078,577 | B2 | 7/2015 | He et al. |
| 9,078,584 | B2 | 7/2015 | Jorge et al. |
| 9,079,039 | B2 | 7/2015 | Carlson et al. |
| 9,079,940 | B2 | 7/2015 | Deisseroth et al. |
| 9,081,488 | B2 | 7/2015 | Soederstroem |
| 9,081,882 | B2 | 7/2015 | Taylor |
| 9,081,890 | B2 | 7/2015 | An et al. |
| 9,082,169 | B2 | 7/2015 | Thomson et al. |
| 9,084,584 | B2 | 7/2015 | Weiland et al. |
| 9,084,885 | B2 | 7/2015 | Deisseroth et al. |
| 9,084,896 | B2 | 7/2015 | Kokones et al. |
| 9,084,900 | B2 | 7/2015 | Hershey et al. |
| 9,087,147 | B1 | 7/2015 | Fonte |
| 9,089,310 | B2 | 7/2015 | Isenhart et al. |
| 9,089,400 | B2 | 7/2015 | Nofzinger |
| 9,089,683 | B2 | 7/2015 | Mishelevich |
| 9,089,707 | B2 | 7/2015 | Kilgard et al. |
| 9,089,713 | B2 | 7/2015 | John |
| 9,089,719 | B2 | 7/2015 | Simon et al. |
| 9,091,785 | B2 | 7/2015 | Donderici et al. |
| 9,092,556 | B2 | 7/2015 | Amble et al. |
| 9,092,895 | B2 | 7/2015 | Ross et al. |
| 9,095,266 | B1 | 8/2015 | Fu |
| 9,095,268 | B2 | 8/2015 | Kurtz et al. |
| 9,095,295 | B2 | 8/2015 | Eagleman et al. |

(56)  References Cited

U.S. PATENT DOCUMENTS

| | | | |
|---|---|---|---|
| 9,095,303 B2 | 8/2015 | Osorio |
| 9,095,314 B2 | 8/2015 | Osorio et al. |
| 9,095,618 B2 | 8/2015 | Satchi-Fainaro et al. |
| 9,095,713 B2 | 8/2015 | Foster et al. |
| 9,100,758 B2 | 8/2015 | Adachi et al. |
| 9,101,263 B2 | 8/2015 | Jung et al. |
| 9,101,276 B2 | 8/2015 | Georgopoulos |
| 9,101,279 B2 | 8/2015 | Ritchey et al. |
| 9,101,690 B2 | 8/2015 | Deisseroth et al. |
| 9,101,759 B2 | 8/2015 | Delp et al. |
| 9,101,766 B2 | 8/2015 | Nekhendzy |
| 9,102,717 B2 | 8/2015 | Huang et al. |
| 9,107,586 B2 | 8/2015 | Tran |
| 9,107,595 B1 | 8/2015 | Smyth |
| 9,108,041 B2 | 8/2015 | Craig |
| 9,113,777 B2 | 8/2015 | Mittal |
| 9,113,801 B2 | 8/2015 | DiLorenzo |
| 9,113,803 B2 | 8/2015 | Zhang |
| 9,113,830 B2 | 8/2015 | Galen et al. |
| 9,116,201 B2 | 8/2015 | Shah et al. |
| 9,116,835 B1 | 8/2015 | Smyth |
| 9,118,775 B2 | 8/2015 | Lim et al. |
| 9,119,533 B2 | 9/2015 | Ghaffari |
| 9,119,551 B2 | 9/2015 | Qi et al. |
| 9,119,583 B2 | 9/2015 | Tass |
| 9,119,597 B2 | 9/2015 | Dripps et al. |
| 9,119,598 B2 | 9/2015 | Engelbrecht et al. |
| 9,121,964 B2 | 9/2015 | Lewis et al. |
| 9,125,574 B2 | 9/2015 | Zia et al. |
| 9,125,581 B2 | 9/2015 | Wu et al. |
| 9,125,788 B2 | 9/2015 | Tee et al. |
| 9,126,050 B2 | 9/2015 | Simon et al. |
| 9,131,864 B2 | 9/2015 | Korenberg |
| 9,133,024 B2 | 9/2015 | Phan et al. |
| 9,133,709 B2 | 9/2015 | Huh et al. |
| 9,135,221 B2 | 9/2015 | Shahaf et al. |
| 9,135,400 B2 | 9/2015 | McIntyre et al. |
| 9,138,156 B2 | 9/2015 | Wu et al. |
| 9,138,175 B2 | 9/2015 | Ernst et al. |
| 9,138,183 B2 | 9/2015 | McKenna et al. |
| 9,138,579 B2 | 9/2015 | Wolpaw et al. |
| 9,138,580 B2 | 9/2015 | Ignagni et al. |
| 9,142,145 B2 | 9/2015 | Tuchschmid et al. |
| 9,142,185 B2 | 9/2015 | Fateh |
| 9,144,392 B2 | 9/2015 | Santosh et al. |
| RE45,766 E | 10/2015 | Lindsay |
| 9,149,195 B2 | 10/2015 | Hadley |
| 9,149,197 B2 | 10/2015 | Taylor |
| 9,149,210 B2 | 10/2015 | Sahasrabudhe et al. |
| 9,149,214 B2 | 10/2015 | Adachi et al. |
| 9,149,226 B2 | 10/2015 | Jadidi |
| 9,149,255 B2 | 10/2015 | Rothberg et al. |
| 9,149,577 B2 | 10/2015 | Robertson et al. |
| 9,149,599 B2 | 10/2015 | Walter et al. |
| 9,149,719 B2 | 10/2015 | Guan et al. |
| 9,152,757 B2 | 10/2015 | Taylor |
| 9,155,373 B2 | 10/2015 | Allen et al. |
| 9,155,484 B2 | 10/2015 | Baker et al. |
| 9,155,487 B2 | 10/2015 | Linderman et al. |
| 9,155,521 B2 | 10/2015 | Rothberg et al. |
| 9,161,715 B2 | 10/2015 | Jung et al. |
| 9,162,051 B2 | 10/2015 | Morrell |
| 9,162,052 B2 | 10/2015 | Morrell |
| 9,165,472 B2 | 10/2015 | Hagedorn et al. |
| 9,167,970 B2 | 10/2015 | Gratton et al. |
| 9,167,974 B2 | 10/2015 | Taylor |
| 9,167,976 B2 | 10/2015 | Wingeier et al. |
| 9,167,977 B2 | 10/2015 | Wingeier et al. |
| 9,167,978 B2 | 10/2015 | Wingeier et al. |
| 9,167,979 B2 | 10/2015 | Skidmore et al. |
| 9,171,353 B2 | 10/2015 | Vija et al. |
| 9,171,366 B2 | 10/2015 | Declerck et al. |
| 9,173,582 B2 | 11/2015 | Popovic et al. |
| 9,173,609 B2 | 11/2015 | Nelson |
| 9,173,610 B2 | 11/2015 | Navakatikyan |
| 9,174,045 B2 | 11/2015 | Simon et al. |
| 9,174,055 B2 | 11/2015 | Davis et al. |
| 9,174,066 B2 | 11/2015 | Simon et al. |
| 9,175,095 B2 | 11/2015 | Deisseroth et al. |
| 9,177,379 B1 | 11/2015 | Biagiotti et al. |
| 9,177,416 B2 | 11/2015 | Sharp |
| 9,179,850 B2 | 11/2015 | Wingeier et al. |
| 9,179,854 B2 | 11/2015 | Doidge et al. |
| 9,179,855 B2 | 11/2015 | Burdea et al. |
| 9,179,858 B2 | 11/2015 | Hasson et al. |
| 9,179,875 B2 | 11/2015 | Hua |
| 9,179,876 B2 | 11/2015 | Ochs et al. |
| 9,183,351 B2 | 11/2015 | Shusterman |
| 9,186,060 B2 | 11/2015 | De Graff et al. |
| 9,186,106 B2 | 11/2015 | Osorio |
| 9,186,503 B2 | 11/2015 | Lindenthaler et al. |
| 9,186,510 B2 | 11/2015 | Gliner et al. |
| 9,187,745 B2 | 11/2015 | Deisseroth et al. |
| 9,192,300 B2 | 11/2015 | Jung et al. |
| 9,192,309 B1 | 11/2015 | Hopenfeld et al. |
| 9,198,563 B2 | 12/2015 | Ferren et al. |
| 9,198,612 B2 | 12/2015 | Fueyo et al. |
| 9,198,621 B2 | 12/2015 | Fernstrom et al. |
| 9,198,624 B2 | 12/2015 | Funane et al. |
| 9,198,637 B2 | 12/2015 | Rothberg et al. |
| 9,198,707 B2 | 12/2015 | McKay et al. |
| 9,198,733 B2 | 12/2015 | Neal, II et al. |
| 9,204,796 B2 | 12/2015 | Tran |
| 9,204,835 B2 | 12/2015 | Parsey et al. |
| 9,204,838 B2 | 12/2015 | Osorio |
| 9,204,998 B2 | 12/2015 | Kilgard et al. |
| 9,208,430 B2 | 12/2015 | Solari |
| 9,208,557 B2 | 12/2015 | Pautot |
| 9,208,558 B2 | 12/2015 | Dean et al. |
| 9,211,076 B2 | 12/2015 | Kim |
| 9,211,077 B2 | 12/2015 | Jung et al. |
| 9,211,212 B2 | 12/2015 | Nofzinger et al. |
| 9,211,411 B2 | 12/2015 | Wu et al. |
| 9,211,417 B2 | 12/2015 | Heldman et al. |
| 9,213,074 B2 | 12/2015 | van der Kouwe et al. |
| 9,213,076 B2 | 12/2015 | Liu |
| 9,215,298 B2 | 12/2015 | Schiff |
| 9,215,978 B2 | 12/2015 | Knight et al. |
| 9,220,910 B2 | 12/2015 | Colborn |
| 9,220,917 B2 | 12/2015 | Boyden et al. |
| 9,221,755 B2 | 12/2015 | Teegarden et al. |
| 9,226,672 B2 | 1/2016 | Taylor |
| 9,227,056 B1 | 1/2016 | Heldman et al. |
| 9,229,080 B2 | 1/2016 | Lin |
| 9,230,065 B2 | 1/2016 | Hasegawa et al. |
| 9,230,539 B2 | 1/2016 | Pakhomov |
| 9,232,910 B2 | 1/2016 | Alshaer et al. |
| 9,232,984 B2 | 1/2016 | Guthart et al. |
| 9,233,244 B2 | 1/2016 | Pal et al. |
| 9,233,245 B2 | 1/2016 | Lamensdorf et al. |
| 9,233,246 B2 | 1/2016 | Simon et al. |
| 9,233,258 B2 | 1/2016 | Simon et al. |
| 9,235,679 B2 | 1/2016 | Taylor |
| 9,235,685 B2 | 1/2016 | McIntyre et al. |
| 9,238,142 B2 | 1/2016 | Heldman et al. |
| 9,238,150 B2 | 1/2016 | Deisseroth et al. |
| 9,241,647 B2 | 1/2016 | Osorio et al. |
| 9,241,665 B2 | 1/2016 | deCharms |
| 9,242,067 B2 | 1/2016 | Shore et al. |
| 9,242,092 B2 | 1/2016 | Simon et al. |
| 9,247,890 B2 | 2/2016 | Turnbull et al. |
| 9,247,911 B2 | 2/2016 | Galloway et al. |
| 9,247,924 B2 | 2/2016 | Rothberg et al. |
| 9,248,003 B2 | 2/2016 | Wright et al. |
| 9,248,280 B2 | 2/2016 | Moffitt et al. |
| 9,248,286 B2 | 2/2016 | Simon et al. |
| 9,248,288 B2 | 2/2016 | Panken et al. |
| 9,248,290 B2 | 2/2016 | Mashiach |
| 9,248,291 B2 | 2/2016 | Mashiach |
| 9,248,296 B2 | 2/2016 | Carcieri et al. |
| 9,249,200 B2 | 2/2016 | Deisseroth et al. |
| 9,249,234 B2 | 2/2016 | Deisseroth et al. |
| 9,251,566 B1 | 2/2016 | Bajic |
| 9,254,097 B2 | 2/2016 | Espy et al. |

(56)                References Cited

U.S. PATENT DOCUMENTS 9,254,099 B2   2/2016  Connor
9,254,383 B2   2/2016  Simon et al.
9,254,387 B2   2/2016  Blum et al.
9,256,982 B2   2/2016  Sharp et al.
9,259,177 B2   2/2016  Drew et al.
9,259,482 B2   2/2016  Satchi-Fainaro et al.
9,259,591 B2   2/2016  Brown et al.
9,261,573 B1   2/2016  Radparvar et al.
9,265,458 B2   2/2016  Stack
9,265,660 B2   2/2016  Kilgard et al.
9,265,661 B2   2/2016  Kilgard et al.
9,265,662 B2   2/2016  Kilgard et al.
9,265,663 B2   2/2016  Kilgard et al.
9,265,931 B2   2/2016  Morrell
9,265,943 B2   2/2016  Yun et al.
9,265,946 B2   2/2016  Morrell
9,265,965 B2   2/2016  Fox et al.
9,265,974 B2   2/2016  You et al.
9,268,014 B2   2/2016  Rothberg et al.
9,268,015 B2   2/2016  Rothberg et al.
9,268,902 B2   2/2016  Taylor et al.
9,271,651 B2   3/2016  Avinash et al.
9,271,657 B2   3/2016  Taylor
9,271,660 B2   3/2016  Luo et al.
9,271,674 B2   3/2016  Deisseroth et al.
9,271,679 B2   3/2016  Cho et al.
9,272,091 B2   3/2016  Skelton et al.
9,272,139 B2   3/2016  Hamilton et al.
9,272,145 B2   3/2016  Kilgard et al.
9,272,153 B2   3/2016  Blum et al.
9,273,035 B2   3/2016  Teegarden et al.
9,275,191 B2   3/2016  Dean et al.
9,275,451 B2   3/2016  Ben-Haim et al.
9,277,871 B2   3/2016  Keenan et al.
9,277,873 B2   3/2016  Sarma et al.
9,278,159 B2   3/2016  Deisseroth et al.
9,278,231 B2   3/2016  Vasishta
9,280,784 B2   3/2016  Barnett et al.
9,282,927 B2   3/2016  Hyde et al.
9,282,930 B2   3/2016  Machon et al.
9,282,934 B2   3/2016  Liley et al.
9,283,279 B2   3/2016  Satchi-Fainaro et al.
9,283,394 B2   3/2016  Whitehurst et al.
9,284,353 B2   3/2016  Deisseroth et al.
9,285,249 B2   3/2016  Schober et al.
9,289,143 B2   3/2016  Wingeier et al.
9,289,595 B2   3/2016  Floyd et al.
9,289,599 B2   3/2016  Craig
9,289,603 B1   3/2016  Giuffrida et al.
9,289,609 B2   3/2016  Moffitt
9,292,471 B2   3/2016  Fung et al.
9,292,858 B2   3/2016  Marci et al.
9,292,920 B2   3/2016  Dean et al.
9,295,838 B2   3/2016  Starr et al.
9,296,382 B2   3/2016  Fung et al.
9,302,069 B2   4/2016  Tass et al.
9,302,093 B2   4/2016  Mashiach
9,302,103 B1   4/2016  Nirenberg
9,302,109 B2   4/2016  Sabesan
9,302,110 B2   4/2016  Kokones et al.
9,302,114 B2   4/2016  Rossi
9,302,116 B2   4/2016  Vo-Dinh et al.
9,305,376 B2   4/2016  Lee et al.
9,307,925 B2   4/2016  Russell et al.
9,307,944 B2   4/2016  Colman et al.
9,308,372 B2   4/2016  Sparks et al.
9,308,392 B2   4/2016  Deisseroth et al.
9,309,296 B2   4/2016  Deisseroth et al.
9,310,985 B2   4/2016  Blum et al.
9,311,335 B2   4/2016  Simon
9,314,190 B1   4/2016  Giuffrida et al.
9,314,613 B2   4/2016  Mashiach
9,314,633 B2   4/2016  Osorio et al.
9,314,635 B2   4/2016  Libbus
9,320,449 B2   4/2016  Gu
9,320,450 B2   4/2016  Badower
9,320,451 B2   4/2016  Feldkamp et al.
9,320,900 B2   4/2016  DiLorenzo
9,320,913 B2   4/2016  Dimino et al.
9,320,914 B2   4/2016  Toselli et al.
9,322,895 B2   4/2016  Santosh et al.
9,326,705 B2   5/2016  Derchak
9,326,720 B2   5/2016  McLaughlin
9,326,742 B2   5/2016  Hirschman et al.
9,327,069 B2   5/2016  Foster et al.
9,327,070 B2   5/2016  Skelton et al.
9,328,107 B2   5/2016  Teegarden et al.
9,329,758 B2   5/2016  Guzak et al.
9,330,206 B2   5/2016  Dean et al.
9,330,523 B2   5/2016  Sutton et al.
9,331,841 B2   5/2016  Kim et al.
9,332,939 B2   5/2016  Osorio
9,333,334 B2   5/2016  Jeffery et al.
9,333,347 B2   5/2016  Simon et al.
9,333,350 B2   5/2016  Rise et al.
9,336,302 B1   5/2016  Swamy
9,336,535 B2   5/2016  Pradeep et al.
9,336,611 B2   5/2016  Bilgic et al.
9,339,200 B2   5/2016  Fonte
9,339,227 B2   5/2016  D'arcy et al.
9,339,641 B2   5/2016  Rajguru et al.
9,339,654 B2   5/2016  Kilgard et al.
9,340,589 B2   5/2016  Deisseroth et al.
9,345,412 B2   5/2016  Horne
9,345,609 B2   5/2016  Hyde et al.
9,345,886 B2   5/2016  Kilgard et al.
9,345,901 B2   5/2016  Peterchev
9,348,974 B2   5/2016  Goetz
9,349,178 B1   5/2016  Itu et al.
9,351,640 B2   5/2016  Tran
9,351,651 B2   5/2016  Nagasaka
9,352,145 B2   5/2016  Whitehurst et al.
9,352,152 B2   5/2016  Lindenthaler et al.
9,352,156 B2   5/2016  Lane et al.
9,357,240 B2   5/2016  Pradeep et al.
9,357,298 B2   5/2016  Hiroe
9,357,941 B2   6/2016  Simon
9,357,949 B2   6/2016  Drew
9,357,970 B2   6/2016  Clark et al.
9,358,361 B2   6/2016  Hyde et al.
9,358,381 B2   6/2016  Simon et al.
9,358,392 B2   6/2016  Mashiach
9,358,393 B1   6/2016  Lozano
9,358,398 B2   6/2016  Moffitt et al.
9,359,449 B2   6/2016  Deisseroth et al.
9,360,472 B2   6/2016  Deisseroth et al.
9,364,462 B2   6/2016  Simpson, Jr.
9,364,665 B2   6/2016  Bokil et al.
9,364,674 B2   6/2016  Cook et al.
9,364,679 B2   6/2016  John
9,365,628 B2   6/2016  Deisseroth et al.
9,367,131 B2   6/2016  Klappert et al.
9,367,738 B2   6/2016  Harumatsu et al.
9,368,018 B2   6/2016  Kangas et al.
9,368,265 B2   6/2016  Park et al.
9,370,309 B2   6/2016  Ko et al.
9,370,667 B2   6/2016  Schmidt
9,375,145 B2   6/2016  Chin et al.
9,375,151 B1   6/2016  Hopenfeld et al.
9,375,171 B2   6/2016  Teixeira
9,375,564 B2   6/2016  Wingeier et al.
9,375,571 B2   6/2016  Errico et al.
9,375,573 B2   6/2016  Dilorenzo
9,377,348 B2   6/2016  Kataoka
9,377,515 B2   6/2016  Kim et al.
9,380,976 B2   7/2016  Stack
9,381,346 B2   7/2016  Lee et al.
9,381,352 B2   7/2016  Yun et al.
9,383,208 B2   7/2016  Mohanty
9,387,320 B2   7/2016  Wingeier et al.
9,387,338 B2   7/2016  Burnett
9,390,233 B2   7/2016  Fueyo et al.
9,392,955 B2   7/2016  Folkerts et al.
9,393,406 B2   7/2016  Ollivier

(56)         References Cited

U.S. PATENT DOCUMENTS

| | | |
|---|---|---|
| 9,393,418 B2 | 7/2016 | Giuffrida et al. |
| 9,394,347 B2 | 7/2016 | Deisseroth et al. |
| 9,395,425 B2 | 7/2016 | Diamond et al. |
| 9,396,533 B2 | 7/2016 | Skidmore |
| 9,396,669 B2 | 7/2016 | Karkanias et al. |
| 9,398,873 B2 | 7/2016 | Van Dooren et al. |
| 9,399,126 B2 | 7/2016 | Pal et al. |
| 9,399,133 B2 | 7/2016 | Besio |
| 9,399,134 B2 | 7/2016 | Simon et al. |
| 9,399,144 B2 | 7/2016 | Howard |
| 9,401,021 B1 | 7/2016 | Biagiotti et al. |
| 9,401,033 B2 | 7/2016 | Bajic |
| 9,402,558 B2 | 8/2016 | John et al. |
| 9,402,994 B2 | 8/2016 | Chow et al. |
| 9,403,000 B2 | 8/2016 | Lyons et al. |
| 9,403,001 B2 | 8/2016 | Simon et al. |
| 9,403,009 B2 | 8/2016 | Mashiach |
| 9,403,010 B2 | 8/2016 | Fried et al. |
| 9,403,038 B2 | 8/2016 | Tyler |
| 9,405,366 B2 | 8/2016 | Segal |
| 9,408,530 B2 | 8/2016 | Ferren et al. |
| 9,409,013 B2 | 8/2016 | Mashiach et al. |
| 9,409,022 B2 | 8/2016 | Jaax et al. |
| 9,409,028 B2 | 8/2016 | Whitehurst et al. |
| 9,410,885 B2 | 8/2016 | Schober et al. |
| 9,411,033 B2 | 8/2016 | He et al. |
| 9,411,935 B2 | 8/2016 | Moffitt et al. |
| 9,412,076 B2 | 8/2016 | Sapiro et al. |
| 9,412,233 B1 | 8/2016 | Bagherzadeh et al. |
| 9,414,029 B2 | 8/2016 | Miyazaki et al. |
| 9,414,749 B2 | 8/2016 | Semenov |
| 9,414,763 B2 | 8/2016 | Semenov |
| 9,414,764 B2 | 8/2016 | Semenov |
| 9,414,776 B2 | 8/2016 | Sillay et al. |
| 9,414,780 B2 | 8/2016 | Rhoads |
| 9,414,907 B2 | 8/2016 | Wortz et al. |
| 9,415,215 B2 | 8/2016 | Mashiach |
| 9,415,216 B2 | 8/2016 | Mashiach |
| 9,415,219 B2 | 8/2016 | Simon et al. |
| 9,415,222 B2 | 8/2016 | DiLorenzo |
| 9,415,233 B2 | 8/2016 | Pilla et al. |
| 9,418,368 B2 | 8/2016 | Jung et al. |
| 9,420,970 B2 | 8/2016 | Dagum |
| 9,421,258 B2 | 8/2016 | Deisseroth et al. |
| 9,421,372 B2 | 8/2016 | Mashiach et al. |
| 9,421,373 B2 | 8/2016 | DiLorenzo |
| 9,421,379 B2 | 8/2016 | Zhu |
| 9,424,761 B2 | 8/2016 | Tuchschmid et al. |
| 9,427,474 B2 | 8/2016 | Satchi-Fainaro et al. |
| 9,427,581 B2 | 8/2016 | Simon et al. |
| 9,427,585 B2 | 8/2016 | Gliner |
| 9,427,598 B2 | 8/2016 | Pilla et al. |
| 9,430,615 B2 | 8/2016 | Michaelis et al. |
| 9,432,777 B2 | 8/2016 | Lunner et al. |
| 9,433,797 B2 | 9/2016 | Pilla et al. |
| 9,434,692 B2 | 9/2016 | Xiong et al. |
| 9,436,989 B2 | 9/2016 | Uber, III |
| 9,438,650 B2 | 9/2016 | Serena |
| 9,439,150 B2 | 9/2016 | Carlson et al. |
| 9,440,063 B2 | 9/2016 | Ho et al. |
| 9,440,064 B2 | 9/2016 | Wingeier et al. |
| 9,440,070 B2 | 9/2016 | Goldwasser et al. |
| 9,440,084 B2 | 9/2016 | Davis et al. |
| 9,440,089 B2 | 9/2016 | Pilla et al. |
| 9,440,646 B2 | 9/2016 | Fung et al. |
| 9,442,088 B2 | 9/2016 | Feldkamp et al. |
| 9,442,525 B2 | 9/2016 | Choi et al. |
| 9,443,141 B2 | 9/2016 | Mirowski et al. |
| 9,444,998 B2 | 9/2016 | Kim et al. |
| 9,445,713 B2 | 9/2016 | Douglas et al. |
| 9,445,730 B2 | 9/2016 | Snyder et al. |
| 9,445,739 B1 | 9/2016 | Payton et al. |
| 9,445,763 B2 | 9/2016 | Davis et al. |
| 9,446,238 B2 | 9/2016 | Lozano |
| 9,448,289 B2 | 9/2016 | Wang et al. |
| 9,449,147 B2 | 9/2016 | Taylor |
| 9,451,303 B2 | 9/2016 | Kothuri et al. |
| 9,451,734 B2 | 9/2016 | Onuma et al. |
| 9,451,883 B2 | 9/2016 | Gallant et al. |
| 9,451,886 B2 | 9/2016 | Teixeira |
| 9,451,899 B2 | 9/2016 | Ritchey et al. |
| 9,452,287 B2 | 9/2016 | Rosenbluth et al. |
| 9,453,215 B2 | 9/2016 | Deisseroth et al. |
| 9,454,646 B2 | 9/2016 | Siefert |
| 9,458,208 B2 | 10/2016 | Deisseroth et al. |
| 9,459,597 B2 | 10/2016 | Kahn et al. |
| 9,460,400 B2 | 10/2016 | De Bruin et al. |
| 9,462,733 B2 | 10/2016 | Hokari |
| 9,462,956 B2 | 10/2016 | Pandia et al. |
| 9,462,975 B2 | 10/2016 | Sackner et al. |
| 9,462,977 B2 | 10/2016 | Horseman |
| 9,463,327 B2 | 10/2016 | Lempka et al. |
| 9,468,541 B2 | 10/2016 | Contreras-Vidal et al. |
| 9,468,761 B2 | 10/2016 | Frei et al. |
| 9,470,728 B2 | 10/2016 | George et al. |
| 9,471,978 B2 | 10/2016 | Chen et al. |
| 9,472,000 B2 | 10/2016 | Dempsey et al. |
| 9,474,481 B2 | 10/2016 | Dagum |
| 9,474,852 B2 | 10/2016 | Lozano et al. |
| 9,474,903 B2 | 10/2016 | Chen et al. |
| 9,475,502 B2 | 10/2016 | Fung et al. |
| RE46,189 E | 11/2016 | Prichep et al. |
| RE46,209 E | 11/2016 | Gong et al. |
| 9,480,402 B2 | 11/2016 | Leuthardt et al. |
| 9,480,425 B2 | 11/2016 | Culver et al. |
| 9,480,812 B1 | 11/2016 | Thompson |
| 9,480,841 B2 | 11/2016 | Hershey et al. |
| 9,480,845 B2 | 11/2016 | Harris et al. |
| 9,480,854 B2 | 11/2016 | Von Ohlsen et al. |
| 9,483,117 B2 | 11/2016 | Karkkainen et al. |
| 9,483,613 B2 | 11/2016 | Fueyo et al. |
| 9,486,168 B2 | 11/2016 | Bonmassar et al. |
| 9,486,381 B2 | 11/2016 | Juto et al. |
| 9,486,389 B2 | 11/2016 | Tass |
| 9,486,618 B2 | 11/2016 | Wingeier et al. |
| 9,486,632 B2 | 11/2016 | Saab |
| 9,489,854 B2 | 11/2016 | Haruta et al. |
| 9,492,084 B2 | 11/2016 | Behar et al. |
| 9,492,114 B2 | 11/2016 | Reiman |
| 9,492,120 B2 | 11/2016 | Horseman |
| 9,492,313 B2 | 11/2016 | Nofzinger |
| 9,492,656 B2 | 11/2016 | Chow et al. |
| 9,492,678 B2 | 11/2016 | Chow |
| 9,495,684 B2 | 11/2016 | Jung et al. |
| 9,497,017 B1 | 11/2016 | Kim et al. |
| 9,498,134 B1 | 11/2016 | Trobaugh et al. |
| 9,498,628 B2 | 11/2016 | Kaemmerer et al. |
| 9,498,634 B2 | 11/2016 | Ridder |
| 9,500,722 B2 | 11/2016 | Takahashi |
| 9,501,829 B2 | 11/2016 | Carlton et al. |
| 9,504,390 B2 | 11/2016 | Osorio |
| 9,504,410 B2 | 11/2016 | Gal |
| 9,504,420 B2 | 11/2016 | Davis et al. |
| 9,504,788 B2 | 11/2016 | Hyde et al. |
| 9,505,402 B2 | 11/2016 | Fung et al. |
| 9,505,817 B2 | 11/2016 | Deisseroth et al. |
| 9,510,790 B2 | 12/2016 | Kang et al. |
| 9,513,398 B2 | 12/2016 | Wilson et al. |
| 9,517,020 B2 | 12/2016 | Shacham-Diamand et al. |
| 9,517,031 B2 | 12/2016 | Jung |
| 9,517,222 B2 | 12/2016 | Goodenowe |
| 9,519,981 B2 | 12/2016 | Sudarsky et al. |
| 9,521,958 B2 | 12/2016 | Nagasaka et al. |
| 9,522,085 B2 | 12/2016 | Kilgard et al. |
| 9,522,278 B1 | 12/2016 | Heldman et al. |
| 9,522,282 B2 | 12/2016 | Chow et al. |
| 9,522,288 B2 | 12/2016 | Deisseroth et al. |
| 9,526,419 B2 | 12/2016 | Derchak et al. |
| 9,526,902 B2 | 12/2016 | Blum et al. |
| 9,526,906 B2 | 12/2016 | Mashiach |
| 9,526,913 B2 | 12/2016 | Vo-Dinh et al. |
| 9,526,914 B2 | 12/2016 | Vo-Dinh et al. |
| 9,533,113 B2 | 1/2017 | Lain et al. |
| 9,533,144 B2 | 1/2017 | Bahmer |

(56)                    References Cited

U.S. PATENT DOCUMENTS

| | | | |
|---|---|---|---|
| 9,533,147 B2 | 1/2017 | Osorio |
| 9,533,148 B2 | 1/2017 | Carcieri |
| 9,533,150 B2 | 1/2017 | Nudo et al. |
| 9,533,151 B2 | 1/2017 | Craig |
| 9,534,044 B2 | 1/2017 | El-Agnaf |
| 9,538,635 B1 | 1/2017 | Beran |
| 9,538,948 B2 | 1/2017 | Dagum |
| 9,538,951 B2 | 1/2017 | Osorio |
| 9,539,118 B2 | 1/2017 | Leuthardt et al. |
| 9,541,383 B2 | 1/2017 | Abovitz et al. |
| 9,545,221 B2 | 1/2017 | Adhikari et al. |
| 9,545,222 B2 | 1/2017 | Derchak et al. |
| 9,545,225 B2 | 1/2017 | Cavuoto et al. |
| 9,545,226 B2 | 1/2017 | Osorio |
| 9,545,285 B2 | 1/2017 | Ghaffari et al. |
| 9,545,510 B2 | 1/2017 | Kokones et al. |
| 9,545,515 B2 | 1/2017 | Wolpaw et al. |
| 9,549,691 B2 | 1/2017 | Tran |
| 9,550,064 B2 | 1/2017 | Mashiach |
| 9,556,149 B2 | 1/2017 | Krishnan et al. |
| 9,556,487 B2 | 1/2017 | Umansky et al. |
| 9,557,439 B2 | 1/2017 | Wilson et al. |
| 9,558,558 B2 | 1/2017 | Stehle et al. |
| 9,560,458 B2 | 1/2017 | Lunner et al. |
| 9,560,967 B2 | 2/2017 | Hyde et al. |
| 9,560,984 B2 | 2/2017 | Pradeep et al. |
| 9,560,986 B2 | 2/2017 | Varcoe |
| 9,561,380 B2 | 2/2017 | Carcieri et al. |
| 9,562,988 B2 | 2/2017 | Wilson et al. |
| 9,563,273 B2 | 2/2017 | Mann |
| 9,563,740 B2 | 2/2017 | Abdelghani et al. |
| 9,563,950 B2 | 2/2017 | Raj |
| 9,566,426 B2 | 2/2017 | Simon et al. |
| 9,567,327 B2 | 2/2017 | Xiong et al. |
| 9,568,564 B2 | 2/2017 | Ma et al. |
| 9,568,635 B2 | 2/2017 | Suhami |
| 9,572,996 B2 | 2/2017 | Tass et al. |
| 9,577,992 B2 | 2/2017 | Zizi et al. |
| 9,578,425 B2 | 2/2017 | Hakansson |
| 9,579,035 B2 | 2/2017 | Sarkela |
| 9,579,048 B2 | 2/2017 | Rayner et al. |
| 9,579,247 B2 | 2/2017 | Juto et al. |
| 9,579,457 B2 | 2/2017 | Osorio |
| 9,579,506 B2 | 2/2017 | Osorio |
| 9,582,072 B2 | 2/2017 | Connor |
| 9,582,152 B2 | 2/2017 | Gulaka et al. |
| 9,582,925 B2 | 2/2017 | Durand et al. |
| 9,584,928 B2 | 2/2017 | Laudanski et al. |
| 9,585,581 B1 | 3/2017 | Mullins et al. |
| 9,585,723 B2 | 3/2017 | Taylor |
| 9,586,047 B2 | 3/2017 | Osorio et al. |
| 9,586,053 B2 | 3/2017 | Moffitt et al. |
| 9,588,203 B2 | 3/2017 | Zhu et al. |
| 9,588,490 B2 | 3/2017 | Tsang |
| 9,590,986 B2 | 3/2017 | Zizi et al. |
| 9,592,003 B2 | 3/2017 | Osorio et al. |
| 9,592,004 B2 | 3/2017 | DiLorenzo et al. |
| 9,592,384 B2 | 3/2017 | Tass |
| 9,592,387 B2 | 3/2017 | Skelton et al. |
| 9,592,389 B2 | 3/2017 | Moffitt |
| 9,592,409 B2 | 3/2017 | Yoo et al. |
| 9,596,224 B2 | 3/2017 | Woods et al. |
| 9,597,493 B2 | 3/2017 | Wingeier et al. |
| 9,597,494 B2 | 3/2017 | Wingeier et al. |
| 9,597,501 B1 | 3/2017 | Danilov et al. |
| 9,597,504 B1 | 3/2017 | Danilov et al. |
| 9,600,138 B2 | 3/2017 | Thomas et al. |
| 9,600,778 B2 | 3/2017 | Sapiro et al. |
| 9,604,056 B2 | 3/2017 | Starr et al. |
| 9,604,067 B2 | 3/2017 | Kothandaraman et al. |
| 9,604,073 B2 | 3/2017 | Deisseroth et al. |
| 9,607,023 B1 | 3/2017 | Swamy |
| 9,607,377 B2 | 3/2017 | Lovberg et al. |
| 9,609,453 B2 | 3/2017 | Jabri |
| 9,610,442 B2 | 4/2017 | Yoo et al. |
| 9,610,456 B2 | 4/2017 | Linke et al. |
| 9,610,459 B2 | 4/2017 | Burnett et al. |
| 9,612,295 B2 | 4/2017 | Toda et al. |
| 9,613,184 B2 | 4/2017 | Giftakis et al. |
| 9,613,186 B2 | 4/2017 | Fonte |
| 9,615,746 B2 | 4/2017 | Horseman |
| 9,615,749 B2 | 4/2017 | Clifton et al. |
| 9,615,789 B2 | 4/2017 | Deisseroth et al. |
| 9,616,166 B2 | 4/2017 | Kalafut et al. |
| 9,616,227 B2 | 4/2017 | Lindenthaler et al. |
| 9,618,591 B1 | 4/2017 | Radparvar et al. |
| 9,622,660 B2 | 4/2017 | Le et al. |
| 9,622,672 B2 | 4/2017 | Yoshida et al. |
| 9,622,675 B2 | 4/2017 | Leyde et al. |
| 9,622,676 B2 | 4/2017 | Masmanidis et al. |
| 9,622,700 B2 | 4/2017 | Sahasrabudhe et al. |
| 9,622,702 B2 | 4/2017 | Badower et al. |
| 9,622,703 B2 | 4/2017 | Badower et al. |
| 9,623,240 B2 | 4/2017 | Simon et al. |
| 9,623,241 B2 | 4/2017 | Wagner et al. |
| 9,626,756 B2 | 4/2017 | Dean et al. |
| 9,629,548 B2 | 4/2017 | Sachanandani et al. |
| 9,629,568 B2 | 4/2017 | Hagedorn et al. |
| 9,629,976 B1 | 4/2017 | Acton |
| 9,630,004 B2 | 4/2017 | Rajguru et al. |
| 9,630,008 B2 | 4/2017 | McLaughlin et al. |
| 9,630,011 B2 | 4/2017 | Lipani |
| 9,630,029 B2 | 4/2017 | Wurster et al. |
| 9,636,019 B2 | 5/2017 | Hendler et al. |
| 9,636,185 B2 | 5/2017 | Quaid et al. |
| 9,640,167 B2 | 5/2017 | DeFranks et al. |
| 9,641,665 B2 | 5/2017 | Lee et al. |
| 9,642,552 B2 | 5/2017 | Hua |
| 9,642,553 B2 | 5/2017 | Hokari |
| 9,642,554 B2 | 5/2017 | Simola et al. |
| 9,642,699 B2 | 5/2017 | Wortz et al. |
| 9,643,015 B2 | 5/2017 | Moffitt et al. |
| 9,643,017 B2 | 5/2017 | Carcieri et al. |
| 9,643,019 B2 | 5/2017 | Higgins et al. |
| 9,646,248 B1 | 5/2017 | Benvenuto et al. |
| 9,649,030 B2 | 5/2017 | Gross et al. |
| 9,649,036 B2 | 5/2017 | Teixeira |
| 9,649,439 B2 | 5/2017 | John |
| 9,649,493 B2 | 5/2017 | Mashiach |
| 9,649,494 B2 | 5/2017 | Gerber et al. |
| 9,649,501 B2 | 5/2017 | Best |
| 9,651,368 B2 | 5/2017 | Abovitz et al. |
| 9,651,706 B2 | 5/2017 | Mandviwala et al. |
| 9,652,626 B2 | 5/2017 | Son et al. |
| 9,652,871 B2 | 5/2017 | Han et al. |
| 9,655,573 B2 | 5/2017 | Majewski et al. |
| 9,655,669 B2 | 5/2017 | Palti et al. |
| 9,656,069 B1 | 5/2017 | Danilov et al. |
| 9,656,075 B2 | 5/2017 | Osorio |
| 9,656,078 B1 | 5/2017 | Danilov et al. |
| 9,656,096 B2 | 5/2017 | Pilla |
| 9,659,186 B2 | 5/2017 | Pinsky et al. |
| 9,659,229 B2 | 5/2017 | Clifton et al. |
| 9,662,049 B2 | 5/2017 | Scarantino et al. |
| 9,662,069 B2 | 5/2017 | De Graff et al. |
| 9,662,083 B2 | 5/2017 | Sakaue |
| 9,662,490 B2 | 5/2017 | Tracey et al. |
| 9,662,492 B1 | 5/2017 | Tucker et al. |
| 9,662,502 B2 | 5/2017 | Giuffrida et al. |
| 9,664,856 B2 | 5/2017 | Nagasaka |
| 9,665,824 B2 | 5/2017 | Chang et al. |
| 9,665,987 B2 | 5/2017 | Fateh |
| 9,668,694 B2 | 6/2017 | Badower |
| 9,669,185 B2 | 6/2017 | Nofzinger |
| 9,669,239 B2 | 6/2017 | Carpentier |
| 9,672,302 B2 | 6/2017 | Dean et al. |
| 9,672,617 B2 | 6/2017 | Dean et al. |
| 9,674,621 B2 | 6/2017 | Bahmer |
| 9,675,254 B2 | 6/2017 | Semenov |
| 9,675,255 B2 | 6/2017 | Semenov |
| 9,675,292 B2 | 6/2017 | Fadem |
| 9,675,794 B2 | 6/2017 | Miller |
| 9,675,809 B2 | 6/2017 | Chow |
| 9,681,814 B2 | 6/2017 | Galloway et al. |

(56)  References Cited

U.S. PATENT DOCUMENTS

| | | |
|---|---|---|
| 9,681,820 B2 | 6/2017 | Wagner |
| 9,682,232 B2 | 6/2017 | Shore et al. |
| 9,682,241 B2 | 6/2017 | Hyde et al. |
| 9,684,051 B2 | 6/2017 | Nieminen et al. |
| 9,684,335 B2 | 6/2017 | Kim et al. |
| 9,685,600 B2 | 6/2017 | Washington, II et al. |
| 9,687,187 B2 | 6/2017 | Dagum |
| 9,687,562 B2 | 6/2017 | Satchi-Fainaro et al. |
| 9,693,684 B2 | 7/2017 | Lopez et al. |
| 9,693,724 B2 | 7/2017 | Dagum |
| 9,693,725 B2 | 7/2017 | Soza |
| 9,693,734 B2 | 7/2017 | Horseman |
| 9,694,155 B2 | 7/2017 | Panova et al. |
| 9,694,178 B2 | 7/2017 | Ruffini et al. |
| 9,694,197 B2 | 7/2017 | Segal |
| 9,697,330 B2 | 7/2017 | Taylor |
| 9,697,336 B2 | 7/2017 | Hyde et al. |
| 9,700,256 B2 | 7/2017 | Osorio et al. |
| 9,700,716 B2 | 7/2017 | Faltys et al. |
| 9,700,723 B2 | 7/2017 | Sabesan |
| 9,704,205 B2 | 7/2017 | Akutagawa et al. |
| 9,706,910 B1 | 7/2017 | Blaha et al. |
| 9,706,925 B2 | 7/2017 | Taylor |
| 9,706,957 B2 | 7/2017 | Wu et al. |
| 9,706,963 B2 | 7/2017 | Gupta et al. |
| 9,707,372 B2 | 7/2017 | Smith |
| 9,707,390 B2 | 7/2017 | Ahmed |
| 9,707,391 B2 | 7/2017 | Ahmed |
| 9,707,396 B2 | 7/2017 | Su et al. |
| 9,710,788 B2 | 7/2017 | Horseman |
| 9,712,736 B2 | 7/2017 | Kearns et al. |
| 9,713,428 B2 | 7/2017 | Chon et al. |
| 9,713,433 B2 | 7/2017 | Gadot et al. |
| 9,713,444 B2 | 7/2017 | Severson |
| 9,713,712 B2 | 7/2017 | Wingeier et al. |
| 9,715,032 B2 | 7/2017 | Song et al. |
| 9,717,461 B2 | 8/2017 | Yu et al. |
| 9,717,904 B2 | 8/2017 | Simon et al. |
| 9,717,920 B1 | 8/2017 | Heldman et al. |
| 9,724,517 B2 | 8/2017 | Giftakis et al. |
| 9,729,252 B2 | 8/2017 | Tyler et al. |
| 9,732,039 B2 | 8/2017 | Xiong et al. |
| 9,734,589 B2 | 8/2017 | Yu et al. |
| 9,734,601 B2 | 8/2017 | Bresler et al. |
| 9,734,632 B2 | 8/2017 | Thomas et al. |
| 9,737,230 B2 | 8/2017 | Sarma et al. |
| 9,740,710 B2 | 8/2017 | Han et al. |
| 9,740,946 B2 | 8/2017 | Varkuti et al. |
| 9,741,114 B2 | 8/2017 | Varkuti |
| 9,743,197 B2 | 8/2017 | Petersen et al. |
| 9,743,835 B2 | 8/2017 | Taylor |
| 9,744,358 B2 | 8/2017 | Hehrmann et al. |
| 9,763,592 B2 | 9/2017 | Le et al. |
| 9,878,155 B1 * | 1/2018 | Phillips ................ A61B 5/0036 |
| 2001/0003799 A1 | 6/2001 | Boveja |
| 2001/0009975 A1 | 7/2001 | Tsukada et al. |
| 2001/0014818 A1 | 8/2001 | Kennedy |
| 2001/0020127 A1 | 9/2001 | Oshio et al. |
| 2001/0021800 A1 | 9/2001 | Balkin et al. |
| 2001/0029391 A1 | 10/2001 | Gluckman et al. |
| 2001/0049480 A1 | 12/2001 | John et al. |
| 2001/0051774 A1 | 12/2001 | Littrup et al. |
| 2001/0051787 A1 | 12/2001 | Haller et al. |
| 2002/0000808 A1 | 1/2002 | Nichols |
| 2002/0005784 A1 | 1/2002 | Balkin et al. |
| 2002/0006875 A1 | 1/2002 | Mcfetridge |
| 2002/0013612 A1 | 1/2002 | Whitehurst |
| 2002/0013613 A1 | 1/2002 | Haller et al. |
| 2002/0016552 A1 | 2/2002 | Granger et al. |
| 2002/0017905 A1 | 2/2002 | Conti |
| 2002/0017994 A1 | 2/2002 | Balkin et al. |
| 2002/0024450 A1 | 2/2002 | Townsend et al. |
| 2002/0032375 A1 | 3/2002 | Bauch et al. |
| 2002/0033454 A1 | 3/2002 | Cheng et al. |
| 2002/0035317 A1 | 3/2002 | Cheng et al. |
| 2002/0035338 A1 | 3/2002 | Dear et al. |
| 2002/0037095 A1 | 3/2002 | Cheng |
| 2002/0042563 A1 | 4/2002 | Becerra et al. |
| 2002/0052539 A1 | 5/2002 | Haller et al. |
| 2002/0055675 A1 | 5/2002 | Llinas et al. |
| 2002/0058867 A1 | 5/2002 | Breiter et al. |
| 2002/0059159 A1 | 5/2002 | Cook |
| 2002/0072776 A1 | 6/2002 | Osorio et al. |
| 2002/0072782 A1 | 6/2002 | Osorio et al. |
| 2002/0077536 A1 | 6/2002 | Diab et al. |
| 2002/0082513 A1 | 6/2002 | Ennen et al. |
| 2002/0082665 A1 | 6/2002 | Haller et al. |
| 2002/0085174 A1 | 7/2002 | Bolger et al. |
| 2002/0087201 A1 | 7/2002 | Firlik et al. |
| 2002/0091319 A1 | 7/2002 | Moehring et al. |
| 2002/0091335 A1 | 7/2002 | John et al. |
| 2002/0091419 A1 | 7/2002 | Firlik et al. |
| 2002/0095099 A1 | 7/2002 | Quyen et al. |
| 2002/0097332 A1 | 7/2002 | Martin et al. |
| 2002/0099273 A1 | 7/2002 | Bocionek et al. |
| 2002/0099295 A1 | 7/2002 | Gil et al. |
| 2002/0099306 A1 | 7/2002 | Shaw et al. |
| 2002/0099412 A1 | 7/2002 | Fischell et al. |
| 2002/0099417 A1 | 7/2002 | Naritoku et al. |
| 2002/0099418 A1 | 7/2002 | Naritoku et al. |
| 2002/0103428 A1 | 8/2002 | deCharms |
| 2002/0103429 A1 | 8/2002 | deCharms |
| 2002/0103512 A1 | 8/2002 | Echauz et al. |
| 2002/0107454 A1 | 8/2002 | Collura et al. |
| 2002/0112732 A1 | 8/2002 | Blazey et al. |
| 2002/0117176 A1 | 8/2002 | Mantzaridis et al. |
| 2002/0128540 A1 | 9/2002 | Kim et al. |
| 2002/0128544 A1 | 9/2002 | Diab et al. |
| 2002/0128638 A1 | 9/2002 | Chauvet et al. |
| 2002/0138013 A1 | 9/2002 | Guerrero et al. |
| 2002/0151771 A1 | 10/2002 | Braun et al. |
| 2002/0151939 A1 | 10/2002 | Rezai |
| 2002/0158631 A1 | 10/2002 | Kandori et al. |
| 2002/0173714 A1 | 11/2002 | Tsukada et al. |
| 2002/0177882 A1 | 11/2002 | DiLorenzo |
| 2002/0182574 A1 | 12/2002 | Freer |
| 2002/0183607 A1 | 12/2002 | Bauch et al. |
| 2002/0183644 A1 | 12/2002 | Levendowski et al. |
| 2002/0188330 A1 | 12/2002 | Gielen et al. |
| 2002/0193670 A1 | 12/2002 | Garfield et al. |
| 2003/0001098 A1 | 1/2003 | Stoddart et al. |
| 2003/0004429 A1 | 1/2003 | Price |
| 2003/0009078 A1 | 1/2003 | Fedorovskaya et al. |
| 2003/0009096 A1 | 1/2003 | Lahteenmaki |
| 2003/0013981 A1 | 1/2003 | Gevins et al. |
| 2003/0018277 A1 | 1/2003 | He |
| 2003/0018278 A1 | 1/2003 | Jordan |
| 2003/0023183 A1 | 1/2003 | Williams |
| 2003/0023282 A1 | 1/2003 | Barrett et al. |
| 2003/0028081 A1 | 2/2003 | Blazey et al. |
| 2003/0028121 A1 | 2/2003 | Blazey et al. |
| 2003/0028348 A1 | 2/2003 | Wenzel et al. |
| 2003/0031357 A1 | 2/2003 | Wenzel et al. |
| 2003/0032870 A1 | 2/2003 | Farwell |
| 2003/0032888 A1 | 2/2003 | Dewan |
| 2003/0032889 A1 | 2/2003 | Wells |
| 2003/0035301 A1 | 2/2003 | Gardiner et al. |
| 2003/0036689 A1 | 2/2003 | Diab et al. |
| 2003/0040660 A1 | 2/2003 | Jackowski et al. |
| 2003/0045914 A1 | 3/2003 | Cohen et al. |
| 2003/0046018 A1 | 3/2003 | Kohlmorgen et al. |
| 2003/0055355 A1 | 3/2003 | Viertio-Oja |
| 2003/0068605 A1 | 4/2003 | Kullok et al. |
| 2003/0070685 A1 | 4/2003 | Patton et al. |
| 2003/0074032 A1 | 4/2003 | Gliner |
| 2003/0081818 A1 | 5/2003 | Fujimaki |
| 2003/0083596 A1 | 5/2003 | Kramer et al. |
| 2003/0083716 A1 | 5/2003 | Nicolelis et al. |
| 2003/0088274 A1 | 5/2003 | Gliner et al. |
| 2003/0093004 A1 | 5/2003 | Sosa et al. |
| 2003/0093005 A1 | 5/2003 | Tucker |
| 2003/0093129 A1 | 5/2003 | Nicolelis et al. |
| 2003/0097159 A1 | 5/2003 | Schiff et al. |
| 2003/0097161 A1 | 5/2003 | Firlik et al. |

(56)                    References Cited

U.S. PATENT DOCUMENTS

| | | |
|---|---|---|
| 2003/0100844 A1 | 5/2003 | Miller et al. |
| 2003/0105408 A1 | 6/2003 | Gotman et al. |
| 2003/0114886 A1 | 6/2003 | Gluckman et al. |
| 2003/0120140 A1 | 6/2003 | Bango |
| 2003/0120172 A1 | 6/2003 | Foust et al. |
| 2003/0125786 A1 | 7/2003 | Gliner et al. |
| 2003/0128801 A1 | 7/2003 | Eisenberg et al. |
| 2003/0130706 A1 | 7/2003 | Sheffield et al. |
| 2003/0130709 A1 | 7/2003 | D.C. et al. |
| 2003/0135128 A1 | 7/2003 | Suffin et al. |
| 2003/0139681 A1 | 7/2003 | Melker et al. |
| 2003/0144601 A1 | 7/2003 | Prichep |
| 2003/0149351 A1 | 8/2003 | Nowinski et al. |
| 2003/0149678 A1 | 8/2003 | Cook |
| 2003/0153818 A1 | 8/2003 | Bocionek et al. |
| 2003/0158466 A1 | 8/2003 | Lynn et al. |
| 2003/0158495 A1 | 8/2003 | Hogan |
| 2003/0158496 A1 | 8/2003 | Keirsbilck et al. |
| 2003/0158497 A1 | 8/2003 | Graham et al. |
| 2003/0158587 A1 | 8/2003 | Esteller et al. |
| 2003/0160622 A1 | 8/2003 | Duensing et al. |
| 2003/0163027 A1 | 8/2003 | Balkin et al. |
| 2003/0163028 A1 | 8/2003 | Balkin et al. |
| 2003/0167019 A1 | 9/2003 | Viertio-Oja et al. |
| 2003/0171658 A1 | 9/2003 | Keirsbilck et al. |
| 2003/0171685 A1 | 9/2003 | Lesser et al. |
| 2003/0171689 A1 | 9/2003 | Millan et al. |
| 2003/0176804 A1 | 9/2003 | Melker |
| 2003/0181791 A1 | 9/2003 | Thomas et al. |
| 2003/0181821 A1 | 9/2003 | Greenwald et al. |
| 2003/0181954 A1 | 9/2003 | Rezai |
| 2003/0181955 A1 | 9/2003 | Gielen et al. |
| 2003/0185408 A1 | 10/2003 | Causevic et al. |
| 2003/0187359 A1 | 10/2003 | Njemanze |
| 2003/0195429 A1 | 10/2003 | Wilson |
| 2003/0195574 A1 | 10/2003 | Osorio et al. |
| 2003/0199749 A1 | 10/2003 | Lowery, Jr. et al. |
| 2003/0204135 A1 | 10/2003 | Bystritsky |
| 2003/0216654 A1 | 11/2003 | Xu et al. |
| 2003/0225335 A1 | 12/2003 | Njemanze |
| 2003/0225340 A1 | 12/2003 | Collura |
| 2003/0229291 A1 | 12/2003 | Collura |
| 2003/0233039 A1 | 12/2003 | Shao et al. |
| 2003/0233250 A1 | 12/2003 | Joffe et al. |
| 2003/0234781 A1 | 12/2003 | Laidlaw et al. |
| 2003/0236458 A1 | 12/2003 | Hochman |
| 2003/0236557 A1 | 12/2003 | Whitehurst et al. |
| 2003/0236558 A1 | 12/2003 | Whitehurst et al. |
| 2004/0002635 A1 | 1/2004 | Hargrove et al. |
| 2004/0006265 A1 | 1/2004 | Alhussiny |
| 2004/0006376 A1 | 1/2004 | Falci |
| 2004/0010203 A1 | 1/2004 | Bibian et al. |
| 2004/0015204 A1 | 1/2004 | Whitehurst et al. |
| 2004/0015205 A1 | 1/2004 | Whitehurst et al. |
| 2004/0019257 A1 | 1/2004 | Meadows |
| 2004/0019370 A1 | 1/2004 | Gliner et al. |
| 2004/0024287 A1 | 2/2004 | Patton et al. |
| 2004/0030585 A1 | 2/2004 | Sariel |
| 2004/0034299 A1 | 2/2004 | Kandori et al. |
| 2004/0039268 A1 | 2/2004 | Barbour et al. |
| 2004/0049124 A1 | 3/2004 | Kullok et al. |
| 2004/0049484 A1 | 3/2004 | Kamba |
| 2004/0059203 A1 | 3/2004 | Guerrero et al. |
| 2004/0059241 A1 | 3/2004 | Suffin |
| 2004/0064020 A1 | 4/2004 | Diab et al. |
| 2004/0064066 A1 | 4/2004 | John et al. |
| 2004/0068164 A1 | 4/2004 | Diab et al. |
| 2004/0068172 A1 | 4/2004 | Nowinski et al. |
| 2004/0068199 A1 | 4/2004 | Echauz et al. |
| 2004/0072133 A1 | 4/2004 | Kullok et al. |
| 2004/0073098 A1 | 4/2004 | Geva et al. |
| 2004/0073129 A1 | 4/2004 | Caldwell et al. |
| 2004/0073273 A1 | 4/2004 | Gluckman et al. |
| 2004/0077960 A1 | 4/2004 | Tanaka et al. |
| 2004/0077967 A1 | 4/2004 | Jordan |
| 2004/0078056 A1 | 4/2004 | Zangen et al. |
| 2004/0079372 A1 | 4/2004 | John et al. |
| 2004/0082862 A1 | 4/2004 | Chance |
| 2004/0082876 A1 | 4/2004 | Viertio-Oja et al. |
| 2004/0088732 A1 | 5/2004 | Martin et al. |
| 2004/0092809 A1 | 5/2004 | DeCharms |
| 2004/0096395 A1 | 5/2004 | Xiong et al. |
| 2004/0097802 A1 | 5/2004 | Cohen |
| 2004/0101146 A1 | 5/2004 | Laitinen et al. |
| 2004/0116784 A1 | 6/2004 | Gavish |
| 2004/0116791 A1 | 6/2004 | Miyauchi |
| 2004/0116798 A1 | 6/2004 | Cancro et al. |
| 2004/0116825 A1 | 6/2004 | Sturzebecher |
| 2004/0117098 A1 | 6/2004 | Ryu et al. |
| 2004/0122787 A1 | 6/2004 | Avinash et al. |
| 2004/0122790 A1 | 6/2004 | Walker et al. |
| 2004/0127803 A1 | 7/2004 | Berkes et al. |
| 2004/0131998 A1 | 7/2004 | Marom et al. |
| 2004/0133118 A1 | 7/2004 | Llinas |
| 2004/0133119 A1 | 7/2004 | Osorio et al. |
| 2004/0133120 A1 | 7/2004 | Frei et al. |
| 2004/0133248 A1 | 7/2004 | Frei et al. |
| 2004/0133390 A1 | 7/2004 | Osorio et al. |
| 2004/0138516 A1 | 7/2004 | Osorio et al. |
| 2004/0138517 A1 | 7/2004 | Osorio et al. |
| 2004/0138518 A1 | 7/2004 | Rise et al. |
| 2004/0138536 A1 | 7/2004 | Frei et al. |
| 2004/0138580 A1 | 7/2004 | Frei et al. |
| 2004/0138581 A1 | 7/2004 | Frei et al. |
| 2004/0138647 A1 | 7/2004 | Osorio et al. |
| 2004/0138711 A1 | 7/2004 | Osorio et al. |
| 2004/0138721 A1 | 7/2004 | Osorio et al. |
| 2004/0140811 A1 | 7/2004 | Conti |
| 2004/0143170 A1 | 7/2004 | DuRousseau |
| 2004/0144925 A1 | 7/2004 | Stoddart et al. |
| 2004/0145370 A1 | 7/2004 | Conti |
| 2004/0151368 A1 | 8/2004 | Cruickshank et al. |
| 2004/0152958 A1 | 8/2004 | Frei et al. |
| 2004/0152995 A1 | 8/2004 | Cox et al. |
| 2004/0153129 A1 | 8/2004 | Pless et al. |
| 2004/0158119 A1 | 8/2004 | Osorio et al. |
| 2004/0158298 A1 | 8/2004 | Gliner et al. |
| 2004/0158300 A1 | 8/2004 | Gardiner |
| 2004/0166536 A1 | 8/2004 | Kerkman et al. |
| 2004/0167418 A1 | 8/2004 | Nguyen et al. |
| 2004/0172089 A1 | 9/2004 | Whitehurst et al. |
| 2004/0172091 A1 | 9/2004 | Rezai |
| 2004/0172094 A1 | 9/2004 | Cohen et al. |
| 2004/0181162 A1 | 9/2004 | Wilson |
| 2004/0184024 A1 | 9/2004 | Katura et al. |
| 2004/0186542 A1 | 9/2004 | van Venrooij et al. |
| 2004/0193037 A1 | 9/2004 | Tsukada et al. |
| 2004/0193068 A1 | 9/2004 | Burton et al. |
| 2004/0193220 A1 | 9/2004 | Whitehurst et al. |
| 2004/0195512 A1 | 10/2004 | Crosetto |
| 2004/0199482 A1 | 10/2004 | Wilson |
| 2004/0204636 A1 | 10/2004 | Diab et al. |
| 2004/0204637 A1 | 10/2004 | Diab et al. |
| 2004/0204656 A1 | 10/2004 | Tolvanen-Laakso et al. |
| 2004/0204659 A1 | 10/2004 | John et al. |
| 2004/0210127 A1 | 10/2004 | Kandori et al. |
| 2004/0210146 A1 | 10/2004 | Diab et al. |
| 2004/0210156 A1 | 10/2004 | Hogan |
| 2004/0215082 A1 | 10/2004 | Chance |
| 2004/0220494 A1 | 11/2004 | Sturzebecher |
| 2004/0220782 A1 | 11/2004 | Cook |
| 2004/0225179 A1 | 11/2004 | Kaplan et al. |
| 2004/0230105 A1 | 11/2004 | Geva et al. |
| 2004/0243017 A1 | 12/2004 | Causevic |
| 2004/0243182 A1 | 12/2004 | Cohen et al. |
| 2004/0254493 A1 | 12/2004 | Chervin et al. |
| 2004/0260169 A1 | 12/2004 | Sternnickel |
| 2004/0260356 A1 | 12/2004 | Kara et al. |
| 2004/0263162 A1 | 12/2004 | Kandori et al. |
| 2004/0267152 A1 | 12/2004 | Pineda |
| 2005/0004489 A1 | 1/2005 | Sarkela et al. |
| 2005/0007091 A1 | 1/2005 | Makeig et al. |
| 2005/0010091 A1 | 1/2005 | Woods et al. |
| 2005/0010116 A1 | 1/2005 | Korhonen et al. |

(56) References Cited

U.S. PATENT DOCUMENTS

| 2005/0015205 A1 | 1/2005 | Repucci et al. |
| 2005/0018858 A1 | 1/2005 | John |
| 2005/0019734 A1 | 1/2005 | Peled |
| 2005/0020483 A1 | 1/2005 | Oksenberg et al. |
| 2005/0020918 A1 | 1/2005 | Wilk et al. |
| 2005/0021105 A1 | 1/2005 | Firlik et al. |
| 2005/0025704 A1 | 2/2005 | Keirsbilck et al. |
| 2005/0027284 A1 | 2/2005 | Lozano et al. |
| 2005/0032827 A1 | 2/2005 | Oksenberg et al. |
| 2005/0033122 A1 | 2/2005 | Balkin et al. |
| 2005/0033154 A1 | 2/2005 | deCharms |
| 2005/0033174 A1 | 2/2005 | Moehring et al. |
| 2005/0033379 A1 | 2/2005 | Lozano et al. |
| 2005/0038354 A1 | 2/2005 | Miller et al. |
| 2005/0043774 A1 | 2/2005 | Devlin et al. |
| 2005/0049651 A1 | 3/2005 | Whitehurst et al. |
| 2005/0059689 A1 | 3/2005 | Oksenberg et al. |
| 2005/0059874 A1 | 3/2005 | Fuchs et al. |
| 2005/0060001 A1 | 3/2005 | Singhal et al. |
| 2005/0060007 A1 | 3/2005 | Goetz |
| 2005/0060008 A1 | 3/2005 | Goetz |
| 2005/0060009 A1 | 3/2005 | Goetz |
| 2005/0060010 A1 | 3/2005 | Goetz |
| 2005/0065412 A1 | 3/2005 | Shiomi et al. |
| 2005/0065427 A1 | 3/2005 | Magill et al. |
| 2005/0075568 A1 | 4/2005 | Moehring |
| 2005/0079474 A1 | 4/2005 | Lowe |
| 2005/0079636 A1 | 4/2005 | White et al. |
| 2005/0080124 A1 | 4/2005 | Teegarden et al. |
| 2005/0080349 A1 | 4/2005 | Okada et al. |
| 2005/0080828 A1 | 4/2005 | Johnson |
| 2005/0085744 A1 | 4/2005 | Beverina et al. |
| 2005/0096311 A1 | 5/2005 | Suffin et al. |
| 2005/0096517 A1 | 5/2005 | Diab et al. |
| 2005/0106713 A1 | 5/2005 | Phan et al. |
| 2005/0107654 A1 | 5/2005 | Riehl |
| 2005/0113713 A1 | 5/2005 | Foust et al. |
| 2005/0118286 A1 | 6/2005 | Suffin et al. |
| 2005/0119547 A1 | 6/2005 | Shastri et al. |
| 2005/0119586 A1 | 6/2005 | Coyle et al. |
| 2005/0124848 A1 | 6/2005 | Holzner |
| 2005/0124851 A1 | 6/2005 | Patton et al. |
| 2005/0124863 A1 | 6/2005 | Cook |
| 2005/0131311 A1 | 6/2005 | Leuthardt et al. |
| 2005/0135102 A1 | 6/2005 | Gardiner et al. |
| 2005/0136002 A1 | 6/2005 | Fossheim et al. |
| 2005/0137494 A1 | 6/2005 | Viertio-Oja |
| 2005/0137645 A1 | 6/2005 | Voipio et al. |
| 2005/0144042 A1 | 6/2005 | Joffe et al. |
| 2005/0148828 A1 | 7/2005 | Lindsay |
| 2005/0148893 A1 | 7/2005 | Misczynski et al. |
| 2005/0148894 A1 | 7/2005 | Misczynski et al. |
| 2005/0148895 A1 | 7/2005 | Misczynski et al. |
| 2005/0149123 A1 | 7/2005 | Lesser et al. |
| 2005/0149157 A1 | 7/2005 | Hunter et al. |
| 2005/0153268 A1* | 7/2005 | Junkin ..................... G09B 5/00 434/321 |
| 2005/0154290 A1 | 7/2005 | Langleben |
| 2005/0154419 A1 | 7/2005 | Whitehurst et al. |
| 2005/0154425 A1 | 7/2005 | Boveja et al. |
| 2005/0154426 A1 | 7/2005 | Boveja et al. |
| 2005/0156602 A1 | 7/2005 | Conti |
| 2005/0159670 A1 | 7/2005 | Sneddon |
| 2005/0159671 A1 | 7/2005 | Sneddon |
| 2005/0165458 A1 | 7/2005 | Boveja et al. |
| 2005/0167588 A1 | 8/2005 | Donnangelo |
| 2005/0171410 A1 | 8/2005 | Hjelt et al. |
| 2005/0182287 A1 | 8/2005 | Becker |
| 2005/0182288 A1 | 8/2005 | Zabara |
| 2005/0182389 A1 | 8/2005 | LaPorte et al. |
| 2005/0182450 A1 | 8/2005 | Hunter et al. |
| 2005/0182453 A1 | 8/2005 | Whitehurst et al. |
| 2005/0182456 A1 | 8/2005 | Ziobro et al. |
| 2005/0182467 A1 | 8/2005 | Hunter et al. |
| 2005/0182468 A1 | 8/2005 | Hunter et al. |
| 2005/0182469 A1 | 8/2005 | Hunter et al. |
| 2005/0187600 A1 | 8/2005 | Hunter et al. |
| 2005/0192514 A1 | 9/2005 | Kearby et al. |
| 2005/0192644 A1 | 9/2005 | Boveja et al. |
| 2005/0192647 A1 | 9/2005 | Hunter et al. |
| 2005/0197590 A1 | 9/2005 | Osorio et al. |
| 2005/0197675 A1 | 9/2005 | David et al. |
| 2005/0197678 A1 | 9/2005 | Boveja et al. |
| 2005/0209512 A1 | 9/2005 | Heruth et al. |
| 2005/0209517 A1 | 9/2005 | Diab et al. |
| 2005/0209654 A1 | 9/2005 | Boveja et al. |
| 2005/0209664 A1 | 9/2005 | Hunter et al. |
| 2005/0209665 A1 | 9/2005 | Hunter et al. |
| 2005/0209666 A1 | 9/2005 | Hunter et al. |
| 2005/0215889 A1 | 9/2005 | Patterson |
| 2005/0216070 A1 | 9/2005 | Boveja et al. |
| 2005/0216071 A1 | 9/2005 | Devlin et al. |
| 2005/0222522 A1 | 10/2005 | Heruth et al. |
| 2005/0222639 A1 | 10/2005 | Seifritz et al. |
| 2005/0228451 A1 | 10/2005 | Jaax et al. |
| 2005/0228785 A1 | 10/2005 | Wolcott et al. |
| 2005/0240087 A1 | 10/2005 | Keenan et al. |
| 2005/0240229 A1 | 10/2005 | Whitehurst et al. |
| 2005/0240253 A1 | 10/2005 | Tyler et al. |
| 2005/0244045 A1 | 11/2005 | Eriksson |
| 2005/0245796 A1 | 11/2005 | Woods et al. |
| 2005/0251055 A1 | 11/2005 | Zhirnov et al. |
| 2005/0251220 A1 | 11/2005 | Barrett et al. |
| 2005/0256378 A1 | 11/2005 | Takai et al. |
| 2005/0256385 A1 | 11/2005 | Diab et al. |
| 2005/0256418 A1 | 11/2005 | Mietus et al. |
| 2005/0267011 A1 | 12/2005 | Deisseroth et al. |
| 2005/0267343 A1 | 12/2005 | Woods et al. |
| 2005/0267344 A1 | 12/2005 | Woods et al. |
| 2005/0267362 A1 | 12/2005 | Mietus et al. |
| 2005/0267542 A1 | 12/2005 | David et al. |
| 2005/0273017 A1 | 12/2005 | Gordon |
| 2005/0277813 A1 | 12/2005 | Katz et al. |
| 2005/0277912 A1 | 12/2005 | John |
| 2005/0283053 A1 | 12/2005 | deCharms |
| 2005/0283090 A1 | 12/2005 | Wells |
| 2006/0004298 A1 | 1/2006 | Kennedy et al. |
| 2006/0004422 A1 | 1/2006 | De Ridder |
| 2006/0009704 A1 | 1/2006 | Okada et al. |
| 2006/0009815 A1 | 1/2006 | Boveja et al. |
| 2006/0014753 A1 | 1/2006 | Shamloo et al. |
| 2006/0015034 A1 | 1/2006 | Martinerie et al. |
| 2006/0015153 A1 | 1/2006 | Gliner et al. |
| 2006/0018525 A1 | 1/2006 | Barbour |
| 2006/0020184 A1 | 1/2006 | Woods et al. |
| 2006/0036152 A1 | 2/2006 | Kozel |
| 2006/0036153 A1 | 2/2006 | Laken |
| 2006/0041201 A1 | 2/2006 | Behbehani et al. |
| 2006/0047187 A1 | 3/2006 | Goyal et al. |
| 2006/0047216 A1 | 3/2006 | Dorr et al. |
| 2006/0047324 A1 | 3/2006 | Tass |
| 2006/0047325 A1 | 3/2006 | Thimineur et al. |
| 2006/0051814 A1 | 3/2006 | Jackowski et al. |
| 2006/0052386 A1 | 3/2006 | Wieloch et al. |
| 2006/0052657 A9 | 3/2006 | Zabara |
| 2006/0052706 A1 | 3/2006 | Hynynen et al. |
| 2006/0058590 A1 | 3/2006 | Shaw et al. |
| 2006/0058683 A1 | 3/2006 | Chance |
| 2006/0058856 A1 | 3/2006 | Morrell |
| 2006/0061544 A1 | 3/2006 | Min et al. |
| 2006/0064138 A1 | 3/2006 | Velasco et al. |
| 2006/0064139 A1 | 3/2006 | Chung et al. |
| 2006/0064140 A1 | 3/2006 | Whitehurst et al. |
| 2006/0069059 A1 | 3/2006 | Schaller et al. |
| 2006/0069415 A1 | 3/2006 | Cameron et al. |
| 2006/0074290 A1 | 4/2006 | Chen et al. |
| 2006/0074298 A1 | 4/2006 | Borsook et al. |
| 2006/0074334 A1 | 4/2006 | Coyle |
| 2006/0074822 A1 | 4/2006 | Eda et al. |
| 2006/0078183 A1 | 4/2006 | deCharms |
| 2006/0079936 A1 | 4/2006 | Boveja et al. |
| 2006/0082727 A1 | 4/2006 | Bolger et al. |
| 2006/0084858 A1 | 4/2006 | Marks |
| 2006/0084877 A1 | 4/2006 | Ujhazy et al. |

(56)                    References Cited

U.S. PATENT DOCUMENTS

| | | |
|---|---|---|
| 2006/0087746 A1 | 4/2006 | Lipow |
| 2006/0089541 A1 | 4/2006 | Braun et al. |
| 2006/0089549 A1 | 4/2006 | Diab et al. |
| 2006/0094968 A1 | 5/2006 | Drew |
| 2006/0094970 A1 | 5/2006 | Drew |
| 2006/0094971 A1 | 5/2006 | Drew |
| 2006/0094972 A1 | 5/2006 | Drew |
| 2006/0095091 A1 | 5/2006 | Drew |
| 2006/0095092 A1 | 5/2006 | Drew |
| 2006/0100526 A1 | 5/2006 | Yamamoto et al. |
| 2006/0100530 A1 | 5/2006 | Kliot et al. |
| 2006/0100671 A1 | 5/2006 | Ridder |
| 2006/0102171 A1 | 5/2006 | Gavish |
| 2006/0106274 A1 | 5/2006 | Thomas et al. |
| 2006/0106326 A1 | 5/2006 | Krebs et al. |
| 2006/0106430 A1 | 5/2006 | Fowler et al. |
| 2006/0106434 A1 | 5/2006 | Padgitt et al. |
| 2006/0111644 A1 | 5/2006 | Guttag et al. |
| 2006/0116556 A1 | 6/2006 | Duhamel |
| 2006/0122481 A1 | 6/2006 | Sievenpiper et al. |
| 2006/0129022 A1 | 6/2006 | Venza et al. |
| 2006/0129202 A1 | 6/2006 | Armstrong |
| 2006/0129277 A1 | 6/2006 | Wu et al. |
| 2006/0129324 A1 | 6/2006 | Rabinoff et al. |
| 2006/0135879 A1 | 6/2006 | Liley |
| 2006/0135880 A1 | 6/2006 | Sarkela |
| 2006/0136135 A1 | 6/2006 | Little et al. |
| 2006/0142802 A1 | 6/2006 | Armstrong |
| 2006/0149144 A1 | 7/2006 | Lynn et al. |
| 2006/0149160 A1 | 7/2006 | Kofol et al. |
| 2006/0149337 A1 | 7/2006 | John |
| 2006/0152227 A1 | 7/2006 | Hammer |
| 2006/0153396 A1 | 7/2006 | John |
| 2006/0155206 A1 | 7/2006 | Lynn |
| 2006/0155207 A1 | 7/2006 | Lynn et al. |
| 2006/0155348 A1 | 7/2006 | deCharms |
| 2006/0155495 A1 | 7/2006 | Osorio et al. |
| 2006/0161071 A1 | 7/2006 | Lynn et al. |
| 2006/0161075 A1 | 7/2006 | Kurtz |
| 2006/0161217 A1 | 7/2006 | Jaax et al. |
| 2006/0161218 A1 | 7/2006 | Danilov |
| 2006/0161384 A1 | 7/2006 | Osorio et al. |
| 2006/0167370 A1 | 7/2006 | Greenwald et al. |
| 2006/0167497 A1 | 7/2006 | Armstrong et al. |
| 2006/0167564 A1 | 7/2006 | Flaherty et al. |
| 2006/0167722 A1 | 7/2006 | MRF Struys et al. |
| 2006/0170424 A1 | 8/2006 | Kasevich |
| 2006/0173259 A1 | 8/2006 | Flaherty et al. |
| 2006/0173364 A1 | 8/2006 | Clancy et al. |
| 2006/0173493 A1 | 8/2006 | Armstrong et al. |
| 2006/0173494 A1 | 8/2006 | Armstrong et al. |
| 2006/0173495 A1 | 8/2006 | Armstrong et al. |
| 2006/0173510 A1 | 8/2006 | Besio et al. |
| 2006/0176062 A1 | 8/2006 | Yang et al. |
| 2006/0178709 A1 | 8/2006 | Foster et al. |
| 2006/0184058 A1 | 8/2006 | Silberstein |
| 2006/0184059 A1 | 8/2006 | Jadidi |
| 2006/0188134 A1 | 8/2006 | Quist |
| 2006/0189866 A1 | 8/2006 | Thomas et al. |
| 2006/0189880 A1 | 8/2006 | Lynn et al. |
| 2006/0189882 A1 | 8/2006 | Thomas |
| 2006/0189899 A1 | 8/2006 | Flaherty et al. |
| 2006/0191543 A1 | 8/2006 | Becker et al. |
| 2006/0195039 A1 | 8/2006 | Drew et al. |
| 2006/0195154 A1 | 8/2006 | Jaax et al. |
| 2006/0195155 A1 | 8/2006 | Firlik et al. |
| 2006/0200013 A1 | 9/2006 | Smith et al. |
| 2006/0200016 A1 | 9/2006 | Diab et al. |
| 2006/0200034 A1 | 9/2006 | Ricci et al. |
| 2006/0200035 A1 | 9/2006 | Ricci et al. |
| 2006/0200206 A1 | 9/2006 | Firlik et al. |
| 2006/0204532 A1 | 9/2006 | John |
| 2006/0206033 A1 | 9/2006 | Guerrero et al. |
| 2006/0206108 A1 | 9/2006 | Hempel |
| 2006/0206155 A1 | 9/2006 | Ben-David et al. |
| 2006/0206165 A1 | 9/2006 | Jaax et al. |
| 2006/0206174 A1 | 9/2006 | Honeycutt et al. |
| 2006/0212090 A1 | 9/2006 | Lozano et al. |
| 2006/0212091 A1 | 9/2006 | Lozano et al. |
| 2006/0217609 A1 | 9/2006 | Diab et al. |
| 2006/0217781 A1 | 9/2006 | John |
| 2006/0217816 A1 | 9/2006 | Pesaran et al. |
| 2006/0224216 A1 | 10/2006 | Pless et al. |
| 2006/0224421 A1 | 10/2006 | St. Ores et al. |
| 2006/0225437 A1 | 10/2006 | Kazami |
| 2006/0229164 A1 | 10/2006 | Einav |
| 2006/0233390 A1 | 10/2006 | Causevic et al. |
| 2006/0235315 A1 | 10/2006 | Akselrod et al. |
| 2006/0235324 A1 | 10/2006 | Lynn |
| 2006/0235484 A1 | 10/2006 | Jaax et al. |
| 2006/0235489 A1 | 10/2006 | Drew et al. |
| 2006/0239482 A1 | 10/2006 | Hatoum |
| 2006/0241373 A1 | 10/2006 | Strychacz et al. |
| 2006/0241382 A1 | 10/2006 | Li et al. |
| 2006/0241562 A1 | 10/2006 | John et al. |
| 2006/0241718 A1 | 10/2006 | Tyler et al. |
| 2006/0247728 A1 | 11/2006 | Foster et al. |
| 2006/0251303 A1 | 11/2006 | He et al. |
| 2006/0252978 A1 | 11/2006 | Vesely et al. |
| 2006/0252979 A1 | 11/2006 | Vesely et al. |
| 2006/0258896 A1 | 11/2006 | Haber et al. |
| 2006/0258950 A1 | 11/2006 | Hargrove et al. |
| 2006/0259077 A1 | 11/2006 | Pardo et al. |
| 2006/0265022 A1 | 11/2006 | John et al. |
| 2006/0276695 A9 | 12/2006 | Lynn et al. |
| 2006/0281543 A1 | 12/2006 | Sutton et al. |
| 2006/0281980 A1 | 12/2006 | Randlov et al. |
| 2006/0282123 A1 | 12/2006 | Hunter et al. |
| 2006/0287691 A1 | 12/2006 | Drew |
| 2006/0293578 A1 | 12/2006 | Rennaker |
| 2006/0293721 A1 | 12/2006 | Tarver et al. |
| 2006/0293723 A1 | 12/2006 | Whitehurst et al. |
| 2007/0000372 A1 | 1/2007 | Rezai et al. |
| 2007/0005115 A1 | 1/2007 | Lozano et al. |
| 2007/0005391 A1 | 1/2007 | Repucci et al. |
| 2007/0007454 A1 | 1/2007 | Stoddart et al. |
| 2007/0008172 A1 | 1/2007 | Hewett et al. |
| 2007/0014454 A1 | 1/2007 | Sawyer et al. |
| 2007/0015985 A1 | 1/2007 | Tolvanen-Laakso et al. |
| 2007/0016095 A1 | 1/2007 | Low et al. |
| 2007/0016264 A1 | 1/2007 | Falci |
| 2007/0019846 A1 | 1/2007 | Bullitt et al. |
| 2007/0021673 A1 | 1/2007 | Arbel et al. |
| 2007/0021675 A1 | 1/2007 | Childre et al. |
| 2007/0021800 A1 | 1/2007 | Whitehurst et al. |
| 2007/0025608 A1 | 2/2007 | Armstrong |
| 2007/0027486 A1 | 2/2007 | Armstrong |
| 2007/0027498 A1 | 2/2007 | Maschino et al. |
| 2007/0027499 A1 | 2/2007 | Maschino et al. |
| 2007/0027500 A1 | 2/2007 | Maschino et al. |
| 2007/0027501 A1 | 2/2007 | Jensen et al. |
| 2007/0031798 A1 | 2/2007 | Gottfried |
| 2007/0032733 A1 | 2/2007 | Burton |
| 2007/0032737 A1 | 2/2007 | Causevic et al. |
| 2007/0032834 A1 | 2/2007 | Gliner et al. |
| 2007/0036355 A1 | 2/2007 | Terauchi et al. |
| 2007/0036402 A1 | 2/2007 | Cahill et al. |
| 2007/0038067 A1 | 2/2007 | Kandori et al. |
| 2007/0038264 A1 | 2/2007 | Jaax et al. |
| 2007/0038382 A1 | 2/2007 | Keenan |
| 2007/0043392 A1 | 2/2007 | Gliner et al. |
| 2007/0043401 A1 | 2/2007 | John |
| 2007/0049844 A1 | 3/2007 | Rosenfeld |
| 2007/0049988 A1 | 3/2007 | Carbunaru et al. |
| 2007/0050715 A1 | 3/2007 | Behar |
| 2007/0055145 A1 | 3/2007 | Zelnik et al. |
| 2007/0060830 A1 | 3/2007 | Le et al. |
| 2007/0060831 A1 | 3/2007 | Le et al. |
| 2007/0060954 A1 | 3/2007 | Cameron et al. |
| 2007/0060974 A1 | 3/2007 | Lozano |
| 2007/0060984 A1 | 3/2007 | Webb et al. |
| 2007/0066403 A1 | 3/2007 | Conkwright |
| 2007/0066914 A1 | 3/2007 | Le et al. |
| 2007/0066915 A1 | 3/2007 | Frei et al. |

(56) References Cited

U.S. PATENT DOCUMENTS

| | | |
|---|---|---|
| 2007/0066997 A1 | 3/2007 | He et al. |
| 2007/0067003 A1 | 3/2007 | Sanchez et al. |
| 2007/0067004 A1 | 3/2007 | Boveja et al. |
| 2007/0072857 A1 | 3/2007 | Teegarden et al. |
| 2007/0078134 A1 | 4/2007 | Teegarden et al. |
| 2007/0081712 A1 | 4/2007 | Huang et al. |
| 2007/0083128 A1 | 4/2007 | Cote et al. |
| 2007/0093721 A1 | 4/2007 | Lynn et al. |
| 2007/0093870 A1 | 4/2007 | Maschino |
| 2007/0100246 A1 | 5/2007 | Hyde |
| 2007/0100251 A1 | 5/2007 | Prichep |
| 2007/0100278 A1 | 5/2007 | Frei et al. |
| 2007/0100377 A1 | 5/2007 | Armstrong et al. |
| 2007/0100378 A1 | 5/2007 | Maschino |
| 2007/0100389 A1 | 5/2007 | Jaax et al. |
| 2007/0100392 A1 | 5/2007 | Maschino et al. |
| 2007/0100398 A1 | 5/2007 | Sloan |
| 2007/0100666 A1 | 5/2007 | Stivoric et al. |
| 2007/0112404 A1 | 5/2007 | Mann et al. |
| 2007/0118197 A1 | 5/2007 | Loeb |
| 2007/0127793 A1 | 6/2007 | Beckett et al. |
| 2007/0129647 A1 | 6/2007 | Lynn |
| 2007/0129769 A1 | 6/2007 | Bourget et al. |
| 2007/0129774 A1 | 6/2007 | Bourget et al. |
| 2007/0135724 A1 | 6/2007 | Ujhazy et al. |
| 2007/0135728 A1 | 6/2007 | Snyder et al. |
| 2007/0138886 A1 | 6/2007 | Krebs et al. |
| 2007/0142862 A1 | 6/2007 | Dilorenzo |
| 2007/0142873 A1 | 6/2007 | Esteller et al. |
| 2007/0142874 A1 | 6/2007 | John |
| 2007/0149860 A1 | 6/2007 | Lynn et al. |
| 2007/0150024 A1 | 6/2007 | Leyde et al. |
| 2007/0150025 A1 | 6/2007 | Dilorenzo et al. |
| 2007/0150026 A1 | 6/2007 | Bourget et al. |
| 2007/0150029 A1 | 6/2007 | Bourget et al. |
| 2007/0156180 A1 | 7/2007 | Jaax et al. |
| 2007/0156457 A1 | 7/2007 | Brown |
| 2007/0159185 A1 | 7/2007 | Yang et al. |
| 2007/0161919 A1 | 7/2007 | DiLorenzo |
| 2007/0162085 A1 | 7/2007 | DiLorenzo |
| 2007/0162086 A1 | 7/2007 | DiLorenzo |
| 2007/0165915 A1 | 7/2007 | Fuchs |
| 2007/0167694 A1 | 7/2007 | Causevic et al. |
| 2007/0167723 A1 | 7/2007 | Park et al. |
| 2007/0167853 A1 | 7/2007 | Melker et al. |
| 2007/0167858 A1 | 7/2007 | Virtanen et al. |
| 2007/0167991 A1 | 7/2007 | DiLorenzo |
| 2007/0173733 A1 | 7/2007 | Le et al. |
| 2007/0173902 A1 | 7/2007 | Maschino et al. |
| 2007/0179395 A1 | 8/2007 | Sotos et al. |
| 2007/0179396 A1 | 8/2007 | Le et al. |
| 2007/0179534 A1 | 8/2007 | Firlik et al. |
| 2007/0179558 A1 | 8/2007 | Gliner et al. |
| 2007/0179734 A1 | 8/2007 | Chmiel et al. |
| 2007/0184507 A1 | 8/2007 | Jackowski et al. |
| 2007/0191688 A1 | 8/2007 | Lynn |
| 2007/0191691 A1 | 8/2007 | Polanco |
| 2007/0191697 A1 | 8/2007 | Lynn et al. |
| 2007/0191704 A1 | 8/2007 | DeCharms |
| 2007/0191727 A1 | 8/2007 | Fadem |
| 2007/0197930 A1 | 8/2007 | Sarkela |
| 2007/0198063 A1 | 8/2007 | Hunter et al. |
| 2007/0203401 A1 | 8/2007 | Gordon et al. |
| 2007/0203448 A1 | 8/2007 | Melker et al. |
| 2007/0208212 A1 | 9/2007 | DiLorenzo |
| 2007/0208269 A1 | 9/2007 | Mumford et al. |
| 2007/0209669 A1 | 9/2007 | Derchak |
| 2007/0213785 A1 | 9/2007 | Osorio et al. |
| 2007/0213786 A1 | 9/2007 | Sackellares et al. |
| 2007/0225581 A1 | 9/2007 | Diab et al. |
| 2007/0225674 A1 | 9/2007 | Molnar et al. |
| 2007/0225774 A1 | 9/2007 | Eskandar et al. |
| 2007/0225932 A1 | 9/2007 | Halford |
| 2007/0233192 A1 | 10/2007 | Craig |
| 2007/0233193 A1 | 10/2007 | Craig |
| 2007/0238934 A1 | 10/2007 | Viswanathan |
| 2007/0239059 A1 | 10/2007 | McIver |
| 2007/0244387 A1 | 10/2007 | Rodriguez Ponce et al. |
| 2007/0244407 A1 | 10/2007 | Osorio |
| 2007/0249918 A1 | 10/2007 | Diab et al. |
| 2007/0249949 A1 | 10/2007 | Hadley |
| 2007/0249952 A1 | 10/2007 | Rubin et al. |
| 2007/0250119 A1 | 10/2007 | Tyler et al. |
| 2007/0250138 A1 | 10/2007 | Nofzinger |
| 2007/0255122 A1 | 11/2007 | Vol et al. |
| 2007/0255135 A1 | 11/2007 | Kalafut et al. |
| 2007/0255155 A1 | 11/2007 | Drew et al. |
| 2007/0255320 A1 | 11/2007 | Inman et al. |
| 2007/0255379 A1 | 11/2007 | Williams et al. |
| 2007/0255531 A1 | 11/2007 | Drew |
| 2007/0259323 A1 | 11/2007 | Brown et al. |
| 2007/0260151 A1 | 11/2007 | Clifford |
| 2007/0265508 A1 | 11/2007 | Sheikhzadeh-Nadjar et al. |
| 2007/0265533 A1 | 11/2007 | Tran |
| 2007/0273504 A1 | 11/2007 | Tran |
| 2007/0273611 A1 | 11/2007 | Torch |
| 2007/0276270 A1 | 11/2007 | Tran |
| 2007/0276278 A1 | 11/2007 | Coyle et al. |
| 2007/0276279 A1 | 11/2007 | Echauz et al. |
| 2007/0276441 A1 | 11/2007 | Goetz |
| 2007/0276609 A1 | 11/2007 | Greenwald |
| 2007/0280508 A1 | 12/2007 | Ernst et al. |
| 2007/0282228 A1 | 12/2007 | Einav et al. |
| 2007/0287896 A1 | 12/2007 | Derchak et al. |
| 2007/0291832 A1 | 12/2007 | Diab et al. |
| 2007/0293760 A1 | 12/2007 | Schaafsma |
| 2007/0299370 A1 | 12/2007 | Bystritsky |
| 2007/0299371 A1 | 12/2007 | Einav et al. |
| 2008/0001600 A1 | 1/2008 | deCharms |
| 2008/0001735 A1 | 1/2008 | Tran |
| 2008/0004514 A1 | 1/2008 | Diab et al. |
| 2008/0004550 A1 | 1/2008 | Einav et al. |
| 2008/0004904 A1 | 1/2008 | Tran |
| 2008/0009685 A1 | 1/2008 | Kim et al. |
| 2008/0009772 A1 | 1/2008 | Tyler et al. |
| 2008/0013747 A1 | 1/2008 | Tran |
| 2008/0015458 A1 | 1/2008 | Buarque de Macedo et al. |
| 2008/0015459 A1 | 1/2008 | Llinas |
| 2008/0021332 A1 | 1/2008 | Brainard |
| 2008/0021336 A1 | 1/2008 | Dobak |
| 2008/0021340 A1 | 1/2008 | Sarkela |
| 2008/0021341 A1 | 1/2008 | Harris et al. |
| 2008/0021342 A1 | 1/2008 | Echauz et al. |
| 2008/0021345 A1 | 1/2008 | Kern et al. |
| 2008/0027347 A1 | 1/2008 | Harris et al. |
| 2008/0027348 A1 | 1/2008 | Harris et al. |
| 2008/0027515 A1 | 1/2008 | Harris et al. |
| 2008/0033266 A1 | 2/2008 | Diab et al. |
| 2008/0033291 A1 | 2/2008 | Rousso et al. |
| 2008/0033297 A1 | 2/2008 | Sliwa |
| 2008/0033502 A1 | 2/2008 | Harris et al. |
| 2008/0033503 A1 | 2/2008 | Fowler et al. |
| 2008/0033508 A1 | 2/2008 | Frei et al. |
| 2008/0033513 A1 | 2/2008 | Man et al. |
| 2008/0036752 A1 | 2/2008 | Diab et al. |
| 2008/0039677 A1 | 2/2008 | Adams |
| 2008/0039698 A1 | 2/2008 | Burton |
| 2008/0039737 A1 | 2/2008 | Breiter et al. |
| 2008/0039904 A1 | 2/2008 | Bulkes et al. |
| 2008/0042067 A1 | 2/2008 | Rousso et al. |
| 2008/0045775 A1 | 2/2008 | Lozano |
| 2008/0045823 A1 | 2/2008 | Diab et al. |
| 2008/0045844 A1 | 2/2008 | Arbel et al. |
| 2008/0046012 A1 | 2/2008 | Covalin et al. |
| 2008/0046035 A1 | 2/2008 | Fowler et al. |
| 2008/0049376 A1 | 2/2008 | Stevenson et al. |
| 2008/0051669 A1 | 2/2008 | Meyer et al. |
| 2008/0051858 A1 | 2/2008 | Haber et al. |
| 2008/0058664 A1 | 3/2008 | Mirro |
| 2008/0058668 A1 | 3/2008 | Seyed Momen et al. |
| 2008/0058773 A1 | 3/2008 | John |
| 2008/0064934 A1 | 3/2008 | Frei et al. |
| 2008/0065183 A1 | 3/2008 | Whitehurst et al. |
| 2008/0069446 A1 | 3/2008 | Ancelin |

(56) References Cited

U.S. PATENT DOCUMENTS

| | | | |
|---|---|---|---|
| 2008/0071150 A1 | 3/2008 | Miesel et al. | |
| 2008/0071326 A1 | 3/2008 | Heruth et al. | |
| 2008/0074307 A1 | 3/2008 | Boric-Lubecke et al. | |
| 2008/0077010 A1 | 3/2008 | Cohen-Solal et al. | |
| 2008/0077015 A1 | 3/2008 | Boric-Lubecke et al. | |
| 2008/0077191 A1 | 3/2008 | Morrell | |
| 2008/0081963 A1 | 4/2008 | Naghavi et al. | |
| 2008/0082018 A1 | 4/2008 | Sackner et al. | |
| 2008/0086182 A1 | 4/2008 | Ben-David et al. | |
| 2008/0091118 A1 | 4/2008 | Georgopoulos | |
| 2008/0091240 A1 | 4/2008 | Ben-David et al. | |
| 2008/0097197 A1 | 4/2008 | Kalafut et al. | |
| 2008/0097235 A1 | 4/2008 | Ofek et al. | |
| 2008/0097553 A1 | 4/2008 | John | |
| 2008/0097785 A1 | 4/2008 | Ali | |
| 2008/0103547 A1 | 5/2008 | Okun et al. | |
| 2008/0103548 A1 | 5/2008 | Fowler et al. | |
| 2008/0109050 A1 | 5/2008 | John | |
| 2008/0119716 A1 | 5/2008 | Boric-Lubecke et al. | |
| 2008/0119747 A1 | 5/2008 | Mietus et al. | |
| 2008/0119763 A1 | 5/2008 | Wiener | |
| 2008/0119900 A1 | 5/2008 | DiLorenzo | |
| 2008/0123927 A1 | 5/2008 | Miga et al. | |
| 2008/0125669 A1 | 5/2008 | Suffin et al. | |
| 2008/0125829 A1 | 5/2008 | Velasco et al. | |
| 2008/0125830 A1 | 5/2008 | Morrell | |
| 2008/0125831 A1 | 5/2008 | Morrell | |
| 2008/0128626 A1 | 6/2008 | Rousso et al. | |
| 2008/0132383 A1 | 6/2008 | Einav et al. | |
| 2008/0139953 A1 | 6/2008 | Baker et al. | |
| 2008/0140141 A1 | 6/2008 | Ben-David et al. | |
| 2008/0140149 A1 | 6/2008 | John et al. | |
| 2008/0140403 A1 | 6/2008 | Hughes et al. | |
| 2008/0147137 A1 | 6/2008 | Cohen et al. | |
| 2008/0154111 A1 | 6/2008 | Wu et al. | |
| 2008/0154126 A1 | 6/2008 | Culver et al. | |
| 2008/0154148 A1 | 6/2008 | Chung et al. | |
| 2008/0154331 A1 | 6/2008 | John et al. | |
| 2008/0154332 A1 | 6/2008 | Rezai | |
| 2008/0157980 A1 | 7/2008 | Sachanandani et al. | |
| 2008/0161700 A1 | 7/2008 | Sachanandani et al. | |
| 2008/0161879 A1 | 7/2008 | Firlik et al. | |
| 2008/0161880 A1 | 7/2008 | Firlik et al. | |
| 2008/0161881 A1 | 7/2008 | Firlik et al. | |
| 2008/0161886 A1 | 7/2008 | Stevenson et al. | |
| 2008/0161894 A1 | 7/2008 | Ben-David et al. | |
| 2008/0162182 A1 | 7/2008 | Cazares et al. | |
| 2008/0167535 A1 | 7/2008 | Stivoric et al. | |
| 2008/0167540 A1 | 7/2008 | Korhonen et al. | |
| 2008/0167569 A1 | 7/2008 | Ermes et al. | |
| 2008/0167571 A1 | 7/2008 | Gevins | |
| 2008/0177195 A1 | 7/2008 | Armitstead | |
| 2008/0177196 A1 | 7/2008 | Burdick et al. | |
| 2008/0177197 A1 | 7/2008 | Lee et al. | |
| 2008/0183072 A1 | 7/2008 | Robertson et al. | |
| 2008/0183097 A1 | 7/2008 | Leyde et al. | |
| 2008/0188765 A1 | 8/2008 | Stolarski et al. | |
| 2008/0194981 A1 | 8/2008 | Sarkela et al. | |
| 2008/0195166 A1 | 8/2008 | Sun et al. | |
| 2008/0200831 A1 | 8/2008 | Sturzebecher | |
| 2008/0208072 A1 | 8/2008 | Fadem et al. | |
| 2008/0208073 A1 | 8/2008 | Causevic | |
| 2008/0208280 A1 | 8/2008 | Lindenthaler et al. | |
| 2008/0208285 A1 | 8/2008 | Fowler et al. | |
| 2008/0214902 A1 | 9/2008 | Lee et al. | |
| 2008/0215112 A1 | 9/2008 | Firlik et al. | |
| 2008/0219917 A1 | 9/2008 | Koruga | |
| 2008/0221400 A1 | 9/2008 | Lee et al. | |
| 2008/0221401 A1 | 9/2008 | Derchak et al. | |
| 2008/0221441 A1 | 9/2008 | Bjornerud et al. | |
| 2008/0221472 A1 | 9/2008 | Lee et al. | |
| 2008/0221969 A1 | 9/2008 | Lee et al. | |
| 2008/0228077 A1 | 9/2008 | Wilk et al. | |
| 2008/0228100 A1 | 9/2008 | Navakatikyan | |
| 2008/0228239 A1 | 9/2008 | Tyler et al. | |
| 2008/0229408 A1 | 9/2008 | Dinges et al. | |
| 2008/0230702 A1 | 9/2008 | Rousso et al. | |
| 2008/0230705 A1 | 9/2008 | Rousso et al. | |
| 2008/0234113 A1 | 9/2008 | Einav | |
| 2008/0234601 A1 | 9/2008 | Wexelman | |
| 2008/0235469 A1 | 9/2008 | Drew | |
| 2008/0241804 A1 | 10/2008 | Pennebaker | |
| 2008/0242521 A1 | 10/2008 | Einav | |
| 2008/0242976 A1 | 10/2008 | Robertson et al. | |
| 2008/0243005 A1 | 10/2008 | Jung et al. | |
| 2008/0243014 A1 | 10/2008 | Moussavi et al. | |
| 2008/0243017 A1 | 10/2008 | Moussavi et al. | |
| 2008/0243021 A1 | 10/2008 | Causevic et al. | |
| 2008/0244003 A1* | 10/2008 | Springer | G09B 5/00 |
| | | | 700/94 |
| 2008/0247618 A1 | 10/2008 | Laine et al. | |
| 2008/0249430 A1 | 10/2008 | John et al. | |
| 2008/0249589 A1 | 10/2008 | Cornejo Cruz et al. | |
| 2008/0255469 A1 | 10/2008 | Shieh et al. | |
| 2008/0255816 A1 | 10/2008 | Neville | |
| 2008/0255949 A1 | 10/2008 | Genco et al. | |
| 2008/0257349 A1 | 10/2008 | Hedner et al. | |
| 2008/0260212 A1 | 10/2008 | Moskal et al. | |
| 2008/0262327 A1 | 10/2008 | Kato | |
| 2008/0262367 A1 | 10/2008 | Mugler et al. | |
| 2008/0262371 A1 | 10/2008 | Causevic | |
| 2008/0269542 A1 | 10/2008 | Zabara | |
| 2008/0269652 A1* | 10/2008 | Reiner | A61M 21/00 |
| | | | 601/15 |
| 2008/0269812 A1 | 10/2008 | Gerber et al. | |
| 2008/0269833 A1 | 10/2008 | Scott et al. | |
| 2008/0269834 A1 | 10/2008 | Byerman et al. | |
| 2008/0269840 A1 | 10/2008 | Scott et al. | |
| 2008/0269843 A1 | 10/2008 | Gerber et al. | |
| 2008/0275327 A1 | 11/2008 | Faarbaek et al. | |
| 2008/0275340 A1 | 11/2008 | Beach et al. | |
| 2008/0275526 A1 | 11/2008 | Lozano | |
| 2008/0279436 A1 | 11/2008 | Razifar et al. | |
| 2008/0281238 A1 | 11/2008 | Oohashi et al. | |
| 2008/0281381 A1 | 11/2008 | Gerber et al. | |
| 2008/0281667 A1 | 11/2008 | Chen et al. | |
| 2008/0286453 A1 | 11/2008 | Koruga | |
| 2008/0287774 A1 | 11/2008 | Katz-Brull | |
| 2008/0287821 A1 | 11/2008 | Jung et al. | |
| 2008/0288018 A1 | 11/2008 | Rezai et al. | |
| 2008/0294019 A1 | 11/2008 | Tran | |
| 2008/0294063 A1 | 11/2008 | Bibian et al. | |
| 2008/0298653 A1 | 12/2008 | Amunts et al. | |
| 2008/0298659 A1 | 12/2008 | Spence et al. | |
| 2008/0304691 A1 | 12/2008 | Lai | |
| 2008/0304731 A1 | 12/2008 | Kimura | |
| 2008/0306365 A1 | 12/2008 | Bunce et al. | |
| 2008/0310697 A1 | 12/2008 | Razifar et al. | |
| 2008/0311549 A1 | 12/2008 | Belitsiotis | |
| 2008/0317317 A1 | 12/2008 | Shekhar et al. | |
| 2008/0319326 A1 | 12/2008 | Behbehani et al. | |
| 2008/0319505 A1 | 12/2008 | Boyden et al. | |
| 2009/0005654 A1 | 1/2009 | Jung et al. | |
| 2009/0005667 A1 | 1/2009 | Cui et al. | |
| 2009/0005675 A1 | 1/2009 | Grunwald et al. | |
| 2009/0006001 A1 | 1/2009 | Niculescu et al. | |
| 2009/0009284 A1 | 1/2009 | Sako | |
| 2009/0012387 A1 | 1/2009 | Hanson et al. | |
| 2009/0018407 A1 | 1/2009 | Jung et al. | |
| 2009/0018419 A1 | 1/2009 | Torch | |
| 2009/0018429 A1 | 1/2009 | Saliga et al. | |
| 2009/0018431 A1 | 1/2009 | Feiweier et al. | |
| 2009/0018432 A1 | 1/2009 | He et al. | |
| 2009/0018462 A1 | 1/2009 | Bell | |
| 2009/0022825 A1 | 1/2009 | Kerkman et al. | |
| 2009/0024007 A1 | 1/2009 | Lee et al. | |
| 2009/0024050 A1 | 1/2009 | Jung et al. | |
| 2009/0030476 A1 | 1/2009 | Hargrove | |
| 2009/0030930 A1 | 1/2009 | Pradeep et al. | |
| 2009/0033333 A1 | 2/2009 | Gribova et al. | |
| 2009/0036781 A1 | 2/2009 | Utsugi et al. | |
| 2009/0036791 A1 | 2/2009 | Plenz | |
| 2009/0036950 A1 | 2/2009 | Armstrong et al. | |
| 2009/0039889 A1 | 2/2009 | Wilt et al. | |

(56) References Cited

U.S. PATENT DOCUMENTS

| | | |
|---|---|---|
| 2009/0043221 A1 | 2/2009 | Kaplan et al. |
| 2009/0048507 A1 | 2/2009 | Feiweier et al. |
| 2009/0048530 A1 | 2/2009 | Sarkela et al. |
| 2009/0054788 A1 | 2/2009 | Hauger et al. |
| 2009/0054800 A1 | 2/2009 | Martinerie et al. |
| 2009/0054801 A1 | 2/2009 | Hinrikus et al. |
| 2009/0054946 A1 | 2/2009 | Sommer et al. |
| 2009/0054958 A1 | 2/2009 | Nofzinger |
| 2009/0058660 A1 | 3/2009 | Torch |
| 2009/0062660 A1 | 3/2009 | Chance |
| 2009/0062670 A1 | 3/2009 | Sterling et al. |
| 2009/0062676 A1 | 3/2009 | Kruglikov et al. |
| 2009/0062679 A1 | 3/2009 | Tan et al. |
| 2009/0062680 A1 | 3/2009 | Sandford |
| 2009/0062696 A1 | 3/2009 | Nathan et al. |
| 2009/0062698 A1 | 3/2009 | Einav et al. |
| 2009/0069707 A1 | 3/2009 | Sandford |
| 2009/0074279 A1 | 3/2009 | Razifar et al. |
| 2009/0076339 A1 | 3/2009 | Quintin et al. |
| 2009/0076399 A1 | 3/2009 | Arbel et al. |
| 2009/0076400 A1 | 3/2009 | Diab et al. |
| 2009/0076406 A1 | 3/2009 | Graham et al. |
| 2009/0076407 A1 | 3/2009 | John et al. |
| 2009/0076567 A1 | 3/2009 | Fowler et al. |
| 2009/0078875 A1 | 3/2009 | Rousso et al. |
| 2009/0082688 A1 | 3/2009 | Wagner |
| 2009/0082689 A1 | 3/2009 | Guttag et al. |
| 2009/0082690 A1 | 3/2009 | Phillips et al. |
| 2009/0082829 A1 | 3/2009 | Panken et al. |
| 2009/0083071 A1 | 3/2009 | Phillips et al. |
| 2009/0088658 A1 | 4/2009 | Luo et al. |
| 2009/0088680 A1 | 4/2009 | Aravanis et al. |
| 2009/0093403 A1 | 4/2009 | Zhang et al. |
| 2009/0093862 A1 | 4/2009 | Gliner et al. |
| 2009/0094305 A1 | 4/2009 | Johnson |
| 2009/0099474 A1 | 4/2009 | Pineda et al. |
| 2009/0099627 A1 | 4/2009 | Molnar et al. |
| 2009/0099783 A1 | 4/2009 | Reisberg |
| 2009/0105785 A1 | 4/2009 | Wei et al. |
| 2009/0112117 A1 | 4/2009 | Rewari |
| 2009/0112273 A1 | 4/2009 | Wingeier et al. |
| 2009/0112277 A1 | 4/2009 | Wingeier et al. |
| 2009/0112278 A1 | 4/2009 | Wingeier et al. |
| 2009/0112279 A1 | 4/2009 | Wingeier et al. |
| 2009/0112280 A1 | 4/2009 | Wingeier et al. |
| 2009/0112281 A1 | 4/2009 | Miyazawa et al. |
| 2009/0112523 A1 | 4/2009 | Townsend et al. |
| 2009/0118593 A1 | 5/2009 | Jung et al. |
| 2009/0118610 A1 | 5/2009 | Karmarkar et al. |
| 2009/0118622 A1 | 5/2009 | Durkin et al. |
| 2009/0118636 A1 | 5/2009 | Collura |
| 2009/0118780 A1 | 5/2009 | DiLorenzo |
| 2009/0118786 A1 | 5/2009 | Meadows et al. |
| 2009/0118787 A1 | 5/2009 | Moffitt et al. |
| 2009/0119154 A1 | 5/2009 | Jung et al. |
| 2009/0124869 A1 | 5/2009 | Hu et al. |
| 2009/0124921 A1 | 5/2009 | Milgramm et al. |
| 2009/0124922 A1 | 5/2009 | Milgramm et al. |
| 2009/0124923 A1 | 5/2009 | Sackellares et al. |
| 2009/0131995 A1 | 5/2009 | Sloan et al. |
| 2009/0132275 A1 | 5/2009 | Jung et al. |
| 2009/0137915 A1 | 5/2009 | Childre et al. |
| 2009/0137923 A1 | 5/2009 | Suffin et al. |
| 2009/0143654 A1 | 6/2009 | Funane et al. |
| 2009/0148019 A1 | 6/2009 | Hamada et al. |
| 2009/0149148 A1 | 6/2009 | Kurtz et al. |
| 2009/0149736 A1 | 6/2009 | Skidmore et al. |
| 2009/0156907 A1 | 6/2009 | Jung et al. |
| 2009/0156954 A1 | 6/2009 | Cox et al. |
| 2009/0156955 A1 | 6/2009 | Jung et al. |
| 2009/0156956 A1 | 6/2009 | Milgramm et al. |
| 2009/0157323 A1 | 6/2009 | Jung et al. |
| 2009/0157481 A1 | 6/2009 | Jung et al. |
| 2009/0157482 A1 | 6/2009 | Jung et al. |
| 2009/0157625 A1 | 6/2009 | Jung et al. |
| 2009/0157660 A1 | 6/2009 | Jung et al. |
| 2009/0157662 A1 | 6/2009 | Suffin et al. |
| 2009/0157751 A1 | 6/2009 | Jung et al. |
| 2009/0157813 A1 | 6/2009 | Jung et al. |
| 2009/0163777 A1 | 6/2009 | Jung et al. |
| 2009/0163980 A1 | 6/2009 | Stevenson |
| 2009/0163981 A1 | 6/2009 | Stevenson et al. |
| 2009/0163982 A1 | 6/2009 | deCharms |
| 2009/0164131 A1 | 6/2009 | Jung et al. |
| 2009/0164132 A1 | 6/2009 | Jung et al. |
| 2009/0164302 A1 | 6/2009 | Jung et al. |
| 2009/0164401 A1 | 6/2009 | Jung et al. |
| 2009/0164403 A1 | 6/2009 | Jung et al. |
| 2009/0164458 A1 | 6/2009 | Jung et al. |
| 2009/0164503 A1 | 6/2009 | Jung et al. |
| 2009/0164549 A1 | 6/2009 | Jung et al. |
| 2009/0171164 A1 | 7/2009 | Jung et al. |
| 2009/0171232 A1 | 7/2009 | Hu et al. |
| 2009/0171240 A1 | 7/2009 | Aguilar et al. |
| 2009/0171405 A1 | 7/2009 | Craig |
| 2009/0172540 A1 | 7/2009 | Jung et al. |
| 2009/0177050 A1 | 7/2009 | Griffiths et al. |
| 2009/0177090 A1 | 7/2009 | Grunwald et al. |
| 2009/0177108 A1 | 7/2009 | Shieh et al. |
| 2009/0177144 A1 | 7/2009 | Masmanidis et al. |
| 2009/0179642 A1 | 7/2009 | deCharms |
| 2009/0182211 A1 | 7/2009 | Diab et al. |
| 2009/0187230 A1 | 7/2009 | Dilorenzo |
| 2009/0191131 A1 | 7/2009 | Fossheim et al. |
| 2009/0192394 A1 | 7/2009 | Guttag et al. |
| 2009/0192556 A1 | 7/2009 | Wu et al. |
| 2009/0198144 A1 | 8/2009 | Phillips et al. |
| 2009/0198145 A1 | 8/2009 | Chow |
| 2009/0204015 A1 | 8/2009 | Phillips et al. |
| 2009/0209831 A1 | 8/2009 | Kucharczyk et al. |
| 2009/0209835 A1 | 8/2009 | Diab et al. |
| 2009/0209845 A1 | 8/2009 | Christen et al. |
| 2009/0210018 A1 | 8/2009 | Lozano |
| 2009/0216091 A1 | 8/2009 | Arndt |
| 2009/0216146 A1 | 8/2009 | Teicher et al. |
| 2009/0216288 A1 | 8/2009 | Schiff et al. |
| 2009/0220425 A1 | 9/2009 | Moxon et al. |
| 2009/0220429 A1 | 9/2009 | Johnsen et al. |
| 2009/0221904 A1 | 9/2009 | Shealy et al. |
| 2009/0221928 A1* | 9/2009 | Einav .................. A61B 5/4076 601/5 |
| 2009/0221930 A1 | 9/2009 | Laken |
| 2009/0227876 A1 | 9/2009 | Tran |
| 2009/0227877 A1 | 9/2009 | Tran |
| 2009/0227882 A1 | 9/2009 | Foo |
| 2009/0227889 A2 | 9/2009 | John et al. |
| 2009/0234419 A1 | 9/2009 | Maschino et al. |
| 2009/0240119 A1 | 9/2009 | Schwaibold et al. |
| 2009/0243756 A1 | 10/2009 | Stevenson et al. |
| 2009/0246138 A1 | 10/2009 | Santosh et al. |
| 2009/0247893 A1 | 10/2009 | Lapinlampi et al. |
| 2009/0247894 A1 | 10/2009 | Causevic |
| 2009/0259277 A1 | 10/2009 | Cornejo Cruz et al. |
| 2009/0261832 A1 | 10/2009 | DePavia et al. |
| 2009/0264785 A1 | 10/2009 | Causevic et al. |
| 2009/0264789 A1 | 10/2009 | Molnar et al. |
| 2009/0264952 A1 | 10/2009 | Jassemidis et al. |
| 2009/0264954 A1 | 10/2009 | Rise et al. |
| 2009/0264955 A1 | 10/2009 | Giftakis et al. |
| 2009/0264956 A1 | 10/2009 | Rise et al. |
| 2009/0264957 A1 | 10/2009 | Giftakis et al. |
| 2009/0264958 A1 | 10/2009 | Hsu et al. |
| 2009/0264967 A1 | 10/2009 | Giftakis et al. |
| 2009/0267758 A1 | 10/2009 | Hyde et al. |
| 2009/0270687 A1 | 10/2009 | Hyde et al. |
| 2009/0270688 A1 | 10/2009 | Hyde et al. |
| 2009/0270692 A1 | 10/2009 | Hyde et al. |
| 2009/0270693 A1 | 10/2009 | Hyde et al. |
| 2009/0270694 A1 | 10/2009 | Hyde et al. |
| 2009/0270754 A1 | 10/2009 | Moridaira |
| 2009/0270758 A1 | 10/2009 | Eagleman et al. |
| 2009/0270786 A1 | 10/2009 | Hyde et al. |
| 2009/0270944 A1 | 10/2009 | Whitehurst et al. |
| 2009/0271011 A1 | 10/2009 | Hyde et al. |

(56) References Cited

U.S. PATENT DOCUMENTS

| | | |
|---|---|---|
| 2009/0271120 A1 | 10/2009 | Hyde et al. |
| 2009/0271122 A1 | 10/2009 | Hyde et al. |
| 2009/0271347 A1 | 10/2009 | Hyde et al. |
| 2009/0275853 A1 | 11/2009 | Sarkela |
| 2009/0276011 A1 | 11/2009 | Hyde et al. |
| 2009/0276012 A1 | 11/2009 | Hyde et al. |
| 2009/0280153 A1 | 11/2009 | Hunter et al. |
| 2009/0281400 A1 | 11/2009 | McCraty et al. |
| 2009/0281448 A1 | 11/2009 | Wright et al. |
| 2009/0281594 A1 | 11/2009 | King et al. |
| 2009/0287035 A1 | 11/2009 | Dietrich et al. |
| 2009/0287107 A1 | 11/2009 | Beck-Nielsen et al. |
| 2009/0287108 A1 | 11/2009 | Levy |
| 2009/0287271 A1 | 11/2009 | Blum et al. |
| 2009/0287272 A1 | 11/2009 | Kokones et al. |
| 2009/0287273 A1 | 11/2009 | Carlton et al. |
| 2009/0287274 A1 | 11/2009 | De Ridder |
| 2009/0287467 A1 | 11/2009 | Sparks et al. |
| 2009/0290767 A1 | 11/2009 | Jung et al. |
| 2009/0290772 A1 | 11/2009 | Avinash et al. |
| 2009/0292180 A1 | 11/2009 | Mirow |
| 2009/0292478 A1 | 11/2009 | Avinash et al. |
| 2009/0292551 A1 | 11/2009 | Sirohey et al. |
| 2009/0292713 A1 | 11/2009 | Jung et al. |
| 2009/0292724 A1 | 11/2009 | Jung et al. |
| 2009/0297000 A1 | 12/2009 | Shahaf et al. |
| 2009/0299126 A1 | 12/2009 | Fowler et al. |
| 2009/0299169 A1 | 12/2009 | deCharms |
| 2009/0299435 A1 | 12/2009 | Gliner et al. |
| 2009/0304582 A1 | 12/2009 | Rousso et al. |
| 2009/0306491 A1 | 12/2009 | Haggers |
| 2009/0306531 A1 | 12/2009 | Leuthardt et al. |
| 2009/0306532 A1 | 12/2009 | Tucker |
| 2009/0306534 A1 | 12/2009 | Pizzagalli |
| 2009/0306741 A1 | 12/2009 | Hogle et al. |
| 2009/0311655 A1 | 12/2009 | Karkanias et al. |
| 2009/0312595 A1 | 12/2009 | Leuthardt et al. |
| 2009/0312624 A1 | 12/2009 | Berridge et al. |
| 2009/0312646 A1 | 12/2009 | Binder et al. |
| 2009/0312663 A1 | 12/2009 | John et al. |
| 2009/0312664 A1 | 12/2009 | Rodriguez Villegas et al. |
| 2009/0312668 A1 | 12/2009 | Leuthardt et al. |
| 2009/0312808 A1 | 12/2009 | Tyler et al. |
| 2009/0312817 A1 | 12/2009 | Hogle et al. |
| 2009/0312998 A1 | 12/2009 | Berckmans et al. |
| 2009/0316925 A1 | 12/2009 | Eisenfeld et al. |
| 2009/0316968 A1 | 12/2009 | Fueyo et al. |
| 2009/0316969 A1 | 12/2009 | Fueyo et al. |
| 2009/0318773 A1 | 12/2009 | Jung et al. |
| 2009/0318779 A1 | 12/2009 | Tran |
| 2009/0318794 A1 | 12/2009 | DeCharms |
| 2009/0319000 A1 | 12/2009 | Firlik et al. |
| 2009/0319001 A1 | 12/2009 | Schiff |
| 2009/0319002 A1 | 12/2009 | Simon |
| 2009/0319004 A1 | 12/2009 | Sabel |
| 2009/0322331 A1 | 12/2009 | Buracas |
| 2009/0323049 A1 | 12/2009 | Addison et al. |
| 2009/0326353 A1 | 12/2009 | Watson et al. |
| 2009/0326604 A1 | 12/2009 | Tyler et al. |
| 2009/0326605 A1 | 12/2009 | Morrell |
| 2009/0327068 A1 | 12/2009 | Pradeep et al. |
| 2010/0003656 A1 | 1/2010 | Kilgard et al. |
| 2010/0004500 A1 | 1/2010 | Gliner et al. |
| 2010/0004705 A1 | 1/2010 | Kilgard et al. |
| 2010/0004717 A1 | 1/2010 | Kilgard et al. |
| 2010/0004762 A1 | 1/2010 | Leuthardt et al. |
| 2010/0004977 A1 | 1/2010 | Marci et al. |
| 2010/0010289 A1 | 1/2010 | Clare |
| 2010/0010316 A1 | 1/2010 | Fueyo et al. |
| 2010/0010363 A1 | 1/2010 | Fueyo et al. |
| 2010/0010364 A1 | 1/2010 | Verbitskiy |
| 2010/0010365 A1 | 1/2010 | Terao et al. |
| 2010/0010366 A1 | 1/2010 | Silberstein |
| 2010/0010383 A1 | 1/2010 | Skelton et al. |
| 2010/0010388 A1 | 1/2010 | Panken et al. |
| 2010/0010391 A1 | 1/2010 | Skelton et al. |
| 2010/0010392 A1 | 1/2010 | Skelton et al. |
| 2010/0010571 A1 | 1/2010 | Skelton et al. |
| 2010/0010572 A1 | 1/2010 | Skelton et al. |
| 2010/0010573 A1 | 1/2010 | Skelton et al. |
| 2010/0010574 A1 | 1/2010 | Skelton et al. |
| 2010/0010575 A1 | 1/2010 | Skelton et al. |
| 2010/0010576 A1 | 1/2010 | Skelton et al. |
| 2010/0010577 A1 | 1/2010 | Skelton et al. |
| 2010/0010578 A1 | 1/2010 | Skelton et al. |
| 2010/0010579 A1 | 1/2010 | Skelton et al. |
| 2010/0010580 A1 | 1/2010 | Skelton et al. |
| 2010/0010584 A1 | 1/2010 | Skelton et al. |
| 2010/0010585 A1 | 1/2010 | Davis et al. |
| 2010/0010587 A1 | 1/2010 | Skelton et al. |
| 2010/0010588 A1 | 1/2010 | Skelton et al. |
| 2010/0010589 A1 | 1/2010 | Skelton et al. |
| 2010/0010590 A1 | 1/2010 | Skelton et al. |
| 2010/0010844 A1 | 1/2010 | Isaksen |
| 2010/0014730 A1 | 1/2010 | Hahn et al. |
| 2010/0014732 A1 | 1/2010 | Vija et al. |
| 2010/0015583 A1 | 1/2010 | Leuthardt et al. |
| 2010/0016783 A1 | 1/2010 | Bourke, Jr. et al. |
| 2010/0017001 A1 | 1/2010 | Leuthardt et al. |
| 2010/0021378 A1 | 1/2010 | Rousso et al. |
| 2010/0022820 A1 | 1/2010 | Leuthardt et al. |
| 2010/0023089 A1 | 1/2010 | DiLorenzo |
| 2010/0028841 A1* | 2/2010 | Eatough ................. G09B 5/065 |
| | | 434/362 |
| 2010/0030073 A1 | 2/2010 | Kalafut |
| 2010/0030089 A1 | 2/2010 | Hyde et al. |
| 2010/0030097 A1 | 2/2010 | Silberstein |
| 2010/0030287 A1 | 2/2010 | Jaax et al. |
| 2010/0036211 A1 | 2/2010 | La Rue et al. |
| 2010/0036233 A1 | 2/2010 | Zhu et al. |
| 2010/0036276 A1 | 2/2010 | Ochs |
| 2010/0036453 A1 | 2/2010 | Hulvershorn et al. |
| 2010/0041949 A1 | 2/2010 | Tolkowsky |
| 2010/0041958 A1 | 2/2010 | Leuthardt et al. |
| 2010/0041962 A1 | 2/2010 | Causevic et al. |
| 2010/0041964 A1 | 2/2010 | Hyde et al. |
| 2010/0042011 A1 | 2/2010 | Doidge et al. |
| 2010/0042578 A1 | 2/2010 | Leuthardt et al. |
| 2010/0043795 A1 | 2/2010 | Ujhazy et al. |
| 2010/0045467 A1 | 2/2010 | Sachanandani et al. |
| 2010/0049069 A1 | 2/2010 | Tarassenko et al. |
| 2010/0049075 A1 | 2/2010 | Bolger et al. |
| 2010/0049276 A1 | 2/2010 | Blum et al. |
| 2010/0049482 A1 | 2/2010 | He et al. |
| 2010/0056276 A1 | 3/2010 | Silberstein |
| 2010/0056854 A1* | 3/2010 | Chang ................... A61M 21/00 |
| | | 600/28 |
| 2010/0056939 A1 | 3/2010 | Tarassenko et al. |
| 2010/0057159 A1 | 3/2010 | Lozano |
| 2010/0057160 A1 | 3/2010 | De Ridder |
| 2010/0057655 A1 | 3/2010 | Jacobson et al. |
| 2010/0063368 A1 | 3/2010 | Leuthardt et al. |
| 2010/0063563 A1 | 3/2010 | Craig |
| 2010/0068751 A1 | 3/2010 | Eberle |
| 2010/0069724 A1 | 3/2010 | Leuthardt et al. |
| 2010/0069739 A1 | 3/2010 | deCharms |
| 2010/0069762 A1 | 3/2010 | Mietus et al. |
| 2010/0069775 A1 | 3/2010 | Milgramm et al. |
| 2010/0069777 A1 | 3/2010 | Marks |
| 2010/0069780 A1 | 3/2010 | Schuette et al. |
| 2010/0070001 A1 | 3/2010 | Goetz |
| 2010/0076249 A1 | 3/2010 | Leuthardt et al. |
| 2010/0076253 A1 | 3/2010 | Altman et al. |
| 2010/0076274 A1 | 3/2010 | Severson |
| 2010/0076333 A9 | 3/2010 | Burton et al. |
| 2010/0076334 A1 | 3/2010 | Rothblatt |
| 2010/0076338 A1 | 3/2010 | Kwak |
| 2010/0076525 A1 | 3/2010 | Skelton et al. |
| 2010/0079292 A1 | 4/2010 | Lynn et al. |
| 2010/0080432 A1 | 4/2010 | Lilja et al. |
| 2010/0081860 A1 | 4/2010 | Leuthardt et al. |
| 2010/0081861 A1 | 4/2010 | Leuthardt et al. |
| 2010/0082506 A1 | 4/2010 | Avinash et al. |
| 2010/0087719 A1 | 4/2010 | Benni |

(56)               References Cited

U.S. PATENT DOCUMENTS

| | | |
|---|---|---|
| 2010/0087900 A1 | 4/2010 | Flint |
| 2010/0090835 A1 | 4/2010 | Liu et al. |
| 2010/0092934 A1 | 4/2010 | Silberstein |
| 2010/0094103 A1 | 4/2010 | Kaplan et al. |
| 2010/0094152 A1 | 4/2010 | Semmlow |
| 2010/0094154 A1 | 4/2010 | Schalk et al. |
| 2010/0094155 A1 | 4/2010 | Prichep |
| 2010/0098289 A1 | 4/2010 | Tognoli et al. |
| 2010/0099954 A1 | 4/2010 | Dickinson et al. |
| 2010/0099975 A1 | 4/2010 | Faro et al. |
| 2010/0100036 A1 | 4/2010 | Leuthardt et al. |
| 2010/0100164 A1 | 4/2010 | Johnson et al. |
| 2010/0106041 A1 | 4/2010 | Ghovanloo et al. |
| 2010/0106043 A1 | 4/2010 | Robinson et al. |
| 2010/0106044 A1 | 4/2010 | Linderman |
| 2010/0106217 A1 | 4/2010 | Colborn |
| 2010/0113959 A1 | 5/2010 | Pascual-Leone et al. |
| 2010/0114190 A1 | 5/2010 | Bendett et al. |
| 2010/0114192 A1 | 5/2010 | Jaax et al. |
| 2010/0114193 A1 | 5/2010 | Lozano et al. |
| 2010/0114237 A1 | 5/2010 | Giftakis et al. |
| 2010/0114272 A1 | 5/2010 | Haidarliu et al. |
| 2010/0114813 A1 | 5/2010 | Zalay et al. |
| 2010/0121415 A1 | 5/2010 | Skelton et al. |
| 2010/0125219 A1 | 5/2010 | Harris et al. |
| 2010/0125304 A1 | 5/2010 | Faltys |
| 2010/0125561 A1 | 5/2010 | Leuthardt et al. |
| 2010/0130811 A1 | 5/2010 | Leuthardt et al. |
| 2010/0130812 A1 | 5/2010 | Martel |
| 2010/0130869 A1 | 5/2010 | Hauger et al. |
| 2010/0130878 A1 | 5/2010 | Lasso et al. |
| 2010/0131030 A1 | 5/2010 | Firlik et al. |
| 2010/0131034 A1 | 5/2010 | Gliner et al. |
| 2010/0132448 A1 | 6/2010 | Donadille et al. |
| 2010/0134113 A1 | 6/2010 | DePavia et al. |
| 2010/0135556 A1 | 6/2010 | Razifar et al. |
| 2010/0137728 A1 | 6/2010 | Govari |
| 2010/0137937 A1 | 6/2010 | John et al. |
| 2010/0142774 A1 | 6/2010 | Ben-Haim et al. |
| 2010/0143256 A1 | 6/2010 | Suffin et al. |
| 2010/0145215 A1 | 6/2010 | Pradeep et al. |
| 2010/0145219 A1 | 6/2010 | Grey |
| 2010/0145427 A1 | 6/2010 | Gliner et al. |
| 2010/0145428 A1 | 6/2010 | Cameron et al. |
| 2010/0152621 A1 | 6/2010 | Janna et al. |
| 2010/0160737 A1 | 6/2010 | Shachar et al. |
| 2010/0163027 A1 | 7/2010 | Hyde et al. |
| 2010/0163028 A1 | 7/2010 | Hyde et al. |
| 2010/0163035 A1 | 7/2010 | Hyde et al. |
| 2010/0165593 A1 | 7/2010 | Townsend et al. |
| 2010/0168053 A1 | 7/2010 | Kurtz |
| 2010/0168525 A1 | 7/2010 | Hyde et al. |
| 2010/0168529 A1 | 7/2010 | Hyde et al. |
| 2010/0168602 A1 | 7/2010 | Hyde et al. |
| 2010/0172567 A1 | 7/2010 | Prokoski |
| 2010/0174161 A1 | 7/2010 | Lynn |
| 2010/0174533 A1 | 7/2010 | Pakhomov |
| 2010/0179415 A1 | 7/2010 | Wenzel et al. |
| 2010/0179447 A1 | 7/2010 | Hunt |
| 2010/0185113 A1 | 7/2010 | Peot et al. |
| 2010/0189318 A1 | 7/2010 | Chang et al. |
| 2010/0191095 A1 | 7/2010 | Felblinger et al. |
| 2010/0191124 A1 | 7/2010 | Prokoski |
| 2010/0191139 A1 | 7/2010 | Jacquin et al. |
| 2010/0191304 A1 | 7/2010 | Scott |
| 2010/0191305 A1 | 7/2010 | Imran et al. |
| 2010/0195770 A1 | 8/2010 | Ricci et al. |
| 2010/0197610 A1 | 8/2010 | Lian et al. |
| 2010/0197993 A1 | 8/2010 | Vasishta |
| 2010/0198090 A1 | 8/2010 | Hudson et al. |
| 2010/0198098 A1 | 8/2010 | Osorio et al. |
| 2010/0198101 A1 | 8/2010 | Song et al. |
| 2010/0198282 A1 | 8/2010 | Rogers |
| 2010/0198296 A1 | 8/2010 | Ignagni et al. |
| 2010/0198519 A1 | 8/2010 | Wilt et al. |
| 2010/0204604 A1 | 8/2010 | Liley et al. |
| 2010/0204614 A1 | 8/2010 | Lindquist et al. |
| 2010/0204748 A1 | 8/2010 | Lozano et al. |
| 2010/0204749 A1 | 8/2010 | Thimineur et al. |
| 2010/0204750 A1 | 8/2010 | Hargrove et al. |
| 2010/0217100 A1 | 8/2010 | LeBoeuf et al. |
| 2010/0217146 A1 | 8/2010 | Osvath |
| 2010/0217341 A1 | 8/2010 | John et al. |
| 2010/0217348 A1 | 8/2010 | DiLorenzo |
| 2010/0219820 A1 | 9/2010 | Skidmore et al. |
| 2010/0222640 A1 | 9/2010 | Anderson et al. |
| 2010/0222694 A1 | 9/2010 | Causevic |
| 2010/0222845 A1 | 9/2010 | Goetz |
| 2010/0224188 A1 | 9/2010 | John et al. |
| 2010/0231221 A1 | 9/2010 | Rosthal et al. |
| 2010/0231327 A1 | 9/2010 | Johnson et al. |
| 2010/0234705 A1 | 9/2010 | Lynn |
| 2010/0234752 A1 | 9/2010 | Sullivan et al. |
| 2010/0234753 A1 | 9/2010 | Ma |
| 2010/0238763 A1 | 9/2010 | Gzara et al. |
| 2010/0241020 A1 | 9/2010 | Zaidel et al. |
| 2010/0241195 A1 | 9/2010 | Meadows et al. |
| 2010/0241449 A1 | 9/2010 | Firminger et al. |
| 2010/0245093 A1 | 9/2010 | Kobetski et al. |
| 2010/0248275 A1 | 9/2010 | Jackowski et al. |
| 2010/0249573 A1 | 9/2010 | Marks |
| 2010/0249627 A1 | 9/2010 | Zhang et al. |
| 2010/0249635 A1 | 9/2010 | Van Der Reijden |
| 2010/0249638 A1 | 9/2010 | Liley |
| 2010/0256592 A1 | 10/2010 | Gerber et al. |
| 2010/0258126 A1 | 10/2010 | Ujhazy et al. |
| 2010/0260402 A1 | 10/2010 | Axelsson et al. |
| 2010/0261977 A1 | 10/2010 | Seely |
| 2010/0261993 A1 | 10/2010 | Van Der Kouwe et al. |
| 2010/0262377 A1 | 10/2010 | Jensen |
| 2010/0268055 A1 | 10/2010 | Jung et al. |
| 2010/0268057 A1 | 10/2010 | Firminger et al. |
| 2010/0268108 A1 | 10/2010 | Firminger et al. |
| 2010/0268288 A1 | 10/2010 | Hunter et al. |
| 2010/0274106 A1 | 10/2010 | Heruth et al. |
| 2010/0274141 A1 | 10/2010 | Patangay et al. |
| 2010/0274147 A1 | 10/2010 | Patangay et al. |
| 2010/0274303 A1 | 10/2010 | Bukhman |
| 2010/0274305 A1 | 10/2010 | Gliner et al. |
| 2010/0274308 A1 | 10/2010 | Scott |
| 2010/0274577 A1 | 10/2010 | Firminger et al. |
| 2010/0274578 A1 | 10/2010 | Firminger et al. |
| 2010/0280332 A1 | 11/2010 | Hyde et al. |
| 2010/0280334 A1 | 11/2010 | Carlson et al. |
| 2010/0280335 A1 | 11/2010 | Carlson et al. |
| 2010/0280372 A1 | 11/2010 | Poolman et al. |
| 2010/0280403 A1 | 11/2010 | Erdogmus et al. |
| 2010/0280500 A1 | 11/2010 | Skelton et al. |
| 2010/0280571 A1 | 11/2010 | Sloan |
| 2010/0280574 A1 | 11/2010 | Carlson et al. |
| 2010/0280579 A1 | 11/2010 | Denison et al. |
| 2010/0286549 A1 | 11/2010 | John et al. |
| 2010/0286747 A1* | 11/2010 | Sabesan ............... A61B 5/4094<br>607/45 |
| 2010/0292602 A1 | 11/2010 | Worrell et al. |
| 2010/0292752 A1 | 11/2010 | Bardakjian et al. |
| 2010/0293002 A1 | 11/2010 | Firminger et al. |
| 2010/0293115 A1 | 11/2010 | Seyed Momen |
| 2010/0298624 A1 | 11/2010 | Becker |
| 2010/0298735 A1 | 11/2010 | Suffin |
| 2010/0303101 A1 | 12/2010 | Lazar et al. |
| 2010/0305962 A1 | 12/2010 | Firminger et al. |
| 2010/0305963 A1 | 12/2010 | Firminger et al. |
| 2010/0312188 A1 | 12/2010 | Robertson et al. |
| 2010/0312579 A1 | 12/2010 | Firminger et al. |
| 2010/0318025 A1 | 12/2010 | John |
| 2010/0318160 A1 | 12/2010 | Stevenson et al. |
| 2010/0322488 A1 | 12/2010 | Virtue et al. |
| 2010/0322497 A1 | 12/2010 | Dempsey et al. |
| 2010/0324441 A1 | 12/2010 | Hargrove et al. |
| 2010/0331649 A1 | 12/2010 | Chou |
| 2010/0331715 A1 | 12/2010 | Addison et al. |
| 2010/0331976 A1 | 12/2010 | Pesaran et al. |
| 2011/0004115 A1 | 1/2011 | Shahaf et al. |

(56) References Cited

U.S. PATENT DOCUMENTS

| | | |
|---|---|---|
| 2011/0004270 A1 | 1/2011 | Sheffield et al. |
| 2011/0004283 A1 | 1/2011 | Stevenson et al. |
| 2011/0004412 A1 | 1/2011 | Shahaf et al. |
| 2011/0007129 A1 | 1/2011 | Martin et al. |
| 2011/0009715 A1 | 1/2011 | O' Reilly et al. |
| 2011/0009729 A1 | 1/2011 | Shin et al. |
| 2011/0009752 A1 | 1/2011 | Chen et al. |
| 2011/0009777 A1 | 1/2011 | Reichow et al. |
| 2011/0009920 A1 | 1/2011 | Whitehurst et al. |
| 2011/0009928 A1 | 1/2011 | Gerber et al. |
| 2011/0015209 A1 | 1/2011 | Shamloo et al. |
| 2011/0015469 A1 | 1/2011 | Walter et al. |
| 2011/0015501 A1 | 1/2011 | Lynn et al. |
| 2011/0015515 A1 | 1/2011 | deCharms |
| 2011/0015536 A1 | 1/2011 | Milgramm et al. |
| 2011/0015539 A1 | 1/2011 | deCharms |
| 2011/0021899 A1 | 1/2011 | Arps et al. |
| 2011/0021970 A1 | 1/2011 | Vo-Dinh et al. |
| 2011/0022981 A1 | 1/2011 | Mahajan et al. |
| 2011/0028798 A1 | 2/2011 | Hyde et al. |
| 2011/0028799 A1 | 2/2011 | Hyde et al. |
| 2011/0028802 A1 | 2/2011 | Addison et al. |
| 2011/0028825 A1 | 2/2011 | Douglas et al. |
| 2011/0028827 A1 | 2/2011 | Sitaram et al. |
| 2011/0028859 A1 | 2/2011 | Chian |
| 2011/0029038 A1 | 2/2011 | Hyde et al. |
| 2011/0029044 A1 | 2/2011 | Hyde et al. |
| 2011/0034812 A1 | 2/2011 | Patangay et al. |
| 2011/0034821 A1 | 2/2011 | Ekpar |
| 2011/0034822 A1 | 2/2011 | Phillips et al. |
| 2011/0034912 A1 | 2/2011 | de Graff et al. |
| 2011/0035231 A1 | 2/2011 | Firminger et al. |
| 2011/0038515 A1 | 2/2011 | Jacquin et al. |
| 2011/0038850 A1 | 2/2011 | Bagnol et al. |
| 2011/0040202 A1 | 2/2011 | Luo et al. |
| 2011/0040356 A1 | 2/2011 | Schiffer |
| 2011/0040546 A1 | 2/2011 | Gerber et al. |
| 2011/0040547 A1 | 2/2011 | Gerber et al. |
| 2011/0040713 A1 | 2/2011 | Colman et al. |
| 2011/0043759 A1 | 2/2011 | Bushinsky |
| 2011/0046451 A1 | 2/2011 | Horn et al. |
| 2011/0046473 A1 | 2/2011 | Pradeep et al. |
| 2011/0046491 A1 | 2/2011 | Diamond |
| 2011/0050232 A1 | 3/2011 | Wilt et al. |
| 2011/0054272 A1 | 3/2011 | Derchak |
| 2011/0054279 A1 | 3/2011 | Reisfeld et al. |
| 2011/0054345 A1 | 3/2011 | Nagatani |
| 2011/0054562 A1 | 3/2011 | Gliner |
| 2011/0054569 A1 | 3/2011 | Zitnik et al. |
| 2011/0060382 A1 | 3/2011 | Jaax et al. |
| 2011/0066005 A1 | 3/2011 | Rotenberg |
| 2011/0066041 A1 | 3/2011 | Pandia et al. |
| 2011/0066042 A1 | 3/2011 | Pandia et al. |
| 2011/0066053 A1 | 3/2011 | Yazicioglu |
| 2011/0074396 A1 | 3/2011 | Liao et al. |
| 2011/0077503 A1 | 3/2011 | Bonilha et al. |
| 2011/0077538 A1 | 3/2011 | Liu et al. |
| 2011/0077548 A1 | 3/2011 | Torch |
| 2011/0077721 A1 | 3/2011 | Whitehurst et al. |
| 2011/0082154 A1 | 4/2011 | Oksenberg et al. |
| 2011/0082360 A1 | 4/2011 | Fuchs et al. |
| 2011/0082381 A1 | 4/2011 | Uthman et al. |
| 2011/0082522 A1 | 4/2011 | Bourget et al. |
| 2011/0087125 A1 | 4/2011 | Causevic |
| 2011/0087127 A1 | 4/2011 | Sarkela et al. |
| 2011/0092800 A1 | 4/2011 | Yoo et al. |
| 2011/0092834 A1 | 4/2011 | Yazicioglu et al. |
| 2011/0092839 A1 | 4/2011 | Alshaer et al. |
| 2011/0092882 A1 | 4/2011 | Firlik et al. |
| 2011/0093033 A1 | 4/2011 | Nekhendzy |
| 2011/0098583 A1 | 4/2011 | Pandia et al. |
| 2011/0098778 A1 | 4/2011 | Thimineur et al. |
| 2011/0105859 A1 | 5/2011 | Popovic et al. |
| 2011/0105915 A1 | 5/2011 | Bauer et al. |
| 2011/0105938 A1 | 5/2011 | Hardt |
| 2011/0105998 A1 | 5/2011 | Zhang et al. |
| 2011/0106206 A1 | 5/2011 | Schiff |
| 2011/0106750 A1 | 5/2011 | Pradeep et al. |
| 2011/0110868 A1 | 5/2011 | Akhtari et al. |
| 2011/0112379 A1 | 5/2011 | Li et al. |
| 2011/0112381 A1 | 5/2011 | Sun et al. |
| 2011/0112394 A1 | 5/2011 | Mishelevich |
| 2011/0112426 A1 | 5/2011 | Causevic |
| 2011/0112427 A1 | 5/2011 | Phillips et al. |
| 2011/0112590 A1 | 5/2011 | Wu et al. |
| 2011/0115624 A1 | 5/2011 | Tran |
| 2011/0118536 A1 | 5/2011 | Phillips et al. |
| 2011/0118618 A1 | 5/2011 | John et al. |
| 2011/0118619 A1 | 5/2011 | Burton et al. |
| 2011/0119212 A1 | 5/2011 | De Bruin et al. |
| 2011/0125046 A1 | 5/2011 | Burton et al. |
| 2011/0125048 A1 | 5/2011 | Causevic et al. |
| 2011/0125077 A1 | 5/2011 | Denison et al. |
| 2011/0125078 A1 | 5/2011 | Denison et al. |
| 2011/0125203 A1 | 5/2011 | Simon et al. |
| 2011/0125238 A1 | 5/2011 | Nofzinger |
| 2011/0129129 A1 | 6/2011 | Avinash et al. |
| 2011/0130615 A1 | 6/2011 | Mishelevich |
| 2011/0130643 A1 | 6/2011 | Derchak et al. |
| 2011/0130675 A1 | 6/2011 | Bibian et al. |
| 2011/0137371 A1 | 6/2011 | Giftakis et al. |
| 2011/0137381 A1 | 6/2011 | Lee et al. |
| 2011/0144520 A1 | 6/2011 | Causevic et al. |
| 2011/0144521 A1 | 6/2011 | Molnar et al. |
| 2011/0150253 A1 | 6/2011 | Corona-Strauss et al. |
| 2011/0152284 A1 | 6/2011 | Wieloch et al. |
| 2011/0152710 A1 | 6/2011 | Kim et al. |
| 2011/0152729 A1 | 6/2011 | Oohashi et al. |
| 2011/0152967 A1 | 6/2011 | Simon et al. |
| 2011/0152988 A1 | 6/2011 | Whitehurst et al. |
| 2011/0160543 A1 | 6/2011 | Parsey et al. |
| 2011/0160607 A1 | 6/2011 | John et al. |
| 2011/0160608 A1 | 6/2011 | Hargrove |
| 2011/0160795 A1 | 6/2011 | Osorio |
| 2011/0160796 A1 | 6/2011 | Lane et al. |
| 2011/0161011 A1 | 6/2011 | Hasson et al. |
| 2011/0162645 A1 | 7/2011 | John et al. |
| 2011/0166430 A1 | 7/2011 | Harris et al. |
| 2011/0166471 A1 | 7/2011 | Drew et al. |
| 2011/0166546 A1 | 7/2011 | Jaax et al. |
| 2011/0172500 A1 | 7/2011 | Van Dooren et al. |
| 2011/0172509 A1 | 7/2011 | Chance |
| 2011/0172553 A1* | 7/2011 | John ................... A61B 5/4833 |
| | | 600/544 |
| 2011/0172554 A1 | 7/2011 | Leyde et al. |
| 2011/0172562 A1 | 7/2011 | Sahasrabudhe et al. |
| 2011/0172564 A1 | 7/2011 | Drew |
| 2011/0172567 A1 | 7/2011 | Panken et al. |
| 2011/0172725 A1 | 7/2011 | Wells et al. |
| 2011/0172732 A1 | 7/2011 | Maschino |
| 2011/0172738 A1 | 7/2011 | Davis et al. |
| 2011/0172739 A1 | 7/2011 | Mann et al. |
| 2011/0172743 A1 | 7/2011 | Davis et al. |
| 2011/0172927 A1 | 7/2011 | Sahasrabudhe et al. |
| 2011/0178359 A1 | 7/2011 | Hirschman et al. |
| 2011/0178441 A1 | 7/2011 | Tyler |
| 2011/0178442 A1 | 7/2011 | Mishelevich |
| 2011/0178581 A1 | 7/2011 | Haber et al. |
| 2011/0181422 A1 | 7/2011 | Tran |
| 2011/0182501 A1 | 7/2011 | Mercier et al. |
| 2011/0184305 A1 | 7/2011 | Liley |
| 2011/0184487 A1 | 7/2011 | Alberts et al. |
| 2011/0184650 A1 | 7/2011 | Hymel |
| 2011/0190569 A1 | 8/2011 | Simon et al. |
| 2011/0190600 A1 | 8/2011 | McKenna et al. |
| 2011/0190846 A1 | 8/2011 | Ruffini et al. |
| 2011/0191275 A1 | 8/2011 | Lujan et al. |
| 2011/0191350 A1 | 8/2011 | Zhang et al. |
| 2011/0196693 A1 | 8/2011 | Hargrove et al. |
| 2011/0201944 A1 | 8/2011 | Higgins et al. |
| 2011/0207988 A1 | 8/2011 | Ruohonen et al. |
| 2011/0208012 A1 | 8/2011 | Gerber et al. |
| 2011/0208094 A1 | 8/2011 | Mishelevich |
| 2011/0208264 A1 | 8/2011 | Gliner et al. |

(56)          References Cited

U.S. PATENT DOCUMENTS

| | | |
|---|---|---|
| 2011/0208539 A1 | 8/2011 | Lynn |
| 2011/0213200 A1 | 9/2011 | Mishelevich |
| 2011/0213222 A1 | 9/2011 | Leyde et al. |
| 2011/0217240 A1 | 9/2011 | Ferris |
| 2011/0218405 A1 | 9/2011 | Avinash et al. |
| 2011/0218453 A1 | 9/2011 | Hirata et al. |
| 2011/0218456 A1 | 9/2011 | Graham et al. |
| 2011/0218950 A1 | 9/2011 | Mirowski et al. |
| 2011/0224569 A1 | 9/2011 | Isenhart et al. |
| 2011/0224570 A1 | 9/2011 | Causevic |
| 2011/0224571 A1 | 9/2011 | Pascual-Leone et al. |
| 2011/0224602 A1 | 9/2011 | Struijk et al. |
| 2011/0224749 A1 | 9/2011 | Ben-David et al. |
| 2011/0229005 A1 | 9/2011 | Den Harder et al. |
| 2011/0230701 A1 | 9/2011 | Simon et al. |
| 2011/0230738 A1 | 9/2011 | Chance |
| 2011/0230755 A1 | 9/2011 | MacFarlane et al. |
| 2011/0230938 A1 | 9/2011 | Simon et al. |
| 2011/0238130 A1 | 9/2011 | Bourget et al. |
| 2011/0238136 A1 | 9/2011 | Bourget et al. |
| 2011/0245709 A1 | 10/2011 | Greenwald |
| 2011/0245734 A1 | 10/2011 | Wagner et al. |
| 2011/0251583 A1 | 10/2011 | Miyazawa et al. |
| 2011/0251985 A1 | 10/2011 | Waxman et al. |
| 2011/0256520 A1 | 10/2011 | Siefert |
| 2011/0257501 A1 | 10/2011 | Huys et al. |
| 2011/0257517 A1 | 10/2011 | Guttag et al. |
| 2011/0257519 A1 | 10/2011 | Bj rnerud et al. |
| 2011/0263962 A1 | 10/2011 | Marks |
| 2011/0263968 A1 | 10/2011 | Quattrocki-Knight et al. |
| 2011/0263995 A1 | 10/2011 | Chen |
| 2011/0264182 A1 | 10/2011 | Cowley |
| 2011/0270074 A1 | 11/2011 | deCharms |
| 2011/0270095 A1 | 11/2011 | Bukhman |
| 2011/0270096 A1 | 11/2011 | Osorio et al. |
| 2011/0270117 A1 | 11/2011 | Warwick et al. |
| 2011/0270346 A1 | 11/2011 | Frei et al. |
| 2011/0270347 A1 | 11/2011 | Frei et al. |
| 2011/0270348 A1 | 11/2011 | Goetz |
| 2011/0270579 A1 | 11/2011 | Watson et al. |
| 2011/0270914 A1 | 11/2011 | Jung et al. |
| 2011/0275927 A1 | 11/2011 | Wagner et al. |
| 2011/0276107 A1 | 11/2011 | Simon et al. |
| 2011/0276112 A1 | 11/2011 | Simon et al. |
| 2011/0282225 A1 | 11/2011 | Anderson et al. |
| 2011/0282230 A9 | 11/2011 | Liley |
| 2011/0282234 A1 | 11/2011 | Ochs |
| 2011/0288119 A1 | 11/2011 | Chesworth et al. |
| 2011/0288400 A1 | 11/2011 | Russell et al. |
| 2011/0288424 A1 | 11/2011 | Kanai et al. |
| 2011/0288431 A1 | 11/2011 | Alshaer et al. |
| 2011/0293193 A1 | 12/2011 | Garg et al. |
| 2011/0295142 A1 | 12/2011 | Chakravarthy et al. |
| 2011/0295143 A1 | 12/2011 | Leuthardt et al. |
| 2011/0295166 A1 | 12/2011 | Dalton |
| 2011/0295338 A1 | 12/2011 | Rickert et al. |
| 2011/0295344 A1 | 12/2011 | Wells et al. |
| 2011/0295345 A1 | 12/2011 | Wells et al. |
| 2011/0295346 A1 | 12/2011 | Wells et al. |
| 2011/0295347 A1 | 12/2011 | Wells et al. |
| 2011/0298706 A1* | 12/2011 | Mann .......... H04W 88/02 345/157 |
| 2011/0301436 A1 | 12/2011 | Teixeira |
| 2011/0301439 A1 | 12/2011 | Albert et al. |
| 2011/0301441 A1 | 12/2011 | Bandic et al. |
| 2011/0301448 A1 | 12/2011 | deCharms |
| 2011/0301486 A1 | 12/2011 | Van Hek et al. |
| 2011/0301487 A1 | 12/2011 | Abeyratne et al. |
| 2011/0301488 A1 | 12/2011 | Schuette et al. |
| 2011/0301529 A1 | 12/2011 | Zhang et al. |
| 2011/0306845 A1 | 12/2011 | Osorio |
| 2011/0306846 A1 | 12/2011 | Osorio |
| 2011/0307029 A1 | 12/2011 | Hargrove |
| 2011/0307030 A1 | 12/2011 | John |
| 2011/0307079 A1 | 12/2011 | Oweiss et al. |
| 2011/0308789 A1 | 12/2011 | Zhang et al. |
| 2011/0311021 A1 | 12/2011 | Tsukagoshi |
| 2011/0311489 A1 | 12/2011 | Deisseroth et al. |
| 2011/0313268 A1 | 12/2011 | Kokones et al. |
| 2011/0313274 A1 | 12/2011 | Subbarao |
| 2011/0313308 A1 | 12/2011 | Zavoronkovs et al. |
| 2011/0313487 A1 | 12/2011 | Kokones et al. |
| 2011/0313760 A1 | 12/2011 | Ricci et al. |
| 2011/0319482 A1 | 12/2011 | Blower et al. |
| 2011/0319724 A1 | 12/2011 | Cox |
| 2011/0319726 A1 | 12/2011 | Sachanandani et al. |
| 2011/0319975 A1 | 12/2011 | Ho et al. |
| 2012/0003615 A1 | 1/2012 | Ochs |
| 2012/0004518 A1 | 1/2012 | D'Souza et al. |
| 2012/0004561 A1 | 1/2012 | John |
| 2012/0004564 A1 | 1/2012 | Daniel |
| 2012/0004579 A1 | 1/2012 | Luo et al. |
| 2012/0004749 A1 | 1/2012 | Abeyratne et al. |
| 2012/0010493 A1 | 1/2012 | Semenov |
| 2012/0010536 A1 | 1/2012 | Bolger et al. |
| 2012/0011927 A1 | 1/2012 | Badri et al. |
| 2012/0016218 A1 | 1/2012 | Lau et al. |
| 2012/0016252 A1 | 1/2012 | Melker et al. |
| 2012/0016336 A1 | 1/2012 | Whitehurst et al. |
| 2012/0016430 A1 | 1/2012 | Lozano |
| 2012/0016432 A1 | 1/2012 | Westendorp et al. |
| 2012/0016435 A1 | 1/2012 | Rom |
| 2012/0021394 A1 | 1/2012 | deCharms |
| 2012/0022336 A1 | 1/2012 | Teixeira |
| 2012/0022340 A1 | 1/2012 | Heruth et al. |
| 2012/0022343 A1 | 1/2012 | Shastri et al. |
| 2012/0022350 A1 | 1/2012 | Teixeira |
| 2012/0022351 A1 | 1/2012 | Starr |
| 2012/0022365 A1 | 1/2012 | Mansfield |
| 2012/0022384 A1 | 1/2012 | Teixeira |
| 2012/0022392 A1 | 1/2012 | Leuthardt et al. |
| 2012/0022611 A1 | 1/2012 | Firlik et al. |
| 2012/0022844 A1 | 1/2012 | Teixeira |
| 2012/0022884 A1 | 1/2012 | Chillemi |
| 2012/0029320 A1 | 2/2012 | Watson et al. |
| 2012/0029378 A1 | 2/2012 | Low |
| 2012/0029379 A1 | 2/2012 | Sivadas |
| 2012/0029591 A1 | 2/2012 | Simon et al. |
| 2012/0029601 A1 | 2/2012 | Simon et al. |
| 2012/0035428 A1 | 2/2012 | Roberts et al. |
| 2012/0035431 A1 | 2/2012 | Sun et al. |
| 2012/0035433 A1 | 2/2012 | Chance |
| 2012/0035698 A1 | 2/2012 | Johnson et al. |
| 2012/0035765 A1 | 2/2012 | Sato et al. |
| 2012/0036004 A1 | 2/2012 | Pradeep et al. |
| 2012/0041279 A1 | 2/2012 | Freeman et al. |
| 2012/0041318 A1 | 2/2012 | Taylor |
| 2012/0041319 A1 | 2/2012 | Taylor et al. |
| 2012/0041320 A1 | 2/2012 | Taylor |
| 2012/0041321 A1 | 2/2012 | Taylor et al. |
| 2012/0041322 A1 | 2/2012 | Taylor et al. |
| 2012/0041323 A1 | 2/2012 | Taylor et al. |
| 2012/0041324 A1 | 2/2012 | Taylor et al. |
| 2012/0041330 A1 | 2/2012 | Prichep et al. |
| 2012/0041498 A1 | 2/2012 | Gliner et al. |
| 2012/0041735 A1 | 2/2012 | Taylor |
| 2012/0041739 A1 | 2/2012 | Taylor |
| 2012/0046531 A1 | 2/2012 | Hua |
| 2012/0046535 A1 | 2/2012 | Lin et al. |
| 2012/0046711 A1 | 2/2012 | Osorio |
| 2012/0046715 A1 | 2/2012 | Moffitt et al. |
| 2012/0046971 A1 | 2/2012 | Walker et al. |
| 2012/0052469 A1 | 3/2012 | Sobel et al. |
| 2012/0052905 A1 | 3/2012 | Lim et al. |
| 2012/0053394 A1 | 3/2012 | Honeycutt |
| 2012/0053433 A1 | 3/2012 | Chamoun et al. |
| 2012/0053449 A1 | 3/2012 | Moses et al. |
| 2012/0053473 A1 | 3/2012 | Johnson et al. |
| 2012/0053476 A1 | 3/2012 | Hopenfeld |
| 2012/0053478 A1 | 3/2012 | Johnson et al. |
| 2012/0053479 A1 | 3/2012 | Hopenfeld |
| 2012/0053483 A1 | 3/2012 | Doidge et al. |
| 2012/0053491 A1 | 3/2012 | Nathan et al. |
| 2012/0053508 A1 | 3/2012 | Wu et al. |

(56)     References Cited

U.S. PATENT DOCUMENTS

| | | |
|---|---|---|
| 2012/0053919 A1 | 3/2012 | Taylor |
| 2012/0053921 A1 | 3/2012 | Taylor |
| 2012/0059246 A1 | 3/2012 | Taylor |
| 2012/0059273 A1 | 3/2012 | Meggiolaro et al. |
| 2012/0059431 A1 | 3/2012 | Williams et al. |
| 2012/0060851 A1 | 3/2012 | Amberg |
| 2012/0065536 A1 | 3/2012 | Causevic et al. |
| 2012/0070044 A1 | 3/2012 | Avinash et al. |
| 2012/0071771 A1 | 3/2012 | Behar |
| 2012/0078115 A1 | 3/2012 | Lonky |
| 2012/0078323 A1 | 3/2012 | Osorio |
| 2012/0078327 A1 | 3/2012 | Sloan et al. |
| 2012/0080305 A1 | 4/2012 | Koruga |
| 2012/0083668 A1 | 4/2012 | Pradeep et al. |
| 2012/0083690 A1 | 4/2012 | Semenov |
| 2012/0083700 A1 | 4/2012 | Osorio |
| 2012/0083701 A1 | 4/2012 | Osorio |
| 2012/0083708 A1 | 4/2012 | Rajdev et al. |
| 2012/0088987 A1 | 4/2012 | Braun et al. |
| 2012/0088992 A1 | 4/2012 | Armitstead |
| 2012/0089004 A1 | 4/2012 | Hsu et al. |
| 2012/0089205 A1 | 4/2012 | Boyden et al. |
| 2012/0092156 A1 | 4/2012 | Tran |
| 2012/0092157 A1 | 4/2012 | Tran |
| 2012/0095352 A1 | 4/2012 | Tran |
| 2012/0095357 A1 | 4/2012 | Tran |
| 2012/0100514 A1 | 4/2012 | Desain et al. |
| 2012/0101326 A1 | 4/2012 | Simon et al. |
| 2012/0101387 A1 | 4/2012 | Ji et al. |
| 2012/0101401 A1 | 4/2012 | Faul et al. |
| 2012/0101402 A1 | 4/2012 | Nguyen |
| 2012/0101430 A1 | 4/2012 | Robertson et al. |
| 2012/0101544 A1 | 4/2012 | Hoberman et al. |
| 2012/0108909 A1 | 5/2012 | Slobounov et al. |
| 2012/0108918 A1 | 5/2012 | Jarvik et al. |
| 2012/0108995 A1 | 5/2012 | Pradeep et al. |
| 2012/0108997 A1 | 5/2012 | Guan et al. |
| 2012/0108998 A1 | 5/2012 | Molnar et al. |
| 2012/0108999 A1 | 5/2012 | Leininger et al. |
| 2012/0109020 A1 | 5/2012 | Wagner et al. |
| 2012/0116149 A1 | 5/2012 | Pilla et al. |
| 2012/0116179 A1 | 5/2012 | Drew et al. |
| 2012/0116235 A1 | 5/2012 | Trumble et al. |
| 2012/0116244 A1 | 5/2012 | McIntyre et al. |
| 2012/0116475 A1 | 5/2012 | Nelson et al. |
| 2012/0116741 A1 | 5/2012 | Choi et al. |
| 2012/0123232 A1 | 5/2012 | Najarian et al. |
| 2012/0123290 A1 | 5/2012 | Kidmose et al. |
| 2012/0125337 A1 | 5/2012 | Asanoi |
| 2012/0128683 A1 | 5/2012 | Shantha |
| 2012/0130204 A1 | 5/2012 | Basta et al. |
| 2012/0130228 A1 | 5/2012 | Zellers et al. |
| 2012/0130229 A1 | 5/2012 | Zellers et al. |
| 2012/0130300 A1 | 5/2012 | Stavchansky et al. |
| 2012/0130641 A1 | 5/2012 | Morrison et al. |
| 2012/0136242 A1 | 5/2012 | Qi et al. |
| 2012/0136274 A1 | 5/2012 | Burdea et al. |
| 2012/0136605 A1 | 5/2012 | Addison et al. |
| 2012/0143038 A1 | 6/2012 | Georgopoulos |
| 2012/0143074 A1 | 6/2012 | Shin et al. |
| 2012/0143075 A1 | 6/2012 | Tansey |
| 2012/0143104 A1 | 6/2012 | Tee et al. |
| 2012/0143285 A1 | 6/2012 | Wang et al. |
| 2012/0145152 A1 | 6/2012 | Lain et al. |
| 2012/0149042 A1 | 6/2012 | Jackowski et al. |
| 2012/0149997 A1 | 6/2012 | Diab et al. |
| 2012/0150255 A1 | 6/2012 | Lindenthaler et al. |
| 2012/0150257 A1 | 6/2012 | Aur et al. |
| 2012/0150262 A1 | 6/2012 | Gliner et al. |
| 2012/0150516 A1 | 6/2012 | Taylor et al. |
| 2012/0150545 A1 | 6/2012 | Simon |
| 2012/0157804 A1 | 6/2012 | Rogers et al. |
| 2012/0157963 A1 | 6/2012 | Imran |
| 2012/0158092 A1 | 6/2012 | Thimineur et al. |
| 2012/0159656 A1 | 6/2012 | Gerber et al. |
| 2012/0162002 A1 | 6/2012 | Semenov |
| 2012/0163689 A1 | 6/2012 | Bottger et al. |
| 2012/0164613 A1 | 6/2012 | Jung et al. |
| 2012/0165624 A1 | 6/2012 | Diab et al. |
| 2012/0165631 A1 | 6/2012 | Diab et al. |
| 2012/0165696 A1 | 6/2012 | Arns |
| 2012/0165898 A1 | 6/2012 | Moffitt |
| 2012/0165899 A1 | 6/2012 | Gliner |
| 2012/0165904 A1 | 6/2012 | Lee et al. |
| 2012/0172682 A1 | 7/2012 | Linderman et al. |
| 2012/0172689 A1 | 7/2012 | Albert et al. |
| 2012/0172743 A1 | 7/2012 | Aguilar et al. |
| 2012/0177716 A1 | 7/2012 | Ho et al. |
| 2012/0179071 A1 | 7/2012 | Skelton |
| 2012/0179228 A1 | 7/2012 | DeCharms |
| 2012/0184801 A1 | 7/2012 | Simon et al. |
| 2012/0184826 A1 | 7/2012 | Keenan et al. |
| 2012/0185020 A1 | 7/2012 | Simon et al. |
| 2012/0191000 A1 | 7/2012 | Adachi et al. |
| 2012/0191158 A1 | 7/2012 | Craig |
| 2012/0191542 A1 | 7/2012 | Nurmi |
| 2012/0195860 A1 | 8/2012 | Walker et al. |
| 2012/0197092 A1 | 8/2012 | Luo et al. |
| 2012/0197153 A1 | 8/2012 | Kraus et al. |
| 2012/0197163 A1 | 8/2012 | Mishelevich |
| 2012/0197322 A1 | 8/2012 | Skelton et al. |
| 2012/0203079 A1 | 8/2012 | McLaughlin |
| 2012/0203087 A1 | 8/2012 | McKenna et al. |
| 2012/0203130 A1 | 8/2012 | Bernhard |
| 2012/0203131 A1 | 8/2012 | DiLorenzo |
| 2012/0203133 A1 | 8/2012 | Jadidi |
| 2012/0203725 A1 | 8/2012 | Stoica |
| 2012/0207362 A1 | 8/2012 | Fueyo et al. |
| 2012/0209126 A1 | 8/2012 | Amos et al. |
| 2012/0209136 A1 | 8/2012 | Ma |
| 2012/0209139 A1 | 8/2012 | John |
| 2012/0209346 A1 | 8/2012 | Bikson et al. |
| 2012/0212353 A1 | 8/2012 | Fung et al. |
| 2012/0215114 A1 | 8/2012 | Gratton et al. |
| 2012/0215448 A1 | 8/2012 | Hu et al. |
| 2012/0219195 A1 | 8/2012 | Wu et al. |
| 2012/0219507 A1 | 8/2012 | Santosh et al. |
| 2012/0220843 A1 | 8/2012 | Diab et al. |
| 2012/0220889 A1 | 8/2012 | Sullivan et al. |
| 2012/0221310 A1 | 8/2012 | Sarrafzadeh et al. |
| 2012/0226091 A1 | 9/2012 | Mishelevich |
| 2012/0226130 A1 | 9/2012 | De Graff et al. |
| 2012/0226185 A1 | 9/2012 | Chung et al. |
| 2012/0226334 A1 | 9/2012 | Gardiner et al. |
| 2012/0232327 A1 | 9/2012 | Lozano et al. |
| 2012/0232376 A1 | 9/2012 | Crevecoeur et al. |
| 2012/0232433 A1 | 9/2012 | Mishelevich |
| 2012/0238890 A1 | 9/2012 | Baker et al. |
| 2012/0242501 A1 | 9/2012 | Tran et al. |
| 2012/0245464 A1 | 9/2012 | Tran |
| 2012/0245474 A1 | 9/2012 | Ofek et al. |
| 2012/0245481 A1 | 9/2012 | Blanco et al. |
| 2012/0245493 A1 | 9/2012 | Mishelevich |
| 2012/0245655 A1 | 9/2012 | Spitzer et al. |
| 2012/0249274 A1 | 10/2012 | Toda et al. |
| 2012/0253101 A1 | 10/2012 | Wang et al. |
| 2012/0253141 A1 | 10/2012 | Addison et al. |
| 2012/0253168 A1 | 10/2012 | Hu et al. |
| 2012/0253219 A1 | 10/2012 | Suffin et al. |
| 2012/0253249 A1 | 10/2012 | Wilson |
| 2012/0253261 A1 | 10/2012 | Poletto et al. |
| 2012/0253421 A1 | 10/2012 | Gliner et al. |
| 2012/0253429 A1 | 10/2012 | Schiffer |
| 2012/0253434 A1 | 10/2012 | Nissila et al. |
| 2012/0253442 A1 | 10/2012 | Gliner et al. |
| 2012/0259249 A1 | 10/2012 | Khuri-Yakub et al. |
| 2012/0262250 A1 | 10/2012 | Stevenson et al. |
| 2012/0262558 A1 | 10/2012 | Boger et al. |
| 2012/0263393 A1 | 10/2012 | Yahil |
| 2012/0265080 A1 | 10/2012 | Yu et al. |
| 2012/0265262 A1 | 10/2012 | Osorio |
| 2012/0265267 A1 | 10/2012 | Blum et al. |
| 2012/0265270 A1 | 10/2012 | Cornejo Cruz et al. |
| 2012/0265271 A1 | 10/2012 | Goetz |

(56)　　　　　References Cited

U.S. PATENT DOCUMENTS

| | | |
|---|---|---|
| 2012/0268272 A1 | 10/2012 | Lee et al. |
| 2012/0269385 A1 | 10/2012 | Lee et al. |
| 2012/0271148 A1 | 10/2012 | Nelson |
| 2012/0271151 A1 | 10/2012 | Voilette et al. |
| 2012/0271183 A1 | 10/2012 | Sachanandani et al. |
| 2012/0271189 A1 | 10/2012 | Nelson et al. |
| 2012/0271190 A1 | 10/2012 | Mortensen et al. |
| 2012/0271374 A1 | 10/2012 | Nelson et al. |
| 2012/0271375 A1 | 10/2012 | Wu et al. |
| 2012/0271376 A1 | 10/2012 | Kokones et al. |
| 2012/0271377 A1 | 10/2012 | Hagedorn et al. |
| 2012/0271380 A1 | 10/2012 | Roberts et al. |
| 2012/0277545 A1 | 11/2012 | Teixeira |
| 2012/0277548 A1 | 11/2012 | Burton |
| 2012/0277816 A1 | 11/2012 | Zhang et al. |
| 2012/0277833 A1 | 11/2012 | Gerber et al. |
| 2012/0283502 A1 | 11/2012 | Mishelevich et al. |
| 2012/0283604 A1 | 11/2012 | Mishelevich |
| 2012/0288143 A1 | 11/2012 | Ernst et al. |
| 2012/0289854 A1 | 11/2012 | Yamada et al. |
| 2012/0289869 A1 | 11/2012 | Tyler |
| 2012/0290058 A1 | 11/2012 | Langevin et al. |
| 2012/0296182 A1 | 11/2012 | Hornero Sanchez et al. |
| 2012/0296241 A1 | 11/2012 | Mishelevich |
| 2012/0296253 A1 | 11/2012 | Mathews et al. |
| 2012/0296569 A1 | 11/2012 | Shahaf et al. |
| 2012/0302842 A1 | 11/2012 | Kurtz et al. |
| 2012/0302845 A1 | 11/2012 | Lynn et al. |
| 2012/0302856 A1 | 11/2012 | Chang et al. |
| 2012/0302867 A1 | 11/2012 | Ichimura |
| 2012/0302894 A1 | 11/2012 | Diab et al. |
| 2012/0302912 A1 | 11/2012 | Moffitt et al. |
| 2012/0303080 A1 | 11/2012 | Ben-David et al. |
| 2012/0303087 A1 | 11/2012 | Moffitt et al. |
| 2012/0310050 A1 | 12/2012 | Osorio |
| 2012/0310100 A1 | 12/2012 | Galen et al. |
| 2012/0310105 A1 | 12/2012 | Feingold et al. |
| 2012/0310106 A1 | 12/2012 | Cavuoto |
| 2012/0310107 A1 | 12/2012 | Doidge et al. |
| 2012/0310298 A1 | 12/2012 | Besio et al. |
| 2012/0316622 A1 | 12/2012 | Whitehurst et al. |
| 2012/0316630 A1 | 12/2012 | Firlik et al. |
| 2012/0316793 A1 | 12/2012 | Jung et al. |
| 2012/0321152 A1 | 12/2012 | Carroll |
| 2012/0321160 A1 | 12/2012 | Carroll |
| 2012/0321759 A1 | 12/2012 | Marinkovich et al. |
| 2012/0323108 A1 | 12/2012 | Carroll |
| 2012/0323132 A1 | 12/2012 | Warner et al. |
| 2012/0330109 A1 | 12/2012 | Tran |
| 2012/0330369 A1 | 12/2012 | Osorio et al. |
| 2013/0006124 A1 | 1/2013 | Eyal et al. |
| 2013/0006332 A1 | 1/2013 | Sommer et al. |
| 2013/0009783 A1 | 1/2013 | Tran |
| 2013/0011819 A1 | 1/2013 | Horseman |
| 2013/0012786 A1 | 1/2013 | Horseman |
| 2013/0012787 A1 | 1/2013 | Horseman |
| 2013/0012788 A1 | 1/2013 | Horseman |
| 2013/0012789 A1 | 1/2013 | Horseman |
| 2013/0012790 A1 | 1/2013 | Horseman |
| 2013/0012802 A1 | 1/2013 | Horseman |
| 2013/0012804 A1 | 1/2013 | deCharms |
| 2013/0012830 A1 | 1/2013 | Leininger et al. |
| 2013/0013327 A1 | 1/2013 | Horseman |
| 2013/0013339 A1 | 1/2013 | Goldman et al. |
| 2013/0013667 A1 | 1/2013 | Serena |
| 2013/0018435 A1 | 1/2013 | De Ridder |
| 2013/0018438 A1 | 1/2013 | Chow |
| 2013/0018439 A1 | 1/2013 | Chow et al. |
| 2013/0018440 A1 | 1/2013 | Chow et al. |
| 2013/0018592 A1 | 1/2013 | Mollicone et al. |
| 2013/0018596 A1 | 1/2013 | Bottger et al. |
| 2013/0019325 A1 | 1/2013 | Deisseroth et al. |
| 2013/0023783 A1 | 1/2013 | Snyder et al. |
| 2013/0028496 A1 | 1/2013 | Panin et al. |
| 2013/0030241 A1 | 1/2013 | Smith |
| 2013/0030257 A1 | 1/2013 | Nakata et al. |
| 2013/0031038 A1 | 1/2013 | Horne |
| 2013/0034837 A1 | 2/2013 | Clapp et al. |
| 2013/0035579 A1 | 2/2013 | Le et al. |
| 2013/0039498 A1 | 2/2013 | Adachi et al. |
| 2013/0041235 A1 | 2/2013 | Rogers et al. |
| 2013/0041281 A1 | 2/2013 | Park et al. |
| 2013/0046151 A1 | 2/2013 | Bsoul et al. |
| 2013/0046193 A1 | 2/2013 | Guttag et al. |
| 2013/0046358 A1 | 2/2013 | Leyde |
| 2013/0046715 A1 | 2/2013 | Castermans et al. |
| 2013/0053656 A1 | 2/2013 | Mollicone et al. |
| 2013/0054214 A1 | 2/2013 | Taylor |
| 2013/0054215 A1 | 2/2013 | Stubna et al. |
| 2013/0058548 A1 | 3/2013 | Garg et al. |
| 2013/0060110 A1 | 3/2013 | Lynn et al. |
| 2013/0060125 A1 | 3/2013 | Zeman et al. |
| 2013/0060158 A1 | 3/2013 | Perez-Velazquez et al. |
| 2013/0063434 A1 | 3/2013 | Miga et al. |
| 2013/0063550 A1 | 3/2013 | Ritchey et al. |
| 2013/0064438 A1 | 3/2013 | Taylor et al. |
| 2013/0066350 A1 | 3/2013 | Mishelevich |
| 2013/0066391 A1 | 3/2013 | Hulvershorn et al. |
| 2013/0066392 A1 | 3/2013 | Simon et al. |
| 2013/0066394 A1 | 3/2013 | Saab |
| 2013/0066395 A1 | 3/2013 | Simon et al. |
| 2013/0066618 A1 | 3/2013 | Taylor et al. |
| 2013/0069780 A1 | 3/2013 | Tran et al. |
| 2013/0070929 A1 | 3/2013 | Adachi et al. |
| 2013/0072292 A1 | 3/2013 | Sutton et al. |
| 2013/0072775 A1 | 3/2013 | Rogers et al. |
| 2013/0072780 A1 | 3/2013 | Espy et al. |
| 2013/0072807 A1 | 3/2013 | Tran |
| 2013/0072996 A1 | 3/2013 | Kilgard et al. |
| 2013/0073022 A1 | 3/2013 | Ollivier |
| 2013/0076885 A1 | 3/2013 | Kobetski et al. |
| 2013/0079606 A1 | 3/2013 | McGonigle et al. |
| 2013/0079621 A1 | 3/2013 | Shoham et al. |
| 2013/0079647 A1 | 3/2013 | McGonigle et al. |
| 2013/0079656 A1 | 3/2013 | Dripps et al. |
| 2013/0079657 A1 | 3/2013 | Ochs et al. |
| 2013/0080127 A1 | 3/2013 | Shahaf et al. |
| 2013/0080489 A1 | 3/2013 | Ochs et al. |
| 2013/0085678 A1 | 4/2013 | Jung et al. |
| 2013/0089503 A1 | 4/2013 | Deisseroth et al. |
| 2013/0090454 A1 | 4/2013 | Deisseroth et al. |
| 2013/0090706 A1 | 4/2013 | Nudo et al. |
| 2013/0091941 A1 | 4/2013 | Huh et al. |
| 2013/0095459 A1 | 4/2013 | Tran |
| 2013/0096391 A1 | 4/2013 | Osorio et al. |
| 2013/0096393 A1 | 4/2013 | Osorio et al. |
| 2013/0096394 A1 | 4/2013 | Gupta et al. |
| 2013/0096408 A1 | 4/2013 | He et al. |
| 2013/0096441 A1 | 4/2013 | Osorio |
| 2013/0096453 A1 | 4/2013 | Chung et al. |
| 2013/0096454 A1 | 4/2013 | Jang et al. |
| 2013/0096839 A1 | 4/2013 | Osorio et al. |
| 2013/0096840 A1 | 4/2013 | Osorio et al. |
| 2013/0102833 A1 | 4/2013 | John et al. |
| 2013/0102877 A1 | 4/2013 | Mori et al. |
| 2013/0102897 A1 | 4/2013 | Kalafut et al. |
| 2013/0102907 A1 | 4/2013 | Funane et al. |
| 2013/0102919 A1 | 4/2013 | Schiff |
| 2013/0104066 A1 | 4/2013 | Soederstroem |
| 2013/0109995 A1 | 5/2013 | Rothman et al. |
| 2013/0109996 A1 | 5/2013 | Turnbull et al. |
| 2013/0110616 A1 | 5/2013 | Bakalash et al. |
| 2013/0113816 A1 | 5/2013 | Sudarsky et al. |
| 2013/0116520 A1 | 5/2013 | Roham et al. |
| 2013/0116540 A1 | 5/2013 | Li et al. |
| 2013/0116561 A1 | 5/2013 | Rothberg et al. |
| 2013/0116578 A1 | 5/2013 | An et al. |
| 2013/0116588 A1 | 5/2013 | Yazicioglu et al. |
| 2013/0116748 A1 | 5/2013 | Bokil et al. |
| 2013/0118494 A1 | 5/2013 | Ujhazy et al. |
| 2013/0120246 A1 | 5/2013 | Schuette et al. |
| 2013/0121984 A1 | 5/2013 | Haslett et al. |
| 2013/0123568 A1 | 5/2013 | Hamilton et al. |
| 2013/0123584 A1 | 5/2013 | Sun et al. |

(56) References Cited

U.S. PATENT DOCUMENTS

| | | | |
|---|---|---|---|
| 2013/0123607 A1 | 5/2013 | Leuthardt et al. | |
| 2013/0123684 A1 | 5/2013 | Giuffrida et al. | |
| 2013/0127708 A1 | 5/2013 | Jung et al. | |
| 2013/0127980 A1 | 5/2013 | Haddick et al. | |
| 2013/0130799 A1 | 5/2013 | Van Hulle et al. | |
| 2013/0131438 A1 | 5/2013 | Brewer et al. | |
| 2013/0131461 A1 | 5/2013 | Jorge et al. | |
| 2013/0131537 A1* | 5/2013 | Tam ...................... | A61B 5/377 |
| | | | 600/544 |
| 2013/0131746 A1 | 5/2013 | Simon et al. | |
| 2013/0131753 A1 | 5/2013 | Simon et al. | |
| 2013/0131755 A1 | 5/2013 | Panken et al. | |
| 2013/0132029 A1 | 5/2013 | Mollicone et al. | |
| 2013/0137717 A1 | 5/2013 | Chesworth et al. | |
| 2013/0137936 A1 | 5/2013 | Baker, Jr. et al. | |
| 2013/0137938 A1 | 5/2013 | Peters | |
| 2013/0138002 A1 | 5/2013 | Weng et al. | |
| 2013/0138176 A1 | 5/2013 | Goetz | |
| 2013/0138177 A1 | 5/2013 | DeRidder | |
| 2013/0141103 A1 | 6/2013 | Roshtal et al. | |
| 2013/0144106 A1 | 6/2013 | Phillips et al. | |
| 2013/0144107 A1 | 6/2013 | Phillips et al. | |
| 2013/0144108 A1 | 6/2013 | Phillips et al. | |
| 2013/0144183 A1 | 6/2013 | John et al. | |
| 2013/0144192 A1 | 6/2013 | Mischelevich et al. | |
| 2013/0144353 A1 | 6/2013 | Lozano | |
| 2013/0144537 A1 | 6/2013 | Schalk et al. | |
| 2013/0150650 A1 | 6/2013 | Phillips et al. | |
| 2013/0150651 A1 | 6/2013 | Phillips et al. | |
| 2013/0150659 A1 | 6/2013 | Shaw et al. | |
| 2013/0150702 A1 | 6/2013 | Hokari | |
| 2013/0150921 A1 | 6/2013 | Singhal et al. | |
| 2013/0151163 A1 | 6/2013 | Taylor et al. | |
| 2013/0158883 A1 | 6/2013 | Hasegawa et al. | |
| 2013/0159041 A1 | 6/2013 | Jayaraman et al. | |
| 2013/0165766 A1 | 6/2013 | Nishikawa et al. | |
| 2013/0165804 A1 | 6/2013 | Johnson et al. | |
| 2013/0165812 A1 | 6/2013 | Aksenova et al. | |
| 2013/0165846 A1 | 6/2013 | Peyman | |
| 2013/0165996 A1 | 6/2013 | Meadows et al. | |
| 2013/0167360 A1 | 7/2013 | Masmanidis et al. | |
| 2013/0172663 A1 | 7/2013 | Leonard | |
| 2013/0172686 A1 | 7/2013 | Addison et al. | |
| 2013/0172691 A1 | 7/2013 | Tran | |
| 2013/0172716 A1 | 7/2013 | Lozano et al. | |
| 2013/0172763 A1 | 7/2013 | Wheeler | |
| 2013/0172767 A1 | 7/2013 | Dripps et al. | |
| 2013/0172772 A1 | 7/2013 | Alshaer et al. | |
| 2013/0172774 A1 | 7/2013 | Crowder et al. | |
| 2013/0178693 A1 | 7/2013 | Neuvonen et al. | |
| 2013/0178718 A1 | 7/2013 | Tran et al. | |
| 2013/0178733 A1 | 7/2013 | Langleben | |
| 2013/0178913 A1 | 7/2013 | Lozano | |
| 2013/0182860 A1 | 7/2013 | Adachi et al. | |
| 2013/0184218 A1 | 7/2013 | Paul et al. | |
| 2013/0184516 A1 | 7/2013 | Genereux et al. | |
| 2013/0184552 A1 | 7/2013 | Westermann et al. | |
| 2013/0184558 A1 | 7/2013 | Gallant et al. | |
| 2013/0184597 A1 | 7/2013 | Hopenfeld | |
| 2013/0184603 A1 | 7/2013 | Rothman | |
| 2013/0184639 A1 | 7/2013 | Whitehurst et al. | |
| 2013/0184728 A1 | 7/2013 | Mischelevich | |
| 2013/0184781 A1 | 7/2013 | Eskandar et al. | |
| 2013/0184786 A1 | 7/2013 | Goetz | |
| 2013/0184792 A1 | 7/2013 | Simon et al. | |
| 2013/0184997 A1 | 7/2013 | Mott | |
| 2013/0185144 A1 | 7/2013 | Pradeep et al. | |
| 2013/0185145 A1 | 7/2013 | Pradeep et al. | |
| 2013/0188830 A1 | 7/2013 | Ernst et al. | |
| 2013/0188854 A1 | 7/2013 | Bilgic et al. | |
| 2013/0189663 A1 | 7/2013 | Tuchschmid et al. | |
| 2013/0190577 A1 | 7/2013 | Brunner et al. | |
| 2013/0190642 A1 | 7/2013 | Muesch et al. | |
| 2013/0197321 A1 | 8/2013 | Wilson | |
| 2013/0197322 A1 | 8/2013 | Tran | |
| 2013/0197328 A1 | 8/2013 | Diab et al. | |
| 2013/0197339 A1 | 8/2013 | Bardakjian et al. | |
| 2013/0197401 A1 | 8/2013 | Sato et al. | |
| 2013/0197944 A1 | 8/2013 | Drew et al. | |
| 2013/0203019 A1 | 8/2013 | Nolen | |
| 2013/0204085 A1 | 8/2013 | Alexander et al. | |
| 2013/0204122 A1 | 8/2013 | Hendler et al. | |
| 2013/0204144 A1 | 8/2013 | Colborn et al. | |
| 2013/0204150 A1 | 8/2013 | Similowski et al. | |
| 2013/0211183 A1 | 8/2013 | Schiffer | |
| 2013/0211224 A1 | 8/2013 | Isenhart et al. | |
| 2013/0211238 A1 | 8/2013 | DeCharms | |
| 2013/0211276 A1 | 8/2013 | Luo et al. | |
| 2013/0211291 A1 | 8/2013 | Tran | |
| 2013/0211728 A1 | 8/2013 | Taylor et al. | |
| 2013/0217982 A1 | 8/2013 | Behzadi | |
| 2013/0218043 A1 | 8/2013 | Yoshida | |
| 2013/0218053 A1 | 8/2013 | Kaiser et al. | |
| 2013/0218232 A1 | 8/2013 | Giftakis et al. | |
| 2013/0218233 A1 | 8/2013 | Warschewske et al. | |
| 2013/0218819 A1 | 8/2013 | Lujan et al. | |
| 2013/0221961 A1 | 8/2013 | Liu | |
| 2013/0223709 A1 | 8/2013 | Wagner | |
| 2013/0225940 A1 | 8/2013 | Fujita et al. | |
| 2013/0225953 A1 | 8/2013 | Oliviero et al. | |
| 2013/0225992 A1 | 8/2013 | Osorio | |
| 2013/0226261 A1 | 8/2013 | Sparks et al. | |
| 2013/0226408 A1 | 8/2013 | Fung et al. | |
| 2013/0226464 A1 | 8/2013 | Marci et al. | |
| 2013/0231574 A1 | 9/2013 | Tran | |
| 2013/0231580 A1 | 9/2013 | Chen et al. | |
| 2013/0231709 A1 | 9/2013 | Lozano | |
| 2013/0231716 A1 | 9/2013 | Skelton et al. | |
| 2013/0231721 A1 | 9/2013 | DeCharms | |
| 2013/0231947 A1 | 9/2013 | Shusterman | |
| 2013/0234823 A1 | 9/2013 | Kahn et al. | |
| 2013/0235550 A1 | 9/2013 | Stevenson et al. | |
| 2013/0237541 A1 | 9/2013 | Teegarden et al. | |
| 2013/0237874 A1 | 9/2013 | Zoicas | |
| 2013/0238049 A1 | 9/2013 | Simon et al. | |
| 2013/0238050 A1 | 9/2013 | Simon et al. | |
| 2013/0238053 A1 | 9/2013 | Ignagni et al. | |
| 2013/0238063 A1 | 9/2013 | Nofzinger | |
| 2013/0242262 A1 | 9/2013 | Lewis | |
| 2013/0243287 A1 | 9/2013 | Thomson et al. | |
| 2013/0244323 A1 | 9/2013 | Deisseroth et al. | |
| 2013/0245416 A1 | 9/2013 | Yarmush et al. | |
| 2013/0245422 A1 | 9/2013 | D'arcy et al. | |
| 2013/0245424 A1 | 9/2013 | deCharms | |
| 2013/0245464 A1 | 9/2013 | Colborn et al. | |
| 2013/0245466 A1 | 9/2013 | Sachanandani et al. | |
| 2013/0245485 A1 | 9/2013 | Mashour et al. | |
| 2013/0245486 A1 | 9/2013 | Simon et al. | |
| 2013/0245711 A1 | 9/2013 | Simon et al. | |
| 2013/0245712 A1 | 9/2013 | Simon et al. | |
| 2013/0245886 A1 | 9/2013 | Fung et al. | |
| 2013/0251641 A1 | 9/2013 | Akhtari et al. | |
| 2013/0253363 A1 | 9/2013 | Juffali et al. | |
| 2013/0253612 A1 | 9/2013 | Chow | |
| 2013/0255586 A1 | 10/2013 | Gerashchenko | |
| 2013/0261490 A1 | 10/2013 | Truccolo et al. | |
| 2013/0261506 A1 | 10/2013 | Mishelevich | |
| 2013/0261703 A1 | 10/2013 | Chow et al. | |
| 2013/0266163 A1 | 10/2013 | Morikawa et al. | |
| 2013/0267760 A1 | 10/2013 | Jin | |
| 2013/0267866 A1 | 10/2013 | Nakashima et al. | |
| 2013/0267928 A1 | 10/2013 | Imran et al. | |
| 2013/0274562 A1 | 10/2013 | Ghaffari et al. | |
| 2013/0274580 A1 | 10/2013 | Madsen et al. | |
| 2013/0274586 A1 | 10/2013 | Miyazaki et al. | |
| 2013/0274625 A1 | 10/2013 | Sarma et al. | |
| 2013/0275159 A1 | 10/2013 | Seely | |
| 2013/0281758 A1 | 10/2013 | Solvason et al. | |
| 2013/0281759 A1 | 10/2013 | Hagedorn et al. | |
| 2013/0281811 A1 | 10/2013 | Imran | |
| 2013/0281879 A1 | 10/2013 | Raniere | |
| 2013/0281890 A1 | 10/2013 | Mishelevich | |
| 2013/0282075 A1 | 10/2013 | De Ridder | |
| 2013/0282339 A1 | 10/2013 | Ricci et al. | |

(56)          References Cited

U.S. PATENT DOCUMENTS

| | | |
|---|---|---|
| 2013/0289360 A1 | 10/2013 | Hyde et al. |
| 2013/0289364 A1 | 10/2013 | Colman et al. |
| 2013/0289385 A1 | 10/2013 | Lozano et al. |
| 2013/0289386 A1 | 10/2013 | Deisseroth et al. |
| 2013/0289401 A1 | 10/2013 | Colbaugh et al. |
| 2013/0289413 A1 | 10/2013 | Ochs et al. |
| 2013/0289417 A1 | 10/2013 | Grunwald et al. |
| 2013/0289424 A1 | 10/2013 | Brockway et al. |
| 2013/0289433 A1 | 10/2013 | Jin et al. |
| 2013/0289653 A1 | 10/2013 | Kilgard et al. |
| 2013/0289669 A1 | 10/2013 | Deisseroth et al. |
| 2013/0293844 A1 | 11/2013 | Gross et al. |
| 2013/0295016 A1 | 11/2013 | Gerber et al. |
| 2013/0296406 A1 | 11/2013 | Deisseroth et al. |
| 2013/0296637 A1 | 11/2013 | Kilgard et al. |
| 2013/0300573 A1 | 11/2013 | Brown et al. |
| 2013/0303828 A1 | 11/2013 | Hargrove |
| 2013/0303934 A1 | 11/2013 | Collura |
| 2013/0304153 A1 | 11/2013 | Hargrove et al. |
| 2013/0304159 A1 | 11/2013 | Simon et al. |
| 2013/0304472 A1 | 11/2013 | Pakhomov |
| 2013/0308099 A1 | 11/2013 | Stack |
| 2013/0309278 A1 | 11/2013 | Peyman |
| 2013/0310422 A1 | 11/2013 | Brown et al. |
| 2013/0310660 A1 | 11/2013 | Zuckerman-Stark et al. |
| 2013/0310909 A1 | 11/2013 | Simon et al. |
| 2013/0314243 A1 | 11/2013 | Le |
| 2013/0317380 A1 | 11/2013 | Liley et al. |
| 2013/0317382 A1 | 11/2013 | Le |
| 2013/0317384 A1 | 11/2013 | Le |
| 2013/0317474 A1 | 11/2013 | Rezai et al. |
| 2013/0317568 A1 | 11/2013 | Skelton |
| 2013/0317580 A1 | 11/2013 | Simon et al. |
| 2013/0318546 A1 | 11/2013 | Kothuri et al. |
| 2013/0324880 A1 | 12/2013 | Adachi et al. |
| 2013/0330428 A1 | 12/2013 | Geng |
| 2013/0338449 A1 | 12/2013 | Warwick et al. |
| 2013/0338450 A1 | 12/2013 | Osorio et al. |
| 2013/0338459 A1 | 12/2013 | Lynn et al. |
| 2013/0338518 A1 | 12/2013 | Zoica |
| 2013/0338526 A1 | 12/2013 | Howard |
| 2013/0338738 A1 | 12/2013 | Garcia Molina et al. |
| 2013/0338803 A1 | 12/2013 | Maoz et al. |
| 2013/0339043 A1 | 12/2013 | Bakar et al. |
| 2013/0344465 A1 | 12/2013 | Dickinson et al. |
| 2013/0345522 A1 | 12/2013 | Sun et al. |
| 2013/0345523 A1 | 12/2013 | Diab et al. |
| 2014/0000630 A1 | 1/2014 | Ford |
| 2014/0003696 A1 | 1/2014 | Taghva |
| 2014/0005518 A1 | 1/2014 | Ko et al. |
| 2014/0005743 A1 | 1/2014 | Giuffrida et al. |
| 2014/0005744 A1 | 1/2014 | Hershey et al. |
| 2014/0005988 A1 | 1/2014 | Brockway |
| 2014/0012061 A1 | 1/2014 | Song et al. |
| 2014/0012110 A1 | 1/2014 | Watson et al. |
| 2014/0012133 A1 | 1/2014 | Sverdlik et al. |
| 2014/0012153 A1 | 1/2014 | Greenwald |
| 2014/0015852 A1 | 1/2014 | Kantartzis et al. |
| 2014/0018649 A1 | 1/2014 | Jespersen et al. |
| 2014/0018792 A1 | 1/2014 | Gang et al. |
| 2014/0019165 A1 | 1/2014 | Horseman |
| 2014/0023999 A1 | 1/2014 | Greder |
| 2014/0025133 A1 | 1/2014 | Lozano |
| 2014/0025396 A1 | 1/2014 | Horseman |
| 2014/0025397 A1 | 1/2014 | Horseman |
| 2014/0029830 A1 | 1/2014 | Vija et al. |
| 2014/0031703 A1 | 1/2014 | Rayner et al. |
| 2014/0031889 A1 | 1/2014 | Mashiach |
| 2014/0031903 A1 | 1/2014 | Mashiach |
| 2014/0032512 A1 | 1/2014 | Drew et al. |
| 2014/0038147 A1 | 2/2014 | Morrow |
| 2014/0039279 A1 | 2/2014 | Jarvik et al. |
| 2014/0039290 A1 | 2/2014 | De Graff et al. |
| 2014/0039336 A1 | 2/2014 | Osorio et al. |
| 2014/0039571 A1 | 2/2014 | Wolpaw et al. |
| 2014/0039577 A1 | 2/2014 | Kothandaraman et al. |
| 2014/0039578 A1 | 2/2014 | Whitehurst et al. |
| 2014/0039975 A1 | 2/2014 | Hill |
| 2014/0046203 A1 | 2/2014 | Osorio et al. |
| 2014/0046208 A1 | 2/2014 | Sejdic et al. |
| 2014/0046407 A1 | 2/2014 | Ben-Ezra et al. |
| 2014/0051044 A1 | 2/2014 | Badower et al. |
| 2014/0051960 A1 | 2/2014 | Badower et al. |
| 2014/0051961 A1 | 2/2014 | Badower et al. |
| 2014/0052213 A1 | 2/2014 | Osorio |
| 2014/0055284 A1 | 2/2014 | Tran et al. |
| 2014/0056815 A1 | 2/2014 | Peyman |
| 2014/0057232 A1 | 2/2014 | Wetmore et al. |
| 2014/0058189 A1 | 2/2014 | Stubbeman |
| 2014/0058218 A1 | 2/2014 | Randlov et al. |
| 2014/0058219 A1 | 2/2014 | Kiraly |
| 2014/0058241 A1 | 2/2014 | Apparies et al. |
| 2014/0058289 A1 | 2/2014 | Panken et al. |
| 2014/0058292 A1 | 2/2014 | Alford et al. |
| 2014/0058528 A1 | 2/2014 | Contreras-Vidal et al. |
| 2014/0062472 A1 | 3/2014 | Nishikawa |
| 2014/0063054 A1 | 3/2014 | Osterhout et al. |
| 2014/0063055 A1 | 3/2014 | Osterhout et al. |
| 2014/0066739 A1 | 3/2014 | He et al. |
| 2014/0066763 A2 | 3/2014 | Rothberg et al. |
| 2014/0066796 A1 | 3/2014 | Davis et al. |
| 2014/0067740 A1 | 3/2014 | Solari |
| 2014/0070958 A1 | 3/2014 | Foo |
| 2014/0072127 A1 | 3/2014 | Adachi et al. |
| 2014/0072130 A1 | 3/2014 | Adachi et al. |
| 2014/0073863 A1 | 3/2014 | Engelbrecht et al. |
| 2014/0073864 A1 | 3/2014 | Engelbrecht et al. |
| 2014/0073866 A1 | 3/2014 | Engelbrecht et al. |
| 2014/0073870 A1 | 3/2014 | Engelbrecht et al. |
| 2014/0073875 A1 | 3/2014 | Engelbrecht et al. |
| 2014/0073876 A1 | 3/2014 | Rodriguez-Llorente et al. |
| 2014/0073877 A1 | 3/2014 | Wooder |
| 2014/0073878 A1 | 3/2014 | Engelbrecht et al. |
| 2014/0073898 A1 | 3/2014 | Engelbrecht et al. |
| 2014/0073948 A1 | 3/2014 | Engelbrecht et al. |
| 2014/0073949 A1 | 3/2014 | Engelbrecht et al. |
| 2014/0073951 A1 | 3/2014 | Engelbrecht et al. |
| 2014/0073953 A1 | 3/2014 | Engelbrecht et al. |
| 2014/0073954 A1 | 3/2014 | Engelbrecht et al. |
| 2014/0073955 A1 | 3/2014 | Engelbrecht et al. |
| 2014/0073956 A1 | 3/2014 | Engelbrecht et al. |
| 2014/0073960 A1 | 3/2014 | Rodriguez-Llorente et al. |
| 2014/0073961 A1 | 3/2014 | Rodriguez-Llorente et al. |
| 2014/0073963 A1 | 3/2014 | Engelbrecht et al. |
| 2014/0073965 A1 | 3/2014 | Engelbrecht et al. |
| 2014/0073966 A1 | 3/2014 | Engelbrecht et al. |
| 2014/0073967 A1 | 3/2014 | Engelbrecht et al. |
| 2014/0073968 A1 | 3/2014 | Engelbrecht et al. |
| 2014/0073974 A1 | 3/2014 | Engelbrecht |
| 2014/0073975 A1 | 3/2014 | Engelbrecht et al. |
| 2014/0074060 A1 | 3/2014 | Imran |
| 2014/0074179 A1 | 3/2014 | Heldman et al. |
| 2014/0074180 A1 | 3/2014 | Heldman et al. |
| 2014/0074188 A1 | 3/2014 | Armstrong et al. |
| 2014/0077612 A1 | 3/2014 | Onuma et al. |
| 2014/0077946 A1 | 3/2014 | Tran |
| 2014/0081071 A1 | 3/2014 | Simon et al. |
| 2014/0081114 A1 | 3/2014 | Shachar et al. |
| 2014/0081115 A1 | 3/2014 | Gu |
| 2014/0081347 A1 | 3/2014 | Nelson et al. |
| 2014/0081353 A1 | 3/2014 | Cook et al. |
| 2014/0088341 A1 | 3/2014 | Altman et al. |
| 2014/0088377 A1 | 3/2014 | Manzke et al. |
| 2014/0094710 A1 | 4/2014 | Sarma et al. |
| 2014/0094719 A1 | 4/2014 | Mishelevich |
| 2014/0094720 A1 | 4/2014 | Tyler |
| 2014/0098981 A1 | 4/2014 | Lunner et al. |
| 2014/0100467 A1 | 4/2014 | Baker et al. |
| 2014/0100633 A1 | 4/2014 | Mann et al. |
| 2014/0101084 A1 | 4/2014 | Li et al. |
| 2014/0104059 A1 | 4/2014 | Tran |
| 2014/0105436 A1 | 4/2014 | Adachi et al. |
| 2014/0107397 A1 | 4/2014 | Simon et al. |
| 2014/0107398 A1 | 4/2014 | Simon et al. |

(56)                    References Cited

U.S. PATENT DOCUMENTS

| | | |
|---|---|---|
| 2014/0107401 A1 | 4/2014 | Anderson et al. |
| 2014/0107464 A1 | 4/2014 | Aksenova et al. |
| 2014/0107519 A1 | 4/2014 | Musha et al. |
| 2014/0107521 A1 | 4/2014 | Galan |
| 2014/0107525 A1 | 4/2014 | Tass |
| 2014/0107728 A1 | 4/2014 | Fried et al. |
| 2014/0107935 A1 | 4/2014 | Taylor |
| 2014/0111335 A1 | 4/2014 | Kleiss et al. |
| 2014/0113367 A1 | 4/2014 | Deisseroth et al. |
| 2014/0114165 A1 | 4/2014 | Walker et al. |
| 2014/0114205 A1 | 4/2014 | Braun et al. |
| 2014/0114207 A1 | 4/2014 | Patterson |
| 2014/0114242 A1 | 4/2014 | Eckle |
| 2014/0114889 A1 | 4/2014 | Dagum |
| 2014/0119621 A1 | 5/2014 | Uber |
| 2014/0121446 A1 | 5/2014 | Phillips et al. |
| 2014/0121476 A1 | 5/2014 | Tran et al. |
| 2014/0121554 A1 | 5/2014 | Sarma et al. |
| 2014/0121565 A1 | 5/2014 | Kim |
| 2014/0122379 A1 | 5/2014 | Moffitt et al. |
| 2014/0128762 A1 | 5/2014 | Han et al. |
| 2014/0128763 A1 | 5/2014 | Fadem |
| 2014/0128764 A1 | 5/2014 | Gandhi |
| 2014/0128938 A1 | 5/2014 | Craig |
| 2014/0133720 A1 | 5/2014 | Lee et al. |
| 2014/0133722 A1 | 5/2014 | Lee et al. |
| 2014/0135642 A1 | 5/2014 | Ekpar |
| 2014/0135680 A1 | 5/2014 | Peyman |
| 2014/0135873 A1 | 5/2014 | An et al. |
| 2014/0135879 A1 | 5/2014 | Flint |
| 2014/0135886 A1 | 5/2014 | Cook et al. |
| 2014/0136585 A1 | 5/2014 | Brockway |
| 2014/0140567 A1 | 5/2014 | LeBoeuf et al. |
| 2014/0142448 A1 | 5/2014 | Bae et al. |
| 2014/0142653 A1 | 5/2014 | Osorio |
| 2014/0142654 A1 | 5/2014 | Simon et al. |
| 2014/0142669 A1 | 5/2014 | Cook et al. |
| 2014/0143064 A1 | 5/2014 | Tran |
| 2014/0148479 A1 | 5/2014 | Chesworth et al. |
| 2014/0148657 A1 | 5/2014 | Hendler et al. |
| 2014/0148693 A1 | 5/2014 | Taylor |
| 2014/0148716 A1 | 5/2014 | Hopenfeld et al. |
| 2014/0148723 A1 | 5/2014 | Nierenberg et al. |
| 2014/0148726 A1 | 5/2014 | Wagner |
| 2014/0148872 A1 | 5/2014 | Goldwasser et al. |
| 2014/0151563 A1 | 6/2014 | Rousso et al. |
| 2014/0152673 A1 | 6/2014 | Lynn et al. |
| 2014/0154647 A1 | 6/2014 | Nolen |
| 2014/0154650 A1 | 6/2014 | Stack |
| 2014/0155430 A1 | 6/2014 | Chesworth et al. |
| 2014/0155706 A1 | 6/2014 | Kochs et al. |
| 2014/0155714 A1 | 6/2014 | Gavish |
| 2014/0155730 A1 | 6/2014 | Bansal et al. |
| 2014/0155740 A1 | 6/2014 | Semenov |
| 2014/0155770 A1 | 6/2014 | Taylor |
| 2014/0155772 A1 | 6/2014 | Frei et al. |
| 2014/0155952 A1 | 6/2014 | Lozano et al. |
| 2014/0156000 A1 | 6/2014 | Campin et al. |
| 2014/0159862 A1 | 6/2014 | Yang et al. |
| 2014/0161352 A1 | 6/2014 | Buyens et al. |
| 2014/0163328 A1 | 6/2014 | Geva et al. |
| 2014/0163330 A1 | 6/2014 | Horseman |
| 2014/0163331 A1 | 6/2014 | Horseman |
| 2014/0163332 A1 | 6/2014 | Horseman |
| 2014/0163333 A1 | 6/2014 | Horseman |
| 2014/0163335 A1 | 6/2014 | Horseman |
| 2014/0163336 A1 | 6/2014 | Horseman |
| 2014/0163337 A1 | 6/2014 | Horseman |
| 2014/0163368 A1 | 6/2014 | Rousso et al. |
| 2014/0163385 A1 | 6/2014 | Kelleher et al. |
| 2014/0163409 A1 | 6/2014 | Arndt |
| 2014/0163425 A1 | 6/2014 | Tran |
| 2014/0163627 A1 | 6/2014 | Starr et al. |
| 2014/0163643 A1 | 6/2014 | Craig |
| 2014/0163893 A1 | 6/2014 | Harumatsu et al. |
| 2014/0163897 A1 | 6/2014 | Lynn et al. |
| 2014/0171749 A1 | 6/2014 | Chin et al. |
| 2014/0171757 A1 | 6/2014 | Kawato et al. |
| 2014/0171819 A1 | 6/2014 | Patterson |
| 2014/0171820 A1 | 6/2014 | Causevic |
| 2014/0174277 A1 | 6/2014 | Mann |
| 2014/0175261 A1 | 6/2014 | Addison et al. |
| 2014/0176944 A1 | 6/2014 | Addison et al. |
| 2014/0179980 A1 | 6/2014 | Phillips et al. |
| 2014/0180088 A1 | 6/2014 | Rothberg et al. |
| 2014/0180092 A1 | 6/2014 | Rothberg et al. |
| 2014/0180093 A1 | 6/2014 | Rothberg et al. |
| 2014/0180094 A1 | 6/2014 | Rothberg et al. |
| 2014/0180095 A1 | 6/2014 | Rothberg et al. |
| 2014/0180096 A1 | 6/2014 | Rothberg et al. |
| 2014/0180097 A1 | 6/2014 | Rothberg et al. |
| 2014/0180099 A1 | 6/2014 | Rothberg et al. |
| 2014/0180100 A1 | 6/2014 | Rothberg et al. |
| 2014/0180112 A1 | 6/2014 | Rothberg et al. |
| 2014/0180113 A1 | 6/2014 | Rothberg et al. |
| 2014/0180145 A1 | 6/2014 | Kanai et al. |
| 2014/0180153 A1 | 6/2014 | Zia et al. |
| 2014/0180160 A1 | 6/2014 | Brown et al. |
| 2014/0180161 A1 | 6/2014 | Bolger et al. |
| 2014/0180176 A1 | 6/2014 | Rothberg et al. |
| 2014/0180177 A1 | 6/2014 | Rothberg et al. |
| 2014/0180194 A1 | 6/2014 | Lozano |
| 2014/0180358 A1 | 6/2014 | Giftakis et al. |
| 2014/0180597 A1 | 6/2014 | Brown et al. |
| 2014/0184550 A1 | 7/2014 | Hennessey et al. |
| 2014/0187901 A1 | 7/2014 | Cui et al. |
| 2014/0187994 A1 | 7/2014 | Thornton |
| 2014/0188006 A1 | 7/2014 | Alshaer et al. |
| 2014/0188770 A1 | 7/2014 | Agrafioti et al. |
| 2014/0193336 A1 | 7/2014 | Rousso et al. |
| 2014/0194702 A1 | 7/2014 | Tran |
| 2014/0194720 A1 | 7/2014 | Hua |
| 2014/0194726 A1 | 7/2014 | Mishelevich et al. |
| 2014/0194758 A1 | 7/2014 | Korenberg |
| 2014/0194759 A1 | 7/2014 | Weiland et al. |
| 2014/0194768 A1 | 7/2014 | Nierenberg et al. |
| 2014/0194769 A1 | 7/2014 | Nierenberg et al. |
| 2014/0194780 A1 | 7/2014 | Alshaer et al. |
| 2014/0194793 A1 | 7/2014 | Nakata et al. |
| 2014/0200414 A1 | 7/2014 | Osorio |
| 2014/0200432 A1 | 7/2014 | Banerji et al. |
| 2014/0200623 A1 | 7/2014 | Lindenthaler et al. |
| 2014/0203797 A1 | 7/2014 | Stivoric et al. |
| 2014/0206981 A1 | 7/2014 | Nagasaka |
| 2014/0207224 A1 | 7/2014 | Simon |
| 2014/0207432 A1 | 7/2014 | Taylor |
| 2014/0211593 A1 | 7/2014 | Tyler et al. |
| 2014/0213842 A1 | 7/2014 | Simon et al. |
| 2014/0213843 A1 | 7/2014 | Pilla et al. |
| 2014/0213844 A1 | 7/2014 | Pilla et al. |
| 2014/0213937 A1 | 7/2014 | Bianchi et al. |
| 2014/0213961 A1 | 7/2014 | Whitehurst et al. |
| 2014/0214135 A1 | 7/2014 | Ben-David et al. |
| 2014/0214330 A1 | 7/2014 | Iyer et al. |
| 2014/0214335 A1 | 7/2014 | Siefert |
| 2014/0221726 A1 | 8/2014 | Pilla et al. |
| 2014/0221866 A1 | 8/2014 | Quy |
| 2014/0222113 A1 | 8/2014 | Gliner et al. |
| 2014/0222406 A1 | 8/2014 | Taylor |
| 2014/0226131 A1 | 8/2014 | Lopez et al. |
| 2014/0226888 A1 | 8/2014 | Skidmore |
| 2014/0228620 A1 | 8/2014 | Vasishta |
| 2014/0228649 A1 | 8/2014 | Rayner et al. |
| 2014/0228651 A1 | 8/2014 | Causevic et al. |
| 2014/0228653 A1 | 8/2014 | Kiraly |
| 2014/0228702 A1 | 8/2014 | Shahaf et al. |
| 2014/0232516 A1 | 8/2014 | Stivoric et al. |
| 2014/0235826 A1 | 8/2014 | Deisseroth et al. |
| 2014/0235965 A1 | 8/2014 | Tran |
| 2014/0236039 A1 | 8/2014 | Strokova Aksenova et al. |
| 2014/0236077 A1 | 8/2014 | Robertson et al. |
| 2014/0236272 A1 | 8/2014 | Simon et al. |
| 2014/0236492 A1 | 8/2014 | Taylor |
| 2014/0237073 A1 | 8/2014 | Schiff |

(56)                    References Cited

U.S. PATENT DOCUMENTS

| | | |
|---|---|---|
| 2014/0243608 A1 | 8/2014 | Hunt |
| 2014/0243613 A1 | 8/2014 | Osorio |
| 2014/0243614 A1 | 8/2014 | Rothberg et al. |
| 2014/0243621 A1 | 8/2014 | Weng et al. |
| 2014/0243628 A1 | 8/2014 | Ochs et al. |
| 2014/0243647 A1 | 8/2014 | Clark et al. |
| 2014/0243652 A1 | 8/2014 | Pashko |
| 2014/0243663 A1 | 8/2014 | Taylor |
| 2014/0243694 A1 | 8/2014 | Baker et al. |
| 2014/0243714 A1 | 8/2014 | Ward et al. |
| 2014/0243926 A1 | 8/2014 | Carcieri |
| 2014/0243934 A1 | 8/2014 | Vo-Dinh et al. |
| 2014/0245191 A1 | 8/2014 | Serena |
| 2014/0247970 A1 | 9/2014 | Taylor |
| 2014/0249360 A1 | 9/2014 | Jaeger et al. |
| 2014/0249396 A1 | 9/2014 | Shacham-Diamand et al. |
| 2014/0249429 A1 | 9/2014 | Tran |
| 2014/0249445 A1 | 9/2014 | Deadwyler et al. |
| 2014/0249447 A1 | 9/2014 | Sereno et al. |
| 2014/0249454 A1 | 9/2014 | Carpentier |
| 2014/0249608 A1 | 9/2014 | Rogers |
| 2014/0249791 A1 | 9/2014 | Taylor |
| 2014/0249792 A1 | 9/2014 | Taylor |
| 2014/0257047 A1 | 9/2014 | Sillay et al. |
| 2014/0257073 A1 | 9/2014 | Machon et al. |
| 2014/0257118 A1 | 9/2014 | DiLorenzo et al. |
| 2014/0257128 A1 | 9/2014 | Moxon et al. |
| 2014/0257132 A1 | 9/2014 | Kilgard et al. |
| 2014/0257147 A1 | 9/2014 | John et al. |
| 2014/0257430 A1 | 9/2014 | Kilgard et al. |
| 2014/0257437 A1 | 9/2014 | Simon et al. |
| 2014/0257438 A1 | 9/2014 | Simon et al. |
| 2014/0266696 A1 | 9/2014 | Addison et al. |
| 2014/0266787 A1 | 9/2014 | Tran |
| 2014/0270438 A1 | 9/2014 | Declerck et al. |
| 2014/0271483 A1 | 9/2014 | Satchi-Fainaro et al. |
| 2014/0275716 A1 | 9/2014 | Connor |
| 2014/0275741 A1 | 9/2014 | Vandenbelt et al. |
| 2014/0275807 A1 | 9/2014 | Redei |
| 2014/0275847 A1 | 9/2014 | Perryman et al. |
| 2014/0275851 A1 | 9/2014 | Amble et al. |
| 2014/0275886 A1 | 9/2014 | Teixeira |
| 2014/0275889 A1 | 9/2014 | Addison et al. |
| 2014/0275891 A1 | 9/2014 | Muehlemann et al. |
| 2014/0275944 A1 | 9/2014 | Semenov |
| 2014/0276012 A1 | 9/2014 | Semenov |
| 2014/0276013 A1 | 9/2014 | Muehlemann et al. |
| 2014/0276014 A1 | 9/2014 | Khanicheh et al. |
| 2014/0276090 A1 | 9/2014 | Breed |
| 2014/0276123 A1 | 9/2014 | Yang |
| 2014/0276130 A1 | 9/2014 | Mirelman et al. |
| 2014/0276181 A1 | 9/2014 | Sun et al. |
| 2014/0276183 A1 | 9/2014 | Badower |
| 2014/0276185 A1 | 9/2014 | Carlson et al. |
| 2014/0276187 A1 | 9/2014 | Iasemidis et al. |
| 2014/0276194 A1 | 9/2014 | Osorio |
| 2014/0276549 A1 | 9/2014 | Osorio |
| 2014/0276702 A1 | 9/2014 | McKay et al. |
| 2014/0276944 A1 | 9/2014 | Farritor et al. |
| 2014/0277255 A1 | 9/2014 | Sabesan |
| 2014/0277256 A1 | 9/2014 | Osorio |
| 2014/0277282 A1 | 9/2014 | Jaax |
| 2014/0277286 A1 | 9/2014 | Cinbis |
| 2014/0277582 A1 | 9/2014 | Leuthardt et al. |
| 2014/0279341 A1 | 9/2014 | Bhardwaj et al. |
| 2014/0279746 A1 | 9/2014 | De Bruin et al. |
| 2014/0280189 A1* | 9/2014 | Tang ...................... G06F 7/22 |
| | | 707/741 |
| 2014/0288381 A1 | 9/2014 | Faarbaek et al. |
| 2014/0288614 A1 | 9/2014 | Hagedorn et al. |
| 2014/0288620 A1 | 9/2014 | DiLorenzo |
| 2014/0288953 A1 | 9/2014 | Lynn et al. |
| 2014/0289172 A1 | 9/2014 | Rothman et al. |
| 2014/0296646 A1 | 10/2014 | Wingeier et al. |
| 2014/0296655 A1 | 10/2014 | Akhbardeh et al. |
| 2014/0296724 A1 | 10/2014 | Guttag et al. |
| 2014/0296733 A1 | 10/2014 | Omurtag et al. |
| 2014/0296750 A1 | 10/2014 | Einav et al. |
| 2014/0297397 A1 | 10/2014 | Bakalash et al. |
| 2014/0300532 A1 | 10/2014 | Karkkainen et al. |
| 2014/0303424 A1 | 10/2014 | Glass |
| 2014/0303425 A1 | 10/2014 | Pilla et al. |
| 2014/0303452 A1 | 10/2014 | Ghaffari |
| 2014/0303453 A1 | 10/2014 | Seely et al. |
| 2014/0303454 A1 | 10/2014 | Clifton et al. |
| 2014/0303486 A1 | 10/2014 | Baumgartner et al. |
| 2014/0303508 A1 | 10/2014 | Plotnik-Peleg et al. |
| 2014/0303511 A1 | 10/2014 | Sajda et al. |
| 2014/0304773 A1 | 10/2014 | Woods et al. |
| 2014/0309484 A1 | 10/2014 | Chang |
| 2014/0309614 A1 | 10/2014 | Frei et al. |
| 2014/0309881 A1 | 10/2014 | Fung et al. |
| 2014/0309943 A1 | 10/2014 | Grundlehner et al. |
| 2014/0313303 A1 | 10/2014 | Davis et al. |
| 2014/0315169 A1 | 10/2014 | Bohbot |
| 2014/0316191 A1 | 10/2014 | de Zambotti et al. |
| 2014/0316192 A1 | 10/2014 | de Zambotti et al. |
| 2014/0316217 A1 | 10/2014 | Purdon et al. |
| 2014/0316221 A1 | 10/2014 | Rothman |
| 2014/0316230 A1 | 10/2014 | Denison et al. |
| 2014/0316235 A1 | 10/2014 | Davis et al. |
| 2014/0316243 A1 | 10/2014 | Niedermeyer |
| 2014/0316248 A1 | 10/2014 | deCharms |
| 2014/0316278 A1 | 10/2014 | Addison et al. |
| 2014/0323849 A1 | 10/2014 | Deisseroth et al. |
| 2014/0323899 A1 | 10/2014 | Silberstein |
| 2014/0323900 A1 | 10/2014 | Bibian et al. |
| 2014/0323924 A1 | 10/2014 | Mishelevich |
| 2014/0323946 A1 | 10/2014 | Bourke, Jr. et al. |
| 2014/0324118 A1 | 10/2014 | Simon et al. |
| 2014/0324138 A1 | 10/2014 | Wentz et al. |
| 2014/0328487 A1 | 11/2014 | Hiroe |
| 2014/0330093 A1 | 11/2014 | Pedro |
| 2014/0330102 A1 | 11/2014 | Zbrzeski et al. |
| 2014/0330157 A1 | 11/2014 | Snook |
| 2014/0330159 A1 | 11/2014 | Costa et al. |
| 2014/0330268 A1 | 11/2014 | Palti et al. |
| 2014/0330334 A1 | 11/2014 | Errico et al. |
| 2014/0330335 A1 | 11/2014 | Errico et al. |
| 2014/0330336 A1 | 11/2014 | Errico et al. |
| 2014/0330337 A1 | 11/2014 | Linke et al. |
| 2014/0330345 A1 | 11/2014 | John |
| 2014/0330357 A1 | 11/2014 | Stevenson et al. |
| 2014/0330394 A1 | 11/2014 | Leuthardt et al. |
| 2014/0330404 A1 | 11/2014 | Abdelghani et al. |
| 2014/0330580 A1 | 11/2014 | Grima et al. |
| 2014/0335489 A1 | 11/2014 | DeCharms |
| 2014/0336473 A1 | 11/2014 | Greco |
| 2014/0336489 A1 | 11/2014 | Angotzi et al. |
| 2014/0336514 A1 | 11/2014 | Peyman |
| 2014/0336547 A1 | 11/2014 | Tass et al. |
| 2014/0336730 A1 | 11/2014 | Simon et al. |
| 2014/0340084 A1 | 11/2014 | Alon |
| 2014/0343397 A1 | 11/2014 | Kim et al. |
| 2014/0343399 A1 | 11/2014 | Posse |
| 2014/0343408 A1 | 11/2014 | Tolkowsky |
| 2014/0343463 A1 | 11/2014 | Mishelevich |
| 2014/0343882 A1 | 11/2014 | Taulu et al. |
| 2014/0347265 A1 | 11/2014 | Aimone et al. |
| 2014/0347491 A1 | 11/2014 | Connor |
| 2014/0348183 A1 | 11/2014 | Kim et al. |
| 2014/0348412 A1 | 11/2014 | Taylor |
| 2014/0350353 A1 | 11/2014 | Connor |
| 2014/0350369 A1 | 11/2014 | Budiman et al. |
| 2014/0350380 A1 | 11/2014 | Eidelberg |
| 2014/0350431 A1 | 11/2014 | Hagedorn |
| 2014/0350436 A1 | 11/2014 | Nathan et al. |
| 2014/0350634 A1 | 11/2014 | Grill et al. |
| 2014/0350636 A1 | 11/2014 | King et al. |
| 2014/0350864 A1 | 11/2014 | Fang et al. |
| 2014/0354278 A1 | 12/2014 | Subbarao |
| 2014/0355859 A1 | 12/2014 | Taylor et al. |
| 2014/0357507 A1 | 12/2014 | Umansky et al. |
| 2014/0357932 A1 | 12/2014 | Lozano |

(56) References Cited

U.S. PATENT DOCUMENTS

| | | |
|---|---|---|
| 2014/0357935 A1 | 12/2014 | Ilmoniemi et al. |
| 2014/0357936 A1 | 12/2014 | Simon et al. |
| 2014/0357962 A1 | 12/2014 | Harrington et al. |
| 2014/0358024 A1 | 12/2014 | Nelson et al. |
| 2014/0358025 A1 | 12/2014 | Parhi et al. |
| 2014/0358067 A1 | 12/2014 | Deisseroth et al. |
| 2014/0358193 A1 | 12/2014 | Lyons et al. |
| 2014/0358199 A1 | 12/2014 | Lim |
| 2014/0364721 A1 | 12/2014 | Lee et al. |
| 2014/0364746 A1 | 12/2014 | Addison et al. |
| 2014/0369537 A1 | 12/2014 | Pontoppidan et al. |
| 2014/0370479 A1 | 12/2014 | Gazzaley |
| 2014/0371515 A1 | 12/2014 | John |
| 2014/0371516 A1 | 12/2014 | Tsai et al. |
| 2014/0371544 A1 | 12/2014 | Wu et al. |
| 2014/0371573 A1 | 12/2014 | Komoto et al. |
| 2014/0371599 A1 | 12/2014 | Wu et al. |
| 2014/0371611 A1 | 12/2014 | Kim |
| 2014/0371984 A1 | 12/2014 | Fung et al. |
| 2014/0378809 A1 | 12/2014 | Weitnauer et al. |
| 2014/0378810 A1 | 12/2014 | Davis et al. |
| 2014/0378815 A1 | 12/2014 | Huang et al. |
| 2014/0378830 A1 | 12/2014 | Li |
| 2014/0378851 A1 | 12/2014 | Frei et al. |
| 2014/0378941 A1 | 12/2014 | Su et al. |
| 2014/0379620 A1 | 12/2014 | Sarrafzadeh et al. |
| 2015/0002815 A1 | 1/2015 | Gross et al. |
| 2015/0003698 A1 | 1/2015 | Davis et al. |
| 2015/0003699 A1 | 1/2015 | Davis et al. |
| 2015/0005592 A1 | 1/2015 | Osorio |
| 2015/0005594 A1 | 1/2015 | Chamoun et al. |
| 2015/0005640 A1 | 1/2015 | Davis et al. |
| 2015/0005644 A1 | 1/2015 | Rhoads |
| 2015/0005646 A1 | 1/2015 | Balakrishnan et al. |
| 2015/0005660 A1 | 1/2015 | Kraus et al. |
| 2015/0005680 A1 | 1/2015 | Lipani |
| 2015/0005839 A1 | 1/2015 | Sabesan et al. |
| 2015/0005840 A1 | 1/2015 | Pal et al. |
| 2015/0005841 A1 | 1/2015 | Pal et al. |
| 2015/0006186 A1 | 1/2015 | Davis et al. |
| 2015/0008916 A1 | 1/2015 | Le Prado et al. |
| 2015/0010223 A1 | 1/2015 | Sapiro et al. |
| 2015/0011866 A1 | 1/2015 | Baumgartner |
| 2015/0011877 A1 | 1/2015 | Baumgartner |
| 2015/0011907 A1 | 1/2015 | Purdon et al. |
| 2015/0012054 A1 | 1/2015 | Kilgard et al. |
| 2015/0012057 A1 | 1/2015 | Carlson et al. |
| 2015/0012111 A1 | 1/2015 | Contreras-Vidal et al. |
| 2015/0012466 A1 | 1/2015 | Sapiro et al. |
| 2015/0016618 A1 | 1/2015 | Adachi et al. |
| 2015/0017115 A1 | 1/2015 | Satchi-Fainaro et al. |
| 2015/0018665 A1 | 1/2015 | Jasanoff et al. |
| 2015/0018699 A1 | 1/2015 | Zeng et al. |
| 2015/0018702 A1 | 1/2015 | Galloway et al. |
| 2015/0018705 A1 | 1/2015 | Barlow et al. |
| 2015/0018706 A1 | 1/2015 | Segal |
| 2015/0018758 A1 | 1/2015 | John |
| 2015/0018893 A1 | 1/2015 | Kilgard et al. |
| 2015/0018905 A1 | 1/2015 | Nofzinger et al. |
| 2015/0019241 A1 | 1/2015 | Bennett et al. |
| 2015/0019266 A1 | 1/2015 | Stempora |
| 2015/0024356 A1 | 1/2015 | Hillyer et al. |
| 2015/0025351 A1 | 1/2015 | Govari |
| 2015/0025408 A1 | 1/2015 | Wingeier et al. |
| 2015/0025410 A1 | 1/2015 | Wolpaw et al. |
| 2015/0025421 A1 | 1/2015 | Wagner et al. |
| 2015/0025422 A1 | 1/2015 | Tyler |
| 2015/0025610 A1 | 1/2015 | Wingeier et al. |
| 2015/0025917 A1 | 1/2015 | Stempora |
| 2015/0026446 A1 | 1/2015 | Kim et al. |
| 2015/0029087 A1 | 1/2015 | Klappert et al. |
| 2015/0030220 A1 | 1/2015 | Cho et al. |
| 2015/0032017 A1 | 1/2015 | Babaeizadeh et al. |
| 2015/0032044 A9 | 1/2015 | Peyman |
| 2015/0032178 A1 | 1/2015 | Simon et al. |
| 2015/0033245 A1 | 1/2015 | Klappert et al. |
| 2015/0033258 A1 | 1/2015 | Klappert et al. |
| 2015/0033259 A1 | 1/2015 | Klappert et al. |
| 2015/0033262 A1 | 1/2015 | Klappert et al. |
| 2015/0033266 A1 | 1/2015 | Klappert et al. |
| 2015/0033363 A1 | 1/2015 | Pinsky et al. |
| 2015/0035959 A1 | 2/2015 | Amble et al. |
| 2015/0038804 A1 | 2/2015 | Younes |
| 2015/0038812 A1 | 2/2015 | Ayaz et al. |
| 2015/0038822 A1 | 2/2015 | Wingeier et al. |
| 2015/0038869 A1 | 2/2015 | Simon et al. |
| 2015/0039066 A1 | 2/2015 | Wingeier et al. |
| 2015/0039110 A1 | 2/2015 | Abeyratne et al. |
| 2015/0042477 A1 | 2/2015 | Kobetski et al. |
| 2015/0044138 A1 | 2/2015 | Lansbergen et al. |
| 2015/0045606 A1 | 2/2015 | Hagedorn et al. |
| 2015/0045607 A1 | 2/2015 | Hakansson |
| 2015/0045686 A1 | 2/2015 | Lynn |
| 2015/0051655 A1 | 2/2015 | Kilgard et al. |
| 2015/0051656 A1 | 2/2015 | Kilgard et al. |
| 2015/0051657 A1 | 2/2015 | Kilgard et al. |
| 2015/0051658 A1 | 2/2015 | Kilgard et al. |
| 2015/0051659 A1 | 2/2015 | Kilgard et al. |
| 2015/0051663 A1 | 2/2015 | Hagedorn |
| 2015/0051668 A1 | 2/2015 | Bahmer |
| 2015/0057512 A1 | 2/2015 | Kapoor |
| 2015/0057715 A1 | 2/2015 | Kilgard et al. |
| 2015/0065803 A1 | 3/2015 | Douglas et al. |
| 2015/0065831 A1 | 3/2015 | Popovic et al. |
| 2015/0065838 A1 | 3/2015 | Wingeier et al. |
| 2015/0065839 A1 | 3/2015 | Farah et al. |
| 2015/0065845 A1 | 3/2015 | Takiguchi |
| 2015/0066124 A1 | 3/2015 | Stevenson et al. |
| 2015/0068069 A1 | 3/2015 | Tran et al. |
| 2015/0069846 A1 | 3/2015 | Hokari |
| 2015/0071907 A1 | 3/2015 | Crombez et al. |
| 2015/0072394 A1 | 3/2015 | Deisseroth et al. |
| 2015/0073141 A1 | 3/2015 | Teegarden et al. |
| 2015/0073237 A1 | 3/2015 | Osorio |
| 2015/0073249 A1 | 3/2015 | Musha |
| 2015/0073294 A1 | 3/2015 | Zhang et al. |
| 2015/0073306 A1 | 3/2015 | Abeyratne et al. |
| 2015/0073505 A1 | 3/2015 | Errico et al. |
| 2015/0073722 A1 | 3/2015 | Taylor et al. |
| 2015/0080327 A1 | 3/2015 | Paul et al. |
| 2015/0080671 A1 | 3/2015 | Christensen et al. |
| 2015/0080674 A1 | 3/2015 | Drew et al. |
| 2015/0080695 A1 | 3/2015 | Rogers et al. |
| 2015/0080703 A1 | 3/2015 | Reiman |
| 2015/0080746 A1 | 3/2015 | Bleich et al. |
| 2015/0080753 A1 | 3/2015 | Miyazaki et al. |
| 2015/0080985 A1 | 3/2015 | Yun et al. |
| 2015/0081226 A1 | 3/2015 | Baki |
| 2015/0081299 A1 | 3/2015 | Jasinschi et al. |
| 2015/0087931 A1 | 3/2015 | Banerjee et al. |
| 2015/0088015 A1 | 3/2015 | Taylor |
| 2015/0088024 A1* | 3/2015 | Sackellares ............ A61B 5/291 600/544 |
| 2015/0088093 A1 | 3/2015 | Goetz |
| 2015/0088120 A1 | 3/2015 | Garcia et al. |
| 2015/0088224 A1 | 3/2015 | Goldwasser et al. |
| 2015/0088228 A1 | 3/2015 | Moffitt |
| 2015/0088478 A1 | 3/2015 | Taylor |
| 2015/0091730 A1 | 4/2015 | Kangas et al. |
| 2015/0091791 A1 | 4/2015 | Segal |
| 2015/0092949 A1 | 4/2015 | Adachi et al. |
| 2015/0093729 A1 | 4/2015 | Plans et al. |
| 2015/0094962 A1 | 4/2015 | Hoegh et al. |
| 2015/0096564 A1 | 4/2015 | Cosnek |
| 2015/0099941 A1 | 4/2015 | Tran |
| 2015/0099946 A1 | 4/2015 | Sahin |
| 2015/0099959 A1 | 4/2015 | Bonmassar et al. |
| 2015/0099962 A1 | 4/2015 | Weiss et al. |
| 2015/0103360 A1 | 4/2015 | Addison et al. |
| 2015/0105631 A1 | 4/2015 | Tran et al. |
| 2015/0105641 A1 | 4/2015 | Austin et al. |
| 2015/0105701 A1 | 4/2015 | Mayer et al. |
| 2015/0105837 A1 | 4/2015 | Aguilar Domingo |
| 2015/0105844 A1 | 4/2015 | Tass et al. |

(56)                References Cited

U.S. PATENT DOCUMENTS

| | | |
|---|---|---|
| 2015/0112222 A1 | 4/2015 | Sun et al. |
| 2015/0112403 A1 | 4/2015 | Ruffini et al. |
| 2015/0112409 A1 | 4/2015 | Hagedorn |
| 2015/0112899 A1 | 4/2015 | Dagum |
| 2015/0119652 A1 | 4/2015 | Hyde et al. |
| 2015/0119658 A1 | 4/2015 | Osorio |
| 2015/0119689 A1 | 4/2015 | Pascual-Leone et al. |
| 2015/0119698 A1 | 4/2015 | Eyal et al. |
| 2015/0119743 A1 | 4/2015 | Maksym et al. |
| 2015/0119745 A1 | 4/2015 | Similowski et al. |
| 2015/0119746 A1 | 4/2015 | Conradsen |
| 2015/0119794 A1 | 4/2015 | Peyman |
| 2015/0119898 A1 | 4/2015 | Desalles et al. |
| 2015/0119956 A1 | 4/2015 | Libbus et al. |
| 2015/0120007 A1 | 4/2015 | Guez et al. |
| 2015/0123653 A1 | 5/2015 | Nagasaka |
| 2015/0124220 A1 | 5/2015 | Gross et al. |
| 2015/0126821 A1 | 5/2015 | Kempfner et al. |
| 2015/0126845 A1 | 5/2015 | Jin et al. |
| 2015/0126848 A1 | 5/2015 | Baker et al. |
| 2015/0126873 A1 | 5/2015 | Connor |
| 2015/0133716 A1 | 5/2015 | Suhami et al. |
| 2015/0133811 A1 | 5/2015 | Suzuki et al. |
| 2015/0133812 A1 | 5/2015 | deCharms |
| 2015/0133830 A1 | 5/2015 | Dirks et al. |
| 2015/0134031 A1 | 5/2015 | Moffitt et al. |
| 2015/0134264 A1 | 5/2015 | Tansey |
| 2015/0137817 A1 | 5/2015 | Wilson et al. |
| 2015/0137988 A1 | 5/2015 | Gravenstein et al. |
| 2015/0140528 A1 | 5/2015 | Sikstrom et al. |
| 2015/0141529 A1 | 5/2015 | Hargrove |
| 2015/0141773 A1 | 5/2015 | Einav et al. |
| 2015/0141789 A1 | 5/2015 | Knight et al. |
| 2015/0141794 A1 | 5/2015 | Foo |
| 2015/0142082 A1 | 5/2015 | Simon et al. |
| 2015/0145519 A1 | 5/2015 | Lee et al. |
| 2015/0145676 A1 | 5/2015 | Adhikari et al. |
| 2015/0148617 A1 | 5/2015 | Friedman |
| 2015/0148619 A1 | 5/2015 | Berg et al. |
| 2015/0148700 A1 | 5/2015 | Mhuircheartaigh et al. |
| 2015/0148878 A1 | 5/2015 | Yoo et al. |
| 2015/0150122 A1 | 5/2015 | Son et al. |
| 2015/0150473 A1 | 6/2015 | Knight et al. |
| 2015/0150475 A1 | 6/2015 | Varcoe |
| 2015/0150530 A1 | 6/2015 | Taylor et al. |
| 2015/0150753 A1 | 6/2015 | Racette |
| 2015/0151142 A1 | 6/2015 | Tyler et al. |
| 2015/0153477 A1 | 6/2015 | Wikelski et al. |
| 2015/0154721 A1 | 6/2015 | Thompson |
| 2015/0154764 A1 | 6/2015 | Xie et al. |
| 2015/0154889 A1 | 6/2015 | Tuchschmid et al. |
| 2015/0157235 A1 | 6/2015 | Jelen et al. |
| 2015/0157266 A1 | 6/2015 | Machon et al. |
| 2015/0157271 A1 | 6/2015 | Zhang |
| 2015/0157859 A1 | 6/2015 | Besio |
| 2015/0161326 A1 | 6/2015 | Taylor et al. |
| 2015/0161348 A1 | 6/2015 | Taylor et al. |
| 2015/0161738 A1 | 6/2015 | Stempora |
| 2015/0164349 A1 | 6/2015 | Gopalakrishnan et al. |
| 2015/0164362 A1 | 6/2015 | Morrow |
| 2015/0164375 A1 | 6/2015 | Schindhelm et al. |
| 2015/0164404 A1 | 6/2015 | Euliano et al. |
| 2015/0164431 A1 | 6/2015 | Terry et al. |
| 2015/0165226 A1 | 6/2015 | Simon et al. |
| 2015/0165239 A1 | 6/2015 | Mishelevich |
| 2015/0167459 A1 | 6/2015 | Sen et al. |
| 2015/0174362 A1 | 6/2015 | Panova et al. |
| 2015/0174398 A1 | 6/2015 | Chow et al. |
| 2015/0174403 A1 | 6/2015 | Pal et al. |
| 2015/0174405 A1 | 6/2015 | Kilgard et al. |
| 2015/0174406 A1 | 6/2015 | Lamensdorf et al. |
| 2015/0174407 A1 | 6/2015 | Osorio |
| 2015/0174418 A1 | 6/2015 | Tyler et al. |
| 2015/0177413 A1 | 6/2015 | Wilt et al. |
| 2015/0178631 A1 | 6/2015 | Thomas et al. |
| 2015/0178978 A1 | 6/2015 | Durand et al. |
| 2015/0181840 A1 | 7/2015 | Tupin, Jr. et al. |
| 2015/0182417 A1 | 7/2015 | Nagatani |
| 2015/0182753 A1 | 7/2015 | Harris et al. |
| 2015/0182756 A1 | 7/2015 | Peyman |
| 2015/0186923 A1 | 7/2015 | Gurumoorthy et al. |
| 2015/0190062 A1 | 7/2015 | Han et al. |
| 2015/0190070 A1 | 7/2015 | Bonmassar et al. |
| 2015/0190077 A1 | 7/2015 | Kim et al. |
| 2015/0190085 A1 | 7/2015 | Nathan et al. |
| 2015/0190094 A1 | 7/2015 | Lee et al. |
| 2015/0190636 A1 | 7/2015 | Simon et al. |
| 2015/0190637 A1 | 7/2015 | Simon et al. |
| 2015/0192532 A1 | 7/2015 | Clevenson et al. |
| 2015/0192776 A1 | 7/2015 | Lee et al. |
| 2015/0196213 A1 | 7/2015 | Pandia et al. |
| 2015/0196246 A1 | 7/2015 | Osorio |
| 2015/0196249 A1 | 7/2015 | Brown et al. |
| 2015/0196800 A1 | 7/2015 | Macri et al. |
| 2015/0199010 A1 | 7/2015 | Coleman et al. |
| 2015/0199121 A1 | 7/2015 | Gulaka et al. |
| 2015/0200046 A1 | 7/2015 | Park et al. |
| 2015/0201849 A1 | 7/2015 | Taylor |
| 2015/0201879 A1 | 7/2015 | Hargrove |
| 2015/0202330 A1 | 7/2015 | Yang et al. |
| 2015/0202428 A1 | 7/2015 | Miller |
| 2015/0202447 A1 | 7/2015 | Afshar et al. |
| 2015/0203822 A1 | 7/2015 | Tremolada et al. |
| 2015/0206051 A1 | 7/2015 | McIntosh et al. |
| 2015/0206174 A1 | 7/2015 | Barnett et al. |
| 2015/0208940 A1 | 7/2015 | Addison et al. |
| 2015/0208975 A1 | 7/2015 | Ghajar |
| 2015/0208978 A1 | 7/2015 | Osorio et al. |
| 2015/0208982 A1 | 7/2015 | Ho et al. |
| 2015/0208994 A1 | 7/2015 | Rapoport |
| 2015/0212168 A1 | 7/2015 | Shah et al. |
| 2015/0213012 A1 | 7/2015 | Marvit et al. |
| 2015/0213019 A1 | 7/2015 | Marvit et al. |
| 2015/0213020 A1 | 7/2015 | Marvit et al. |
| 2015/0213191 A1 | 7/2015 | Abdelghani et al. |
| 2015/0215412 A1 | 7/2015 | Marvit et al. |
| 2015/0216436 A1 | 8/2015 | Bosl et al. |
| 2015/0216439 A1 | 8/2015 | Muraskin et al. |
| 2015/0216468 A1 | 8/2015 | Vidal-Naquet et al. |
| 2015/0216469 A1 | 8/2015 | DiLorenzo et al. |
| 2015/0216762 A1 | 8/2015 | Oohashi et al. |
| 2015/0217082 A1 | 8/2015 | Kang et al. |
| 2015/0219729 A1 | 8/2015 | Takahashi |
| 2015/0219732 A1 | 8/2015 | Diamond et al. |
| 2015/0220486 A1 | 8/2015 | Karakonstantis et al. |
| 2015/0220830 A1 | 8/2015 | Li et al. |
| 2015/0223721 A1 | 8/2015 | De Ridder |
| 2015/0223731 A1 | 8/2015 | Sahin |
| 2015/0223743 A1 | 8/2015 | Pathangay et al. |
| 2015/0223905 A1 | 8/2015 | Karmarkar et al. |
| 2015/0226813 A1 | 8/2015 | Yu et al. |
| 2015/0227702 A1 | 8/2015 | Krishna et al. |
| 2015/0227793 A1 | 8/2015 | Ernst et al. |
| 2015/0230719 A1 | 8/2015 | Berg et al. |
| 2015/0230744 A1 | 8/2015 | Faubert et al. |
| 2015/0230750 A1 | 8/2015 | McDarby et al. |
| 2015/0231330 A1 | 8/2015 | Lozano et al. |
| 2015/0231395 A1 | 8/2015 | Saab |
| 2015/0231397 A1 | 8/2015 | Nudo, Jr. et al. |
| 2015/0231405 A1 | 8/2015 | Okada |
| 2015/0231408 A1 | 8/2015 | Williams et al. |
| 2015/0234477 A1 | 8/2015 | Abovitz et al. |
| 2015/0235088 A1 | 8/2015 | Abovitz et al. |
| 2015/0235370 A1 | 8/2015 | Abovitz et al. |
| 2015/0235441 A1 | 8/2015 | Abovitz et al. |
| 2015/0235447 A1 | 8/2015 | Abovitz et al. |
| 2015/0238104 A1 | 8/2015 | Tass |
| 2015/0238106 A1 | 8/2015 | Lappalainen et al. |
| 2015/0238112 A1 | 8/2015 | Park et al. |
| 2015/0238137 A1 | 8/2015 | Eyal et al. |
| 2015/0238693 A1 | 8/2015 | Skelton et al. |
| 2015/0238761 A1 | 8/2015 | Sabesan |
| 2015/0238765 A1 | 8/2015 | Zhu |
| 2015/0241705 A1 | 8/2015 | Abovitz et al. |

(56)　　　　References Cited

U.S. PATENT DOCUMENTS

| | | |
|---|---|---|
| 2015/0241916 A1 | 8/2015 | Choi et al. |
| 2015/0241959 A1 | 8/2015 | Abovitz et al. |
| 2015/0242575 A1 | 8/2015 | Abovitz et al. |
| 2015/0242608 A1 | 8/2015 | Kim et al. |
| 2015/0242943 A1 | 8/2015 | Abovitz et al. |
| 2015/0243100 A1 | 8/2015 | Abovitz et al. |
| 2015/0243105 A1 | 8/2015 | Abovitz et al. |
| 2015/0243106 A1 | 8/2015 | Abovitz et al. |
| 2015/0245781 A1 | 9/2015 | Hua |
| 2015/0245800 A1 | 9/2015 | Sorensen et al. |
| 2015/0246238 A1 | 9/2015 | Moses et al. |
| 2015/0247723 A1 | 9/2015 | Abovitz et al. |
| 2015/0247921 A1 | 9/2015 | Rothberg et al. |
| 2015/0247975 A1 | 9/2015 | Abovitz et al. |
| 2015/0247976 A1 | 9/2015 | Abovitz et al. |
| 2015/0248167 A1 | 9/2015 | Turbell et al. |
| 2015/0248169 A1 | 9/2015 | Abovitz et al. |
| 2015/0248170 A1 | 9/2015 | Abovitz et al. |
| 2015/0248470 A1 | 9/2015 | Coleman et al. |
| 2015/0248615 A1 | 9/2015 | Parra et al. |
| 2015/0248764 A1 | 9/2015 | Keskin et al. |
| 2015/0248765 A1 | 9/2015 | Criminisi et al. |
| 2015/0248787 A1 | 9/2015 | Abovitz et al. |
| 2015/0248788 A1 | 9/2015 | Abovitz et al. |
| 2015/0248789 A1 | 9/2015 | Abovitz et al. |
| 2015/0248791 A1 | 9/2015 | Abovitz et al. |
| 2015/0248792 A1 | 9/2015 | Abovitz et al. |
| 2015/0248793 A1 | 9/2015 | Abovitz et al. |
| 2015/0250393 A1 | 9/2015 | Tran |
| 2015/0250401 A1 | 9/2015 | Tveit |
| 2015/0250415 A1 | 9/2015 | Leininger et al. |
| 2015/0251016 A1 | 9/2015 | Vo-Dinh et al. |
| 2015/0253391 A1 | 9/2015 | Toda et al. |
| 2015/0253410 A1 | 9/2015 | Warfield et al. |
| 2015/0254413 A1 | 9/2015 | Soederstroem |
| 2015/0257645 A1 | 9/2015 | Bae et al. |
| 2015/0257648 A1 | 9/2015 | Semenov |
| 2015/0257649 A1 | 9/2015 | Semenov |
| 2015/0257673 A1 | 9/2015 | Lawrence et al. |
| 2015/0257674 A1 | 9/2015 | Jordan et al. |
| 2015/0257700 A1 | 9/2015 | Fu |
| 2015/0257712 A1 | 9/2015 | Sarrafzadeh et al. |
| 2015/0262016 A1 | 9/2015 | Rothblatt |
| 2015/0264492 A1 | 9/2015 | Laudanski et al. |
| 2015/0265164 A1 | 9/2015 | Gopalakrishnan et al. |
| 2015/0265207 A1 | 9/2015 | Wu et al. |
| 2015/0265583 A1 | 9/2015 | Chesworth et al. |
| 2015/0265830 A1 | 9/2015 | Simon et al. |
| 2015/0265836 A1 | 9/2015 | Simon et al. |
| 2015/0269825 A1 | 9/2015 | Tran |
| 2015/0272448 A1 | 10/2015 | Fonte et al. |
| 2015/0272461 A1 | 10/2015 | Morimoto et al. |
| 2015/0272465 A1 | 10/2015 | Ishii |
| 2015/0272496 A1 | 10/2015 | Klappert et al. |
| 2015/0272510 A1 | 10/2015 | Chin |
| 2015/0272652 A1 | 10/2015 | Ghaffari et al. |
| 2015/0273211 A1 | 10/2015 | Ollivier |
| 2015/0273223 A1 | 10/2015 | John |
| 2015/0282705 A1 | 10/2015 | Avital |
| 2015/0282730 A1 | 10/2015 | Knight et al. |
| 2015/0282749 A1 | 10/2015 | Zand et al. |
| 2015/0282755 A1 | 10/2015 | Deriche et al. |
| 2015/0282760 A1 | 10/2015 | Badower et al. |
| 2015/0283019 A1 | 10/2015 | Feingold |
| 2015/0283265 A1 | 10/2015 | Peyman |
| 2015/0283379 A1 | 10/2015 | Venkatesan |
| 2015/0283393 A1 | 10/2015 | Schmidt |
| 2015/0287223 A1 | 10/2015 | Bresler et al. |
| 2015/0289217 A1 | 10/2015 | Ban et al. |
| 2015/0289779 A1 | 10/2015 | Fischl et al. |
| 2015/0289813 A1 | 10/2015 | Lipov |
| 2015/0289929 A1 | 10/2015 | Toth et al. |
| 2015/0290419 A1 | 10/2015 | Kare et al. |
| 2015/0290420 A1 | 10/2015 | Nofzinger |
| 2015/0290453 A1 | 10/2015 | Tyler et al. |
| 2015/0290454 A1 | 10/2015 | Tyler et al. |
| 2015/0293004 A1 | 10/2015 | Adolphi et al. |
| 2015/0294067 A1 | 10/2015 | Kare et al. |
| 2015/0294074 A1 | 10/2015 | Kawato et al. |
| 2015/0294085 A1 | 10/2015 | Kare et al. |
| 2015/0294086 A1 | 10/2015 | Kare et al. |
| 2015/0294445 A1 | 10/2015 | Sakaue |
| 2015/0296288 A1 | 10/2015 | Anastas |
| 2015/0297106 A1 | 10/2015 | Pasley et al. |
| 2015/0297108 A1 | 10/2015 | Chase et al. |
| 2015/0297109 A1 | 10/2015 | Garten et al. |
| 2015/0297139 A1 | 10/2015 | Toth |
| 2015/0297141 A1 | 10/2015 | Siegel et al. |
| 2015/0297444 A1 | 10/2015 | Tass |
| 2015/0297719 A1 | 10/2015 | Deisseroth et al. |
| 2015/0297889 A1 | 10/2015 | Simon et al. |
| 2015/0297893 A1 | 10/2015 | Kokones et al. |
| 2015/0301218 A1 | 10/2015 | Donderici |
| 2015/0304048 A1 | 10/2015 | Kim et al. |
| 2015/0304101 A1 | 10/2015 | Gupta et al. |
| 2015/0305685 A1 | 10/2015 | Shahaf et al. |
| 2015/0305686 A1 | 10/2015 | Coleman et al. |
| 2015/0305689 A1 | 10/2015 | Gourmelon et al. |
| 2015/0305799 A1 | 10/2015 | Trieu |
| 2015/0305800 A1 | 10/2015 | Trieu |
| 2015/0305801 A1 | 10/2015 | Trieu |
| 2015/0306057 A1 | 10/2015 | Goodenowe |
| 2015/0306340 A1 | 10/2015 | Giap et al. |
| 2015/0306390 A1 | 10/2015 | Zalay et al. |
| 2015/0306391 A1 | 10/2015 | Wu et al. |
| 2015/0306392 A1 | 10/2015 | Sabesan |
| 2015/0309563 A1 | 10/2015 | Connor |
| 2015/0309582 A1 | 10/2015 | Gupta |
| 2015/0310862 A1 | 10/2015 | Dauphin et al. |
| 2015/0313496 A1* | 11/2015 | Connor .................. A61B 5/369 |
| | | 600/301 |
| 2015/0313498 A1 | 11/2015 | Coleman et al. |
| 2015/0313535 A1 | 11/2015 | Alshaer et al. |
| 2015/0313539 A1 | 11/2015 | Connor |
| 2015/0313540 A1 | 11/2015 | Deuchar et al. |
| 2015/0313949 A1 | 11/2015 | Cutillo |
| 2015/0313971 A1 | 11/2015 | Haslett et al. |
| 2015/0315554 A1 | 11/2015 | Shekdar et al. |
| 2015/0317447 A1 | 11/2015 | Helleputte et al. |
| 2015/0317796 A1 | 11/2015 | Schett et al. |
| 2015/0320591 A1 | 11/2015 | Smith et al. |
| 2015/0321000 A1 | 11/2015 | Rosenbluth et al. |
| 2015/0324544 A1 | 11/2015 | Maslowski et al. |
| 2015/0324545 A1 | 11/2015 | Fonte |
| 2015/0324692 A1 | 11/2015 | Ritchey et al. |
| 2015/0325151 A1 | 11/2015 | Tuchschmid et al. |
| 2015/0327813 A1 | 11/2015 | Fu |
| 2015/0327837 A1 | 11/2015 | Qi et al. |
| 2015/0328330 A1 | 11/2015 | Satchi-Fainaro et al. |
| 2015/0328455 A1 | 11/2015 | Meadows et al. |
| 2015/0331929 A1 | 11/2015 | El-Saban et al. |
| 2015/0332015 A1 | 11/2015 | Taylor |
| 2015/0335281 A1 | 11/2015 | Scroggins |
| 2015/0335288 A1 | 11/2015 | Toth et al. |
| 2015/0335292 A1 | 11/2015 | Mittal |
| 2015/0335294 A1 | 11/2015 | Witcher et al. |
| 2015/0335295 A1 | 11/2015 | Park et al. |
| 2015/0335303 A1 | 11/2015 | Chandelier et al. |
| 2015/0335876 A1 | 11/2015 | Jeffery et al. |
| 2015/0335877 A1 | 11/2015 | Jeffery et al. |
| 2015/0338915 A1 | 11/2015 | Publicover et al. |
| 2015/0339363 A1 | 11/2015 | Moldoveanu et al. |
| 2015/0339459 A1 | 11/2015 | Taylor |
| 2015/0342472 A1 | 12/2015 | Semenov |
| 2015/0342478 A1 | 12/2015 | Galen et al. |
| 2015/0342493 A1 | 12/2015 | Hardt |
| 2015/0343215 A1 | 12/2015 | De Ridder |
| 2015/0343222 A1 | 12/2015 | Kilgard et al. |
| 2015/0343242 A1 | 12/2015 | Tyler et al. |
| 2015/0351655 A1* | 12/2015 | Coleman .............. A61B 5/0205 |
| | | 600/595 |
| 2015/0351690 A1 | 12/2015 | Toth et al. |
| 2015/0351701 A1 | 12/2015 | Moxon et al. |
| 2015/0352362 A1 | 12/2015 | Craig |

(56)  References Cited

U.S. PATENT DOCUMENTS

| 2015/0352363 A1 | 12/2015 | McIntyre et al. |
| 2015/0359431 A1 | 12/2015 | Bakalash et al. |
| 2015/0359441 A1 | 12/2015 | Giovangrandi et al. |
| 2015/0359450 A1 | 12/2015 | Lee et al. |
| 2015/0359452 A1 | 12/2015 | Giovangrandi et al. |
| 2015/0359467 A1 | 12/2015 | Tran |
| 2015/0359486 A1 | 12/2015 | Kovacs et al. |
| 2015/0359492 A1 | 12/2015 | Giovangrandi et al. |
| 2015/0360026 A1 | 12/2015 | Wagner |
| 2015/0360030 A1 | 12/2015 | Cartledge et al. |
| 2015/0360039 A1 | 12/2015 | Lempka et al. |
| 2015/0363941 A1 | 12/2015 | Taylor |
| 2015/0366482 A1 | 12/2015 | Lee |
| 2015/0366497 A1 | 12/2015 | Cavuoto et al. |
| 2015/0366503 A1 | 12/2015 | Sjaaheim et al. |
| 2015/0366504 A1 | 12/2015 | Connor |
| 2015/0366516 A1 | 12/2015 | Dripps et al. |
| 2015/0366518 A1 | 12/2015 | Sampson |
| 2015/0366656 A1 | 12/2015 | Wortz et al. |
| 2015/0366659 A1 | 12/2015 | Wortz et al. |
| 2015/0369864 A1 | 12/2015 | Marlow et al. |
| 2015/0370320 A1 | 12/2015 | Connor |
| 2015/0370325 A1 | 12/2015 | Jarosiewicz et al. |
| 2015/0374250 A1 | 12/2015 | Hatano et al. |
| 2015/0374285 A1 | 12/2015 | Chang et al. |
| 2015/0374292 A1 | 12/2015 | Wyeth et al. |
| 2015/0374300 A1 | 12/2015 | Najarian et al. |
| 2015/0374973 A1 | 12/2015 | Morrell |
| 2015/0374983 A1 | 12/2015 | Simon et al. |
| 2015/0374986 A1 | 12/2015 | Bahmer |
| 2015/0374987 A1 | 12/2015 | Bahmer |
| 2015/0374993 A1 | 12/2015 | Morrell |
| 2015/0375006 A1 | 12/2015 | Denison et al. |
| 2015/0379230 A1 | 12/2015 | Taylor |
| 2015/0379370 A1 | 12/2015 | Clifton et al. |
| 2015/0379878 A1 | 12/2015 | Walter et al. |
| 2015/0380009 A1 | 12/2015 | Chang et al. |
| 2016/0000348 A1 | 1/2016 | Kitajo et al. |
| 2016/0000354 A1 | 1/2016 | Hagedorn et al. |
| 2016/0000383 A1 | 1/2016 | Lee et al. |
| 2016/0001065 A1 | 1/2016 | Wingeier et al. |
| 2016/0001096 A1 | 1/2016 | Mishelevich |
| 2016/0001098 A1 | 1/2016 | Wingeier et al. |
| 2016/0002523 A1 | 1/2016 | Huh et al. |
| 2016/0004298 A1 | 1/2016 | Mazed et al. |
| 2016/0004396 A1 | 1/2016 | Gulaka et al. |
| 2016/0004821 A1 | 1/2016 | Fueyo et al. |
| 2016/0004957 A1 | 1/2016 | Solari |
| 2016/0005235 A1 | 1/2016 | Fateh |
| 2016/0005320 A1 | 1/2016 | deCharms et al. |
| 2016/0007899 A1 | 1/2016 | Durkee et al. |
| 2016/0007904 A1 | 1/2016 | Vardy |
| 2016/0007915 A1 | 1/2016 | Berka et al. |
| 2016/0007918 A1 | 1/2016 | Badower et al. |
| 2016/0007945 A1 | 1/2016 | Taylor |
| 2016/0008489 A1 | 1/2016 | Korzus |
| 2016/0008568 A1 | 1/2016 | Attia et al. |
| 2016/0008598 A1 | 1/2016 | McLaughlin et al. |
| 2016/0008600 A1 | 1/2016 | Hershey et al. |
| 2016/0008620 A1 | 1/2016 | Stubbeman |
| 2016/0008632 A1 | 1/2016 | Wetmore et al. |
| 2016/0012011 A1 | 1/2016 | Llinas et al. |
| 2016/0012583 A1 | 1/2016 | Cales et al. |
| 2016/0012749 A1 | 1/2016 | Connor |
| 2016/0015281 A1 | 1/2016 | McKenna et al. |
| 2016/0015289 A1 | 1/2016 | Simon et al. |
| 2016/0015307 A1 | 1/2016 | Kothuri |
| 2016/0015673 A1 | 1/2016 | Goodenowe |
| 2016/0016014 A1 | 1/2016 | Wagner et al. |
| 2016/0019434 A1 | 1/2016 | Caldwell |
| 2016/0019693 A1 | 1/2016 | Silbersweig et al. |
| 2016/0022141 A1 | 1/2016 | Mittal et al. |
| 2016/0022156 A1 | 1/2016 | Kovacs et al. |
| 2016/0022164 A1 | 1/2016 | Brockway et al. |
| 2016/0022165 A1 | 1/2016 | Sackellares et al. |
| 2016/0022167 A1 | 1/2016 | Simon |
| 2016/0022168 A1 | 1/2016 | Luczak et al. |
| 2016/0022206 A1 | 1/2016 | Simon et al. |
| 2016/0022207 A1 | 1/2016 | Roberts et al. |
| 2016/0022981 A1 | 1/2016 | Wingeier et al. |
| 2016/0023016 A1 | 1/2016 | Bonmassar et al. |
| 2016/0026913 A1 | 1/2016 | Moon et al. |
| 2016/0027178 A1 | 1/2016 | Yu et al. |
| 2016/0027293 A1 | 1/2016 | Esteller et al. |
| 2016/0027342 A1 | 1/2016 | Ben-Haim |
| 2016/0027423 A1 | 1/2016 | Deuel et al. |
| 2016/0029896 A1 | 2/2016 | Lee et al. |
| 2016/0029917 A1 | 2/2016 | Baker et al. |
| 2016/0029918 A1 | 2/2016 | Baker et al. |
| 2016/0029946 A1 | 2/2016 | Simon et al. |
| 2016/0029950 A1 | 2/2016 | Chang et al. |
| 2016/0029958 A1 | 2/2016 | Le et al. |
| 2016/0029959 A1 | 2/2016 | Le et al. |
| 2016/0029965 A1 | 2/2016 | Simon |
| 2016/0029998 A1 | 2/2016 | Brister et al. |
| 2016/0030666 A1 | 2/2016 | Lozano et al. |
| 2016/0030702 A1 | 2/2016 | Yang |
| 2016/0030749 A1 | 2/2016 | Carcieri et al. |
| 2016/0030750 A1 | 2/2016 | Bokil et al. |
| 2016/0030834 A1 | 2/2016 | Brown et al. |
| 2016/0031479 A1 | 2/2016 | Fung et al. |
| 2016/0035093 A1 | 2/2016 | Kateb et al. |
| 2016/0038037 A1 | 2/2016 | Kovacs |
| 2016/0038038 A1 | 2/2016 | Kovacs |
| 2016/0038042 A1 | 2/2016 | Mulligan et al. |
| 2016/0038043 A1 | 2/2016 | Mulligan et al. |
| 2016/0038049 A1 | 2/2016 | Geva et al. |
| 2016/0038069 A1 | 2/2016 | Stack |
| 2016/0038091 A1 | 2/2016 | Krishnaswamy et al. |
| 2016/0038559 A1 | 2/2016 | Palmer et al. |
| 2016/0038770 A1 | 2/2016 | Tyler et al. |
| 2016/0040514 A1 | 2/2016 | Rahmani et al. |
| 2016/0044841 A1 | 2/2016 | Chamberlain |
| 2016/0045128 A1 | 2/2016 | Sitt et al. |
| 2016/0045150 A1 | 2/2016 | Leininger et al. |
| 2016/0045162 A1 | 2/2016 | De Graff et al. |
| 2016/0045731 A1 | 2/2016 | Simon et al. |
| 2016/0045756 A1 | 2/2016 | Phillips et al. |
| 2016/0048659 A1 | 2/2016 | Pereira et al. |
| 2016/0048948 A1 | 2/2016 | Bajic |
| 2016/0048965 A1 | 2/2016 | Stehle et al. |
| 2016/0051161 A1 | 2/2016 | Labyt et al. |
| 2016/0051162 A1 | 2/2016 | Durand et al. |
| 2016/0051187 A1 | 2/2016 | Damadian |
| 2016/0051195 A1 | 2/2016 | Pang et al. |
| 2016/0051793 A1 | 2/2016 | Gibson-Horn |
| 2016/0051812 A1 | 2/2016 | Montgomery, Jr. et al. |
| 2016/0051818 A1 | 2/2016 | Simon et al. |
| 2016/0055236 A1 | 2/2016 | Frank et al. |
| 2016/0055304 A1 | 2/2016 | Russell et al. |
| 2016/0055415 A1 | 2/2016 | Baxi |
| 2016/0055842 A1 | 2/2016 | DeFranks et al. |
| 2016/0058301 A1 | 3/2016 | Shusterman |
| 2016/0058304 A1 | 3/2016 | Emblem et al. |
| 2016/0058322 A1 | 3/2016 | Brister et al. |
| 2016/0058354 A1 | 3/2016 | Phan et al. |
| 2016/0058359 A1 | 3/2016 | Osorio |
| 2016/0058366 A1 | 3/2016 | Choi et al. |
| 2016/0058376 A1 | 3/2016 | Baek et al. |
| 2016/0058392 A1 | 3/2016 | Hasson et al. |
| 2016/0058673 A1 | 3/2016 | Francis |
| 2016/0060926 A1 | 3/2016 | Kim et al. |
| 2016/0062459 A1 | 3/2016 | Publicover et al. |
| 2016/0063207 A1 | 3/2016 | Schmidt |
| 2016/0063883 A1 | 3/2016 | Jeyanandarajan |
| 2016/0065724 A1 | 3/2016 | Lee et al. |
| 2016/0065840 A1 | 3/2016 | Kim et al. |
| 2016/0066788 A1 | 3/2016 | Tran et al. |
| 2016/0066789 A1 | 3/2016 | Rogers et al. |
| 2016/0066828 A1 | 3/2016 | Phan et al. |
| 2016/0066838 A1* | 3/2016 | DeCharms ........... A61B 5/4064 |
|  |  | 434/236 |
| 2016/0067485 A1 | 3/2016 | Lindenthaler et al. |
| 2016/0067492 A1 | 3/2016 | Wolpaw et al. |

(56)  References Cited

U.S. PATENT DOCUMENTS

| | | |
|---|---|---|
| 2016/0067494 A1 | 3/2016 | Lipani |
| 2016/0067496 A1 | 3/2016 | Gliner et al. |
| 2016/0067526 A1 | 3/2016 | Yang |
| 2016/0070436 A1 | 3/2016 | Thomas et al. |
| 2016/0073886 A1 | 3/2016 | Connor |
| 2016/0073916 A1 | 3/2016 | Aksenova et al. |
| 2016/0073947 A1 | 3/2016 | Anderson |
| 2016/0073991 A1 | 3/2016 | Taylor |
| 2016/0074657 A1 | 3/2016 | Kwan et al. |
| 2016/0074660 A1 | 3/2016 | Osorio et al. |
| 2016/0074661 A1 | 3/2016 | Lipani |
| 2016/0077547 A1 | 3/2016 | Aimone et al. |
| 2016/0078780 A1 | 3/2016 | Alexander et al. |
| 2016/0081577 A1 | 3/2016 | Sridhar et al. |
| 2016/0081610 A1 | 3/2016 | Osorio et al. |
| 2016/0081613 A1 | 3/2016 | Braun et al. |
| 2016/0081616 A1 | 3/2016 | Li |
| 2016/0081625 A1 | 3/2016 | Kim et al. |
| 2016/0081793 A1 | 3/2016 | Galstian et al. |
| 2016/0082180 A1 | 3/2016 | Toth et al. |
| 2016/0082319 A1 | 3/2016 | Macri et al. |
| 2016/0084925 A1 | 3/2016 | Le Prado et al. |
| 2016/0085302 A1 | 3/2016 | Publicover et al. |
| 2016/0086622 A1 | 3/2016 | Yamamoto |
| 2016/0087603 A1 | 3/2016 | Ricci et al. |
| 2016/0089031 A1 | 3/2016 | Hu |
| 2016/0091448 A1 | 3/2016 | Soleimani |
| 2016/0095546 A1 | 4/2016 | Sahasrabudhe et al. |
| 2016/0095838 A1 | 4/2016 | Satchi-Fainaro et al. |
| 2016/0096025 A1 | 4/2016 | Moffitt et al. |
| 2016/0097824 A1 | 4/2016 | Fujii et al. |
| 2016/0100769 A1 | 4/2016 | Kim et al. |
| 2016/0101260 A1 | 4/2016 | Austin et al. |
| 2016/0102500 A1 | 4/2016 | Donderici et al. |
| 2016/0103487 A1 | 4/2016 | Crawford et al. |
| 2016/0103963 A1 | 4/2016 | Mishra |
| 2016/0104006 A1 | 4/2016 | Son et al. |
| 2016/0106331 A1 | 4/2016 | Zorick et al. |
| 2016/0106344 A1 | 4/2016 | Nazari |
| 2016/0106513 A1 | 4/2016 | De Stavola et al. |
| 2016/0106950 A1 | 4/2016 | Vasapollo |
| 2016/0106997 A1 | 4/2016 | Arendash et al. |
| 2016/0107309 A1 | 4/2016 | Walsh et al. |
| 2016/0107653 A1 | 4/2016 | Fung et al. |
| 2016/0109851 A1 | 4/2016 | Tsang |
| 2016/0109959 A1 | 4/2016 | Heo |
| 2016/0110517 A1 | 4/2016 | Taylor |
| 2016/0110866 A1 | 4/2016 | Taylor |
| 2016/0110867 A1 | 4/2016 | Taylor |
| 2016/0112022 A1 | 4/2016 | Butts |
| 2016/0112684 A1 | 4/2016 | Connor |
| 2016/0113517 A1 | 4/2016 | Lee et al. |
| 2016/0113528 A1 | 4/2016 | Taylor |
| 2016/0113539 A1 | 4/2016 | Sinharay et al. |
| 2016/0113545 A1 | 4/2016 | Kim et al. |
| 2016/0113567 A1 | 4/2016 | Osvath et al. |
| 2016/0113569 A1 | 4/2016 | Zhao et al. |
| 2016/0113587 A1 | 4/2016 | Kothe et al. |
| 2016/0113726 A1 | 4/2016 | Taylor |
| 2016/0114165 A1 | 4/2016 | Levine et al. |
| 2016/0116472 A1 | 4/2016 | Ay |
| 2016/0116553 A1 | 4/2016 | Kim et al. |
| 2016/0117815 A1 | 4/2016 | Taylor |
| 2016/0117816 A1 | 4/2016 | Taylor |
| 2016/0117819 A1 | 4/2016 | Taylor |
| 2016/0119726 A1 | 4/2016 | Pontoppidan et al. |
| 2016/0120048 A1 | 4/2016 | Seo et al. |
| 2016/0120428 A1 | 5/2016 | Yoshida et al. |
| 2016/0120432 A1 | 5/2016 | Sridhar et al. |
| 2016/0120433 A1 | 5/2016 | Hughes et al. |
| 2016/0120434 A1 | 5/2016 | Park et al. |
| 2016/0120436 A1 | 5/2016 | Silberstein |
| 2016/0120437 A1 | 5/2016 | Graham et al. |
| 2016/0120457 A1 | 5/2016 | Wu et al. |
| 2016/0120464 A1 | 5/2016 | Lau et al. |
| 2016/0120480 A1 | 5/2016 | Turnbull et al. |
| 2016/0121074 A1 | 5/2016 | Ashby |
| 2016/0121114 A1 | 5/2016 | Simon et al. |
| 2016/0121116 A1 | 5/2016 | Simon et al. |
| 2016/0125228 A1 | 5/2016 | Son et al. |
| 2016/0125572 A1 | 5/2016 | Yoo et al. |
| 2016/0128589 A1 | 5/2016 | Tabib-Azar |
| 2016/0128596 A1 | 5/2016 | Morshed et al. |
| 2016/0128597 A1 | 5/2016 | Lin et al. |
| 2016/0128632 A1 | 5/2016 | Wiebe et al. |
| 2016/0128661 A1 | 5/2016 | Taylor |
| 2016/0128864 A1 | 5/2016 | Nofzinger et al. |
| 2016/0129249 A1 | 5/2016 | Yun et al. |
| 2016/0131723 A1 | 5/2016 | Nagasaka |
| 2016/0132654 A1 | 5/2016 | Rothman et al. |
| 2016/0133015 A1 | 5/2016 | Taylor |
| 2016/0135691 A1 | 5/2016 | Dripps et al. |
| 2016/0135727 A1 | 5/2016 | Osorio |
| 2016/0135748 A1 | 5/2016 | Lin et al. |
| 2016/0135754 A1 | 5/2016 | Marshall et al. |
| 2016/0136423 A1 | 5/2016 | Simon et al. |
| 2016/0136427 A1 | 5/2016 | De Ridder |
| 2016/0136429 A1 | 5/2016 | Massoumi et al. |
| 2016/0136430 A1 | 5/2016 | Moffitt et al. |
| 2016/0136443 A1 | 5/2016 | Grandhe et al. |
| 2016/0139215 A1 | 5/2016 | Fujii |
| 2016/0140306 A1 | 5/2016 | Hua et al. |
| 2016/0140313 A1 | 5/2016 | Taylor |
| 2016/0140707 A1 | 5/2016 | Abe et al. |
| 2016/0140834 A1 | 5/2016 | Tran |
| 2016/0140975 A1 | 5/2016 | Kamamoto et al. |
| 2016/0143540 A1 | 5/2016 | Gencer et al. |
| 2016/0143541 A1 | 5/2016 | He et al. |
| 2016/0143554 A1 | 5/2016 | Lim et al. |
| 2016/0143560 A1 | 5/2016 | Grunwald et al. |
| 2016/0143574 A1 | 5/2016 | Jones et al. |
| 2016/0143582 A1 | 5/2016 | Connor |
| 2016/0143594 A1 | 5/2016 | Moorman et al. |
| 2016/0144175 A1 | 5/2016 | Simon et al. |
| 2016/0144186 A1 | 5/2016 | Kaemmerer et al. |
| 2016/0147964 A1 | 5/2016 | Corey et al. |
| 2016/0148077 A1 | 5/2016 | Cox et al. |
| 2016/0148371 A1 | 5/2016 | Itu et al. |
| 2016/0148372 A1 | 5/2016 | Itu et al. |
| 2016/0148400 A1 | 5/2016 | Bajic |
| 2016/0148531 A1 | 5/2016 | Bleich et al. |
| 2016/0150988 A1 | 6/2016 | Prerau et al. |
| 2016/0151014 A1 | 6/2016 | Ujhazy et al. |
| 2016/0151018 A1 | 6/2016 | Machon et al. |
| 2016/0151628 A1 | 6/2016 | Simon et al. |
| 2016/0152233 A1 | 6/2016 | Fung et al. |
| 2016/0155005 A1 | 6/2016 | Varkuti et al. |
| 2016/0157742 A1 | 6/2016 | Huang et al. |
| 2016/0157773 A1 | 6/2016 | Baek et al. |
| 2016/0157777 A1 | 6/2016 | Attal et al. |
| 2016/0157828 A1 | 6/2016 | Sumi et al. |
| 2016/0158553 A1 | 6/2016 | Panken et al. |
| 2016/0158554 A1 | 6/2016 | Graig |
| 2016/0162652 A1 | 6/2016 | Siekmeier |
| 2016/0164813 A1 | 6/2016 | Anderson et al. |
| 2016/0165852 A1 | 6/2016 | Goldfain |
| 2016/0165853 A1 | 6/2016 | Goldfain |
| 2016/0166169 A1 | 6/2016 | Badower et al. |
| 2016/0166197 A1 | 6/2016 | Venkatraman et al. |
| 2016/0166199 A1 | 6/2016 | Sun et al. |
| 2016/0166205 A1 | 6/2016 | Ernst et al. |
| 2016/0166207 A1 | 6/2016 | Falconer |
| 2016/0166208 A1 | 6/2016 | Girouard et al. |
| 2016/0166219 A1 | 6/2016 | Majewski et al. |
| 2016/0167672 A1 | 6/2016 | Krueger |
| 2016/0168137 A1 | 6/2016 | Van Leyen et al. |
| 2016/0170996 A1 | 6/2016 | Frank et al. |
| 2016/0170998 A1 | 6/2016 | Frank et al. |
| 2016/0171514 A1 | 6/2016 | Frank et al. |
| 2016/0174099 A1 | 6/2016 | Goldfain |
| 2016/0174862 A1 | 6/2016 | Yu et al. |
| 2016/0174863 A1 | 6/2016 | Foerster et al. |
| 2016/0174867 A1 | 6/2016 | Hatano et al. |
| 2016/0174907 A1 | 6/2016 | Colman et al. |

(56)                    References Cited

U.S. PATENT DOCUMENTS

| | | |
|---|---|---|
| 2016/0175557 A1 | 6/2016 | Tass |
| 2016/0175607 A1 | 6/2016 | Deisseroth et al. |
| 2016/0176053 A1 | 6/2016 | Rognini et al. |
| 2016/0178392 A1 | 6/2016 | Goldfain |
| 2016/0180042 A1 | 6/2016 | Menon et al. |
| 2016/0180054 A1 | 6/2016 | Luo et al. |
| 2016/0180055 A1 | 6/2016 | Fonte |
| 2016/0183812 A1 | 6/2016 | Zhang et al. |
| 2016/0183828 A1 | 6/2016 | Ouyang et al. |
| 2016/0183861 A1 | 6/2016 | Hayes et al. |
| 2016/0183881 A1 | 6/2016 | Keenan et al. |
| 2016/0184029 A1 | 6/2016 | Peng et al. |
| 2016/0184596 A1 | 6/2016 | Fried et al. |
| 2016/0184599 A1 | 6/2016 | Segal |
| 2016/0187524 A1 | 6/2016 | Suhami |
| 2016/0191517 A1 | 6/2016 | Bae et al. |
| 2016/0192841 A1 | 7/2016 | Inagaki et al. |
| 2016/0192842 A1 | 7/2016 | Inagaki |
| 2016/0192847 A1 | 7/2016 | Inagaki |
| 2016/0192879 A1 | 7/2016 | Yamashita |
| 2016/0193499 A1 | 7/2016 | Kim et al. |
| 2016/0196185 A1 | 7/2016 | Gu et al. |
| 2016/0196393 A1 | 7/2016 | Avinash et al. |
| 2016/0196635 A1 | 7/2016 | Cho et al. |
| 2016/0196758 A1 | 7/2016 | Causevic et al. |
| 2016/0198950 A1 | 7/2016 | Gross et al. |
| 2016/0198963 A1 | 7/2016 | Addison et al. |
| 2016/0198966 A1 | 7/2016 | Uematsu et al. |
| 2016/0198968 A1 | 7/2016 | Plenz et al. |
| 2016/0198973 A1 | 7/2016 | Fukuda et al. |
| 2016/0199241 A1 | 7/2016 | Rapoport |
| 2016/0199577 A1 | 7/2016 | Hyde et al. |
| 2016/0199656 A1 | 7/2016 | Phillips |
| 2016/0199662 A1 | 7/2016 | Wundrich et al. |
| 2016/0202755 A1 | 7/2016 | Connor |
| 2016/0203597 A1 | 7/2016 | Chang et al. |
| 2016/0203726 A1 | 7/2016 | Hibbs et al. |
| 2016/0204937 A1 | 7/2016 | Edwards et al. |
| 2016/0205450 A1 | 7/2016 | Gartseev et al. |
| 2016/0205489 A1 | 7/2016 | Jabri |
| 2016/0206236 A1 | 7/2016 | Dilorenzo et al. |
| 2016/0206241 A1 | 7/2016 | Cho et al. |
| 2016/0206380 A1 | 7/2016 | Sparks et al. |
| 2016/0206581 A1 | 7/2016 | Wittkowski |
| 2016/0206671 A1 | 7/2016 | Geng |
| 2016/0206871 A1 | 7/2016 | Weisend |
| 2016/0206877 A1 | 7/2016 | Hargrove |
| 2016/0206880 A1 | 7/2016 | Koubeissi |
| 2016/0210872 A1 | 7/2016 | Roberts et al. |
| 2016/0213261 A1 | 7/2016 | Fleischer et al. |
| 2016/0213276 A1 | 7/2016 | Gadot et al. |
| 2016/0213314 A1 | 7/2016 | Zuckerman-Stark et al. |
| 2016/0213317 A1 | 7/2016 | Richardson et al. |
| 2016/0213947 A1 | 7/2016 | Han et al. |
| 2016/0216760 A1 | 7/2016 | Trutna et al. |
| 2016/0217586 A1 | 7/2016 | Dickrell et al. |
| 2016/0217595 A1 | 7/2016 | Han et al. |
| 2016/0219345 A1 | 7/2016 | Knight et al. |
| 2016/0220133 A1 | 8/2016 | Inagaki |
| 2016/0220134 A1 | 8/2016 | Inagaki |
| 2016/0220136 A1 | 8/2016 | Schultz |
| 2016/0220163 A1 | 8/2016 | Yamada et al. |
| 2016/0220166 A1 | 8/2016 | Thornton |
| 2016/0220439 A1 | 8/2016 | Wojciechowski et al. |
| 2016/0220821 A1 | 8/2016 | O'Connell et al. |
| 2016/0220836 A1* | 8/2016 | Parks ..................... A61N 2/006 |
| 2016/0220837 A1 | 8/2016 | Jin |
| 2016/0220850 A1 | 8/2016 | Tyler |
| 2016/0222073 A1 | 8/2016 | Deisseroth et al. |
| 2016/0223622 A1 | 8/2016 | Yu et al. |
| 2016/0223627 A1 | 8/2016 | Shah et al. |
| 2016/0223703 A1 | 8/2016 | Wu et al. |
| 2016/0224757 A1 | 8/2016 | Melkonyan |
| 2016/0224803 A1 | 8/2016 | Frank et al. |
| 2016/0228019 A1 | 8/2016 | Grunwald et al. |
| 2016/0228028 A1 | 8/2016 | Van Der Kooi et al. |
| 2016/0228029 A1 | 8/2016 | Ware |
| 2016/0228059 A1 | 8/2016 | Badower |
| 2016/0228064 A1 | 8/2016 | Jung et al. |
| 2016/0228204 A1 | 8/2016 | Quaid et al. |
| 2016/0228640 A1 | 8/2016 | Pindado et al. |
| 2016/0228702 A1 | 8/2016 | Kempe et al. |
| 2016/0228705 A1 | 8/2016 | Crowder et al. |
| 2016/0231401 A1 | 8/2016 | Wang et al. |
| 2016/0232330 A1 | 8/2016 | Dowson |
| 2016/0232625 A1 | 8/2016 | Akutagawa et al. |
| 2016/0232667 A1 | 8/2016 | Taylor |
| 2016/0232811 A9 | 8/2016 | Connor |
| 2016/0235323 A1 | 8/2016 | Tadi et al. |
| 2016/0235324 A1 | 8/2016 | Mershin et al. |
| 2016/0235341 A1 | 8/2016 | Choi et al. |
| 2016/0235351 A1 | 8/2016 | Intrator |
| 2016/0235352 A1 | 8/2016 | DiLorenzo |
| 2016/0235359 A1 | 8/2016 | Cho et al. |
| 2016/0235980 A1 | 8/2016 | Berman et al. |
| 2016/0235983 A1 | 8/2016 | Berman et al. |
| 2016/0238673 A1 | 8/2016 | Honkura |
| 2016/0239084 A1 | 8/2016 | Connor |
| 2016/0239966 A1 | 8/2016 | Parsey et al. |
| 2016/0239968 A1 | 8/2016 | Parsey et al. |
| 2016/0240212 A1 | 8/2016 | Wilson et al. |
| 2016/0240765 A1 | 8/2016 | Washington et al. |
| 2016/0242645 A1 | 8/2016 | Muller |
| 2016/0242659 A1 | 8/2016 | Yamashita et al. |
| 2016/0242665 A1 | 8/2016 | Galloway et al. |
| 2016/0242669 A1 | 8/2016 | Muraskin et al. |
| 2016/0242670 A1 | 8/2016 | Suzuki et al. |
| 2016/0242690 A1 | 8/2016 | Principe et al. |
| 2016/0242699 A1 | 8/2016 | Das et al. |
| 2016/0243362 A1 | 8/2016 | Hehrmann et al. |
| 2016/0243381 A1 | 8/2016 | Alford et al. |
| 2016/0245670 A1 | 8/2016 | Nelson et al. |
| 2016/0245766 A1 | 8/2016 | Nelson et al. |
| 2016/0245952 A1 | 8/2016 | Dupuis et al. |
| 2016/0246939 A1 | 8/2016 | Taylor |
| 2016/0247064 A1 | 8/2016 | Yoo et al. |
| 2016/0248434 A1 | 8/2016 | Govari |
| 2016/0248994 A1 | 8/2016 | Liu |
| 2016/0249826 A1 | 9/2016 | Derchak |
| 2016/0249841 A1 | 9/2016 | Gerber et al. |
| 2016/0249846 A1 | 9/2016 | Yoo et al. |
| 2016/0249857 A1 | 9/2016 | Choi et al. |
| 2016/0249864 A1 | 9/2016 | Kang et al. |
| 2016/0250355 A1 | 9/2016 | Macknik |
| 2016/0250465 A1 | 9/2016 | Simon et al. |
| 2016/0250473 A1 | 9/2016 | Alberts et al. |
| 2016/0256063 A1 | 9/2016 | Friedman et al. |
| 2016/0256086 A1 | 9/2016 | Byrd et al. |
| 2016/0256105 A1 | 9/2016 | Boyle et al. |
| 2016/0256108 A1 | 9/2016 | Yun et al. |
| 2016/0256109 A1 | 9/2016 | Semenov |
| 2016/0256112 A1 | 9/2016 | Brockway et al. |
| 2016/0256118 A1 | 9/2016 | Iyer et al. |
| 2016/0256130 A1 | 9/2016 | Hamilton et al. |
| 2016/0256690 A1 | 9/2016 | Cecchi et al. |
| 2016/0256691 A1 | 9/2016 | Cecchi et al. |
| 2016/0256693 A1 | 9/2016 | Parramon |
| 2016/0257957 A1 | 9/2016 | Greenberg et al. |
| 2016/0259085 A1 | 9/2016 | Wilson et al. |
| 2016/0259905 A1 | 9/2016 | Park et al. |
| 2016/0260216 A1 | 9/2016 | Wu et al. |
| 2016/0261962 A1 | 9/2016 | Petersen et al. |
| 2016/0262623 A1 | 9/2016 | Semenov |
| 2016/0262664 A1 | 9/2016 | Linderman |
| 2016/0262680 A1 | 9/2016 | Martucci et al. |
| 2016/0262685 A1 | 9/2016 | Wagner et al. |
| 2016/0262695 A1 | 9/2016 | Zhang et al. |
| 2016/0262703 A1 | 9/2016 | Maccallum |
| 2016/0263318 A1 | 9/2016 | Osorio |
| 2016/0263376 A1 | 9/2016 | Yoo et al. |
| 2016/0263380 A1 | 9/2016 | Starr et al. |
| 2016/0263393 A1 | 9/2016 | Vo-Dinh et al. |
| 2016/0267809 A1 | 9/2016 | deCharms et al. |
| 2016/0270656 A1 | 9/2016 | Samec et al. |

(56)                References Cited

U.S. PATENT DOCUMENTS

| | | |
|---|---|---|
| 2016/0270723 A1 | 9/2016 | Deisseroth et al. |
| 2016/0274660 A1 | 9/2016 | Publicover et al. |
| 2016/0275536 A1 | 9/2016 | Anderson |
| 2016/0278651 A1 | 9/2016 | Lu et al. |
| 2016/0278653 A1 | 9/2016 | Clark et al. |
| 2016/0278662 A1 | 9/2016 | Brister et al. |
| 2016/0278672 A1 | 9/2016 | Cho et al. |
| 2016/0278687 A1 | 9/2016 | Xia |
| 2016/0278697 A1 | 9/2016 | John et al. |
| 2016/0278713 A1 | 9/2016 | Shoaran et al. |
| 2016/0278736 A1 | 9/2016 | Hamilton et al. |
| 2016/0278870 A1 | 9/2016 | Quaid et al. |
| 2016/0279021 A1 | 9/2016 | Hyde et al. |
| 2016/0279022 A1 | 9/2016 | Hyde et al. |
| 2016/0279023 A1 | 9/2016 | Hyde et al. |
| 2016/0279024 A1 | 9/2016 | Hyde et al. |
| 2016/0279025 A1 | 9/2016 | Hyde et al. |
| 2016/0279267 A1 | 9/2016 | Deisseroth et al. |
| 2016/0279410 A1 | 9/2016 | Simon et al. |
| 2016/0279417 A1 | 9/2016 | Kilgard et al. |
| 2016/0279435 A1 | 9/2016 | Hyde et al. |
| 2016/0282113 A1 | 9/2016 | Lee |
| 2016/0282941 A1 | 9/2016 | Aksenova et al. |
| 2016/0284082 A1 | 9/2016 | Varkuti |
| 2016/0287117 A1 | 10/2016 | Breakspear et al. |
| 2016/0287118 A1 | 10/2016 | Sarma et al. |
| 2016/0287120 A1 | 10/2016 | Sun et al. |
| 2016/0287142 A1 | 10/2016 | Han et al. |
| 2016/0287157 A1 | 10/2016 | Simpson |
| 2016/0287162 A1 | 10/2016 | Bardakjian et al. |
| 2016/0287166 A1 | 10/2016 | Tran |
| 2016/0287169 A1 | 10/2016 | Kortelainen et al. |
| 2016/0287308 A1 | 10/2016 | Grant et al. |
| 2016/0287334 A1 | 10/2016 | Grant et al. |
| 2016/0287436 A1 | 10/2016 | Wingeier et al. |
| 2016/0287869 A1 | 10/2016 | Errico et al. |
| 2016/0287871 A1 | 10/2016 | Bardakjian et al. |
| 2016/0287889 A1 | 10/2016 | Bokil et al. |
| 2016/0287895 A1 | 10/2016 | Deisseroth et al. |
| 2016/0296157 A1 | 10/2016 | Girouard |
| 2016/0296287 A1 | 10/2016 | Taylor |
| 2016/0296746 A1 | 10/2016 | Wingeier et al. |
| 2016/0298449 A1 | 10/2016 | Orban |
| 2016/0299568 A1 | 10/2016 | Segal |
| 2016/0300252 A1 | 10/2016 | Frank et al. |
| 2016/0300352 A1 | 10/2016 | Raj |
| 2016/0302683 A1 | 10/2016 | Lawrence et al. |
| 2016/0302704 A9 | 10/2016 | Lynn et al. |
| 2016/0302709 A1 | 10/2016 | Mossbridge |
| 2016/0302711 A1 | 10/2016 | Frank et al. |
| 2016/0302720 A1 | 10/2016 | John et al. |
| 2016/0302737 A1 | 10/2016 | Watson et al. |
| 2016/0303322 A1 | 10/2016 | John |
| 2016/0303396 A9 | 10/2016 | Deisseroth et al. |
| 2016/0303397 A1 | 10/2016 | Hirschman et al. |
| 2016/0303402 A1 | 10/2016 | Tyler |
| 2016/0306844 A1 | 10/2016 | Frank et al. |
| 2016/0306942 A1 | 10/2016 | Rapaka et al. |
| 2016/0310031 A1 | 10/2016 | Sarkar |
| 2016/0310070 A1 | 10/2016 | Sabesan |
| 2016/0310071 A1 | 10/2016 | Kim |
| 2016/0313408 A1 | 10/2016 | Hatano et al. |
| 2016/0313417 A1 | 10/2016 | Kawabata et al. |
| 2016/0313418 A1 | 10/2016 | Fujii et al. |
| 2016/0313798 A1 | 10/2016 | Connor |
| 2016/0317056 A1 | 11/2016 | Moon et al. |
| 2016/0317060 A1 | 11/2016 | Connor |
| 2016/0317077 A1 | 11/2016 | Sillay |
| 2016/0317383 A1 | 11/2016 | Stanfield et al. |
| 2016/0317824 A1 | 11/2016 | Moffitt et al. |
| 2016/0320210 A1 | 11/2016 | Nelson et al. |
| 2016/0321742 A1 | 11/2016 | Phillips et al. |
| 2016/0324445 A1 | 11/2016 | Kim et al. |
| 2016/0324457 A1 | 11/2016 | Dagum |
| 2016/0324465 A1 | 11/2016 | Osvath et al. |
| 2016/0324478 A1 | 11/2016 | Goldstein |
| 2016/0324580 A1 | 11/2016 | Esterberg |
| 2016/0324677 A1 | 11/2016 | Hyde et al. |
| 2016/0324942 A1 | 11/2016 | Lester et al. |
| 2016/0325111 A1 | 11/2016 | Bourke, Jr. et al. |
| 2016/0331264 A1 | 11/2016 | Helms-Tillery et al. |
| 2016/0331307 A1 | 11/2016 | Purdon et al. |
| 2016/0331952 A1 | 11/2016 | Faltys et al. |
| 2016/0331970 A1 | 11/2016 | Lozano |
| 2016/0331974 A1 | 11/2016 | Lyons et al. |
| 2016/0331982 A1 | 11/2016 | Chow et al. |
| 2016/0334475 A1 | 11/2016 | Ueno |
| 2016/0334534 A1 | 11/2016 | Mandviwala et al. |
| 2016/0334866 A9 | 11/2016 | Mazed et al. |
| 2016/0338608 A1 | 11/2016 | Nagasaka et al. |
| 2016/0338634 A1 | 11/2016 | Neu et al. |
| 2016/0338644 A1 | 11/2016 | Connor |
| 2016/0338798 A1 | 11/2016 | Vora et al. |
| 2016/0338825 A1 | 11/2016 | Wortz et al. |
| 2016/0339237 A1 | 11/2016 | Ahmed et al. |
| 2016/0339238 A1 | 11/2016 | Ahmed et al. |
| 2016/0339239 A1 | 11/2016 | Yoo et al. |
| 2016/0339242 A1 | 11/2016 | Cook et al. |
| 2016/0339243 A1 | 11/2016 | Wingeier et al. |
| 2016/0339300 A1 | 11/2016 | Todasco |
| 2016/0341684 A1 | 11/2016 | Choi |
| 2016/0342241 A1 | 11/2016 | Chung et al. |
| 2016/0342762 A1 | 11/2016 | Goetz |
| 2016/0345856 A1 | 12/2016 | Semenov |
| 2016/0345895 A1 | 12/2016 | Loetsch et al. |
| 2016/0345901 A1 | 12/2016 | Connor |
| 2016/0345911 A1 | 12/2016 | Leuthardt et al. |
| 2016/0346530 A1 | 12/2016 | Jeffery et al. |
| 2016/0346542 A1 | 12/2016 | Simon et al. |
| 2016/0351069 A1 | 12/2016 | Faubert et al. |
| 2016/0354003 A1 | 12/2016 | Baker et al. |
| 2016/0354027 A1 | 12/2016 | Benson et al. |
| 2016/0356911 A1 | 12/2016 | Wilson et al. |
| 2016/0357003 A1 | 12/2016 | Hauger et al. |
| 2016/0357256 A1 | 12/2016 | Siefert |
| 2016/0360100 A1 | 12/2016 | Kim et al. |
| 2016/0360965 A1 | 12/2016 | Tran |
| 2016/0360970 A1 | 12/2016 | Tzvieli et al. |
| 2016/0361021 A1 | 12/2016 | Salehizadeh et al. |
| 2016/0361027 A1 | 12/2016 | Jang et al. |
| 2016/0361041 A1 | 12/2016 | Barsimantov et al. |
| 2016/0361532 A1 | 12/2016 | Wingeier et al. |
| 2016/0361534 A9 | 12/2016 | Weisend |
| 2016/0361540 A9 | 12/2016 | Simon et al. |
| 2016/0361546 A1 | 12/2016 | Salam et al. |
| 2016/0363483 A1 | 12/2016 | Tzvieli et al. |
| 2016/0364859 A1 | 12/2016 | Taylor |
| 2016/0364860 A1 | 12/2016 | Taylor |
| 2016/0364861 A1 | 12/2016 | Taylor |
| 2016/0366462 A1 | 12/2016 | Klappert et al. |
| 2016/0367138 A1 | 12/2016 | Kim et al. |
| 2016/0367186 A1 | 12/2016 | Freeman et al. |
| 2016/0367195 A1 | 12/2016 | Park et al. |
| 2016/0367198 A1 | 12/2016 | Chon et al. |
| 2016/0367204 A1 | 12/2016 | Won et al. |
| 2016/0367209 A1 | 12/2016 | Odry et al. |
| 2016/0367808 A9 | 12/2016 | Simon et al. |
| 2016/0367812 A1 | 12/2016 | De Ridder |
| 2016/0371387 A1 | 12/2016 | Serena |
| 2016/0371455 A1 | 12/2016 | Taylor |
| 2016/0371721 A1 | 12/2016 | Bogdon et al. |
| 2016/0374581 A1 | 12/2016 | Jensen |
| 2016/0374616 A1 | 12/2016 | Mullins et al. |
| 2016/0374618 A1 | 12/2016 | Giovangrandi |
| 2016/0374990 A1 | 12/2016 | Teegarden et al. |
| 2016/0375245 A1 | 12/2016 | Frei et al. |
| 2016/0375259 A1 | 12/2016 | Davis et al. |
| 2016/0378608 A1 | 12/2016 | Kong et al. |
| 2016/0378965 A1 | 12/2016 | Choe et al. |
| 2017/0000324 A1 | 1/2017 | Samec et al. |
| 2017/0000325 A1 | 1/2017 | Samec et al. |
| 2017/0000326 A1 | 1/2017 | Samec et al. |
| 2017/0000329 A1 | 1/2017 | Samec et al. |
| 2017/0000330 A1 | 1/2017 | Samec et al. |

(56)                    References Cited

U.S. PATENT DOCUMENTS

| | | |
|---|---|---|
| 2017/0000331 A1 | 1/2017 | Samec et al. |
| 2017/0000332 A1 | 1/2017 | Samec et al. |
| 2017/0000333 A1 | 1/2017 | Samec et al. |
| 2017/0000334 A1 | 1/2017 | Samec et al. |
| 2017/0000335 A1 | 1/2017 | Samec et al. |
| 2017/0000337 A1 | 1/2017 | Samec et al. |
| 2017/0000340 A1 | 1/2017 | Samec et al. |
| 2017/0000341 A1 | 1/2017 | Samec et al. |
| 2017/0000342 A1 | 1/2017 | Samec et al. |
| 2017/0000343 A1 | 1/2017 | Samec et al. |
| 2017/0000345 A1 | 1/2017 | Samec et al. |
| 2017/0000404 A1 | 1/2017 | Leininger et al. |
| 2017/0000422 A1 | 1/2017 | Moturu et al. |
| 2017/0000454 A1 | 1/2017 | Samec et al. |
| 2017/0000683 A1 | 1/2017 | Samec et al. |
| 2017/0001016 A1 | 1/2017 | De Ridder |
| 2017/0001032 A1 | 1/2017 | Samec et al. |
| 2017/0006931 A1 | 1/2017 | Guez et al. |
| 2017/0007111 A1 | 1/2017 | Samec et al. |
| 2017/0007115 A1 | 1/2017 | Samec et al. |
| 2017/0007116 A1 | 1/2017 | Samec et al. |
| 2017/0007122 A1 | 1/2017 | Samec et al. |
| 2017/0007123 A1 | 1/2017 | Samec et al. |
| 2017/0007165 A1 | 1/2017 | Jain et al. |
| 2017/0007173 A1 | 1/2017 | Adamczyk et al. |
| 2017/0007182 A1 | 1/2017 | Samec et al. |
| 2017/0007450 A1 | 1/2017 | Samec et al. |
| 2017/0007799 A1 | 1/2017 | Samec et al. |
| 2017/0007820 A9 | 1/2017 | Simon et al. |
| 2017/0007828 A1 | 1/2017 | Monteiro |
| 2017/0007843 A1 | 1/2017 | Samec et al. |
| 2017/0010469 A1 | 1/2017 | Samec et al. |
| 2017/0010470 A1 | 1/2017 | Samec et al. |
| 2017/0013562 A1 | 1/2017 | Lim et al. |
| 2017/0014037 A1 | 1/2017 | Coppola et al. |
| 2017/0014080 A1 | 1/2017 | Barber et al. |
| 2017/0014083 A1 | 1/2017 | Diab et al. |
| 2017/0014625 A1 | 1/2017 | Rosenbluth et al. |
| 2017/0014630 A1 | 1/2017 | Fried et al. |
| 2017/0017083 A1 | 1/2017 | Samec et al. |
| 2017/0020434 A1 | 1/2017 | Walker et al. |
| 2017/0020447 A1 | 1/2017 | Grossman et al. |
| 2017/0020454 A1 | 1/2017 | Keteyian et al. |
| 2017/0020627 A1 | 1/2017 | Tesar et al. |
| 2017/0021158 A1 | 1/2017 | Wingeier et al. |
| 2017/0021161 A1 | 1/2017 | De Ridder |
| 2017/0024886 A1 | 1/2017 | Dickrell et al. |
| 2017/0027467 A1 | 2/2017 | Hagedorn |
| 2017/0027517 A9 | 2/2017 | Le et al. |
| 2017/0027521 A1 | 2/2017 | Geva et al. |
| 2017/0027539 A1 | 2/2017 | Uber |
| 2017/0027651 A1 | 2/2017 | Esterberg |
| 2017/0027812 A1 | 2/2017 | Hyde et al. |
| 2017/0028563 A1 | 2/2017 | Hemken |
| 2017/0031440 A1 | 2/2017 | Randolph |
| 2017/0031441 A1 | 2/2017 | Muller et al. |
| 2017/0032098 A1 | 2/2017 | Ghorbanian et al. |
| 2017/0032221 A1 | 2/2017 | Wu et al. |
| 2017/0032524 A1 | 2/2017 | Dickrell et al. |
| 2017/0032527 A1 | 2/2017 | Murthy et al. |
| 2017/0032544 A1 | 2/2017 | Dempsey et al. |
| 2017/0034638 A1 | 2/2017 | Anastas |
| 2017/0035309 A1 | 2/2017 | Kang et al. |
| 2017/0035317 A1 | 2/2017 | Jung et al. |
| 2017/0035344 A1 | 2/2017 | Tzvieli et al. |
| 2017/0035392 A1 | 2/2017 | Grunwald et al. |
| 2017/0036024 A1 | 2/2017 | Hershey et al. |
| 2017/0039591 A1 | 2/2017 | Knight et al. |
| 2017/0039706 A1 | 2/2017 | Mikhno et al. |
| 2017/0041699 A1 | 2/2017 | Mackellar et al. |
| 2017/0042430 A1 | 2/2017 | Kovacs |
| 2017/0042444 A1 | 2/2017 | Bardy et al. |
| 2017/0042469 A1 | 2/2017 | Prerau et al. |
| 2017/0042474 A1 | 2/2017 | Widge et al. |
| 2017/0042475 A1 | 2/2017 | Verghese et al. |
| 2017/0042476 A1 | 2/2017 | Reiman |
| 2017/0042485 A1 | 2/2017 | Chung et al. |
| 2017/0042713 A1 | 2/2017 | Nurmikko et al. |
| 2017/0042827 A1 | 2/2017 | Margel et al. |
| 2017/0043160 A1 | 2/2017 | Goodall et al. |
| 2017/0043166 A1 | 2/2017 | Choi et al. |
| 2017/0043167 A1 | 2/2017 | Widge et al. |
| 2017/0043178 A1 | 2/2017 | Vo-Dinh et al. |
| 2017/0045601 A1 | 2/2017 | Akhtari |
| 2017/0046052 A1 | 2/2017 | Lee et al. |
| 2017/0046971 A1 | 2/2017 | Moreno |
| 2017/0050046 A1 | 2/2017 | Walder et al. |
| 2017/0052170 A1 | 2/2017 | Shekdar et al. |
| 2017/0053082 A1 | 2/2017 | Pereira et al. |
| 2017/0053088 A1 | 2/2017 | Walker et al. |
| 2017/0053092 A1 | 2/2017 | Taylor |
| 2017/0053461 A1 | 2/2017 | Pal et al. |
| 2017/0053513 A1 | 2/2017 | Savolainen et al. |
| 2017/0053665 A1 | 2/2017 | Quatieri, Jr. et al. |
| 2017/0055839 A1 | 3/2017 | Levinson et al. |
| 2017/0055898 A1 | 3/2017 | Bandyopadhyay et al. |
| 2017/0055900 A1 | 3/2017 | Jain et al. |
| 2017/0055913 A1 | 3/2017 | Bandyopadhyay et al. |
| 2017/0056363 A1 | 3/2017 | Goodenowe |
| 2017/0056467 A1 | 3/2017 | Deisseroth et al. |
| 2017/0056642 A1 | 3/2017 | Moffitt et al. |
| 2017/0056655 A1 | 3/2017 | Lineaweaver |
| 2017/0056663 A1 | 3/2017 | Kaemmerer et al. |
| 2017/0060298 A1 | 3/2017 | Hwang et al. |
| 2017/0061034 A1 | 3/2017 | Ritchey et al. |
| 2017/0061589 A1 | 3/2017 | Kuo et al. |
| 2017/0061760 A1 | 3/2017 | Lee et al. |
| 2017/0065199 A1 | 3/2017 | Meisel |
| 2017/0065218 A1 | 3/2017 | Leininger et al. |
| 2017/0065229 A1 | 3/2017 | Howard |
| 2017/0065349 A1 | 3/2017 | Ourselin et al. |
| 2017/0065379 A1 | 3/2017 | Cowburn et al. |
| 2017/0065638 A1 | 3/2017 | Fraser |
| 2017/0065816 A1 | 3/2017 | Wingeier et al. |
| 2017/0066806 A1 | 3/2017 | Deisseroth et al. |
| 2017/0067323 A1 | 3/2017 | Katterbauer et al. |
| 2017/0069306 A1 | 3/2017 | Asaei et al. |
| 2017/0071495 A1 | 3/2017 | Denison et al. |
| 2017/0071521 A1 | 3/2017 | Mestha et al. |
| 2017/0071523 A1 | 3/2017 | Jain et al. |
| 2017/0071529 A1 | 3/2017 | Haugland et al. |
| 2017/0071532 A1 | 3/2017 | Greco |
| 2017/0071537 A1 | 3/2017 | Jain et al. |
| 2017/0071546 A1 | 3/2017 | Jain et al. |
| 2017/0071551 A1 | 3/2017 | Jain et al. |
| 2017/0071552 A1 | 3/2017 | Harpe et al. |
| 2017/0076452 A1 | 3/2017 | Yui et al. |
| 2017/0079538 A1 | 3/2017 | Liang et al. |
| 2017/0079543 A1 | 3/2017 | Sadeghian-Motahar |
| 2017/0079573 A1 | 3/2017 | Osorio |
| 2017/0079588 A1 | 3/2017 | Ghaffari et al. |
| 2017/0079589 A1 | 3/2017 | Ghaffari et al. |
| 2017/0079596 A1 | 3/2017 | Teixeira |
| 2017/0080050 A1 | 3/2017 | Deisseroth et al. |
| 2017/0080234 A1 | 3/2017 | Gillespie et al. |
| 2017/0080256 A1 | 3/2017 | Kim et al. |
| 2017/0080320 A1 | 3/2017 | Smith |
| 2017/0084175 A1 | 3/2017 | Sedlik et al. |
| 2017/0084187 A1 | 3/2017 | Mollicone et al. |
| 2017/0085547 A1 | 3/2017 | De Aguiar et al. |
| 2017/0085855 A1 | 3/2017 | Roberts et al. |
| 2017/0086672 A1 | 3/2017 | Tran |
| 2017/0086695 A1 | 3/2017 | Mullins et al. |
| 2017/0086727 A1 | 3/2017 | Dagum |
| 2017/0086729 A1 | 3/2017 | Bruno |
| 2017/0086763 A1 | 3/2017 | Verma et al. |
| 2017/0087302 A1 | 3/2017 | Osorio |
| 2017/0087330 A1 | 3/2017 | Kahn et al. |
| 2017/0087354 A1 | 3/2017 | Stevenson et al. |
| 2017/0087355 A1 | 3/2017 | Stevenson et al. |
| 2017/0087356 A1 | 3/2017 | Stevenson et al. |
| 2017/0087364 A1 | 3/2017 | Cartledge et al. |
| 2017/0087367 A1 | 3/2017 | Weisend |
| 2017/0090475 A1 | 3/2017 | Choi et al. |

(56)                    References Cited

U.S. PATENT DOCUMENTS

| | | | |
|---|---|---|---|
| 2017/0091418 A1 | 3/2017 | Chen et al. |
| 2017/0091567 A1 | 3/2017 | Wang et al. |
| 2017/0094385 A1 | 3/2017 | Lee et al. |
| 2017/0095157 A1 | 4/2017 | Tzvieli et al. |
| 2017/0095174 A1 | 4/2017 | Fokas et al. |
| 2017/0095199 A1 | 4/2017 | Kranck |
| 2017/0095670 A1 | 4/2017 | Ghaffari et al. |
| 2017/0095676 A1 | 4/2017 | Caparso et al. |
| 2017/0095721 A1 | 4/2017 | Bleich et al. |
| 2017/0099479 A1 | 4/2017 | Browd et al. |
| 2017/0099713 A1 | 4/2017 | Perez et al. |
| 2017/0100051 A1 | 4/2017 | Honkura |
| 2017/0100540 A1 | 4/2017 | Hyde et al. |
| 2017/0100591 A1 | 4/2017 | Nudo et al. |
| 2017/0103440 A1 | 4/2017 | Xing et al. |
| 2017/0105647 A1 | 4/2017 | Duffy |
| 2017/0106193 A1 | 4/2017 | Carcieri |
| 2017/0107575 A1 | 4/2017 | Umansky et al. |
| 2017/0108926 A1 | 4/2017 | Moon et al. |
| 2017/0112379 A1 | 4/2017 | Swiston et al. |
| 2017/0112403 A1 | 4/2017 | Doidge et al. |
| 2017/0112427 A1 | 4/2017 | Simon et al. |
| 2017/0112446 A1 | 4/2017 | Dagum |
| 2017/0112577 A1 | 4/2017 | Bonutti et al. |
| 2017/0112671 A1 | 4/2017 | Goldstein |
| 2017/0112947 A1 | 4/2017 | Abebe |
| 2017/0113042 A1 | 4/2017 | Goodall et al. |
| 2017/0113046 A1 | 4/2017 | Fried et al. |
| 2017/0113056 A1 | 4/2017 | Stocco et al. |
| 2017/0113057 A1 | 4/2017 | Goodall et al. |
| 2017/0117866 A1 | 4/2017 | Stevenson et al. |
| 2017/0119270 A1 | 5/2017 | Juan et al. |
| 2017/0119271 A1 | 5/2017 | Leuthardt et al. |
| 2017/0119994 A1 | 5/2017 | Argaman |
| 2017/0120041 A1 | 5/2017 | Wenger et al. |
| 2017/0120043 A1 | 5/2017 | John |
| 2017/0120052 A9 | 5/2017 | Simon et al. |
| 2017/0120054 A1 | 5/2017 | Moffitt et al. |
| 2017/0120066 A1 | 5/2017 | Phillips et al. |
| 2017/0127727 A1 | 5/2017 | Davidson et al. |
| 2017/0127946 A1 | 5/2017 | Levinson et al. |
| 2017/0128006 A1 | 5/2017 | Seo et al. |
| 2017/0128015 A1 | 5/2017 | Rogers et al. |
| 2017/0128032 A1 | 5/2017 | Buchert et al. |
| 2017/0131293 A1 | 5/2017 | Haslett et al. |
| 2017/0132816 A1 | 5/2017 | Aston et al. |
| 2017/0133576 A1 | 5/2017 | Marcus et al. |
| 2017/0133577 A1 | 5/2017 | Cybart et al. |
| 2017/0135594 A1 | 5/2017 | Hartings et al. |
| 2017/0135597 A1 | 5/2017 | Mann |
| 2017/0135604 A1 | 5/2017 | Kent et al. |
| 2017/0135626 A1 | 5/2017 | Singer |
| 2017/0135629 A1 | 5/2017 | Kent et al. |
| 2017/0135631 A1 | 5/2017 | Zuckerman-Stark et al. |
| 2017/0135633 A1 | 5/2017 | Connor |
| 2017/0135640 A1 | 5/2017 | Gunasekar et al. |
| 2017/0136238 A1 | 5/2017 | Hartig et al. |
| 2017/0136240 A1 | 5/2017 | Mogul |
| 2017/0136264 A1 | 5/2017 | Hyde et al. |
| 2017/0136265 A1 | 5/2017 | Hyde et al. |
| 2017/0138132 A1 | 5/2017 | Wilson et al. |
| 2017/0140124 A1 | 5/2017 | Sehgal et al. |
| 2017/0143231 A1 | 5/2017 | Ostberg et al. |
| 2017/0143249 A1 | 5/2017 | Davis et al. |
| 2017/0143255 A1 | 5/2017 | Babaeizadeh et al. |
| 2017/0143257 A1 | 5/2017 | Kent et al. |
| 2017/0143259 A1 | 5/2017 | Kent et al. |
| 2017/0143266 A1 | 5/2017 | Kovacs et al. |
| 2017/0143267 A1 | 5/2017 | Kovacs et al. |
| 2017/0143268 A1 | 5/2017 | Kovacs et al. |
| 2017/0143273 A1 | 5/2017 | Osorio et al. |
| 2017/0143280 A1 | 5/2017 | Kent et al. |
| 2017/0143282 A1 | 5/2017 | Kovacs et al. |
| 2017/0143442 A1 | 5/2017 | Tesar et al. |
| 2017/0143550 A1 | 5/2017 | Kilgard et al. |
| 2017/0143960 A1 | 5/2017 | Kent et al. |
| 2017/0143963 A1 | 5/2017 | Osorio |
| 2017/0143966 A1 | 5/2017 | Reymers et al. |
| 2017/0143986 A1 | 5/2017 | Deisseroth et al. |
| 2017/0146386 A1 | 5/2017 | Wiard et al. |
| 2017/0146387 A1 | 5/2017 | Wiard et al. |
| 2017/0146390 A1 | 5/2017 | Kovacs |
| 2017/0146391 A1 | 5/2017 | Kovacs et al. |
| 2017/0146615 A1 | 5/2017 | Wolf et al. |
| 2017/0146801 A1 | 5/2017 | Stempora |
| 2017/0147578 A1 | 5/2017 | Hecht et al. |
| 2017/0147754 A1 | 5/2017 | Kovacs |
| 2017/0148213 A1 | 5/2017 | Thomas et al. |
| 2017/0148240 A1 | 5/2017 | Kovacs et al. |
| 2017/0148340 A1 | 5/2017 | Popa-Simil et al. |
| 2017/0148592 A1 | 5/2017 | Tabib-Azir |
| 2017/0149945 A1 | 5/2017 | Lee et al. |
| 2017/0150896 A9 | 6/2017 | Lu et al. |
| 2017/0150916 A1 | 6/2017 | Osorio |
| 2017/0150921 A1 | 6/2017 | Yun et al. |
| 2017/0150925 A1 | 6/2017 | Jung |
| 2017/0151433 A1 | 6/2017 | Simon et al. |
| 2017/0151435 A1 | 6/2017 | Deadwyler et al. |
| 2017/0151436 A1 | 6/2017 | Flaherty et al. |
| 2017/0154167 A1 | 6/2017 | Ovtchinnikov |
| 2017/0156593 A1 | 6/2017 | Ferber et al. |
| 2017/0156606 A1 | 6/2017 | Ferber et al. |
| 2017/0156622 A1 | 6/2017 | Mahoor et al. |
| 2017/0156655 A1 | 6/2017 | Austin et al. |
| 2017/0156662 A1 | 6/2017 | Goodall et al. |
| 2017/0156674 A1 | 6/2017 | Hochman |
| 2017/0157343 A1 | 6/2017 | Davidson et al. |
| 2017/0157402 A1 | 6/2017 | Osorio |
| 2017/0157410 A1 | 6/2017 | Moffitt et al. |
| 2017/0160360 A1 | 6/2017 | Deisseroth et al. |
| 2017/0162072 A1 | 6/2017 | Horseman et al. |
| 2017/0164861 A1 | 6/2017 | Cahan et al. |
| 2017/0164862 A1 | 6/2017 | Dolev et al. |
| 2017/0164876 A1 | 6/2017 | Hyde et al. |
| 2017/0164878 A1 | 6/2017 | Connor |
| 2017/0164893 A1 | 6/2017 | Narayan et al. |
| 2017/0164894 A1 | 6/2017 | Yoo et al. |
| 2017/0164895 A1 | 6/2017 | Howard |
| 2017/0164901 A1 | 6/2017 | Shusterman |
| 2017/0165020 A1 | 6/2017 | Martel |
| 2017/0165481 A1 | 6/2017 | Menon |
| 2017/0165496 A1 | 6/2017 | Pilla et al. |
| 2017/0168121 A1 | 6/2017 | Yu et al. |
| 2017/0168566 A1 | 6/2017 | Osterhout et al. |
| 2017/0168568 A1 | 6/2017 | Petrov |
| 2017/0169714 A1 | 6/2017 | Lin et al. |
| 2017/0171441 A1 | 6/2017 | Kearns et al. |
| 2017/0172414 A1 | 6/2017 | Nierenberg et al. |
| 2017/0172446 A1 | 6/2017 | Kuzum et al. |
| 2017/0172499 A1 | 6/2017 | Yoo |
| 2017/0172501 A1 | 6/2017 | Badower et al. |
| 2017/0172520 A1 | 6/2017 | Kannan et al. |
| 2017/0172527 A1 | 6/2017 | Uber |
| 2017/0173262 A1 | 6/2017 | Veltz |
| 2017/0173326 A1 | 6/2017 | Bloch et al. |
| 2017/0173391 A1 | 6/2017 | Wiebe et al. |
| 2017/0177023 A1 | 6/2017 | Simon et al. |
| 2017/0178001 A1 | 6/2017 | Anderson et al. |
| 2017/0178340 A1 | 6/2017 | Schadewaldt et al. |
| 2017/0180558 A1 | 6/2017 | Li et al. |
| 2017/0181252 A1 | 6/2017 | Wouhaybi et al. |
| 2017/0181693 A1 | 6/2017 | Kim et al. |
| 2017/0182176 A1 | 6/2017 | Satchi-Fainaro et al. |
| 2017/0182285 A1 | 6/2017 | Tyler et al. |
| 2017/0182312 A1 | 6/2017 | Durand et al. |
| 2017/0185149 A1 | 6/2017 | Oluwafemi et al. |
| 2017/0185714 A1 | 6/2017 | Halter et al. |
| 2017/0185741 A1 | 6/2017 | Moffitt et al. |
| 2017/0188862 A1 | 7/2017 | Kale et al. |
| 2017/0188865 A1 | 7/2017 | Nierenberg et al. |
| 2017/0188866 A1 | 7/2017 | Kale et al. |
| 2017/0188868 A1 | 7/2017 | Kale et al. |
| 2017/0188869 A1 | 7/2017 | Kale et al. |
| 2017/0188870 A1 | 7/2017 | Hilty |

(56)                References Cited

U.S. PATENT DOCUMENTS

| | | | |
|---|---|---|---|
| 2017/0188872 A1 | 7/2017 | Hughes et al. |
| 2017/0188876 A1 | 7/2017 | Marci et al. |
| 2017/0188905 A1 | 7/2017 | Lee et al. |
| 2017/0188916 A1 | 7/2017 | Wang et al. |
| 2017/0188922 A1 | 7/2017 | Lee et al. |
| 2017/0188932 A1 | 7/2017 | Singer et al. |
| 2017/0188933 A1 | 7/2017 | Huggins et al. |
| 2017/0188947 A1 | 7/2017 | Connor |
| 2017/0188992 A1 | 7/2017 | O'Brien et al. |
| 2017/0189685 A1 | 7/2017 | Steinke et al. |
| 2017/0189686 A1 | 7/2017 | Steinke et al. |
| 2017/0189687 A1 | 7/2017 | Steinke et al. |
| 2017/0189688 A1 | 7/2017 | Steinke et al. |
| 2017/0189689 A1 | 7/2017 | Steinke et al. |
| 2017/0189691 A1 | 7/2017 | De Ridder |
| 2017/0189700 A1 | 7/2017 | Moffitt et al. |
| 2017/0189707 A1 | 7/2017 | Zabara |
| 2017/0190765 A1 | 7/2017 | El-Agnaf |
| 2017/0193161 A1 | 7/2017 | Sapiro et al. |
| 2017/0193831 A1 | 7/2017 | Walter et al. |
| 2017/0196497 A1 | 7/2017 | Ray et al. |
| 2017/0196501 A1 | 7/2017 | Watson et al. |
| 2017/0196503 A1 | 7/2017 | Narayan et al. |
| 2017/0196519 A1 | 7/2017 | Miller et al. |
| 2017/0197080 A1 | 7/2017 | Wagner et al. |
| 2017/0197081 A1 | 7/2017 | Charlesworth et al. |
| 2017/0197086 A1 | 7/2017 | Howard et al. |
| 2017/0198017 A1 | 7/2017 | Deisseroth et al. |
| 2017/0198349 A1 | 7/2017 | Rice |
| 2017/0199251 A1 | 7/2017 | Fujii et al. |
| 2017/0202474 A1 | 7/2017 | Banerjee et al. |
| 2017/0202475 A1 | 7/2017 | Leuthardt |
| 2017/0202476 A1 | 7/2017 | Desain et al. |
| 2017/0202518 A1 | 7/2017 | Furman et al. |
| 2017/0202621 A1 | 7/2017 | Taylor |
| 2017/0202633 A1 | 7/2017 | Liu |
| 2017/0203154 A1 | 7/2017 | Solinsky |
| 2017/0205259 A1 | 7/2017 | Jang et al. |
| 2017/0206654 A1 | 7/2017 | Shiroishi et al. |
| 2017/0206691 A1 | 7/2017 | Harrises et al. |
| 2017/0206913 A1 | 7/2017 | Nahman et al. |
| 2017/0209043 A1 | 7/2017 | Gross et al. |
| 2017/0209044 A1 | 7/2017 | Ito et al. |
| 2017/0209053 A1 | 7/2017 | Pantelopoulos et al. |
| 2017/0209062 A1 | 7/2017 | Iwasaki et al. |
| 2017/0209083 A1 | 7/2017 | Zarandi et al. |
| 2017/0209094 A1 | 7/2017 | Derchak et al. |
| 2017/0209225 A1 | 7/2017 | Wu |
| 2017/0209389 A1 | 7/2017 | Toth et al. |
| 2017/0209737 A1 | 7/2017 | Tadi et al. |
| 2017/0212188 A1 | 7/2017 | Kikitsu et al. |
| 2017/0213339 A1 | 7/2017 | Hibbard et al. |
| 2017/0214786 A1 | 7/2017 | Lee et al. |
| 2017/0216595 A1 | 8/2017 | Geva et al. |
| 2017/0221206 A1 | 8/2017 | Han et al. |
| 2017/0224990 A1 | 8/2017 | Goldwasser et al. |
| 2017/0224994 A1 | 8/2017 | Kilgard et al. |
| 2017/0231560 A1 | 8/2017 | Hyde et al. |
| 2017/0239486 A1 | 8/2017 | Suryavanshi |
| 2017/0239489 A1 | 8/2017 | Bourke, Jr. et al. |
| 2018/0089531 A1* | 3/2018 | Geva ................... G06V 10/454 |
| 2019/0070386 A1* | 3/2019 | Raut ...................... A61B 5/375 |

FOREIGN PATENT DOCUMENTS

| | | |
|---|---|---|
| WO | WO2000025668 A1 | 9/2003 |
| WO | WO2001087153 A1 | 9/2003 |

* cited by examiner

Dendritic Tree

Flow of Current in

EEG Reading

Fig. 4 One second of EEG signal

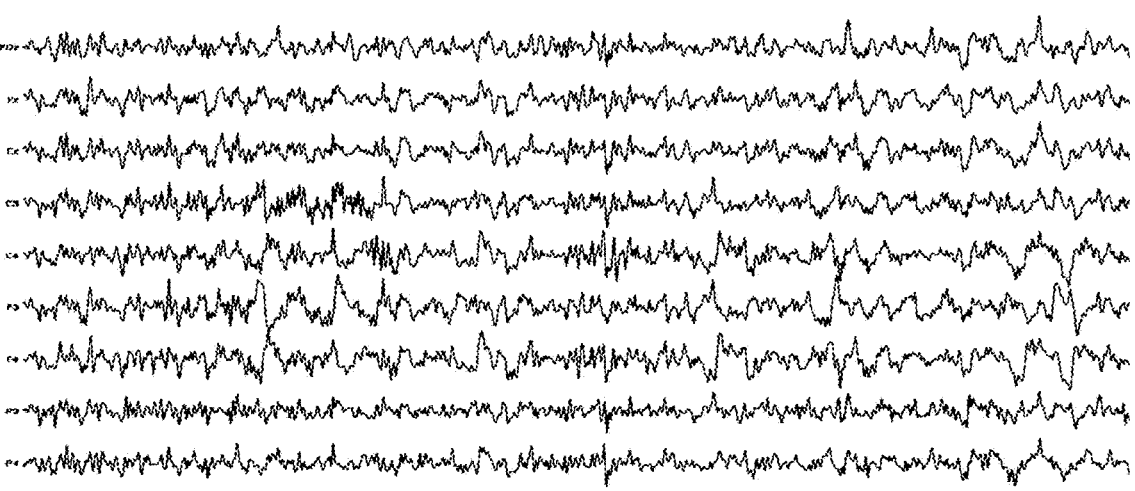
Fig. 5 Brain Wave Patterns
Delta waves
0.1 - 4 Hz
Theta waves
4 - 8 Hz
Mu rhythm
8 - 12 Hz
Sensorimotor
rhythm
12.5 - 15.5 Hz
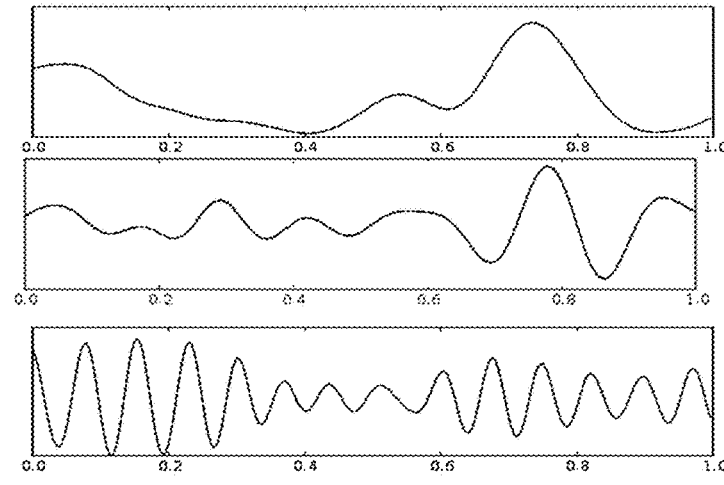
Alpha Waves
8-14 HZ
Beta waves
14-30 Hz
Gamma waves
30->50 Hz
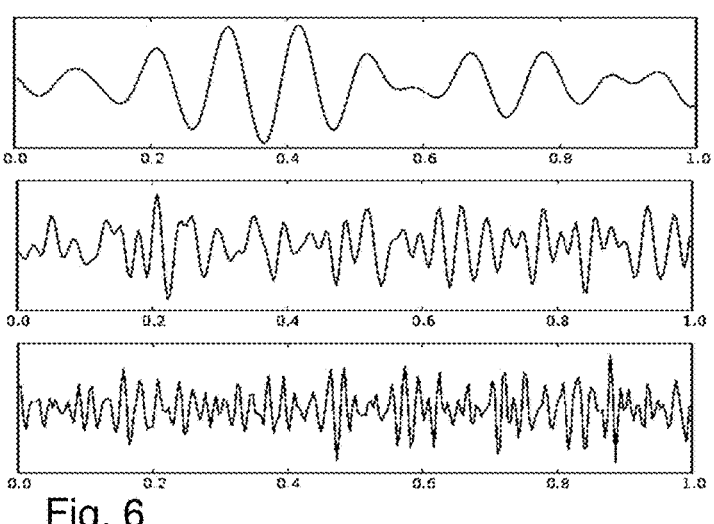
Fig. 6

Figures 7, 8:
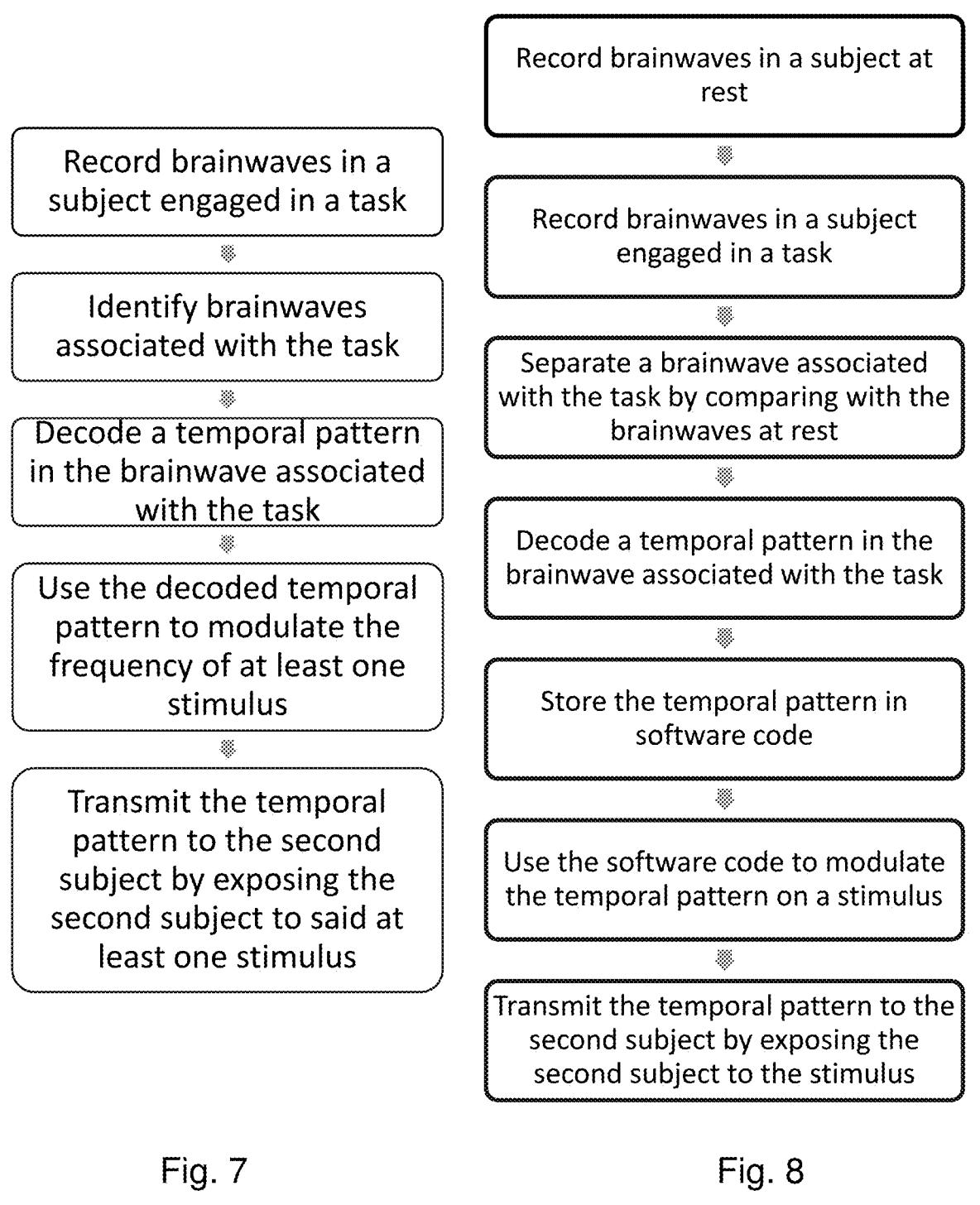

Record brainwaves in a subject at rest

Record brainwaves in a subject engaged in a task

Separate a brainwave associated with the task by comparing with the brainwaves at rest Decode a temporal pattern in the brainwave associated with the task Store the temporal pattern in software code Use the software code to modulate the temporal pattern on a stimulus Transmit the temporal pattern to the second subject by exposing the second subject to the stimulus Record brainwaves in a subject engaged in a task Identify brainwaves associated with the task Decode a temporal pattern in the brainwave associated with the task Use the decoded temporal pattern to modulate the frequency of at least one stimulus Transmit the temporal pattern to the second subject by exposing the second subject to said at least one stimulus

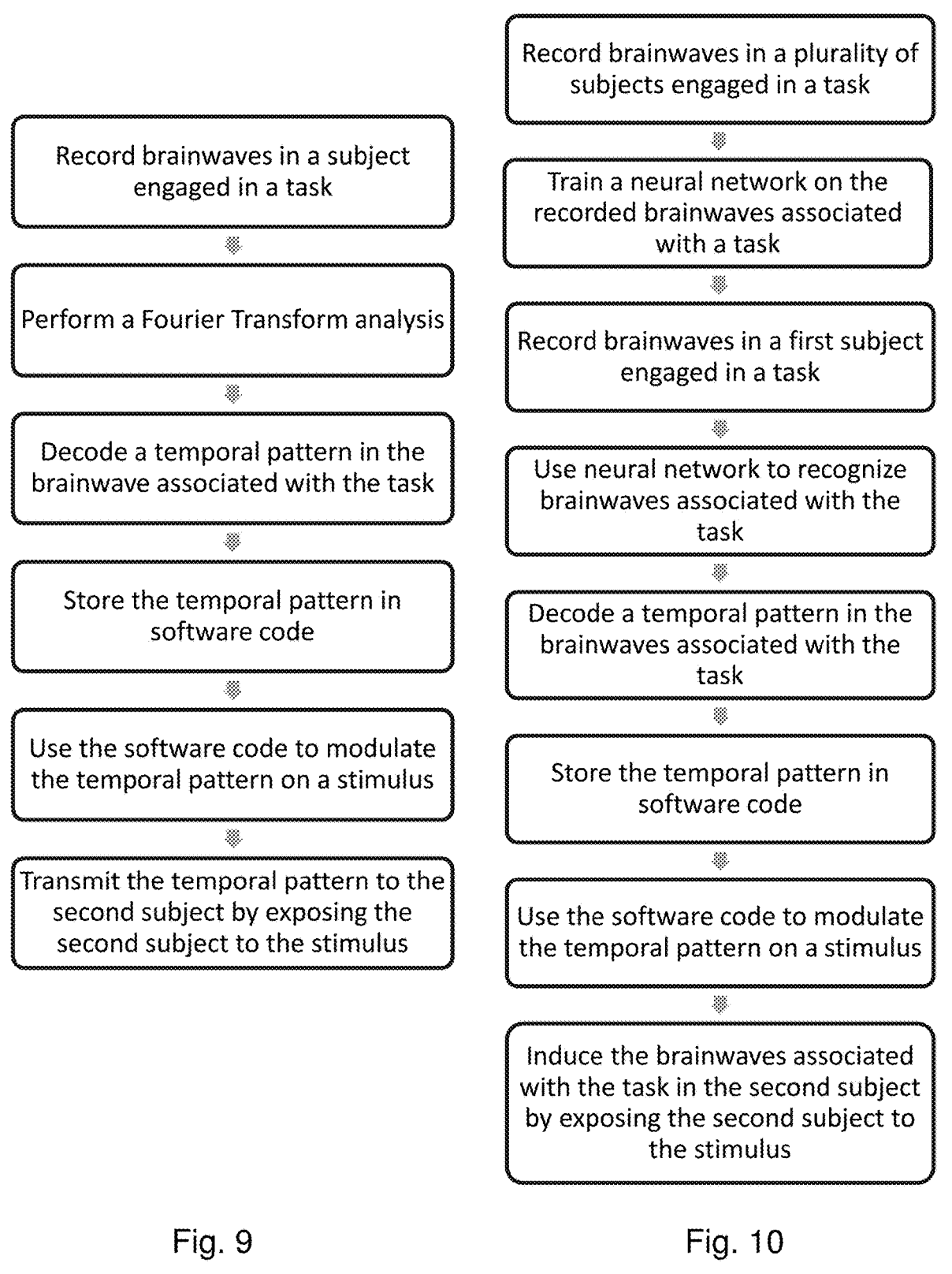

Record brainwaves in a subject engaged in a task

↓

Perform a Fourier Transform analysis

↓

Decode a temporal pattern in the brainwave associated with the task

↓

Store the temporal pattern in software code

↓

Use the software code to modulate the temporal pattern on a stimulus

↓

Transmit the temporal pattern to the second subject by exposing the second subject to the stimulus

Record brainwaves in a plurality of subjects engaged in a task

↓

Train a neural network on the recorded brainwaves associated with a task

↓

Record brainwaves in a first subject engaged in a task

↓

Use neural network to recognize brainwaves associated with the task

↓

Decode a temporal pattern in the brainwaves associated with the task

↓

Store the temporal pattern in software code

↓

Use the software code to modulate the temporal pattern on a stimulus

↓

Induce the brainwaves associated with the task in the second subject by exposing the second subject to the stimulus

Fig. 10

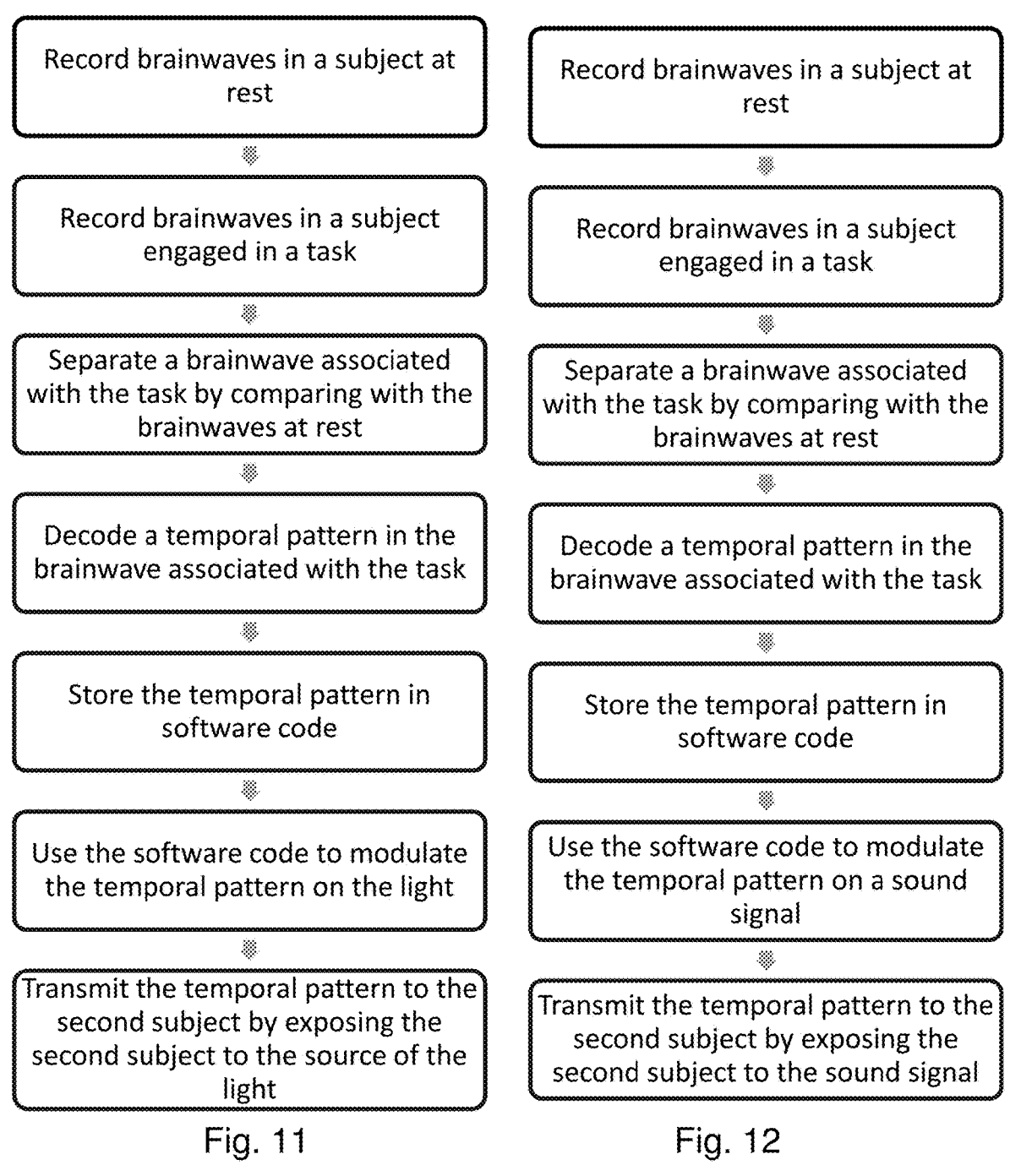

Record brainwaves in a subject at rest

Record brainwaves in a subject engaged in a task

Separate a brainwave associated with the task by comparing with the brainwaves at rest Decode a temporal pattern in the brainwave associated with the task Store the temporal pattern in software code Use the software code to modulate the temporal pattern on the light Transmit the temporal pattern to the second subject by exposing the second subject to the source of the light

Fig. 11

Record brainwaves in a subject at rest

Record brainwaves in a subject engaged in a task

Separate a brainwave associated with the task by comparing with the brainwaves at rest Decode a temporal pattern in the brainwave associated with the task Store the temporal pattern in software code Use the software code to modulate the temporal pattern on a sound signal Transmit the temporal pattern to the second subject by exposing the second subject to the sound signal

Fig. 12

Record brainwaves in a subject
engaged in a task

Identify brainwaves associated with
the task

Decode a temporal pattern in the
brainwave associated with the task

Use the decoded temporal pattern
to entrain the brainwaves of the
second subject BrainWave RT BOLD (Blood Oxygen Level Dependent) fMRI studies acquired with synchronized stimuli Brain Entrainment Frequency Following Response (or FFR) Brain Response to 10 Hz Entrainment Brainwave Entrainment Brainwaves during inefficient problem solving and stress 3D Rendering                                    Peak Indicators 40Hz 30Hz 20Hz 10Hz 0Hz 0Hz 10Hz 20Hz 30Hz 40Hz

Fig. 18

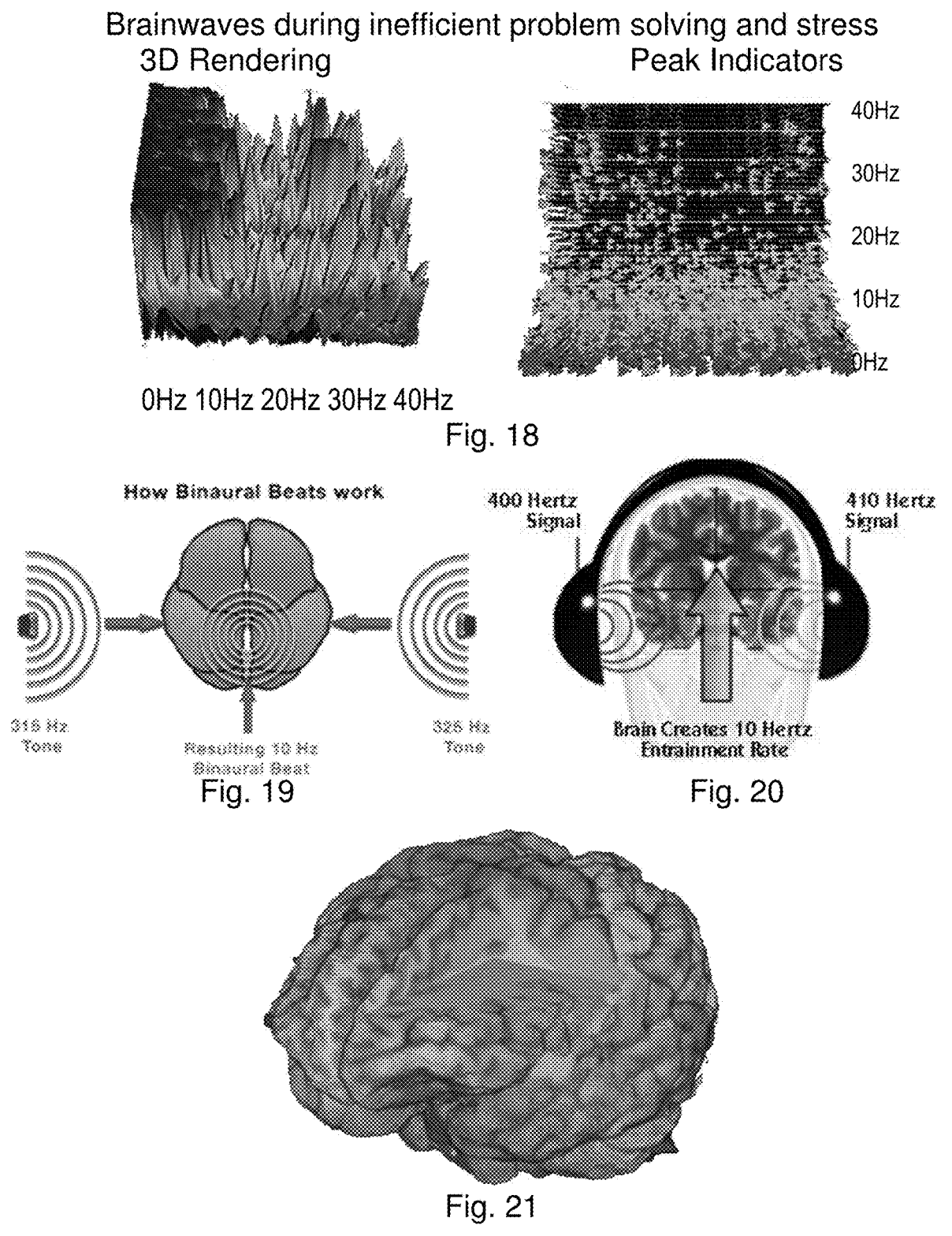

How Binaural Beats work

315 Hz
Tone

Resulting 10 Hz
Binaural Beat

325 Hz
Tone

Fig. 19

400 Hertz
Signal

410 Hertz
Signal

Brain Creates 10 Hertz
Entrainment Rate

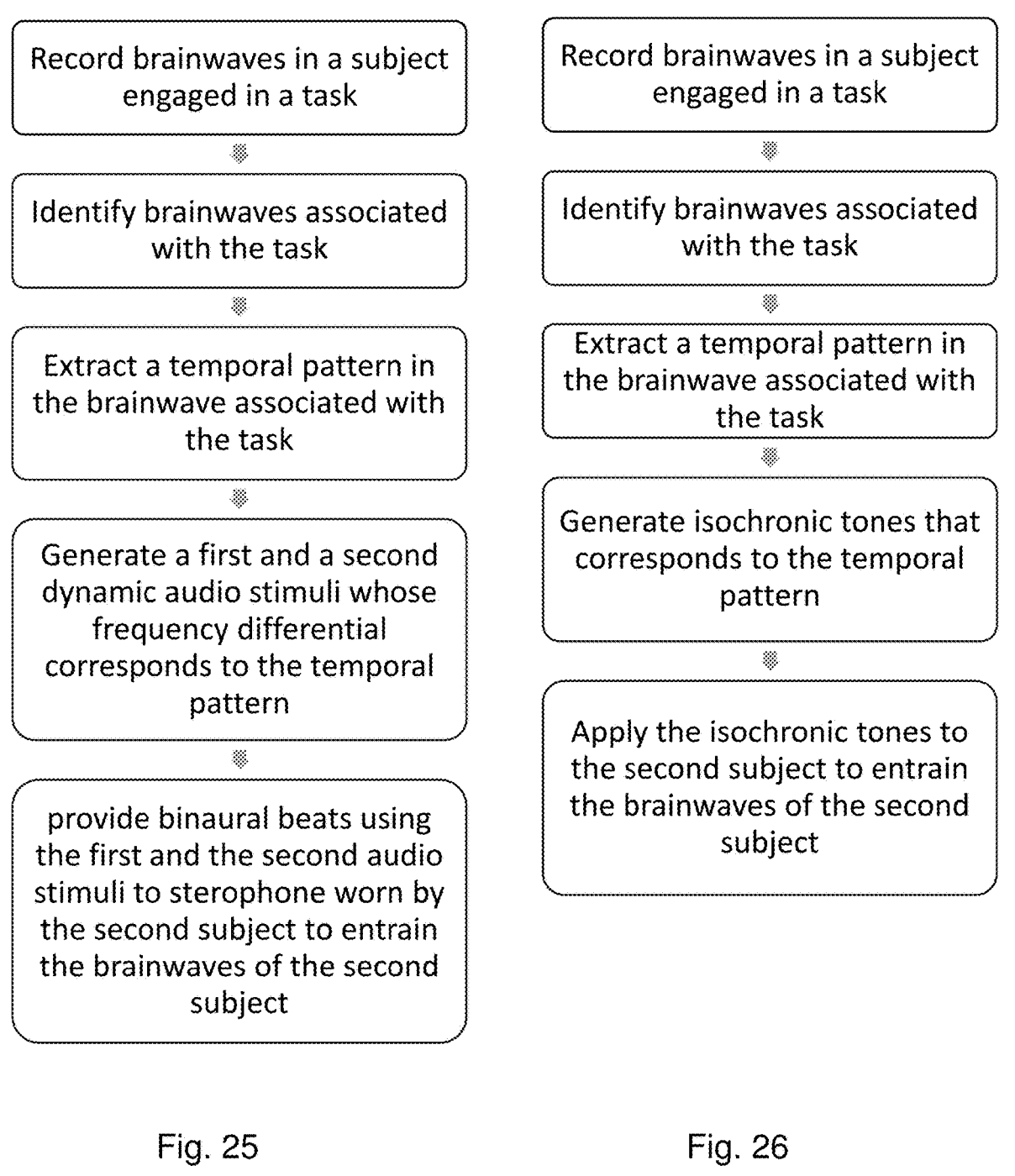

Record brainwaves in a subject engaged in a task

Identify brainwaves associated with the task

Extract a temporal pattern in the brainwave associated with the task

Generate a first and a second dynamic audio stimuli whose frequency differential corresponds to the temporal pattern provide binaural beats using the first and the second audio stimuli to sterophone worn by the second subject to entrain the brainwaves of the second subject

Fig. 25

Record brainwaves in a subject engaged in a task

Identify brainwaves associated with the task

Extract a temporal pattern in the brainwave associated with the task

Generate isochronic tones that corresponds to the temporal pattern

Apply the isochronic tones to the second subject to entrain the brainwaves of the second subject

Fig. 26

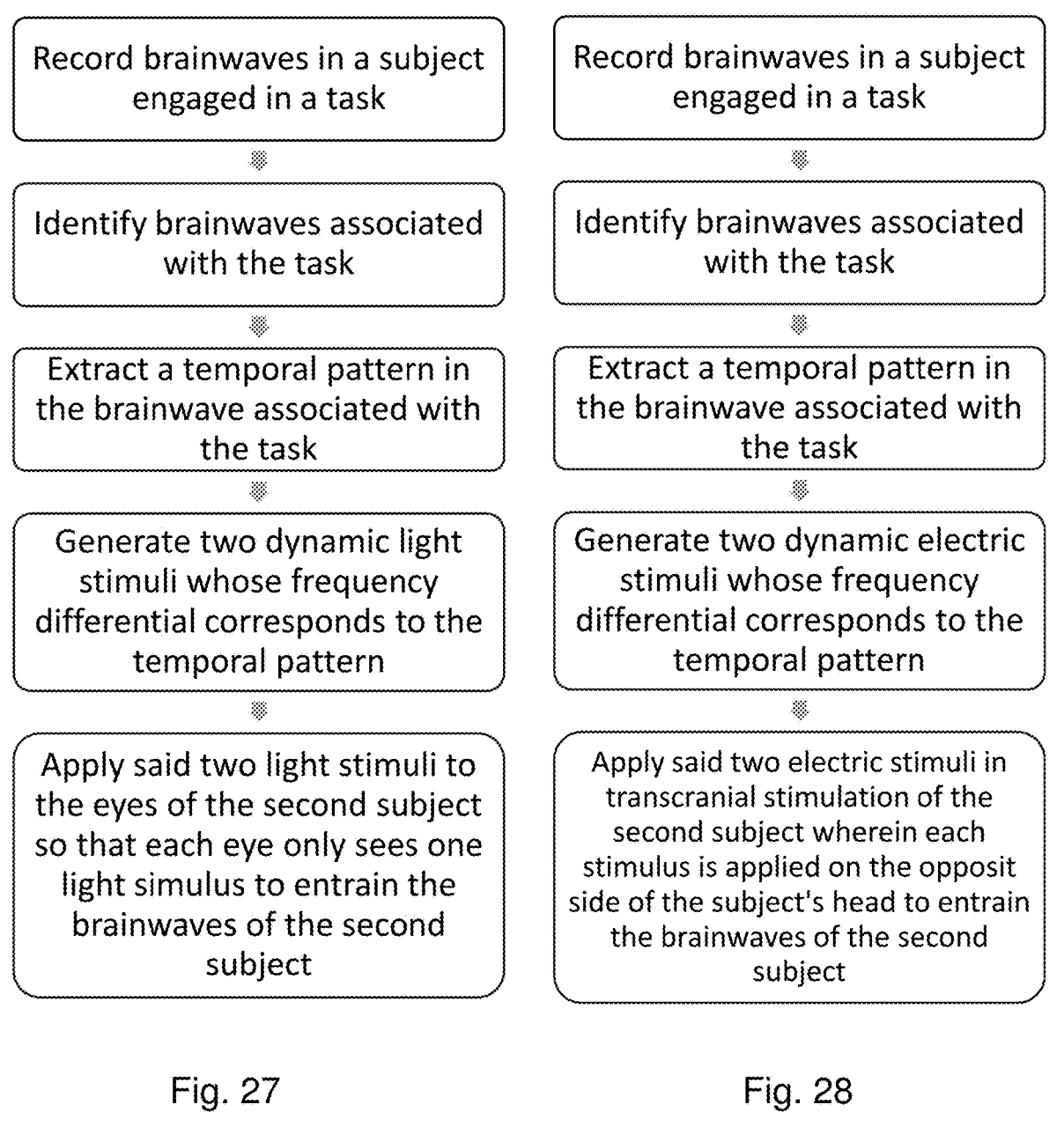

Record brainwaves in a subject engaged in a task

Identify brainwaves associated with the task

Extract a temporal pattern in the brainwave associated with the task

Generate two dynamic light stimuli whose frequency differential corresponds to the temporal pattern Apply said two light stimuli to the eyes of the second subject so that each eye only sees one light simulus to entrain the brainwaves of the second subject

Fig. 27

Record brainwaves in a subject engaged in a task

Identify brainwaves associated with the task

Extract a temporal pattern in the brainwave associated with the task

Generate two dynamic electric stimuli whose frequency differential corresponds to the temporal pattern Apply said two electric stimuli in transcranial stimulation of the second subject wherein each stimulus is applied on the opposit side of the subject's head to entrain the brainwaves of the second subject

Fig. 28

METHOD AND APPARATUS FOR NEUROENHANCEMENT

CROSS REFERENCE TO RELATED APPLICATIONS

The present application is a Division of U.S. patent application Ser. No. 16/134,309, filed Sep. 18, 2018, now U.S. Pat. No. 11,723,579, issued Aug. 15, 2023, which claims benefit of priority from U.S. Provisional Application No. 62/560,502, filed Sep. 19, 2017, and from U.S. Provisional Application No. 62/568,610, filed Oct. 5, 2017, and from U.S. Provisional Application No. 62/594,452, filed Dec. 4, 2017, each of which is expressly incorporated herein in its entirety, including any references cited therein. Each reference and document cited herein is expressly incorporated herein by reference in its entirety, for all purposes.

FIELD OF THE INVENTION

The present invention generally relates to the field of neuroenhancement and more specifically to systems and methods for determining brain activity patterns corresponding to tasks, and inducing brain activity patterns of the desired type in a subject through, inter alia, brain entrainment.

BACKGROUND OF THE INVENTION

Brain—The brain is a key part of the central nervous system, enclosed in the skull. In humans, and mammals more generally, the brain controls both autonomic processes, as well as cognitive processes. The brain (and to a lesser extent, the spinal cord) controls all volitional functions of the body and interprets information from the outside world. Intelligence, memory, emotions, speech, thoughts, movements and creativity are controlled by the brain. The central nervous system also controls autonomic functions and many homeostatic and reflex actions, such as breathing, heart rate, etc. The human brain consists of the cerebrum, cerebellum, and brainstem. The brainstem includes the midbrain, the pons, and the medulla oblongata. Sometimes the diencephalon, the caudal part of the forebrain, is included.

The brainstem provides the main motor and sensory innervation to the face and neck via the cranial nerves. Of the twelve pairs of cranial nerves, ten pairs come from the brainstem. This is an extremely important part of the brain, as the nerve connections of the motor and sensory systems from the main part of the brain to the rest of the body pass through the brainstem. This includes the corticospinal tract (motor), the posterior column-medial lemniscus pathway (fine touch, vibration sensation, and proprioception), and the spinothalamic tract (pain, temperature, itch, and crude touch). The brainstem also plays an important role in the regulation of cardiac and respiratory function. It also regulates the central nervous system and is pivotal in maintaining consciousness and regulating the sleep cycle. The brainstem has many basic functions including heart rate, breathing, sleeping, and eating. The skull imposes a barrier to electrical access to the brain functions, and in a healthy human, breaching the dura to access the brain is highly disfavored. The result is that electrical readings of brain activity are filtered by the dura, the cerebrospinal fluid, the skull, the scalp, skin appendages (e.g., hair), resulting in a loss of potential spatial resolution and amplitude of signals emanating from the brain. While magnetic fields resulting from brain electrical activity are accessible, the spatial resolution using feasible sensors is also limited.

The brain is composed of neurons and other cell types in connected networks that integrate sensory inputs, control movements, facilitate learning and memory, activate and express emotions, and control all other behavioral and cognitive functions. Neurons communicate primarily through electrochemical pulses that transmit signals between connected cells within and between brain areas. Thus, the desire to noninvasively capture and replicate neural activity associated with cognitive states has been a subject of interest to behavioral and cognitive neuroscientists.

Technological advances now allow for non-invasive recording of large quantities of information from the brain at multiple spatial and temporal scales. Examples include electroencephalogram ("EEG") data using multi-channel electrode arrays placed on the scalp or inside the brain, functional data using functional magnetic resonance imaging ("fMRI") and magnetoencephalography ("MEG"), and others. Noninvasive neuromodulation technologies have also been developed that can modulate the pattern of neural activity, and thereby cause altered behavior, cognitive states, perception, and motor output. Integration of noninvasive measurement and neuromodulation techniques for identifying and transplanting brain states from neural activity would be very valuable for clinical therapies, such as brain stimulation and related technologies often attempting to treat disorders of cognition. However, to date, no such systems and methods have been developed.

The brain is a key part of the central nervous system, and is enclosed in the skull. In humans, and mammals more generally, the brain controls both autonomic processes, as well as cognitive processes. The brain (and to a lesser extent, the spinal cord) controls all volitional functions of the body and interprets information from the outside world. Intelligence, memory, emotions, speech, thoughts, movements and creativity are controlled by the brain. The central nervous system also controls autonomic functions and many homeostatic and reflex actions, such as breathing, heart rate, etc. The human brain consists of the cerebrum, cerebellum, and brainstem. The brainstem includes the midbrain, the pons, and the medulla oblongata. Sometimes the diencephalon, the caudal part of the forebrain, is included.

The brainstem provides the main motor and sensory innervation to the face and neck via the cranial nerves. Of the twelve pairs of cranial nerves, ten pairs come from the brainstem. This is an extremely important part of the brain, as the nerve connections of the motor and sensory systems from the main part of the brain to the rest of the body pass through the brainstem. This includes the corticospinal tract (motor), the posterior column-medial lemniscus pathway (fine touch, vibration sensation, and proprioception), and the spinothalamic tract (pain, temperature, itch, and crude touch). The brainstem also plays an important role in the regulation of cardiac and respiratory function. It also regulates the central nervous system and is pivotal in maintaining consciousness and regulating the sleep cycle. The brainstem has many basic functions including heart rate, breathing, sleeping, and eating.

The function of the skull is to protect delicate brain tissue from injury. The skull consists of eight fused bones: the frontal, two parietal, two temporal, sphenoid, occipital and ethmoid. The face is formed by 14 paired bones including the maxilla, zygoma, nasal, palatine, lacrimal, inferior nasal conchae, mandible, and vomer. The bony skull is separated from the brain by the dura, a membranous organ, which in turn contains cerebrospinal fluid. The cortical surface of the brain typically is not subject to localized pressure from the skull. The skull therefore imposes a barrier to electrical access to the brain functions, and in a healthy human, breaching the dura to access the brain is highly disfavored. The result is that electrical readings of brain activity are filtered by the dura, the cerebrospinal fluid, the skull, the scalp, skin appendages (e.g., hair), resulting in a loss of potential spatial resolution and amplitude of signals emanating from the brain. While magnetic fields resulting from brain electrical activity are accessible, the spatial resolution using feasible sensors is also limited.

The cerebrum is the largest part of the brain and is composed of right and left hemispheres. It performs higher functions, such as interpreting inputs from the senses, as well as speech, reasoning, emotions, learning, and fine control of movement. The surface of the cerebrum has a folded appearance called the cortex. The human cortex contains about 70% of the nerve cells (neurons) and gives an appearance of gray color (grey matter). Beneath the cortex are long connecting fibers between neurons, called axons, which make up the white matter.

The cerebellum is located behind the cerebrum and brainstem. It coordinates muscle movements, helps to maintain balance and posture. The cerebellum may also be involved in some cognitive functions such as attention and language, as well as in regulating fear and pleasure responses. There is considerable evidence that the cerebellum plays an essential role in some types of motor learning. The tasks where the cerebellum most clearly comes into play are those in which it is necessary to make fine adjustments to the way an action is performed. There is dispute about whether learning takes place within the cerebellum itself, or whether it merely serves to provide signals that promote learning in other brain structures.

The brain communicates with the body through the spinal cord and twelve pairs of cranial nerves. Ten of the twelve pairs of cranial nerves that control hearing, eye movement, facial sensations, taste, swallowing and movement of the face, neck, shoulder and tongue muscles originate in the brainstem. The cranial nerves for smell and vision originate in the cerebrum.

The right and left hemispheres of the brain are joined by a structure consisting of fibers called the corpus callosum. Each hemisphere controls the opposite side of the body. Not all functions of the hemispheres are shared.

The cerebral hemispheres have distinct structures, which divide the brain into lobes. Each hemisphere has four lobes: frontal, temporal, parietal, and occipital. There are very complex relationships between the lobes of the brain and between the right and left hemispheres. There are very complex relationships between the lobes of the brain and between the right and left hemispheres. Frontal lobes control judgment, planning, problem-solving, behavior, emotions, personality, speech, self-awareness, concentration, intelligence, body movements; Temporal lobes control understanding of language, memory, organization and hearing; Parietal lobes control interpretation of language; input from vision, hearing, sensory, and motor; temperature, pain, tactile signals, memory, spatial and visual perception; Occipital lobes interpret visual input (movement, light, color).

A neuron is a fundamental unit of the nervous system, which comprises the autonomic nervous system and the central nervous system.

Brain structures and particular areas within brain structures include but are not limited to Hindbrain structures (e.g., Myelencephalon structures (e.g., Medulla oblongata, Medullary pyramids, Olivary body, Inferior olivary nucleus, Respiratory center, Cuneate nucleus, Gracile nucleus, Intercalated nucleus, Medullary cranial nerve nuclei, Inferior salivatory nucleus, Nucleus ambiguous, Dorsal nucleus of vagus nerve, Hypoglossal nucleus, Solitary nucleus, etc.), Metencephalon structures (e.g., Pons, Pontine cranial nerve nuclei, chief or pontine nucleus of the trigeminal nerve sensory nucleus (V), Motor nucleus for the trigeminal nerve (V), Abducens nucleus (VI), Facial nerve nucleus (VII), vestibulocochlear nuclei (vestibular nuclei and cochlear nuclei) (VIII), Superior salivatory nucleus, Pontine tegmentum, Respiratory centers, Pneumotaxic center, Apneustic center, Pontine micturition center (Barrington's nucleus), Locus coeruleus, Pedunculopontine nucleus, Laterodorsal tegmental nucleus, Tegmental pontine reticular nucleus, Superior olivary complex, Paramedian pontine reticular formation, Cerebellar peduncles, Superior cerebellar peduncle, Middle cerebellar peduncle, Inferior cerebellar peduncle, Fourth ventricle, Cerebellum, Cerebellar vermis, Cerebellar hemispheres, Anterior lobe, Posterior lobe, Flocculonodular lobe, Cerebellar nuclei, Fastigial nucleus, Interposed nucleus, Globose nucleus, Emboliform nucleus, Dentate nucleus, etc.)), Midbrain structures (e.g., Tectum, Corpora quadrigemina, inferior colliculi, superior colliculi, Pretectum, Tegmentum, Periaqueductal gray, Parabrachial area, Medial parabrachial nucleus, Lateral parabrachial nucleus, Subparabrachial nucleus (Kolliker-Fuse nucleus), Rostral interstitial nucleus of medial longitudinal fasciculus, Midbrain reticular formation, Dorsal raphe nucleus, Red nucleus, Ventral tegmental area, Substantia nigra, Pars compacta, Pars reticulata, Interpeduncular nucleus, Cerebral peduncle, Cms cerebri, Mesencephalic cranial nerve nuclei, Oculomotor nucleus (III), Trochlear nucleus (IV), Mesencephalic duct (cerebral aqueduct, aqueduct of Sylvius), etc.), Forebrain structures (e.g., Diencephalon, Epithalamus structures (e.g., Pineal body, Habenular nuclei, Stria medullares, Taenia thalami, etc.) Third ventricle, Thalamus structures (e.g., Anterior nuclear group, Anteroventral nucleus (aka ventral anterior nucleus), Anterodorsal nucleus, Anteromedial nucleus, Medial nuclear group, Medial dorsal nucleus, Midline nuclear group, Paratenial nucleus, Reuniens nucleus, Rhomboidal nucleus, Intralaminar nuclear group, Centromedial nucleus, Parafascicular nucleus, Paracentral nucleus, Central lateral nucleus, Central medial nucleus, Lateral nuclear group, Lateral dorsal nucleus, Lateral posterior nucleus, Pulvinar, Ventral nuclear group, Ventral anterior nucleus, Ventrallateral nucleus, Ventral posterior nucleus, Ventral posterior lateral nucleus, Ventral posterior medial nucleus, Metathalamus, Medial geniculate body, Lateral geniculate body, Thalamic reticular nucleus, etc.), Hypothalamus structures (e.g., Anterior, Medial area, Parts of preoptic area, Medial preoptic nucleus, Suprachiasmatic nucleus, Paraventricular nucleus, Supraoptic nucleus (mainly), Anterior hypothalamic nucleus, Lateral area, Parts of preoptic area, Lateral preoptic nucleus, Anterior part of Lateral nucleus, Part of supraoptic nucleus, Other nuclei of preoptic area, median preoptic nucleus, periventricular preoptic nucleus, Tuberal, Medial area, Dorsomedial hypothalamic nucleus, Ventromedial nucleus, Arcuate nucleus, Lateral area, Tuberal part of Lateral nucleus, Lateral tuberal nuclei, Posterior, Medial area, Mammillary nuclei (part of mammillary bodies), Posterior nucleus, Lateral area, Posterior part of Lateral nucleus, Optic chiasm, Subfornical organ, Periventricular nucleus, Pituitary stalk, Tuber cinereum, Tuberal nucleus, Tuberomammillary nucleus, Tuberal region, Mammillary bodies, Mammillary nucleus, etc.), Subthalamus structures (e.g., Thalamic nucleus, Zona incerta, etc.), Pituitary gland structures (e.g., neurohypophysis, Pars intermedia (Intermediate Lobe), adenohypophysis, etc.), Telencephalon structures, white matter structures (e.g., Corona radiata, Internal capsule, External capsule, Extreme capsule, Arcuate fasciculus, Uncinate fasciculus, Perforant Path, etc.), Subcortical structures (e.g., Hippocampus (Medial Temporal Lobe), Dentate gyrus, Cornu ammonis (CA fields), Cornu ammonis area 1, Cornu ammonis area 2, Cornu ammonis area 3, Cornu ammonis area 4, Amygdala (limbic system) (limbic lobe), Central nucleus (autonomic nervous system), Medial nucleus (accessory olfactory system), Cortical and basomedial nuclei (main olfactory system), Lateral[disambiguation needed] and basolateral nuclei (frontotemporal cortical system), Claustrum, Basal ganglia, Striatum, Dorsal striatum (aka neostriatum), Putamen, Caudate nucleus, Ventral striatum, Nucleus accumbens, Olfactory tubercle, Globus pallidus (forms nucleus lentiformis with putamen), Subthalamic nucleus, Basal forebrain, Anterior perforated substance, Substantia innominata, Nucleus basalis, Diagonal band of Broca, Medial septal nuclei, etc.), Rhinencephalon structures (e.g., Olfactory bulb, Piriform cortex, Anterior olfactory nucleus, Olfactorytract, Anterior commissure, Uncus, etc.), Cerebral cortex structures (e.g., Frontal lobe, Cortex, Primary motor cortex (Precentral gyrus, M1), Supplementary motor cortex, Premotor cortex, Prefrontal cortex, Gyri, Superiorfrontal gyrus, Middle frontal gyrus, Inferiorfrontal gyrus, Brodmann areas: 4, 6, 8, 9, 10, 11, 12, 24, 25, 32, 33, 44, 45, 46, 47, Parietallobe, Cortex, Primary somatosensory cortex (S1), Secondary somatosensory cortex (S2), Posterior parietal cortex, Gyri, Postcentral gyrus (Primary somesthetic area), Other, Precuneus, Brodmann areas 1, 2, 3 (Primary somesthetic area); 5, 7, 23, 26, 29, 31, 39, 40, Occipitallobe, Cortex, Primary visual cortex (V), V2, V3, V4, V5/MT, Gyri, Lateral occipital gyrus, Cuneus, Brodmann areas 17 (VI, primary visual cortex); 18, 19, Temporal lobe, Cortex, Primary auditory cortex (A), secondary auditory cortex (A2), Inferior temporal cortex, Posterior inferior temporal cortex, Superior temporal gyrus, Middle temporal gyrus, Inferior temporal gyrus, Entorhinal Cortex, Perirhinal Cortex, Parahippocampal gyrus, Fusiform gyrus, Brodmann areas: 9, 20, 21, 22, 27, 34, 35, 36, 37, 38, 41, 42, Medial superior temporal area (MST), Insular cortex, Cingulate cortex, Anterior cingulate, Posterior cingulate, Retrosplenial cortex, Indusium griseum, Subgenual area 25, Brodmann areas 23, 24; 26, 29, 30 (retrosplenial areas); 31, 32, etc.)).

Neurons—Neurons are electrically excitable cells that receive, process, and transmit information, and based on that information sends a signal to other neurons, muscles, or glands through electrical and chemical signals. These signals between neurons occurvia specialized connections called synapses. Neurons can connect to each other to form neural networks. The basic purpose of a neuron is to receive incoming information and, based upon that information send a signal to other neurons, muscles, or glands. Neurons are designed to rapidly send signals across physiologically long distances. They do this using electrical signals called nerve impulses or action potentials. When a nerve impulse reaches the end of a neuron, it triggers the release of a chemical, e.g., neurotransmitter. The neurotransmitter travels rapidly across the short gap between cells (the synapse) and acts to signal the adjacent cell. See www.biologyreference.com/Mo-Nu/Neuron.html#ixzz5AVxCuM5a.

Neurons can receive thousands of inputs from other neurons through synapses. Synaptic integration is a mechanism whereby neurons integrate these inputs before the generation of a nerve impulse, or action potential. The ability of synaptic inputs to effect neuronal output is determined by a number of factors: Size, shape and relative timing of electrical potentials generated by synaptic inputs; the geometric structure of the target neuron; the physical location of synaptic inputs within that structure; and the expression of voltage-gated channels in different regions of the neuronal membrane.

Neurons within a neural network receive information from, and send information to, many other cells, at specialized junctions called synapses. Synaptic integration is the computational process by which an individual neuron processes its synaptic inputs and converts them into an output signal. Synaptic potentials occur when neurotransmitter binds to and opens ligand-operated channels in the dendritic membrane, allowing ions to move into or out of the cell according to their electrochemical gradient. Synaptic potentials can be either excitatory or inhibitory depending on the direction and charge of ion movement. Action potentials occur if the summed synaptic inputs to a neuron reach a threshold level of depolarization and trigger regenerative opening of voltage-gated ion channels. Synaptic potentials are often brief and of small amplitude, therefore summation of inputs in time (temporal summation) or from multiple synaptic inputs (spatial summation) is usually required to reach action potential firing threshold.

There are two types of synapses: electrical synapses and chemical synapses. Electrical synapses are a direct electrical coupling between two cells mediated by gap junctions, which are pores constructed of connexin proteins—essentially result in the passing of a gradient potential (may be depolarizing or hyperpolarizing) between two cells.

Electrical synapses are very rapid (no synaptic delay). It is a passive process where signal can degrade with distance and may not produce a large enough depolarization to initiate an action potential in the postsynaptic cell. Electrical synapses are bidirectional, i.e., postsynaptic cell can actually send messages to the presynaptic cell.

Chemical synapses are a coupling between two cells through neuro-transmitters, ligand or voltage gated channels, receptors. They are influenced by the concentration and types of ions on either side of the membrane. Among the neurotransmitters, Glutamate, sodium, potassium, and calcium are positively charged. GABA and chloride are negatively charged. Neurotransmitter junctions provide an opportunity for pharmacological intervention, and many different drugs, including illicit drugs, act at synapses.

An excitatory postsynaptic potential (EPSP) is a postsynaptic potential that makes the postsynaptic neuron more likely to fire an action potential. An electrical charge (hyperpolarization) in the membrane of a postsynaptic neuron is caused by the binding of an inhibitory neurotransmitter from a presynaptic cell to a postsynaptic receptor. It makes it more difficult for a postsynaptic neuron to generate an action potential. An electrical change (depolarization) in the membrane of a postsynaptic neuron occurs, caused by the binding of an excitatory neurotransmitter from a presynaptic cell to a postsynaptic receptor. It makes it more likely for a postsynaptic neuron to generate an action potential. In a neuronal synapse that uses glutamate as receptor, for example, receptors open ion channels that are non-selectively permeable to cations. When these glutamate receptors are activated, both Na+ and K+ flow across the postsynaptic membrane. The reversal potential (Erev) for the post-synaptic current is approximately 0 mV. The resting potential of neurons is approximately −60 mV. The resulting EPSP will depolarize the post synaptic membrane potential, bringing it toward 0 mV.

An inhibitory postsynaptic potential (IPSP) is a kind of synaptic potential that makes a postsynaptic neuron less likely to generate an action potential. An example of inhibitory post synaptic s action is a neuronal synapse that uses gamma-Aminobutyric acid (γ-Aminobutyric acid, or GABA) as its transmitter. At such synapses, the GABA receptors typically open channels that are selectively permeable to Cl−. When these channels open, negatively charged chloride ions can flow across the membrane. The postsynaptic neuron has a resting potential of −60 mV and an action potential threshold of −40 mV. Transmitter release at this synapse will inhibit the postsynaptic cell. Since $E_a$ is more negative than the action potential threshold, e.g., −70 mV, it reduces the probability that the postsynaptic cell will fire an action potential.

Some types of neurotransmitters, such as glutamate, consistently result in EPSPs. Others, such as GABA, consistently result in IPSPs. The action potential lasts about one millisecond (1 msec). In contrast, the EPSPs and IPSPs can last as long as 5 to 10 msec. This allows the effect of one postsynaptic potential to build upon the next and so on.

Membrane leakage, and to a lesser extent, potentials per se, can be influenced by external electrical and magnetic fields. These fields may be generated focally, such as through implanted electrodes, or less specifically, such as through transcranial stimulation. Transcranial stimulation may be subthreshold or superthreshold. In the former case, the external stimulation acts to modulate resting membrane potential, making nerves more or less excitable. Such stimulation may be direct current or alternating current. In the latter case, this will tend to synchronize neuron depolarization with the signals. Superthreshold stimulation can be painful (at least because the stimulus directly excites pain neurons) and must be pulsed. Since this has correspondence to electroconvulsive therapy, superthreshold transcranial stimulation is sparingly used.

A number of neurotransmitters are known, as are pharmaceutical interventions and therapies that influence these compounds. Typically, the major neurotransmitters are small monoamine molecules, such as dopamine, epinephrine, norepinephrine, serotonin, GABA, histamine, etc., as well as acetylcholine. In addition, neurotransmitters also include amino acids, gas molecules such as nitric oxide, carbon monoxide, carbon dioxide, and hydrogen sulfide, as well as peptides. The presence, metabolism, and modulation of these molecules may influence learning and memory. Supply of neurotransmitter precursors, control of oxidative and mental stress conditions, and other influences on learning and memory-related brain chemistry, may be employed to facilitate memory, learning, and learning adaption transfer.

The neuropeptides, as well as their respective receptors, are widely distributed throughout the mammalian central nervous system. During learning and memory processes, besides structural synaptic remodeling, changes are observed at molecular and metabolic levels with the alterations in neurotransmitter and neuropeptide synthesis and release. While there is a consensus that brain cholinergic neurotransmission plays a critical role in the processes related to learning and memory, it is also well known that these functions are influenced by a tremendous number of neuropeptides and non-peptide molecules. Arginine vasopressin (AVP), oxytocin, angiotensin II, insulin, growth factors, serotonin (5-HT), melanin-concentrating hormone, histamine, bombesin and gastrin-releasing peptide (GRP), glucagon-like peptide-1 (GLP-1), cholecystokinin (CCK), dopamine, corticotropin-releasing factor (CRF) have modulatory effects on learning and memory. Among these peptides, CCK, 5-HT, and CRF play strategic roles in the modulation of memory processes under stressful conditions. CRF is accepted as the main neuropeptide involved in both physical and emotional stress, with a protective role during stress, possibly through the activation of the hypothalamo-pituitary (HPA) axis. The peptide CCK has been proposed to facilitate memory processing, and CCK-like immunoreactivity in the hypothalamus was observed upon stress exposure, suggesting that CCK may participate in the central control of stress response and stress-induced memory dysfunction. On the other hand, 5-HT appears to play a role in behaviors that involve a high cognitive demand and stress exposure activates serotonergic systems in a variety of brain regions. See: Mehmetali Gülpinar, Berrak C Yeğen, "The Physiology of Learning and Memory: Role of Peptides and Stress", Current Protein and Peptide Science, 2004(5), www.researchgate.net/publication/8147320_The_Physiology_of_Learning_and_Memory_Role_of_Peptides_and_Stress. Deep brain stimulation is described in NIH Research Matters, "A noninvasive deep brain stimulation technique", (2017), Brainworks, "QEEG Brain Mapping"; Carmon, A., Mor, J., & Goldberg, J. (1976). Evoked cerebral responses to noxious thermal stimuli in humans. Experimental Brain Research, 25(1), 103-107.

Mental State—A mental state is a state of mind that a subject is in. Some mental states are pure and unambiguous, while humans are capable of complex states that are a combination of mental representations, which may have in their pure state contradictory characteristics. There are several paradigmatic states of mind that a subject has: love, hate, pleasure, fear, and pain. Mental states can also include a waking state, a sleeping state, a flow (or being in the "zone"), and a mood (a mental state). A mental state is a hypothetical state that corresponds to thinking and feeling, and consists of a conglomeration of mental representations. A mental state is related to an emotion, though it can also relate to cognitive processes. Because the mental state itself is complex and potentially possess inconsistent attributes, clear interpretation of mental state through external analysis (other than self-reporting) is difficult or impossible. However, a number of studies report that certain attributes of mental state or thought processes may in fact be determined through passive monitoring, such as EEG, with some degree of statistical reliability. In most studies, the characterization of mental state was an endpoint, and the raw signals, after statistically classification or semantic labelling, are superseded and the remaining signal energy treated as noise. Current technology does not permit a precise abstract encoding or characterization of the full range of mental states based on neural correlates of mental state.

Neural Correlates—A neural correlate of a mental state is an electro-neuro-biological state or the state assumed by some biophysical subsystem of the brain, whose presence necessarily and regularly correlates with such specific mental state. All properties credited to the en.wikipedia.org/wiki/Mind, including consciousness, emotion, and desires are thought to have direct neural correlates. For our purposes, neural correlates of a mental state can be defined as the minimal set of neuronal oscillations that correspond to the given mental state. Neuroscientists use empirical approaches to discover neural correlates of subjective mental states.

Brainwaves—At the root of all our thoughts, emotions, and behaviors is the communication between neurons within our brains, a rhythmic or repetitive neural activity in the central nervous system. The oscillation can be produced by a single neuron or by synchronized electrical pulses from ensembles of neurons communicating with each other. The interaction between neurons can give rise to oscillations at a different frequency than the firing frequency of individual neurons. The synchronized activity of large numbers of neurons produces macroscopic oscillations, which can be observed in an electroencephalogram. They are divided into bandwidths to describe their purported functions or functional relationships. Oscillatory activity in the brain is widely observed at different levels of organization and is thought to play a key role in processing neural information. Numerous experimental studies support a functional role of neural oscillations. A unified interpretation, however, is still not determined. Neural oscillations and synchronization have been linked to many cognitive functions such as information transfer, perception, motor control and memory.

Electroencephalographic (EEG) signals are relatively easy and safe to acquire, have along history of analysis, and can have high dimensionality, e.g., up to 128 or 256 separate recording electrodes. While the information represented in each electrode is not independent of the others, and the noise in the signals high, there is much information available through such signals that has not been fully characterized to date.

Brain waves have been widely studied in neural activity generated by large groups of neurons, mostly by EEG. In general, EEG signals reveal oscillatory activity (groups of neurons periodically firing in synchrony), in specific frequency bands: alpha (7.5-12.5 Hz) that can be detected from the occipital lobe during relaxed wakefulness and which increases when the eyes are closed; delta (1-4 Hz), theta (4-8 Hz), beta (13-30 Hz), low gamma (30-70 Hz), and high gamma (70-150 Hz) frequency bands, where faster rhythms such as gamma activity have been linked to cognitive processing. Higher frequencies imply multiple groups of neurons firing in coordination, either in parallel or in series, or both, since individual neurons do not fire at rates of 100 Hz. Neural oscillations of specific characteristics have been linked to cognitive states, such as awareness and consciousness and different sleep stages.

The functional role of neural oscillations is still not fully understood; however, they have been shown to correlate with emotional responses, motor control, and a number of cognitive functions including information transfer, perception, and memory. Specifically, neural oscillations, in particular theta activity, are extensively linked to memory function, and coupling between theta and gamma activity is considered to be vital for memory functions, including episodic memory. Electroencephalography (EEG) has been most widely used in the study of neural activity generated by large groups of neurons, known as neural ensembles, including investigations of the changes that occur in electroencephalographic profiles during cycles of sleep and wakefulness. EEG signals change dramatically during sleep and show a transition from faster frequencies to increasingly slower frequencies, indicating a relationship between the frequency of neural oscillations and cognitive states including awareness and consciousness.

It is a useful analogy to think of brainwaves as musical notes. Like in symphony, the higher and lower frequencies link and cohere with each other through harmonics, especially when one considers that neurons may be coordinated not only based on transitions, but also on phase delay. Oscillatory activity is observed throughout the central nervous system at all levels of organization. The dominant neuro oscillation frequency is associated with a respective mental state.

The functions of brain waves are wide-ranging and vary for different types of oscillatory activity. Neural oscillations also play an important role in many neurological disorders.

In standard EEG recording practice, 19 recording electrodes are placed uniformly on the scalp (the International 10-20 System). In addition, one or two reference electrodes (often placed on earlobes) and a ground electrode (often placed on the nose to provide amplifiers with reference voltages) are required. However, additional electrodes may add minimal useful information unless supplemented by computer algorithms to reduce raw EEG data to a manageable form. When large numbers of electrodes are employed, the potential at each location may be measured with respect to the average of all potentials (the common average reference), which often provides a good estimate of potential at infinity. The common average reference is not appropriate when electrode coverage is sparse (perhaps less than 64 electrodes). See, Paul L. Nunez and Ramesh Srinivasan (2007) Electroencephalogram. Scholarpedia, 2(2):1348, scholarpedia.org/article/Electroencephalogram. Dipole localization algorithms may be useful to determine spatial emission patterns in EEG.

Scalp potential may be expressed as a volume integral of dipole moment per unit volume over the entire brain provided P(r,t) is defined generally rather than in columnar terms. For the important case of dominant cortical sources, scalp potential may be approximated by the following integral over the cortical volume $\Theta$, $VS(r,t)=\iiint \Theta G(r,r') \cdot P(r',t)d\Theta(r')$. If the volume element $d\Theta(r')$ is defined in terms of cortical columns, the volume integral may be reduced to an integral over the folded cortical surface. The time-dependence of scalp potential is the weighted sum of all dipole time variations in the brain, although deep dipole volumes typically make negligible contributions.

The vector Green's function G(r,r') contains all geometric and conductive information about the head volume conductor and weights the integral accordingly. Thus, each scalar component of the Green's function is essentially an inverse electrical distance between each source component and scalp location. For the idealized case of sources in an infinite medium of constant conductivity, the electrical distance equals the geometric distance. The Green's function accounts for the tissue's finite spatial extent and its inhomogeneity and anisotropy. The forward problem in EEG consists of choosing a head model to provide G(r,r') and carrying out the integral for some assumed source distribution. The inverse problem consists of using the recorded scalp potential distribution VS(r,t) plus some constraints (usual assumptions) on P(r,t) to find the best fit source distribution P(r,t). Since the inverse problem has no unique solution, any inverse solution depends critically on the chosen constraints, for example, only one or two isolated sources, distributed sources confined to the cortex, or spatial and temporal smoothness criteria.

High-resolution EEG uses the experimental scalp potential VS(r,t) to predict the potential on the dura surface (the unfolded membrane surrounding the cerebral cortex) VD(r,t). This may be accomplished using a head model Green's function G(r,r') or by estimating the surface Laplacian with either spherical or 3D splines. These two approaches typically provide very similar dura potentials VD(r,t); the estimates of dura potential distribution are unique subject to head model, electrode density, and noise issues.

In an EEG recording system, each electrode is connected to one input of a differential amplifier (one amplifier per pair of electrodes); a common system reference electrode (or synthesized reference) is connected to the other input of each differential amplifier. These amplifiers amplify the voltage between the active electrode and the reference (typically 1,000-100,000 times, or 60-100 dB of voltage gain). The amplified signal is digitized via an analog-to-digital converter, after being passed through an anti-aliasing filter. Analog-to-digital sampling typically occurs at 256-512 Hz in clinical scalp EEG; sampling rates of up to 20 kHz are used in some research applications. The EEG signals can be captured with open source hardware such as OpenBCI, and the signal can be processed by freely available EEG software such as EEGLAB or the Neurophysiological Bio-marker Toolbox. Atypical adult human EEG signal is about 10 μV to 100 μV in amplitude when measured from the scalp and is about 10-20 mV when measured from subdural electrodes.

Delta wave (en.wikipedia.org/wiki/Delta_wave) is the frequency range up to 4 Hz. It tends to be the highest in amplitude and the slowest waves. It is normally seen in adults in NREM (en.wikipedia.org/wiki/NREM). It is also seen normally in babies. It may occur focally with subcortical lesions and in general distribution with diffuse lesions, metabolic encephalopathy hydrocephalus or deep midline lesions. It is usually most prominent frontally in adults (e.g., FIRDA-frontal intermittent rhythmic delta) and posteriorly in children (e.g., OIRDA-occipital intermittent rhythmic delta).

Theta is the frequency range from 4 Hz to 7 Hz. Theta is normally seen in young children. It may be seen in drowsiness or arousal in older children and adults; it can also be seen in meditation. Excess theta for age represents abnormal activity. It can be seen as a focal disturbance in focal subcortical lesions; it can be seen in generalized distribution in diffuse disorder or metabolic encephalopathy or deep midline disorders or some instances of hydrocephalus. On the contrary, this range has been associated with reports of relaxed, meditative, and creative states.

Alpha is the frequency range from 7 Hz to 14 Hz. This was the "posterior basic rhythm" (also called the "posterior dominant rhythm" or the "posterior alpha rhythm"), seen in the posterior regions of the head on both sides, higher in amplitude on the dominant side. It emerges with the closing of the eyes and with relaxation and attenuates with eye opening or mental exertion. The posterior basic rhythm is actually slower than 8 Hz in young children (therefore technically in the theta range). In addition to the posterior basic rhythm, there are other normal alpha rhythms such as the sensorimotor, or mu rhythm (alpha activity in the contralateral sensory and motor cortical areas) that emerges when the hands and arms are idle; and the "third rhythm" (alpha activity in the temporal or frontal lobes). Alpha can be abnormal; for example, an EEG that has diffuse alpha occurring in coma and is not responsive to external stimuli is referred to as "alpha coma."

Beta is the frequency range from 15 Hz to about 30 Hz. It is usually seen on both sides in symmetrical distribution and is most evident frontally. Beta activity is closely linked to motor behavior and is generally attenuated during active movements. Low-amplitude beta with multiple and varying frequencies is often associated with active, busy or anxious thinking and active concentration. Rhythmic beta with a dominant set of frequencies is associated with various pathologies, such as Dup15q syndrome, and drug effects, especially benzodiazepines. It may be absent or reduced in areas of cortical damage. It is the dominant rhythm in patients who are alert or anxious or who have their eyes open.

Gamma is the frequency range approximately 30-100 Hz. Gamma rhythms are thought to represent binding of different populations of neurons together into a network to carry out a certain cognitive or motor function.

Mu range is 8-13 Hz and partly overlaps with other frequencies. It reflects the synchronous firing of motor neurons in a rest state. Mu suppression is thought to reflect motor mirror neuron systems, because when an action is observed, the pattern extinguishes, possibly because of the normal neuronal system and the mirror neuron system "go out of sync" and interfere with each other. (en.wikipedia.org/wiki/Electroencephalography). See:

Abeles M, Local Cortical Circuits (1982) New York: Springer-Verlag.

Braitenberg V and Schuz A (1991) Anatomy of the Cortex. Statistics and Geometry. New York: Springer-Verlag.

Ebersole J S (1997) Defining epileptogenic foci: past, present, future. J. Clin. Neurophysiology 14: 470-483.

Edelman G M and Tononi G (2000) A Universe of Consciousness, New York: Basic Books.

Freeman W J (1975) Mass Action in the Nervous System, New York: Academic Press.

Gevins A S and Cutillo B A (1995) Neuroelectric measures of mind. In: P L Nunez (Au), Neocortical Dynamics and Human EEG Rhythms. NY: Oxford U. Press, pp. 304-338.

Gevins A S, Le J, Martin N, Brickett P, Desmond J, and Reutter B (1994) High resolution EEG: 124-channel recording, spatial enhancement, and MRI integration methods. Electroencephalography and Clin. Neurophysiology 90: 337-358.

Gevins A S, Smith M E, McEvoy L and Yu D (1997) High-resolution mapping of cortical activation related to working memory: effects of task difficulty, type of processing, and practice. Cerebral Cortex 7: 374-385.

Haken H (1983) Synergetics: An Introduction, 3rd Edition, Springer-Verlag.

Haken H (1999) What can synergetics contribute to the understanding of brain functioning? In: Analysis of Neurophysiological Brain Functioning, C Uhl (Ed), Berlin: Springer-Verlag, pp 7-40.

Ingber L (1995) Statistical mechanics of multiple scales of neocortical interactions. In: P L Nunez (Au), Neocortical Dynamics and Human EEG Rhythms. NY: Oxford U. Press, 628-681.

Izhikevich E M (1999) Weakly connected quasi-periodic oscillators, FM interactions, and multiplexing in the brain, SIAM J. Applied Mathematics 59: 2193-2223.

Jirsa V K and Haken H (1997) A derivation of a macroscopic field theory of the brain from the quasi-microscopic neural dynamics. Physica D 99: 503-526.

Jirsa V K and Kelso J A S (2000) Spatiotemporal pattern formation in continuous systems with heterogeneous connection topologies. Physical Review E 62: 8462-8465.

Katznelson R D (1981) Normal modes of the brain: Neuroanatomical basis and a physiological theoretical model. In PL Nunez (Au), Electric Fields of the Brain: The Neurophysics of EEG, 1st Edition, NY: Oxford U. Press, pp 401-442.

Klimesch W (1996) Memory processes, brain oscillations and EEG synchronization. International J. Psychophysiology 24: 61-100.

Law S K, Nunez P L and Wijesinghe R S (1993) High resolution EEG using spline generated surface Laplacians on spherical and ellipsoidal surfaces. IEEE Transactions on Biomedical Engineering 40:145-153.

Liley D T J, Cadusch P J and Dafilis M P (2002) A spatially continuous mean field theory of electrocortical activity network. Computation in Neural Systems 13: 67-113.

Malmuvino J and Plonsey R (1995) Bioelectromagetism. NY: Oxford U. Press.

Niedermeyer E and Lopes da Silva F H (Eds) (2005) Electroencephalography. Basic Principals, Clin. Applications, and Related Fields. Fifth Edition. London: Williams and Wilkins.

Nunez P L (1989) Generation of human EEG by a combination of long and short range neocortical interactions. Brain Topography 1:199-215.

Nunez P L (1995) Neocortical Dynamics and Human EEG Rhythms. NY: Oxford U. Press.

Nunez P L (2000) Toward a large-scale quantitative description of neocortical dynamic function and EEG (Target article), Behavioral and Brain Sciences 23:371-398.

Nunez P L (2000) Neocortical dynamic theory should be as simple as possible, but not simpler (Response to 18 commentaries on target article), Behavioral and Brain Sciences 23: 415-437.

Nunez P L (2002) EEG. In VS Ramachandran (Ed) Encyclopedia of the Human Brain, La Jolla: Academic Press, 169-179.

Nunez P L and Silberstein R B (2001) On the relationship of synaptic activity to macroscopic measurements: Does co-registration of EEG with fMRI make sense? Brain Topog. 13:79-96.

Nunez P L and Srinivasan R (2006) Electric Fields of the Brain: The Neurophysics of EEG, 2nd Edition, NY: Oxford U. Press.

Nunez P L and Srinivasan R (2006) A theoretical basis for standing and traveling brain waves measured with human EEG with implications for an integrated consciousness. Clin. Neurophysiology 117: 2424-2435.

Nunez P L, Srinivasan R, Westdorp A F, Wijesinghe R S, Tucker D M, Silberstein R B, and Cadusch P J (1997) EEG coherency I: Statistics, reference electrode, volume conduction, Laplacians, cortical imaging, and interpretation at multiple scales. Electroencephalography and Clin. Neurophysiology 103: 516-527.

Nunez P L. Wingeier B M and Silberstein R B (2001) Spatial-temporal structures of human alpha rhythms: theory, micro-current sources, multiscale measurements, and global binding of local networks, Human Brain Mapping 13:125-164.

Nuwer M (1997) Assessment of digital EEG, quantitative EEG, and EEG brain mapping: report of the American Academy of Neurology and the American Clin. Neurophysiology Society. Neurology 49: 277-292.

Penfield W and Jasper H D (1954) Epilepsy and the Functional Anatomy of the Human Brain. London: Little, Brown and Co.

Robinson P A, Rennie C J, Rowe D L and O'Conner S C (2004) Estimation of multiscale neurophysiologic parameters by electroencephalographic means. Human Brain Mapping 23: 53-72.

Scott A C (1995) Stairway to the Mind. New York: Springer-Verlag.

Silberstein R B, Danieli F and Nunez P L (2003) Fronto-parietal evoked potential synchronization is increased during mental rotation, NeuroReport 14: 67-71.

Silberstein R B, Song J, Nunez P L and Park W (2004) Dynamic sculpting of brain functional connectivity is correlated with performance, Brain Topography 16: 240-254.

Srinivasan R and Petrovic S (2006) MEG phase follows conscious perception during binocular rivalry induced by visual stream segregation. Cerebral Cortex, 16: 597-608.

Srinivasan R, Nunez P L and Silberstein R B (1998) Spatial filtering and neocortical dynamics: estimates of EEG coherence. IEEE Trans. on Biomedical Engineering, 45: 814-825.

Srinivasan R, Russell D P, Edelman G M, and Tononi G (1999) Frequency tagging competing stimuli in binocular rivalry reveals increased synchronization of neuromagnetic responses during conscious perception. J. Neuroscience 19: 5435-5448.

Uhl C (Ed) (1999) Analysis of Neurophysiological Brain Functioning. Berlin: Springer-Verlag, Wingeier B M, Nunez P L and Silberstein R B (2001) Spherical harmonic decomposition applied to spatial-temporal analysis of human high-density electroencephalogram. Physical Review E 64: 051916-1 to 9.

en.wikipedia.org/wiki/Electroencephalography

TABLE 1

| Band | Freq. (Hz) | Location | Normally | Pathologically |
|---|---|---|---|---|
| | | Comparison of EEG bands | | |
| Delta | <4 | frontally in adults, posteriorly in children; high-amplitude waves | adult slow-wave sleep in babies Has been found during some continuous-attention tasks | subcortical lesions diffuse lesions metabolic encephalopathy hydrocephalus deep midline lesions |
| Theta | 4-7 | Found in locations not related to task at hand | higher in young children drowsiness in adults and teens idling Associated with inhibition of elicited responses (has been found to spike in situations where a person is actively trying to repress a response or action). | focal subcortical lesions metabolic encephalopathy deep midline disorders some instances of hydrocephalus |
| Alpha | 8-15 | posterior regions of head, both sides, higher in amplitude on dominant side. Central sites (c3-c4) at rest | relaxed/reflecting closing the eyes Also associated with inhibition control, seemingly with the purpose of timing inhibitory activity in different locations across the brain. | Coma |

TABLE 1-continued

Comparison of EEG bands

| Band | Freq. (Hz) | Location | Normally | Pathologically |
|------|-----------|----------|----------|----------------|
| Beta | 16-31 | both sides, symmetrical distribution, most evident frontally; low-amplitude waves | range span: active calm → intense → stressed → mild obsessive active thinking, focus, high alert, anxious | Benzodiazepines (en.wikipedia.org/wiki/ Benzodiazepines) Dup15q syndrome |
| Gamma | >32 | Somatosensory cortex | Displays during cross-modal sensory processing (perception that combines two different senses, such as sound and sight) Also is shown during short-term memory matching of recognized objects, sounds, or tactile sensations | A decrease in gamma-band activity may be associated with cognitive decline, especially when related to the theta band; however, this has not been proven for use as a clinical diagnostic measurement |
| Mu | 8-12 | Sensorimotor cortex | Shows rest-state motor neurons. | Mu suppression could indicate that motor mirror neurons are working. Deficits in Mu suppression, and thus in mirror neurons, might play a role in autism. |

EEG AND qEEG—An EEG electrode will mainly detect the neuronal activity in the brain region just beneath it. However, the electrodes receive the activity from thousands of neurons. One square millimeter of cortex surface, for example, has more than 100,000 neurons. It is only when the input to a region is synchronized with electrical activity occurring at the same time that simple periodic waveforms in the EEG become distinguishable. The temporal pattern associated with specific brainwaves can be digitized and encoded a non-transient memory, and embodied in or referenced by, computer software.

EEG (electroencephalography) and MEG (magnetoencephalography) are available technologies to monitor brain electrical activity. Each generally has sufficient temporal resolution to follow dynamic changes in brain electrical activity. Electroencephalography (EEG) and quantitative electroencephalography (qEEG) are electrophysiological monitoring methods that analyze the electrical activity of the brain to measure and display patterns that correspond to cognitive states and/or diagnostic information. It is typically noninvasive, with the electrodes placed on the scalp, although invasive electrodes are also used in some cases. EEG signals may be captured and analyzed by a mobile device, often referred as "brain wearables". There are a variety of "brain wearables" readily available on the market today. EEGs can be obtained with a non-invasive method where the aggregate oscillations of brain electric potentials are recorded with numerous electrodes attached to the scalp of a person. Most EEG signals originate in the brain's outer layer (the cerebral cortex), believed largely responsible for our thoughts, emotions, and behavior. Cortical synaptic action generates electrical signals that change in the 10 to 100-millisecond range. Transcutaneous EEG signals are limited by the relatively insulating nature of the skull surrounding the brain, the conductivity of the cerebrospinal fluid and brain tissue, relatively low amplitude of individual cellular electrical activity, and distances between the cellular current flows and the electrodes. EEG is characterized by: (1) Voltage; (2) Frequency; (3) Spatial location; (4) Interhemispheric symmetries; (5) Reactivity (reaction to state change); (6) Character of waveform occurrence (random, serial, continuous); and (7) Morphology of transient events. EEGs can be separated into two main categories. Spontaneous EEG which occur in the absence of specific sensory stimuli and evoked potentials (EPs) which are associated with sensory stimuli like repeated light flashes, auditory tones, finger pressure or mild electric shocks. The latter is recorded for example by time averaging to remove effects of spontaneous EEG. Non-sensory triggered potentials are also known. EP's typically are time synchronized with the trigger, and thus have an organization principle. Event-related potentials (ERPs) provide evidence of a direct link between cognitive events and brain electrical activity in a wide range of cognitive paradigms. It has generally been held that an ERP is the result of a set of discrete stimulus-evoked brain events. Event-related potentials (ERPs) are recorded in the same way as EPs, but occur at longer latencies from the stimuli and are more associated with an endogenous brain state.

Typically, a magnetic sensor with sufficient sensitivity to individual cell depolarization or small groups is a superconducting quantum interference device (SQIUD), which requires cryogenic temperature operation, either at liquid nitrogen temperatures (high temperature superconductors, HTS) or at liquid helium temperatures (low temperature superconductors, LTS). However, current research shows possible feasibility of room temperature superconductors (20 C). Magnetic sensing has an advantage, due to the dipole nature of sources, of having better potential volumetric localization; however, due to this added information, complexity of signal analysis is increased.

In general, the electromagnetic signals detected represent action potentials, an automatic response of a nerve cell to depolarization beyond a threshold, which briefly opens conduction channels. The cells have ion pumps which seek to maintain a depolarized state. Once triggered, the action potential propagates along the membrane in two-dimensions, causing a brief high level of depolarizing ion flow. There is a quiescent period after depolarization that generally prevents oscillation within a single cell. Since the exon extends from the body of the neuron, the action potential will typically proceed along the length of the axon, which terminates in a synapse with another cell. While direct electrical connections between cells occur, often the axon releases a neurotransmitter compound into the synapse, which causes a depolarization or hyperpolarization of the target cell. Indeed, the result may also be release of a hormone or peptide, which may have a local or more distant effect.

The electrical fields detectable externally tend to not include signals which low frequency signals, such as static levels of polarization, or cumulative depolarizating or hyperpolarizing effects between action potentials. In myelinated tracts, the current flows at the segments tend to be small, and therefore the signals from individual cells are small. Therefore, the largest signal components are from the synapses and cell bodies. In the cerebrum and cerebellum, these structures are mainly in the cortex, which is largely near the skull, making electroencephalography useful, since it provides spatial discrimination based on electrode location. However, deep signals are attenuated, and poorly localized. Magnetoencephalography detects dipoles, which derive from current flow, rather than voltage changes. In the case of a radially or spherically symmetric current flow within a short distance, the dipoles will tend to cancel, while net current flows long axons will reinforce. Therefore, an electroencephalogram reads a different signal than a magnetoencephalogram.

EEG-based studies of emotional specificity at the single-electrode level demonstrated that asymmetric activity at the frontal site, especially in the alpha (8-12 Hz) band, is associated with emotion. Voluntary facial expressions of smiles of enjoyment produce higher left frontal activation. Decreased left frontal activity is observed during the voluntary facial expressions of fear. In addition to alpha band activity, theta band power at the frontal midline (Fm) has also been found to relate to emotional states. Pleasant (as opposed to unpleasant) emotions are associated with an increase in frontal midline theta power. Many studies have sought to utilize pattern classification, such as neural networks, statistical classifiers, clustering algorithms, etc., to differentiate between various emotional states reflected in EEG.

EEG-based studies of emotional specificity at the single-electrode level demonstrated that asymmetric activity at the frontal site, especially in the alpha (8-12 Hz) band, is associated with emotion. Ekman and Davidson found that voluntary facial expressions of smiles of enjoyment produced higher left frontal activation (Ekman P, Davidson R J (1993) Voluntary Smiling Changes Regional Brain Activity. Psychol Sci 4: 342-345). Another study by Coan et al. found decreased left frontal activity during the voluntary facial expressions of fear (Coan J A, Allen J J, Harmon-Jones E (2001) Voluntary facial expression and hemispheric asymmetry over the frontal cortex. Psychophysiology 38: 912-925). In addition to alpha band activity, theta band power at the frontal midline (Fm) has also been found to relate to emotional states. Sammler and colleagues, for example, showed that pleasant (as opposed to unpleasant) emotion is associated with an increase in frontal midline theta power (Sammler D, Grigutsch M, Fritz T, Koelsch S (2007) Music and emotion: Electrophysiological correlates of the processing of pleasant and unpleasant music. Psychophysiology 44: 293-304). To further demonstrate whether these emotion-specific EEG characteristics are strong enough to differentiate between various emotional states, some studies have utilized a pattern classification analysis approach. See, for example:

Dan N, Xiao-Wei W, Li-Chen S, Bao-Liang L. EEG-based emotion recognition during watching movies; 2011-04-27 2011-05-01. 2011: 667-670;

Lin Y P, Wang C H, Jung T P, Wu T L, Jeng S K, (2010) EEG-Based Emotion Recognition in Music Listening. IEEE T Bio Med Eng 57:1798-1806;

Murugappan M, Nagarajan R, Yaacob S (2010) Classification of human emotion from EEG using discrete wavelet transform. J Biomed Sci Eng 3: 390-396;

Murugappan M, Nagarajan R, Yaacob S (2011) Combining Spatial Filtering and Wavelet Transform for Classifying Human Emotions Using EEG Signals. J Med. Bio. Eng. 31:45-51.

Detecting different emotional states by EEG may be more appropriate using EEG-based functional connectivity. There are various ways to estimate EEG-based functional brain connectivity: correlation, coherence and phase synchronization indices between each pair of EEG electrodes had been used. (Brazier M A, Casby J U (1952) Cross-correlation and autocorrelation studies of electroencephalographic potentials. Electroen clin neuro 4: 201-211). Coherence gives information similar to correlation, but also includes the covariation between two signals as a function of frequency. (Cantero J L, Atienza M, Salas R M, Gomez C M (1999) Alpha EEG coherence in different brain states: an electrophysiological index of the arousal level in human subjects. Neuroscilett 271:167-70.) The assumption is that higher correlation indicates a stronger relationship between two signals. (Guevara M A, Corsi-Cabrera M (1996) EEG coherence or EEG correlation? Int J Psychophysiology 23:145-153; Cantero J L, Atienza M, Salas R M, Gomez C M (1999) Alpha EEG coherence in different brain states: an electrophysiological index of the arousal level in human subjects. Neurosci lett 271:167-70; Adler G, Brassen S, Jajcevic A (2003) EEG coherence in Alzheimer's dementia. J Neural Transm 110:1051-1058; Deeny S P, Hillman C H, Janelle C M, Hatfield B D (2003) Cortico-cortical communication and superior performance in skilled marksmen: An EEG coherence analysis. J Sport Exercise Psy 25:188-204.) Phase synchronization among the neuronal groups estimated based on the phase difference between two signals is another way to estimate the EEG-based functional connectivity among brain areas. It is. (Franaszczuk P J, Bergey G K (1999) An autoregressive method for the measurement of synchronization of interictal and ictal EEG signals. Biol Cybern 81: 3-9.)

A number of groups have examined emotional specificity using EEG-based functional brain connectivity. For example, Shin and Park showed that, when emotional states become more negative at high room temperatures, correlation coefficients between the channels in temporal and occipital sites increase (Shin J-H, Park D-H. (2011) Analysis for Characteristics of Electroencephalogram (EEG) and Influence of Environmental Factors According to Emotional Changes. In Lee G, Howard D, Ślęzak D, editors. Convergence and Hybrid Information Technology. Springer Berlin Heidelberg, 488-500.) Hinrichs and Machleidt demonstrated that coherence decreases in the alpha band during sadness, compared to happiness (Hinrichs H, Machleidt W (1992) Basic emotions reflected in EEG-coherences. Int J Psychophysiol 13: 225-232). Miskovic and Schmidt found that EEG coherence between the prefrontal cortex and the posterior cortex increased while viewing highly emotionally arousing (i.e., threatening) images, compared to viewing neutral images (Miskovic V, Schmidt L A (2010) Cross-regional cortical synchronization during affective image viewing. Brain Res 1362:102-111). Costa and colleagues applied the synchronization index to detect interaction in different brain sites under different emotional states (Costa T, Rognoni E, Galati D (2006) EEG phase synchronization during emotional response to positive and negative film stimuli. Neurosci Lett 406:159-164). Costa's results showed an overall increase in the synchronization index among frontal channels during emotional stimulation, particularly during negative emotion (i.e., sadness). Furthermore, phase synchronization patterns were found to differ between positive and negative emotions. Costa also found that sadness was more synchronized than happiness at each frequency band and was associated with a wider synchronization both between the right and left frontal sites and within the left hemisphere. In contrast, happiness was associated with a wider synchronization between the frontal and occipital sites.

Different connectivity indices are sensitive to different characteristics of EEG signals. Correlation is sensitive to phase and polarity, but is independent of amplitudes. Changes in both amplitude and phase lead to a change in coherence (Guevara M A, Corsi-Cabrera M (1996) EEG coherence or EEG correlation? Int J Psychophysiol 23:145-153). The phase synchronization index is only sensitive to a change in phase (Lachaux J P, Rodriguez E, Martinerie J, Varela F J (1999) Measuring phase synchrony in brain signals. Hum Brain Mapp 8:194-208).

A number of studies have tried to classify emotional states by means of recording and statistically analyzing EEG signals from the central nervous systems. See for example:

Lin Y P, Wang C H, Jung T P, Wu T L, Jeng S K, et al. (2010) EEG-Based Emotion Recognition in Music Listening. IEEE T Bio Med Eng 57:1798-1806 [PubMed].

Murugappan M, Nagarajan R, Yaacob S (2010) Classification of human emotion from EEG using discrete wavelet transform. J Biomed Sci Eng 3: 390-396.

Murugappan M, Nagarajan R, Yaacob S (2011) Combining Spatial Filtering and Wavelet Transform for Classifying Human Emotions Using EEG Signals. J Med. Bio. Eng. 31:45-51.

Berkman E, Wong D K, Guimaraes M P, Uy E T, Gross J J, et al. (2004) Brain wave recognition of emotions in EEG. Psychophysiology 41: S71-S71.

Chanel G, Kronegg J, Grandjean D, Pun T (2006) Emotion assessment: Arousal evaluation using EEG's and peripheral physiological signals. Multimedia Content Representation, Classification and Security 4105: 530-537.

Hagiwara KlaM (2003) A Feeling Estimation System Using a Simple Electroencephalograph. IEEE International Conference on Systems, Man and Cybernetics. 4204-4209.

You-Yun Lee and Shulan Hsieh studied different emotional states by means of EEG-based functional connectivity patterns. They used emotional film clips to elicit three different emotional states.

The dimensional theory of emotion, which asserts that there are neutral, positive, and negative emotional states, may be used to classify emotional states, because numerous studies have suggested that the responses of the central nervous system correlate with emotional valence and arousal. (See for example, Davidson R J (1993) Cerebral Asymmetry and Emotion—Conceptual and Methodological Conundrums. Cognition Emotion 7:115-138; Jones N A, Fox N A (1992) Electroencephalogram asymmetry during emotionally evocative films and its relation to positive and negative affectivity. Brain Cogn 20: 280-299 [PubMed]; Schmidt L A, Trainor U (2001) Frontal brain electrical activity (EEG) distinguishes valence and intensity of musical emotions. Cognition Emotion 15:487-500; Tomarken A J, Davidson R J, Henriques J B (1990) Resting frontal brain asymmetry predicts affective responses to films. J Pers Soc Psychol 59: 791-801.) As suggested by Mauss and Robins (2009), "measures of emotional responding appear to be structured along dimensions (e.g., valence, arousal) rather than discrete emotional states (e.g., sadness, fear, anger)".

EEG-based functional connectivity change was found to be significantly different among emotional states of neutral, positive, or negative. Lee Y-Y, Hsieh S (2014) Classifying Different Emotional States by Means of EEG-Based Functional Connectivity Patterns. PLoS ONE 9(4): e95415. doi.org/10.1371/journal.pone.0095415. A connectivity pattern may be detected by pattern classification analysis using Quadratic Discriminant Analysis. The results indicated that the classification rate was better than chance. They concluded that estimating EEG-based functional connectivity provides a useful tool for studying the relationship between brain activity and emotional states.

Emotions affects learning. Intelligent Tutoring Systems (ITS) learner model initially composed of a cognitive module was extended to include a psychological module and an emotional module. Alicia Heraz et al. introduced an emomental agent. It interacts with an ITS to communicate the emotional state of the learner based upon his mental state. The mental state was obtained from the learner's brainwaves. The agent learns to predict the learner's emotions by using machine learning techniques. (Alicia Heraz, Ryad Razaki; Claude Frasson, "Using machine learning to predict learner emotional state from brainwaves" Advanced Learning Technologies, 2007. ICALT 2007. Seventh IEEE International Conference on Advanced Learning Technologies (ICALT 2007)) See also:

Ella T. Mampusti, Jose S. Ng, Jarren James I. Quinto, Grizelda L. Teng, Merlin Teodosia C. Suarez, Rhia S. Trogo, "Measuring Academic Affective States of Students via Brainwave Signals", *Knowledge and Systems Engineering (KSE)* 2011 *Third International Conference on*, pp. 226-231, 2011

Judith J. Azcarraga, John Francis Ibanez Jr., Ianne Robert Lim, Nestor Lumanas Jr., "Use of Personality Profile in Predicting Academic Emotion Based on Brainwaves Signals and Mouse Behavior", *Knowledge and Systems Engineering (KSE)* 2011 *Third International Conference on*, pp. 239-244, 2011.

Yi-Hung Liu, Chien-Te Wu, Yung-Hwa Kao, Ya-Ting Chen, "Single-trial EEG-based emotion recognition using kernel Eigen-emotion pattern and adaptive support vector machine", *Engineering in Medicine and Biology Society (EMBC)* 2013 *35th Annual International Conference of the IEEE*, pp. 4306-4309, 2013, ISSN 1557-170X.

Thong Tri Vo, Nam Phuong Nguyen, Toi Vo Van, *IFMBE Proceedings*, vol. 63, pp. 621, 2018, ISSN 1680-0737, ISBN 978-981-10-4360-4.

Adrian Rodriguez Aguiñaga, Miguel Angel Lopez Ramirez, Lecture *Notes in Computer Science*, vol. 9456, pp. 177, 2015, ISSN 0302-9743, ISBN 978-3-319-26507-0.

Judith Azcarraga, Merlin Teodosia Suarez, "Recognizing Student Emotions using Brainwaves and Mouse Behavior Data", *International Journal of Distance Education Technologies*, vol. 11, pp. 1, 2013, ISSN 1539-3100.

Tri Thong Vo, Phuong Nam Nguyen, Van Toi Vo, *IFMBE Proceedings*, vol. 61, pp. 67, 2017, ISSN 1680-0737, ISBN 978-981-10-4219-5.

Alicia Heraz, Claude Frasson, *Lecture Notes in Computer Science*, vol. 5535, pp. 367, 2009, ISSN 0302-9743, ISBN 978-3-642-02246-3.

Hamwira Yaacob, Wahab Abdul, Norhaslinda Kamaruddin, "Classification of EEG signals using MLP based on categorical and dimensional perceptions of emotions",

*Information and Communication Technology for the Muslim World (ICT4M) 2013 5th International Conference on*, pp. 1-6, 2013.

Yuan-Pin Lin, Chi-Hong Wang, Tzyy-PingJung, Tien-Lin Wu, Shyh-KangJeng, Jeng-Ren Duann, Jyh-Horng Chen, "EEG-Based Emotion Recognition in Music Listening", *Biomedical Engineering IEEE Transactions on*, vol. 57, pp. 1798-1806, 2010, ISSN 0018-9294.

Yi-Hung Liu, Wei-Teng Cheng, Yu-Tsung Hsiao, Chien-Te Wu, Mu-DerJeng, "EEG-based emotion recognition based on kernel Fisher's discriminant analysis and spectral powers", *Systems Man and Cybernetics (SMC) 2014 IEEE International Conference on*, pp. 2221-2225, 2014.

Using EEG to assess the emotional state has numerous practical applications. One of the first such applications was the development of a travel guide based on emotions by measuring brainwaves by the Singapore tourism group. "By studying the brainwaves of a family on vacation, the researchers drew up the Singapore Emotion Travel Guide, which advises future visitors of the emotions they can expect to experience at different attractions." (www.lonelyplanet-.com/news/2017/04/12/singapore-emotion-travel-guide) Joel Pearson at University of New South Wales and his group developed the protocol of measuring brainwaves of travelers using EEG and decoding specific emotional states.

Another recently released application pertains to virtual reality (VR) technology. On Sep. 18, 2017 Looxid Labs launched a technology that harnesses EEG from a subject waring a VR headset. Looxid Labs intention is to factor in brain waves into VR applications in order to accurately infer emotions. Other products such as MindMaze and even Samsung have tried creating similar applications through facial muscles recognition. (scottamyx.com/2017/10/13/looxid-labs-vr-brain-waves-human-emotions). According to its website (looxidlabs.com/device-2/), the Looxid Labs Development Kit provides a VR headset embedded with miniaturized eye and brain sensors. It uses 6 EEG channels: Fp1, Fp2, AF7, AF8, AF3, AF4 in international 10-20 system.

To assess a user's state of mind, a computer may be used to analyze the EEG signals. However, the emotional states of a brain are complex, and the brain waves associated with specific emotions seem to change over time. Wei-Long Zheng at Shanghai Jiao Tong University used machine learning to identify the emotional brain states and to repeat it reliably. The machine learning algorithm found a set of patterns that clearly distinguished positive, negative, and neutral emotions that worked for different subjects and for the same subjects over time with an accuracy of about 80 percent. (See Wei-Long Zheng, Jia-Yi Zhu, Bao-Liang Lu, Identifying Stable Patterns over Time for Emotion Recognition from EEG, arxiv.org/abs/1601.02197; see also How One Intelligent Machine Learned to Recognize Human Emotions, MIT Technology Review, Jan. 23, 2016.)

MEG—Magnetoencephalography (MEG) is a functional neuroimaging technique for mapping brain activity by recording magnetic fields produced by electrical currents occurring naturally in the brain, using very sensitive magnetometers. Arrays of SQUIDs (superconducting quantum interference devices) are currently the most common magnetometer, while the SERF (spin exchange relaxation-free) magnetometer is being investigated (Hämäläinen, Matti; Hari, Riitta; Ilmoniem, Risto J.; Knuutila, Jukka; Lounasmaa, Olli V. (1993). "*Magnetoencephalography-theory, instrumentation, and applications to noninvasive studies of the working human brain*". Reviews of Modern Physics. 65 (2): 413-497. ISSN 0034-6861. doi:10.1103/RevMod- Phys.65.413.) It is known that "neuronal activity causes local changes in cerebral blood flow, blood volume, and blood oxygenation" (Dynamic magnetic resonance imaging of human brain activity during primary sensory stimulation. K. K. Kwong, J. W. Belliveau, D. A. Chesler, I. E. Goldberg, R. M. Weisskoff, B. P. Poncelet, D. N. Kennedy, B. E. Hoppel, M. S. Cohen, and R. Turner). Using "a 122-channel D.C. SQUID magnetometer with a helmet-shaped detector array covering the subject's head" it has been shown that the "system allows simultaneous recording of magnetic activity all over the head." (122-channel squid instrument for investigating the magnetic signals from the human brain.) A. I. Ahonen, M. S. Hämäläinen, M. J. Kajola, J. E. T. Knuutila, P. P. Laine, O. V. Lounasmaa, L. T. Parkkonen, J. T. Simola, and C. D. Tesche Physica Scripta, Volume 1993, T49A).

In some cases, magnetic fields cancel, and thus the detectable electrical activity may fundamentally differ from the detectable electrical activity obtained via EEG. However, the main types of brain rhythms are detectable by both methods.

See: U.S. Pat. Nos. 5,059,814; 5,118,606; 5,136,687; 5,224,203; 5,303,705; 5,325,862; 5,461,699; 5,522,863; 5,640,493; 5,715,821; 5,719,561; 5,722,418; 5,730,146; 5,736,543; 5,737,485; 5,747,492; 5,791,342; 5,816,247; 6,497,658; 6,510,340; 6,654,729; 6,893,407; 6,950,697; 8,135,957; 8,620,206; 8,644,754; 9,118,775; 9,179,875; 9,642,552; 20030018278; 20030171689; 20060293578; 20070156457; 20070259323; 20080015458; 20080154148; 20080229408; 20100010365; 20100076334; 20100090835; 20120046531; 20120052905; 20130041281; 20150081299; 20150262016. See EP1304073A2; EP1304073A3; WO2000025668A1; and WO2001087153A1.

MEGs seek to detect the magnetic dipole emission from an electrical discharge in cells, e.g., neural action potentials. Typical sensors for MEGs are superconducting quantum interference devices (SQUIDs). These currently require cooling to liquid nitrogen or liquid helium temperatures. However, the development of room temperature, or near room temperature superconductors, and miniature cryocoolers, may permit field deployments and portable or mobile detectors. Because MEGs are less influenced by medium conductivity and dielectric properties, and because they inherently detect the magnetic field vector, MEG technology permits volumetric mapping of brain activity and distinction of complementary activity that might suppress detectable EEG signals. MEG technology also supports vector mapping of fields, since magnetic emitters are inherently dipoles, and therefore a larger amount of information is inherently available.

See, U.S. Pat. Nos. 4,862,359; 5,027,817; 5,198,977; 5,230,346; 5,269,315; 5,309,923; 5,325,862; 5,331,970; 5,546,943; 5,568,816; 5,662,109; 5,724,987; 5,797,853; 5,840,040; 5,845,639; 6,042,548; 6,080,164; 6,088,611; 6,097,980; 6,144,872; 6,161,031; 6,171,239; 6,240,308; 6,241,686; 6,280,393; 6,309,361; 6,319,205; 6,322,515; 6,356,781; 6,370,414; 6,377,833; 6,385,479; 6,390,979; 6,402,689; 6,419,629; 6,466,816; 6,490,472; 6,526,297; 6,527,715; 6,530,884; 6,547,746; 6,551,243; 6,553,252; 6,622,036; 6,644,976; 6,648,880; 6,663,571; 6,684,098; 6,697,660; 6,728,564; 6,740,032; 6,743,167; 6,773,400; 6,907,280; 6,947,790; 6,950,698; 6,963,770; 6,963,771; 6,996,261; 7,010,340; 7,011,814; 7,022,083; 7,092,748; 7,104,947; 7,105,824; 7,120,486; 7,130,673; 7,171,252; 7,177,675; 7,231,245; 7,254,500; 7,283,861; 7,286,871; 7,338,455; 7,346,395; 7,378,056; 7,461,045; 7,489,964; 7,490,085; 7,499,745; 7,510,699; 7,539,528; 7,547,284; 7,565,193; 7,567,693; 7,577,472; 7,613,502; 7,627,370;

7,647,098; 7,653,433; 7,697,979; 7,729,755; 7,754,190;
7,756,568; 7,766,827; 7,769,431; 7,778,692; 7,787,937;
7,787,946; 7,794,403; 7,831,305; 7,840,250; 7,856,264;
7,860,552; 7,899,524; 7,904,139; 7,904,144; 7,933,645;
7,962,204; 7,983,740; 7,986,991; 8,000,773; 8,000,793;
8,002,553; 8,014,847; 8,036,434; 8,065,360; 8,069,125;
8,086,296; 8,121,694; 8,190,248; 8,190,264; 8,197,437;
8,224,433; 8,233,682; 8,233,965; 8,236,038; 8,262,714;
8,280,514; 8,295,914; 8,306,607; 8,306,610; 8,313,441;
8,326,433; 8,337,404; 8,346,331; 8,346,342; 8,356,004;
8,358,818; 8,364,271; 8,380,289; 8,380,290; 8,380,314;
8,391,942; 8,391,956; 8,423,125; 8,425,583; 8,429,225;
8,445,851; 8,457,746; 8,467,878; 8,473,024; 8,498,708;
8,509,879; 8,527,035; 8,532,756; 8,538,513; 8,543,189;
8,554,325; 8,562,951; 8,571,629; 8,586,932; 8,591,419;
8,606,349; 8,606,356; 8,615,479; 8,626,264; 8,626,301;
8,632,750; 8,644,910; 8,655,817; 8,657,756; 8,666,478;
8,679,009; 8,684,926; 8,690,748; 8,696,722; 8,706,205;
8,706,241; 8,706,518; 8,712,512; 8,717,430; 8,725,669;
8,738,395; 8,761,869; 8,761,889; 8,768,022; 8,805,516;
8,814,923; 8,831,731; 8,834,546; 8,838,227; 8,849,392;
8,849,632; 8,852,103; 8,855,773; 8,858,440; 8,868,174;
8,888,702; 8,915,741; 8,918,162; 8,938,289; 8,938,290;
8,951,189; 8,951,192; 8,956,277; 8,965,513; 8,977,362;
8,989,836; 8,998,828; 9,005,126; 9,020,576; 9,022,936;
9,026,217; 9,026,218; 9,028,412; 9,033,884; 9,037,224;
9,042,201; 9,050,470; 9,067,052; 9,072,905; 9,084,896;
9,089,400; 9,089,683; 9,092,556; 9,095,266; 9,101,276;
9,107,595; 9,116,835; 9,133,024; 9,144,392; 9,149,255;
9,155,521; 9,167,970; 9,167,976; 9,167,977; 9,167,978;
9,171,366; 9,173,609; 9,179,850; 9,179,854; 9,179,858;
9,179,875; 9,192,300; 9,198,637; 9,198,707; 9,204,835;
9,211,077; 9,211,212; 9,213,074; 9,242,067; 9,247,890;
9,247,924; 9,248,288; 9,254,097; 9,254,383; 9,268,014;
9,268,015; 9,271,651; 9,271,674; 9,282,930; 9,289,143;
9,302,110; 9,308,372; 9,320,449; 9,322,895; 9,326,742;
9,332,939; 9,336,611; 9,339,227; 9,357,941; 9,367,131;
9,370,309; 9,375,145; 9,375,564; 9,387,320; 9,395,425;
9,402,558; 9,403,038; 9,414,029; 9,436,989; 9,440,064;
9,463,327; 9,470,728; 9,471,978; 9,474,852; 9,486,632;
9,492,313; 9,560,967; 9,579,048; 9,592,409; 9,597,493;
9,597,494; 9,615,789; 9,616,166; 9,655,573; 9,655,669;
9,662,049; 9,662,492; 9,669,185; 9,675,292; 9,682,232;
9,687,187; 9,707,396; 9,713,433; 9,713,444; 20010020127;
20010021800; 20010051774; 20020005784; 20020016552;
20020017994; 20020042563; 20020058867; 20020099273;
20020099295; 20020103428; 20020103429; 20020128638;
20030001098; 20030009096; 20030013981; 20030032870;
20030040660; 20030068605; 20030074032; 20030093004;
20030093005; 20030120140; 20030128801; 20030135128;
20030153818; 20030163027; 20030163028; 20030181821;
20030187359; 20030204135; 20030225335; 20030236458;
20040030585; 20040059241; 20040072133; 20040077960;
20040092809; 20040096395; 20040097802; 20040116798;
20040122787; 20040122790; 20040144925; 20040204656;
20050004489; 20050007091; 20050027284; 20050033122;
20050033154; 20050033379; 20050079474; 20050079636;
20050106713; 20050107654; 20050119547; 20050131311;
20050136002; 20050159670; 20050159671; 20050182456;
20050192514; 20050222639; 20050283053; 20060004422;
20060015034; 20060018525; 20060036152; 20060036153;
20060051814; 20060052706; 20060058683; 20060074290;
20060074298; 20060078183; 20060084858; 20060100526;
20060111644; 20060116556; 20060122481; 20060129324;
20060173510; 20060189866; 20060241373; 20060241382;
20070005115; 20070007454; 20070008172; 20070015985;
20070032737; 20070055145; 20070100251; 20070138886;

20070179534; 20070184507; 20070191704; 20070191727;
20070203401; 20070239059; 20070250138; 20070255135;
20070293760; 20070299370; 20080001600; 20080021332;
20080021340; 20080033297; 20080039698; 20080039737;
20080042067; 20080058664; 20080091118; 20080097197;
20080123927; 20080125669; 20080128626; 20080154126;
20080167571; 20080221441; 20080230702; 20080230705;
20080249430; 20080255949; 20080275340; 20080306365;
20080311549; 20090012387; 20090018407; 20090018431;
20090018462; 20090024050; 20090048507; 20090054788;
20090054800; 20090054958; 20090062676; 20090078875;
20090082829; 20090099627; 20090112117; 20090112273;
20090112277; 20090112278; 20090112279; 20090112280;
20090118622; 20090131995; 20090137923; 20090156907;
20090156955; 20090157323; 20090157481; 20090157482;
20090157625; 20090157662; 20090157751; 20090157813;
20090163777; 20090164131; 20090164132; 20090171164;
20090172540; 20090177050; 20090179642; 20090191131;
20090209845; 20090216091; 20090220429; 20090221928;
20090221930; 20090246138; 20090264785; 20090267758;
20090270694; 20090287271; 20090287272; 20090287273;
20090287274; 20090287467; 20090292180; 20090292713;
20090292724; 20090299169; 20090304582; 20090306531;
20090306534; 20090318773; 20090318794; 20100021378;
20100030073; 20100036233; 20100036453; 20100041962;
20100042011; 20100049276; 20100069739; 20100069777;
20100076274; 20100082506; 20100087719; 20100094154;
20100094155; 20100099975; 20100106043; 20100113959;
20100114193; 20100114237; 20100130869; 20100143256;
20100163027; 20100163028; 20100163035; 20100168525;
20100168529; 20100168602; 20100189318; 20100191095;
20100191124; 20100204748; 20100248275; 20100249573;
20100261993; 20100298735; 20100324441; 20110004115;
20110004412; 20110009777; 20110015515; 20110015539;
20110028859; 20110034821; 20110046491; 20110054345;
20110054562; 20110077503; 20110092800; 20110092882;
20110112394; 20110112426; 20110119212; 20110125048;
20110125238; 20110129129; 20110144521; 20110160543;
20110160607; 20110160608; 20110161011; 20110178359;
20110178441; 20110178442; 20110207988; 20110208094;
20110213200; 20110218405; 20110230738; 20110257517;
20110263962; 20110263968; 20110270074; 20110270914;
20110275927; 20110295143; 20110295166; 20110301448;
20110306845; 20110306846; 20110307029; 20110313268;
20110313487; 20120004561; 20120021394; 20120022343;
20120022884; 20120035765; 20120046531; 20120046971;
20120053449; 20120053483; 20120078327; 20120083700;
20120108998; 20120130228; 20120130229; 20120149042;
20120150545; 20120163689; 20120165899; 20120165904;
20120197163; 20120215114; 20120219507; 20120226091;
20120226185; 20120232327; 20120232433; 20120245493;
20120253219; 20120253434; 20120265267; 20120271148;
20120271151; 20120271376; 20120283502; 20120283604;
20120296241; 20120296253; 20120296569; 20120302867;
20120310107; 20120310298; 20120316793; 20130012804;
20130063434; 20130066350; 20130066391; 20130066394;
20130072780; 20130079621; 20130085678; 20130096441;
20130096454; 20130102897; 20130109996; 20130110616;
20130116561; 20130131755; 20130138177; 20130172716;
20130178693; 20130184728; 20130188854; 20130204085;
20130211238; 20130226261; 20130231580; 20130238063;
20130245422; 20130245424; 20130245486; 20130261506;
20130274586; 20130281879; 20130281890; 20130289386;
20130304153; 20140000630; 20140005518; 20140031703;
20140057232; 20140058241; 20140058292; 20140066763;
20140081115; 20140088377; 20140094719; 20140094720;
20140111335; 20140114207; 20140119621; 20140128763;

20140135642; 20140148657; 20140151563; 20140155952; 20140163328; 20140163368; 20140163409; 20140171749; 20140171757; 20140171819; 20140180088; 20140180092; 20140180093; 20140180094; 20140180095; 20140180096; 20140180097; 20140180099; 20140180100; 20140180112; 20140180113; 20140180176; 20140180177; 20140193336; 20140194726; 20140200414; 20140211593; 20140228649; 20140228702; 20140243614; 20140243652; 20140243714; 20140249360; 20140249445; 20140257073; 20140270438; 20140275807; 20140275851; 20140275891; 20140276013; 20140276014; 20140276187; 20140276702; 20140279746; 20140296646; 20140296655; 20140303425; 20140303486; 20140316248; 20140323849; 20140330268; 20140330394; 20140335489; 20140336489; 20140340084; 20140343397; 20140357962; 20140364721; 20140371573; 20140378830; 20140378941; 20150011866; 20150011877; 20150018665; 20150018905; 20150024356; 20150025408; 20150025422; 20150025610; 20150029087; 20150033245; 20150033258; 20150033259; 20150033262; 20150033266; 20150035959; 20150038812; 20150038822; 20150038869; 20150039066; 20150073237; 20150080753; 20150088120; 20150119658; 20150119689; 20150119698; 20150140528; 20150141529; 20150141773; 20150150473; 20150151142; 20150157266; 20150165239; 20150174418; 20150182417; 20150196800; 20150201879; 20150208994; 20150219732; 20150223721; 20150227702; 20150230744; 20150246238; 20150247921; 20150257700; 20150290420; 20150297106; 20150297893; 20150305799; 20150305800; 20150305801; 20150306340; 20150313540; 20150317796; 20150320591; 20150327813; 20150335281; 20150335294; 20150339363; 20150343242; 20150359431; 20150360039; 20160001065; 20160001096; 20160001098; 20160008620; 20160008632; 20160015289; 20160022165; 20160022167; 20160022168; 20160022206; 20160027342; 20160029946; 20160029965; 20160038049; 20160038559; 20160048659; 20160051161; 20160051162; 20160058354; 20160058392; 20160066828; 20160066838; 20160081613; 20160100769; 20160120480; 20160128864; 20160143541; 20160143574; 20160151018; 20160151628; 20160157828; 20160158553; 20160166219; 20160184599; 20160196393; 20160199241; 20160203597; 20160206380; 20160206871; 20160206877; 20160213276; 20160235324; 20160235980; 20160235983; 20160239966; 20160239968; 20160245670; 20160245766; 20160270723; 20160278687; 20160287118; 20160287436; 20160296746; 20160302720; 20160303397; 20160303402; 20160320210; 20160339243; 20160341684; 20160361534; 20160366462; 20160371721; 20170021161; 20170027539; 20170032098; 20170039706; 20170042474; 20170043167; 20170065349; 20170079538; 20170080320; 20170085855; 20170086729; 20170086763; 20170087367; 20170091418; 20170112403; 20170112427; 20170112446; 20170112577; 20170147578; 20170151435; 20170160360; 20170164861; 20170164862; 20170164893; 20170164894; 20170172527; 20170173262; 20170185714; 20170188862; 20170188866; 20170188868; 20170188869; 20170188932; 20170189691; 20170196501; and 20170202633.

Allen, Philip B., et al. High-temperature superconductivity. Springer Science & Business Media, 2012; Fausti, Daniele, et al. "Light-induced superconductivity in a stripe-ordered cuprate." Science 331.6014 (2011): 189-191;

Inoue, Mitsuteru, et al. "Investigating the use of magnonic crystals as extremely sensitive magnetic field sensors at room temperature." Applied Physics Letters 98.13 (2011): 132511;

Kaiser, Stefan, et al. "Optically induced coherent transport far above T c in underdoped YBa 2 Cu3 0 6+δ." Physical Review B 89.18 (2014): 184516;

Malik, M. A., and B. A. Malik. "High Temperature Super-conductivity: Materials, Mechanism and Applications." Bulgarian J. Physics 41.4 (2014).

Mankowsky, Roman, et al. "Nonlinear lattice dynamics as a basis for enhanced superconductivity in YBa2Cu306. 5." arXiv preprint arXiv:1405.2266 (2014);

Mcfetridge, Grant. "Room temperature superconductor." U.S. Pub. App. No. 20020006875.

Mitrano, Matteo, et al. "Possible light-induced supercon-ductivity in K3C60 at high temperature." Nature 530.7591 (2016):461-464;

Mourachkine, Andrei. Room-temperature superconductiv-ity. Cambridge Int Science Publishing, 2004;

Narlikar, Anant V., ed. High Temperature Superconductivity 2. Springer Science & Business Media, 2013; Pickett, Warren E. "Design for a room-temperature superconduc-tor." J. superconductivity and novel magnetism 19.3 (2006):291-297;

Sleight, Arthur W. "Room temperature superconductors." Accounts of chemical research 28.3 (1995): 103-108.

Hämäläinen, Matti; Hari, Riitta; Ilmoniemi, Risto J.; Knuu-tila, Jukka; Lounasmaa, Olli V. (1993). "Magnetoen-cephalography-theory, instrumentation, and applications to noninvasive studies of the working human brain". Reviews of Modern Physics. 65 (2): 413-497. ISSN 0034-6861. doi:10.1103/RevModPhys.65.413.

EEGs and MEGs can monitor the state of consciousness. For example, states of deep sleep are associated with slower EEG oscillations of larger amplitude. Various signal analysis methods allow for robust identifications of dis-tinct sleep stages, depth of anesthesia, epileptic seizures and connections to detailed cognitive events.

Positron Emission Tomography (PET) Scan-A PET scan is an imaging test that helps reveal how tissues and organs are functioning (Bailey, D. L; D. W Townsend; P. E. Valk; M. N. Maisey (2005). Positron Emission Tomography: Basic Sciences. Secaucus, NJ: Springer-Verlag. ISBN 1-85233-798-2.). A PET scan uses a radioactive drug (positron-emitting tracer) to show this activity. It uses this radiation to produce 3-D, images colored for the different activity of the brain. See, e.g.: Jarden, Jens O., Vijay Dhawan, Alexander Poltorak, Jerome B. Posner, and David A. Rottenberg. "Positron emission tomographic measurement of blood-to-brain and blood-to-tumor trans-port of 82Rb: The effect of dexamethasone and whole-brain radiation therapy." Annals of neurology 18, no. 6 (1985): 636-646.

Dhawan, V. I. J. A. Y., A. Poltorak, J. R. Moeller, J. O. Jarden, S. C. Strother, H. Thaler, and D. A. Rottenberg. "Positron emission tomographic measurement of blood-to-brain and blood-to-tumour transport of 82Rb. I: Error analysis and computer simulations." Physics in medicine and biology 34, no. 12 (1989): 1773.

U.S. Pat. Nos. 4,977,505; 5,331,970; 5,568,816; 5,724, 987; 5,825,830; 5,840,040; 5,845,639; 6,053,739; 6,132, 724; 6,161,031; 6,226,418; 6,240,308; 6,266,453; 6,364, 845; 6,408,107; 6,490,472; 6,547,746; 6,615,158; 6,633, 686; 6,644,976; 6,728,424; 6,775,405; 6,885,886; 6,947, 790; 6,996,549; 7,117,026; 7,127,100; 7,150,717; 7,254, 500; 7,309,315; 7,355,597; 7,367,807; 7,383,237; 7,483, 747; 7,583,857; 7,627,370; 7,647,098; 7,678,047; 7,738, 683; 7,778,490; 7,787,946; 7,876,938; 7,884,101; 7,890, 155; 7,901,211; 7,904,144; 7,961,922; 7,983,762; 7,986, 991; 8,002,553; 8,069,125; 8,090,164; 8,099,299; 8,121, 361; 8,126,228; 8,126,243; 8,148,417; 8,148,418; 8,150, 796; 8,160,317; 8,167,826; 8,170,315; 8,170,347; 8,175, 359; 8,175,360; 8,175,686; 8,180,125; 8,180,148; 8,185,

186; 8,195,593; 8,199,982; 8,199,985; 8,233,689; 8,233,965; 8,249,815; 8,303,636; 8,306,610; 8,311,747; 8,311,748; 8,311,750; 8,315,812; 8,315,813; 8,315,814; 8,321,150; 8,356,004; 8,358,818; 8,374,411; 8,379,947; 8,386,188; 8,388,529; 8,423,118; 8,430,816; 8,463,006; 8,473,024; 8,496,594; 8,520,974; 8,523,779; 8,538,108; 8,571,293; 8,574,279; 8,577,103; 8,588,486; 8,588,552; 8,594,950; 8,606,356; 8,606,361; 8,606,530; 8,606,592; 8,615,479; 8,630,812; 8,634,616; 8,657,756; 8,664,258; 8,675,936; 8,675,983; 8,680,119; 8,690,748; 8,706,518; 8,724,871; 8,725,669; 8,734,356; 8,734,357; 8,738,395; 8,754,238; 8,768,022; 8,768,431; 8,785,441; 8,787,637; 8,795,175; 8,812,245; 8,812,246; 8,838,201; 8,838,227; 8,861,819; 8,868,174; 8,871,797; 8,913,810; 8,915,741; 8,918,162; 8,934,685; 8,938,102; 8,980,891; 8,989,836; 9,025,845; 9,034,911; 9,037,224; 9,042,201; 9,053,534; 9,064,036; 9,076,212; 9,078,564; 9,081,882; 9,082,169; 9,087,147; 9,095,266; 9,138,175; 9,144,392; 9,149,197; 9,152,757; 9,167,974; 9,171,353; 9,171,366; 9,177,379; 9,177,416; 9,179,854; 9,186,510; 9,198,612; 9,198,624; 9,204,835; 9,208,430; 9,208,557; 9,211,077; 9,221,755; 9,226,672; 9,235,679; 9,256,982; 9,268,902; 9,271,657; 9,273,035; 9,275,451; 9,282,930; 9,292,858; 9,295,838; 9,305,376; 9,311,335; 9,320,449; 9,328,107; 9,339,200; 9,339,227; 9,367,131; 9,370,309; 9,390,233; 9,396,533; 9,401,021; 9,402,558; 9,412,076; 9,418,368; 9,434,692; 9,436,989; 9,449,147; 9,451,303; 9,471,978; 9,472,000; 9,483,613; 9,495,684; 9,556,149; 9,558,558; 9,560,967; 9,563,950; 9,567,327; 9,582,152; 9,585,723; 9,600,138; 9,600,778; 9,604,056; 9,607,377; 9,613,186; 9,652,871; 9,662,083; 9,697,330; 9,706,925; 9,717,461; 9,729,252; 9,732,039; 9,734,589; 9,734,601; 9,734,632; 9,740,710; 9,740,946; 9,741,114; 9,743,835; RE45336; RE45337; 20020032375; 20020183607; 20030013981; 20030028348; 20030031357; 20030032870; 20030068605; 20030128801; 20030233039; 20030233250; 20030234781; 20040049124; 20040072133; 20040116798; 20040151368; 20040184024; 20050007091; 20050065412; 20050080124; 20050096311; 20050118286; 20050144042; 20050215889; 20050244045; 20060015153; 20060074290; 20060084858; 20060129324; 20060188134; 20070019846; 20070032737; 20070036402; 20070072857; 20070078134; 20070081712; 20070100251; 20070127793; 20070280508; 20080021340; 20080069446; 20080123927; 20080167571; 20080219917; 20080221441; 20080241804; 20080247618; 20080249430; 20080279436; 20080281238; 20080286453; 20080287774; 20080287821; 20080298653; 20080298659; 20080310697; 20080317317; 20090018407; 20090024050; 20090036781; 20090048507; 20090054800; 20090074279; 20090099783; 20090143654; 20090148019; 20090156907; 20090156955; 20090157323; 20090157481; 20090157482; 20090157625; 20090157660; 20090157751; 20090157813; 20090163777; 20090164131; 20090164132; 20090164302; 20090164401; 20090164403; 20090164458; 20090164503; 20090164549; 20090171164; 20090172540; 20090221904; 20090246138; 20090264785; 20090267758; 20090270694; 20090271011; 20090271120; 20090271122; 20090271347; 20090290772; 20090292180; 20090292478; 20090292551; 20090299435; 20090312595; 20090312668; 20090316968; 20090316969; 20090318773; 20100004762; 20100010316; 20100010363; 20100014730; 20100014732; 20100015583; 20100017001; 20100022820; 20100030089; 20100036233; 20100041958; 20100041962; 20100041964; 20100042011; 20100042578; 20100063368; 20100069724; 20100069777; 20100076249; 20100080432; 20100081860; 20100081861; 20100094155; 20100100036; 20100125561; 20100130811; 20100130878; 20100135556; 20100142774; 20100163027; 20100163028; 20100163035;

20100168525; 20100168529; 20100168602; 20100172567; 20100179415; 20100189318; 20100191124; 20100219820; 20100241449; 20100249573; 20100260402; 20100268057; 20100268108; 20100274577; 20100274578; 20100280332; 20100293002; 20100305962; 20100305963; 20100312579; 20100322488; 20100322497; 20110028825; 20110035231; 20110038850; 20110046451; 20110077503; 20110125048; 20110152729; 20110160543; 20110229005; 20110230755; 20110263962; 20110293193; 20120035765; 20120041318; 20120041319; 20120041320; 20120041321; 20120041322; 20120041323; 20120041324; 20120041498; 20120041735; 20120041739; 20120053919; 20120053921; 20120059246; 20120070044; 20120080305; 20120128683; 20120150516; 20120207362; 20120226185; 20120263393; 20120283502; 20120288143; 20120302867; 20120316793; 20120321152; 20120321160; 20120323108; 20130018596; 20130028496; 20130054214; 20130058548; 20130063434; 20130064438; 20130066618; 20130085678; 20130102877; 20130102907; 20130116540; 20130144192; 20130151163; 20130188830; 20130197401; 20130211728; 20130226464; 20130231580; 20130237541; 20130243287; 20130245422; 20130274586; 20130318546; 20140003696; 20140005518; 20140018649; 20140029830; 20140058189; 20140063054; 20140063055; 20140067740; 20140081115; 20140107935; 20140119621; 20140133720; 20140133722; 20140148693; 20140155770; 20140163627; 20140171757; 20140194726; 20140207432; 20140211593; 20140222113; 20140222406; 20140226888; 20140236492; 20140243663; 20140247970; 20140249791; 20140249792; 20140257073; 20140270438; 20140343397; 20140348412; 20140350380; 20140355859; 20140371573; 20150010223; 20150012466; 20150019241; 20150029087; 20150033245; 20150033258; 20150033259; 20150033262; 20150033266; 20150073141; 20150073722; 20150080753; 20150088015; 20150088478; 20150150530; 20150150753; 20150157266; 20150161326; 20150161348; 20150174418; 20150196800; 20150199121; 20150201849; 20150216762; 20150227793; 20150257700; 20150272448; 20150287223; 20150294445; 20150297106; 20150306340; 20150317796; 20150324545; 20150327813; 20150332015; 20150335303; 20150339459; 20150343242; 20150363941; 20150379230; 20160004396; 20160004821; 20160004957; 20160007945; 20160019693; 20160027178; 20160027342; 20160035093; 20160038049; 20160038770; 20160048965; 20160067496; 20160070436; 20160073991; 20160082319; 20160110517; 20160110866; 20160110867; 20160113528; 20160113726; 20160117815; 20160117816; 20160117819; 20160128661; 20160133015; 20160140313; 20160140707; 20160151018; 20160155005; 20160166205; 20160180055; 20160203597; 20160213947; 20160217586; 20160217595; 20160232667; 20160235324; 20160239966; 20160239968; 20160246939; 20160263380; 20160284082; 20160296287; 20160300352; 20160302720; 20160364859; 20160364860; 20160364861; 20160366462; 20160367209; 20160371455; 20160374990; 20170024886; 20170027539; 20170032524; 20170032527; 20170032544; 20170039706; 20170053092; 20170061589; 20170076452; 20170085855; 20170091418; 20170112577; 20170128032; 20170147578; 20170148213; 20170168566; 20170178340; 20170193161; 20170198349; 20170202621; 20170213339; 20170216595; 20170221206; and 20170231560.

Functional Magnetic Resonance Imaging fMRI (fMRI)—
fMRI is a functional neuroimaging procedure using MRI technology that measures brain activity by detecting changes associated with blood flow ("Magnetic Resonance, a critical peer-reviewed introduction; functional MRI". *European Magnetic Resonance Forum*. Retrieved 17 Nov. 2014; Huettel, Song & McCarthy (2009)).

Yukiyasu Kamitani et al., Neuron (DOI:10.1016fj.neuron.2008.11.004) used an image of brain activity taken in a functional MRI scanner to recreate a black-and-white image from scratch. See also 'Mind-reading' software could record your dreams" By Celeste Biever. New Scientist, 12 Dec. 2008. (www.newscientist.com/article/dn16267-mind-reading-software-could-record-your-dreams/)

See, U.S. Pat. Nos. 6,622,036; 7,120,486; 7,177,675; 7,209,788; 7,489,964; 7,697,979; 7,754,190; 7,856,264; 7,873,411; 7,962,204; 8,060,181; 8,224,433; 8,315,962; 8,320,649; 8,326,433; 8,356,004; 8,380,314; 8,386,312; 8,392,253; 8,532,756; 8,562,951; 8,626,264; 8,632,750; 8,655,817; 8,679,009; 8,684,742; 8,684,926; 8,698,639; 8,706,241; 8,725,669; 8,831,731; 8,849,632; 8,855,773; 8,868,174; 8,915,871; 8,918,162; 8,939,903; 8,951,189; 8,951,192; 9,026,217; 9,037,224; 9,042,201; 9,050,470; 9,072,905; 9,084,896; 9,095,266; 9,101,276; 9,101,279; 9,135,221; 9,161,715; 9,192,300; 9,230,065; 9,248,286; 9,248,288; 9,265,458; 9,265,974; 9,292,471; 9,296,382; 9,302,110; 9,308,372; 9,345,412; 9,367,131; 9,420,970; 9,440,646; 9,451,899; 9,454,646; 9,463,327; 9,468,541; 9,474,481; 9,475,502; 9,489,854; 9,505,402; 9,538,948; 9,579,247; 9,579,457; 9,615,746; 9,693,724; 9,693,734; 9,694,155; 9,713,433; 9,713,444; 20030093129; 20030135128; 20040059241; 20050131311; 20050240253; 20060015034; 20060074822; 20060129324; 20060161218; 20060167564; 20060189899; 20060241718; 20070179534; 20070244387; 20080009772; 20080091118; 20080125669; 20080228239; 20090006001; 20090009284; 20090030930; 20090062676; 20090062679; 20090082829; 20090132275; 20090137923; 20090157662; 20090164132; 20090209845; 20090216091; 20090220429; 20090270754; 20090287271; 20090287272; 20090287273; 20090287467; 20090290767; 20090292713; 20090297000; 20090312808; 20090312817; 20090312998; 20090318773; 20090326604; 20090327068; 20100036233; 20100049276; 20100076274; 20100094154; 20100143256; 20100145215; 20100191124; 20100298735; 20110004412; 20110028827; 20110034821; 20110092882; 20110106750; 20110119212; 20110256520; 20110306845; 20110306846; 20110313268; 20110313487; 20120035428; 20120035765; 20120052469; 20120060851; 20120083668; 20120108909; 20120165696; 20120203725; 20120212353; 20120226185; 20120253219; 20120265267; 20120271376; 20120296569; 20130031038; 20130063550; 20130080127; 20130085678; 20130130799; 20130131755; 20130158883; 20130185145; 20130218053; 20130226261; 20130226408; 20130245886; 20130253363; 20130338803; 20140058528; 20140114889; 20140135642; 20140142654; 20140154650; 20140163328; 20140163409; 20140171757; 20140200414; 20140200432; 20140211593; 20140214335; 20140243652; 20140276549; 20140279746; 20140309881; 20140315169; 20140347265; 20140371984; 20150024356; 20150029087; 20150033245; 20150033258; 20150033259; 20150033262; 20150033266; 20150038812; 20150080753; 20150094962; 20150112899; 20150119658; 20150164431; 20150174362; 20150174418; 20150196800; 20150227702; 20150248470; 20150257700; 20150290453; 20150290454; 20150297893; 20150305685; 20150324692; 20150327813; 20150339363; 20150343242; 20150351655; 20150359431; 20150360039; 20150366482; 20160015307; 20160027342; 20160031479; 20160038049; 20160048659; 20160051161; 20160051162; 20160055304; 20160107653; 20160120437; 20160144175; 20160152233; 20160158553; 20160206380; 20160213276; 20160262680; 20160263318; 20160302711; 20160306942; 20160324457; 20160357256; 20160366462; 20170027812; 20170031440; 20170032098; 20170042474; 20170043160;

20170043167; 20170061034; 20170065349; 20170085547; 20170086727; 20170087302; 20170091418; 20170113046; 20170188876; 20170196501; 20170202476; 20170202518; and 20170206913.

Functional near infrared spectroscopy (fNIRS)—fNIR is a non-invasive imaging method involving the quantification of chromophore concentration resolved from the measurement of near infrared (NIR) light attenuation or temporal or phasic changes. NIR spectrum light takes advantage of the optical window in which skin, tissue, and bone are mostly transparent to NIR light in the spectrum of 700-900 nm, while hemoglobin (Hb) and deoxygenated-hemoglobin (deoxy-Hb) are stronger absorbers of light. Differences in the absorption spectra of deoxy-Hb and oxy-Hb allow the measurement of relative changes in hemoglobin concentration through the use of light attenuation at multiple wavelengths. Two or more wavelengths are selected, with one wavelength above and one below the isosbestic point of 810 nm at which deoxy-Hb and oxy-Hb have identical absorption coefficients. Using the modified Beer-Lambert law (mBLL), relative concentration can be calculated as a function of total photon path length. Typically, the light emitter and detector are placed ipsilaterally on the subject's skull so recorded measurements are due to back-scattered (reflected) light following elliptical pathways. The use of fNIR as a functional imaging method relies on the principle of neurovascular coupling also known as the haemodynamic response or blood-oxygen-level dependent (BOLD) response. This principle also forms the core of fMRI techniques. Through neuro-vascular coupling, neuronal activity is linked to related changes in localized cerebral blood flow. fNIR and fMRI are sensitive to similar physiologic changes and are often comparative methods. Studies relating fMRI and fNIR show highly correlated results in cognitive tasks. fNIR has several advantages in cost and portability over fMRI, but cannot be used to measure cortical activity more than 4 cm deep due to limitations in light emitter power and has more limited spatial resolution. fNIR includes the use of diffuse optical tomography (DOT/NIRDOT) for functional purposes. Multiplexing fNIRS channels can allow 2D topographic functional maps of brain activity (e.g. with Hitachi ETG-4000 or Artinis Oxymon) while using multiple emitter spacings may be used to build 3D tomographic maps. Note that fNIR is generally not capable of directly detecting neuron discharge, and therefore the technique is useful for determining metabolic activity level in different areas of the brain.

Beste Yuksel and Robert Jacob, Brain Automated Chorales (BACh), ACM CHI 2016, DOI: 10.1145/2858036.2858388, provides a system that helps beginners learn to play Bach chorales on piano by measuring how hard their brains are working. This is accomplished by estimating the brain's workload using functional Near-Infrared Spectroscopy (fNIRS), a technique that measures oxygen levels in the brain—in this case in the prefrontal cortex. A brain that's working hard pulls in more oxygen. Sensors strapped to the player's forehead talk to a computer, which delivers the new music, one line at a time. See also "Mind-reading tech helps beginners quickly learn to play Bach." By Anna Nowogrodzki, New Scientist, 9 Feb. 2016 available online at www.newscientist.com/article/2076899-mind-reading-tech-helps-beginners-quickly-learn-to-play-bach/.

LORETA—Low-resolution brain electromagnetic tomography often referred as LORETA is a functional imaging technology usually using a linearly constrained minimum variance vector beamformer in the time-frequency domain as described in Gross et al., "Dynamic imaging of coherent sources: Studying neural interactions in the human brain",
PNAS 98, 694-699, 2001. It allows to the image (mostly 3D)
evoked and induced oscillatory activity in a variable time-
frequency range, where time is taken relative to a triggered
event. There are three categories of imaging related to the
technique used for LORETA. See, wiki.besa.de/index.
php?title=Source_Analysis_3D_Imaging#Multiple_
Source_Beamformer_0.28MSBF.29. The Multiple Source
Beamformer (MSBF) is a tool for imaging brain activity. It
is applied in the time-frequency domain and based on
single-trial data. Therefore, it can image not only evoked,
but also induced activity, which is not visible in time-domain
averages of the data. Dynamic Imaging of Coherent Sources
(DICS) can find coherence between any two pairs of voxels
in the brain or between an external source and brain voxels.
DICS requires time-frequency-transformed data and can
find coherence for evoked and induced activity. The follow-
ing imaging methods provides an image of brain activity
based on a distributed multiple source model: CLARA is an
iterative application of LORETA images, focusing the
obtained 3D image in each iteration step. LAURA uses a
spatial weighting function that has the form of a local
autoregressive function. LORETA has the 3D Laplacian
operator implemented as spatial weighting prior. sLORETA
is an unweighted minimum norm that is standardized by the
resolution matrix. swLORETA is equivalent to sLORETA,
except for an additional depth weighting. SSLOFO is an
iterative application of standardized minimum norm images
with consecutive shrinkage of the source space. A User-
defined volume image allows experimenting with the dif-
ferent imaging techniques. It is possible to specify user-
defined parameters for the family of distributed source
images to create a new imaging technique. If no individual
MRI is available, the minimum norm image is displayed on
a standard brain surface and computed for standard source
locations. If available, an individual brain surface is used to
construct the distributed source model and to image the
brain activity. Unlike classical LORETA, cortical LORETA
is not computed in a 3D volume, but on the cortical surface.
Unlike classical CLARA, cortical CLARA is not computed
in a 3D volume, but on the cortical surface. The Multiple
Source Probe Scan (MSPS) is a tool for the validation of a
discrete multiple source model. The Source Sensitivity
image displays the sensitivity of a selected source in the
current discrete source model and is, therefore, data inde-
pendent.

See U.S. Pat. Nos.: 4,562,540; 4,594,662; 5,650,726;
5,859,533; 6,026,173; 6,182,013; 6,294,917; 6,332,087;
6,393,363; 6,534,986; 6,703,838; 6,791,331; 6,856,830;
6,863,127; 7,030,617; 7,092,748; 7,119,553; 7,170,294;
7,239,731; 7,276,916; 7,286,871; 7,295,019; 7,353,065;
7,363,164; 7,454,243; 7,499,894; 7,648,498; 7,804,441;
7,809,434; 7,841,986; 7,852,087; 7,937,222; 8,000,795;
8,046,076; 8,131,526; 8,174,430; 8,188,749; 8,244,341;
8,263,574; 8,332,191; 8,346,365; 8,362,780; 8,456,166;
8,538,700; 8,565,883; 8,593,154; 8,600,513; 8,706,205;
8,711,655; 8,731,987; 8,756,017; 8,761,438; 8,812,237;
8,829,908; 8,958,882; 9,008,970; 9,035,657; 9,069,097;
9,072,449; 9,091,785; 9,092,895; 9,121,964; 9,133,709;
9,165,472; 9,179,854; 9,320,451; 9,367,738; 9,414,749;
9,414,763; 9,414,764; 9,442,088; 9,468,541; 9,513,398;
9,545,225; 9,557,439; 9,562,988; 9,568,635; 9,651,706;
9,675,254; 9,675,255; 9,675,292; 9,713,433; 9,715,032;
20020000808; 20020017905; 20030018277; 20030093004;
20040097802; 20040116798; 20040131998; 20040140811;
20040145370; 20050156602; 20060058856; 20060069059;
20060136135; 20060149160; 20060152227; 20060170424;

20060176062; 20060184058; 20060206108; 20070060974;
20070159185; 20070191727; 20080033513; 20080097235;
20080125830; 20080125831; 20080183072; 20080242976;
20080255816; 20080281667; 20090039889; 20090054801;
20090082688; 20090099783; 20090216146; 20090261832;
20090306534; 20090312663; 20100010366; 20100030097;
20100042011; 20100056276; 20100092934; 20100132448;
20100134113; 20100168053; 20100198519; 20100231221;
20100238763; 20110004115; 20110050232; 20110160607;
20110308789; 20120010493; 20120011927; 20120016430;
20120083690; 20120130641; 20120150257; 20120162002;
20120215448; 20120245474; 20120268272; 20120269385;
20120296569; 20130091941; 20130096408; 20130141103;
20130231709; 20130289385; 20130303934; 20140015852;
20140025133; 20140058528; 20140066739; 20140107519;
20140128763; 20140155740; 20140161352; 20140163328;
20140163893; 20140228702; 20140243714; 20140275944;
20140276012; 20140323899; 20150051663; 20150112409;
20150119689; 20150137817; 20150145519; 20150157235;
20150167459; 20150177413; 20150248615; 20150257648;
20150257649; 20150301218; 20150342472; 20160002523;
20160038049; 20160040514; 20160051161; 20160051162;
20160091448; 20160102500; 20160120436; 20160136427;
20160187524; 20160213276; 20160220821; 20160223703;
20160235983; 20160245952; 20160256109; 20160259085;
20160262623; 20160298449; 20160334534; 20160345856;
20160356911; 20160367812; 20170001016; 20170067323;
20170138132; and 20170151436.

Neurofeedback—Neurofeedback (NFB), also called neu-
rotherapy or neurobiofeedback, is a type of biofeedback that
uses real-time displays of brain activity-most commonly
electroencephalography (EEG), to teach self-regulation of
brain function. Typically, sensors are placed on the scalp to
measure activity, with measurements displayed using video
displays or sound. The feedback may be in various other
forms as well. Typically, the feedback is sought to be
presented through primary sensory inputs, but this is not a
limitation on the technique.

The applications of neurofeedback to enhance perfor-
mance extend to the arts in fields such as music, dance, and
acting. A study with conservatory musicians found that
alpha-theta training benefitted the three music domains of
musicality, communication, and technique. Historically,
alpha-theta training, a form of neurofeedback, was created to
assist creativity by inducing hypnagogia, a "borderline wak-
ing state associated with creative insights", through facili-
tation of neural connectivity. Alpha-theta training has also
been shown to improve novice singing in children. Alpha-
theta neurofeedback, in conjunction with heart rate variabil-
ity training, a form of biofeedback, has also produced
benefits in dance by enhancing performance in competitive
ballroom dancing and increasing cognitive creativity in
contemporary dancers. Additionally, neurofeedback has also
been shown to instill a superior flow state in actors, possibly
due to greater immersion while performing.

Several studies of brain wave activity in experts while
performing a task related to their respective area of expertise
revealed certain characteristic telltale signs of so-called
"flow" associated with top-flight performance. Mihaly
Csikszentmihalyi (University of Chicago) found that the
most skilled chess players showed less EEG activity in the
prefrontal cortex, which is typically associated with higher
cognitive processes such as working memory and verbal-
ization, during a game.

Chris Berka et al., Advanced Brain Monitoring, Carlsbad,
California, The International J. Sport and Society, vol 1, p
87, looked at the brain waves of Olympic archers and professional golfers. A few seconds before the archers fired off an arrow or the golfers hit the ball, the team spotted a small increase in alpha band patterns. This may correspond to the contingent negative variation observed in evoked potential studies, and the Bereitschaftspotential or BP (from German, "readiness potential"), also called the pre-motor potential or readiness potential (RP), a measure of activity in the motor cortex and supplementary motor area of the brain leading up to voluntary muscle movement. Berka also trained novice marksmen using neurofeedback. Each person was hooked up to electrodes that tease out and display specific brain waves, along with a monitor that measured their heartbeat. By controlling their breathing and learning to deliberately manipulate the waveforms on the screen in front of them, the novices managed to produce the alpha waves characteristic of the flow state. This, in turn, helped them improve their accuracy at hitting the targets.

Low Energy Neurofeedback System (LENS)—The LENS, or Low Energy Neurofeedback System, uses a very low power electromagnetic field, to carry feedback to the person receiving it. The feedback travels down the same wires carrying the brain waves to the amplifier and computer. Although the feedback signal is weak, it produces a measurable change in the brainwaves without conscious effort from the individual receiving the feedback. The system is software controlled, to receive input from EEG electrodes, to control the stimulation. Through the scalp. Neurofeedback uses a feedback frequency that is different from, but correlates with, the dominant brainwave frequency. When exposed to this feedback frequency, the EEG amplitude distribution changes in power. Most of the time the brain waves reduce in power; but at times they also increase in power. In either case the result is a changed brainwave state, and much greater ability for the brain to regulate itself.

Content-Based Brainwave Analysis—Memories are not unique. Janice Chen, Nature Neuroscience, DOI: 10.1038/nn.4450, showed that when people describe the episode from Sherlock Holmes drama, their brain activity patterns were almost exactly the same as each other's, for each scene. Moreover, there's also evidence that, when a person tells someone else about it, they implant that same activity into their brain as well. Moreover, research in which people who have not seen a movie listen to someone else's description of it, Chen et al. have found that the listener's brain activity looks much like that of the person who has seen it. See also "Our brains record and remember things in exactly the same way" by Andy Coghlan, New Scientist, Dec. 5, 2016 (www.newscientist.com/article/2115093-our-brains-record-and-remember-things-in-exactly-the-same-way/)

Brian Pasley, Frontiers in Neuroengineering, doi.org/whb, developed a technique for reading thoughts. The team hypothesized that hearing speech and thinking to oneself might spark some of the same neural signatures in the brain. They supposed that an algorithm trained to identify speech heard out loud might also be able to identify words that are thought. In the experiment, the decoder trained on speech was able to reconstruct which words several of the volunteers were thinking, using neural activity alone. See also "Hearing our inner voice" by Helen Thomson. New Scientist, Oct. 29, 2014 (www.newscientist.com/article/mg22429934-000-brain-decoder-can-eavesdrop-on-your-inner-voice/)

Jack Gallant et al. were able to detect which of a set of images someone was looking at from a brain scan, using software that compared the subject's brain activity while looking at an image with that captured while they were looking at "training" photographs. The program then picked the most likely match from a set of previously unseen pictures.

Ann Graybiel and Mark Howe used electrodes to analyze brainwaves in the ventromedial striatum of rats while they were taught to navigate a maze. As rats were learning the task, their brain activity showed bursts of fast gamma waves. Once the rats mastered the task, their brainwaves slowed to almost a quarter of their initial frequency, becoming beta waves. Graybiel's team posited that this transition reflects when learning becomes a habit.

Bernard Balleine, Proceedings of the National Academy of Sciences, DOI: 10.1073/pnas.1113158108. See also "Habits form when brainwaves slow down" by Wendy Zukerman. New Scientist, Sep. 26, 2011 (www.newscientist.com/article/dn20964-habits-form-when-brainwaves-slow-down/) posits that the slower brainwaves may be the brain weeding out excess activity to refine behavior. He suggests it might be possible to boost the rate at which they learn a skill by enhancing such beta-wave activity.

U.S. Pat. No. 9,763,592 provides a system for instructing a user behavior change comprising: collecting and analyzing bioelectrical signal datasets; and providing a behavior change suggestion based upon the analysis. A stimulus may be provided to prompt an action by the user, which may be visual, auditory, or haptic. See also U.S. Pat. No. 9,622,660, 20170041699; 20130317384; 20130317382; 20130314243; 20070173733; and 20070066914.

The chess game is a good example of a cognitive task which needs a lot of training and experience. A number of EEG studies have been done on chess players. Pawel Stepien, Wlodzimierz Klonowski and Nikolay Suvorov, Nonlinear analysis of EEG in chess players, EPJ Nonlinear Biomedical Physics 20153:1, showed better applicability of Higuchi Fractal Dimension method for analysis of EEG signals related to chess tasks than that of Sliding Window Empirical Mode Decomposition. The paper shows that the EEG signal during the game is more complex, non-linear, and non-stationary even when there are no significant differences between the game and relaxed state in the contribution of different EEG bands to total power of the signal. There is the need of gathering more data from more chess experts and of comparing them with data from novice chess players. See also Junior, L. R. S., Cesar, F. H. G., Rocha, F. T., and Thomaz, C. E. EEG and Eye Movement Maps of Chess Players. Proceedings of the Sixth International Conference on Pattern Recognition Applications and Methods. (ICPRAM 2017) pp. 343-441. (fei.edu.br/-cet/icpraml7_LaercioJunior.pdf).

Estimating EEG-based functional connectivity provides a useful tool for studying the relationship between brain activity and emotional states. See You-Yun Lee, Shulan Hsieh. Classifying Different Emotional States by Means of EEG-Based Functional Connectivity Patterns. Apr. 17, 2014, (doi.org/10.1371/journal.pone.0095415), which aimed to classify different emotional states by means of EEG-based functional connectivity patterns, and showed that the EEG-based functional connectivity change was significantly different among emotional states. Furthermore, the connectivity pattern was detected by pattern classification analysis using Quadratic Discriminant Analysis. The results indicated that the classification rate was better than chance. Estimating EEG-based functional connectivity provides a useful tool for studying the relationship between brain activity and emotional states.

Neuromodulation/Neuroenhancement—Neuromodulation is the alteration of nerve activity through targeted delivery of a stimulus, such as electrical stimulation or chemical agents, to specific neurological sites in the body. It is carried out to normalize—or modulate—nervous tissue function. Neuromodulation is an evolving therapy that can involve a range of electromagnetic stimuli such as a magnetic field (TMS, rTMS), an electric current (TES, e.g., tDCS, HD-tDCS, tACS, electrosleep), or a drug instilled directly in the subdural space (intrathecal drug delivery). Emerging applications involve targeted introduction of genes or gene regulators and light (optogenetics). The most clinical experience has been with electrical stimulation. Neuromodulation, whether electrical or magnetic, employs the body's natural biological response by stimulating nerve cell activity that can influence populations of nerves by releasing transmitters, such as dopamine, or other chemical messengers such as the peptide Substance P, that can modulate the excitability and firing patterns of neural circuits. There may also be more direct electrophysiological effects on neural membranes. According to some applications, the end effect is a "normalization" of a neural network function from its perturbed state. Presumed mechanisms of action for neurostimulation include depolarizing blockade, stochastic normalization of neural firing, axonal blockade, reduction of neural firing keratosis, and suppression of neural network oscillations. Although the exact mechanisms of neurostimulation are not known, the empirical effectiveness has led to considerable application clinically.

Neuroenhancement refers to the targeted enhancement and extension of cognitive and affective abilities based on an understanding of their underlying neurobiology in healthy persons who do not have any mental illness. As such, it can be thought of as an umbrella term that encompasses pharmacological and non-pharmacological methods of improving cognitive, affective, and motor functionality, as well as the overarching ethico-legal discourse that accompanies these aims. Critically, for any agent to qualify as a neuroenhancer, it must reliably engender substantial cognitive, affective, or motor benefits beyond normal functioning in healthy individuals (or in select groups of individuals having pathology), whilst causing few side effects: at most at the level of commonly used comparable legal substances or activities, such as caffeine, alcohol, and sleep-deprivation. Pharmacological neuroenhancement agents include the well-validated nootropics, such as racetam, vinpocetine, and phosphatidylserine, as well as other drugs used for treating patients suffering from neurological disorders. Non-pharmacological measures include non-invasive brain stimulation, which has been employed to improve various cognitive and affective functions, and brain-machine interfaces, which hold much potential to extend the repertoire of motor and cognitive actions available to humans.

Brain Stimulation—Non-invasive brain stimulation (NIBS) bypasses the correlative approaches of other imaging techniques, making it possible to establish a causal relationship between cognitive processes and the functioning of specific brain areas. NIBS can provide information about where a particular process occurs. NIBS offers the opportunity to study brain mechanisms beyond process localization, providing information about when activity in a given brain region is involved in a cognitive process, and even how it is involved. When using NIBS to explore cognitive processes, it is important to understand not only how NIBS functions but also the functioning of the neural structures themselves. Non-invasive brain stimulation (NIBS) methods, which include transcranial magnetic stimulation (TMS) and transcranial electric stimulation (TES), are used in cognitive neuroscience to induce transient changes in brain activity and thereby alter the behavior of the subject.

The application of NIBS aims at establishing the role of a given cortical area in an ongoing specific motor, perceptual or cognitive process. Physically, NIBS techniques affect neuronal states through different mechanisms. In TMS, a solenoid (coil) is used to deliver a strong and transient magnetic field, or "pulse," to induce a transitory electric current at the cortical surface beneath the coil. The pulse causes the rapid and above-threshold depolarization of cell membranes affected by the current, followed by the transynaptic depolarization or hyperpolarization of interconnected neurons. Therefore, strong TMS can induce a current that elicits action potentials in neurons, while weak (subthreshold) can modify susceptibility of cells to depolarization. A complex set of coils can deliver a complex 3D excitation field. By contrast, in TES techniques, the stimulation involves the application of weak electrical currents directly to the scalp through a pair of electrodes. As a result, TES induces a subthreshold polarization of cortical neurons that is too weak to generate an action potential. (Superthreshold tES corresponds to electroconvulsive therapy, which is a currently disfavored, but apparently effective treatment for depression). However, by changing the intrinsic neuronal excitability, TES can induce changes in the resting membrane potential and the postsynaptic activity of cortical neurons. This, in turn, can alter the spontaneous firing rate of neurons and modulate their response to afferent signals, leading to changes in synaptic efficacy. The typical application of NIBS involves different types of protocols: TMS can be delivered as a single pulse (spTMS) at a precise time, as pairs of pulses separated by a variable interval, or as a series of stimuli in conventional or patterned protocols of repetitive TMS (rTMS). In TES, different protocols are established by the electrical current used and by its polarity, which can be direct (anodal or cathodal transcranial direct current stimulation: tDCS), alternating at a fix frequency (transcranial alternating current stimulation: tACS), oscillating transcranial direct current stimulation (osc-tDCS), high-definition transcranial direct current stimulation (HD-tDCS), or at random frequencies (transcranial random noise stimulation: tRNS).

In general, the final effects of NIBS on the central nervous system depend on a lengthy list of parameters (e.g., frequency, temporal characteristics, intensity, geometric configuration of the coil/electrode, current direction), when it is delivered before (off-line) or during (on-line) the task as part of the experimental procedure. In addition, these factors interact with several variables related to the anatomy (e.g., properties of the brain tissue and its location), as well as physiological (e.g., gender and age) and cognitive states of the stimulated area/subject. The entrainment hypothesis, suggests the possibility of inducing a particular oscillation frequency in the brain using an external oscillatory force (e.g., rTMS, but also tACS). The physiological basis of oscillatory cortical activity lies in the timing of the interacting neurons; when groups of neurons synchronize their firing activities, brain rhythms emerge, network oscillations are generated, and the basis for interactions between brain areas may develop. Because of the variety of experimental protocols for brain stimulation, limits on descriptions of the actual protocols employed, and limited controls, consistency of reported studies is lacking, and extrapolability is limited. Thus, while there is some consensus in various aspects of the effects of extra cranial brain stimulation, the results achieved have a degree of uncertainty dependent on details of implementation. On the other hand, within a specific experimental protocol, it is possible to obtain statistically significant and repeatable results. This implies that feedback control might be effective to control implementation of the stimulation for a given purpose; however, prior studies that employ feedback control are lacking.

Changes in the neuronal threshold result from changes in membrane permeability (Liebetanz et al., 2002), which influence the response of the task-related network. The same mechanism of action may be responsible for both TES methods and TMS, i.e., the induction of noise in the system. However, the neural activity induced by TES will be highly influenced by the state of the system because it is a neuro-modulatory method (Paulus, 2011), and its effect will depend on the activity of the stimulated area. Therefore, the final result will depend strongly on the task characteristics, the system state and the way in which TES will interact with such a state.

In TMS, the magnetic pulse causes a rapid increase in current flow, which can in some cases cause and above-threshold depolarization of cell membranes affected by the current, triggering an action potential, and leading to the trans-synaptic depolarization or hyperpolarization of connected cortical neurons, depending on their natural response to the firing of the stimulated neuron(s). Therefore, TMS activates a neural population that, depending on several factors, can be congruent (facilitate) or incongruent (inhibit) with task execution. TES induces a polarization of cortical neurons at a subthreshold level that is too weak to evoke an action potential. However, by inducing a polarity shift in the intrinsic neuronal excitability, TES can alter the spontaneous firing rate of neurons and modulate the response to afferent signals.

In this sense, TES-induced effects are even more bound to the state of the stimulated area that is determined by the conditions. In short, NIBS leads to a stimulation-induced modulation of the state that can be substantially defined as noise induction. Induced noise will not be just random activity, but will depend on the interaction of many parameters, from the characteristics of the stimulation to the state.

Although the types and number of neurons "triggered" by NIBS are theoretically random, the induced change in neuronal activity is likely to be correlated with ongoing activity, yet even if we are referring to a non-deterministic process, the noise introduced will not be a totally random element. Because it will be partially determined by the experimental variables, the level of noise that will be introduced by the stimulation and by the context can be estimated, as well as the interaction between the two levels of noise (stimulation and context). Known transcranial stimulation does not permit stimulation with a focused and highly targeted signal to a clearly defined area of the brain to establish a unique brain-behavior relationship; therefore, the known introduced stimulus activity in the brain stimulation is 'noise.' Cosmetic neuroscience has emerged as a new field of research. Roy Hamilton, Samuel Messing, and Anjan Chatterjee, "Rethinking the thinking cap—Ethics of neural enhancement using noninvasive brain stimulation." Neurology, Jan. 11, 2011, vol. 76 no. 2 187-193. (www.neurology.org/content/76/2/187.) discuss the use noninvasive brain stimulation techniques such as transcranial magnetic stimulation and transcranial direct current stimulation to enhance neurologic function: cognitive skills, mood, and social cognition.

Electrical brain stimulation (EBS), orfocal brain stimulation (FBS), is a form of clinical neurobiology electrotherapy used to stimulate a neuron or neural network in the brain through the direct or indirect excitation of cell membranes using an electric current. See, en.wikipedia.org/wiki/Electrical_brain_stimulation; U.S. Pat. Nos. 7,753,836; 7,94673; 8,545,378; 9,345,901; 9,610,456; 9,694,178; 20140330337; 20150112403; and 20150119689.

Motor skills can be affected by CNS stimulation.

See, U.S. Pub. App. Nos. U.S. Pat. Nos. 5,343,871; 5,742,748; 6,057,846; 6,390,979; 6,644,976; 6,656,137; 7,063,535; 7,558,622; 7,618,381; 7,733,224; 7,829,562; 7,863,272; 8,016,597; 8,065,240; 8,069,125; 8,108,036; 8,126,542; 8,150,796; 8,195,593; 8,356,004; 8,449,471; 8,461,988; 8,525,673; 8,525,687; 8,531,291; 8,591,419; 8,606,592; 8,615,479; 8,680,991; 8,682,449; 8,706,518; 8,747,336; 8,750,971; 8,764,651; 8,784,109; 8,858,440; 8,862,236; 8,938,289; 8,962,042; 9,005,649; 9,064,036; 9,107,586; 9,125,788; 9,138,579; 9,149,599; 9,173,582; 9,204,796; 9,211,077; 9,265,458; 9,351,640; 9,358,361; 9,380,976; 9,403,038; 9,418,368; 9,468,541; 9,495,684; 9,545,515; 9,549,691; 9,560,967; 9,577,992; 9,590,986; 20030068605; 20040072133; 20050020483; 20050032827; 20050059689; 20050153268; 20060014753; 20060052386; 20060106326; 20060191543; 20060229164; 20070031798; 20070138886; 20070276270; 20080001735; 20080004904; 20080243005; 20080287821; 20080294019; 20090005654; 20090018407; 20090024050; 20090118593; 20090119154; 20090132275; 20090156907; 20090156955; 20090157323; 20090157481; 20090157482; 20090157625; 20090157660; 20090157751; 20090157813; 20090163777; 20090164131; 20090164132; 20090164302; 20090164401; 20090164403; 20090164458; 20090164503; 20090164549; 20090171164; 20090172540; 20090221928; 20090267758; 20090271011; 20090271120; 20090271347; 20090312595; 20090312668; 20090318773; 20090318779; 20090319002; 20100004762; 20100015583; 20100017001; 20100022820; 20100041958; 20100042578; 20100063368; 20100069724; 20100076249; 20100081860; 20100081861; 20100100036; 20100125561; 20100130811; 20100145219; 20100163027; 20100163035; 20100168525; 20100168602; 20100280332; 20110015209; 20110015469; 20110082154; 20110105859; 20110115624; 20110152284; 20110178441; 20110181422; 20110288119; 20120092156; 20120092157; 20120130300; 20120143104; 20120164613; 20120177716; 20120316793; 20120330109; 20130009783; 20130018592; 20130034837; 20130053656; 20130054215; 20130085678; 20130121984; 20130132029; 20130137717; 20130144537; 20130184728; 20130184997; 20130211291; 20130231574; 20130281890; 20130289385; 20130330428; 20140039571; 20140058528; 20140077946; 20140094720; 20140104059; 20140148479; 20140155430; 20140163425; 20140207224; 20140235965; 20140249429; 20150025410; 20150025422; 20150068069; 20150071907; 20150141773; 20150208982; 20150265583; 20150290419; 20150294067; 20150294085; 20150294086; 20150359467; 20150379878; 20160001096; 20160007904; 20160007915; 20160030749; 20160030750; 20160067492; 20160074657; 20160120437; 20160140834; 20160198968; 20160206671; 20160220821; 20160303402; 20160351069; 20160360965; 20170046971; 20170065638; 20170080320; 20170084187; 20170086672; 20170112947; 20170127727; 20170131293; 20170143966; 20170151436; 20170157343; and 20170193831.

See:

Abraham, W. C., 2008. Metaplasticity: tuning synapses and networks for plasticity. Nature Reviews Neuroscience 9, 387.

Abrahamyan, A., Clifford, C. W., Arabzadeh, E., Harris, J. A., 2011. Improving visual sensitivity with subthreshold transcranial magnetic stimulation. J. Neuroscience 31, 3290-3294.

Adrian, E. D., 1928. The Basis of Sensation. W. W. Norton, New York.

Amassian, V. E., Cracco, R. Q., Maccabee, P. J., Cracco, J. B., Rudell, A., Eberle, L., 1989. Suppression of visual perception by magnetic coil stimulation of human occipital cortex. Electroencephalography and Clin. Neurophysiology 74, 458-462.

Amassian, V. E., Eberle, L., Maccabee, P. J., Cracco, R. Q., 1992. Modelling magnetic coil excitation of human cerebral cortex with a peripheral nerve immersed in a brain-shaped volume conductor: the significance of fiber bending in excitation. Electroencephalography and Clin. Neurophysiology 85, 291-301.

Antal, A., Boros, K., Poreisz, C., Chaieb, L., Terney, D., Paulus, W., 2008. Comparatively weak after-effects of transcranial alternating current stimulation (tACS) on cortical excitability in humans. Brain Stimulation 1, 97-105.

Antal, A., Nitsche, M. A., Kruse, W., Kincses, T. Z., Hoffmann, K. P., Paulus, W., 2004. Direct current stimulation over V5 enhances visuomotor coordination by improving motion perception in humans. J. Cognitive Neuroscience 16, 521-527.

Ashbridge, E., Walsh, V., Cowey, A., 1997. Temporal aspects of visual search studied by transcranial magnetic stimulation. Neuropsychologia 35, 1121-1131.

Barker, A. T., Freeston, I. L., Jalinous, R., Jarratt, J. A., 1987. Magnetic stimulation of the human brain and peripheral nervous system: an introduction and the results of an initial clinical evaluation. Neurosurgery 20, 100-109.

Barker, A. T., Jalinous, R., Freeston, I. L., 1985. Non-invasive magnetic stimulation of human motor cortex. Lancet 1, 1106-1107.

Bi, G., Poo, M., 2001. Synaptic modification by correlated activity: Hebb's postulate revisited. Annual Review of Neuroscience 24, 139-166.

Bialek, W., Rieke, F., 1992. Reliability and information transmission in spiking neurons. Trends in Neurosciences 15, 428-434.

Bienenstock, E. L., Cooper, L. N., Munro, P. W., 1982. Theory for the development of neuron selectivity: orientation specificity and binocular interaction in visual cortex. J. Neuroscience 2, 32-48.

Bindman, L. J., Lippold, O. C., Milne, A. R., 1979. Prolonged changes in excitability of pyramidal tract neurons in the cat: a post-synaptic mechanism. J. Physiology 286, 457-477.

Bindman, L. J., Lippold, O. C., Redfeam, J. W., 1962. Long-lasting changes in the level of the electrical activity of the cerebral cortex produced by polarizing currents. Nature 196, 584-585.

Bindman, L. J., Lippold, O. C., Redfeam, J. W., 1964. The action of brief polarizing currents on the cerebral cortex of the rat (1) during current flow and (2) in the production of long-lasting after-effects. J. Physiology 172, 369-382.

Brignani, D., Ruzzoli, M., Mauri, P., Miniussi, C., 2013. Is transcranial alternating current stimulation effective in modulating brain oscillations? PLoS ONE 8, e56589.

Buzsaki, G., 2006. Rhythms of the Brain. Oxford University Press, Oxford.

Canolty, R. T., Knight, R. T., 2010. The functional role of cross-frequency coupling. Trends in Cognitive Sciences 14, 506-515.

Carandini, M., Ferster, D., 1997. A tonic hyperpolarization underlying contrast adaptation in catvisual cortex. Science 276, 949-952.

Cattaneo, L., Sandrini, M., Schwarzbach, J., 2010. State-dependent TMS reveals a hierarchical representation of observed acts in the temporal, parietal, and premotor cortices. Cerebral Cortex 20, 2252-2258.

Cattaneo, Z., Rota, F., Vecchi, T., Silvanto, J., 2008. Using state-dependency of trans-cranial magnetic stimulation (TMS) to investigate letter selectivity in the left posterior parietal cortex: a comparison of TMS-priming and TMS-adaptation paradigms. Eur. J. Neuroscience 28, 1924-1929.

Chambers, C. D., Payne, J. M., Stokes, M. G., Mattingley, J. B., 2004. Fast and slow parietal pathways mediate spatial attention. Nature Neuroscience 7, 217-218.

Corthout, E., Uttl, B., Walsh, V., Hallett, M., Cowey, A., 1999. Timing of activity in early visual cortex as revealed by transcranial magnetic stimulation. Neuroreport 10, 2631-2634.

Creutzfeldt, O. D., Fromm, G. H., Kapp, H., 1962. Influence of transcortical d-c currents on cortical neuronal activity. Experimental Neurology 5, 436-452.

Deans, J. K., Powell, A. D., Jefferys, J. G., 2007. Sensitivity of coherent oscillations in rat hippocampus to AC electric fields. J. Physiology 583, 555-565.

Dockery, C. A., Hueckel-Weng, R., Birbaumer, N., Plewnia, C., 2009. Enhancement of planning ability by transcranial direct current stimulation. J. Neuroscience 29, 7271-7277.

Ermentrout, G. B., Galan, R. F., Urban, N. N., 2008. Reliability, synchrony and noise. Trends in Neurosciences 31, 428-434.

Epstein, C. M., Rothwell, J. C., 2003. Therapeutic uses of rTMS. Cambridge University Press, Cambridge, pp. 246-263.

Faisal, A. A., Selen, L. P., Wolpert, D. M., 2008. Noise in the nervous system. Nature Reviews Neuroscience 9, 292-303.

Ferbert, A., Caramia, D., Priori, A., Bertolasi, L., Rothwell, J. C., 1992. Cortical projection to erector spinae muscles in man as assessed by focal transcranial magnetic stimulation. Electroencephalography and Clin. Neurophysiology 85, 382-387.

Fertonani, A., Pirulli, C., Miniussi, C., 2011. Random noise stimulation improves neuroplasticity in perceptual learning. J. Neuroscience 31, 15416-15423. Feurra, M., Galli, G., Rossi, S., 2012. Transcranial alternating current stimulation affects decision making. Frontiers in Systems Neuroscience 6, 39.

Guyonneau, R., Vanrullen, R., Thorpe, S. J., 2004. Temporal codes and sparse representations: a key to understanding rapid processing in the visual system. J. Physiology, Paris 98, 487-497.

Hallett, M., 2000. Transcranial magnetic stimulation and the human brain. Nature 406, 147-150.

Harris, I. M., Miniussi, C., 2003. Parietal lobe contribution to mental rotation demonstrated with rTMS. J. Cognitive Neuroscience 15, 315-323.

Harris, J. A., Clifford, C. W., Miniussi, C., 2008. The functional effect of transcranial magnetic stimulation: signal suppression or neural noise generation. J. Cognitive Neuroscience 20, 734-740.

Hebb, D. O., 1949. The Organization of Behavior; A Neuropsychological Theory. Wiley, New York.

Hutcheon, B., Yarom, Y., 2000. Resonance, oscillation and the intrinsic frequency preferences of neurons. Trends in Neurosciences 23, 216-222.

Jacobson, L., Koslowsky, M., Lavidor, M., 2011. tDCS polarity effects in motor and cognitive domains: a meta-analytical review. Experimental Brain Research 216, 1-10.

Joundi, R. A., Jenkinson, N., Brittain, J. S., Aziz, T. Z., Brown, P., 2012. Driving oscillatory activity in the human cortex enhances motor performance. Current Biology 22, 403-407.

Kahn, I., Pascual-Leone, A., Theoret, H., Fregni, F., Clark, D., Wagner, A. D., 2005. Transient disruption of ventro-lateral prefrontal cortex during verbal encoding affects subsequent memory performance. J. Neurophysiology 94, 688-698.

Kanai, R., Chaieb, L., Antal, A., Walsh, V., Paulus, W., 2008. Frequency-dependent electrical stimulation of the visual cortex. Current Biology 18, 1839-1843.

Kitajo, K., Doesburg, S. M., Yamanaka, K., Nozaki, D., Ward, L. M., Yamamoto, Y., 2007. Noise-induced large-scale phase synchronization of human-brain activity associated with behavioral stochastic resonance. EPL—Europhysics Letters, 80.

Kitajo, K., Nozaki, D., Ward, L. M., Yamamoto, Y., 2003. Behavioral stochastic resonance within the human brain. Physical Review Letters 90, 218103.

Landi, D., Rossini, P. M., 2010. Cerebral restorative plasticity from normal aging to brain diseases: a never-ending story. Restorative Neurology and Neuroscience 28, 349-366.

Lang, N., Rothkegel, H., Reiber, H., Hasan, A., Sueske, E., Tergau, F., Ehrenreich, H., Wuttke, W., Paulus, W., 2011. Circadian modulation of GABA-mediated cortical inhibition. Cerebral Cortex 21, 2299-2306.

Laycock, R., Crewther, D. P., Fitzgerald, P. B., Crewther, S. G., 2007. Evidence for fast signals and later processing in human V1/V2 and V5/MT+. A TMS study of motion perception. J. Neurophysiology 98, 1253-1262.

Liebetanz, D., Nitsche, M. A., Tergau, F., Paulus, W., 2002. Pharmacological approach to the mechanisms of transcranial DC-stimulation-induced after-effects of human motor cortex excitability. Brain 125, 2238-2247.

Longtin, A., 1997. Autonomous stochastic resonance in bursting neurons. Physical Review E 55, 868-876.

Manenti, R., Cappa, S. F., Rossini, P. M., Miniussi, C., 2008. The role of the prefrontal cortex in sentence comprehension: an rTMS study. Cortex 44, 337-344.

Marzi, C. A., Miniussi, C., Maravita, A., Bertolasi, L., Zanette, G., Rothwell, J. C., Sanes, J. N., 1998. Transcranial magnetic stimulation selectively impairs interhemispheric transfer of visuo-motor information in humans. Experimental Brain Research 118, 435-438.

Masquelier, T., Thorpe, S. J., 2007. Unsupervised learning of visual features through spike timing dependent plasticity. PLOS Computational Biology 3, e31.

Miniussi, C., Brignani, D., Pellicciari, M. C., 2012a. Combining transcranial electrical stimulation with electroencephalography: a multimodal approach. Clin. EEG and Neuroscience 43, 184-191.

Miniussi, C., Paulus, W., Rossini, P. M., 2012b. Transcranial Brain Stimulation. CRC Press, Boca Raton, FL.

Miniussi, C., Ruzzoli, M., Walsh, V., 2010. The mechanism of transcranial magnetic stimulation in cognition. Cortex 46, 128-130.

Moliadze, V., Zhao, Y., Eysel, U., Funke, K., 2003. Effect of transcranial magnetic stimulation on single-unit activity in the cat primary visual cortex. J. Physiology 553, 665-679.

Moss, F., Ward, L. M., Sannita, W. G., 2004. Stochastic resonance and sensory information processing: a tutorial and review of application. Clin. Neurophysiology 115, 267-281.

Mottaghy, F. M., Gangitano, M., Krause, BJ., Pascual-Leone, A., 2003. Chronometry of parietal and prefrontal activations in verbal working memory revealed by transcranial magnetic stimulation. Neuroimage 18, 565-575.

Nachmias, J., Sansbury, R. V., 1974. Grating contrast: discrimination may be better than detection. Vision Research 14, 1039-1042.

Nitsche, M. A., Cohen, L. G., Wassermann, E. M., Priori, A., Lang, N., Antal, A., Paulus, W., Hummel, F., Boggio, P. S., Fregni, F., Pascual-Leone, A., 2008. Transcranial direct current stimulation: state of the art 2008. Brain Stimulation 1, 206-223.

Nitsche, M. A., Liebetanz, D., Lang, N., Antal, A., Tergau, F., Paulus, W., 2003a. Safety criteria for transcranial direct current stimulation (tDCS) in humans. Clin. Neurophysiology 114, 2220-2222, author reply 2222-2223.

Nitsche, M. A., Niehaus, L., Hoffmann, K. T., Hengst, S., Liebetanz, D., Paulus, W., Meyer, B. U., 2004. MRI study of human brain exposed to weak direct current stimulation of the frontal cortex. Clin. Neurophysiology 115, 2419-2423.

Nitsche, M. A., Nitsche, M. S., Klein, C. C., Tergau, F., Rothwell, J. C., Paulus, W., 2003b. Level of action of cathodal DC polarisation induced inhibition of the human motor cortex. Clin. Neurophysiology 114, 600-604.

Nitsche, M. A., Paulus, W., 2000. Excitability changes induced in the human motor cortex by weak transcranial direct current stimulation. J. Physiology 527 (Pt 3), 633-639.

Nitsche, M. A., Paulus, W., 2011. Transcranial direct current stimulation—update 2011. Restorative Neurology and Neuroscience 29, 463-492.

Nitsche, M. A., Seeber, A., Frommann, K., Klein, C. C., Rochford, C., Nitsche, M. S., Fricke, K., Liebetanz, D., Lang, N., Antal, A., Paulus, W., Tergau, F., 2005. Modulating parameters of excitability during and after transcranial direct current stimulation of the human motor cortex. J. Physiology 568, 291-303.

Pascual-Leone, A., Walsh, V., Rothwell, J., 2000. Transcranial magnetic stimulation in cognitive neuroscience-virtual lesion, chronometry, and functional connectivity. Current Opinion in Neurobiology 10, 232-237.

Pasley, B. N., Allen, E. A., Freeman, R. D., 2009. State-dependent variability of neuronal responses to transcranial magnetic stimulation of the visual cortex. Neuron 62, 291-303.

Paulus, W., 2011. Transcranial electrical stimulation (TES-tDCS; tRNS, tACS) methods. Neuropsychological Rehabilitation 21, 602-617.

Plewnia, C., Rilk, A. J., Soekadar, S. R., Arfeller, C., Huber, H. S., Sauseng, P., Hummel, F., Gerloff, C., 2008. Enhancement of long-range EEG coherence by synchronous bifocal transcranial magnetic stimulation. European J. Neuroscience 27, 1577-1583.

Pogosyan, A., Gaynor, L. D., Eusebio, A., Brown, P., 2009. Boosting cortical activity at Beta-band frequencies slows movement in humans. Current Biology 19, 1637-1641.

Priori, A., Berardelli, A., Rona, S., Accornero, N., Manfredi, M., 1998. Polarization of the human motor cortex through the scalp. Neuroreport 9, 2257-2260.

Radman, T., Datta, A., Peterchev, A. V., 2007. In vitro modulation of endogenous rhythms by AC electric fields: syncing with clinical brain stimulation. J. Physiology 584, 369-370.

Rahnev, D. A., Maniscalco, B., Luber, B., Lau, H., Lisanby, S. H., 2012. Direct injection of noise to the visual cortex decreases accuracy but increases decision confidence. J. Neurophysiology 107, 1556-1563.

Reato, D., Rahman, A., Bikson, M., Parra, L. C., 2010. Low-intensity electrical stimulation affects network dynamics by modulating population rate and spike timing. J. Neuroscience 30, 15067-15079.

Ridding, M. C., Ziemann, U., 2010. Determinants of the induction of cortical plasticity by non-invasive brain stimulation in healthy subjects. J. Physiology 588, 2291-2304.

Rosanova, M., Casali, A., Bellina, V., Resta, F., Mariotti, M., Massimini, M., 2009. Natural frequencies of human corticothalamic circuits. J. Neuroscience 29, 7679-7685.

Rossi, S., Hallett, M., Rossini, P. M., Pascual-Leone, A., Safety of TMS Consensus Group, 2009. Safety, ethical considerations, and application guidelines for the use of transcranial magnetic stimulation in clinical practice and research. Clin. Neurophysiology 120, 2008-2039.

Roth, B. J., 1994. Mechanisms for electrical stimulation of excitable tissue. Critical Rev. in Biomedical Engineering 22, 253-305.

Rothwell, J. C., Day, B. L., Thompson, P. D., Dick, J. P., Marsden, C. D., 1987. Some experiences of techniques for stimulation of the human cerebral motor cortex through the scalp. Neurosurgery 20, 156-163.

Ruohonen, J., 2003. Background physics for magnetic stimulation. Supplements to Clin. Neurophysiology 56, 3-12.

Ruzzoli, M., Abrahamyan, A., Clifford, C. W., Marzi, C. A., Miniussi, C., Harris, J. A., 2011. The effect of TMS on visual motion sensitivity: an increase in neural noise or a decrease in signal strength. J. Neurophysiology 106, 138-143.

Ruzzoli, M., Marzi, C. A., Miniussi, C., 2010. The neural mechanisms of the effects of transcranial magnetic stimulation on perception. J. Neurophysiology 103, 2982-2989.

Sack, A. T., Linden, D. E., 2003. Combining transcranial magnetic stimulation and functional imaging in cognitive brain research: possibilities and limitations. Brain Research: Brain Research Reviews 43, 41-56.

Sandrini, M., Umilta, C., Rusconi, E., 2011. The use of transcranial magnetic stimulation in cognitive neuroscience: a new synthesis of methodological issues. Neuroscience and Biobehavioral Reviews 35, 516-536.

Schutter, D. J., Hortensius, R., 2010. Retinal origin of phosphenes to transcranial alternating current stimulation. Clin. Neurophysiology 121, 1080-1084.

Schwarzkopf, D. S., Silvanto, J., Rees, G., 2011. Stochastic resonance effects reveal the neural mechanisms of transcranial magnetic stimulation. J. Neuro-science 31, 3143-3147.

Schwiedrzik, C. M., 2009. Retina or visual cortex? The site of phosphane induction by transcranial alternating current stimulation. Frontiers in Integrative Neuro-science 3, 6.

Sclar, G., Lennie, P., DePriest, D. D., 1989. Contrast adaptation in striate cortex of macaque. Vision Research 29, 747-755.

Seyal, M., Masuoka, L. K., Browne, J. K., 1992. Suppression of cutaneous perception by magnetic pulse stimulation of the human brain. Electroencephalography and Clin. Neurophysiology 85, 397-401.

Siebner, H. R., Lang, N., Rizzo, V., Nitsche, M. A., Paulus, W., Lemon, R. N., Rothwell, J. C., 2004. Preconditioning of low-frequency repetitive transcranial magnetic stimulation with transcranial direct current stimulation: evidence for homeostatic plasticity in the human motor cortex. The J. Neuroscience 24, 3379-3385.

Silvanto, J., Muggleton, N., Walsh, V., 2008. State-dependency in brain stimulation studies of perception and cognition. Trends in Cognitive Sciences 12, 447-454.

Silvanto, J., Muggleton, N. G., Cowey, A., Walsh, V., 2007. Neural adaptation reveals state-dependent effects of transcranial magnetic stimulation. Eur. J. Neuroscience 25, 1874-1881.

Solomon, J. A., 2009. The history of dipper functions. Attention, Perception, and Psychophysics 71, 435-443.

Stein, R. B., Gossen, E. R., Jones, K. E., 2005. Neuronal variability: noise or part of the signal? Nature Rev. Neuroscience 6, 389-397.

Terney, D., Chaieb, L., Moliadze, V., Antal, A., Paulus, W., 2008. Increasing human brain excitability by transcranial high-frequency random noise stimulation. J. Neuroscience 28, 14147-14155.

Thut, G., Miniussi, C., 2009. New insights into rhythmic brain activity from TMS-EEG studies. Trends in Cognitive Sciences 13, 182-189.

Thut, G., Miniussi, C., Gross, J., 2012. The functional importance of rhythmic activity in the brain. Current Biology 22, R658-R663.

Thut, G., Schyns, P. G., Gross, J., 2011a. Entrainment of perceptually relevant brain oscillations by non-invasive rhythmic stimulation of the human brain. Front. Psychology 2, 170.

Thut, G., Veniero, D., Romei, V., Miniussi, C., Schyns, P., Gross, J., 2011b. Rhythmic TMS causes local entrainment of natural oscillatory signatures. Current Biology 21, 1176-1185.

Vallar, G., Bolognini, N., 2011. Behavioural facilitation following brain stimulation: implications for neurorehabilitation. Neuropsychological Rehabilitation 21, 618-649.

Varela, F., Lachaux, J. P., Rodriguez, E., Martinerie, J., 2001. The brainweb: phase synchronization and large-scale integration. Nature Reviews Neuroscience 2, 229-239.

Veniero, D., Brignani, D., Thut, G., Miniussi, C., 2011. Alpha-generation as basic response-signature to transcranial magnetic stimulation (TMS) targeting the human resting motor cortex: a TMS/EEG co-registration study. Psychophysiology 48, 1381-1389.

Walsh, V., Cowey, A., 2000. Transcranial magnetic stimulation and cognitive neuroscience. Nature Rev. Neuroscience 1, 73-79.

Walsh, V., Ellison, A., Battelli, L., Cowey, A., 1998. Task-specific impairments and enhancements induced by magnetic stimulation of human visual area V5. Proceedings: Biological Sciences 265, 537-543.

Walsh, V., Pascual-Leone, A., 2003. Transcranial Magnetic Stimulation: A Neurochronometrics of Mind. MIT Press, Cambridge, MA.

Walsh, V., Rushworth, M., 1999. A primer of magnetic stimulation as a tool for neuropsychology. Neuropsychologia 37, 125-135.

Ward, LM., Doesburg, S. M., Kitajo, K., MacLean, S. E., Roggeveen, A. B., 2006. Neural synchrony in stochastic resonance, attention, and consciousness. Canadian J. Experimental Psychology 60, 319-326.

Wassermann, E. M., Epstein, C., Ziemann, U., Walsh, V., Paus, T., Lisanby, S., 2008. Handbook of Transcranial Stimulation. Oxford University Press, Oxford, UK.

Waterston, M. L., Pack, C. C., 2010. Improved discrimination of visual stimuli following repetitive transcranial magnetic stimulation. PLoS ONE 5, e10354.

Wu, S., Amari, S., Nakahara, H., 2002. Population coding and decoding in a neural field: a computational study. Neural Computation 14, 999-1026.

Zaehle, T., Rach, S., Herrmann, C. S., 2010. Transcranial alternating current stimulation enhances individual alpha activity in human EEG. PLoS ONE 5, e13766.

Transcranial Electrical Stimulation (TES)—TES (tDCS, HD-tDCS, osc-tDCS, tACS, and tRNS) is a set of noninvasive method of cortical stimulation, using weak direct currents to polarize target brain regions. The most used and best-known method is tDCS, as all considerations for the use of tDCS have been extended to the other TES methods. The hypotheses concerning the application of tDCS in cognition are very similar to those of TMS, with the exception that tDCS was never considered a virtual lesion method. tDCS can increase or decrease cortical excitability in the stimulated brain regions and facilitate or inhibit behavior accordingly. TES does not induce action potentials but instead modulates the neuronal response threshold so that it can be defined as subthreshold stimulation.

Michael A. Nitsche, and Armin Kibele. "Noninvasive brain stimulation and neural entrainment enhance athletic performance—a review." J. Cognitive Enhancement 1.1 (2017): 73-79, discusses that non-invasive brain stimulation (NIBS) bypasses the correlative approaches of other imaging techniques, making it possible to establish a causal relationship between cognitive processes and the functioning of specific brain areas. NIBS can provide information about where a particular process occurs. NIBS offers the opportunity to study brain mechanisms beyond process localization, providing information about when activity in a given brain region is involved in a cognitive process, and even how it is involved. When using NIBS to explore cognitive processes, it is important to understand not only how NIBS functions but also the functioning of the neural structures themselves. Non-invasive brain stimulation (NIBS) methods, which include transcranial magnetic stimulation (TMS) and transcranial electric stimulation (TES), are used in cognitive neuroscience to induce transient changes in brain activity and thereby alter the behavior of the subject. The application of NIBS aims at establishing the role of a given cortical area in an ongoing specific motor, perceptual or cognitive process (Hallett, 2000; Walsh and Cowey, 2000). Physically, NIBS techniques affect neuronal states through different mechanisms. In TMS, a solenoid (coil) is used to deliver a strong and transient magnetic field, or "pulse," to induce a transitory electric current at the cortical surface beneath the coil. (US 2004078056) The pulse causes the rapid and above-threshold depolarization of cell membranes affected by the current (Barker et al., 1985, 1987), followed by the transynaptic depolarization or hyperpolarization of interconnected neurons. Therefore, TMS induces a current that elicits action potentials in neurons. A complex set of coils can deliver a complex 3D excitation field. By contrast, in TES techniques, the stimulation involves the application of weak electrical currents directly to the scalp through a pair of electrodes (Nitsche and Paulus, 2000; Priori et al., 1998). As a result, TES induces a subthreshold polarization of cortical neurons that is too weak to generate an action potential. However, by changing the intrinsic neuronal excitability, TES can induce changes in the resting membrane potential and the postsynaptic activity of cortical neurons. This, in turn, can alter the spontaneous firing rate of neurons and modulate their response to afferent signals (Bindman et al., 1962, 1964, 1979; Creutzfeldt et al., 1962), leading to changes in synaptic efficacy. The typical application of NIBS involves different types of protocols: TMS can be delivered as a single pulse (spTMS) at a precise time, as pairs of pulses separated by a variable interval, or as a series of stimuli in conventional or patterned protocols of repetitive TMS (rTMS) (for a complete classification see Rossi et al., 2009). In TES, different protocols are established by the electrical current used and by its polarity, which can be direct (anodal or cathodal transcranial direct current stimulation: tDCS), high-definition transcranial direct current stimulation (HD-tDCS), oscillating transcranial direct current stimulation (osc-tDCS), alternating at a fix frequency (transcranial alternating current stimulation: tACS) or at random frequencies (transcranial random noise stimulation: tRNS) (Nitsche et al., 2008; Paulus, 2011). In general, the final effects of NIBS on the central nervous system depend on a lengthy list of parameters (e.g., frequency, temporal characteristics, intensity, geometric configuration of the coil/electrode, current direction), when it is delivered before (off-line) or during (on-line) the task as part of the experimental procedure (e.g., Jacobson et al., 2011; Nitsche and Paulus, 2011; Sandrini et al., 2011). In addition, these factors interact with several variables related to the anatomy (e.g., properties of the brain tissue and its location, Radman et al., 2007), as well as physiological (e.g., gender and age, Landi and Rossini, 2010; Lang et al., 2011; Ridding and Ziemann, 2010) and cognitive (e.g., Miniussi et al., 2010; Silvanto et al., 2008; Walsh et al., 1998) states of the stimulated area/subject.

Transcranial Direct Current Stimulation (tDCS)—Cranial electrotherapy stimulation (CES) is a form of non-invasive brain stimulation that applies a small, pulsed electric current across a person's head to treat a variety of conditions such as anxiety, depression and insomnia. See, en.wikipedia.org/wiki/Cranial_electrotherapy_stimulation. Transcranial direct current stimulation (tDCS) is a form of neurostimulation that uses constant, low current delivered to the brain area of interest via electrodes on the scalp. It was originally developed to help patients with brain injuries or psychiatric conditions like major depressive disorder. tDCS appears to have some potential for treating depression. See, en.wikipedia.org/wiki/Transcranial_direct-current_stimulation.

tDCS is being studied for acceleration of learning. The mild electrical shock (usually, a 2-milliamp current) is used to depolarize the neuronal membranes, making the cells more excitable and responsive to inputs. Weisend, Experimental Brain Research, vol 213, p 9 (DARPA) showed that tDCS accelerates the formation of new neural pathways during the time that someone practices a skill. tDCS appears to bring about the flow state. The movements of the subjects become more automatic; they report calm, focused concentration, and their performance improves immediately. (See Adee, Sally, "Zap your brain into the zone: Fast track to pure focus", New Scientist, No. 2850, Feb. 1, 2012, www.newscientist.com/article/mg21328501-600-zap-your-brain-into-the-zone-fast-track-to-pure-focus).

U.S. Pat. Nos. 7,856,264; 8,706,241; 8,725,669; 9,037,224; 9,042,201; 9,095,266; 9,248,286; 9,349,178; 9,629,568; 9,693,725; 9,713,433; 20040195512; 20070179534; 20110092882; 20110311021; 20120165696; 20140142654; 20140200432; 20140211593; 20140316243; 20140347265; 20150099946; 20150174418; 20150257700; 20150327813; 20150343242; 20150351655; 20160000354; 20160038049;

20160113569; 20160144175; 20160148371; 20160148372; 20160180042; 20160213276; 20160228702; and 20160235323.

Reinhart, Robert M G. "Disruption and rescue of intera-real theta phase coupling and adaptive behavior." Proceedings of the National Academy of Sciences (2017): provide evidence for a causal relation between interareal theta phase synchronization in frontal cortex and multiple components of adaptive human behavior. Reinhart's results support the idea that the precise timing of rhythmic population activity spatially distributed in frontal cortex conveys information to direct behavior. Given prior work showing that phase synchronization can change spike time-dependent plasticity, together with Reihart's findings showing stimulation effects on neural activity and behavior can outlast a 20-min period of electrical stimulation, it is reasonable to suppose that the externally modulated interareal coupling changed behavior by causing neuroplastic modifications in functional connectivity. Reinhart suggests that we may be able to noninvasively intervene in the temporal coupling of distant rhythmic activity in the human brain to optimize (or impede) the postsynaptic effect of spikes from one area on the other, improving (or impairing) the cross-area communication necessary for cognitive action control and learning. Moreover, these neuroplastic alterations in functional connectivity were induced with a 0° phase, suggesting that inducing synchronization does not require a meticulous accounting of the communication delay between regions such as MFC and IPFC to effectively modify behavior and learning. This conforms to work showing that despite long axonal conduction delays between distant brain areas, theta phase synchronizations at 0° phase lag can occur between these regions and underlie meaningful functions of cognition and action. It is also possible that a third subcortical or posterior region with a nonzero time lag interacted with these two frontal areas to drive changes in goal-directed behavior.

Alexander W H & Brown J W (2011) Medial prefrontal cortex as an action-outcome predictor. Nature Neuroscience 14(10):1338-1344.
Alexander W H & Brown J W (2015) Hierarchical error representation: A computational model of anterior cingulate and dorsolateral prefrontal cortex. Neural Computation 27:2354-2410.
Anguera J A, et al. (2013) Video game training enhances cognitive control in older adults. Nature 501:97-101.
Aron A R, Fletcher P C, Bullmore E T, Sahakian B J, Robbins T W (2003) Stop-signal inhibition disrupted by damage to right inferiorfrontal gyrus in humans. Nat Neurosci 6:115-116.
Au J, et al. (2015) Improving fluid intelligence with training on working memory: a meta-analysis. Psychonomic Bulletin & Review 22:366-377.
Bellman R, Kalaba R (1959) A mathematical theory of adaptive control processes. Proc Natl Acad Sci USA 45:1288-1290.
Bibbig A, Traub R D, Whittington M A (2002) Long-range synchronization of gamma and beta oscillations and the plasticity of excitatory and inhibitory synapses: A network model. J Neurophysiol 88:1634-1654.
Botvinick M M (2012) Hierarchical reinforcement learning and decision making. Current Opinion in Neurobiology 22(6):956-962.
Botvinick M M, Braver T S, Barch D M, Carter C S, & Cohen J D (2001) Conflict monitoring and cognitive control. Psychological Review 108(3):624-652.
Bryck R L & Fisher P A (2012) Training the brain: practical applications of neural plasticity from the intersection of cognitive neuroscience, developmental psychology, and prevention science. American Psychologist 67:87-100.
Cavanagh J F, Cohen M X, & Allen J J (2009) Prelude to and resolution of an error: EEG phase synchrony reveals cognitive control dynamics during action monitoring. Journal of Neuroscience 29(1):98-105.
Cavanagh J F, Frank M J (2014) Frontal theta as a mechanism for cognitive control. Trends Cogn Sci 18:414-421.
Christie G J, Tata M S (2009) Right frontal cortex generates reward-related theta-band oscillatory activity. Neuroimage 48:415-422.
Cohen M X, Wilmes K, Vijver Iv (2011) Cortical electrophysiological network dynamics of feedback learning. Trends Cogn Sci 15:558-566.
Corbett A, et al. (2015) The effect of an online cognitive training package in healthy older adults: An online randomized controlled trial. J Am Med Dir Assoc 16:990-997.
Dale A M & Sereno M I (1993) Improved localization of cortical activity by combining EEG and MEG with MRI cortical surface reconstruction: A linear approach. Journal of Cognitive Neuroscience 5:162-176.
Dalley J W, Robbins T W (2017) Fractionating impulsivity: Neuropsychiatric implications. Nat Rev Neurosci 18:158-171.
Delorme A & Makeig S (2004) EEGLAB: An open source toolbox for analysis of single-trial EEG dynamics including independent component analysis. Journal of Neuroscience Methods 134(1):9-21.
Diamond A & Lee K (2011) Interventions and programs demonstrated to aid executive function development in children 4-12 years of age. Science 333:959964.
Engel A K, Fries P, Singer W (2001) Dynamic predictions: Oscillations and synchrony in top-down processing. Nat Rev Neurosci 2:704-716.
Fairclough S H & Houston K (2004) A metabolic measure of mental effort. Biological Psychology 66:177-190.
Fell J, Axmacher N (2011) The role of phase synchronization in memory processes. Nat Rev Neurosci 12:105-118.
Fitzgerald K D, et al. (2005) Error-related hyperactivity of the anterior cingulate cortex in obsessive-compulsive disorder. Biol Psychiatry 57:287-294.
Foti D, Weinberg A, Dien J, Hajcak G (2011) Event-related potential activity in the basal ganglia differentiates rewards from nonrewards: Temporospatial principal components analysis and source localization of the feedback negativity. Hum Brain Mapp 32:2207-2216.
Fuchs M, Drenckhahn R, Wischmann H A, & Wagner M (1998) An improved boundary element method for realistic volume-conductor modeling. IEEE Trans Biomed Eng 45(8):980-997.
Gailliot M T & Baumeister R F (2007) The physiology of willpower: linking blood glucose to self-control. Personality and Social Psychology Review 11(4):303-327.
Gandiga P, Hummel F, & Cohen L (2006) Transcranial DC stimulation (tDCS): A tool for double-blind sham-controlled clinical studies in brain stimulation. Clinical Neurophysiology 117(4):845-850.
Gregoriou G G, Gotts S J, Zhou H, Desimone R (2009) High-frequency, long-range coupling between prefrontal and visual cortex during attention. Science 324:1207-1210.
Hillman C H, Erickson K I, & Kramer A F (2008) Be smart, exercise your heart: exercise effects on brain and cognition. Nature Reviews Neuroscience 9(1):5865.

Holroyd C B& Yeung N (2012) Motivation of extended behaviors by anterior cingulate cortex. Trends in Cognitive Sciences 16:122-128.

Inzlicht M, Schmeichel B J, & Macrae C N (2014) Why self-control seems (but may not be) limited. Trends in Cognitive Sciences 18(3):127-133.

Jennings J R & Wood C C (1976) The e-adjustment procedure for repeated measures analyses of variance. Psychophysiology 13:277-278.

Kanai R, Chaieb L, Antal A, Walsh V, & Paulus W (2008) Frequency-dependent electrical stimulation of the visual cortex. Current Biology 18(23):1839-1843.

Kayser J & Tenke C E (2006) Principal components analysis of Laplacian waveforms as a generic method for identifying estimates: II. Adequacy of low density estimates. Clinical Neurophysiology 117:369-380.

Kramer A F & Erickson K I (2007) Capitalizing on cortical plasticity: influence of physical activity on cognition and brain function. Trends in Cognitive Sciences 11:342-348.

Kurland J, Baldwin K, Tauer C (2010) Treatment-induced neuroplasticity following intensive naming therapy in a case of chronic wernicke's aphasia. Aphasiology 24: 737-751.

Lachaux J P, Rodriguez E, Martinerie J, & Varela F J (1999) Measuring phase synchrony in brain signals. Human Brain Mapping 8:194-208.

Lennie P (2003) The cost of cortical computation. Current Biology 13:493-497.

Luft C D B, Nolte G, & Bhattacharya J (2013) High-learners present larger midfrontal theta power and connectivity in response to incorrect performance feedback. Journal of Neuroscience 33(5):2029-2038.

Luft C D B, Nolte G, Bhattacharya J (2013) High-learners present larger mid-frontal theta power and connectivity in response to incorrect performance feedback. J Neurosci 33:2029-2038.

Marco-Pallares J, et al. (2008) Human oscillatory activity associated to reward processing in a gambling task. Neuropsychologia 46:241-248.

Marcora S M, Staiano W, & Manning V (2009) Mental fatigue impairs physical performance in humans. Journal of Applied Physiology 106:857-864.

Miltner W H R, Braun C H, & Coles M G H (1997) Event-related brain potentials following incorrect feedback in a time-estimation task: evidence for a "generic" neural system for error detection. Journal of Cognitive Neuroscience 9:788-798.

Noury N, Hipp J F, Siegel M (2016) Physiological processes non-linearly affect electrophysiological recordings during transcranial electric stimulation. Neuroimage 140: 99-109.

Oostenveld R, Fries P, Maris E, & Schoffelen J M (2011) FieldTrip: Open source software for advanced analysis of MEG, EEG, and invasive electrophysiological data. Computational Intelligence and Neuroscience 2011:1-9.

Owen A M, et al. (2010) Putting brain training to the test. Nature 465:775-778.

Pascual-Marqui R D (2002) Standardized low-resolution brain electromagnetic tomography (sLORETA): technical details. Methods & Findings in Experimental & Clinical Pharmacology 24:5-12.

Paulus W (2010) On the difficulties of separating retinal from cortical origins of phosphenes when using transcranial alternating current stimulation (tACS). Clinical Neurophysiology 121:987-991.

Poreisz C, Boros K, Antal A, & Paulus W (2007) Safety aspects of transcranial direct current stimulation concerning healthy subjects and patients. Brain Research Bulletin 72(4-6):208-214.

Raichle M E & Mintun M A (2006) Brain work and brain imaging. Annual Review of Neuroscience 29:449-476.

Reinhart R M G &Woodman G F (2014) Causal control of medial-frontal cortex governs electrophysiological and behavioral indices of performance monitoring and learning. Journal of Neuroscience 34(12):4214-4227.

Reinhart R M G & Woodman G F (2015) Enhancing long-term memory with stimulation tunes visual attention in one trial. Proceedings of the National Academy of Sciences of the USA 112(2):625-630.

Reinhart R M G, Cosman J, Fukuda K, & Woodman G F (2017) Using transcranial direct-current stimulation (tDCS) to understand cognitive processing. Attention, Perception & Psychophysics 79(1):3-23.

Reinhart R M G, Woodman G F (2014) Oscillatory coupling reveals the dynamic reorganization of large-scale neural networks as cognitive demands change. J Cogn Neurosci 26:175-188.

Reinhart R M G, Xiao W, McClenahan L, & Woodman G F (2016) Electrical stimulation of visual cortex can immediately improve spatial vision. Current Biology 25(14): 1867-1872.

Reinhart R M G, Zhu J, Park S, & Woodman G F (2015) Medial-frontal stimulation enhances learning in schizophrenia by restoring prediction-error signaling. Journal of Neuroscience 35(35):12232-12240.

Reinhart R M G, Zhu J, Park S, & Woodman G F (2015) Synchronizing theta oscillations with direct-current stimulation strengthens adaptive control in the human brain. Proceedings of the National Academy of Sciences of the USA 112(30):9448-9453.

Ridderinkhof K R, Ullsperger M, Crone E A, & Nieuwenhuis S (2004) The role of the medial frontal cortex in cognitive control. Science 306:443-447.

Salinas E, Sejnowski T J (2001) Correlated neuronal activity and the flow of neural information. Nat Rev Neurosci 2:539-550.

SchnitzlerA, Gross J (2005) Normal and pathological oscillatory communication in the brain. Nat Rev Neurosci 6:285-296.

Schutter D J & Hortensius R (2010) Retinal origin of phosphenes to transcranial alternating current stimulation. Clinical Neurophysiology 121(7):1080-1084.

Shallice T, Gazzaniga M S (2004) The fractionation of supervisory control. The Cognitive Neuroscience (MIT Press, Cambridge, M A), pp 943-956.

Shenhav A, Botvinick M M, & Cohen J D (2013) The expected value of control: An integrative theory of anterior cingulate cortex function. Neuron 79:217-240.

Shenhav A, Cohen J, & Botvinick M M (2016) Dorsal anterior cingulate cortex and the value of control. Nature Neuroscience 19:1286-1291.

Siegel M, Donner T H, Engel A K (2012) Spectral fingerprints of large-scale neuronal interactions. Nat Rev Neurosci 13:121-134.

Srinivasan R, Winter W R, Ding J, & Nunez P L (2007) EEG and MEG coherence: measures of functional connectivity at distinct spatial scales of neocortical dynamics. Journal of Neuroscience Methods 166(1):41-52.

Tang Y, et al. (2010) Short term mental training induces white-matter changes in the anterior cingulate. Proceedings of the National Academy of Sciences 107:16649-16652.

Tang Y Y, et al. (2009) Central and autonomic nervous system interaction is altered by short term meditation. Proceedings of the National Academy of Sciences 106: 8865-8870.

Thrane G, Friborg O, Anke A, Indredavik B (2014) A meta-analysis of constraint-induced movement therapy after stroke. J Rehabil Med 46:833-842.

Uhlhaas P J, Singer W (2006) Neural synchrony in brain disorders: Relevance for cognitive dysfunctions and pathophysiology. Neuron 52:155-168.

Uhlhaas P J, Singer W (2010) Abnormal neural oscillations and synchrony in schizophrenia. Nat Rev Neurosci 11:100-113.

van de Vijver I, Ridderinkhof K R, & Cohen M X (2011) Frontal oscillatory dynamics predict feedback learning and action adjustment. Journal of Cognitive Neuroscience 23:4106-4121.

van Driel J, Ridderinkhof K R, & Cohen M X (2012) Not all errors are alike: Theta and alpha EEG dynamics relate to differences in error-processing dynamics. Journal of Neuroscience 32(47):16795-16806.

van Meel C S, Heslenfeld D J, Oosterlaan J, Sergeant J A (2007) Adaptive control deficits in attention-deficit/hyperactivity disorder (ADHD): The role of error processing. Psychiatry Res 151:211-220.

Varela F, Lachaux J P, Rodriguez E, Martinerie J (2001) The brainweb: Phase synchronization and large-scale integration. Nat Rev Neurosci 2:229-239.

Velligan D I, Ritch J L, Sui D, DiCocco M, Huntzinger C D (2002) Frontal systems behavior scale in schizophrenia: Relationships with psychiatric symptomatology, cognition and adaptive function. Psychiatry Res 113:227-236.

Vicente R, Gollo L L, Mirasso C R, Fischer I, Pipa G (2008) Dynamical relaying can yield zero time lag neuronal synchrony despite long conduction delays. Proc Natl Acad Sci USA 105:17157-17162.

Wagner M, Fuchs M, & Kastner J (2007) SWARM: sLORETA-weighted accurate minimum norm inverse solutions. International Congress Series 1300:185-188.

Wang X J (2010) Neurophysiological and computational principles of cortical rhythms in cognition. Physiol Rev 90:1195-1268.

Wolpert D M, Diedrichsen J, & Flanagan J R (2011) Principles of sensorimotor learning. Nature Rev. Neuroscience 12:739-751.

Xue S, Tang Y Y, Tang R, & Posner M I (2014) Short-term meditation induces changes in brain resting EEG theta networks. Brain & Cognition 87:1-6

Zatorre R J, Fields R D, &Johansen-Berg H (2012) Plasticity in gray and white: neuroimaging changes in brain structure during learning. Nature Neuroscience 15(4):528-536. See, Daniel Stevenson. "Intro to Transcranial Direct Current Stimulation (tDCS)" (Mar. 26, 2017) (www.slideshare.net/DanielStevenson27/intro-to-transcranial-direct-curent-stimulation-tdcs).

High-Definition-tDCS—High-Definition transcranial Direct Current Stimulation (HD-tDCS) was invented at The City University of New York with the introduction of the 4×1 HD-tDCS montage. The 4×1 HD-tDCS montage allows precise targeting of cortical structures. The region of current flow is circumscribed by the area of the 4× ring, such that decreasing ring radius increases focality. 4×1 HD-tDCS allows for unifocal stimulation, meaning the polarity of the center 1× electrode will determine the direction of neuro-modulation under the ring. This is in contrast to conventional tDCS where the need for one anode and one cathode always produces bidirectional modulation (even when an extra-cephalic electrode is used). 4×1 HD-tDCS thus provides the ability not only to select a cortical brain region to target, but to modulate the excitability of that brain region with a designed polarity without having to consider return counter-electrode flow.

Transcranial Alternative Current Stimulation (tACS)—Transcranial alternating current stimulation (tACS) is a noninvasive means by which alternating electrical current applied through the skin and skull entrains in a frequency-specific fashion the neural oscillations of the underlying brain. See, en.wikipedia.org/wiki/Transcranial_alternating_current_stimulation U.S. Pub. App. No. 20170197081 discloses transdermal electrical stimulation of nerves to modify or induce a cognitive state using transdermal electrical stimulation (TES).

Transcranial alternating current stimulation (tACS) is a noninvasive means by which alternating electrical current applied through the skin and skull entrains in a frequency-specific fashion the neural oscillations of the underlying brain.

See, en.wikipedia.org/wiki/Transcranial_alternating_current_stimulation; U.S. Pat. Nos. 6,804,558; 7,149,773; 7,181,505; 7,278,966; 9,042,201; 9,629,568; 9,713,433; 20010051787; 20020013613; 20020052539; 20020082665; 20050171410; 20140211593; 20140316243; 20150174418; 20150343242; 20160000354; 20160038049; 20160106513; 20160213276; 20160228702; 20160232330; 20160235323; and 20170113056.

Transcranial Random Noise Stimulation (tRNS)—Transcranial random noise stimulation (tRNS) is a non-invasive brain stimulation technique and a form of transcranial electrical stimulation (TES). See, en.wikipedia.org/wiki/Transcranial_random_noise_stimulation; U.S. Pat. Nos. 9,198,733; 9,713,433; 20140316243; 20160038049; and 20160213276.

The stimulus may comprise transcranial pulsed current stimulation (tPCS). See:

Shapour Jaberzadeh, Andisheh Bastani, Maryam Zoghi, "Anodal transcranial pulsed current stimulation: A novel technique to enhance corticospinal excitability," Clin. Neurophysiology, Volume 125, Issue 2, February 2014, Pages 344-351, doi.org/10.1016fj.clinph.2013.08.025; earthpulse.net/tpcs-transcranial-pulsed-current-stimulation/; help.foc.us/article/16-tpcs-transcranial-pulsed-current-stimulation.

Transcranial Magnetic Stimulation (TMS)—Transcranial magnetic stimulation (TMS) is a method in which a changing magnetic field is used to cause electric current to flow in a small region of the brain via electromagnetic induction. During a TMS procedure, a magnetic field generator, or "coil", is placed near the head of the person receiving the treatment. The coil is connected to a pulse generator, or stimulator, that delivers a changing electric current to the coil. TMS is used diagnostically to measure the connection between the central nervous system and skeletal muscle to evaluate damage in a wide variety of disease states, including stroke, multiple sclerosis, amyotrophic lateral sclerosis, movement disorders, and motor neuron diseases. Evidence is available suggesting that TMS is useful in treating neuropathic pain, major depressive disorder, and other conditions. See, en.wikipedia.org/wiki/Transcranial_magnetic_stimulation, See U.S. Pat. Nos. 4,296,756; 4,367,527; 5,069,218; 5,088,497; 5,359,363; 5,384,588; 5,459,536; 5,711,305; 5,877,801; 5,891,131; 5,954,662; 5,971,923; 6,188,924; 6,259,399; 6,487,441; 6,603,502; 7,714,936; 7,844,324; 7,856,264; 8,221,330; 8,655,817; 8,706,241; 8,725,669; 8,914,115; 9,037,224; 9,042,201; 9,095,266; 9,149, 195; 9,248,286; 9,265,458; 9,414,776; 9,445,713; 9,713, 433; 20020097332; 20040088732; 20070179534; 20070249949; 20080194981; 20090006001; 20110004412; 20110007129; 20110087127; 20110092882; 20110119212; 20110137371; 20120165696; 20120296569; 20130339043; 20140142654; 20140163328; 20140200432; 20140211593; 20140257047; 20140279746; 20140316243; 20140350369; 20150065803; 20150099946; 20150148617; 20150174418; 20150257700; 20150327813; 20150343242; 20150351655; 20160038049; 20160140306; 20160144175; 20160213276; 20160235323; 20160284082; 20160306942; 20160317077; 20170084175; and 20170113056.

Pulsed electromagnetic field (PEMF)—PEMF, when applied to the brain is referred to as Transcranial magnetic stimulation, and has been FDA approved since 2008 for use in people who failed to respond to antidepressants. Weak magnetic stimulation of the brain is often called transcranial pulsed electromagnetic field (tPEMF) therapy. See, en.wikipedia.org/wiki/Pulsed_electromagnetic_field_therapy, U.S. Pat. Nos. 7,280,861; 8,343,027; 8,415,123; 8,430,805; 8,435,166; 8,571,642; 8,657,732; 8,775,340; 8,961,385; 8,968,172; 9,002,477; 9,005,102; 9,278,231; 9,320,913; 9,339,641; 9,387,338; 9,415,233; 9,427,598; 9,433,797; 9,440,089; 9,610,459; 9,630,004; 9,656,096; 20030181791; 20060129022; 20100057655; 20100197993; 20120101544; 20120116149; 20120143285; 20120253101; 20130013339; 20140213843; 20140213844; 20140221726; 20140228620; 20140303425; 20160235983; 20170087367; and 20170165496.

Deep Brain Stimulation (DBS)—DBS is a neurosurgical procedure involving the implantation of a medical device called a neurostimulator (sometimes referred to as a 'brain pacemaker'), which sends electrical impulses, through implanted electrodes, to specific targets in the brain (brain nuclei) for the treatment of movement and neuropsychiatric disorders. See, en.wikipedia.org/wiki/Deep_brain_stimulation; See, U.S. Pat. Nos. 6,539,263; 6,671,555; 6,959,215; 6,990,377; 7,006,872; 7,010,351; 7,024,247; 7,079,977; 7,146,211; 7,146,217; 7,149,572; 7,174,206; 7,184,837; 7,209,787; 7,221,981; 7,231,254; 7,236,830; 7,236,831; 7,239,926; 7,242,983; 7,242,984; 7,252,090; 7,257,439; 7,267,644; 7,277,758; 7,280,867; 7,282,030; 7,299,096; 7,302,298; 7,305,268; 7,313,442; 7,321,837; 7,324,851; 7,346,382; 7,353,064; 7,403,820; 7,437,196; 7,463,927; 7,483,747; 7,499,752; 7,565,199; 7,565,200; 7,577,481; 7,582,062; 7,594,889; 7,603,174; 7,606,405; 7,610,096; 7,617,002; 7,620,456; 7,623,928; 7,624,293; 7,629,889; 7,670,838; 7,672,730; 7,676,263; 7,680,526; 7,680,540; 7,684,866; 7,684,867; 7,715,919; 7,725,192; 7,729,773; 7,742,820; 7,747,325; 7,747,326; 7,756,584; 7,769,464; 7,775,993; 7,822,481; 7,831,305; 7,853,322; 7,853,323; 7,853,329; 7,856,264; 7,860,548; 7,894,903; 7,899,545; 7,904,134; 7,908,009; 7,917,206; 7,917,225; 7,930,035; 7,933,646; 7,945,330; 7,957,797; 7,957,809; 7,976,465; 7,983,762; 7,991,477; 8,000,794; 8,000,795; 8,005,534; 8,027,730; 8,031,076; 8,032,229; 8,050,768; 8,055,348; 8,065,012; 8,073,546; 8,082,033; 8,092,549; 8,121,694; 8,126,567; 8,126,568; 8,135,472; 8,145,295; 8,150,523; 8,150,524; 8,160,680; 8,180,436; 8,180,601; 8,187,181; 8,195,298; 8,195,300; 8,200,340; 8,223,023; 8,229,559; 8,233,990; 8,239,029; 8,244,347; 8,249,718; 8,262,714; 8,280,517; 8,290,596; 8,295,934; 8,295,935; 8,301,257; 8,303,636; 8,308,661; 8,315,703; 8,315,710; 8,326,420; 8,326,433; 8,332,038; 8,332,041; 8,346,365; 8,364,271; 8,364,272; 8,374,703; 8,379,952; 8,380,314; 8,388,555; 8,396,565; 8,398,692; 8,401,666; 8,412,335; 8,433,414; 8,437,861; 8,447,392; 8,447,411; 8,456,309; 8,463,374;

8,463,387; 8,467,877; 8,475,506; 8,504,150; 8,506,469; 8,512,219; 8,515,549; 8,515,550; 8,538,536; 8,538,543; 8,543,214; 8,554,325; 8,565,883; 8,565,886; 8,574,279; 8,579,786; 8,579,834; 8,583,238; 8,583,252; 8,588,899; 8,588,929; 8,588,933; 8,589,316; 8,594,798; 8,603,790; 8,606,360; 8,606,361; 8,644,945; 8,649,845; 8,655,817; 8,660,642; 8,675,945; 8,676,324; 8,676,330; 8,684,921; 8,690,748; 8,694,087; 8,694,092; 8,696,722; 8,700,174; 8,706,237; 8,706,241; 8,708,934; 8,716,447; 8,718,777; 8,725,243; 8,725,669; 8,729,040; 8,731,656; 8,734,498; 8,738,136; 8,738,140; 8,751,008; 8,751,011; 8,755,901; 8,758,274; 8,761,889; 8,762,065; 8,768,718; 8,774,923; 8,781,597; 8,788,033; 8,788,044; 8,788,055; 8,792,972; 8,792,991; 8,805,518; 8,815,582; 8,821,559; 8,825,166; 8,831,731; 8,834,392; 8,834,546; 8,843,201; 8,843,210; 8,849,407; 8,849,632; 8,855,773; 8,855,775; 8,868,172; 8,868,173; 8,868,201; 8,886,302; 8,892,207; 8,900,284; 8,903,486; 8,903,494; 8,906,360; 8,909,345; 8,910,638; 8,914,115; 8,914,119; 8,918,176; 8,918,178; 8,918,183; 8,926,959; 8,929,991; 8,932,562; 8,934,979; 8,936,629; 8,938,290; 8,942,817; 8,945,006; 8,951,203; 8,956,363; 8,958,870; 8,962,589; 8,965,513; 8,965,514; 8,974,365; 8,977,362; 8,983,155; 8,983,620; 8,983,628; 8,983,629; 8,989,871; 9,008,780; 9,011,329; 9,014,823; 9,020,598; 9,020,612; 9,020,789; 9,022,930; 9,026,217; 9,037,224; 9,037,254; 9,037,256; 9,042,201; 9,042,988; 9,043,001; 9,044,188; 9,050,470; 9,050,471; 9,061,153; 9,063,643; 9,072,832; 9,072,870; 9,072,905; 9,079,039; 9,079,940; 9,081,488; 9,084,885; 9,084,896; 9,084,900; 9,089,713; 9,095,266; 9,101,690; 9,101,759; 9,101,766; 9,113,801; 9,126,050; 9,135,400; 9,149,210; 9,167,976; 9,167,977; 9,167,978; 9,173,609; 9,174,055; 9,175,095; 9,179,850; 9,179,875; 9,186,510; 9,187,745; 9,198,563; 9,204,838; 9,211,411; 9,211,417; 9,215,298; 9,220,917; 9,227,056; 9,233,245; 9,233,246; 9,235,685; 9,238,142; 9,238,150; 9,248,280; 9,248,286; 9,248,288; 9,248,296; 9,249,200; 9,249,234; 9,254,383; 9,254,387; 9,259,591; 9,271,674; 9,272,091; 9,272,139; 9,272,153; 9,278,159; 9,284,353; 9,289,143; 9,289,595; 9,289,603; 9,289,609; 9,295,838; 9,302,103; 9,302,110; 9,302,114; 9,302,116; 9,308,372; 9,308,392; 9,309,296; 9,310,985; 9,314,190; 9,320,900; 9,320,914; 9,327,070; 9,333,350; 9,340,589; 9,348,974; 9,352,156; 9,357,949; 9,358,381; 9,358,398; 9,359,449; 9,360,472; 9,364,665; 9,364,679; 9,365,628; 9,375,564; 9,375,571; 9,375,573; 9,381,346; 9,387,320; 9,393,406; 9,393,418; 9,394,347; 9,399,134; 9,399,144; 9,403,001; 9,403,010; 9,408,530; 9,411,935; 9,414,776; 9,415,219; 9,415,222; 9,421,258; 9,421,373; 9,421,379; 9,427,581; 9,427,585; 9,439,150; 9,440,063; 9,440,064; 9,440,070; 9,440,084; 9,452,287; 9,453,215; 9,458,208; 9,463,327; 9,474,903; 9,480,841; 9,480,845; 9,486,632; 9,498,628; 9,501,829; 9,505,817; 9,517,020; 9,522,278; 9,522,288; 9,526,902; 9,526,913; 9,526,914; 9,533,148; 9,533,150; 9,538,951; 9,545,510; 9,561,380; 9,566,426; 9,579,247; 9,586,053; 9,592,004; 9,592,387; 9,592,389; 9,597,493; 9,597,494; 9,597,501; 9,597,504; 9,604,056; 9,604,067; 9,604,073; 9,613,184; 9,615,789; 9,622,675; 9,622,700; 9,623,240; 9,623,241; 9,629,548; 9,630,011; 9,636,185; 9,642,552; 9,643,015; 9,643,017; 9,643,019; 9,649,439; 9,649,494; 9,649,501; 9,656,069; 9,656,078; 9,662,502; 9,697,336; 9,706,957; 9,713,433; 9,717,920; 9,724,517; 9,729,252; 20020087201; 20020091419; 20020188330; 20030088274; 20030097159; 20030097161; 20030125786; 20030130706; 20030181955; 20040133118; 20040133119; 20040133120; 20040133248; 20040133390; 20040138516; 20040138517; 20040138518; 20040138536; 20040138580; 20040138581; 20040138647; 20040138711; 20040152958;

US 12,605,104 B2

55

20040158119; 20040158298; 20050021105; 20050060001;
20050060007; 20050060008; 20050060009; 20050060010;
20050065427; 20050124848; 20050154425; 20050154426;
20050182389; 20050209512; 20050222522; 20050240253;
20050267011; 20060004422; 20060015153; 20060064138;
20060069415; 20060100671; 20060106274; 20060106430;
20060149337; 20060155348; 20060155495; 20060161218;
20060161384; 20060167370; 20060195155; 20060200206;
20060212090; 20060217781; 20060224421; 20060239482;
20060241718; 20070000372; 20070014454; 20070025608;
20070027486; 20070027498; 20070027499; 20070027500;
20070027501; 20070032834; 20070043401; 20070060974;
20070066915; 20070100278; 20070100389; 20070100392;
20070100398; 20070118197; 20070129769; 20070129774;
20070142874; 20070150026; 20070150029; 20070179534;
20070179558; 20070225774; 20070250119; 20070276441;
20080009772; 20080015459; 20080033503; 20080033508;
20080045775; 20080046012; 20080046035; 20080058773;
20080064934; 20080071150; 20080071326; 20080097553;
20080103547; 20080103548; 20080109050; 20080125829;
20080154331; 20080154332; 20080157980; 20080161700;
20080161879; 20080161880; 20080161881; 20080162182;
20080183097; 20080208285; 20080215112; 20080228239;
20080269812; 20080269843; 20080275526; 20080281381;
20080288018; 20090018462; 20090076567; 20090082829;
20090093862; 20090099627; 20090105785; 20090112273;
20090112277; 20090112278; 20090112279; 20090112280;
20090118786; 20090118787; 20090163982; 20090192556;
20090210018; 20090216288; 20090234419; 20090264789;
20090264954; 20090264955; 20090264956; 20090264957;
20090264958; 20090264967; 20090281594; 20090287035;
20090287271; 20090287272; 20090287273; 20090287274;
20090287467; 20090299126; 20090299435; 20090306491;
20090306741; 20090312808; 20090312817; 20090319000;
20090319001; 20090326604; 20100004500; 20100010383;
20100010388; 20100010391; 20100010392; 20100010571;
20100010572; 20100010573; 20100010574; 20100010575;
20100010576; 20100010577; 20100010578; 20100010579;
20100010580; 20100010584; 20100010585; 20100010587;
20100010588; 20100010589; 20100010590; 20100016783;
20100045467; 20100049276; 20100057159; 20100057160;
20100070001; 20100076525; 20100114237; 20100114272;
20100121415; 20100131030; 20100145427; 20100191305;
20100198090; 20100222845; 20100241020; 20100256592;
20100274106; 20100274141; 20100274147; 20100274305;
20100280334; 20100280335; 20100280500; 20100280571;
20100280574; 20100280579; 20100292602; 20110004270;
20110009928; 20110021970; 20110022981; 20110028798;
20110028799; 20110034812; 20110040356; 20110040546;
20110040547; 20110082522; 20110092882; 20110093033;
20110106206; 20110112590; 20110119212; 20110137371;
20110137381; 20110160796; 20110172554; 20110172562;
20110172564; 20110172567; 20110172738; 20110172743;
20110172927; 20110184487; 20110191275; 20110208012;
20110208264; 20110213222; 20110230701; 20110238130;
20110238136; 20110245734; 20110257501; 20110270348;
20110275927; 20110276107; 20110307030; 20110307079;
20110313268; 20110313487; 20110319726; 20110319975;
20120016430; 20120016432; 20120016435; 20120022340;
20120022611; 20120041498; 20120046531; 20120046715;
20120053508; 20120089205; 20120108998; 20120109020;
20120116244; 20120116475; 20120157963; 20120165696;
20120165898; 20120179071; 20120179228; 20120184801;
20120185020; 20120195860; 20120197322; 20120209346;
20120253421; 20120253429; 20120253442; 20120265267;
20120271148; 20120271183; 20120271189; 20120271374;
20120271375; 20120271376; 20120271380; 20120277833;

56

20120289869; 20120290058; 20120302912; 20120303087;
20120310050; 20120316630; 20130018435; 20130066392;
20130066394; 20130066395; 20130073022; 20130090706;
20130102919; 20130104066; 20130116578; 20130116748;
20130123568; 20130123684; 20130131746; 20130131753;
20130131755; 20130138176; 20130138177; 20130144353;
20130150921; 20130178913; 20130184781; 20130184792;
20130197401; 20130211183; 20130218232; 20130218819;
20130226261; 20130231709; 20130231716; 20130231721;
20130238049; 20130238050; 20130245466; 20130245486;
20130245711; 20130245712; 20130281758; 20130281811;
20130282075; 20130289385; 20130310909; 20130317474;
20130317568; 20130317580; 20130338526; 20130338738;
20140005743; 20140005744; 20140025133; 20140039577;
20140058289; 20140066796; 20140074060; 20140074179;
20140074180; 20140081071; 20140081347; 20140107397;
20140107398; 20140107728; 20140122379; 20140135642;
20140135886; 20140142654; 20140142669; 20140148872;
20140163627; 20140180194; 20140180358; 20140194720;
20140194726; 20140211593; 20140213842; 20140222113;
20140237073; 20140243613; 20140243926; 20140243934;
20140249396; 20140249445; 20140257047; 20140257437;
20140257438; 20140276185; 20140277282; 20140277286;
20140279746; 20140296646; 20140309614; 20140323924;
20140323946; 20140324118; 20140324138; 20140330334;
20140330335; 20140330345; 20140350634; 20140350636;
20140358024; 20140358199; 20140364721; 20140371515;
20150005680; 20150012057; 20150018699; 20150025408;
20150025421; 20150025610; 20150032178; 20150038822;
20150039066; 20150065831; 20150073505; 20150088224;
20150088228; 20150119689; 20150119898; 20150134031;
20150142082; 20150174406; 20150174418; 20150190636;
20150190637; 20150196246; 20150202447; 20150223721;
20150231395; 20150231397; 20150238693; 20150238765;
20150245781; 20150251016; 20150254413; 20150257700;
20150265207; 20150265830; 20150265836; 20150273211;
20150273223; 20150283379; 20150290453; 20150290454;
20150297893; 20150306391; 20150321000; 20150327813;
20150343215; 20150343242; 20150352363; 20150360026;
20150360039; 20150366482; 20150374983; 20160001065;
20160001096; 20160001098; 20160008600; 20160008632;
20160016014; 20160030666; 20160030749; 20160030750;
20160038049; 20160044841; 20160058359; 20160066789;
20160067494; 20160067496; 20160067526; 20160074661;
20160095546; 20160096025; 20160106997; 20160120437;
20160121114; 20160121116; 20160136429; 20160136430;
20160136443; 20160144175; 20160144186; 20160147964;
20160151628; 20160158553; 20160184596; 20160199662;
20160206380; 20160213276; 20160213314; 20160220821;
20160220850; 20160228204; 20160228640; 20160228702;
20160228705; 20160235323; 20160249846; 20160250473;
20160256690; 20160256691; 20160256693; 20160263380;
20160263393; 20160278870; 20160279410; 20160279417;
20160287436; 20160287869; 20160287889; 20160296746;
20160303322; 20160317077; 20160317824; 20160325111;
20160331970; 20160339243; 20160342762; 20160346542;
20160361540; 20160367808; 20160375259; 20170007820;
20170007828; 20170014625; 20170014630; 20170021161;
20170036024; 20170042474; 20170042713; 20170043167;
20170043178; 20170050046; 20170056642; 20170056663;
20170065349; 20170079573; 20170080234; 20170095670;
20170095676; 20170100591; 20170106193; 20170113046;
20170120043; 20170120052; 20170120054; 20170136238;
20170143966; 20170151433; 20170151435; 20170151436;
20170156622; 20170157410; 20170164895; 20170165481;
20170173326; 20170182285; 20170185741; 20170189685;
20170189686; 20170189687; 20170189688; 20170189689;

20170189700; 20170197080; 20170197086; 20170216595; 20170224990; 20170239486; and 20170239489.

Transcranial Pulse Ultrasound (TPU)—TPU uses low intensity, low frequency ultrasound (LILFU) as a method to stimulate the brain. See, en.wikipedia.org/wiki/Transcranial_pulsed_ultrasound; U.S. Pat. Nos. 8,591,419; 8,858,440; 8,903,494; 8,921,320; 9,002,458; 9,014,811; 9,036,844; 9,042,201; 9,061,133; 9,233,244; 9,333,334; 9,399,126; 9,403,038; 9,440,070; 9,630,029; 9,669,239; 20120259249; 20120283502; 20120289869; 20130079621; 20130144192; 20130184218; 20140058219; 20140211593; 20140228653; 20140249454; 20140316243; 20150080327; 20150133716; 20150343242; 20160143541; 20160176053; and 20160220850.

Sensory Stimulation—Light, sound or electromagnetic fields may be used to remotely convey a temporal pattern of brainwaves. See: U.S. Pat. Nos. 5,293,187; 5,422,689; 5,447,166; 5,491,492; 5,546,943; 5,622,168; 5,649,061; 5,720,619; 5,740,812; 5,983,129; 6,050,962; 6,092,058; 6,149,586; 6,325,475; 6,377,833; 6,394,963; 6,428,490; 6,482,165; 6,503,085; 6,520,921; 6,522,906; 6,527,730; 6,556,695; 6,565,518; 6,652,458; 6,652,470; 6,701,173; 6,726,624; 6,743,182; 6,746,409; 6,758,813; 6,843,774; 6,896,655; 6,996,261; 7,037,260; 7,070,571; 7,107,090; 7,120,486; 7,212,851; 7,215,994; 7,260,430; 7,269,455; 7,280,870; 7,392,079; 7,407,485; 7,463,142; 7,478,108; 7,488,294; 7,515,054; 7,567,693; 7,647,097; 7,740,592; 7,751,877; 7,831,305; 7,856,264; 7,881,780; 7,970,734; 7,972,278; 7,974,787; 7,991,461; 8,012,107; 8,032,486; 8,033,996; 8,060,194; 8,095,209; 8,209,224; 8,239,030; 8,262,714; 8,320,649; 8,358,818; 8,376,965; 8,380,316; 8,386,312; 8,386,313; 8,392,250; 8,392,253; 8,392,254; 8,392,255; 8,437,844; 8,464,288; 8,475,371; 8,483,816; 8,494,905; 8,517,912; 8,533,042; 8,545,420; 8,560,041; 8,655,428; 8,672,852; 8,682,687; 8,684,742; 8,694,157; 8,706,241; 8,706,518; 8,738,395; 8,753,296; 8,762,202; 8,764,673; 8,768,022; 8,788,030; 8,790,255; 8,790,297; 8,821,376; 8,838,247; 8,864,310; 8,872,640; 8,888,723; 8,915,871; 8,938,289; 8,938,301; 8,942,813; 8,955,010; 8,955,974; 8,958,882; 8,964,298; 8,971,936; 8,989,835; 8,992,230; 8,998,828; 9,004,687; 9,060,671; 9,101,279; 9,135,221; 9,142,145; 9,165,472; 9,173,582; 9,179,855; 9,208,558; 9,215,978; 9,232,984; 9,241,665; 9,242,067; 9,254,099; 9,271,660; 9,275,191; 9,282,927; 9,292,858; 9,292,920; 9,320,450; 9,326,705; 9,330,206; 9,357,941; 9,396,669; 9,398,873; 9,414,780; 9,414,907; 9,424,761; 9,445,739; 9,445,763; 9,451,303; 9,451,899; 9,454,646; 9,462,977; 9,468,541; 9,483,117; 9,492,120; 9,504,420; 9,504,788; 9,526,419; 9,541,383; 9,545,221; 9,545,222; 9,545,225; 9,560,967; 9,560,984; 9,563,740; 9,582,072; 9,596,224; 9,615,746; 9,622,702; 9,622,703; 9,626,756; 9,629,568; 9,642,699; 9,649,030; 9,651,368; 9,655,573; 9,668,694; 9,672,302; 9,672,617; 9,682,232; 9,693,734; 9,694,155; 9,704,205; 9,706,910; 9,710,788; RE44408; RE45766; 20020024450; 20020103428; 20020103429; 20020112732; 20020128540; 20030028081; 20030028121; 20030070685; 20030083596; 20030100844; 20030120172; 20030149351; 20030158496; 20030158497; 20030171658; 20040019257; 20040024287; 20040068172; 20040092809; 20040101146; 20040116784; 20040143170; 20040267152; 20050010091; 20050019734; 20050025704; 20050038354; 20050113713; 20050124851; 20050148828; 20050228785; 20050240253; 20050245796; 20050267343; 20050267344; 20050283053; 20060020184; 20060061544; 20060078183; 20060087746; 20060102171; 20060129277; 20060161218; 20060189866; 20060200013; 20060241718; 20060252978; 20060252979; 20070050715; 20070179534; 20070191704;

20070238934; 20070273611; 20070282228; 20070299371; 20080004550; 20080009772; 20080058668; 20080081963; 20080119763; 20080123927; 20080132383; 20080228239; 20080234113; 20080234601; 20080242521; 20080255949; 20090018419; 20090058660; 20090062698; 20090076406; 20090099474; 20090112523; 20090221928; 20090267758; 20090270687; 20090270688; 20090270692; 20090270693; 20090270694; 20090270786; 20090281400; 20090287108; 20090297000; 20090299169; 20090311655; 20090312808; 20090312817; 20090318794; 20090326604; 20100004977; 20100010289; 20100010366; 20100041949; 20100069739; 20100069780; 20100163027; 20100163028; 20100163035; 20100165593; 20100168525; 20100168529; 20100168602; 20100268055; 20100293115; 20110004412; 20110009777; 20110015515; 20110015539; 20110043759; 20110054272; 20110077548; 20110092882; 20110105859; 20110130643; 20110172500; 20110218456; 20110256520; 20110270074; 20110301488; 20110307079; 20120004579; 20120021394; 20120036004; 20120071771; 20120108909; 20120108995; 20120136274; 20120150545; 20120203130; 20120262558; 20120271377; 20120310106; 20130012804; 20130046715; 20130063434; 20130063550; 20130080127; 20130120246; 20130127980; 20130185144; 20130189663; 20130204085; 20130211238; 20130226464; 20130242262; 20130245424; 20130281759; 20130289360; 20130293844; 20130308099; 20130318546; 20140058528; 20140155714; 20140171757; 20140200432; 20140214335; 20140221866; 20140243608; 20140243614; 20140243652; 20140276130; 20140276944; 20140288614; 20140296750; 20140300532; 20140303508; 20140304773; 20140313303; 20140315169; 20140316191; 20140316192; 20140316235; 20140316248; 20140323899; 20140335489; 20140343408; 20140347491; 20140350353; 20140350431; 20140364721; 20140378810; 20150002815; 20150003698; 20150003699; 20150005640; 20150005644; 20150006186; 20150012111; 20150038869; 20150045606; 20150051663; 20150099946; 20150112409; 20150120007; 20150124220; 20150126845; 20150126873; 20150133812; 20150141773; 20150145676; 20150154889; 20150174362; 20150196800; 20150213191; 20150223731; 20150234477; 20150235088; 20150235370; 20150235441; 20150235447; 20150241705; 20150241959; 20150242575; 20150242943; 20150243100; 20150243105; 20150243106; 20150247723; 20150247975; 20150247976; 20150248169; 20150248170; 20150248787; 20150248788; 20150248789; 20150248791; 20150248792; 20150248793; 20150290453; 20150290454; 20150305685; 20150306340; 20150309563; 20150313496; 20150313539; 20150324692; 20150325151; 20150335288; 20150339363; 20150351690; 20150366497; 20150366504; 20150366656; 20150366659; 20150369864; 20150370320; 20160000354; 20160004298; 20160005320; 20160007915; 20160008620; 20160012749; 20160015289; 20160022167; 20160022206; 20160029946; 20160029965; 20160038069; 20160051187; 20160051793; 20160066838; 20160073886; 20160077547; 20160078780; 20160106950; 20160112684; 20160120436; 20160143582; 20160166219; 20160167672; 20160176053; 20160180054; 20160198950; 20160199577; 20160202755; 20160216760; 20160220439; 20160228640; 20160232625; 20160232811; 20160235323; 20160239084; 20160248994; 20160249826; 20160256108; 20160267809; 20160270656; 20160287157; 20160302711; 20160306942; 20160313798; 20160317060; 20160317383; 20160324478; 20160324580; 20160334866; 20160338644; 20160338825; 20160339300; 20160345901; 20160357256; 20160360970; 20160363483; 20170000324; 20170000325; 20170000326; 20170000329; 20170000330; 20170000331; 20170000332; 20170000333; 20170000334; 20170000335; 20170000337; 20170000340; 20170000341; 20170000342; 20170000343;

20170000345; 20170000454; 20170000683; 20170001032;
20170006931; 20170007111; 20170007115; 20170007116;
20170007122; 20170007123; 20170007165; 20170007182;
20170007450; 20170007799; 20170007843; 20170010469;
20170010470; 20170017083; 20170020447; 20170020454;
20170020627; 20170027467; 20170027651; 20170027812;
20170031440; 20170032098; 20170035344; 20170043160;
20170055900; 20170060298; 20170061034; 20170071523;
20170071537; 20170071546; 20170071551; 20170080320;
20170086729; 20170095157; 20170099479; 20170100540;
20170103440; 20170112427; 20170112671; 20170113046;
20170113056; 20170119994; 20170135597; 20170135633;
20170136264; 20170136265; 20170143249; 20170143442;
20170148340; 20170156662; 20170162072; 20170164876;
20170164878; 20170168568; 20170173262; 20170173326;
20170177023; 20170188947; 20170202633; 20170209043;
20170209094; and 20170209737.

Light Stimulation—The functional relevance of brain oscillations in the alpha frequency range (8-13 Hz) has been repeatedly investigated through the use of rhythmic visual stimulation. There are two hypotheses on the origin of steady-state visual evoked potential (SSVEP) measured in EEG during rhythmic stimulation: entrainment of brain oscillations and superposition of event-related responses (ERPs). The entrainment but not the superposition hypothesis justifies rhythmic visual stimulation as a means to manipulate brain oscillations, because superposition assumes a linear summation of single responses, independent from ongoing brain oscillations. Participants stimulated with rhythmic flickering light of different frequencies and intensities, and entrainment was measured by comparing the phase coupling of brain oscillations stimulated by rhythmic visual flicker with the oscillations induced by arrhythmic jittered stimulation, varying the time, stimulation frequency, and intensity conditions. Phase coupling was found to be more pronounced with increasing stimulation intensity as well as at stimulation frequencies closer to each participant's intrinsic frequency. Even in a single sequence of an SSVEP, non-linear features (intermittency of phase locking) was found that contradict the linear summation of single responses, as assumed by the superposition hypothesis. Thus, evidence suggests that visual rhythmic stimulation entrains brain oscillations, validating the approach of rhythmic stimulation as a manipulation of brain oscillations. See, Notbohm A, Kurths J, Herrmann C S, Modification of Brain Oscillations via Rhythmic Light Stimulation Provides Evidence for Entrainment but Not for Superposition of Event-Related Responses, Front Hum Neurosci. 2016 Feb. 3; 10:10. doi: 10.3389/fnhum.2016.00010. eCollection 2016.

It is also known that periodic visual stimulation can trigger epileptic seizures.

Cochlear Implant—A cochlear implant is a surgically implanted electronic device that provides a sense of sound to a person who is profoundly deaf or severely hard of hearing in both ears. See, en.wikipedia.org/wiki/Cochlear_implant;

See, U.S. Pat. Nos. 5,999,856; 6,354,299; 6,427,086;
6,430,443; 6,665,562; 6,873,872; 7,359,837; 7,440,806;
7,493,171; 7,610,083; 7,610,100; 7,702,387; 7,747,318;
7,765,088; 7,853,321; 7,890,176; 7,917,199; 7,920,916;
7,957,806; 8,014,870; 8,024,029; 8,065,017; 8,108,033;
8,108,042; 8,140,152; 8,165,687; 8,175,700; 8,195,295;
8,209,018; 8,224,431; 8,315,704; 8,332,024; 8,401,654;
8,433,410; 8,478,417; 8,515,541; 8,538,543; 8,560,041;
8,565,864; 8,574,164; 8,577,464; 8,577,465; 8,577,466;
8,577,467; 8,577,468; 8,577,472; 8,577,478; 8,588,941;
8,594,800; 8,644,946; 8,644,957; 8,652,187; 8,676,325;
8,696,724; 8,700,183; 8,718,776; 8,768,446; 8,768,477;

8,788,057; 8,798,728; 8,798,773; 8,812,126; 8,864,806;
8,868,189; 8,929,999; 8,968,376; 8,989,868; 8,996,120;
9,002,471; 9,044,612; 9,061,132; 9,061,151; 9,095,713;
9,135,400; 9,186,503; 9,235,685; 9,242,067; 9,248,290;
9,248,291; 9,259,177; 9,302,093; 9,314,613; 9,327,069;
9,352,145; 9,352,152; 9,358,392; 9,358,393; 9,403,009;
9,409,013; 9,415,215; 9,415,216; 9,421,372; 9,432,777;
9,501,829; 9,526,902; 9,533,144; 9,545,510; 9,550,064;
9,561,380; 9,578,425; 9,592,389; 9,604,067; 9,616,227;
9,643,017; 9,649,493; 9,674,621; 9,682,232; 9,743,197;
9,744,358; 20010014818; 20010029391; 20020099412;
20030114886; 20040073273; 20050149157; 20050182389;
20050182450; 20050182467; 20050182468; 20050182469;
20050187600; 20050192647; 20050209664; 20050209665;
20050209666; 20050228451; 20050240229; 20060064140;
20060094970; 20060094971; 20060094972; 20060095091;
20060095092; 20060161217; 20060173259; 20060178709;
20060195039; 20060206165; 20060235484; 20060235489;
20060247728; 20060282123; 20060287691; 20070038264;
20070049988; 20070156180; 20070198063; 20070213785;
20070244407; 20070255155; 20070255531; 20080049376;
20080140149; 20080161886; 20080208280; 20080235469;
20080249589; 20090163980; 20090163981; 20090243756;
20090259277; 20090270944; 20090280153; 20100030287;
20100100164; 20100198282; 20100217341; 20100231327;
20100241195; 20100268055; 20100268288; 20100318160;
20110004283; 20110060382; 20110166471; 20110295344;
20110295345; 20110295346; 20110295347; 20120035698;
20120116179; 20120116741; 20120150255; 20120245655;
20120262250; 20120265270; 20130165996; 20130197944;
20130235550; 20140032512; 20140098981; 20140200623;
20140249608; 20140275847; 20140330357; 20140350634;
20150018699; 20150045607; 20150051668; 20150065831;
20150066124; 20150080674; 20150328455; 20150374986;
20150374987; 20160067485; 20160243362; 20160261962;
20170056655; 20170087354; 20170087355; 20170087356;
20170113046; 20170117866; 20170135633; and
20170182312.

Vagus Nerve Stimulation (VNS)—VNS is a medical treatment that involves delivering electrical impulses to the vagus nerve. It is used as an adjunctive treatment for certain types of intractable epilepsy and treatment-resistant depression. See, en.wikipedia.org/wikiNagus_nerve_stimulation;

See, U.S. Pat. Nos. 5,215,086; 5,231,988; 5,299,569;
5,335,657; 5,571,150; 5,928,272; 5,995,868; 6,104,956;
6,167,311; 6,205,359; 6,208,902; 6,248,126; 6,269,270;
6,339,725; 6,341,236; 6,356,788; 6,366,814; 6,418,344;
6,497,699; 6,549,804; 6,556,868; 6,560,486; 6,587,727;
6,591,137; 6,597,954; 6,609,030; 6,622,047; 6,665,562;
6,671,556; 6,684,105; 6,708,064; 6,735,475; 6,782,292;
6,788,975; 6,873,872; 6,879,859; 6,882,881; 6,920,357;
6,961,618; 7,003,352; 7,151,961; 7,155,279; 7,167,751;
7,177,678; 7,203,548; 7,209,787; 7,228,167; 7,231,254;
7,242,984; 7,277,758; 7,292,890; 7,313,442; 7,324,851;
7,346,395; 7,366,571; 7,386,347; 7,389,144; 7,403,820;
7,418,290; 7,422,555; 7,444,184; 7,454,245; 7,457,665;
7,463,927; 7,486,986; 7,493,172; 7,499,752; 7,561,918;
7,620,455; 7,623,927; 7,623,928; 7,630,757; 7,634,317;
7,643,881; 7,653,433; 7,657,316; 7,676,263; 7,680,526;
7,684,858; 7,706,871; 7,711,432; 7,734,355; 7,736,382;
7,747,325; 7,747,326; 7,769,461; 7,783,362; 7,801,601;
7,805,203; 7,840,280; 7,848,803; 7,853,321; 7,853,329;
7,860,548; 7,860,570; 7,865,244; 7,869,867; 7,869,884;
7,869,885; 7,890,185; 7,894,903; 7,899,539; 7,904,134;
7,904,151; 7,904,175; 7,908,008; 7,920,915; 7,925,353;
7,945,316; 7,957,796; 7,962,214; 7,962,219; 7,962,220;
7,974,688; 7,974,693; 7,974,697; 7,974,701; 7,996,079;

8,000,788; 8,027,730; 8,036,745; 8,041,418; 8,041,419; 8,046,076; 8,064,994; 8,068,911; 8,097,926; 8,108,038; 8,112,148; 8,112,153; 8,116,883; 8,150,508; 8,150,524; 8,160,696; 8,172,759; 8,180,601; 8,190,251; 8,190,264; 8,204,603; 8,209,009; 8,209,019; 8,214,035; 8,219,188; 8,224,444; 8,224,451; 8,229,559; 8,239,028; 8,260,426; 8,280,505; 8,306,627; 8,315,703; 8,315,704; 8,326,418; 8,337,404; 8,340,771; 8,346,354; 8,352,031; 8,374,696; 8,374,701; 8,379,952; 8,382,667; 8,401,634; 8,412,334; 8,412,338; 8,417,344; 8,423,155; 8,428,726; 8,452,387; 8,454,555; 8,457,747; 8,467,878; 8,478,428; 8,485,979; 8,489,185; 8,498,699; 8,515,538; 8,536,667; 8,538,523; 8,538,543; 8,548,583; 8,548,594; 8,548,604; 8,560,073; 8,562,536; 8,562,660; 8,565,867; 8,571,643; 8,571,653; 8,588,933; 8,591,419; 8,600,521; 8,603,790; 8,606,360; 8,615,309; 8,630,705; 8,634,922; 8,641,646; 8,644,954; 8,649,871; 8,652,187; 8,660,666; 8,666,501; 8,676,324; 8,676,330; 8,684,921; 8,694,118; 8,700,163; 8,712,547; 8,716,447; 8,718,779; 8,725,243; 8,738,126; 8,744,562; 8,761,868; 8,762,065; 8,768,471; 8,781,597; 8,815,582; 8,827,912; 8,831,732; 8,843,210; 8,849,409; 8,852,100; 8,855,775; 8,858,440; 8,864,806; 8,868,172; 8,868,177; 8,874,205; 8,874,218; 8,874,227; 8,888,702; 8,914,122; 8,918,178; 8,934,967; 8,942,817; 8,945,006; 8,948,855; 8,965,514; 8,968,376; 8,972,004; 8,972,013; 8,983,155; 8,983,628; 8,983,629; 8,985,119; 8,989,863; 8,989,867; 9,014,804; 9,014,823; 9,020,582; 9,020,598; 9,020,789; 9,026,218; 9,031,655; 9,042,201; 9,042,988; 9,043,001; 9,044,188; 9,050,469; 9,056,195; 9,067,054; 9,067,070; 9,079,940; 9,089,707; 9,089,719; 9,095,303; 9,095,314; 9,108,041; 9,113,801; 9,119,533; 9,135,400; 9,138,580; 9,162,051; 9,162,052; 9,174,045; 9,174,066; 9,186,060; 9,186,106; 9,204,838; 9,204,998; 9,220,910; 9,233,246; 9,233,258; 9,235,685; 9,238,150; 9,241,647; 9,242,067; 9,242,092; 9,248,286; 9,249,200; 9,249,234; 9,254,383; 9,259,591; 9,265,660; 9,265,661; 9,265,662; 9,265,663; 9,265,931; 9,265,946; 9,272,145; 9,283,394; 9,284,353; 9,289,599; 9,302,109; 9,309,296; 9,314,633; 9,314,635; 9,320,900; 9,326,720; 9,332,939; 9,333,347; 9,339,654; 9,345,886; 9,358,381; 9,359,449; 9,364,674; 9,365,628; 9,375,571; 9,375,573; 9,381,346; 9,394,347; 9,399,133; 9,399,134; 9,402,994; 9,403,000; 9,403,001; 9,403,038; 9,409,022; 9,409,028; 9,415,219; 9,415,222; 9,427,581; 9,440,063; 9,458,208; 9,468,761; 9,474,852; 9,480,845; 9,492,656; 9,492,678; 9,501,829; 9,504,390; 9,505,817; 9,522,085; 9,522,282; 9,526,902; 9,533,147; 9,533,151; 9,538,951; 9,545,226; 9,545,510; 9,561,380; 9,566,426; 9,579,506; 9,586,047; 9,592,003; 9,592,004; 9,592,409; 9,604,067; 9,604,073; 9,610,442; 9,622,675; 9,623,240; 9,643,017; 9,643,019; 9,656,075; 9,662,069; 9,662,490; 9,675,794; 9,675,809; 9,682,232; 9,682,241; 9,700,256; 9,700,716; 9,700,723; 9,707,390; 9,707,391; 9,717,904; 9,729,252; 9,737,230; 20010003799; 20010029391; 20020013612; 20020072776; 20020072782; 20020099417; 20020099418; 20020151939; 20030023282; 20030045914; 20030083716; 20030114886; 20030181954; 20030195574; 20030236557; 20030236558; 20040015204; 20040015205; 20040073273; 20040138721; 20040153129; 20040172089; 20040172091; 20040172094; 20040193220; 20040243182; 20040260356; 20050027284; 20050033379; 20050043774; 20050049651; 20050137645; 20050149123; 20050149157; 20050154419; 20050154426; 20050165458; 20050182288; 20050182450; 20050182453; 20050182467; 20050182468; 20050182469; 20050187600; 20050192644; 20050192647; 20050197590; 20050197675; 20050197678; 20050209654; 20050209664; 20050209665; 20050209666; 20050216070; 20050216071; 20050251220; 20050267542; 20060009815;

20060047325; 20060052657; 20060064138; 20060064139; 20060064140; 20060079936; 20060111644; 20060129202; 20060142802; 20060155348; 20060167497; 20060173493; 20060173494; 20060173495; 20060195154; 20060206155; 20060212090; 20060212091; 20060217781; 20060224216; 20060259077; 20060282123; 20060293721; 20060293723; 20070005115; 20070021800; 20070043401; 20070060954; 20070060984; 20070066997; 20070067003; 20070067004; 20070093870; 20070100377; 20070100378; 20070100392; 20070112404; 20070150024; 20070150025; 20070162085; 20070173902; 20070198063; 20070213786; 20070233192; 20070233193; 20070255320; 20070255379; 20080021341; 20080027347; 20080027348; 20080027515; 20080033502; 20080039904; 20080065183; 20080077191; 20080086182; 20080091240; 20080125829; 20080140141; 20080147137; 20080154332; 20080161894; 20080167571; 20080183097; 20080269542; 20080269833; 20080269834; 20080269840; 20090018462; 20090036950; 20090054946; 20090088680; 20090093403; 20090118780; 20090163982; 20090171405; 20090187230; 20090234419; 20090276011; 20090276012; 20090280153; 20090326605; 20100003656; 20100004705; 20100004717; 20100057159; 20100063563; 20100106217; 20100114190; 20100114192; 20100114193; 20100125219; 20100125304; 20100145428; 20100191304; 20100198098; 20100198296; 20100204749; 20100268288; 20100274303; 20100274308; 20100292602; 20110009920; 20110021899; 20110028799; 20110029038; 20110029044; 20110034912; 20110054569; 20110077721; 20110092800; 20110098778; 20110105998; 20110125203; 20110130615; 20110137381; 20110152967; 20110152988; 20110160795; 20110166430; 20110166546; 20110172554; 20110172725; 20110172732; 20110172739; 20110178441; 20110178442; 20110190569; 20110201944; 20110213222; 20110224602; 20110224749; 20110230701; 20110230938; 20110257517; 20110264182; 20110270095; 20110270096; 20110270346; 20110270347; 20110276107; 20110276112; 20110282225; 20110295344; 20110295345; 20110295346; 20110295347; 20110301529; 20110307030; 20110311489; 20110319975; 20120016336; 20120016432; 20120029591; 20120029601; 20120046711; 20120059431; 20120078323; 20120083700; 20120083701; 20120101326; 20120116741; 20120158092; 20120179228; 20120184801; 20120185020; 20120191158; 20120203079; 20120209346; 20120226130; 20120232327; 20120265262; 20120303080; 20120310050; 20120316622; 20120330369; 20130006332; 20130018438; 20130018439; 20130018440; 20130019325; 20130046358; 20130066350; 20130066392; 20130066395; 20130072996; 20130089503; 20130090454; 20130096441; 20130131753; 20130165846; 20130178913; 20130184639; 20130184792; 20130204144; 20130225953; 20130225992; 20130231721; 20130238049; 20130238050; 20130238053; 20130244323; 20130245464; 20130245486; 20130245711; 20130245712; 20130253612; 20130261703; 20130274625; 20130281890; 20130289653; 20130289669; 20130296406; 20130296637; 20130304159; 20130309278; 20130310909; 20130317580; 20130338450; 20140039290; 20140039336; 20140039578; 20140046203; 20140046407; 20140052213; 20140056815; 20140058189; 20140058292; 20140074188; 20140081071; 20140081353; 20140094720; 20140100633; 20140107397; 20140107398; 20140113367; 20140128938; 20140135680; 20140135886; 20140142653; 20140142654; 20140142669; 20140155772; 20140155952; 20140163643; 20140213842; 20140213961; 20140214135; 20140235826; 20140236272; 20140243613; 20140243714; 20140257118; 20140257132; 20140257430; 20140257437; 20140257438; 20140275716; 20140276194; 20140277255; 20140277256; 20140288620; 20140303452; 20140324118; 20140330334; 20140330335; 20140330336; 20140336514;

20140336730; 20140343463; 20140357936; 20140358067; 20140358193; 20140378851; 20150005592; 20150005839; 20150012054; 20150018893; 20150025422; 20150032044; 20150032178; 20150051655; 20150051656; 20150051657; 20150051658; 20150051659; 20150057715; 20150072394; 20150073237; 20150073505; 20150119689; 20150119794; 20150119956; 20150142082; 20150148878; 20150157859; 20150165226; 20150174398; 20150174405; 20150174407; 20150182753; 20150182756; 20150190636; 20150190637; 20150196246; 20150202428; 20150208978; 20150216469; 20150231330; 20150238761; 20150265830; 20150265836; 20150283265; 20150297719; 20150297889; 20150306392; 20150343222; 20150352362; 20150360030; 20150366482; 20150374973; 20150374993; 20160001096; 20160008620; 20160012749; 20160030666; 20160045162; 20160045731; 20160051818; 20160058359; 20160074660; 20160081610; 20160114165; 20160121114; 20160121116; 20160135727; 20160136423; 20160144175; 20160151628; 20160158554; 20160175607; 20160199656; 20160199662; 20160206236; 20160222073; 20160232811; 20160243381; 20160249846; 20160250465; 20160263376; 20160279021; 20160279022; 20160279023; 20160279024; 20160279025; 20160279267; 20160279410; 20160279435; 20160287869; 20160287895; 20160303396; 20160303402; 20160310070; 20160331952; 20160331974; 20160331982; 20160339237; 20160339238; 20160339239; 20160339242; 20160346542; 20160361540; 20160361546; 20160367808; 20160375245; 20170007820; 20170027812; 20170043160; 20170056467; 20170056642; 20170066806; 20170079573; 20170080050; 20170087364; 20170095199; 20170095670; 20170113042; 20170113057; 20170120043; 20170120052; 20170143550; 20170143963; 20170143986; 20170150916; 20170150921; 20170151433; 20170157402; 20170164894; 20170189707; 20170198017; and 20170224994.

Brain-To-Brain Interface (B2BI)—A B2BI is a direct communication pathway between the brain of one animal and the brain of another animal. Brain to brain interfaces have been used to help rats collaborate with each other.

It is hypothesized that by using brain-to-brain interfaces (BTBIs) a biological computer, or brain-net, could be constructed using animal brains as its computational units. Initial exploratory work demonstrated collaboration between rats in distant cages linked by signals from cortical microelectrode arrays implanted in their brains. The rats were rewarded when actions were performed by the "decoding rat" which conformed to incoming signals and when signals were transmitted by the "encoding rat" which resulted in the desired action. In the initial experiment the rewarded action was pushing a lever in the remote location corresponding to the position of a lever near alighted LED at the home location. About a month was required for the rats to acclimate themselves to incoming "brainwaves." When a decoding rat was unable to choose the correct lever, the encoding rat noticed (not getting an expected reward), and produced a round of task-related neuron firing that made the second rat more likely to choose the correct lever.

In another study, electrical brain readings were used to trigger a form of magnetic stimulation, to send a brain signal based on brain activity on a subject to a recipient, which caused the recipient to hit the fire button on a computer game.

Brain-To-Computer Interface (BCI)—BCI, sometimes called a neural-control interface (NCI), mind-machine interface (MMI), direct neural interface (DNI), or brain-machine interface (BMI), is a direct communication pathway between an enhanced or wired brain and an external device. BCI differs from neuromodulation in that it allows for bidirectional information flow. BCIs are often directed at researching, mapping, assisting, augmenting, or repairing human cognitive or sensory-motor functions.

Synthetic telepathy, also known as techlepathy or psychotronics (geeldon.wordpress.com/2010/09/06/synthetic-telepathy-also-known-as-techlepathy-or-psychotronics), describes the process of use of brain-computer interfaces by which human thought (as electromagnetic radiation) is intercepted, processed by computer and a return signal generated that is perceptible by the human brain. Dewan, E. M., "Occipital Alpha Rhythm Eye Position and Lens Accommodation." Nature 214, 975-977 (3 Jun. 1967), demonstrates the mental control of Alpha waves, turning them on and off, to produce Morse code representations of words and phrases by thought alone. U.S. Pat. No. 3,951,134 proposes remotely monitoring and altering brainwaves using radio, and references demodulating the waveform, displaying it to an operator for viewing and passing this to a computer for further analysis. In 1988, Farwell, L. A., & Donchin, E. (1988). Talking off the top of your head: toward a mental prosthesis utilizing event-related brain potentials. Electroencephalography and Clinical Neurophysiology, 70(6), 510-523 describes a method of transmitting linguistic information using the P300 response system, which combines matching observed information to what the subject was thinking of. In this case, being able to select a letter of the alphabet that the subject was thinking of. In theory, any input could be used and a lexicon constructed. U.S. Pat. No. 6,011,991 describes a method of monitoring an individual's brain waves remotely, for the purposes of communication, and outlines a system that monitors an individual's brainwaves via a sensor, then transmits this information, specifically by satellite, to a computer for analysis. This analysis would determine if the individual was attempting to communicate a "word, phrase, or thought corresponding to the matched stored normalized signal."

Approaches to synthetic telepathy can be categorized into two major groups, passive and active. Like sonar, the receiver can take part or passively listen. Passive reception is the ability to "read" a signal without first broadcasting a signal. This can be roughly equated to tuning into a radio station—the brain generates electromagnetic radiation which can be received at a distance. That distance is determined by the sensitivity of the receiver, the filters used and the bandwidth required. Most universities would have limited budgets, and receivers, such as EEG (and similar devices), would be used. A related military technology is the surveillance system TEMPEST. Robert G. Malech's approach requires a modulated signal to be broadcast at the target. The method uses an active signal, which is interfered with by the brain's modulation. Thus, the return signal can be used to infer the original brainwave.

Computer mediation falls into two basic categories, interpretative and interactive. Interpretative mediation is the passive analysis of signals coming from the human brain. A computer "reads" the signal then compares that signal against a database of signals and their meanings. Using statistical analysis and repetition, false-positives are reduced over time. Interactive mediation can be in a passive-active mode or active-active mode. In this case, passive and active denote the method of reading and writing to the brain and whether or not they make use of a broadcast signal. Interactive mediation can also be performed manually or via artificial intelligence. Manual interactive mediation involves a human operator producing return signals such as speech or images. A.I. mediation leverages the cognitive system of the subject to identify images, pre-speech, objects, sounds and other artifacts, rather than developing A.I. routines to perform such activities. A.I. based systems may incorporate natural language processing interfaces that produce sensations, mental impressions, humor and conversation to provide a mental picture of a computerized personality. Statistical analysis and machine learning techniques, such as neural networks can be used.

ITV News Service, in March 1991, produced a report of ultrasound piggybacked on a commercial radio broadcast (100 MHz) aimed at entraining the brains of Iraqi troops and creating feelings of despair. U.S. Pat. No. 5,159,703 that refers to a "silent communications system in which nonaural carriers, in the very low or very high audio frequency range or in the adjacent ultrasonic frequency spectrum, are amplitude or frequency modulated with the desired intelligence and propagated acoustically or vibrationally, for inducement into the brain, typically through the use of loudspeakers, earphones or piezoelectric transducers." See:

Dr Nick Begich—Controlling the Human Mind, Earth Pulse Press Anchorage—isbn=1-890693-54-5 cbcg.org/gjcsl.htm %7C God's Judgment Cometh Soon cnslab.ss.uci.edu/muri/research.html, #Dewan, #Farwell-Donchin, #ImaginedSpeechProduction, #Overview, MURI: Synthetic Telepathy daprocess.com/01.welcome.html DaProcess of A Federal Investigation deepthought.newsvine.com/_news/2012/01/01/9865851-nsa-disinformation-watch-the-watchers-with-me deepthought.newsvine.com/_news/2012/01/09/10074589-nsa-disinformation-watch-the-watchers-with-me-part-2 deepthought.newsvine.com/_news/2012/01/16/10169491-the-nsa-behind-the-curtain genamason.wordpress.com/2009/10/18/more-on-synthetic-telepathy/ io9.com/5065304/tips-and-tricks-for-mind-control-from-the-us-military newdawnmagazine.com.au/Article/Brain_Zapping_Part_One.html pinktentacle.com/2008/12/scientists-extract-images-directly-from-brain/Scientists extract images directly from brain timesofindia.indiatimes.com/HealthSci/US_army_developing_synthetic_telepathy/ www.bibliotecapleyades.net/ciencia/ciencia_nonlethalweapons02.htm Eleanor White—New Devices That 'Talk' To The Human Mind Need Debate, Controls www.cbsnews.com/stories/2008/12/31/60 minutes/main 4694713.shtml 60 Minutes: Incredible Research Lets Scientists Get A Glimpse At Your Thoughts www.cbsnews.com/video/watch/?id=5119805n& tag=related;photovideo 60 Minutes: Video—Mind Reading www.charlesrehn.com/charlesrehn/books/aconversation-withamerica/essays/myessays/The %20NSA.doc www.govtrack.us/congress/billtext.xpd?bill=h107-2977 Space Preservation Act of 2001 www.informaworld.com/smpp/content-db=all~content=a785359968 Partial Amnesia for a Narrative Following Application of Theta Frequency Electromagnetic Fields www.msnbc.msn.comfid/27162401/ www.psychology.nottingham.ac.uk/staff/lpxdts/TMS %20info.html Transcranial Magnetic Stimulation www.ravenl.net/silsoun2.htm Psy-Ops Weaponry Used In The Persian Gulf War www.scribd.com/doc/24531011/Operation-Mind-Control www.scribd.com/doc/6508206/synthetic-telepathy-and-the-early-mind-wars www.slavery.org.uk/Bioeffects_of_Selected_Non-Lethal_Weapons.pdf-Bioeffects of selected non-lethal weapons www.sst.ws/tempstandards.php?pab=1_1 TEMPEST measurement standards www.uwe.ac.uk/hlss/research/cpss/Journal_Psycho-Social_Studies/v2-2/SmithC.shtml Journal of Psycho-Social Studies—Vol 2 (2) 2003—On the Need for New Criteria of Diagnosis of Psychosis in the Light of Mind Invasive Technology by Dr. Carole Smith www.wired.com/dangerroom/2009/05/pentagon-preps-soldier-telepathy-push www.wired.com/wired/archive/7.11/persinger.html This Is Your Brain on God Noah, Shachtman—Pentagon's PCs Bend to Your Brain www.wired.com/dangerroom/2007/03/the_us_military Wall, Judy, "Military Use of Mind Control Weapons", NEXUS, 5/06, October-November 1998

Soldier-Telepathy" Drummond, Katie—Pentagon Preps Soldier Telepathy Push U.S. Pat. Nos. 3,951,134; 5,159, 703 Silent subliminal presentation system; U.S. Pat. No. 6,587,729 Apparatus for audibly communicating speech using the radio frequency hearing effect It is known to analyze EEG patterns to extract an indication of certain volitional activity (U.S. Pat. No. 6,011, 991). This technique describes that an EEG recording can be matched against a stored normalized signal using a computer. This matched signal is then translated into the corresponding reference. The patent application describes a method "a system capable of identifying particular nodes in an individual's brain, the firings of which affect characteristics such as appetite, hunger, thirst, communication skills" and "devices mounted to the person (e.g. underneath the scalp) may be energized in a predetermined manner or sequence to remotely cause particular identified brain node(s) to be fired in order to cause a predetermined feeling or reaction in the individual" without technical description of implementation. This patent also describes, that "brain activity [is monitored] byway of electroencephalograph (EEG) methods, magnetoencephalograph (MEG) methods, and the like. For example, see U.S. Pat. Nos. 5,816,247 and 5,325,862. See also, U.S. patents and Pub. App. Nos. U.S. Pat. Nos. 3,951,134; 4,437,064; 4,591,787; 4,613,817; 4,689,559; 4,693,000; 4,700,135; 4,733,180; 4,736,751; 4,749,946; 4,753,246; 4,761,611; 4771,239; 4,801,882; 4,862,359; 4,913,152; 4,937,525; 4,940,058; 4,947,480; 4,949,725; 4,951,674; 4,974,602; 4,982,157; 4,983,912; 4,996,479; 5,008,622; 5,012,190; 5,020,538; 5,061,680; 5,092,835; 5,095,270; 5,126,315; 5,158,932; 5,159,703; 5,159,928; 5,166,614; 5,187,327; 5,198,977; 5,213,338; 5,241,967; 5,243,281; 5,243,517; 5,263,488; 5,265,611; 5,269,325; 5,282,474; 5,283,523; 5,291,888; 5,303,705; 5,307,807; 5,309,095; 5,311,129; 5,323,777; 5,325,862; 5,326,745; 5,339,811; 5,417,211; 5,418,512; 5,442,289; 5,447,154; 5,458,142; 5,469,057; 5,476,438; 5,496,798; 5,513,649; 5,515,301; 5,552,375; 5,579,241; 5,594,849; 5,600,243; 5,601,081; 5,617,856; 5,626,145; 5,656,937; 5,671,740; 5,682,889; 5,701,909; 5,706,402; 5,706,811; 5,729,046; 5,743,854; 5,743,860; 5,752,514; 5,752,911; 5,755,227; 5,761,332; 5,762,611; 5,767,043; 5,771,261; 5,771,893; 5,771,894; 5,797,853; 5,813,993; 5,815,413; 5,842,986; 5,857,978; 5,885,976; 5,921,245; 5,938,598; 5,938,688; 5,970,499; 6,002,254; 6,011,991; 6,023,161; 6,066,084; 6,069,369; 6,080,164; 6,099,319; 6,144,872;

6,154,026; 6,155,966; 6,167,298; 6,167,311; 6,195,576;
6,230,037; 6,239,145; 6,263,189; 6,290,638; 6,354,087;
6,356,079; 6,370,414; 6,374,131; 6,385,479; 6,418,344;
6,442,948; 6,470,220; 6,488,617; 6,516,246; 6,526,415;
6,529,759; 6,538,436; 6,539,245; 6,539,263; 6,544,170;
6,547,746; 6,557,558; 6,587,729; 6,591,132; 6,609,030;
6,611,698; 6,648,822; 6,658,287; 6,665,552; 6,665,553;
6,665,562; 6,684,098; 6,687,525; 6,695,761; 6,697,660;
6,708,051; 6,708,064; 6,708,184; 6,725,080; 6,735,460;
6,774,929; 6,785,409; 6,795,724; 6,804,661; 6,815,949;
6,853,186; 6,856,830; 6,873,872; 6,876,196; 6,885,192;
6,907,280; 6,926,921; 6,947,790; 6,978,179; 6,980,863;
6,983,184; 6,983,264; 6,996,261; 7,022,083; 7,023,206;
7,024,247; 7,035,686; 7,038,450; 7,039,266; 7,039,547;
7,053,610; 7,062,391; 7,092,748; 7,105,824; 7,116,102;
7,120,486; 7,130,675; 7,145,333; 7,171,339; 7,176,680;
7,177,675; 7,183,381; 7,186,209; 7,187,169; 7,190,826;
7,193,413; 7,196,514; 7,197,352; 7,199,708; 7,209,787;
7,218,104; 7,222,964; 7,224,282; 7,228,178; 7,231,254;
7,242,984; 7,254,500; 7,258,659; 7,269,516; 7,277,758;
7,280,861; 7,286,871; 7,313,442; 7,324,851; 7,334,892;
7,338,171; 7,340,125; 7,340,289; 7,346,395; 7,353,064;
7,353,065; 7,369,896; 7,371,365; 7,376,459; 7,394,246;
7,400,984; 7,403,809; 7,403,820; 7,409,321; 7,418,290;
7,420,033; 7,437,196; 7,440,789; 7,453,263; 7,454,387;
7,457,653; 7,461,045; 7,462,155; 7,463,024; 7,466,132;
7,468,350; 7,482,298; 7,489,964; 7,502,720; 7,539,528;
7,539,543; 7,553,810; 7,565,200; 7,565,809; 7,567,693;
7,570,054; 7,573,264; 7,573,268; 7,580,798; 7,603,174;
7,608,579; 7,613,502; 7,613,519; 7,613,520; 7,620,456;
7,623,927; 7,623,928; 7,625,340; 7,627,370; 7,647,098;
7,649,351; 7,653,433; 7,672,707; 7,676,263; 7,678,767;
7,697,979; 7,706,871; 7,715,894; 7,720,519; 7,729,740;
7,729,773; 7,733,973; 7,734,340; 7,737,687; 7,742,820;
7,746,979; 7,747,325; 7,747,326; 7,747,551; 7,756,564;
7,763,588; 7,769,424; 7,771,341; 7,792,575; 7,800,493;
7,801,591; 7,801,686; 7,831,305; 7,834,627; 7,835,787;
7,840,039; 7,840,248; 7,840,250; 7,853,329; 7,856,264;
7,860,552; 7,873,411; 7,881,760; 7,881,770; 7,882,135;
7,891,814; 7,892,764; 7,894,903; 7,895,033; 7,904,139;
7,904,507; 7,908,009; 7,912,530; 7,917,221; 7,917,225;
7,929,693; 7,930,035; 7,932,225; 7,933,727; 7,937,152;
7,945,304; 7,962,204; 7,974,787; 7,986,991; 7,988,969;
8,000,767; 8,000,794; 8,001,179; 8,005,894; 8,010,178;
8,014,870; 8,027,730; 8,029,553; 8,032,209; 8,036,736;
8,055,591; 8,059,879; 8,065,360; 8,069,125; 8,073,631;
8,082,215; 8,083,786; 8,086,563; 8,116,874; 8,116,877;
8,121,694; 8,121,695; 8,150,523; 8,150,796; 8,155,726;
8,160,273; 8,185,382; 8,190,248; 8,190,264; 8,195,593;
8,209,224; 8,212,556; 8,222,378; 8,224,433; 8,229,540;
8,239,029; 8,244,552; 8,244,553; 8,248,069; 8,249,316;
8,270,814; 8,280,514; 8,285,351; 8,290,596; 8,295,934;
8,301,222; 8,301,257; 8,303,636; 8,304,246; 8,305,078;
8,308,646; 8,315,703; 8,334,690; 8,335,715; 8,335,716;
8,337,404; 8,343,066; 8,346,331; 8,350,804; 8,354,438;
8,356,004; 8,364,271; 8,374,412; 8,374,696; 8,380,314;
8,380,316; 8,380,658; 8,386,312; 8,386,313; 8,388,530;
8,392,250; 8,392,251; 8,392,253; 8,392,254; 8,392,255;
8,396,545; 8,396,546; 8,396,744; 8,401,655; 8,406,838;
8,406,848; 8,412,337; 8,423,144; 8,423,297; 8,429,225;
8,431,537; 8,433,388; 8,433,414; 8,433,418; 8,439,845;
8,444,571; 8,445,021; 8,447,407; 8,456,164; 8,457,730;
8,463,374; 8,463,378; 8,463,386; 8,463,387; 8,464,288;
8,467,878; 8,473,345; 8,483,795; 8,484,081; 8,487,760;
8,492,336; 8,494,610; 8,494,857; 8,494,905; 8,498,697;
8,509,904; 8,519,705; 8,527,029; 8,527,035; 8,529,463;
8,532,756; 8,532,757; 8,533,042; 8,538,513; 8,538,536;

8,543,199; 8,548,786; 8,548,852; 8,553,956; 8,554,325;
8,559,645; 8,562,540; 8,562,548; 8,565,606; 8,568,231;
8,571,629; 8,574,279; 8,586,019; 8,587,304; 8,588,933;
8,591,419; 8,593,141; 8,600,493; 8,600,696; 8,603,790;
8,606,592; 8,612,005; 8,613,695; 8,613,905; 8,614,254;
8,614,873; 8,615,293; 8,615,479; 8,615,664; 8,618,799;
8,626,264; 8,628,328; 8,635,105; 8,648,017; 8,652,189;
8,655,428; 8,655,437; 8,655,817; 8,658,149; 8,660,649;
8,666,099; 8,679,009; 8,682,441; 8,690,748; 8,693,765;
8,700,167; 8,703,114; 8,706,205; 8,706,206; 8,706,241;
8,706,518; 8,712,512; 8,716,447; 8,721,695; 8,725,243;
8,725,668; 8,725,669; 8,725,796; 8,731,650; 8,733,290;
8,738,395; 8,762,065; 8,762,202; 8,768,427; 8,768,447;
8,781,197; 8,781,597; 8,786,624; 8,798,717; 8,814,923;
8,815,582; 8,825,167; 8,838,225; 8,838,247; 8,845,545;
8,849,390; 8,849,392; 8,855,775; 8,858,440; 8,868,173;
8,874,439; 8,888,702; 8,893,120; 8,903,494; 8,907,668;
8,914,119; 8,918,176; 8,922,376; 8,933,696; 8,934,965;
8,938,289; 8,948,849; 8,951,189; 8,951,192; 8,954,293;
8,955,010; 8,961,187; 8,974,365; 8,977,024; 8,977,110;
8,977,362; 8,993,623; 9,002,458; 9,014,811; 9,015,087;
9,020,576; 9,026,194; 9,026,218; 9,026,372; 9,031,658;
9,034,055; 9,034,923; 9,037,224; 9,042,074; 9,042,201;
9,042,988; 9,044,188; 9,053,516; 9,063,183; 9,064,036;
9,069,031; 9,072,482; 9,074,976; 9,079,940; 9,081,890;
9,095,266; 9,095,303; 9,095,618; 9,101,263; 9,101,276;
9,102,717; 9,113,801; 9,113,803; 9,116,201; 9,125,581;
9,125,788; 9,138,156; 9,142,185; 9,155,373; 9,161,715;
9,167,979; 9,173,609; 9,179,854; 9,179,875; 9,183,351;
9,192,300; 9,198,621; 9,198,707; 9,204,835; 9,211,076;
9,211,077; 9,213,074; 9,229,080; 9,230,539; 9,233,244;
9,238,150; 9,241,665; 9,242,067; 9,247,890; 9,247,911;
9,248,003; 9,248,288; 9,249,200; 9,249,234; 9,251,566;
9,254,097; 9,254,383; 9,259,482; 9,259,591; 9,261,573;
9,265,943; 9,265,965; 9,271,679; 9,280,784; 9,283,279;
9,284,353; 9,285,249; 9,289,595; 9,302,069; 9,309,296;
9,320,900; 9,329,758; 9,331,841; 9,332,939; 9,333,334;
9,336,535; 9,336,611; 9,339,227; 9,345,609; 9,351,651;
9,357,240; 9,357,298; 9,357,970; 9,358,393; 9,359,449;
9,364,462; 9,365,628; 9,367,738; 9,368,018; 9,370,309;
9,370,667; 9,375,573; 9,377,348; 9,377,515; 9,381,352;
9,383,208; 9,392,955; 9,394,347; 9,395,425; 9,396,669;
9,401,033; 9,402,558; 9,403,038; 9,405,366; 9,410,885;
9,411,033; 9,412,233; 9,415,222; 9,418,368; 9,421,373;
9,427,474; 9,438,650; 9,440,070; 9,445,730; 9,446,238;
9,448,289; 9,451,734; 9,451,899; 9,458,208; 9,460,400;
9,462,733; 9,463,327; 9,468,541; 9,471,978; 9,474,852;
9,480,845; 9,480,854; 9,483,117; 9,486,381; 9,486,389;
9,486,618; 9,486,632; 9,492,114; 9,495,684; 9,497,017;
9,498,134; 9,498,634; 9,500,722; 9,505,817; 9,517,031;
9,517,222; 9,519,981; 9,521,958; 9,534,044; 9,538,635;
9,539,118; 9,556,487; 9,558,558; 9,560,458; 9,560,967;
9,560,984; 9,560,986; 9,563,950; 9,568,564; 9,572,996;
9,579,035; 9,579,048; 9,582,925; 9,584,928; 9,588,203;
9,588,490; 9,592,384; 9,600,138; 9,604,073; 9,612,295;
9,618,591; 9,622,660; 9,622,675; 9,630,008; 9,642,553;
9,642,554; 9,643,019; 9,646,248; 9,649,501; 9,655,573;
9,659,186; 9,664,856; 9,665,824; 9,665,987; 9,675,292;
9,681,814; 9,682,232; 9,684,051; 9,685,600; 9,687,562;
9,694,178; 9,694,197; 9,713,428; 9,713,433; 9,713,444;
9,713,712; D627476; RE44097; RE46209; 20010009975;
20020103428; 20020103429; 20020158631; 20020173714;
20030004429; 20030013981; 20030018277; 20030081818;
20030093004; 20030097159; 20030105408; 20030158495;
20030199749; 20040019370; 20040034299; 20040092809;
20040127803; 20040186542; 20040193037; 20040210127;
20040210156; 20040263162; 20050015205; 20050033154;

20050043774; 20050059874; 20050216071; 20050256378;
20050283053; 20060074822; 20060078183; 20060100526;
20060135880; 20060225437; 20070005391; 20070036355;
20070038067; 20070043392; 20070049844; 20070083128;
20070100251; 20070165915; 20070167723; 20070191704;
20070197930; 20070239059; 20080001600; 20080021340;
20080091118; 20080167571; 20080249430; 20080304731;
20090018432; 20090082688; 20090099783; 20090149736;
20090179642; 20090216288; 20090299169; 20090312624;
20090318794; 20090319001; 20090319004; 20100010366;
20100030097; 20100049482; 20100056276; 20100069739;
20100092934; 20100094155; 20100113959; 20100131034;
20100174533; 20100197610; 20100219820; 20110015515;
20110015539; 20110046491; 20110082360; 20110110868;
20110150253; 20110182501; 20110217240; 20110218453;
20110270074; 20110301448; 20120021394; 20120143104;
20120150262; 20120191542; 20120232376; 20120249274;
20120253168; 20120271148; 20130012804; 20130013667;
20130066394; 20130072780; 20130096453; 20130150702;
20130165766; 20130211238; 20130245424; 20130251641;
20130255586; 20130304472; 20140005518; 20140058241;
20140062472; 20140077612; 20140101084; 20140121565;
20140135873; 20140142448; 20140155730; 20140159862;
20140206981; 20140243647; 20140243652; 20140245191;
20140249445; 20140249447; 20140271483; 20140275891;
20140276013; 20140276014; 20140276187; 20140276702;
20140277582; 20140279746; 20140296733; 20140297397;
20140300532; 20140303424; 20140303425; 20140303511;
20140316248; 20140323899; 20140328487; 20140330093;
20140330394; 20140330580; 20140335489; 20140336489;
20140336547; 20140343397; 20140343882; 20140348183;
20140350380; 20140354278; 20140357507; 20140357932;
20140357935; 20140358067; 20140364721; 20140370479;
20140371573; 20140371611; 20140378815; 20140378830;
20150005840; 20150005841; 20150008916; 20150011877;
20150017115; 20150018665; 20150018702; 20150018705;
20150018706; 20150019266; 20150025422; 20150025917;
20150026446; 20150030220; 20150033363; 20150044138;
20150065838; 20150065845; 20150069846; 20150072394;
20150073237; 20150073249; 20150080695; 20150080703;
20150080753; 20150080985; 20150088024; 20150088224;
20150091730; 20150091791; 20150096564; 20150099962;
20150105844; 20150112403; 20150119658; 20150119689;
20150119698; 20150119745; 20150123653; 20150133811;
20150133812; 20150133830; 20150140528; 20150141529;
20150141773; 20150148619; 20150150473; 20150150475;
20150151142; 20150154721; 20150154764; 20150157271;
20150161738; 20150174403; 20150174418; 20150178631;
20150178978; 20150182417; 20150186923; 20150192532;
20150196800; 20150201879; 20150202330; 20150206051;
20150206174; 20150212168; 20150213012; 20150213019;
20150213020; 20150215412; 20150216762; 20150219729;
20150219732; 20150220830; 20150223721; 20150226813;
20150227702; 20150230719; 20150230744; 20150231330;
20150231395; 20150231405; 20150238104; 20150248615;
20150253391; 20150257700; 20150264492; 20150272461;
20150272465; 20150283393; 20150289813; 20150289929;
20150293004; 20150294074; 20150297108; 20150297139;
20150297444; 20150297719; 20150304048; 20150305799;
20150305800; 20150305801; 20150306057; 20150306390;
20150309582; 20150313496; 20150313971; 20150315554;
20150317447; 20150320591; 20150324544; 20150324692;
20150327813; 20150328330; 20150335281; 20150335294;
20150335876; 20150335877; 20150343242; 20150359431;
20150360039; 20150366503; 20150370325; 20150374250;
20160000383; 20160005235; 20160008489; 20160008598;
20160008620; 20160008632; 20160012011; 20160012583;

20160015673; 20160019434; 20160019693; 20160022165;
20160022168; 20160022207; 20160022981; 20160023016;
20160029958; 20160029959; 20160029998; 20160030666;
20160030834; 20160038049; 20160038559; 20160038770;
20160048659; 20160048948; 20160048965; 20160051161;
20160051162; 20160055236; 20160058322; 20160063207;
20160063883; 20160066838; 20160070436; 20160073916;
20160073947; 20160081577; 20160081793; 20160082180;
20160082319; 20160084925; 20160086622; 20160095838;
20160097824; 20160100769; 20160103487; 20160103963;
20160109851; 20160113587; 20160116472; 20160116553;
20160120432; 20160120436; 20160120480; 20160121074;
20160128589; 20160128632; 20160129249; 20160131723;
20160135748; 20160139215; 20160140975; 20160143540;
20160143541; 20160148077; 20160148400; 20160151628;
20160157742; 20160157777; 20160157828; 20160158553;
20160162652; 20160164813; 20160166207; 20160166219;
20160168137; 20160170996; 20160170998; 20160171514;
20160174862; 20160174867; 20160175557; 20160175607;
20160184599; 20160198968; 20160203726; 20160204937;
20160205450; 20160206581; 20160206871; 20160206877;
20160210872; 20160213276; 20160219345; 20160220163;
20160220821; 20160222073; 20160223622; 20160223627;
20160224803; 20160235324; 20160238673; 20160239966;
20160239968; 20160240212; 20160240765; 20160242665;
20160242670; 20160250473; 20160256130; 20160257957;
20160262680; 20160275536; 20160278653; 20160278662;
20160278687; 20160278736; 20160279267; 20160287117;
20160287308; 20160287334; 20160287895; 20160299568;
20160300252; 20160300352; 20160302711; 20160302720;
20160303396; 20160303402; 20160306844; 20160313408;
20160313417; 20160313418; 20160321742; 20160324677;
20160324942; 20160334475; 20160338608; 20160339300;
20160346530; 20160357003; 20160360970; 20160361532;
20160361534; 20160371387; 20170000422; 20170014080;
20170020454; 20170021158; 20170021161; 20170027517;
20170032527; 20170039591; 20170039706; 20170041699;
20170042474; 20170042476; 20170042827; 20170043166;
20170043167; 20170045601; 20170052170; 20170053082;
20170053088; 20170053461; 20170053665; 20170056363;
20170056467; 20170056655; 20170065199; 20170065349;
20170065379; 20170065816; 20170066806; 20170079538;
20170079543; 20170080050; 20170080256; 20170085547;
20170085855; 20170086729; 20170087367; 20170091418;
20170095174; 20170100051; 20170105647; 20170107575;
20170108926; 20170119270; 20170119271; 20170120043;
20170131293; 20170133576; 20170133577; 20170135640;
20170140124; 20170143986; 20170146615; 20170146801;
20170147578; 20170148213; 20170148592; 20170150925;
20170151435; 20170151436; 20170154167; 20170156674;
20170165481; 20170168121; 20170168568; 20170172446;
20170173391; 20170178001; 20170178340; 20170180558;
20170181252; 20170182176; 20170188932; 20170189691;
20170190765; 20170196519; 20170197081; 20170198017;
20170199251; 20170202476; 20170202518; 20170206654;
20170209044; 20170209062; 20170209225; 20170209389;
and 20170212188.

Brain Entrainment—Brain entrainment, also referred to as brainwave synchronization and neural entrainment, refers to the capacity of the brain to naturally synchronize its brainwave frequencies with the rhythm of periodic external stimuli, most commonly auditory, visual, or tactile. Brainwave entrainment technologies are used to induce various brain states, such as relaxation or sleep, by creating stimuli that occur at regular, periodic intervals to mimic electrical cycles of the brain during the desired states, thereby "training" the brain to consciously alter states. Recurrent acoustic frequencies, flickering lights, or tactile vibrations are the most common examples of stimuli applied to generate different sensory responses. It is hypothesized that listening to these beats of certain frequencies one can induce a desired state of consciousness that corresponds with specific neural activity. Patterns of neural firing, measured in Hz, correspond with alertness states such as focused attention, deep sleep, etc.

Neural oscillations are rhythmic or repetitive electrochemical activity in the brain and central nervous system. Such oscillations can be characterized by their frequency, amplitude and phase. Neural tissue can generate oscillatory activity driven by mechanisms within individual neurons, as well as by interactions between them. They may also adjust frequency to synchronize with the periodic vibration of external acoustic or visual stimuli.

The term 'entrainment' has been used to describe a shared tendency of many physical and biological systems to synchronize their periodicity and rhythm through interaction. This tendency has been identified as specifically pertinent to the study of sound and music generally, and acoustic rhythms specifically. The most ubiquitous and familiar examples of neuromotor entrainment to acoustic stimuli is observable in spontaneous foot or finger tapping to the rhythmic beat of a song. Exogenous rhythmic entrainment, which occurs outside the body, has been identified and documented for a variety of human activities, which include the way people adjust the rhythm of their speech patterns to those of the subject with whom they communicate, and the rhythmic unison of an audience clapping. Even among groups of strangers, the rate of breathing, locomotive and subtle expressive motor movements, and rhythmic speech patterns have been observed to synchronize and entrain, in response to an auditory stimulus, such as a piece of music with a consistent rhythm. Furthermore, motor synchronization to repetitive tactile stimuli occurs in animals, including cats and monkeys as well as humans, with accompanying shifts in electroencephalogram (EEG) readings. Examples of endogenous entrainment, which occurs within the body, include the synchronizing of human circadian sleep-wake cycles to the 24-hour cycle of light and dark, and the frequency following response of humans to sounds and music.

Brainwaves, or neural oscillations, share the fundamental constituents with acoustic and optical waves, including frequency, amplitude and periodicity. The synchronous electrical activity of cortical neural ensembles can synchronize in response to external acoustic or optical stimuli and also entrain or synchronize their frequency and phase to that of a specific stimulus. Brainwave entrainment is a colloquialism for such 'neural entrainment', which is a term used to denote the way in which the aggregate frequency of oscillations produced by the synchronous electrical activity in ensembles of cortical neurons can adjust to synchronize with the periodic vibration of an external stimuli, such as a sustained acoustic frequency perceived as pitch, a regularly repeating pattern of intermittent sounds, perceived as rhythm, or of a regularly rhythmically intermittent flashing light.

Changes in neural oscillations, demonstrable through electroencephalogram (EEG) measurements, are precipitated by listening to music, which can modulate autonomic arousal ergotropically and trophotropically, increasing and decreasing arousal respectively. Musical auditory stimulation has also been demonstrated to improve immune function, facilitate relaxation, improve mood, and contribute to the alleviation of stress.

The Frequency following response (FFR), also referred to as Frequency Following Potential (FFP), is a specific response to hearing sound and music, by which neural oscillations adjust their frequency to match the rhythm of auditory stimuli. The use of sound with intent to influence cortical brainwave frequency is called auditory driving, by which frequency of neural oscillation is 'driven' to entrain with that of the rhythm of a sound source.

See, en.wikipedia.org/wiki/Brainwave_entrainment;

U.S. Pat. Nos. 5,070,399; 5,306,228; 5,409,445; 6,656,137; 7,749,155; 7,819,794; 7,988,613; 8,088,057; 8,167,784; 8,213,670; 8,267,851; 8,298,078; 8,517,909; 8,517,912; 8,579,793; 8,579,795; 8,597,171; 8,636,640; 8,638,950; 8,668,496; 8,852,073; 8,932,218; 8,968,176; 9,330,523; 9,357,941; 9,459,597; 9,480,812; 9,563,273; 9,609,453; 9,640,167; 9,707,372; 20050153268; 20050182287; 20060106434; 20060206174; 20060281543; 20070066403; 20080039677; 20080304691; 20100010289; 20100010844; 20100028841; 20100056854; 20100076253; 20100130812; 20100222640; 20100286747; 20100298624; 20110298706; 20110319482; 20120003615; 20120053394; 20120150545; 20130030241; 20130072292; 20130131537; 20130172663; 20130184516; 20130203019; 20130234823; 20130338738; 20140088341; 20140107401; 20140114242; 20140154647; 20140174277; 20140275741; 20140309484; 20140371516; 20150142082; 20150283019; 20150296288; 20150313496; 20150313949; 20160008568; 20160019434; 20160055842; 20160205489; 20160235980; 20160239084; 20160345901; 20170034638; 20170061760; 20170087330; 20170094385; 20170095157; 20170099713; 20170135597; and 20170149945.

Carter, J., and H. Russell. "A pilot investigation of auditory and visual entrainment of brain wave activity in learning disabled boys." Texas Researcher 4.1 (1993): 65-75;

Casciaro, Francesco, et al. "Alpha-rhythm stimulation using brain entrainment enhances heart rate variability in subjects with reduced HRV." World J. Neuroscience 3.04 (2013): 213;

Helfrich, Randolph F., et al. "Entrainment of brain oscillations by transcranial alternating current stimulation." Current Biology 24.3 (2014): 333-339;

Huang, Tina L., and Christine Charyton. "A comprehensive review of the psychological effects of brainwave entrainment." Alternative therapies in health and medicine 14.5 (2008): 38;

Joyce, Michael, and Dave Siever. "Audio-visual entrainment program as a treatment for behavior disorders in a school setting." J. Neurotherapy 4.2 (2000):9-25;

Keitel, Christian, Cliodhna Quigley, and Philipp Ruhnau. "Stimulus-driven brain oscillations in the alpha range: entrainment of intrinsic rhythms orfrequency-following response?" J. Neuroscience 34.31 (2014): 10137-10140;

Lakatos, Peter, et al. "Entrainment of neuronal oscillations as a mechanism of attentional selection." Science 320.5872 (2008): 110-113;

Mori, Toshio, and Shoichi Kai. "Noise-induced entrainment and stochastic resonance in human brain waves." Physical review letters 88.21 (2002): 218101;

Padmanabhan, R., A. J. Hildreth, and D. Laws. "A prospective, randomised, controlled study examining binaural beat audio and pre-operative anxiety in patients undergoing general anaesthesia for day case surgery." Anaesthesia 60.9 (2005):874-877;

Schalles, Matt D., and Jaime A. Pineda. "Musical sequence learning and EEG correlates of audiomotor processing." Behavioural neurology 2015 (2015). www.hindawi.comfjournals/bn/2015/638202/

Thaut, Michael H., David A. Peterson, and Gerald C. McIntosh. "Temporal entrainment of cognitive functions." Annals of the New York Academy of Sciences 1060.1 (2005): 243-254.

Thut, Gregor, Philippe G. Schyns, and Joachim Gross. "Entrainment of perceptually relevant brain oscillations by non-invasive rhythmic stimulation of the human brain." Frontiers in Psychology 2 (2011);

Trost, Wiebke, et al. "Getting the beat: entrainment of brain activity by musical rhythm and pleasantness." NeuroImage 103 (2014): 55-64;

Will, Udo, and Eric Berg. "Brain wave synchronization and entrainment to periodic acoustic stimuli." Neuroscience letters 424.1 (2007): 55-60; and Zhuang, Tianbao, Hong Zhao, and Zheng Tang. "A study of brainwave entrainment based on EEG brain dynamics." Computer and information science 2.2 (2009): 80.

A baseline correction of event-related time-frequency measure may be made to take pre-event baseline activity into consideration. In general, a baseline period is defined by the average of the values within a time window preceding the time-locking event. There are at least four common methods for baseline correction in time-frequency analysis. The methods include various baseline value normalizations. See, Spencer K M, Nestor P G, Perlmutter R, et al. Neural synchrony indexes disordered perception and cognition in schizophrenia. Proc Natl Acad Sci USA. 2004; 101: 17288-17293;

Hoogenboom N, Schoffelen J M, Oostenveld R, Parkes L M, Fries P. Localizing human visual gamma-band activity in frequency, time and space. Neuroimage. 2006; 29:764-773;

Le Van Quyen M, Foucher J, Lachaux J, et al. Comparison of Hilbert transform and wavelet methods for the analysis of neuronal synchrony. J Neurosci Methods. 2001; 111: 83-98, Lachaux J P, Rodriguez E, Martinerie J, Varela F J. Measuring phase synchrony in brain signals. Hum Brain Mapp. 1999; 8:194-208, Rodriguez E, George N, Lachaux J P, Martinerie J, Renault B, Varela F J. Perception's shadow: long-distance synchronization of human brain activity. Nature. 1999; 397: 430-433., Canolty R T, Edwards E, Dalal S S, et al. High gamma power is phase-locked to theta oscillations in human neocortex. Science. 2006; 313:1626-1628.

The question of whether different emotional states are associated with specific patterns of physiological response has long being a subject of neuroscience research See, for example:

James W (1884.) What is an emotion? Mind 9:188-205; Lacey J I, Bateman D E, Vanlehn R (1953) Autonomic response specificity; an experimental study. Psychosom Med 15: 8-21;

Levenson R W, Heider K, Ekman P, Friesen W V (1992) Emotion and Autonomic Nervous-System Activity in the Minangkabau of West Sumatra. J Pers Soc Psychol 62:972-988.

Some studies have indicated that the physiological correlates of emotions are likely to be found in the central nervous system (CNS). See, for example:

Buck R (1999) The biological affects: A typology. Psychological Review 106:301-336; Izard C E (2007) Basic Emotions, Natural Kinds, Emotion Schemas, and a New Paradigm. Perspect Psychol Sci 2: 260-280;

Panksepp J (2007) Neurologizing the Psychology of Affects How Appraisal-Based Constructivism and Basic Emotion Theory Can Coexist. Perspect Psychol Sci 2: 281-296.

Electroencephalograms (EEG) and functional Magnetic Resonance Imaging, fMRI have been used to study specific brain activity associated with different emotional states. Mauss and Robinson, in their review paper, have indicated that "emotional state is likely to involve circuits rather than any brain region considered in isolation" (Mauss I B, Robinson M D (2009) Measures of emotion: A review. Cogn Emot 23: 209-237.)

The amplitude, latency from the stimulus, and covariance (in the case of multiple electrode sites) of each component can be examined in connection with a cognitive task (ERP) or with no task (EP). Steady-state visually evoked potentials (SSVEPs) use a continuous sinusoidally-modulated flickering light, typically superimposed in front of a TV monitor displaying a cognitive task. The brain response in a narrow frequency band containing the stimulus frequency is measured. Magnitude, phase, and coherence (in the case of multiple electrode sites) may be related to different parts of the cognitive task. Brain entrainment may be detected through EEG or MEG activity.

Brain entrainment may be detected through EEG or MEG activity. See:

Abeln, Vera, et al. "Brainwave entrainment for better sleep and post-sleep state of young elite soccer players-A pilot study." European J. Sport science 14.5 (2014): 393-402;

Acton, George. "Methods for independent entrainment of visual field zones." U.S. Pat. No. 9,629,976. 25 Apr. 2017;

Albouy, Philippe, et al. "Selective entrainment of theta oscillations in the dorsal stream causally enhances auditory working memory performance." Neuron 94.1 (2017): 193-206.

Amengual, J., et al. "P018 Local entrainment and distribution across cerebral networks of natural oscillations elicited in implanted epilepsy patients by intracranial stimulation: Paving the way to develop causal connectomics of the healthy human brain." Clin. Neurophysiology 128.3 (2017): e18;

Argento, Emanuele, et al. "Augmented Cognition via Brainwave Entrainment in Virtual Reality: An Open, Integrated Brain Augmentation in a Neuroscience System Approach." Augmented Human Research 2.1 (2017): 3;

Bello, Nicholas P. "Altering Cognitive and Brain States Through Cortical Entrainment." (2014); Costa-Faidella, Jordi, Elyse S. Sussman, and Carles Escera. "Selective entrainment of brain oscillations drives auditory perceptual organization." NeuroImage (2017);

Börgers, Christoph. "Entrainment by Excitatory Input Pulses." An Introduction to Modeling Neuronal Dynamics. Springer International Publishing, 2017. 183-192;

Calderone, Daniel J., et al. "Entrainment of neural oscillations as a modifiable substrate of attention." Trends in cognitive sciences 18.6 (2014): 300-309;

Casciaro, Francesco, et al. "Alpha-rhythm stimulation using brain entrainment enhances heart rate variability in subjects with reduced HRV." World J. Neuroscience 3.04 (2013): 213;

Chang, Daniel Wonchul. "Method and system for brain entrainment." U.S. Pat. No. 8,636,640. 28 Jan. 2014;

Colzato, Lorenza S., Amengual, Julia L., et al. "Local entrainment of oscillatory activity induced by direct brain stimulation in humans." Scientific Reports 7 (2017);

Conte, Elio, et al. "A Fast Fourier Transform analysis of time series data of heart rate variability during alfa-rhythm stimulation in brain entrainment." NeuroQuantology 11.3 (2013);

Dikker, Suzanne, et al. "Brain-to-brain synchrony tracks real-world dynamic group interactions in the classroom." Current Biology 27.9 (2017): 1375-1380;

Ding, Nai, and Jonathan Z. Simon. "Cortical entrainment to continuous speech: functional roles and interpretations." Frontiers in human neuroscience 8 (2014); Doherty, Cormac. "A comparison of alpha brainwave entrainment, with and without musical accompaniment." (2014);

Falk, Simone, Cosima Lanzilotti, and Daniele Schon. "Tuning neural phase entrainment to speech." J. Cognitive Neuroscience (2017);

Gao, Junling, et al. "Entrainment of chaotic activities in brain and heart during MBSR mindfulness training." Neuroscience letters 616 (2016): 218-223;

Gooding-Williams, Gerard, Hongfang Wang, and Klaus Kessler. "THETA-Rhythm Makes the World Go Round: Dissociative Effects of TMS Theta Versus Alpha Entrainment of Right pTPJ on Embodied Perspective Transformations." Brain Topography (2017): 1-4;

Hanslmayr, Simon, Jonas Matuschek, and Marie-Christin Fellner. "Entrainment of prefrontal beta oscillations induces an endogenous echo and impairs memory formation." Current Biology 24.8 (2014):904-909;

Heideman, Simone G., Erik S. te Woerd, and Peter Praamstra. "Rhythmic entrainment of slow brain activity preceding leg movements." Clin. Neurophysiology 126.2 (2015):348-355;

Helfrich, Randolph F., et al. "Entrainment of brain oscillations by transcranial alternating current stimulation." Current Biology 24.3 (2014): 333-339;

Henry, Molly J., et al. "Aging affects the balance of neural entrainment and top-down neural modulation in the listening brain." Nature Communications 8 (2017): ncomms15801;

Horr, Ninja K., Maria Wimber, and Massimiliano Di Luca. "Perceived time and temporal structure: Neural entrainment to isochronous stimulation increases duration estimates." Neuroimage 132 (2016): 148-156;

Irwin, Rosie. "Entraining Brain Oscillations to Influence Facial Perception." (2015);

Kalyan, Ritu, and Bipan Kaushal. "Binaural Entrainment and Its Effects on Memory." (2016);

Keitel, Anne, et al. "Auditory cortical delta-entrainment interacts with oscillatory power in multiple fronto-parietal networks." NeuroImage 147 (2017):32-42;

Keitel, Christian, Cliodhna Quigley, and Philipp Ruhnau. "Stimulus-driven brain oscillations in the alpha range: entrainment of intrinsic rhythms or frequency-following response?" J. Neuroscience 34.31 (2014): 10137-10140;

Koelsch, Stefan. "Music-evoked emotions: principles, brain correlates, and implications for therapy." Annals of the New York Academy of Sciences 1337.1 (2015): 193-201;

Kosem, Anne, et al. "Neural entrainment reflects temporal predictions guiding speech comprehension." the Eighth Annual Meeting of the Society for the Neurobiology of Language (SNL 2016). 2016;

Lee, Daniel Keewoong, Dongyeup Daniel Synn, and Daniel Chesong Lee. "Intelligent earplug system." U.S. patent application Ser. No. 15/106,989;

Lefournour, Joseph, Ramaswamy Palaniappan, and Ian V. McLoughlin. "Inter-hemispheric and spectral power analyses of binaural beat effects on the brain." Matters 2.9 (2016): e201607000001;

Mai, Guangting, James W. Minett, and William S-Y. Wang. "Delta, theta, beta, and gamma brain oscillations index levels of auditory sentence processing." Neuroimage 133 (2016):516-528;

Marconi, Pier Luigi, et al. "The phase amplitude coupling to assess brain network system integration." Medical Measurements and Applications (MeMeA), 2016 IEEE International Symposium on. IEEE, 2016;

McLaren, Elgin-Skye, and Alissa N. Antle. "Exploring and Evaluating Sound for Helping Children Self-Regulate with a Brain-Computer Application." Proceedings of the 2017 Conference on Interaction Design and Children. ACM, 2017;

Moisa, Marius, et al. "Brain network mechanisms underlying motor enhancement by transcranial entrainment of gamma oscillations." J. Neuroscience 36.47 (2016): 12053-12065;

Molinaro, Nicola, et al. "Out-of-synchrony speech entrainment in developmental dyslexia." Human brain mapping 37.8 (2016):2767-2783;

Moseley, Ralph. "Immersive brain entrainment in virtual worlds: actualizing meditative states." Emerging Trends and Advanced Technologies for Computational Intelligence. Springer International Publishing, 2016.315-346;

Neuling, Toralf, et al. "Friends, not foes: magnetoencephalography as a tool to uncover brain dynamics during transcranial alternating current stimulation." Neuroimage 118 (2015): 406-413;

Notbohm, Annika, Jürgen Kurths, and Christoph S. Herrmann. "Modification of brain oscillations via rhythmic light stimulation provides evidence for entrainment but not for superposition of event-related responses." Frontiers in human neuroscience 10 (2016);

Nozaradan, S., et al. "P943: Neural entrainment to musical rhythms in the human auditory cortex, as revealed by intracerebral recordings." Clin. Neurophysiology 125 (2014): S299;

Palaniappan, Ramaswamy, et al. "Improving the feature stability and classification performance of bimodal brain and heart biometrics." Advances in Signal Processing and Intelligent Recognition Systems. Springer, Cham, 2016. 175-186;

Palaniappan, Ramaswamy, Somnuk Phon-Amnuaisuk, and Chikkannan Eswaran. "On the binaural brain entrainment indicating lower heart rate variability." Int. J. Cardiol 190 (2015): 262-263;

Papagiannakis, G., et al. A virtual reality brainwave entrainment method for human augmentation applications. Technical Report, FORTH-ICS/TR-458, 2015;

Park, Hyojin, et al. "Frontal top-down signals increase coupling of auditory low-frequency oscillations to continuous speech in human listeners." Current Biology 25.12 (2015): 1649-1653;

Perez, Alejandro, Manuel Carreiras, and Jon Andoni Duhabeitia. "Brain-to-brain entrainment: EEG interbrain synchronization while speaking and listening." Scientific Reports 7 (2017);

Riecke, Lars, Alexander T. Sack, and Charles E. Schroeder. "Endogenous delta/theta sound-brain phase entrainment accelerates the buildup of auditory streaming." Current Biology 25.24 (2015): 3196-3201;

Spaak, Eelke, Floris P. de Lange, and Ole Jensen. "Local entrainment of alpha oscillations by visual stimuli causes cyclic modulation of perception." J. Neuroscience 34.10 (2014):3536-3544;

Thaut, Michael H. "The discovery of human auditory-motor entrainment and its role in the development of neurologic music therapy." Progress in brain research 217 (2015): 253-266;

Thaut, Michael H., Gerald C. McIntosh, and Volker Hoemberg. "Neurobiological foundations of neurologic music therapy: rhythmic entrainment and the motor system." Frontiers in psychology 5 (2014);

Thut, G. "T030 Guiding TMS by EEG/MEG to interact with oscillatory brain activity and associated functions." Clin. Neurophysiology 128.3 (2017): e9; Trevino, Guadalupe Villarreal, et al. "The Effect of Audio Visual Entrainment on Pre-Attentive Dysfunctional Processing to Stressful Events in Anxious Individuals." Open J. Medical Psychology 3.05 (2014): 364; Trost, Wiebke, et al. "Getting the beat: entrainment of brain activity by musical rhythm and pleasantness." NeuroImage 103 (2014): 55-64;

Tsai, Shu-Hui, and Yue-Der Lin. "Autonomie feedback with brain entrainment." Awareness Science and Technology and Ubi-Media Computing (iCAST-UMEDIA), 2013 International Joint Conference on. IEEE, 2013;

Vossen, Alexandra, Joachim Gross, and Gregor Thut. "Alpha power increase after transcranial alternating current stimulation at alpha frequency (α-tACS) reflects plastic changes rather than entrainment." Brain Stimulation 8.3 (2015): 499-508;

Witkowski, Matthias, et al. "Mapping entrained brain oscillations during transcranial alternating current stimulation (tACS)." Neuroimage 140 (2016): 89-98;

Zlotnik, Anatoly, Raphael Nagao, and Istvan Z. Kiss Jr-Shin Li. "Phase-selective entrainment of nonlinear oscillator ensembles." Nature Communications 7 (2016).

The entrainment hypothesis (Thut and Miniussi, 2009; Thut et al., 2011a, 2012), suggests the possibility of inducing a particular oscillation frequency in the brain using an external oscillatory force (e.g., rTMS, but also tACS). The physiological basis of oscillatory cortical activity lies in the timing of the interacting neurons; when groups of neurons synchronize their firing activities, brain rhythms emerge, network oscillations are generated, and the basis for interactions between brain areas may develop (Buzsaki, 2006). Because of the variety of experimental protocols for brain stimulation, limits on descriptions of the actual protocols employed, and limited controls, consistency of reported studies is lacking, and extrapolability is limited. Thus, while there is various consensus in various aspects of the effects of extra cranial brain stimulation, the results achieved have a degree of uncertainty dependent on details of implementation. On the other hand, within a specific experimental protocol, it is possible to obtain statistically significant and repeatable results. This implies that feedback control might be effective to control implementation of the stimulation for a given purpose; however, studies that employ feedback control are lacking.

Different cognitive states are associated with different oscillatory patterns in the brain (Buzsaki, 2006; Canolty and Knight, 2010; Varela et al., 2001). Thut et al. (2011b) directly tested the entrainment hypothesis by means of a concurrent EEG-TMS experiment. They first determined the individual source of the parietal-occipital alpha modulation and the individual alpha frequency (magnetoencephalography study). They then applied rTMS at the individual alpha power while recording the EEG activity at rest. The results confirmed the three predictions of the entrainment hypothesis: the induction of a specific frequency after TMS, the enhancement of oscillation during TMS stimulation due to synchronization, and a phase alignment of the induced frequency and the ongoing activity (Thut et al., 2011b).

If associative stimulation is a general principle for human neural plasticity in which the timing and strength of activation are critical factors, it is possible that synchronization within or between areas using an external force to phase/align oscillations can also favor efficient communication and associative plasticity (or alter communication). In this respect associative, cortico-cortical stimulation has been shown to enhance coherence of oscillatory activity between the stimulated areas (Plewnia et al., 2008).

In coherence resonance (Longtin, 1997), the addition of a certain amount of noise in an excitable system results in the most coherent and proficient oscillatory responses. The brain's response to external timing-embedded stimulation can result in a decrease in phase variance and an enhanced alignment (clustering) of the phase components of the ongoing EEG activity (entraining, phase resetting) that can change the signal-to-noise ratio and increase (or decrease) signal efficacy.

If one considers neuron activity within the brain as a set of loosely coupled oscillators, then the various parameters that might be controlled include the size of the region of neurons, frequency of oscillation, resonant frequency or time-constant, oscillator damping, noise, amplitude, coupling to other oscillators, and of course, external influences that may include stimulation and/or power loss. In a human brain, pharmacological intervention may be significant. For example, drugs that alter excitability, such as caffeine, neurotransmitter release and reuptake, nerve conductance, etc. can all influence operation of the neural oscillators. Likewise, sub-threshold external stimulation effects, including DC, AC and magnetic electromagnetic effects, can also influence operation of the neural oscillators.

Phase resetting or shifting can synchronize inputs and favor communication and, eventually, Hebbian plasticity (Hebb, 1949). Thus, rhythmic stimulation may induce a statistically higher degree of coherence in spiking neurons, which facilitates the induction of a specific cognitive process (or hinders that process). Here, the perspective is slightly different (coherence resonance), but the underlining mechanisms are similar to the ones described so far (stochastic resonance), and the additional key factor is the repetition at a specific rhythm of the stimulation.

In the 1970's, the British biophysicist and psychobiologist, C. Maxwell Cade, monitored the brainwave patterns of advanced meditators and 300 of his students. Here he found that the most advanced meditators have a specific brainwave pattern that was different from the rest of his students. He noted that these meditators showed high activity of alpha brainwaves accompanied by beta, theta and even delta waves that were about half the amplitude of the alpha waves. See, Cade "The Awakened Mind: Biofeedback and the Development of Higher States of Awareness" (Dell, 1979). Anna Wise extended Cade's studies, and found that extraordinary achievers which included composers, inventors, artists, athletes, dancers, scientists, mathematicians, CEO's and presidents of large corporations have brainwave patterns differ from average performers, with a specific balance between Beta, Alpha, Theta and Delta brainwaves where Alpha had the strongest amplitude. See, Anna Wise, "The High-Performance Mind: Mastering Brainwaves for Insight, Healing, and Creativity".

Entrainment is plausible because of the characteristics of the demonstrated EEG responses to a single TMS pulse, which have a spectral composition which resemble the spontaneous oscillations of the stimulated cortex. For example, TMS of the "resting" visual (Rosanova et al., 2009) or motor cortices (Veniero et al., 2011) triggers alpha-waves, the natural frequency at the resting state of both types of cortices. With the entrainment hypothesis, the noise generation framework moves to a more complex and extended level in which noise is synchronized with on-going activity.

Nevertheless, the model to explain the outcome will not change, stimulation will interact with the system, and the final result will depend on introducing or modifying the noise level. The entrainment hypothesis makes clear predictions with respect to online repetitive TMS paradigms' frequency engagement as well as the possibility of inducing phase alignment, i.e., a reset of ongoing brain oscillations via external spTMS (Thut et al., 2011a, 2012; Veniero et al., 2011). The entrainment hypothesis is superior to the localization approach in gaining knowledge about how the brain works, rather than where or when a single process occurs. TMS pulses may phase-align the natural, ongoing oscillation of the target cortex. When additional TMS pulses are delivered in synchrony with the phase-aligned oscillation (i.e., at the same frequency), further synchronized phase-alignment will occur, which will bring the oscillation of the target area in resonance with the TMS train. Thus, entrainment may be expected when TMS is frequency-tuned to the underlying brain oscillations (Veniero et al., 2011).

Binaural Beats—Binaural beats are auditory brainstem responses which originate in the superior olivary nucleus of each hemisphere. They result from the interaction of two different auditory impulses, originating in opposite ears, below 1000 Hz and which differ in frequency between one and 30 Hz. For example, if a pure tone of 400 Hz is presented to the right ear and a pure tone of 410 Hz is presented simultaneously to the left ear, an amplitude modulated standing wave of 10 Hz, the difference between the two tones, is experienced as the two wave forms mesh in and out of phase within the superior olivary nuclei. This binaural beat is not heard in the ordinary sense of the word (the human range of hearing is from 20-20,000 Hz). It is perceived as an auditory beat and theoretically can be used to entrain specific neural rhythms through the frequency-following response (FFR)—the tendency for cortical potentials to entrain to or resonate at the frequency of an external stimulus. Thus, it is theoretically possible to utilize a specific binaural-beat frequency as a consciousness management technique to entrain a specific cortical rhythm. The binaural-beat appears to be associated with an electroencephalographic (EEG) frequency-following response in the brain.

Uses of audio with embedded binaural beats that are mixed with music or various pink or background sound are diverse. They range from relaxation, meditation, stress reduction, pain management, improved sleep quality, decrease in sleep requirements, super learning, enhanced creativity and intuition, remote viewing, telepathy, and out-of-body experience and lucid dreaming. Audio embedded with binaural beats is often combined with various meditation techniques, as well as positive affirmations and visualization.

When signals of two different frequencies are presented, one to each ear, the brain detects phase differences between these signals. Under natural circumstances a detected phase difference would provide directional information. The brain processes this anomalous information differently when these phase differences are heard with stereo headphones or speakers. A perceptual integration of the two signals takes place, producing the sensation of a third "beat" frequency. The difference between the signals waxes and wanes as the two different input frequencies mesh in and out of phase. As a result of these constantly increasing and decreasing differences, an amplitude-modulated standing wave—the binaural beat—is heard. The binaural beat is perceived as a fluctuating rhythm at the frequency of the difference between the two auditory inputs. Evidence suggests that the binaural beats are generated in the brainstem's superior olivary nucleus, the first site of contralateral integration in the auditory system. Studies also suggest that the frequency-following response originates from the inferior colliculus. This activity is conducted to the cortex where it can be recorded by scalp electrodes. Binaural beats can easily be heard at the low frequencies (<30 Hz) that are characteristic of the EEG spectrum.

Synchronized brain waves have long been associated with meditative and hypnogogic states, and audio with embedded binaural beats has the ability to induce and improve such states of consciousness. The reason for this is physiological. Each ear is "hardwired" (so to speak) to both hemispheres of the brain. Each hemisphere has its own olivary nucleus (sound-processing center) which receives signals from each ear. In keeping with this physiological structure, when a binaural beat is perceived there are actually two standing waves of equal amplitude and frequency present, one in each hemisphere. So, there are two separate standing waves entraining portions of each hemisphere to the same frequency. The binaural beats appear to contribute to the hemispheric synchronization evidenced in meditative and hypnogogic states of consciousness. Brain function is also enhanced through the increase of cross-collosal communication between the left and right hemispheres of the brain. en.wikipedia.org/wiki/Beat_(acoustics) #Binaural_beats.

Oster, G (October 1973). "Auditory beats in the brain". Scientific American. 229 (4): 94-102. See:

Lane, J. D., Kasian, S. J., Owens, J. E., & Marsh, G. R. (1998). Binaural auditory beats affect vigilance performance and mood. Physiology & behavior, 63(2), 249-252;

Foster, D. S. (1990). EEG and subjective correlates of alpha frequency binaural beats stimulation combined with alpha biofeedback (Doctoral dissertation, Memphis State University);

Kasprzak, C. (2011). Influence of binaural beats on EEG signal. Acta Physica Polonica A, 119(6A), 986-990;

Pratt, H., Starr, A., Michalewski, H. J., Dimitrijevic, A., Bleich, N., & Mittelman, N. (2009). Cortical evoked potentials to an auditory illusion: binaural beats. Clinical Neurophysiology, 120(8), 1514-1524;

Pratt, H., Starr, A., Michalewski, H. J., Dimitrijevic, A., Bleich, N., & Mittelman, N. (2010). A comparison of auditory evoked potentials to acoustic beats and to binaural beats. Hearing research, 262(1), 34-44;

Padmanabhan, R., Hildreth, A. J., & Laws, D. (2005). A prospective, randomised, controlled study examining binaural beat audio and pre-operative anxiety in patients undergoing general anaesthesia for day case surgery. Anaesthesia, 60(9), 874-877;

Reedijk, S. A., Bolders, A., & Hommel, B. (2013). The impact of binaural beats on creativity. Front. in human neuroscience, 7;

Atwater, F. H. (2001). Binaural beats and the regulation of arousal levels. Proceedings of the TANS, 11;

Hink, R. F., Kodera, K., Yamada, O., Kaga, K., & Suzuki, J. (1980). Binaural interaction of a beating frequency-following response. Audiology, 19(1), 36-43;

Gao, X., Cao, H., Ming, D., Qi, H., Wang, X., Wang, X., & Zhou, P. (2014). Analysis of EEG activity in response to binaural beats with different frequencies. International Journal of Psychophysiology, 94(3), 399-406;

Sung, H. C., Lee, W. L., Li, H. M., Lin, C. Y., Wu, Y. Z., Wang, J. J., & Li, T. L. (2017). Familiar Music Listening with Binaural Beats for Older People with Depressive Symptoms in Retirement Homes. Neuropsychiatry, 7(4);

Colzato, L. S., Barone, H., Sellaro, R., & Hommel, B. (2017). More attentional focusing through binaural beats: evidence from the global-local task. Psychological research, 81(1), 271-277;

Mortazavi, S. M. J., Zahraei-Moghadam, S. M., Masoumi, S., Rafati, A., Haghani, M., Mortazavi, S. A. R., & Zehtabian, M. (2017). Short Term Exposure to Binaural Beats Adversely Affects Learning and Memory in Rats. Journal of Biomedical Physics and Engineering.

Brain Entrainment Frequency Following Response (or FFR). See, "Stimulating the Brain with Light and Sound," Transparent Corporation, Neuroprogrammer™3, www.transparentcorp.com/products/np/entrainment.php.

Isochronic Tones—Isochronic tones are regular beats of a single tone that are used alongside monaural beats and binaural beats in the process called brainwave entrainment. At its simplest level, an isochronic tone is a tone that is being turned on and off rapidly. They create sharp, distinctive pulses of sound. www.livingflow.net/isochronic-tones-work/;

Schulze, H. H. (1989). The perception of temporal deviations in isochronic patterns. Attention, Perception, & Psychophysics, 45(4), 291-296;

Oster, G. (1973). Auditory beats in the brain. Scientific American, 229(4), 94-102;

Huang, T. L., & Charyton, C. (2008). A comprehensive review of the psychological effects of brainwave entrainment. Alternative therapies in health and medicine, 14(5), 38;

Trost, W., Fruhholz, S., Schon, D., Labbe, C., Pichon, S., Grandjean, D., & Vuilleumier, P. (2014). Getting the beat: entrainment of brain activity by musical rhythm and pleasantness. NeuroImage, 103, 55-64;

Casciaro, F., Laterza, V., Conte, S., Pieralice, M., Federici, A., Todarello, O., . . . & Conte, E. (2013). Alpha-rhythm stimulation using brain entrainment enhances heart rate variability in subjects with reduced HRV. World Journal of Neuroscience, 3(04), 213;

Conte, E., Conte, S., Santacroce, N., Federici, A., Todarello, O., Orsucci, F., . . . & Laterza, V. (2013). A Fast Fourier Transform analysis of time series data of heart rate variability during alfa-rhythm stimulation in brain entrainment. NeuroQuantology, 11(3);

Doherty, C. (2014). A comparison of alpha brainwave entrainment, with and without musical accompaniment;

Moseley, R. (2015, July). Inducing targeted brain states utilizing merged reality systems. In Science and Information Conference (SAI), 2015 (pp. 657-663). IEEE.

Time-Frequency Analysis—Brian J. Roach and Daniel H. Mathalon, "Event-related EEG time-frequency analysis: an overview of measures and analysis of early gamma band phase locking in schizophrenia. Schizophrenia Bull. USA. 2008; 34:5:907-926, describes a mechanism for EEG time-frequency analysis. Fourier and wavelet transforms (and their inverse) may be performed on EEG signals.

See, U.S. Pat. Nos. 4,407,299; 4,408,616; 4,421,122; 4,493,327; 4,550,736; 4,557,270; 4,579,125; 4,583,190; 4,585,011; 4,610,259; 4,649,482; 4,705,049; 4,736,307; 4,744,029; 4,776,345; 4,792,145; 4,794,533; 4,846,190; 4,862,359; 4,883,067; 4,907,597; 4,924,875; 4,940,058; 5,010,891; 5,020,540; 5,029,082; 5,083,571; 5,092,341; 5,105,354; 5,109,862; 5,218,530; 5,230,344; 5,230,346; 5,233,517; 5,241,967; 5,243,517; 5,269,315; 5,280,791; 5,287,859; 5,309,917; 5,309,923; 5,320,109; 5,339,811; 5,339,826; 5,377,100; 5,406,956; 5,406,957; 5,443,073; 5,447,166; 5,458,117; 5,474,082; 5,555,889; 5,611,350; 5,619,995; 5,632,272; 5,643,325; 5,678,561; 5,685,313; 5,692,517; 5,694,939; 5,699,808; 5,752,521; 5,755,739; 5,771,261; 5,771,897; 5,794,623; 5,795,304; 5,797,840; 5,810,737; 5,813,993; 5,827,195; 5,840,040; 5,846,189; 5,846,208; 5,853,005; 5,871,517; 5,884,626; 5,899,867; 5,916,171; 5,995,868; 6,002,952; 6,011,990; 6,016,444; 6,021,345; 6,032,072; 6,044,292; 6,050,940; 6,052,619; 6,067,462; 6,067,467; 6,070,098; 6,071,246; 6,081,735; 6,097,980; 6,097,981; 6,115,631; 6,117,075; 6,129,681; 6,155,993; 6,157,850; 6,157,857; 6,171,258; 6,195,576; 6,196,972; 6,224,549; 6,236,872; 6,287,328; 6,292,688; 6,293,904; 6,305,943; 6,306,077; 6,309,342; 6,315,736; 6,317,627; 6,325,761; 6,331,164; 6,338,713; 6,343,229; 6,358,201; 6,366,813; 6,370,423; 6,375,614; 6,377,833; 6,385,486; 6,394,963; 6,402,520; 6,475,163; 6,482,165; 6,493,577; 6,496,724; 6,511,424; 6,520,905; 6,520,921; 6,524,249; 6,527,730; 6,529,773; 6,544,170; 6,546,378; 6,547,736; 6,547,746; 6,549,804; 6,556,861; 6,565,518; 6,574,573; 6,594,524; 6,602,202; 6,616,611; 6,622,036; 6,625,485; 6,626,676; 6,650,917; 6,652,470; 6,654,632; 6,658,287; 6,678,548; 6,687,525; 6,699,194; 6,709,399; 6,726,624; 6,731,975; 6,735,467; 6,743,182; 6,745,060; 6,745,156; 6,746,409; 6,751,499; 6,768,920; 6,798,898; 6,801,803; 6,804,661; 6,816,744; 6,819,956; 6,826,426; 6,843,774; 6,865,494; 6,875,174; 6,882,881; 6,886,964; 6,915,241; 6,928,354; 6,931,274; 6,931,275; 6,981,947; 6,985,769; 6,988,056; 6,993,380; 7,011,410; 7,014,613; 7,016,722; 7,037,260; 7,043,293; 7,054,454; 7,089,927; 7,092,748; 7,099,714; 7,104,963; 7,105,824; 7,123,955; 7,128,713; 7,130,691; 7,146,218; 7,150,710; 7,150,715; 7,150,718; 7,163,512; 7,164,941; 7,177,675; 7,190,995; 7,207,948; 7,209,788; 7,215,986; 7,225,013; 7,228,169; 7,228,171; 7,231,245; 7,254,433; 7,254,439; 7,254,500; 7,267,652; 7,269,456; 7,286,871; 7,288,066; 7,297,110; 7,299,088; 7,324,845; 7,328,053; 7,333,619; 7,333,851; 7,343,198; 7,367,949; 7,373,198; 7,376,453; 7,381,185; 7,383,070; 7,392,079; 7,395,292; 7,396,333; 7,399,282; 7,403,814; 7,403,815; 7,418,290; 7,429,247; 7,450,986; 7,454,240; 7,462,151; 7,468,040; 7,469,697; 7,471,971; 7,471,978; 7,489,958; 7,489,964; 7,491,173; 7,496,393; 7,499,741; 7,499,745; 7,509,154; 7,509,161; 7,509,163; 7,510,531; 7,530,955; 7,537,568; 7,539,532; 7,539,533; 7,547,284; 7,558,622; 7,559,903; 7,570,991; 7,572,225; 7,574,007; 7,574,254; 7,593,767; 7,594,122; 7,596,535; 7,603,168; 7,604,603; 7,610,094; 7,623,912; 7,623,928; 7,625,340; 7,630,757; 7,640,055; 7,643,655; 7,647,098; 7,654,948; 7,668,579; 7,668,591; 7,672,717; 7,676,263; 7,678,061; 7,684,856; 7,697,979; 7,702,502; 7,706,871; 7,706,992; 7,711,417; 7,715,910; 7,720,530; 7,727,161; 7,729,753; 7,733,224; 7,734,334; 7,747,325; 7,751,878; 7,754,190; 7,757,690; 7,758,503; 7,764,987; 7,771,364; 7,774,052; 7,774,064; 7,778,693; 7,787,946; 7,794,406; 7,801,592; 7,801,593; 7,803,118; 7,803,119; 7,809,433; 7,811,279; 7,819,812; 7,831,302; 7,853,329; 7,860,561; 7,865,234; 7,865,235; 7,878,965; 7,879,043; 7,887,493; 7,894,890; 7,896,807; 7,899,525; 7,904,144; 7,907,994;

7,909,771; 7,918,779; 7,920,914; 7,930,035; 7,938,782; 7,938,785; 7,941,209; 7,942,824; 7,944,551; 7,962,204; 7,974,696; 7,983,741; 7,983,757; 7,986,991; 7,993,279; 7,996,075; 8,002,553; 8,005,534; 8,005,624; 8,010,347; 8,019,400; 8,019,410; 8,024,032; 8,025,404; 8,032,209; 8,033,996; 8,036,728; 8,036,736; 8,041,136; 8,046,041; 8,046,042; 8,065,011; 8,066,637; 8,066,647; 8,068,904; 8,073,534; 8,075,499; 8,079,953; 8,082,031; 8,086,294; 8,089,283; 8,095,210; 8,103,333; 8,108,036; 8,108,039; 8,114,021; 8,121,673; 8,126,528; 8,128,572; 8,131,354; 8,133,172; 8,137,269; 8,137,270; 8,145,310; 8,152,732; 8,155,736; 8,160,689; 8,172,766; 8,177,726; 8,177,727; 8,180,420; 8,180,601; 8,185,207; 8,187,201; 8,190,227; 8,190,249; 8,190,251; 8,197,395; 8,197,437; 8,200,319; 8,204,583; 8,211,035; 8,214,007; 8,224,433; 8,236,005; 8,239,014; 8,241,213; 8,244,340; 8,244,475; 8,249,698; 8,271,077; 8,280,502; 8,280,503; 8,280,514; 8,285,368; 8,290,575; 8,295,914; 8,296,108; 8,298,140; 8,301,232; 8,301,233; 8,306,610; 8,311,622; 8,314,707; 8,315,970; 8,320,649; 8,323,188; 8,323,189; 8,323,204; 8,328,718; 8,332,017; 8,332,024; 8,335,561; 8,337,404; 8,340,752; 8,340,753; 8,343,026; 8,346,342; 8,346,349; 8,352,023; 8,353,837; 8,354,881; 8,356,594; 8,359,080; 8,364,226; 8,364,254; 8,364,255; 8,369,940; 8,374,690; 8,374,703; 8,380,296; 8,382,667; 8,386,244; 8,391,966; 8,396,546; 8,396,557; 8,401,624; 8,401,626; 8,403,848; 8,425,415; 8,425,583; 8,428,696; 8,437,843; 8,437,844; 8,442,626; 8,449,471; 8,452,544; 8,454,555; 8,461,988; 8,463,007; 8,463,349; 8,463,370; 8,465,408; 8,467,877; 8,473,024; 8,473,044; 8,473,306; 8,475,354; 8,475,368; 8,475,387; 8,478,389; 8,478,394; 8,478,402; 8,480,554; 8,484,270; 8,494,829; 8,498,697; 8,500,282; 8,500,636; 8,509,885; 8,509,904; 8,512,221; 8,512,240; 8,515,535; 8,519,853; 8,521,284; 8,525,673; 8,525,687; 8,527,435; 8,531,291; 8,538,512; 8,538,514; 8,538,705; 8,542,900; 8,543,199; 8,543,219; 8,545,416; 8,545,436; 8,554,311; 8,554,325; 8,560,034; 8,560,073; 8,562,525; 8,562,526; 8,562,527; 8,562,951; 8,568,329; 8,571,642; 8,585,568; 8,588,933; 8,591,419; 8,591,498; 8,597,193; 8,600,502; 8,606,351; 8,606,356; 8,606,360; 8,620,419; 8,628,480; 8,630,699; 8,632,465; 8,632,750; 8,641,632; 8,644,914; 8,644,921; 8,647,278; 8,649,866; 8,652,038; 8,655,817; 8,657,756; 8,660,799; 8,666,467; 8,670,603; 8,672,852; 8,680,991; 8,684,900; 8,684,922; 8,684,926; 8,688,209; 8,690,748; 8,693,756; 8,694,087; 8,694,089; 8,694,107; 8,700,137; 8,700,141; 8,700,142; 8,706,205; 8,706,206; 8,706,207; 8,708,903; 8,712,507; 8,712,513; 8,725,238; 8,725,243; 8,725,311; 8,725,669; 8,727,978; 8,728,001; 8,738,121; 8,744,563; 8,747,313; 8,747,336; 8,750,971; 8,750,974; 8,750,992; 8,755,854; 8,755,856; 8,755,868; 8,755,869; 8,755,871; 8,761,866; 8,761,869; 8,764,651; 8,764,652; 8,764,653; 8,768,447; 8,771,194; 8,775,340; 8,781,193; 8,781,563; 8,781,595; 8,781,597; 8,784,322; 8,786,624; 8,790,255; 8,790,272; 8,792,974; 8,798,735; 8,798,736; 8,801,620; 8,821,408; 8,825,149; 8,825,428; 8,827,917; 8,831,705; 8,838,226; 8,838,227; 8,843,199; 8,843,210; 8,849,390; 8,849,392; 8,849,681; 8,852,100; 8,852,103; 8,855,758; 8,858,440; 8,858,449; 8,862,196; 8,862,210; 8,862,581; 8,868,148; 8,868,163; 8,868,172; 8,868,174; 8,868,175; 8,870,737; 8,880,207; 8,880,576; 8,886,299; 8,888,672; 8,888,673; 8,888,702; 8,888,708; 8,898,037; 8,902,070; 8,903,483; 8,914,100; 8,915,741; 8,915,871; 8,918,162; 8,918,178; 8,922,788; 8,923,958; 8,924,235; 8,932,227; 8,938,301; 8,942,777; 8,948,834; 8,948,860; 8,954,146; 8,958,882; 8,961,386; 8,965,492; 8,968,195; 8,977,362; 8,983,591; 8,983,628; 8,983,629; 8,986,207; 8,989,835; 8,989,836; 8,996,112; 9,008,367; 9,008,754;

9,008,771; 9,014,216; 9,014,453; 9,014,819; 9,015,057; 9,020,576; 9,020,585; 9,020,789; 9,022,936; 9,026,202; 9,028,405; 9,028,412; 9,033,884; 9,037,224; 9,037,225; 9,037,530; 9,042,952; 9,042,958; 9,044,188; 9,055,871; 9,058,473; 9,060,671; 9,060,683; 9,060,695; 9,060,722; 9,060,746; 9,072,482; 9,078,577; 9,084,584; 9,089,310; 9,089,400; 9,095,266; 9,095,268; 9,100,758; 9,107,586; 9,107,595; 9,113,777; 9,113,801; 9,113,830; 9,116,835; 9,119,551; 9,119,583; 9,119,597; 9,119,598; 9,125,574; 9,131,864; 9,135,221; 9,138,183; 9,149,214; 9,149,226; 9,149,255; 9,149,577; 9,155,484; 9,155,487; 9,155,521; 9,165,472; 9,173,582; 9,173,610; 9,179,854; 9,179,876; 9,183,351 RE34015; RE38476; RE38749; RE46189; 20010049480; 20010051774; 20020035338; 20020055675; 20020059159; 20020077536; 20020082513; 20020085174; 20020091319; 20020091335; 20020099295; 20020099306; 20020103512; 20020107454; 20020112732; 20020117176; 20020128544; 20020138013; 20020151771; 20020177882; 20020182574; 20020183644; 20020193670; 20030001098; 20030009078; 20030023183; 20030028121; 20030032888; 20030035301; 20030036689; 20030046018; 20030055355; 20030070685; 20030093004; 20030093129; 20030100844; 20030120172; 20030130709; 20030135128; 20030139681; 20030144601; 20030149678; 20030158466; 20030158496; 20030158587; 20030160622; 20030167019; 20030171658; 20030171685; 20030176804; 20030181821; 20030185408; 20030195429; 20030216654; 20030225340; 20030229291; 20030236458; 20040002635; 20040006265; 20040006376; 20040010203; 20040039268; 20040059203; 20040059241; 20040064020; 20040064066; 20040068164; 20040068199; 20040073098; 20040073129; 20040077967; 20040079372; 20040082862; 20040082876; 20040097802; 20040116784; 20040116791; 20040116798; 20040116825; 20040117098; 20040143170; 20040144925; 20040152995; 20040158300; 20040167418; 20040181162; 20040193068; 20040199482; 20040204636; 20040204637; 20040204659; 20040210146; 20040220494; 20040220782; 20040225179; 20040230105; 20040243017; 20040254493; 20040260169; 20050007091; 20050010116; 20050018858; 20050025704; 20050033154; 20050033174; 20050038354; 20050043774; 20050075568; 20050080349; 20050080828; 20050085744; 20050096517; 20050113713; 20050119586; 20050124848; 20050124863; 20050135102; 20050137494; 20050148893; 20050148894; 20050148895; 20050149123; 20050182456; 20050197590; 20050209517; 20050216071; 20050251055; 20050256385; 20050256418; 20050267362; 20050273017; 20050277813; 20050277912; 20060004298; 20060009704; 20060015034; 20060041201; 20060047187; 20060047216; 20060047324; 20060058590; 20060074334; 20060082727; 20060084877; 20060089541; 20060089549; 20060094968; 20060100530; 20060102171; 20060111644; 20060116556; 20060135880; 20060149144; 20060153396; 20060155206; 20060155207; 20060161071; 20060161075; 20060161218; 20060167370; 20060167722; 20060173364; 20060184059; 20060189880; 20060189882; 20060200016; 20060200034; 20060200035; 20060204532; 20060206033; 20060217609; 20060233390; 20060235315; 20060235324; 20060241562; 20060241718; 20060251303; 20060258896; 20060258950; 20060265022; 20060276695; 20070007454; 20070016095; 20070016264; 20070021673; 20070021675; 20070032733; 20070032737; 20070038382; 20070060830; 20070060831; 20070066914; 20070083128; 20070093721; 20070100246; 20070100251; 20070100666; 20070129647; 20070135724; 20070135728; 20070142862; 20070142873; 20070149860; 20070161919; 20070162086; 20070167694; 20070167853; 20070167858; 20070167991; 20070173733; 20070179396; 20070191688; 20070191691; 20070191697; 20070197930; 20070203448;

20070208212; 20070208269; 20070213786; 20070225581;
20070225674; 20070225932; 20070249918; 20070249952;
20070255135; 20070260151; 20070265508; 20070265533;
20070273504; 20070276270; 20070276278; 20070276279;
20070276609; 20070291832; 20080001600; 20080001735;
20080004514; 20080004904; 20080009685; 20080009772;
20080013747; 20080021332; 20080021336; 20080021340;
20080021342; 20080033266; 20080036752; 20080045823;
20080045844; 20080051669; 20080051858; 20080058668;
20080074307; 20080077010; 20080077015; 20080082018;
20080097197; 20080119716; 20080119747; 20080119900;
20080125669; 20080139953; 20080140403; 20080154111;
20080167535; 20080167540; 20080167569; 20080177195;
20080177196; 20080177197; 20080188765; 20080195166;
20080200831; 20080208072; 20080208073; 20080214902;
20080221400; 20080221472; 20080221969; 20080228100;
20080242521; 20080243014; 20080243017; 20080243021;
20080249430; 20080255469; 20080257349; 20080260212;
20080262367; 20080262371; 20080275327; 20080294019;
20080294063; 20080319326; 20080319505; 20090005675;
20090009284; 20090018429; 20090024007; 20090030476;
20090043221; 20090048530; 20090054788; 20090062660;
20090062670; 20090062676; 20090062679; 20090062680;
20090062696; 20090076339; 20090076399; 20090076400;
20090076407; 20090082689; 20090082690; 20090083071;
20090088658; 20090094305; 20090112281; 20090118636;
20090124869; 20090124921; 20090124922; 20090124923;
20090137915; 20090137923; 20090149148; 20090156954;
20090156956; 20090157662; 20090171232; 20090171240;
20090177090; 20090177108; 20090179642; 20090182211;
20090192394; 20090198144; 20090198145; 20090204015;
20090209835; 20090216091; 20090216146; 20090227876;
20090227877; 20090227882; 20090227889; 20090240119;
20090247893; 20090247894; 20090264785; 20090264952;
20090275853; 20090287107; 20090292180; 20090297000;
20090306534; 20090312663; 20090312664; 20090312808;
20090312817; 20090316925; 20090318779; 20090323049;
20090326353; 20100010364; 20100023089; 20100030073;
20100036211; 20100036276; 20100041962; 20100042011;
20100043795; 20100049069; 20100049075; 20100049482;
20100056939; 20100069762; 20100069775; 20100076333;
20100076338; 20100079292; 20100087900; 20100094103;
20100094152; 20100094155; 20100099954; 20100106044;
20100114813; 20100130869; 20100137728; 20100137937;
20100143256; 20100152621; 20100160737; 20100174161;
20100179447; 20100185113; 20100191124; 20100191139;
20100191305; 20100195770; 20100198098; 20100198101;
20100204614; 20100204748; 20100204750; 20100217100;
20100217146; 20100217348; 20100222694; 20100224188;
20100234705; 20100234752; 20100234753; 20100245093;
20100249627; 20100249635; 20100258126; 20100261977;
20100262377; 20100268055; 20100280403; 20100286549;
20100286747; 20100292752; 20100293115; 20100298735;
20100303101; 20100312188; 20100318025; 20100324441;
20100331649; 20100331715; 20110004115; 20110009715;
20110009729; 20110009752; 20110015501; 20110015536;
20110028802; 20110028859; 20110034822; 20110038515;
20110040202; 20110046473; 20110054279; 20110054345;
20110066005; 20110066041; 20110066042; 20110066053;
20110077538; 20110082381; 20110087125; 20110092834;
20110092839; 20110098583; 20110105859; 20110105915;
20110105938; 20110106206; 20110112379; 20110112381;
20110112426; 20110112427; 20110115624; 20110118536;
20110118618; 20110118619; 20110119212; 20110125046;
20110125048; 20110125238; 20110130675; 20110144520;
20110152710; 20110160607; 20110160608; 20110160795;
20110162645; 20110178441; 20110178581; 20110181422;

20110184650; 20110190600; 20110196693; 20110208539;
20110218453; 20110218950; 20110224569; 20110224570;
20110224602; 20110245709; 20110251583; 20110251985;
20110257517; 20110263995; 20110270117; 20110270579;
20110282234; 20110288424; 20110288431; 20110295142;
20110295143; 20110295338; 20110301436; 20110301439;
20110301441; 20110301448; 20110301486; 20110301487;
20110307029; 20110307079; 20110313308; 20110313760;
20110319724; 20120004561; 20120004564; 20120004749;
20120010536; 20120016218; 20120016252; 20120022336;
20120022350; 20120022351; 20120022365; 20120022384;
20120022392; 20120022844; 20120029320; 20120029378;
20120029379; 20120035431; 20120035433; 20120035765;
20120041330; 20120046711; 20120053433; 20120053491;
20120059273; 20120065536; 20120078115; 20120083700;
20120083701; 20120088987; 20120088992; 20120089004;
20120092156; 20120092157; 20120095352; 20120095357;
20120100514; 20120101387; 20120101401; 20120101402;
20120101430; 20120108999; 20120116235; 20120123232;
20120123290; 20120125337; 20120136242; 20120136605;
20120143074; 20120143075; 20120149997; 20120150545;
20120157963; 20120159656; 20120165624; 20120165631;
20120172682; 20120172689; 20120172743; 20120191000;
20120197092; 20120197153; 20120203087; 20120203130;
20120203131; 20120203133; 20120203725; 20120209126;
20120209136; 20120209139; 20120220843; 20120220889;
20120221310; 20120226334; 20120238890; 20120242501;
20120245464; 20120245481; 20120253141; 20120253219;
20120253249; 20120265080; 20120271190; 20120277545;
20120277548; 20120277816; 20120296182; 20120296569;
20120302842; 20120302845; 20120302856; 20120302894;
20120310100; 20120310105; 20120321759; 20120323132;
20120330109; 20130006124; 20130009783; 20130011819;
20130012786; 20130012787; 20130012788; 20130012789;
20130012790; 20130012802; 20130012830; 20130013327;
20130023783; 20130030257; 20130035579; 20130039498;
20130041235; 20130046151; 20130046193; 20130046715;
20130060110; 20130060125; 20130066392; 20130066394;
20130066395; 20130069780; 20130070929; 20130072807;
20130076885; 20130079606; 20130079621; 20130079647;
20130079656; 20130079657; 20130080127; 20130080489;
20130095459; 20130096391; 20130096393; 20130096394;
20130096408; 20130096441; 20130096839; 20130096840;
20130102833; 20130102897; 20130109995; 20130109996;
20130116520; 20130116561; 20130116588; 20130118494;
20130123584; 20130127708; 20130130799; 20130137936;
20130137938; 20130138002; 20130144106; 20130144107;
20130144108; 20130144183; 20130150650; 20130150651;
20130150659; 20130159041; 20130165812; 20130172686;
20130172691; 20130172716; 20130172763; 20130172767;
20130172772; 20130172774; 20130178718; 20130182860;
20130184552; 20130184558; 20130184603; 20130188854;
20130190577; 20130190642; 20130197321; 20130197322;
20130197328; 20130197339; 20130204150; 20130211224;
20130211276; 20130211291; 20130217982; 20130218043;
20130218053; 20130218233; 20130221961; 20130225940;
20130225992; 20130231574; 20130231580; 20130231947;
20130238049; 20130238050; 20130238063; 20130245422;
20130245486; 20130245711; 20130245712; 20130266163;
20130267760; 20130267866; 20130267928; 20130274580;
20130274625; 20130275159; 20130281811; 20130282339;
20130289401; 20130289413; 20130289417; 20130289424;
20130289433; 20130295016; 20130300573; 20130303828;
20130303934; 20130304153; 20130310660; 20130310909;
20130324880; 20130338449; 20130338459; 20130344465;
20130345522; 20130345523; 20140005988; 20140012061;
20140012110; 20140012133; 20140012153; 20140018792;

20140019165; 20140023999; 20140025396; 20140025397;
20140038147; 20140046208; 20140051044; 20140051960;
20140051961; 20140052213; 20140055284; 20140058241;
20140066739; 20140066763; 20140070958; 20140072127;
20140072130; 20140073863; 20140073864; 20140073866;
20140073870; 20140073875; 20140073876; 20140073877;
20140073878; 20140073898; 20140073948; 20140073949;
20140073951; 20140073953; 20140073954; 20140073955;
20140073956; 20140073960; 20140073961; 20140073963;
20140073965; 20140073966; 20140073967; 20140073968;
20140073974; 20140073975; 20140074060; 20140074179;
20140074180; 20140077946; 20140081114; 20140081115;
20140094720; 20140098981; 20140100467; 20140104059;
20140105436; 20140107464; 20140107519; 20140107525;
20140114165; 20140114205; 20140121446; 20140121476;
20140121554; 20140128762; 20140128764; 20140135879;
20140136585; 20140140567; 20140143064; 20140148723;
20140152673; 20140155706; 20140155714; 20140155730;
20140156000; 20140163328; 20140163330; 20140163331;
20140163332; 20140163333; 20140163335; 20140163336;
20140163337; 20140163385; 20140163409; 20140163425;
20140163897; 20140171820; 20140175261; 20140176944;
20140179980; 20140180088; 20140180092; 20140180093;
20140180094; 20140180095; 20140180096; 20140180097;
20140180099; 20140180100; 20140180112; 20140180113;
20140180145; 20140180153; 20140180160; 20140180161;
20140180176; 20140180177; 20140180597; 20140187994;
20140188006; 20140188770; 20140194702; 20140194758;
20140194759; 20140194768; 20140194769; 20140194780;
20140194793; 20140203797; 20140213937; 20140214330;
20140228651; 20140228702; 20140232516; 20140235965;
20140236039; 20140236077; 20140237073; 20140243614;
20140243621; 20140243628; 20140243694; 20140249429;
20140257073; 20140257147; 20140266696; 20140266787;
20140275886; 20140275889; 20140275891; 20140276013;
20140276014; 20140276090; 20140276123; 20140276130;
20140276181; 20140276183; 20140279746; 20140288381;
20140288614; 20140288953; 20140289172; 20140296724;
20140303453; 20140303454; 20140303508; 20140309943;
20140313303; 20140316217; 20140316221; 20140316230;
20140316235; 20140316278; 20140323900; 20140324118;
20140330102; 20140330157; 20140330159; 20140330334;
20140330404; 20140336473; 20140347491; 20140350431;
20140350436; 20140358025; 20140364721; 20140364746;
20140369537; 20140371544; 20140371599; 20140378809;
20140378810; 20140379620; 20150003698; 20150003699;
20150005592; 20150005594; 20150005640; 20150005644;
20150005660; 20150005680; 20150006186; 20150016618;
20150018758; 20150025351; 20150025422; 20150032017;
20150038804; 20150038869; 20150039110; 20150042477;
20150045686; 20150051663; 20150057512; 20150065839;
20150073237; 20150073306; 20150080671; 20150080746;
20150087931; 20150088024; 20150092949; 20150093729;
20150099941; 20150099962; 20150103360; 20150105631;
20150105641; 20150105837; 20150112222; 20150112409;
20150119652; 20150119743; 20150119746; 20150126821;
20150126845; 20150126848; 20150126873; 20150134264;
20150137988; 20150141529; 20150141789; 20150141794;
20150153477; 20150157235; 20150157266; 20150164349;
20150164362; 20150164375; 20150164404; 20150181840;
20150182417; 20150190070; 20150190085; 20150190636;
20150190637; 20150196213; 20150199010; 20150201879;
20150202447; 20150203822; 20150208940; 20150208975;
20150213191; 20150216436; 20150216468; 20150217082;
20150220486; 20150223743; 20150227702; 20150230750;
20150231408; 20150238106; 20150238112; 20150238137;
20150245800; 20150247921; 20150250393; 20150250401;

20150250415; 20150257645; 20150257673; 20150257674;
20150257700; 20150257712; 20150265164; 20150269825;
20150272465; 20150282730; 20150282755; 20150282760;
20150290420; 20150290453; 20150290454; 20150297106;
20150297141; 20150304101; 20150305685; 20150309563;
20150313496; 20150313535; 20150327813; 20150327837;
20150335292; 20150342478; 20150342493; 20150351655;
20150351701; 20150359441; 20150359450; 20150359452;
20150359467; 20150359486; 20150359492; 20150366497;
20150366504; 20150366516; 20150366518; 20150374285;
20150374292; 20150374300; 20150380009; 20160000348;
20160000354; 20160007915; 20160007918; 20160012749;
20160015281; 20160015289; 20160022141; 20160022156;
20160022164; 20160022167; 20160022206; 20160027293;
20160029917; 20160029918; 20160029946; 20160029950;
20160029965; 20160030702; 20160038037; 20160038038;
20160038049; 20160038091; 20160045150; 20160045756;
20160051161; 20160051162; 20160051187; 20160051195;
20160055415; 20160058301; 20160066788; 20160067494;
20160073886; 20160074661; 20160081577; 20160081616;
20160087603; 20160089031; 20160100769; 20160101260;
20160106331; 20160106344; 20160112022; 20160112684;
20160113539; 20160113545; 20160113567; 20160113587;
20160119726; 20160120433; 20160120434; 20160120464;
20160120480; 20160128596; 20160132654; 20160135691;
20160135727; 20160135754; 20160140834; 20160143554;
20160143560; 20160143594; 20160148531; 20160150988;
20160151014; 20160151018; 20160151628; 20160157742;
20160157828; 20160162652; 20160165852; 20160165853;
20160166169; 20160166197; 20160166199; 20160166208;
20160174099; 20160174863; 20160178392; 20160183828;
20160183861; 20160191517; 20160192841; 20160192842;
20160192847; 20160192879; 20160196758; 20160198963;
20160198966; 20160202755; 20160206877; 20160206880;
20160213276; 20160213314; 20160220133; 20160220134;
20160220136; 20160220166; 20160220836; 20160220837;
20160224757; 20160228019; 20160228029; 20160228059;
20160228705; 20160232811; 20160235324; 20160235351;
20160235352; 20160239084; 20160242659; 20160242690;
20160242699; 20160248434; 20160249841; 20160256063;
20160256112; 20160256118; 20160259905; 20160262664;
20160262685; 20160262695; 20160262703; 20160278651;
20160278697; 20160278713; 20160282941; 20160287120;
20160287157; 20160287162; 20160287166; 20160287871;
20160296157; 20160302683; 20160302704; 20160302709;
20160302720; 20160302737; 20160303402; 20160310031;
20160310070; 20160317056; 20160324465; 20160331264;
20160338634; 20160338644; 20160338798; 20160346542;
20160354003; 20160354027; 20160360965; 20160360970;
20160361021; 20160361041; 20160367204; 20160374581;
20160374618; 20170000404; 20170001016; 20170007165;
20170007173; 20170014037; 20170014083; 20170020434;
20170020447; 20170027467; 20170032098; 20170035392;
20170042430; 20170042469; 20170042475; 20170053513;
20170055839; 20170055898; 20170055913; 20170065199;
20170065218; 20170065229; 20170071495; 20170071523;
20170071529; 20170071532; 20170071537; 20170071546;
20170071551; 20170071552; 20170079538; 20170079596;
20170086672; 20170086695; 20170091567; 20170095721;
20170105647; 20170112379; 20170112427; 20170120066;
20170127946; 20170132816; 20170135597; 20170135604;
20170135626; 20170135629; 20170135631; 20170135633;
20170143231; 20170143249; 20170143255; 20170143257;
20170143259; 20170143266; 20170143267; 20170143268;
20170143273; 20170143280; 20170143282; 20170143960;
20170143963; 20170146386; 20170146387; 20170146390;
20170146391; 20170147754; 20170148240; 20170150896;

20170150916; 20170156593; 20170156606; 20170156655; 20170164878; 20170164901; 20170172414; 20170172501; 20170172520; 20170173262; 20170177023; 20170181693; 20170185149; 20170188865; 20170188872; 20170188947; 20170188992; 20170189691; 20170196497; 20170202474; 20170202518; 20170203154; 20170209053; and 20170209083.

There are many approaches to time-frequency decomposition of EEG data, including the short-term Fourier transform (STFT), (Gabor D. Theory of Communication. J. Inst. Electr. Engrs. 1946; 93:429-457) continuous (Daubechies I. Ten Lectures on Wavelets. Philadelphia, Pa: Society for Industrial and Applied Mathematics; 1992:357. 21. Combes J M, Grossmann A, Tchamitchian P. Wavelets: Time-Frequency Methods and Phase Space-Proceedings of the International Conference; Dec. 14-18, 1987; Marseille, France) or discrete (Mallat S G. A theory for multiresolution signal decomposition: the wavelet representation. IEEE Trans Pattern Anal Mach Intell. 1989; 11:674-693) wavelet transforms, Hilbert transform (Lyons R G. Understanding Digital Signal Processing. 2nd ed. Upper Saddle River, NJ: Prentice Hall PTR; 2004:688), and matching pursuits (Mallat S, Zhang Z. Matching pursuits with time-frequency dictionaries. IEEE Trans. Signal Proc. 1993; 41(12):3397-3415). Prototype analysis systems may be implemented using, for example, MatLab with the Wavelet Toolbox, www.mathworks.com/products/wavelet.html.

See, U.S. Pat. Nos. 6,196,972; 6,338,713; 6,442,421; 6,507,754; 6,524,249; 6,547,736; 6,616,611; 6,816,744; 6,865,494; 6,915,241; 6,936,012; 6,996,261; 7,043,293; 7,054,454; 7,079,977; 7,128,713; 7,146,211; 7,149,572; 7,164,941; 7,209,788; 7,254,439; 7,280,867; 7,282,030; 7,321,837; 7,330,032; 7,333,619; 7,381,185; 7,537,568; 7,559,903; 7,565,193; 7,567,693; 7,604,603; 7,624,293; 7,640,055; 7,715,919; 7,725,174; 7,729,755; 7,751,878; 7,778,693; 7,794,406; 7,797,040; 7,801,592; 7,803,118; 7,803,119; 7,879,043; 7,896,807; 7,899,524; 7,917,206; 7,933,646; 7,937,138; 7,976,465; 8,014,847; 8,033,996; 8,073,534; 8,095,210; 8,137,269; 8,137,270; 8,175,696; 8,177,724; 8,177,726; 8,180,601; 8,187,181; 8,197,437; 8,233,965; 8,236,005; 8,244,341; 8,248,069; 8,249,698; 8,280,514; 8,295,914; 8,326,433; 8,335,664; 8,346,342; 8,355,768; 8,386,312; 8,386,313; 8,392,250; 8,392,253; 8,392,254; 8,392,255; 8,396,542; 8,406,841; 8,406,862; 8,412,655; 8,428,703; 8,428,704; 8,463,374; 8,464,288; 8,475,387; 8,483,815; 8,494,610; 8,494,829; 8,494,905; 8,498,699; 8,509,881; 8,533,042; 8,548,786; 8,571,629; 8,579,786; 8,591,419; 8,606,360; 8,628,480; 8,655,428; 8,666,478; 8,682,422; 8,706,183; 8,706,205; 8,718,747; 8,725,238; 8,738,136; 8,747,382; 8,755,877; 8,761,869; 8,762,202; 8,768,449; 8,781,796; 8,790,255; 8,790,272; 8,821,408; 8,825,149; 8,831,731; 8,843,210; 8,849,392; 8,849,632; 8,855,773; 8,858,440; 8,862,210; 8,862,581; 8,903,479; 8,918,178; 8,934,965; 8,951,190; 8,954,139; 8,955,010; 8,958,868; 8,983,628; 8,983,629; 8,989,835; 9,020,789; 9,026,217; 9,031,644; 9,050,470; 9,060,671; 9,070,492; 9,072,832; 9,072,905; 9,078,584; 9,084,896; 9,095,295; 9,101,276; 9,107,595; 9,116,835; 9,125,574; 9,149,719; 9,155,487; 9,192,309; 9,198,621; 9,204,835; 9,211,417; 9,215,978; 9,232,910; 9,232,984; 9,238,142; 9,242,067; 9,247,911; 9,248,286; 9,254,383; 9,277,871; 9,277,873; 9,282,934; 9,289,603; 9,302,110; 9,307,944; 9,308,372; 9,320,450; 9,336,535; 9,357,941; 9,375,151; 9,375,171; 9,375,571; 9,403,038; 9,415,219; 9,427,581; 9,443,141; 9,451,886; 9,454,646; 9,462,956; 9,462,975; 9,468,541; 9,471,978; 9,480,402; 9,492,084; 9,504,410; 9,522,278; 9,533,113; 9,545,285; 9,560,984; 9,563,740;

9,615,749; 9,616,166; 9,622,672; 9,622,676; 9,622,702; 9,622,703; 9,623,240; 9,636,019; 9,649,036; 9,659,229; 9,668,694; 9,681,814; 9,681,820; 9,682,232; 9,713,428; 20020035338; 20020091319; 20020095099; 20020103428; 20020103429; 20020193670; 20030032889; 20030046018; 20030093129; 20030160622; 20030185408; 20030216654; 20040039268; 20040049484; 20040092809; 20040133119; 20040133120; 20040133390; 20040138536; 20040138580; 20040138711; 20040152958; 20040158119; 20050010091; 20050018858; 20050033174; 20050075568; 20050085744; 20050119547; 20050148893; 20050148894; 20050148895; 20050154290; 20050167588; 20050240087; 20050245796; 20050267343; 20050267344; 20050283053; 20050283090; 20060020184; 20060036152; 20060036153; 20060074290; 20060078183; 20060135879; 20060153396; 20060155495; 20060161384; 20060173364; 20060200013; 20060217816; 20060233390; 20060281980; 20070016095; 20070066915; 20070100278; 20070179395; 20070179734; 20070191704; 20070209669; 20070225932; 20070255122; 20070255135; 20070260151; 20070265508; 20070287896; 20080021345; 20080033508; 20080064934; 20080074307; 20080077015; 20080091118; 20080097197; 20080119716; 20080177196; 20080221401; 20080221441; 20080243014; 20080243017; 20080255949; 20080262367; 20090005667; 20090033333; 20090036791; 20090054801; 20090062676; 20090177144; 20090220425; 20090221930; 20090270758; 20090281448; 20090287271; 20090287272; 20090287273; 20090287467; 20090299169; 20090306534; 20090312646; 20090318794; 20090322331; 20100030073; 20100036211; 20100049276; 20100068751; 20100069739; 20100094152; 20100099975; 20100106041; 20100198090; 20100204604; 20100204748; 20100249638; 20100280372; 20100331976; 20110004115; 20110015515; 20110015539; 20110040713; 20110066041; 20110066042; 20110074396; 20110077538; 20110092834; 20110092839; 20110098583; 20110160543; 20110172725; 20110178441; 20110184305; 20110191350; 20110218950; 20110257519; 20110270074; 20110282230; 20110288431; 20110295143; 20110301441; 20110313268; 20110313487; 20120004518; 20120004561; 20120021394; 20120022343; 20120029378; 20120041279; 20120046535; 20120053473; 20120053476; 20120053478; 20120053479; 20120083708; 20120108918; 20120108997; 20120143038; 20120145152; 20120150545; 20120157804; 20120159656; 20120172682; 20120184826; 20120197153; 20120209139; 20120253261; 20120265267; 20120271151; 20120271376; 20120289869; 20120310105; 20120321759; 20130012804; 20130041235; 20130060125; 20130066392; 20130066395; 20130072775; 20130079621; 20130102897; 20130116520; 20130123607; 20130127708; 20130131438; 20130131461; 20130165804; 20130167360; 20130172716; 20130172772; 20130178733; 20130184597; 20130204122; 20130211238; 20130223709; 20130226261; 20130237874; 20130238049; 20130238050; 20130245416; 20130245424; 20130245485; 20130245486; 20130245711; 20130245712; 20130261490; 20130274562; 20130289364; 20130295016; 20130310422; 20130310909; 20130317380; 20130338518; 20130338803; 20140039279; 20140057232; 20140058218; 20140058528; 20140074179; 20140074180; 20140094710; 20140094720; 20140107521; 20140142654; 20140148657; 20140148716; 20140148726; 20140180153; 20140180160; 20140187901; 20140228702; 20140243647; 20140243714; 20140257128; 20140275807; 20140276130; 20140276187; 20140303454; 20140303508; 20140309614; 20140316217; 20140316248; 20140324118; 20140330334; 20140330335; 20140330336; 20140330404; 20140335489; 20140350634; 20140350864; 20150005646; 20150005660; 20150011907; 20150018665; 20150018699; 20150018702; 20150025422; 20150038869; 20150073294;

20150073306; 20150073505; 20150080671; 20150080695; 20150099962; 20150126821; 20150151142; 20150164431; 20150190070; 20150190636; 20150190637; 20150196213; 20150196249; 20150213191; 20150216439; 20150245800; 20150248470; 20150248615; 20150272652; 20150297106; 20150297893; 20150305686; 20150313498; 20150366482; 20150379370; 20160000348; 20160007899; 20160022167; 20160022168; 20160022207; 20160027423; 20160029965; 20160038042; 20160038043; 20160045128; 20160051812; 20160058304; 20160066838; 20160107309; 20160113587; 20160120428; 20160120432; 20160120437; 20160120457; 20160128596; 20160128597; 20160135754; 20160143594; 20160144175; 20160151628; 20160157742; 20160157828; 20160174863; 20160174907; 20160176053; 20160183881; 20160184029; 20160198973; 20160206380; 20160213261; 20160213317; 20160220850; 20160228028; 20160228702; 20160235324; 20160239966; 20160239968; 20160242645; 20160242665; 20160242669; 20160242690; 20160249841; 20160250355; 20160256063; 20160256105; 20160262664; 20160278653; 20160278713; 20160287117; 20160287162; 20160287169; 20160287869; 20160303402; 20160331264; 20160331307; 20160345895; 20160345911; 20160346542; 20160361041; 20160361546; 20160367186; 20160367198; 20170031440; 20170031441; 20170039706; 20170042444; 20170045601; 20170071521; 20170079588; 20170079589; 20170091418; 20170113046; 20170120041; 20170128015; 20170135594; 20170135626; 20170136240; 20170165020; 20170172446; 20170173326; 20170188870; 20170188905; 20170188916; 20170188922; and 20170196519.

Single instruction, multiple data processors, such as graphic processing units including the nVidia CUDA environment or AMD Firepro high-performance computing environment are known, and may be employed for general purpose computing, finding particular application in data matrix transformations.

See, U.S. Pat. Nos. 5,273,038; 5,503,149; 6,240,308; 6,272,370; 6,298,259; 6,370,414; 6,385,479; 6,490,472; 6,556,695; 6,697,660; 6,801,648; 6,907,280; 6,996,261; 7,092,748; 7,254,500; 7,338,455; 7,346,382; 7,490,085; 7,497,828; 7,539,528; 7,565,193; 7,567,693; 7,577,472; 7,597,665; 7,627,370; 7,680,526; 7,729,755; 7,809,434; 7,840,257; 7,860,548; 7,872,235; 7,899,524; 7,904,134; 7,904,139; 7,907,998; 7,983,740; 7,983,741; 8,000,773; 8,014,847; 8,069,125; 8,233,682; 8,233,965; 8,235,907; 8,248,069; 8,356,004; 8,379,952; 8,406,838; 8,423,125; 8,445,851; 8,553,956; 8,586,932; 8,606,349; 8,615,479; 8,644,910; 8,679,009; 8,696,722; 8,712,512; 8,718,747; 8,761,866; 8,781,557; 8,814,923; 8,821,376; 8,834,546; 8,852,103; 8,870,737; 8,936,630; 8,951,189; 8,951,192; 8,958,882; 8,983,155; 9,005,126; 9,020,586; 9,022,936; 9,028,412; 9,033,884; 9,042,958; 9,078,584; 9,101,279; 9,135,400; 9,144,392; 9,149,255; 9,155,521; 9,167,970; 9,179,854; 9,179,858; 9,198,637; 9,204,835; 9,208,558; 9,211,077; 9,213,076; 9,235,685; 9,242,067; 9,247,924; 9,268,014; 9,268,015; 9,271,651; 9,271,674; 9,275,191; 9,292,920; 9,307,925; 9,322,895; 9,326,742; 9,330,206; 9,368,265; 9,395,425; 9,402,558; 9,414,776; 9,436,989; 9,451,883; 9,451,899; 9,468,541; 9,471,978; 9,480,402; 9,480,425; 9,486,168; 9,592,389; 9,615,789; 9,626,756; 9,672,302; 9,672,617; 9,682,232; 20020033454; 20020035317; 20020037095; 20020042563; 20020058867; 20020103428; 20020103429; 20030018277; 20030093004; 20030128801; 20040082862; 20040092809; 20040096395; 20040116791; 20040116798; 20040122787; 20040122790; 20040166536; 20040215082; 20050007091; 20050020918; 20050033154; 20050079636; 20050119547; 20050154290; 20050222639; 20050240253; 20050283053; 20060036152;

20060036153; 20060052706; 20060058683; 20060074290; 20060078183; 20060084858; 20060149160; 20060161218; 20060241382; 20060241718; 20070191704; 20070239059; 20080001600; 20080009772; 20080033291; 20080039737; 20080042067; 20080097235; 20080097785; 20080128626; 20080154126; 20080221441; 20080228077; 20080228239; 20080230702; 20080230705; 20080249430; 20080262327; 20080275340; 20090012387; 20090018407; 20090022825; 20090024050; 20090062660; 20090078875; 20090118610; 20090156907; 20090156955; 20090157323; 20090157481; 20090157482; 20090157625; 20090157751; 20090157813; 20090163777; 20090164131; 20090164132; 20090171164; 20090172540; 20090179642; 20090209831; 20090221930; 20090246138; 20090299169; 20090304582; 20090306532; 20090306534; 20090312808; 20090312817; 20090318773; 20090318794; 20090322331; 20090326604; 20100021378; 20100036233; 20100041949; 20100042011; 20100049482; 20100069739; 20100069777; 20100082506; 20100113959; 20100249573; 20110015515; 20110015539; 20110028827; 20110077503; 20110118536; 20110125077; 20110125078; 20110129129; 20110160543; 20110161011; 20110172509; 20110172553; 20110178359; 20110190846; 20110218405; 20110224571; 20110230738; 20110257519; 20110263962; 20110263968; 20110270074; 20110288400; 20110301448; 20110306845; 20110306846; 20110313274; 20120021394; 20120022343; 20120035433; 20120053483; 20120163689; 20120165904; 20120215114; 20120219195; 20120219507; 20120245474; 20120253261; 20120253434; 20120289854; 20120310107; 20120316793; 20130012804; 20130060125; 20130063550; 20130085678; 20130096408; 20130110616; 20130116561; 20130123607; 20130131438; 20130131461; 20130178693; 20130178733; 20130184558; 20130211238; 20130221961; 20130245424; 20130274586; 20130289385; 20130289386; 20130303934; 20140058528; 20140066763; 20140119621; 20140151563; 20140155730; 20140163368; 20140171757; 20140180088; 20140180092; 20140180093; 20140180094; 20140180095; 20140180096; 20140180097; 20140180099; 20140180100; 20140180112; 20140180113; 20140180176; 20140180177; 20140184550; 20140193336; 20140200414; 20140243614; 20140257047; 20140275807; 20140303486; 20140315169; 20140316248; 20140323849; 20140335489; 20140343397; 20140343399; 20140343408; 20140364721; 20140378830; 20150011866; 20150038812; 20150051663; 20150099959; 20150112409; 20150119658; 20150119689; 20150148700; 20150150473; 20150196800; 20150200046; 20150219732; 20150223905; 20150227702; 20150247921; 20150248615; 20150253410; 20150289779; 20150290453; 20150290454; 20150313540; 20150317796; 20150324692; 20150366482; 20150375006; 20160005320; 20160027342; 20160029965; 20160051161; 20160051162; 20160055304; 20160058304; 20160058392; 20160066838; 20160103487; 20160120437; 20160120457; 20160143541; 20160157742; 20160184029; 20160196393; 20160228702; 20160231401; 20160239966; 20160239968; 20160260216; 20160267809; 20160270723; 20160302720; 20160303397; 20160317077; 20160345911; 20170027539; 20170039706; 20170045601; 20170061034; 20170085855; 20170091418; 20170112403; 20170113046; 20170120041; 20170160360; 20170164861; 20170169714; 20170172527; and 20170202475.

Statistical analysis may be presented in a form that permits parallelization, which can be efficiently implemented using various parallel processors, a common form of which is a SIMD (single instruction, multiple data) processor, found in typical graphics processors (GPUs).

See, U.S. Pat. Nos. 8,406,890; 8,509,879; 8,542,916; 8,852,103; 8,934,986; 9,022,936; 9,028,412; 9,031,653;

9,033,884; 9,037,530; 9,055,974; 9,149,255; 9,155,521;
9,198,637; 9,247,924; 9,268,014; 9,268,015; 9,367,131;
9,4147,80; 9,420,970; 9,430,615; 9,442,525; 9,444,998;
9,445,763; 9,462,956; 9,474,481; 9,489,854; 9,504,420;
9,510,790; 9,519,981; 9,526,906; 9,538,948; 9,585,581;
9,622,672; 9,641,665; 9,652,626; 9,684,335; 9,687,187;
9,693,684; 9,693,724; 9,706,963; 9,712,736; 20090118622;
20100098289; 20110066041; 20110066042; 20110098583;
20110301441; 20120130204; 20120265271; 20120321759;
20130060158; 20130113816; 20130131438; 20130184786;
20140031889; 20140031903; 20140039975; 20140114889;
20140226131; 20140279341; 20140296733; 20140303424;
20140313303; 20140315169; 20140316235; 20140364721;
20140378810; 20150003698; 20150003699; 20150005640;
20150005644; 20150006186; 20150029087; 20150033245;
20150033258; 20150033259; 20150033262; 20150033266;
20150081226; 20150088093; 20150093729; 20150105701;
20150112899; 20150126845; 20150150122; 20150190062;
20150190070; 20150190077; 20150190094; 20150192776;
20150196213; 20150196800; 20150199010; 20150241916;
20150242608; 20150272496; 20150272510; 20150282705;
20150282749; 20150289217; 20150297109; 20150305689;
20150335295; 20150351655; 20150366482; 20160027342;
20160029896; 20160058366; 20160058376; 20160058673;
20160060926; 20160065724; 20160065840; 20160077547;
20160081625; 20160103487; 20160104006; 20160109959;
20160113517; 20160120048; 20160120428; 20160120457;
20160125228; 20160157773; 20160157828; 20160183812;
20160191517; 20160193499; 20160196185; 20160196635;
20160206241; 20160213317; 20160228064; 20160235341;
20160235359; 20160249857; 20160249864; 20160256086;
20160262680; 20160262685; 20160270656; 20160278672;
20160282113; 20160287142; 20160306942; 20160310071;
20160317056; 20160324445; 20160324457; 20160342241;
20160360100; 20160361027; 20160366462; 20160367138;
20160367195; 20160374616; 20160378608; 20160378965;
20170000324; 20170000325; 20170000326; 20170000329;
20170000330; 20170000331; 20170000332; 20170000333;
20170000334; 20170000335; 20170000337; 20170000340;
20170000341; 20170000342; 20170000343; 20170000345;
20170000454; 20170000683; 20170001032; 20170007111;
20170007115; 20170007116; 20170007122; 20170007123;
20170007182; 20170007450; 20170007799; 20170007843;
20170010469; 20170010470; 20170013562; 20170017083;
20170020627; 20170027521; 20170028563; 20170031440;
20170032221; 20170035309; 20170035317; 20170041699;
20170042485; 20170046052; 20170065349; 20170086695;
20170086727; 20170090475; 20170103440; 20170112446;
20170113056; 20170128006; 20170143249; 20170143442;
20170156593; 20170156606; 20170164893; 20170171441;
20170172499; 20170173262; 20170185714; 20170188933;
20170196503; 20170205259; 20170206913; and
20170214786.

Artificial neural networks have been employed to analyze EEG signals.

See, U.S. Pat. Nos. 9,443,141; 20110218950; 20150248167; 20150248764; 20150248765; 20150310862; 20150331929; 20150338915; 20160026913; 20160062459; 20160085302; 20160125572; 20160247064; 20160274660; 20170053665; 20170069306; 20170173262; and 20170206691.

SUMMARY AND OBJECTS OF THE INVENTION

The present invention generally relates to enhancing and/or accelerating learning or performance of a mental or motor task, and/or enhanced assimilation and retention of information by a subject (e.g., a student) by conveying to the brain of the subject patterns of brainwaves. These brainwaves may be artificial or synthetic, or derived from the brain of a second subject (e.g., a teacher, a trainer, a mentor, a master or person skill and/or knowledgeable in the given task). Typically, the wave patterns of the second subject are derived while the second subject is performing a physical or mental task, e.g., corresponding to the task sought to be learned or performed by the transferee subject.

A special case is where the first and second subjects are the same. For example, brainwave patters are recorded while a subject is learning a task or information. That same pattern my assist in further learning of similar tasks, and/or recall of the previous learning. Also the same pattern may assist in performance of a mental or a motor task previously learnt. Thus, there may be a time delay between acquisition of the brainwave information from the second subject, and exposing the first subject to corresponding stimulation. The signals may be recorded and transmitted.

The temporal pattern may be conveyed or induced non-invasively via light, sound (or ultrasound), transcranial direct current stimulation (tDCS), transcranial magnetic stimulation (TMS), or any other means capable of conveying frequency patterns. In a preferred embodiment, normal human senses are employed to stimulate the subject, such as light, sound, and touch.

This technology may be advantageously used to accelerate learning, or enhance performance, of a new mental skill or task, a new motor skill or task. Still another aspect provides enhanced processing, comprehension, and retention of new information. The technology may be used in humans or animals.

The present technology may employ an event-correlated EEG time and/or frequency analysis performed on neuronal activity patterns. In a time analysis, the signal is analyzed temporally and spatially, generally looking for changes with respect to time and space. In a frequency analysis, over an epoch of analysis, the data, which is typically a time-sequence of samples, is transformed, using e.g., a Fourier transform (FT, or one implementation, the Fast Fourier Transform, FFT), into a frequency domain representation, and the frequencies present during the epoch are analyzed. The window of analysis may be rolling, and so the frequency analysis may be continuous. In a hybrid time-frequency analysis, for example, a wavelet analysis, the data during the epoch is transformed using a "wavelet transform", e.g., the Discrete Wavelet Transform (DWT) or continuous wavelet transform (CWT), which has the ability to construct a time-frequency representation of a signal that offers very good time and frequency localization. Changes in transformed data over time and space may be analyzed. In general, the spatial aspect of the brainwave analysis is anatomically modelled. In most cases, anatomy is considered universal, but in some cases, there are significant differences. For example, brain injury, psychiatric disease, age, race, native language, training, sex, handedness, and other factors may lead to distinct spatial arrangement of brain function, and therefore when transferring activity from one individual to another, it is preferred to normalize the brain anatomy of both individuals by performing standard tasks/tests, and measuring spatial parameters of the EEG or MEG. Note that spatial organization of the brain is highly persistent, absent injury or disease, and therefore this need only be performed infrequently. However, since electrode placement may be inexact, a spatial calibration may be performed after electrode placement.

Different aspects of EEG magnitude and phase relationships may be captured, to reveal details of the neuronal activity. The "time-frequency analysis" reveals the brain's parallel processing of information, with oscillations at various frequencies within various regions of the brain reflecting multiple neural processes co-occurring and interacting. See, Lisman J, Buzsaki G. A neural coding scheme formed by the combined function of gamma and theta oscillations. Schizophr Bull. Jun. 16, 2008; doi:10.1093/schbul/sbn060. Such a time-frequency analysis may take the form of a wavelet transform analysis. This may be used to assist in integrative and dynamically adaptive information processing. Of course, the transform may be essentially lossless and may be performed in any convenient information domain representation. These EEG-based data analyses reveal the frequency-specific neuronal oscillations and their synchronization in brain functions ranging from sensory processing to higher-order cognition. Therefore, these patterns may be selectively analyzed, for transfer to or induction in, a subject.

A statistical clustering analysis may be performed in high dimension space to isolate or segment regions which act as signal sources, and to characterize the coupling between various regions. This analysis may also be used to establish signal types within each brain region, and decision boundaries characterizing transitions between different signal types. These transitions may be state dependent, and therefore the transitions may be detected based on a temporal analysis, rather than merely a concurrent oscillator state.

The various measures make use of the magnitude and/or phase angle information derived from the complex data extracted from the EEG during spectral decomposition and/or temporal/spatial/spectral analysis. Some measures estimate the magnitude or phase consistency of the EEG within one channel across trials, whereas others estimate the consistency of the magnitude or phase differences between channels across trials. Beyond these two families of calculations, there are also measures that examine the coupling between frequencies, within trials and recording sites. Of course, in the realm of time-frequency analysis, many types of relationships can be examined beyond those already mentioned.

These sensory processing specific neuronal oscillations, e.g., brainwave patterns, e.g., of a trainer or a skilled person, are closely connected to the task or the skill the person is engaged with (movements, coordination, learning, thoughts, emotions, moods, biological chemistry, etc.), and can be stored on a tangible medium and/or can be simultaneously conveyed to a trainee making use of the brain's frequency following response nature. See, Galbraith, Gary C., Darlene M. Olfman, and Todd M. Huffman. "Selective attention affects human brain stem frequency-following response." Neuroreport 14, no. 5 (2003): 735-738, journals.lww.com/neuroreport/Abstract/2003/04150/Selective_attention_affects_human_brain_stem.15.aspx.

One of the advantages of transforming the data is the ability to select a transform that separates the information of interest represented in the raw data, from noise or other information. Some transforms preserve the spatial and state transition history, and may be used for a more global analysis. Another advantage of a transform is that it can present the information of interest in a form where relatively simple linear or statistical functions of low order may be applied. In some cases, it is desired to perform an inverse transform on the data. For example, if the raw data includes noise, such as 50 or 60 Hz interference, a frequency transform may be performed, followed by a narrow band filtering of the interference and its higher order intermodulation products. An inverse transform may be performed to return the data to its time-domain representation for further processing. (In the case of simple filtering, a finite impulse response (FIR) or infinite impulse response (IIR) filter could be employed). In other cases, the analysis is continued in the transformed domain.

Transforms may be part of an efficient algorithm to compress data for storage or analysis, by making the representation of the information of interest consume fewer bits of information (if in digital form) and/or allow it to be communication using lower bandwidth. Typically, compression algorithms will not be lossless, and as a result, the compression is irreversible with respect to truncated information.

Typically, the transformation(s) and filtering of the signal are conducted using traditional computer logic, according to defined algorithms. The intermediate stages may be stored and analyzed. However, in some cases, neural networks or deep neural networks may be used, convolutional neural network architectures, or even analog signal processing. According to one set of embodiments, the transforms (if any) and analysis are implemented in a parallel processing environment. Such as using an SIMD processor such as a GPU. Algorithms implemented in such systems are characterized by an avoidance of data-dependent branch instructions, with many threads concurrently executing the same instructions.

EEG signals are analyzed to determine the location (e.g., voxel or brain region) from which an electrical activity pattern is emitted, and the wave pattern characterized. The spatial processing of the EEG signals will typically precede the content analysis, since noise and artifacts may be useful for spatial resolution. Further, the signal from one brain region will typically be noise or interference in the signal analysis from another brain region; so the spatial analysis may represent part of the comprehension analysis. The spatial analysis is typically in the form of a geometrically and/or anatomically-constrained statistical model, employing all of the raw inputs in parallel. For example, where the input data is transcutaneous electroencephalogram information, from 32 EEG electrodes, the 32 input channels, sampled at e.g., 500 sps, 1 ksps or 2 ksps, are processed in a four or higher dimensional matrix, to permit mapping of locations and communication of impulses overtime, space and state.

The matrix processing may be performed in a standard computing environment, e.g., an i7-7920HQ, i7-8700K, or i9-7980XE processor, under the Windows 10 operating system, executing Matlab (Mathworks, Woburn MA) software platform. Alternately, the matrix processing may be performed in a computer cluster or grid or cloud computing environment. The processing may also employ parallel processing, in either a distributed and loosely coupled environment, or asynchronous environment. One preferred embodiment employs a single instruction, multiple data processors, such as a graphics processing unit such as the nVidia CUDA environment or AMD Firepro high-performance computing environment.

Artificial intelligence (AI) and machine learning methods, such as artificial neural networks, deep neural networks, etc., may be implemented to extract the signals of interest. Neural networks act as an optimized statistical classifier and may have arbitrary complexity. A so-called deep neural network having multiple hidden layers may be employed. The processing is typically dependent on labeled training data, such as EEG data, or various processed, transformed, or classified representations of the EEG data. The label represents the task, performance, context, or state of the subject during acquisition. In order to handle the continuous stream of data represented by the EEG, a recurrent neural network architecture may be implemented. Depending preprocessing before the neural network, formal implementations of recurrence may be avoided. A four or more dimensional data matrix may be derived from the traditional spatial-temporal processing of the EEG and fed to a neural network. Since the time parameter is represented in the input data, a neural network temporal memory is not required, though this architecture may require a larger number of inputs. Principal component analysis (PCA, en.wikipedia.org/wiki/Principal_component_analysis), spatial PCA (arxiv.org/pdf/1501.03221v3.pdf, adegenet.r-forge.r-project.org/files/tutorial-spca.pdf, www.ncbi.nlm.nih.gov/pubmed/1510870); and clustering analysis may also be employed (en.wikipedia.org/wiki/Cluster_analysis, see U.S. Pat. Nos. 9,336,302, 9,607,023 and cited references).

In general, a neural network of this type of implementation will, in operation, be able to receive unlabeled EEG data, and produce the output signals representative of the predicted or estimated task, performance, context, or state of the subject during acquisition of the unclassified EEG. Of course, statistical classifiers may be used rather than neural networks.

The analyzed EEG, either by conventional processing, neural network processing, or both, serves two purposes. First, it permits one to deduce which areas of the brain are subject to which kinds of electrical activity under which conditions. Second, it permits feedback during training of a trainee (assuming proper spatial and anatomical correlates between the trainer and trainee), to help the system achieve the desired state, or as may be appropriate, desired series of states and/or state transitions. According to one aspect of the technology, the applied stimulation is dependent on a measured starting state or status (which may represent a complex context and history dependent matrix of parameters), and therefore the target represents a desired complex vector change. Therefore, this aspect of the technology seeks to understand a complex time-space-brain activity associated with an activity or task in a trainer, and to seek a corresponding complex time-space-brain activity associated with the same activity or task in a trainee, such that the complex time-space-brain activity state in the train or is distinct from the corresponding state sought to be achieved in the trainee. This permits transfer of training paradigms from qualitatively different persons, in different contexts, and, to some extent, to achieve a different result.

The conditions of data acquisition from the trainer will include both task data, and sensory-stimulation data. That is, a preferred application of the system is to acquire EEG data from a trainer or skilled individual, which will then be used to transfer learning, or more likely, learning readiness states, to a nave trainee. The goal for the trainee is to produce a set of stimulation parameters that will achieve, in the trainee, the corresponding neural activity resulting in the EEG state of the trainer at the time of or preceding the learning of a skill or a task, or performance of the task.

It is noted that EEG is not the only neural or brain activity or state data that may be acquired, and of course any and all such data may be included within the scope of the technology, and therefore EEG is a representative example only of the types of data that may be used. Other types include fMRI, magnetoencephalogram, motor neuron activity, PET, etc.

While mapping the stimulus-response patterns distinct from the task is not required in the trainer, it is advantageous to do so, because the trainer may be available for an extended period, the stimulus of the trainee may influence the neural activity patterns, and it is likely that the trainer will have correlated stimulus-response neural activity patterns with the trainee(s). It should be noted that the foregoing has suggested that the trainer is a single individual, while in practice, the trainer may be a population of trainers or skilled individuals. The analysis and processing of brain activity data may, therefore, be adaptive, both for each respective individual and for the population as a whole.

For example, the system may determine that not all human subjects have common stimulus-response brain activity correlates, and therefore that the population needs to be segregated and clustered. If the differences may be normalized, then a normalization matrix or other correction may be employed. On the other hand, if the differences do not permit feasible normalization, the population(s) may be segmented, with different trainers for the different segments. For example, in some tasks, male brains have different activity patterns and capabilities than female brains. This, coupled with anatomical differences between the sexes, implies that the system may provide gender-specific implementations. Similarly, age differences may provide a rational and scientific basis for segmentation of the population. However, depending on the size of the information base and matrices required, and some other factors, each system may be provided with substantially all parameters required for the whole population, with a user-specific implementation based on a user profile or initial setup, calibration, and system training session.

According to one aspect of the present invention, a trainer subject is instrumented with sensors to determine localized brain activity during a task, which may be mental or physical. The objective is to identify regions of the brain involved in learning new skills or tasks and the patterns in those regions, which reflect the readiness for learning or the learning itself.

The trainer may be a trained and/or skilled individual, an individual in the course of training, and the training data set may be derived from a classified population of individuals.

The sensors will typically seek to determine neuron firing patterns and brain region excitation patterns, which can be detected by implanted electrodes, transcutaneous electroencephalograms, magnetoencephalograms, and other technologies. Where appropriate, transcutaneous EEG is preferred, since this is non-invasive and relatively simple.

Task performance data is also obtained from the trainer, to provide correlates of physical, mental or result data with sensor data.

The trainer is observed with the sensors in a quiet state, a state in which he or she is learning the skill and/or task at issue, and various control states in which the trainer is at rest or engaged in different activities and learning different tasks. The training data may be obtained for a sufficiently long period of time and over repeated trials to determine the effect of duration. The training data may also be a population statistical result, and need not be derived from only a single individual at a single time.

The sensor data is then processed using a 4D (or higher) model to determine the characteristic location-dependent pattern of brain activity over time associated with learning or performing the skill and/or task of interest. Where the data is derived from a population with various degrees of training in the skill or the task, the model maintains this training state variable dimension.

A trainee is then prepared for the training. The state of learning of the trainee for the task may be assessed. This can include the physical or results level, with metrics about task performance. Further, the transcutaneous EEG (or other brain activity data) of the trainee may be obtained, to determine the starting state for the trainee, as well as activity during performance of the task.

In addition, a set of stimuli, such as visual patterns, acoustic patterns, vestibular, smell, taste, touch (light touch, deep touch, proprioception, stretch, hot, cold, pain, pleasure, electric stimulation, acupuncture, etc.), vagus nerve (e.g., parasympathetic), are imposed on the subject, optionally over a range of baseline brain states, to acquire data defining the effect of individual and various combinations of sensory stimulation on the brain state of the trainee. Population data may also be used for this aspect.

The data from the trainer or population of trainers (see above) may then be processed in conjunction with the trainee or population of trainee data, to extract information defining the optimal sensory stimulation over time of the trainee to achieve the desired brain state to learn the task.

In general, for populations of trainers and trainees, the data processing task is immense. However, the statistical analysis will generally be of a form that permits parallelization of mathematical transforms for processing the data, which can be efficiently implemented using various parallel processors, a common form of which is a SIMD (single instruction, multiple data) processor, found in typical graphics processors (GPUs). Because of the cost-efficiency of GPUs, it is referred to implement the analysis using efficient parallelizable algorithms, even if the computational complexity is nominally greater than a CISC-type processor implementation.

During training of the trainee, the EEG pattern may be monitored to determine if the desired state is achieved through the sensory stimulation. A closed loop feedback control system may be implemented to modify the sensory stimulation seeking to achieve the target. An evolving genetic algorithm may be used to develop a user model, which relates the task, trainee task performance, sensory stimulation, and brain activity patterns, both to optimize the current session of stimulation and learning, as well as to facilitate future sessions, where the skills of the trainee have further developed, and to permit use of the system for a range of tasks.

The stimulus may comprise a chemical messenger or stimulus to alter the subject's level of consciousness or otherwise alter brain chemistry or functioning. The chemical may comprise a hormone or endocrine analog molecule, (such as adrenocorticotropic hormone [ACTH] (4-11)), a stimulant (such as cocaine, caffeine, nicotine, phenethylamines), a psychoactive drug, psychotropic or hallucinogenic substance (a chemical substance that alters brain function, resulting in temporary changes in perception, mood, consciousness and behavior such as pleasantness (e.g. euphoria) or advantageousness (e.g., increased alertness).

While typically, controlled or "illegal" substances are to be avoided, in some cases, these may be appropriate for use. For example, various drugs may alter the state of the brain to enhance or selectively enhance the effect of the stimulation. Such drugs include stimulants (e.g., cocaine, methylphenidate (Ritalin), ephedrine, phenylpropanolamine, amphetamines), narcotics/opiates (opium, morphine, heroin, methadone, oxymorphine, oxycodone, codeine, fentanyl), hallucinogens (lysergic acid diethylamide (LSD), PCP, MDMA (ecstasy), mescaline, psilocybin, magic mushroom (*Psilocybe cubensis*), *Amanita muscaria* mushroom, marijuana/*Cannabis*), *Salvia divinorum*, diphenhydramine (Benadryl), flexeril, tobacco, nicotine, bupropion (Zyban), opiate antagonists, depressants, gamma aminobutyric acid (GABA) agonists or antagonists, NMDA receptor agonists or antagonists, depressants (e.g., alcohol, Xanax; Valium; Halcion; Librium; other benzodiazepines, Ativan; Klonopin; Amytal; Nembutal; Seconal; Phenobarbital, other barbiturates), psychedelics, disassociatives, and deliriants (e.g., a special class of acetylcholine-inhibitor hallucinogen). For example, Carhart-Harris showed using fMRI that LSD and psilocybin caused synchronisation of different parts of the brain that normally work separately by making neurons fire simultaneously. This effect can be used to induce synchronization of various regions of the brain to promote focus and enhanced cognitive function desirable for learning and performance.

It is an object of the present invention to provide a system and method for facilitating a skill-learning process, comprising: determining a neuronal activity pattern, of a skilled subject while engaged in a respective skill; processing the determined neuronal activity pattern with at least one automated processor; and subjecting a subject training in the respective skill to a stimulus selected from the group consisting of one or more of a sensory excitation, a peripheral excitation, a transcranial excitation, and a deep brain stimulation, dependent on the processed electromagnetic determined neuronal activity pattern.

It is yet another object of the present invention to provide a system and method for facilitating a skill or information-learning process, comprising: determining a neuronal activity pattern of a skilled subject with the knowledge of a respective skill or information while engaged in learning this skill or information; processing the determined neuronal activity pattern with at least one automated processor; and subjecting a subject learning the respective skill or information to a stimulus selected from the group consisting of one or more of a sensory excitation, a peripheral excitation, a transcranial excitation, and a deep brain stimulation, dependent on the processed electromagnetic determined neuronal activity pattern.

It is still another object of the present invention to provide a system and method for improving performance of an activity, comprising: determining a neuronal activity pattern, of a skilled subject with mastery of a respective activity while engaged in performing the respective activity; processing the determined neuronal activity pattern with at least one automated processor; and subjecting a subject performing the respective activity to a stimulus selected from the group consisting of one or more of a sensory excitation, a peripheral excitation, a transcranial excitation, and a deep brain stimulation, dependent on the processed electromagnetic determined neuronal activity pattern.

It is also an object of the present invention to provide an apparatus for facilitating a skill learning process, comprising: an input, configured to receive data representing a neuronal activity pattern of a skilled subject while engaged in a respective skill; at least one automated processor, configured to process the determined neuronal activity pattern, to determine neuronal activity patterns selectively associated with successful learning of the skill; and a stimulator, configured to subject a subject training in the respective skill to a stimulus selected from the group consisting of one or more of a sensory excitation, a peripheral excitation, a transcranial excitation, and a deep brain stimulation, dependent on the processed determined neuronal activity pattern.

It is further an object of the present invention to provide an apparatus for facilitating a skill or information learning process, comprising: an input, configured to receive data representing a neuronal activity pattern of a skilled subject while engaged in a respective skill or learning information; at least one automated processor, configured to process the determined neuronal activity pattern, to determine neuronal activity patterns selectively associated with successful learning of the skill or information; and a stimulator, configured to subject a subject training in the respective skill or learning the information to a stimulus selected from the group consisting of one or more of a sensory excitation, a peripheral excitation, a transcranial excitation, and a deep brain stimulation, dependent on the processed determined neuronal activity pattern.

It is also an object of the present invention to provide an apparatus for improving a performance of an activity, comprising: an input, configured to receive data representing a neuronal activity pattern of a skilled subject while engaged in the performance of an activity; at least one automated processor, configured to process the determined neuronal activity pattern, to determine neuronal activity patterns selectively associated with effective performance of the respective activity; and a stimulator, configured to subject a less-experienced subject performing the respective activity to a stimulus selected from the group consisting of one or more of a sensory excitation, a peripheral excitation, a transcranial excitation, and a deep brain stimulation, dependent on the processed determined neuronal activity pattern.

It is a further object of the present invention to provide a system for influencing a brain electrical activity pattern of a subject during training in a task, comprising: an input, configured to determine a target brain activity state for the subject, dependent on the task; at least one processor, configured to generate a stimulation pattern profile adapted to achieve the target brain activity state for the subject, dependent on the task; and a stimulator, configured to output at least one stimulus, proximate to the subject, dependent on the generated stimulation pattern profile.

It is yet a further object of the present invention to provide a system for influencing a brain electrical activity pattern of a subject during learning new information, comprising: an input, configured to determine a target brain activity state for the subject, dependent on the nature of the respective information; at least one processor, configured to generate a stimulation pattern profile adapted to achieve the target brain activity state for the subject, dependent on the task; and a stimulator, configured to output at least one stimulus, proximate to the subject, dependent on the generated stimulation pattern profile.

It is still a further object of the present invention to provide a system for influencing a brain electrical activity pattern of a subject during performing of an activity, comprising: an input, configured to determine a target brain activity state for the subject, dependent on the activity; at least one processor, configured to generate a stimulation pattern profile adapted to achieve the target brain activity state for the subject, dependent on the activity; and a stimulator, configured to output at least one stimulus, proximate to the subject, dependent on the generated stimulation pattern profile.

It is a still further object of the present invention to provide a system for determining a target brain activity state for a subject, dependent on a task, comprising: a first monitor, configured to acquire a brain activity of a first subject during performance of a task; at least one first processor, configured to analyze a spatial brain activity state over time of the first subject; and determine spatial brain activity states of the first subject, which represent readiness for training in the task; a second monitor, configured to acquire a brain activity of a second subject during performance of a variety of activities, under a variety of stimuli; and at least one second processor, configured to: analyze a spatial brain activity state overtime of the second subject; and translate the determined spatial brain activity states of the first subject which represent readiness for training in the task, into a stimulus pattern for the second subject to achieve a spatial brain activity state in the second subject corresponding to readiness for training in the task.

It is a still further object of the present invention to provide a system for determining a target brain activity state for a subject, dependent on a physical activity, comprising: a first monitor, configured to acquire a brain activity of a first subject during performance of a physical activity; at least one first processor, configured to analyze a spatial brain activity state over time of the first subject; and determine spatial brain activity states of the first subject, which represent readiness for training in the task; a second monitor, configured to acquire a brain activity of a second subject during performance of a variety of activities, under a variety of stimuli; and at least one second processor, configured to: analyze a spatial brain activity state over time of the second subject; and translate the determined spatial brain activity states of the first subject which represent readiness for training in the task, into a stimulus pattern for the second subject to achieve a spatial brain activity state in the second subject corresponding to optimal physical activity.

It is a further object to provide a method of teaching a task to a first subject, the method comprising: recording a second subject's brainwaves EEG while at rest; having the second subject perform said task; recording the second subject's brainwaves EEG while performing said task; extracting a predominant temporal pattern associated with said task from the recorded brainwaves by comparing them with the brainwaves at rest; encoding said temporal pattern as a digital code stored in a tangible media; and using said digital code to modulate the temporal pattern on a signal perceptible to the first subject while said first subject is learning said one if a mental and a motor skill, whereby said light signal stimulates in the second subject brain waves having said temporal pattern to accelerate learning of said task.

It is still a further object to provide a method of enhancing performance of a task of a first subject, the method comprising: recording a second subject's brainwaves EEG while at rest; having the second subject perform said task; recording the second subject's brainwaves EEG while performing said task; extracting a predominant temporal pattern associated with said task from the recorded brainwaves by comparing them with the brainwaves at rest; encoding said temporal pattern as a digital code stored in a tangible media; and using said digital code to modulate the temporal pattern on a signal perceptible to the first subject while said first subject is performing said task, whereby said light signal stimulates in the second subject brain waves having said temporal pattern to enhance the performance of said task.

A still further object provides a method of assisted reading a new text by a first subject, the method comprising: recording a second subject's brainwaves EEG while at rest, wherein the second subject is knowledgeable in the subject matter of the text; having the second subject read the text; recording the second subject's brainwaves EEG while reading the text; extracting a predominant temporal pattern associated with reading the text from the recorded brainwaves by comparing them with the brainwaves at rest;

encoding said temporal pattern as a digital code stored in a tangible media; and using said digital code to modulate the temporal pattern on a signal perceptible to the first subject while the first subject is reading, whereby said signal stimulates in the first subject brain waves having said temporal pattern to accelerate reading, comprehension, and retention of the text.

It is another object to provide a computer readable medium, storing therein non-transitory instructions for a programmable processor to perform a process, comprising the computer-implemented steps: synchronizing brain activity data of a subject with at least one event involving the subject; analyzing the brain activity data to determine a selective change in the brain activity data corresponding to a timing of the event; and determine a stimulation pattern adapted to induce a brain activity having a correspondence to the brain activity data associated with the event, based on at least a brain activity model.

The at least one of a sensory excitation, peripheral excitation, and transcranial excitation may be generated based on a digital code. The subjecting of the subject training in the respective skill to the sensory excitation increases a learning rate of the skill in the training subject. Similarly, the subjecting of the subject learning the respective new information to the sensory excitation increases a learning rate of the new information in the learning subject. Likewise, the subjecting of the subject engaged in the respective physical activity to the sensory excitation improves the performance of the respective physical activity in the subject engages in the respective activity.

The method may further comprise determining a neuronal baseline activity of the skilled subject while not engaged in the skill, a neuronal baseline activity of the subject training in the respective skill while not engaged in the skill, a neuronal activity of the skilled subject while engaged in the respective skill, and/or a neuronal activity of the subject training in the respective skill while engaged in the skill.

The method may further comprise determining a neuronal baseline activity of the skilled subject while not engaged in the learning of new information, a neuronal baseline activity of the subject learning respective information while not engaged in the learning, a neuronal activity of the skilled subject while engaged in the learning, and/or a neuronal activity of the subject learning respective information while engaged in the learning.

The method may further comprise determining a neuronal baseline activity of the skilled subject while not engaged in the physical activity, a neuronal baseline activity of the less-experienced subject to be engaged in a physical activity while not engaged in the physical activity, a neuronal activity of the skilled subject while engaged in the respective physical activity, and/or a neuronal activity of the less-experienced subject while engaging in the respective physical activity.

The skilled subject may be at the same level of training as the trainee, or one or more stages advanced beyond the training of the trainee.

The representation of the processed the determined neuronal activity pattern may be stored in memory. The storage could be on a tangible medium as an analog or digital representation. It is possible to store the representation in a data storage and access system either for a permanent backup or further processing the respective representation. The storage can also be in a cloud storage and/or processing system.

The neuronal activity pattern may be obtained by electroencephalography, magnetoencephalography, MRI, fMRI, PET, low-resolution brain electromagnetic tomography, or other electrical or non-electrical means.

The neuronal activity pattern may be obtained by at least one implanted central nervous system (cerebral, spinal) or peripheral nervous system electrode. An implanted neuronal electrode can be either within the peripheral nervous system or the central nervous system. The recording device could be portable or stationary. Either with or without onboard electronics such as signal transmitters and/or amplifiers, etc. The at least one implanted electrode can consist of a microelectrode array featuring more than one recording site. Its main purpose can be for stimulation and/or recoding.

The neuronal activity pattern may be obtained by at least a galvanic skin response. Galvanic skin response or resistance is often also referred as electrodermal activity (EDA), psychogalvanic reflex (PGR), skin conductance response (SCR), sympathetic skin response (SSR) and skin conductance level (SCL) and is the property of the human body that causes continuous variation in the electrical characteristics of the skin.

The stimulus may comprise a sensory excitation. The sensory excitation may by either sensible or insensible. It may be either peripheral or transcranial. It may consist of at least one of a visual, an auditory, a tactile, a proprioceptive, a somatosensory, a cranial nerve, a gustatory, an olfactory, a pain, a compression and a thermal stimulus or a combination of aforesaid. It can, for example, consist of light flashes either within ambient light or aimed at the subject's eyes, 2D or 3D picture noise, modulation of intensity, within the focus of the subject's eye the visual field or within peripheral sight.

The stimulus may comprise a peripheral excitation, a transcranial excitation, a sensible stimulation of a sensory input, an insensible stimulation of a sensory input, a visual stimulus, an auditory stimulus, a tactile stimulus, a proprioceptive stimulus, a somatosensory stimulus, a cranial nerve stimulus, a gustatory stimulus, an olfactory stimulus, a pain stimulus, an electric stimulus, a magnetic stimulus, or a thermal stimulus.

The stimulus may comprise transcranial magnetic stimulation (TMS), cranial electrotherapy stimulation (CES), transcranial direct current stimulation (tDCS), comprise transcranial alternating current stimulation (tACS), transcranial random noise stimulation (tRNS), comprise transcranial pulsed current stimulation (tPCS), pulsed electromagnetic field (PEMF), or noninvasive or invasive deep brain stimulation (DBS), for example.

The stimulus may comprise transcranial pulsed ultrasound (TPU).

The stimulus may comprise a cochlear implant stimulus, spinal cord stimulation (SCS) or a vagus nerve stimulation (VNS), or other direct or indirect cranial or peripheral nerve stimulus.

The stimulus may comprise or achieve brainwave entrainment.

The stimulus may comprise electrical stimulation of the retina, a pacemaker, a stimulation microelectrode array, electrical brain stimulation (EBS), focal brain stimulation (FBS), light, sound, vibrations, an electromagnetic wave. The light stimulus may be emitted by at least one of alight bulb, alight emitting diode (LED), and a laser. The signal may be one of alight ray, a sound wave, and an electromagnetic wave. The signal may be alight signal projected onto the first subject by one of a smart bulb generating ambient light, at least one LED position near the eyes of the first subject and laser generating low-intensity pulses.

The skill may comprise a mental skill. For example, mental skill can be a cognitive skill, an alertness skill, a concentration skill, an attention skill, a focusing skill, a memorization skill, a visualization skill, a relaxation skill, a meditation skill, a speedreading skill, a creative skill, "whole-brain-thinking" skill, an analytical skill, a reasoning skill, a problem-solving skill, a critical thinking skill, an intuitive skill, a leadership skill, a learning skill, a speed-reading skill, a patience skill, a balancing skill, a perception skill, a linguistic or language skill, a language comprehension skill, a quantitative skill, a "fluid intelligence" skill, a pain management skill, a skill of maintaining positive attitude, a foreign language skill, a musical skill, a musical composition skill, a writing skill, a poetry composition skill, a mathematical skill, a science skill, an art skill, a visual art skill, a rhetorical skill, an emotional control skill, an empathy skill, a compassion skill, a motivational skill, people skill, a computational skill, a science skill, or an inventorship skill. See, U.S. patent and Pub. U.S. Pat. Nos. 6,435, 878, 5,911,581, and 20090069707.

The skill may comprise a motor skill, e.g., fine motor, muscular coordination, walking, running, jumping, swimming, dancing, gymnastics, yoga; an athletic or sports skill, a massage skill, martial arts or fighting, shooting, self-defense; speech, singing, playing a musical instrument, penmanship, calligraphy, drawing, painting, visual, auditory, olfactory, game-playing, gambling, sculptor's, craftsman, massage, or assembly.

The technology may be embodied in apparatuses for acquiring the brain activity information from the trainer, processing the brain activity information to reveal a target brain activity state and a set of stimuli, which seek to achieve that state in a trainee, and generating stimuli for the trainee to achieve and maintain the target brain activity state over a period of time and potential state transitions. The generated stimuli may be feedback controlled. A general-purpose computer may be used for the processing of the information, a microprocessor, a FPGA, an ASIC, a system-on-a-chip, or a specialized system, which employs a customized configuration to efficiently achieve the information transformations required. Typically, the trainer and trainee act asynchronously, with the brain activity of the trainer recorded and later processed. However, real-time processing and brain activity transfer are also possible. In the case of a general purpose programmable processor implementation or portions of the technology, computer instructions may be stored on a nontransitory computer readable medium.

It is another object to provide a method of teaching one of a mental skill and a motor skill to a first subject, the method comprising: recording a second subject's brainwaves EEG while at rest; having the second subject perform said one of a mental skill and a motor skill; recording the second subject's brainwaves EEG while performing said one of a mental skill and a motor skill; extracting a predominant temporal pattern associated with said one of a mental skill and a motor skill from the recorded brainwaves by comparing them with the brainwaves at rest; encoding said temporal pattern as a digital code stored in a tangible media; and using said digital code to modulate the temporal pattern on a signal perceptible to the first subject while the first subject is learning said one if a mental and a motor skill, whereby said light signal stimulates in the first subject brain waves having said temporal pattern to accelerate learning of said one if a mental skill and a motor skill.

A further object provides a high-definition transcranial alternating current stimulation (HD-tACS) stimulation of a trainee, having a stimulation frequency, amplitude pattern, spatial pattern, dependent on an existing set of states in the target, and a set of brainwave patterns from a trainor engaged in an activity, adapted to improve the learning or performance of the trainee.

Another object provides a system and method for facilitating a skill-learning process, comprising: determining a neuronal activity pattern, of a skilled subject while engaged in a respective skill; processing the determined neuronal activity pattern with at least one automated processor; and subjecting a subject training in the respective skill to a stimulus selected from the group consisting of one or more of a sensory excitation, a peripheral excitation, a transcranial excitation, and a deep brain stimulation, dependent on the processed electromagnetic determined neuronal activity pattern while the subject is subjected to tES, a psychedelic and/or other pharmaceutical agents.

It is a still further object to provide a method of facilitating a skill learning process, comprising: determining a neuronal activity pattern of a skilled subject while engaged in a respective skill; processing the determined neuronal activity pattern with at least one automated processor; subjecting a subject training in the respective skill to one of transcranial electric stimulation (tES) and magnetic brain stimulation; and subjecting a subject training in the respective skill to a stimulus selected from the group consisting of one or more of a sensory excitation, a peripheral excitation, a transcranial excitation, and a deep brain stimulation, dependent on the processed determined neuronal activity pattern. The transcranial electric stimulation (tES) may be one of transcranial direct current stimulation (tDCS), transcranial alternative current stimulation (tACS), and high-definition transcranial alternative current stimulation (tES).

Another object provides a method of facilitating a skill learning process, comprising: determining a neuronal activity pattern of a skilled subject while engaged in a respective skill; processing the determined neuronal activity pattern with at least one automated processor; subjecting a subject training in the respective skill to one of a pharmaceutical agent and a psychedelic agent; and subjecting a subject training in the respective skill to a stimulus selected from the group consisting of one or more of a sensory excitation, a peripheral excitation, a transcranial excitation, and a deep brain stimulation, dependent on the processed determined neuronal activity pattern.

A further object provides a method of facilitating a mental process, comprising: determining brainwave neural correlates associated with a mental process of a first subject; processing the brainwave neural correlates with at least one automated processor, to extract at least a modulated neural activity pattern; and subjecting a second subject to a stimulus having a modulation selectively dependent on the modulated neural activity pattern.

A computer-readable medium is provided, storing therein non-transitory instructions for a programmable processor to perform a process, comprising the computer-implemented steps of: reading information from a memory representing dynamic neuronal activity patterns selectively associated with the skill or task; and controlling a stimulator, to stimulate a subject with a stimulus selected from the group consisting of one or more of a sensory excitation, a peripheral neural excitation, a transcranial excitation, and a deep brain stimulation, dependent on the dynamic neuronal activity patterns selectively associated with the skill or task, to facilitate performance of the respective skill or task by a stimulated subject.

An apparatus is provided for facilitating a skill or task, comprising: a memory, configured to store automatically processed dynamic neuronal activity pattern, to define dynamic neuronal activity patterns selectively associated with the skill or task; and a stimulator, configured to stimulate a subject with a stimulus selected from the group consisting of one or more of a sensory excitation, a peripheral excitation, a transcranial excitation, and a deep brain stimulation, dependent on the defined dynamic neuronal activity patterns selectively associated with the skill or task, to facilitate performance of the respective skill or task by the subject.

The mental process may comprise a skill or task, the brainwave neural correlates are determined while the first subject is engaged in the skill or task, and the modulated neural activity pattern is selectively associated with the skill or task. The second subject may be engaged in the skill or task in temporal proximity to said subjecting the second subject to the stimulus, and the stimulus comprises at least one of a sensory stimulation and a transcranial stimulation.

The stimulus may be generated based on a digitally coded waveform representing the modulated neural activity pattern.

The method may further comprise determining brainwave neural correlates associated with the mental process of the second subject.

The brainwave neural correlates associated with the mental process of the first subject may be acquired by at least one of electroencephalography, magnetoencephaography, brain electromagnetic tomography, positron emission tomography, and functional magnetic resonance imaging.

The stimulus may be one or more of a peripheral sensory neuron excitation, a cranial nerve stimulation, a transcranial electrical stimulation, a transcranial magnetic stimulation of the second subject, a visual stimulus, and an auditory stimulus. The stimulus may be selected from the group consisting of one or more of a tactile stimulus, a proprioceptive stimulus, a somatosensory stimulus, a gustatory stimulus, an olfactory stimulus, a pain stimulus, a thermal stimulus, spinal cord stimulation (SCS), transcranial pulsed ultrasound (TPU), pulsed electromagnetic field (PEMF), noninvasive deep brain stimulation, cochlear implant stimulus, deep brain stimulation (DBS), electrical stimulation of the retina, pacemaker stimulation, microelectrode array stimulation, vagus nerve stimulation (VNS), electrical brain stimulation (EBS), and focal brain stimulation (FBS). The stimulus may be adapted to achieve brainwave entrainment. The stimulus may be generated based on a digitally coded stimulation waveform. The stimulator may comprise at least one of a sensory neuron stimulator, a transcranial electrical stimulator, a transcranial alternating current stimulator (tACS), a transcranial magnetic stimulation (TMS), a visual stimulator, an auditory stimulator, a tactile stimulator, a proprioceptive stimulator, a somatosensory stimulator, a gustatory stimulator, an olfactory stimulator, a pain stimulator, a thermal stimulator, a spinal cord stimulator, a transcranial pulsed ultrasound (TPU) stimulator, a pulsed electromagnetic field (PEMF) stimulator, a noninvasive deep brain stimulator, a cochlear implant stimulator, a deep brain stimulator, a retinal electrical stimulator, a pacemaker stimulator, a microelectrode array stimulator, a vagus nerve stimulator, an electrical brain stimulator, and a focal brain stimulator. The stimulator may be configured to cause brainwave entrainment. The stimulus may comprise a peripheral or central neural stimulation of the subject with a signal having a modulation corresponding to a neuronal activity pattern defined by a recording of brainwaves of a human.

The mental process may comprise a motor skill. The mental process may comprise at least one of a mental skill, a motor skill, a musical instrument playing skill, a singing skill, a dancing skill, a sports skill, a martial arts skill, a speech skill, a mathematical skill, a calligraphical skill, a drawing skill, a painting skill, a massage skill, an assembly skill, a walking skill, a running skill, a swimming skill, a yoga skill, a fighting skill, a shooting skill, a self-defense skill, an olfactory skill, and a muscular coordination skill.

The apparatus may further comprise an input configured to acquire neural correlates associated with the skill or task of the subject. The neural correlates associated with the task or skill may be acquired by at least one of electroencephalography, magnetoencephaography, brain electromagnetic tomography, positron emission tomography, functional magnetic resonance imaging, an implanted electrode, and galvanic skin response.

The skill or task may comprise at least one of a mental skill, a motor skill, a musical instrument playing skill, a singing skill, a dancing skill, a sports skill, a martial arts skill, a speech skill, a mathematical skill, a calligraphical skill, a drawing skill, a painting skill, a massage skill, an assembly skill, a walking skill, a running skill, a swimming skill, a yoga skill, a fighting skill, a shooting skill, a self-defense skill, an olfactory skill, a muscular coordination skill, a memorization, a native language, a foreign language, literature, arithmetic, algebra, geometry, calculus, mathematics, physics, chemistry, biology, history, economics, geography, a social science, physical education, health, art, and music.

The stimulator may comprise a binaural stimulator configured to at least one of: induce a desired predominant brainwave frequency in the subject; expose the subject to an isochronic tone; and expose the subject to binaural beats.

The stimulator may comprise a binocular stimulator configured to present optical signals having different amplitude modulated optical signals to each respective eye. The stimulator may be configured to concurrently electrically or magnetically stimulate different parts of the subject's brain with signals having different frequencies. The stimulator may comprise an optical illuminator configured to produce optical patterns having a tine-varying intensity pattern corresponding to the dynamic neuronal activity patterns, wherein the dynamic neuronal activity patterns have a waveform corresponding to an acquired brainwave.

The apparatus may further comprise an input configured to receive brainwave signals; and at least one processor configured to process the received brainwave signals to define the dynamic neuronal activity pattern, wherein the received brainwave signals are not from the same subject at the same time.

The processed dynamic neuronal activity pattern may comprise a plurality of frequency patterns of brainwave activity of a human while engaged in different aspects of the skill or task; and the stimulus comprises a sequence of phases respectively representing the plurality of frequency patterns.

The stimulus may comprise a concurrent plurality of stimulation signal frequencies.

The apparatus may further comprise at least one processor configured to analyze an input received from the subject to determine readiness for the task, and to control the stimulator dependent on the determined readiness for the task.

BRIEF DESCRIPTION OF THE DRAWINGS

FIG. 4 shows one second of a typical EEG signal.

FIG. 5 shows a typical EEG reading.

FIG. 6 shows main brainwave patterns.

FIG. 7 shows a flowchart according to one embodiment of the invention.

FIG. 8 shows a flowchart according to one embodiment of the invention.

FIG. 9 shows a flowchart according to one embodiment of the invention.

FIG. 10 shows a flowchart according to one embodiment of the invention.

FIG. 11 shows a flowchart according to one embodiment of the invention.

FIG. 12 shows a flowchart according to one embodiment of the invention.

FIG. 18 shows brainwaves during inefficient problem solving and stress.

FIGS. 19 and 20 show how binaural beats work.

FIG. 21 shows Functional Magnetic Resonance Imaging (fMRI)

FIG. 25 shows a flowchart according to one embodiment of the invention.

FIG. 26 shows a flowchart according to one embodiment of the invention.

FIG. 27 shows a flowchart according to one embodiment of the invention.

FIG. 28 shows a flowchart according to one embodiment of the invention.

DETAILED DESCRIPTION OF THE PREFERRED EMBODIMENTS

Figures 1, 2, 3:
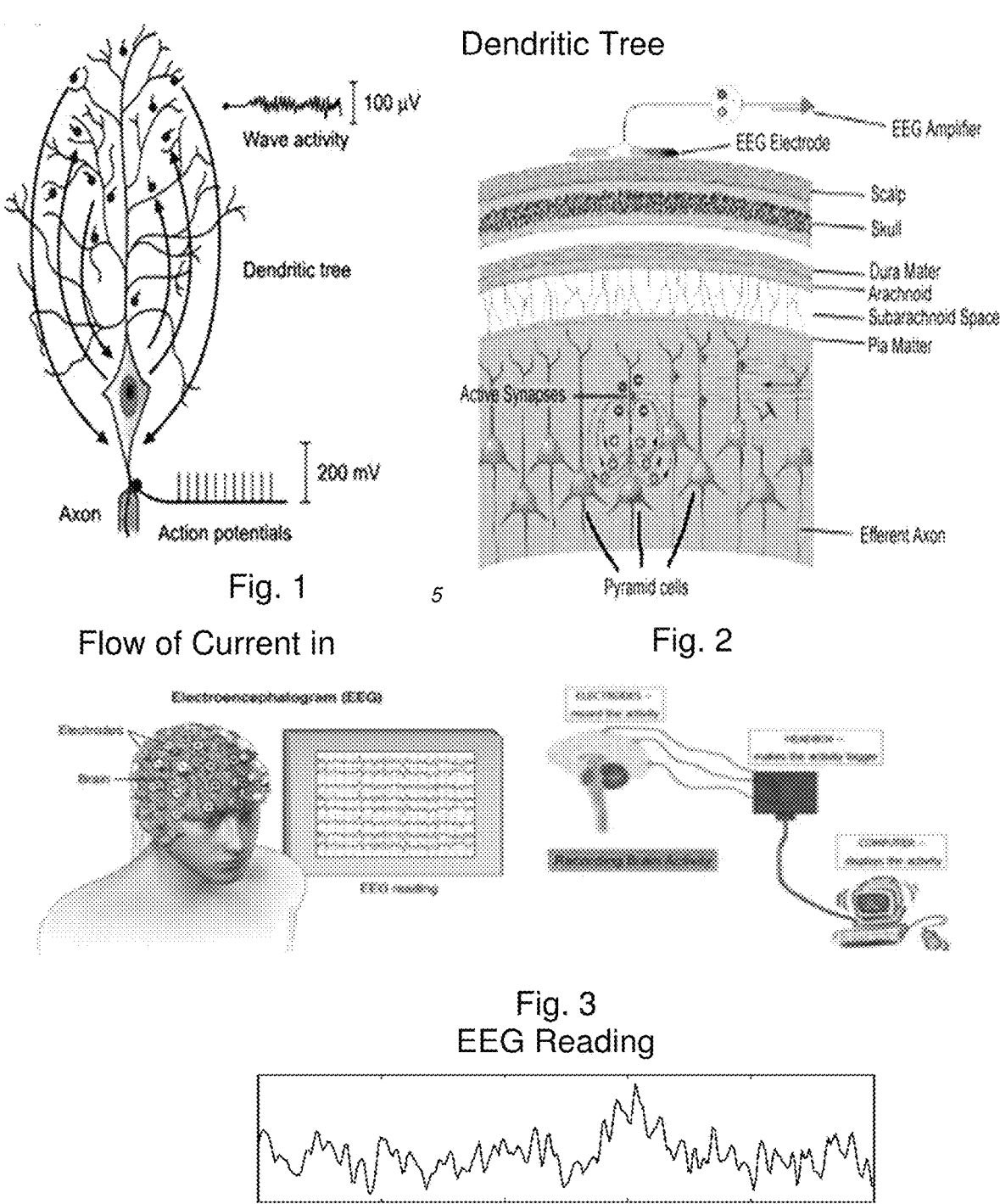
FIG. 1 shows the electric activity of a neuron contributing to a brainwave.
FIG. 2 shows transmission of an electrical signal generated by a neuron through the skull, skin and other tissue to be detectable by an electrode transmitting this signal to EEG amplifier.
FIG. 3 shows an illustration of a typical EEG setup with a subject wearing a cup with electrodes connected to the EEG machine, which is, in turn, connected to a computer screen displaying the EEG.

Hereinafter, embodiments of the present disclosure will be described in detail with reference to the accompanying drawings so that the present disclosure may be readily implemented by those skilled in the art. However, it is to be noted that the present disclosure is not limited to the embodiments but can be embodied in various other ways. In drawings, parts irrelevant to the description are omitted for the simplicity of explanation, and like reference numerals denote like parts through the whole document.

Through the whole document, the term "connected to" or "coupled to" that is used to designate a connection or coupling of one element to another element includes both a case that an element is "directly connected or coupled to" another element and a case that an element is "electronically connected or coupled to" another element via still another element. Further, it is to be understood that the term "comprises or includes" and/or "comprising or including" used in the document means that one or more other components, steps, operation and/or existence or addition of elements are not excluded in addition to the described components, steps, operation and/or elements unless context dictates otherwise.

Through the whole document, the term "unit" or "module" includes a unit implemented by hardware or software and a unit implemented by both of them. One unit may be implemented by two or more pieces of hardware, and two or more units may be implemented by one piece of hardware.

The present invention generally relates to enhancing emotional response by a subject in connection with the received information by conveying to the brain of the subject temporal patterns of brainwaves of a second subject who had experienced such emotional response, said temporal pattern being provided non-invasively via light, sound, transcranial direct current stimulation (tDCS), transcranial alternating current stimulation (tDAS) or HD-tACS, transcranial magnetic stimulation (TMS) or other means capable of conveying frequency patterns.

The transmission of the brain waves can be accomplished through direct electrical contact with the electrodes implanted in the brain or remotely employing light, sound, electromagnetic waves and other non-invasive techniques. Light, sound, or electromagnetic fields may be used to remotely convey the temporal pattern of prerecorded brainwaves to a subject by modulating the encoded temporal frequency on the light, sound or electromagnetic filed signal to which the subject is exposed.

Every activity, mental or motor, every emotion is associated with unique brainwaves having specific spatial and temporal patterns, i.e., a characteristic frequency or a characteristic distribution of frequencies over time and space. Such waves can be read and recorded by several known techniques, including electroencephalography (EEG), magnetoencephalography (MEG), exact low-resolution brain electromagnetic tomography (eLORETA), sensory evoked potentials (SEP), fMRI, functional near-infrared spectroscopy (fNIRS), etc. The cerebral cortex is composed of neurons that are interconnected in networks. Cortical neurons constantly send and receive nerve impulses-electrical activity-even during sleep. The electrical or magnetic activity measured by an EEG or MEG (or another device) device reflects the intrinsic activity of neurons in the cerebral cortex and the information sent to it by subcortical structures and the sense receptors.

"Playing back the brainwaves" to another animal or person by providing decoded temporal pattern through tDCS, tACS, HD-tACS, TMS, or through electrodes implanted in the brain, allows the recipient to learn the task at hand faster. For example, if the brain waves of a mouse navigated a familiar maze are decoded (by EEG or via implanted electrodes), playing this temporal pattern to another mouse unfamiliar with this maze will allow it to learn to navigate this maze faster.

Employing light, sound or electromagnetic field to remotely convey the temporal pattern of brainwaves (which may be prerecorded) to a subject by modulating the encoded temporal frequency on the light, sound or electromagnetic filed signal to which the subject is exposed.

When a group of neurons fires simultaneously, the activity appears as a brainwave. Different brainwave-frequencies are linked to different tasks in the brain.

FIG. 1 shows the electric activity of a neuron contributing to a brainwave.

FIG. 2 shows transmission of an electrical signal generated by a neuron through the skull, skin and other tissue to be detectable by an electrode transmitting this signal to EEG amplifier.

FIG. 3 shows an illustration of a typical EEG setup with a subject wearing a cup with electrodes connected to the EEG machine, which is, in turn, connected to a computer screen displaying the EEG. FIG. 4 shows one second of a typical EEG signal. FIG. 5 shows a typical EEG reading. FIG. 6 shows main brainwave patterns.

FIG. 7 shows a flowchart according to one embodiment of the invention. Brainwaves from a subject engaged in a task are recorded. Brainwaves associated with the task are identified. A temporal pattern in the brainwave associated with the task is decoded. The decoded temporal pattern is used to modulate the frequency of at least one stimulus. The temporal pattern is transmitted to the second subject by exposing the second subject to said at least one stimulus.

FIG. 8 shows a flowchart according to one embodiment of the invention. Brainwaves in a subject at rest and engaged in a task are recorded, and a brainwave characteristic associated with the task is separated by comparing with the brainwaves at rest. A temporal pattern in the brainwave associated with the task is decoded and stored. The stored code is used to modulate the temporal pattern on a stimulus, which is transmitted to the second subject by exposing the second subject to the stimulus FIG. 9 shows a flowchart according to one embodiment of the invention. Brainwaves in a subject engaged in a task are recorded, and a Fourier Transform analysis performed. A temporal pattern in the brainwave associated with the task is then decoded and stored. The stored code is then used to modulate the temporal pattern on a stimulus, which is transmitted to the second subject by exposing the second subject to the stimulus.

FIG. 10 shows a flowchart according to one embodiment of the invention. Brainwaves in a plurality of subjects engaged in a respective task are recorded. A neural network is trained on the recorded brainwaves associated with the task. After the neural network is defined, brainwaves in a first subject engaged in the task are recorded. The neural network is used to recognize brainwaves associated with the task. A temporal pattern in the brainwaves associated with the task is decoded and stored. The code is used to modulate the temporal pattern on a stimulus. Brainwaves associated with the task in a second subject are induced by exposing the second subject to the stimulus FIG. 11 shows a flowchart according to one embodiment of the invention. Brainwaves in a subject both at rest and engaged in a task are recorded. A brainwave pattern associated with the task is separated by comparing with the brainwaves at rest. For example, a filter or optimal filter may be designed to distinguish between the patterns. A temporal pattern in the brainwave associated with the task is decoded, and stored in software code, which is then used to modulate the temporal pattern of light, which is transmitted to the second subject, by exposing the second subject to the source of the light.

FIG. 12 shows a flowchart according to one embodiment of the invention. Brainwaves in a subject at rest and engaged in a task are recoded. A brainwave pattern associated with the task is separated by comparing with the brainwaves at rest. A temporal pattern in the brainwave associated with the task is decoded and stored as a temporal pattern in software code. The software code is used to modulate the temporal pattern on a sound signal. The temporal pattern is transmitted to the second subject by exposing the second subject to the sound signal.

Figures 13, 14:
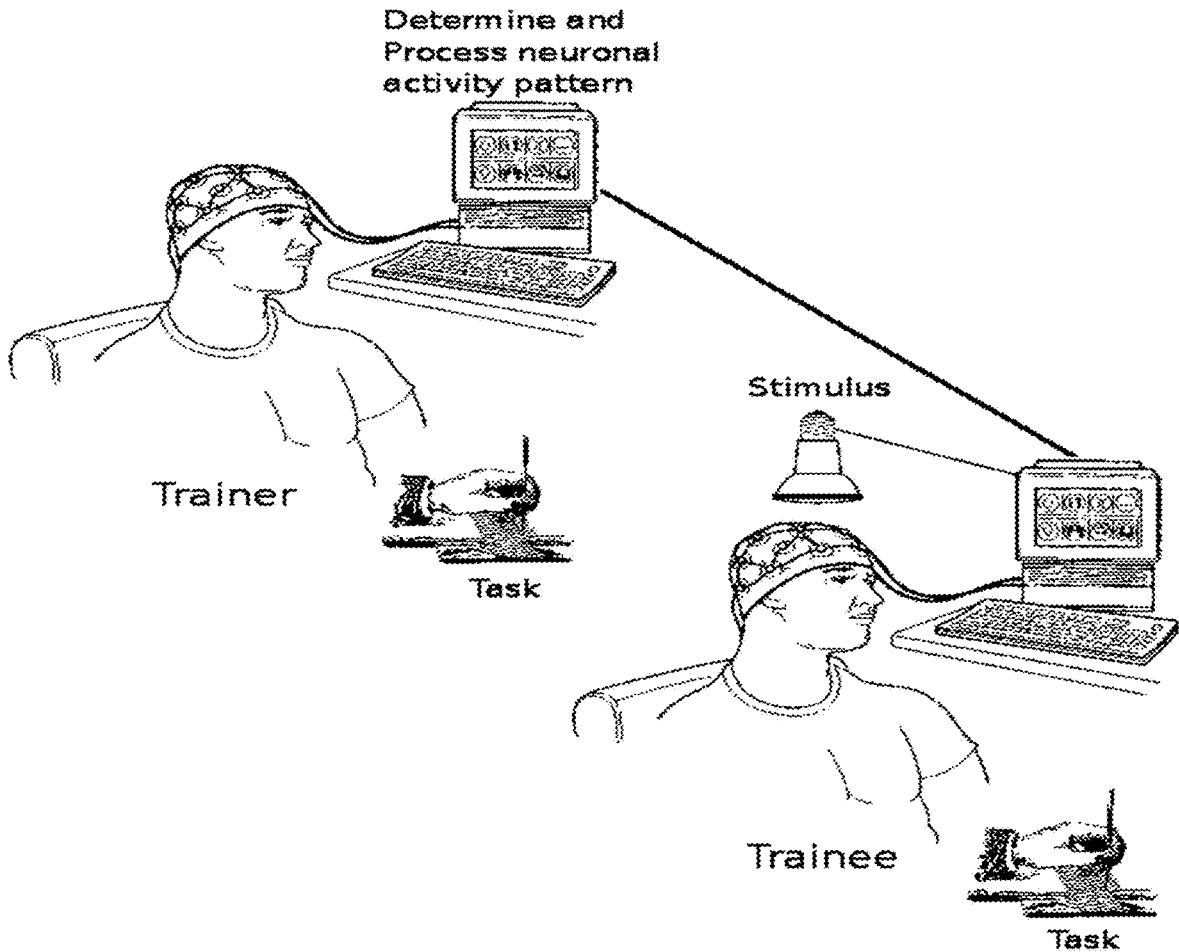
FIG. 13 shows a flowchart according to one embodiment of the invention.
FIG. 14 shows a schematic representation of an apparatus according to one embodiment of the invention.

FIG. 13 shows a flowchart according to one embodiment of the invention. Brainwaves in a subject engaged in a task are recorded, and brainwaves selectively associated with the task are identified. A pattern, e.g., a temporal pattern, in the brainwave associated with the task, is decoded and used to entrain the brainwaves of the second subject.

FIG. 14 shows a schematic representation of an apparatus according to one embodiment of the invention.

Figure 15:
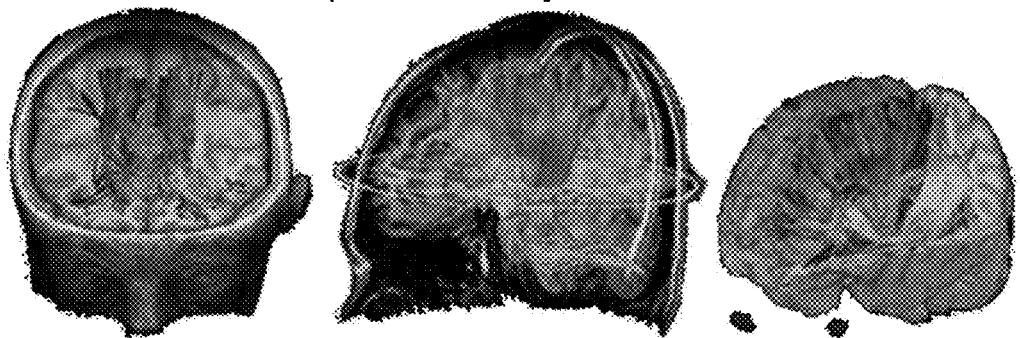
FIG. 15 shows brainwave real-time BOLD (Blood Oxygen Level Dependent) fMRI studies acquired with synchronized stimuli.

FIG. 15 shows brainwave real time BOLD (Blood Oxygen Level Dependent) fMRI studies acquired with synchronized stimuli.

Figure 16:
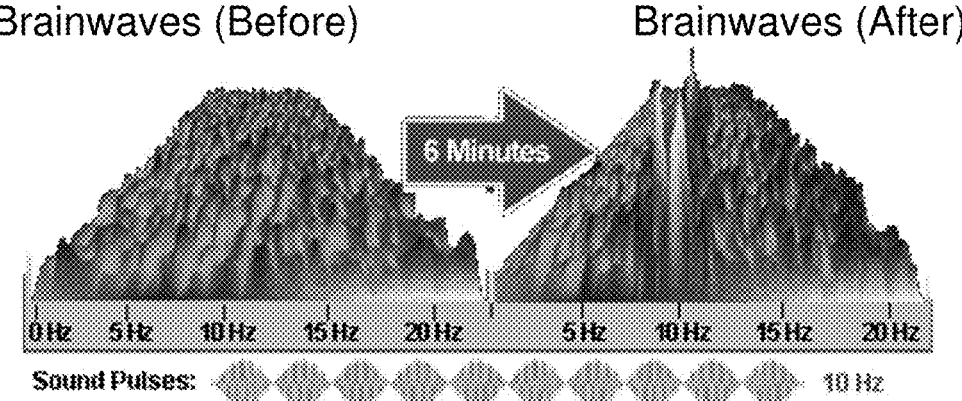
FIG. 16 shows Brain Entrainment Frequency Following Response (or FFR).
Figure 17:
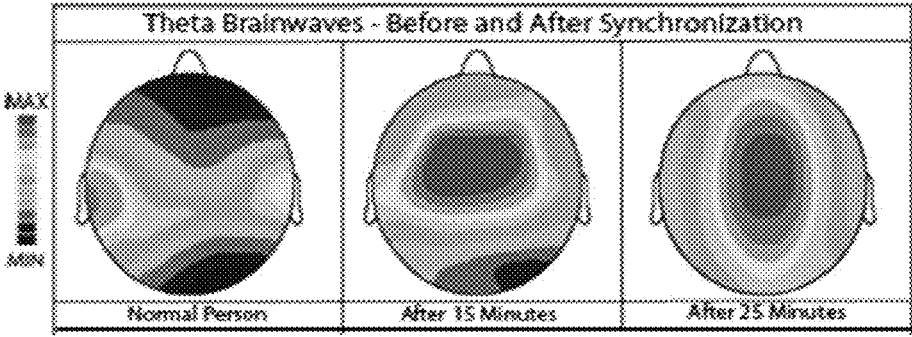
FIG. 17 shows brainwave entrainment before and after synchronization.

FIG. 16 shows FIG. 17 shows brainwave entrainment before and after synchronization. See, Understanding Brainwaves to Expand our Consciousness, fractalenlightenment.com/14794/spirituality/understanding-brainwaves-to-expand-our-consciousness FIG. 18 shows brainwaves during inefficient problem solving and stress.

FIGS. 19 and 20 show how binaural beats work. Binaural beats are perceived when two different pure-tone sine waves, both with frequencies lower than 1500 Hz, with less than a 40 Hz difference between them, are presented to a listener dichotically (one through each ear). See, en.wikipedia.org/wiki/Beat_(acoustics) #Binaural_beats. For example, if a 530 Hz pure tone is presented to a subject's right ear, while a 520 Hz pure tone is presented to the subject's left ear, the listener will perceive the auditory illusion of a third tone, in addition to the two pure-tones presented to each ear. The third sound is called a binaural beat, and in this example would have a perceived pitch correlating to a frequency of 10 Hz, that being the difference between the 530 Hz and 520 Hz pure tones presented to each ear. Binaural-beat perception originates in the inferior colliculus of the midbrain and the superior olivary complex of the brainstem, where auditory signals from each ear are integrated and precipitate electrical impulses along neural pathways through the reticular formation up the midbrain to the thalamus, auditory cortex, and other cortical regions.

FIG. 21 shows Functional Magnetic Resonance Imaging (fMRI)

Figures 22, 23, 24:
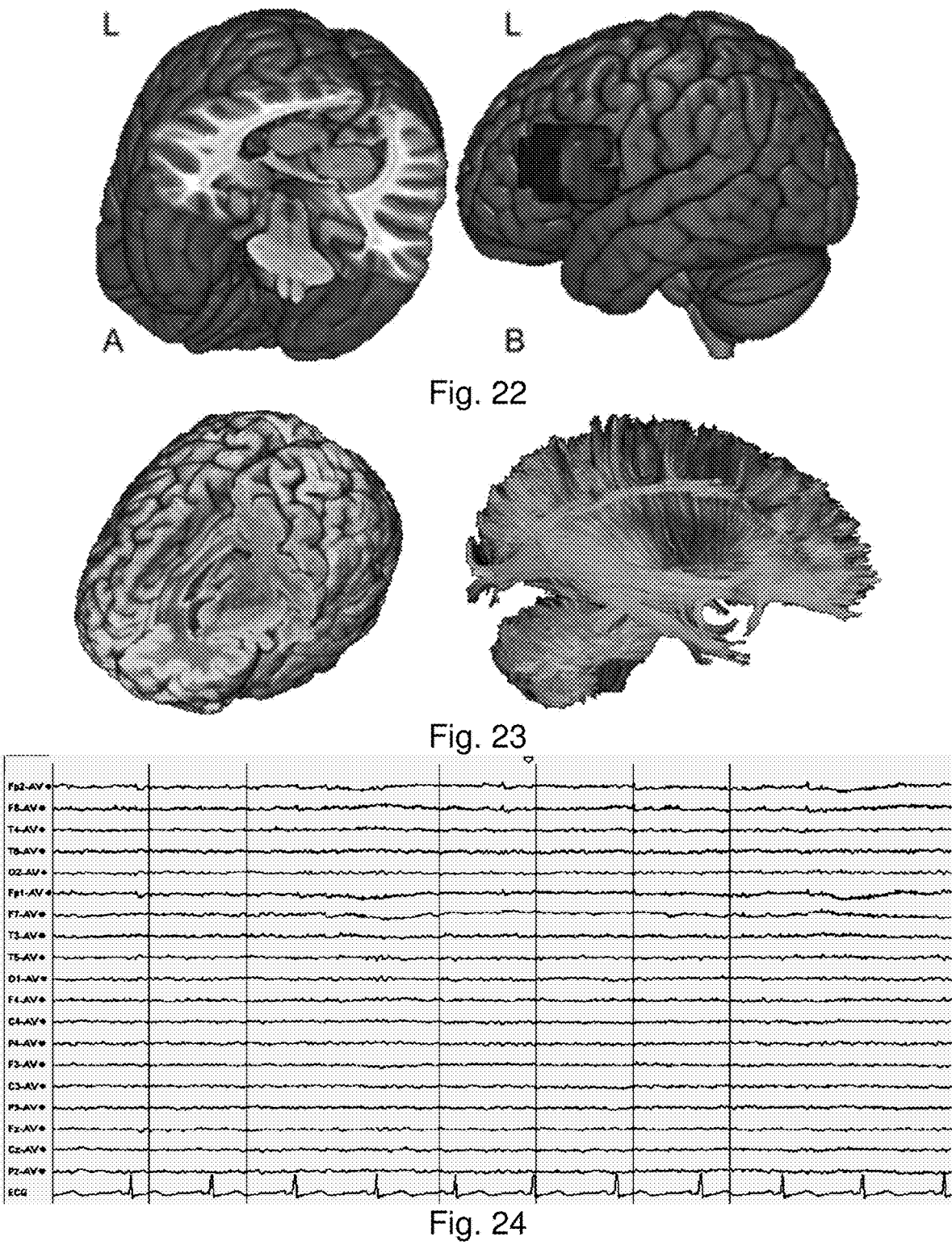
FIG. 22 shows a photo of a brain forming a new idea.
FIG. 23 shows 3D T2 CUBE (SPACENISTA) FLAIR & DSI tractography
FIG. 24 shows an EEG tracing.

FIG. 22 shows a photo of a brain forming a new idea.

FIG. 23 shows 3D T2 CUBE (SPACENISTA) FLAIR & DSI tractography.

FIG. 24 shows The EEG activities for a healthy subject during a working memory task.

FIG. 25 shows a flowchart according to one embodiment of the invention. Brainwaves in a subject engaged in a task are recorded. Brainwaves associated with the task are identified. A temporal pattern in the brainwave associated with the task is extracted. First and second dynamic audio stimuli are generated, whose frequency differential corresponds to the temporal pattern. Binaural beats are provided using the first and the second audio stimuli to stereo headphones worn by the second subject to entrain the brainwaves of the second subject.

FIG. 25 shows a flowchart according to one embodiment of the invention. Brainwaves of a subject engaged in a task are recorded, and brainwaves associated with the task identified. A pattern in the brainwave associated with the task is identified, having a temporal variation. Two dynamic audio stimuli whose frequency differential corresponds to the temporal variation are generated, and applied as a set of binaural bits to the second subject, to entrain the brainwaves of the second subject.

FIG. 26 shows a flowchart according to one embodiment of the invention. Brainwaves of a subject engaged in a task are recorded, and brainwaves associated with the task identified. A pattern in the brainwave associated with the task is identified, having a temporal variation. A series of isochronic tones whose frequency differential corresponds to the temporal variation is generated and applied as a set of stimuli to the second subject, to entrain the brainwaves of the second subject.

FIG. 27 shows a flowchart according to one embodiment of the invention. Brainwaves of a subject engaged in a task are recorded, and brainwaves associated with the task identified. A pattern in the brainwave associated with the task is identified, having a temporal variation. Two dynamic light stimuli whose frequency differential corresponds to the temporal variation are generated, and applied as a set of stimuli to the second subject, wherein each eye sees only one light stimuli, to entrain the brainwaves of the second subject.

FIG. 28 shows a flowchart according to one embodiment of the invention. Brainwaves of a subject engaged in a task are recorded, and brainwaves associated with the task identified. A pattern in the brainwave associated with the task is identified, having a temporal variation. Two dynamic electric stimuli whose frequency differential corresponds to the temporal variation are generated, and applied as transcranial stimulation to the second subject, wherein each electric signal is applied to the opposite side of the subject's head, to entrain the brainwaves of the second subject.

Example 1

We record EEG of a concert pianist while the pianist is playing a particular piece (e.g., Beethoven sonata); then decode the dynamic spatial and/or temporal patterns of the EEG and encode them in software. If a music student wants to learn this particular Beethoven sonata, we use the software with an encoded dynamic temporal pattern to drive "smart bulbs" or another source of light while the student is learning to play this piece from the music sheet. The result is accelerated learning. See FIG. 1.

Example 2

We record EEG of a martial art master while performing a particular move (say Karate or Kong Fu), decode the dynamic spatial and temporal patterns of the EEG and encode them in software. If a karate student wants to learn this particular move, we use the software with an encoded temporal pattern to drive smart bulbs or another source of light while the student is practicing this move. The result is accelerated learning. FIG. 2 represents an embodiment of the invention as applied to learning a drawing task, which is representative of various motor skills.

Example 3

A person is reading a book, and during the course of the reading, brain activity, including electrical or magnetic activity, and optionally other measurements, as acquired. The data is processed to determine the frequency and phase, and dynamic changes of brainwave activity, as well as the spatial location of emission. Based on a brain model, a set of non-invasive stimuli, which may include any and all senses, magnetic nerve or brain stimulation, ultrasound, etc., is devised for a subject who is to read or learn the same book. The subject is provided with the book to read, and the stimuli are presented to the subject synchronized with the progress through the book. Typically, the book is presented to the subject through an electronic reader device, such as a computer or computing pad, to assist in synchronization. The same electronic reader device may produce the temporal pattern of stimulation across the various stimulus modalities. The result is speed reading and improved comprehension and retention of the information. Other examples of skill domains that may be facilitated include learning foreign languages, math, sports or specialized skills. The method of the present invention can be used to accelerate learning of new information, new subjects or fine motor skills.

In this description, several preferred embodiments were discussed. Persons skilled in the art will, undoubtedly, have other ideas as to how the systems and methods described herein may be used. It is understood that this broad invention is not limited to the embodiments discussed herein. Rather, the invention is limited only by the following claims.

The aspects of the invention are intended to be separable and may be implemented in combination, sub-combination, and with various permutations of embodiments. Therefore, the various disclosure herein, including that which is represented by acknowledged prior art, may be combined, sub-combined and permuted in accordance with the teachings hereof, without departing from the spirit and scope of the invention. All references and information sources cited herein are expressly incorporated herein by reference in their entirety.

What is claimed is:

1. An apparatus for facilitating a skill or task, comprising:
a memory, configured to store automatically processed dynamic neuronal electrical activity patterns comprising at least one of a delta rhythm and a theta rhythm selectively associated with the skill or task;
an input configured to receive electroencephalographic signals from a subject;
a parallel processor, configured to perform mathematical transforms for processing of the electroencephalographic signals from the subject in parallel, to at least extract frequency and phase information; and
a stimulator, configured to entrain brainwaves of the subject with at least one sensory stimulus, comprising frequencies dependent on the stored dynamic neuronal activity patterns comprising the at least one of the delta rhythm and the theta rhythm selectively associated with the skill or task, and being dependent on a relative frequency and phase of the stored dynamic neuronal electrical activity patterns comprising the at least one of the delta rhythm and the theta rhythm with respect to the extracted frequency and phase information from the electroencephalographic signals, to facilitate performance of the respective skill or task by the subject.

2. The apparatus according to claim 1, wherein the at least one sensory stimulus comprises a concurrent plurality of frequencies.

3. The apparatus according to claim 1, further comprising an input configured to acquire the dynamic neuronal electrical activity patterns comprising the at least one of the delta rhythm and the theta rhythm associated with the skill or task of the subject.

4. The apparatus according to claim 1, wherein the stimulator comprises at least one sensory stimulator configured to generate at least one of an audio, visual, or audio-visual stimulus.

5. The apparatus according to claim 1, wherein the stimulator is configured to cause brainwave entrainment of the subject with the dynamic neuronal electrical activity patterns comprising the at least one of the delta rhythm and the theta rhythm.

6. The apparatus according to claim 1, wherein the at least one sensory stimulus comprises a central nervous system stimulation of the subject with a signal having a modulation corresponding to a dynamic neuronal electrical activity pattern comprising the at least one of the delta rhythm and the theta rhythm defined by a recording of brainwaves of a human.

7. The apparatus of claim 1, wherein the stimulator is configured to deliver a tactile stimulus in addition to at least one of a visual and an auditory stimulus.

8. The apparatus according to claim 1, wherein the stimulator comprises an optical illuminator configured to produce optical patterns having a time-varying intensity pattern corresponding to the dynamic neuronal electrical activity patterns, wherein the dynamic neuronal electrical activity patterns comprising the at least one of the delta rhythm and the theta rhythm have a waveform corresponding to an acquired brainwave.

9. The apparatus according to claim 1, further comprising:

an input configured to receive electrical brainwave signals; and at least one processor configured to process the received electrical brainwave signals to define the dynamic electrical neuronal activity patterns comprising the at least one of the delta rhythm and the theta rhythm, wherein the received electrical brainwave signals are not from the same subject at the same time.

10. The apparatus according to claim 1, wherein the processed dynamic electrical neuronal activity pattern comprising the at least one of the delta rhythm and the theta rhythm comprises a plurality of sequential frequency patterns of electrical brainwave activity of a human while engaged in different aspects of the skill or task; and the at least one sensory stimulus comprises a sequence of phases respectively representing the plurality of frequency patterns.

11. A system for determining a target brain activity state-dependent neurostimulation pattern, dependent on a task, comprising:

a memory configured to store a model of electrical brainwave activity data comprising a plurality of concurrent waves including at least one of a delta rhythm and a theta rhythm over time of a first subject during a plurality of distinct aspects of performance of the task and transitions between respective aspects of performance of the task, dependent on rhythm frequencies and respective phase differences between the plurality of concurrent waves, for each of the plurality of distinct aspects and transitions between respective aspects;

an input configured to receive brainwaves from a second subject;

a single-instruction multiple-data processor, configured to perform parallel mathematical transforms of the brainwaves from the second subject in parallel, and to determine at least frequency and phase information; and at least one processor configured to determine a sequence of neurostimulation patterns for a multichannel neurostimulator, the multichannel neurostimulator being configured to stimulate a brain of the second subject, associated with a performance of the task by the second subject, with a stimulus comprising the at least one of the delta rhythm and the theta rhythm and being dependent on a relationship of:

the determined frequencies and the phases, and the rhythm frequencies and respective phase differences between the plurality of concurrent waves of the modelled electrical brainwave activity data comprising a plurality of concurrent waves including at least one of an delta rhythm and a theta rhythm over time of the first subject.

12. A computer-readable medium, storing therein non-transitory instructions for a programmable processor to perform a process, comprising the computer-implemented steps of:

reading information from a memory representing dynamic neuronal electrical activity patterns comprising at least one frequency within a range of 1 Hz to 8 Hz selectively associated with the skill or task;

receiving electroencephalographic signals from a subject;

performing mathematical transforms using a parallel processor to process of the electroencephalographic signals from the subject in parallel, to at least extract frequency and phase information; and controlling a neurostimulator, to entrain brainwaves of a subject with at least one sensory stimulus, dependent on the dynamic neuronal electrical activity patterns selectively associated with the skill or task, and a frequency and phase difference of the dynamic neuronal electrical activity patterns from the extracted frequency and phase information, the at least one sensory stimulus comprising the at least one frequency within the range of 1 Hz to 8 Hz, to facilitate performance of the respective skill or task by a stimulated subject.

13. A method for determining a target brain electrical activity state, dependent on a task, comprising:

acquiring electrical brainwave activity data comprising a plurality of concurrent waves including at least one of a delta rhythm and a theta rhythm over time of a first subject during a plurality of distinct aspects of performance of the task and transitions between respective aspects of performance of the task;

analyzing the acquired electrical brainwave activity data comprising the plurality of concurrent waves including the at least one of the delta rhythm and the theta rhythm over time of the first subject, comprising determining rhythm frequencies of the plurality of concurrent waves, and phase differences between the plurality of concurrent waves, including at least one of a delta rhythm and a theta rhythm over time, for each of the plurality of distinct aspects of performance of the task and transitions between respective aspects of performance of the task;

modelling electrical brainwave characteristics of the first subject for each distinct aspect of performance of the task and transitions between respective aspects of performance of the task based on at least the rhythms frequencies of the plurality of concurrent waves and the phase differences between the plurality of concurrent waves;

acquiring second electrical brainwave activity data over time of a second subject;

performing parallel mathematical transforms of the second electrical brainwave activity data an automated parallel processor, configured to determine at least frequency and phase information of the second electrical brainwave activity data;

modelling second electrical brainwave activity data characteristics of the second subject based on at least the frequency and phase information; and determining a sequence of neurostimulation patterns for a multichannel neurostimulator configured to entrain brainwaves of the second subject, associated with a performance of the task by the second subject, with the determined rhythm frequencies of the plurality of concurrent waves, and being dependent on the phase differences between the plurality of concurrent waves, the modelled electrical brainwave activity data characteristics of the first subject, and the modelled second electrical brainwave activity data characteristics of the second subject based on at least the frequency and phase information.

14. The method according to claim 13, wherein the acquired electrical brainwave activity data over time of the first subject and the acquired second electrical brainwave activity of the second subject are each spatially localized.

15. The method according to claim 13, wherein said analyzing comprises performing a mathematical transform of the electrical brainwave activity data to preserve spatial and state transition history.

16. The method according to claim 15, further comprising modifying the mathematically transformed electrical brainwave activity data and performing an inverse mathematical transform on the modified mathematically transformed electrical brainwave activity data.

17. The method according to claim 15, further comprising filtering noise from the mathematically transformed electrical brainwave activity data.

18. The method according to claim 13, further comprising temporally synchronizing the sequence of neurostimulation patterns with the acquired second electrical brainwave activity data over time of the second subject.

19. The method according to claim 13, further comprising normalizing a sequence of neurostimulation patterns based on differences between the modelled electrical brainwave characteristics of the first subject and the modelled second electrical brainwave characteristics of the second subject.

20. The method according to claim 13, wherein the analyzing of the acquired brain activity data over time of the first subject comprises representing the electrical brainwave activity data over time as an at least four dimensional matrix.

21. The method according to claim 13, wherein the analyzing of the acquired brain activity data over time of the first subject comprises processing of the acquired electrical brainwave activity data over time with a convolutional neural network.

22. The method according to claim 13, wherein the multichannel neurostimulator comprises at least one of an audio stimulator and a visual stimulator.

23. The method according to claim 13, further comprising presenting the sequence of neurostimulation patterns to the second subject.

* * * * *